US007809541B2

(12) United States Patent
Cheetham et al.

(10) Patent No.: US 7,809,541 B2
(45) Date of Patent: Oct. 5, 2010

(54) CRYSTAL STRUCTURE OF AURORA-2 PROTEIN AND BINDING POCKETS THEREOF

(75) Inventors: Graham Cheetham, Abingdon (GB); Ronald Knegtel, Abingdon (GB); Lovorka Swenson, Belmont, MA (US); Joyce T. Coll, Westborough, MA (US); Suzanne Renwick, Sunbury on Thames (GB); Peter Weber, Abingdon (GB)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 409 days.

(21) Appl. No.: 12/070,054

(22) Filed: Feb. 13, 2008

(65) Prior Publication Data

US 2009/0287422 A1 Nov. 19, 2009

Related U.S. Application Data

(60) Division of application No. 10/979,375, filed on Nov. 1, 2004, now Pat. No. 7,361,492, which is a continuation of application No. PCT/US03/13605, filed on May 1, 2003.

(60) Provisional application No. 60/377,510, filed on May 1, 2002.

(51) Int. Cl.
G06G 7/58 (2006.01)
C12N 9/12 (2006.01)
(52) U.S. Cl. .......................................... 703/11; 435/194
(58) Field of Classification Search ....................... None
See application file for complete search history.

(56) References Cited

U.S. PATENT DOCUMENTS

| 4,886,646 | A | 12/1989 | Carter et al. |
| 5,096,676 | A | 3/1992 | McPherson et al. |
| 5,130,105 | A | 7/1992 | Carter et al. |
| 5,221,410 | A | 6/1993 | Kushner et al. |
| 5,400,741 | A | 3/1995 | DeTitta et al. |
| 5,884,230 | A | 3/1999 | Srinivasan et al. |
| 7,214,518 | B2 * | 5/2007 | Anderson et al. ........... 435/183 |

FOREIGN PATENT DOCUMENTS

| WO | WO 02/22602 | 3/2002 |
| WO | WO 03/031606 | 4/2003 |

OTHER PUBLICATIONS

Balbes et al., "A Perspective of Modern Methods in Computer-Aided Drug Design", *Rev. in Comp. Chem.*, 5: 337-379 (1994).
Bartlett et al., "CAVEAT: A Program to Facilitate the Structure-Derived Design of Biologically Active Molecules", *Mol. Recog. in Chem. and Biol. Prob.*, 78: 182-196 (1989).
Bayliss, et al., "Structural Basis of Aurora-A Activation by TPX2 at the Mitotic Spindle", *Mol. Cell*, 12: 851-862 (2003).
Bellon, et al., "The Structure of Phosphorylated P38γ is Monomeric and Reveals a Conserved Activation-Loop Conformation", *Structure*, 7: 1057-1065 (1999).
Blundell et al., "Knowledge-Based Prediction of Protein Structures and the Design of Novel Molecules", *Nature*, 326: 347-352 (1987).
Böhm, "The Computer Program LUDI: A New Method for the De Novo Design of Enzyme Inhibitors", *J. Comp. Aid. Molec. Design*, 6: 61-78 (1992).
Brown, et al., "Effects of Phosphorylation of Threonine 160 on Cyclin-Dependent Kinase 2 Structure and Activity", *J. Biol. Chem.*, 274: 8746-8756 (1999).
Brünger et al., "Crystallography & NMR System: A New Software Suite for Macromolecular Structure Determination", *Acta Cryst.*, D54: 905-921 (1998).
Carson, "Ribbons 2.0", *J. Appl. Cryst.*, 24: 958-961 (1991).
Chayen, "A Novel Technique to Control the Rate of Vapour Diffusion, Giving Larger Protein Crystals", *J. Appl. Cryst.*, 30: 198-202 (1997).
Chayen, "The Role of Oil in Macromolecular Crystallization", *Structure*, 5: 1269-1274 (1997).
Chayen, "Comparative Studies of Protein Crystallization by Vapour-Diffusion and Microbatch Techniques", *Acta Cryst.*, D54: 8-15 (1998).
Cheetam et al., "Crystal Structure of Aurora-2, an Oncogenic Serine/Threonine Kinase", *J. Biol. Chem.*, 277: 42419-42422 (2002).
Cohen et al., "Molecular Modeling Software and Methods for Medicinal Chemistry", *J. Med. Chem*, 33: 883-894 (1990).
D' Arcy et al., "A Novel Approach to Crystallising Proteins Under Oil", *J. Cryst. Growth*, 168: 175-180 (1996).
Eisen et al., "HOOK: A Program for Finding Novel Molecular Architectures that Satisfy the Chemical and Steric Requirements of a Macromolecule Binding Site", *Proteins Struct. Funct. Genet.*, 19: 199-221 (1994).
Fetrow and Bryant, "New Programs for Protein Tertiary Structure Prediction", *Bio/Technology*, 11: 479-484 (1993).

(Continued)

*Primary Examiner*—Suzanne M. Noakes
(74) *Attorney, Agent, or Firm*—Ropes & Gray LLP; James F. Haley, Jr.; Raymond M. Doss

(57) ABSTRACT

The present invention provides crystalline molecules or molecular complexes which comprise binding pockets of Aurora-2 or its homologues. The invention also provides crystals comprising Aurora-2. The present invention also relates to a computer comprising a data storage medium encoded with the structural coordinates of Aurora-2 binding pockets and methods of using a computer to evaluate the ability of a compound to bind to the molecule or molecular complex. This invention also provides methods of using the structure coordinates to solve the structure of homologous proteins or protein complexes. In addition, this invention provides methods of using the structure coordinates to screen for and design compounds, including inhibitory compounds, that bind to Aurora-2 or homologues thereof.

6 Claims, 141 Drawing Sheets

OTHER PUBLICATIONS

Fox et al., "A Single Amino Acid Substitution Makes ERK2 Susceptible to Pyridinyl Imidazole Inhibitors of p38 MAP Kinase" *Protein Sci.*, 7: 2249-2255 (1998).

Gerstein and Altman, "Average Core Structures and Variability Measures for Protein Families: Application to the Immunoglobulins", *J. Mol. Biol.*, 251: 161-175 (1995).

Giet and Prigent, "Aurora/Ipl1p-Related Kinases, a New Oncogenic Family of Mitotic Serine-Threonine Kinases", *J. Cell Science*, 112: 3591-3601 (1999).

Gillet et al., "SPROUT: A Program for Structure Generation", *J. Comp. Aid. Molec. Design*, 7: 127-153 (1993).

Goepfert and Brinkley, "The Centrosome-Associated Aurora/Ipl-Like Kinase Family", *Curr. Top. Dev. Biol.*, 49: 331-342 (2000).

Goodford, "A Computational Procedure for Determining Energetically Favorable Binding Sites on Biologically Important Macromolecules", *J. Med. Chem.*, 28: 849-857 (1985).

Goodsell and Olson, "Automated Docking of Substrates to Proteins by Simulated Annealing", *Proteins Struct. Funct. Genet.*, 8: 195-202 (1990).

Greer, "Comparative Modeling of Homologous Proteins", *Methods In Enzymol.*, 202: 239-253 (1991).

Guex and Peitsch, "Swiss-Model and the SwissPdb Viewer: An Environment for Comparative Protein Modeling", *Electrophoresis*, 18: 2714-2723 (1997).

Guida, "Software for Structure-Based Drug Design", *Curr. Opin. Struct. Biol.*, 4: 777-781 (1994).

Hanks et al., "The Protein Kinase Family: Conserved Features and Deduced Phylogeny of the Catalytic Domains", *Science*, 241: 42-52 (1988).

Hanks and Quinn, "Protein Kinase Catalytic Domain Sequence Database: Identification of Conserved Features of Primary Structure and Classification of Family Members", *Methods In Enzymol.*, 200: 38-62 (1991).

Higgins et al., "Using Clustal for Multiple Sequence Alignments", *Methods In Enzymol.*, 266: 383-402 (1996).

Johnson et al., "Knowledge-Based Protein Modeling", *Crit. Rev. Biochem. Mol. Biol.*, 29: 1-68 (1994).

Jones et al., "Improved Methods for Building Protein Models in Electron Density Maps and the Location of Errors in these Models", *Acta Cryst.*, A47: 110-119 (1991).

Kuntz et al., "A Geometric Approach to Macromolecule-Ligand Interactions", *J. Mol. Biol.*, 161: 269-288 (1982).

Lattman, "Use of Rotation and Translation Functions", *Methods In Enzymol.*, 115: 55-77 (1985).

Lauri and Bartlett, "CAVEAT: A Program to Facilitate the Design of Organic Molecules", *J. Comput. Aided Mol. Des.*, 8: 51-66 (1994).

Leslie, "Integration Of Macromolecular Diffraction Data", *Acta Cryst.*, D55: 1696-1702 (1999).

Martin, "3D Database Searching in Drug Design", *J. Med. Chem.*, 35: 2145-2154 (1992).

Meng et al., "Automated Docking with Grid-Based Energy Evaluation", *J. Comp. Chem.*, 13: 505-524 (1992).

Miranker and Karplus, "Functionality Maps of Binding Sites: A Multiple Copy Simultaneous Search Method", *Proteins Struct. Funct. Genet.*, 11: 29-34 (1991).

Miyoshi, et al., "Association Of Centrosomal Kinase *STK15/BTAK* MRNA Expression with Chromosomal Instability in Human Breast Cancers", *Int. J. Cancer*, 92: 370-373 (2001).

Navaza, "*AmoRe*: An Automated Package for Molecular Replacement," *Acta Cryst.*, A50: 157-163 (1994).

Navia and Murcko, "Use of Structural Information in Drug Design", *Curr. Opin. Struct. Biol.*, 2: 202-210 (1992).

Nishibata and Itai, "Automatic Creation of Drug Candidate Structures Based on Receptor Structure. Starting Point for Artificial Lead Generation", *Tetrahedron*, 47: 8985-8990 (1991).

Nowakowski et al., "Structures of the Cancer-Related Aurora-A, FAK, and EphA2 Protein Kinases from Nanovolume Crystallography", *Structure*, 10: 1659-1667 (2002).

Pav et al., "Microtube Batch Protein Crystallization: Applications to Human Immunodeficiency Virus Type 2 (HIV-2) Protease and Human Renin", *Proteins Struct. Funct. Genet.*, 20: 98-102 (1994).

Schnare et al., "Comprehensive Comparison of Structural Characteristics in Eukaryotic Cytoplasmic Large Subunit (23 S-like) Ribosomal RNA", *J. Mol. Biol.*, 256: 701-719 (1996).

Smith and Waterman, "Comparison of Biosequences", *Adv. In App. Math.*, 2: 482-489 (1981).

Szklarz and Halpert, "Use of Homology Modeling in Conjunction with Site-Directed Mutagenesis for Analysis of Structure-Function Relationships of Mammalian Cytochromes P450", *Life Sci.*, 61: 2507-2520 (1997).

Tainer, et al., "The Reactivity of Anti-Peptide Antibodies is a Function of the Atomic Mobility of Sites in a Protein", *Nature*, 312: 127-134 (1984).

ter Haar et al., "Structure of GSK3β Reveals a Primed Phosphorylation Mechanism" *Nat. Struct. Biol.* 8: 593-596 (2001).

Wang et al., "The Structure Of Mitogen-Activated Protein Kinase p38 at 2.1—Å Resolution", *Proc. Natl. Acad. Sci. USA*, 94: 2327-2332 (1997).

Wilson et al., "Crystal Structure of P38 Mitogen-Activated Protein Kinase", *J. Biol. Chem.*, 271: 27696-27700 (1996).

Wishart et al., "Constrained Multiple Sequence Alignment Using XALIGN", *Comput. Appl. Biosci.*, 10: 687-688 (1994).

Xie et al., "Crystal Structure of JNK3: A Kinase Implicated in Neuronal Apoptosis" *Structure*, 6: 983-991 (1998).

Zhang et al., "Atomic Structure of the MAP Kinase ERK2 at 2.3 Å Resolution", *Nature*, 367: 704-711 (1994).

"The *CCP4* Suite: Programs for Protein Crystallography", Collaborative Computational Project, No. 4, *Acta. Cryst.*, D50: 760-763 (1994).

\* cited by examiner

Figure 1A

| | Atom | Type | Resid | # | X | Y | Z | Occ | B | Mol | |
|---|---|---|---|---|---|---|---|---|---|---|---|
| ATOM | 1 | CB | GLN A | 127 | 0.325 | 21.296 | 18.772 | 1.00 | 127.88 | A | C |
| ATOM | 2 | CG | GLN A | 127 | -1.046 | 21.256 | 19.422 | 1.00 | 128.33 | A | C |
| ATOM | 3 | CD | GLN A | 127 | -1.726 | 22.612 | 19.427 | 1.00 | 128.40 | A | C |
| ATOM | 4 | OE1 | GLN A | 127 | -2.899 | 22.730 | 19.780 | 1.00 | 127.91 | A | O |
| ATOM | 5 | NE2 | GLN A | 127 | -0.990 | 23.647 | 19.034 | 1.00 | 127.78 | A | N |
| ATOM | 6 | C | GLN A | 127 | 2.235 | 20.064 | 17.748 | 1.00 | 125.70 | A | C |
| ATOM | 7 | O | GLN A | 127 | 2.597 | 19.151 | 17.005 | 1.00 | 125.94 | A | O |
| ATOM | 8 | N | GLN A | 127 | 1.319 | 19.351 | 19.941 | 1.00 | 126.48 | A | N |
| ATOM | 9 | CA | GLN A | 127 | 0.982 | 19.925 | 18.604 | 1.00 | 127.22 | A | C |
| ATOM | 10 | N | TRP A | 128 | 2.876 | 21.224 | 17.851 | 1.00 | 122.47 | A | N |
| ATOM | 11 | CA | TRP A | 128 | 4.112 | 21.520 | 17.137 | 1.00 | 116.88 | A | C |
| ATOM | 12 | CB | TRP A | 128 | 5.143 | 20.425 | 17.416 | 1.00 | 115.02 | A | C |
| ATOM | 13 | CG | TRP A | 128 | 5.203 | 20.045 | 18.870 | 1.00 | 113.98 | A | C |
| ATOM | 14 | CD2 | TRP A | 128 | 4.931 | 20.893 | 19.998 | 1.00 | 114.80 | A | C |
| ATOM | 15 | CE2 | TRP A | 128 | 5.069 | 20.101 | 21.158 | 1.00 | 114.55 | A | C |
| ATOM | 16 | CE3 | TRP A | 128 | 4.570 | 22.241 | 20.139 | 1.00 | 117.38 | A | C |
| ATOM | 17 | CD1 | TRP A | 128 | 5.500 | 18.817 | 19.380 | 1.00 | 113.92 | A | C |
| ATOM | 18 | NE1 | TRP A | 128 | 5.421 | 18.840 | 20.755 | 1.00 | 114.05 | A | N |
| ATOM | 19 | CZ2 | TRP A | 128 | 4.875 | 20.615 | 22.444 | 1.00 | 116.69 | A | C |
| ATOM | 20 | CZ3 | TRP A | 128 | 4.375 | 22.750 | 21.417 | 1.00 | 118.82 | A | C |
| ATOM | 21 | CH2 | TRP A | 128 | 4.522 | 21.935 | 22.552 | 1.00 | 118.90 | A | C |
| ATOM | 22 | C | TRP A | 128 | 3.997 | 21.765 | 15.640 | 1.00 | 113.95 | A | C |
| ATOM | 23 | O | TRP A | 128 | 3.608 | 20.896 | 14.857 | 1.00 | 110.45 | A | O |
| ATOM | 24 | N | ALA A | 129 | 4.352 | 22.991 | 15.281 | 1.00 | 111.97 | A | N |
| ATOM | 25 | CA | ALA A | 129 | 4.370 | 23.502 | 13.921 | 1.00 | 111.78 | A | C |
| ATOM | 26 | CB | ALA A | 129 | 3.018 | 24.104 | 13.558 | 1.00 | 111.78 | A | C |
| ATOM | 27 | C | ALA A | 129 | 5.412 | 24.594 | 14.095 | 1.00 | 111.90 | A | C |
| ATOM | 28 | O | ALA A | 129 | 5.480 | 25.205 | 15.161 | 1.00 | 110.75 | A | O |
| ATOM | 29 | N | LEU A | 130 | 6.234 | 24.841 | 13.084 | 1.00 | 113.37 | A | N |
| ATOM | 30 | CA | LEU A | 130 | 7.266 | 25.861 | 13.224 | 1.00 | 114.76 | A | C |
| ATOM | 31 | CB | LEU A | 130 | 7.958 | 26.119 | 11.885 | 1.00 | 112.78 | A | C |
| ATOM | 32 | CG | LEU A | 130 | 9.132 | 27.100 | 11.971 | 1.00 | 111.35 | A | C |
| ATOM | 33 | CD1 | LEU A | 130 | 10.120 | 26.630 | 13.032 | 1.00 | 110.44 | A | C |
| ATOM | 34 | CD2 | LEU A | 130 | 9.810 | 27.212 | 10.618 | 1.00 | 112.52 | A | C |
| ATOM | 35 | C | LEU A | 130 | 6.733 | 27.178 | 13.788 | 1.00 | 116.59 | A | C |
| ATOM | 36 | O | LEU A | 130 | 7.501 | 27.999 | 14.290 | 1.00 | 117.26 | A | O |
| ATOM | 37 | N | GLU A | 131 | 5.420 | 27.372 | 13.717 | 1.00 | 117.84 | A | N |
| ATOM | 38 | CA | GLU A | 131 | 4.801 | 28.597 | 14.214 | 1.00 | 117.92 | A | C |
| ATOM | 39 | CB | GLU A | 131 | 3.329 | 28.660 | 13.801 | 1.00 | 122.28 | A | C |
| ATOM | 40 | CG | GLU A | 131 | 2.698 | 30.027 | 14.020 | 1.00 | 129.95 | A | C |
| ATOM | 41 | CD | GLU A | 131 | 1.184 | 29.976 | 14.066 | 1.00 | 134.06 | A | C |
| ATOM | 42 | OE1 | GLU A | 131 | 0.573 | 29.459 | 13.108 | 1.00 | 135.96 | A | O |
| ATOM | 43 | OE2 | GLU A | 131 | 0.606 | 30.458 | 15.063 | 1.00 | 135.89 | A | O- |
| ATOM | 44 | C | GLU A | 131 | 4.884 | 28.741 | 15.732 | 1.00 | 115.10 | A | C |
| ATOM | 45 | O | GLU A | 131 | 5.359 | 29.756 | 16.242 | 1.00 | 114.82 | A | O |
| ATOM | 46 | N | ASP A | 132 | 4.416 | 27.720 | 16.444 | 1.00 | 111.27 | A | N |
| ATOM | 47 | CA | ASP A | 132 | 4.404 | 27.718 | 17.905 | 1.00 | 106.88 | A | C |
| ATOM | 48 | CB | ASP A | 132 | 4.003 | 26.336 | 18.431 | 1.00 | 106.57 | A | C |
| ATOM | 49 | CG | ASP A | 132 | 2.959 | 25.660 | 17.568 | 1.00 | 106.64 | A | C |
| ATOM | 50 | OD1 | ASP A | 132 | 3.274 | 25.329 | 16.406 | 1.00 | 105.58 | A | O |
| ATOM | 51 | OD2 | ASP A | 132 | 1.825 | 25.458 | 18.050 | 1.00 | 107.73 | A | O |
| ATOM | 52 | C | ASP A | 132 | 5.736 | 28.097 | 18.541 | 1.00 | 103.44 | A | C |
| ATOM | 53 | O | ASP A | 132 | 5.832 | 28.192 | 19.765 | 1.00 | 101.89 | A | O |
| ATOM | 54 | N | PHE A | 133 | 6.764 | 28.315 | 17.728 | 1.00 | 99.34 | A | N |
| ATOM | 55 | CA | PHE A | 133 | 8.063 | 28.642 | 18.290 | 1.00 | 96.10 | A | C |
| ATOM | 56 | CB | PHE A | 133 | 9.041 | 27.501 | 18.012 | 1.00 | 93.17 | A | C |
| ATOM | 57 | CG | PHE A | 133 | 8.600 | 26.190 | 18.586 | 1.00 | 90.32 | A | C |
| ATOM | 58 | CD1 | PHE A | 133 | 7.596 | 25.451 | 17.969 | 1.00 | 87.81 | A | C |

Figure 1B

| ATOM | 59 | CD2 | PHE | A | 133 | 9.146 | 25.719 | 19.773 | 1.00 | 91.26 | A | C |
|---|---|---|---|---|---|---|---|---|---|---|---|---|
| ATOM | 60 | CE1 | PHE | A | 133 | 7.139 | 24.265 | 18.528 | 1.00 | 87.69 | A | C |
| ATOM | 61 | CE2 | PHE | A | 133 | 8.696 | 24.533 | 20.342 | 1.00 | 91.81 | A | C |
| ATOM | 62 | CZ | PHE | A | 133 | 7.690 | 23.806 | 19.718 | 1.00 | 89.39 | A | C |
| ATOM | 63 | C | PHE | A | 133 | 8.698 | 29.964 | 17.897 | 1.00 | 95.70 | A | C |
| ATOM | 64 | O | PHE | A | 133 | 8.702 | 30.368 | 16.735 | 1.00 | 95.61 | A | O |
| ATOM | 65 | N | GLU | A | 134 | 9.236 | 30.624 | 18.915 | 1.00 | 94.54 | A | N |
| ATOM | 66 | CA | GLU | A | 134 | 9.921 | 31.899 | 18.788 | 1.00 | 92.75 | A | C |
| ATOM | 67 | CB | GLU | A | 134 | 9.547 | 32.774 | 19.989 | 1.00 | 96.03 | A | C |
| ATOM | 68 | CG | GLU | A | 134 | 9.973 | 34.219 | 19.905 | 1.00 | 100.91 | A | C |
| ATOM | 69 | CD | GLU | A | 134 | 9.406 | 35.063 | 21.033 | 1.00 | 104.28 | A | C |
| ATOM | 70 | OE1 | GLU | A | 134 | 8.193 | 34.954 | 21.307 | 1.00 | 107.44 | A | O |
| ATOM | 71 | OE2 | GLU | A | 134 | 10.169 | 35.843 | 21.640 | 1.00 | 105.04 | A | O |
| ATOM | 72 | C | GLU | A | 134 | 11.391 | 31.487 | 18.853 | 1.00 | 89.51 | A | C |
| ATOM | 73 | O | GLU | A | 134 | 11.829 | 30.964 | 19.873 | 1.00 | 89.68 | A | O |
| ATOM | 74 | N | ILE | A | 135 | 12.149 | 31.698 | 17.779 | 1.00 | 85.75 | A | N |
| ATOM | 75 | CA | ILE | A | 135 | 13.554 | 31.289 | 17.775 | 1.00 | 85.62 | A | C |
| ATOM | 76 | CB | ILE | A | 135 | 13.880 | 30.431 | 16.517 | 1.00 | 86.50 | A | C |
| ATOM | 77 | CG2 | ILE | A | 135 | 12.664 | 29.588 | 16.145 | 1.00 | 86.30 | A | C |
| ATOM | 78 | CG1 | ILE | A | 135 | 14.263 | 31.321 | 15.330 | 1.00 | 86.14 | A | C |
| ATOM | 79 | CD1 | ILE | A | 135 | 14.720 | 30.544 | 14.106 | 1.00 | 81.51 | A | C |
| ATOM | 80 | C | ILE | A | 135 | 14.554 | 32.443 | 17.881 | 1.00 | 84.38 | A | C |
| ATOM | 81 | O | ILE | A | 135 | 14.418 | 33.467 | 17.211 | 1.00 | 83.97 | A | O |
| ATOM | 82 | N | GLY | A | 136 | 15.562 | 32.260 | 18.729 | 1.00 | 83.40 | A | N |
| ATOM | 83 | CA | GLY | A | 136 | 16.565 | 33.291 | 18.928 | 1.00 | 85.07 | A | C |
| ATOM | 84 | C | GLY | A | 136 | 17.894 | 33.051 | 18.236 | 1.00 | 87.82 | A | C |
| ATOM | 85 | O | GLY | A | 136 | 17.980 | 33.076 | 17.008 | 1.00 | 91.47 | A | O |
| ATOM | 86 | N | ARG | A | 137 | 18.932 | 32.813 | 19.032 | 1.00 | 88.84 | A | N |
| ATOM | 87 | CA | ARG | A | 137 | 20.281 | 32.591 | 18.518 | 1.00 | 88.46 | A | C |
| ATOM | 88 | CB | ARG | A | 137 | 21.311 | 32.931 | 19.594 | 1.00 | 89.82 | A | C |
| ATOM | 89 | CG | ARG | A | 137 | 20.773 | 33.763 | 20.745 | 1.00 | 92.84 | A | C |
| ATOM | 90 | CD | ARG | A | 137 | 21.693 | 33.648 | 21.942 | 1.00 | 93.88 | A | C |
| ATOM | 91 | NE | ARG | A | 137 | 23.072 | 33.982 | 21.598 | 1.00 | 94.43 | A | N |
| ATOM | 92 | CZ | ARG | A | 137 | 24.136 | 33.517 | 22.246 | 1.00 | 95.05 | A | C |
| ATOM | 93 | NH1 | ARG | A | 137 | 25.357 | 33.875 | 21.868 | 1.00 | 94.11 | A | N |
| ATOM | 94 | NH2 | ARG | A | 137 | 23.981 | 32.682 | 23.265 | 1.00 | 93.59 | A | N |
| ATOM | 95 | C | ARG | A | 137 | 20.530 | 31.156 | 18.059 | 1.00 | 87.21 | A | C |
| ATOM | 96 | O | ARG | A | 137 | 19.937 | 30.212 | 18.581 | 1.00 | 87.20 | A | O |
| ATOM | 97 | N | PRO | A | 138 | 21.426 | 30.978 | 17.075 | 1.00 | 87.47 | A | N |
| ATOM | 98 | CD | PRO | A | 138 | 22.013 | 32.055 | 16.256 | 1.00 | 88.32 | A | C |
| ATOM | 99 | CA | PRO | A | 138 | 21.779 | 29.662 | 16.532 | 1.00 | 88.68 | A | C |
| ATOM | 100 | CB | PRO | A | 138 | 22.296 | 30.001 | 15.139 | 1.00 | 87.16 | A | C |
| ATOM | 101 | CG | PRO | A | 138 | 22.987 | 31.305 | 15.371 | 1.00 | 89.17 | A | C |
| ATOM | 102 | C | PRO | A | 138 | 22.844 | 28.983 | 17.399 | 1.00 | 89.44 | A | C |
| ATOM | 103 | O | PRO | A | 138 | 23.982 | 28.798 | 16.968 | 1.00 | 92.83 | A | O |
| ATOM | 104 | N | LEU | A | 139 | 22.455 | 28.620 | 18.620 | 1.00 | 86.94 | A | N |
| ATOM | 105 | CA | LEU | A | 139 | 23.339 | 27.974 | 19.592 | 1.00 | 82.18 | A | C |
| ATOM | 106 | CB | LEU | A | 139 | 22.554 | 26.950 | 20.415 | 1.00 | 76.92 | A | C |
| ATOM | 107 | CG | LEU | A | 139 | 21.300 | 27.449 | 21.136 | 1.00 | 75.64 | A | C |
| ATOM | 108 | CD1 | LEU | A | 139 | 20.653 | 26.287 | 21.876 | 1.00 | 78.04 | A | C |
| ATOM | 109 | CD2 | LEU | A | 139 | 21.664 | 28.566 | 22.104 | 1.00 | 75.94 | A | C |
| ATOM | 110 | C | LEU | A | 139 | 24.585 | 27.298 | 19.027 | 1.00 | 82.77 | A | C |
| ATOM | 111 | O | LEU | A | 139 | 25.701 | 27.589 | 19.459 | 1.00 | 82.01 | A | O |
| ATOM | 112 | N | GLY | A | 140 | 24.398 | 26.390 | 18.074 | 1.00 | 83.56 | A | N |
| ATOM | 113 | CA | GLY | A | 140 | 25.535 | 25.697 | 17.496 | 1.00 | 85.06 | A | C |
| ATOM | 114 | C | GLY | A | 140 | 25.410 | 25.446 | 16.007 | 1.00 | 87.56 | A | C |
| ATOM | 115 | O | GLY | A | 140 | 24.315 | 25.495 | 15.449 | 1.00 | 86.09 | A | O |
| ATOM | 116 | N | LYS | A | 141 | 26.539 | 25.168 | 15.365 | 1.00 | 91.22 | A | N |
| ATOM | 117 | CA | LYS | A | 141 | 26.565 | 24.912 | 13.930 | 1.00 | 95.38 | A | C |
| ATOM | 118 | CB | LYS | A | 141 | 27.998 | 25.026 | 13.402 | 1.00 | 97.20 | A | C |
| ATOM | 123 | C | LYS | A | 141 | 26.000 | 23.541 | 13.581 | 1.00 | 98.12 | A | C |

Figure 1C

| ATOM | 124 | O | LYS | A | 141 | 25.228 | 22.959 | 14.344 | 1.00 | 99.43 | A | O |
|---|---|---|---|---|---|---|---|---|---|---|---|---|
| ATOM | 125 | N | GLY | A | 142 | 26.393 | 23.032 | 12.417 | 1.00 | 100.94 | A | N |
| ATOM | 126 | CA | GLY | A | 142 | 25.919 | 21.736 | 11.976 | 1.00 | 104.98 | A | C |
| ATOM | 127 | C | GLY | A | 142 | 25.548 | 21.730 | 10.507 | 1.00 | 108.77 | A | C |
| ATOM | 128 | O | GLY | A | 142 | 24.573 | 22.364 | 10.103 | 1.00 | 108.88 | A | O |
| ATOM | 129 | N | LYS | A | 143 | 26.334 | 21.024 | 9.700 | 1.00 | 112.43 | A | N |
| ATOM | 130 | CA | LYS | A | 143 | 26.062 | 20.935 | 8.272 | 1.00 | 113.18 | A | C |
| ATOM | 131 | CB | LYS | A | 143 | 26.998 | 19.917 | 7.615 | 1.00 | 112.94 | A | C |
| ATOM | 136 | C | LYS | A | 143 | 24.617 | 20.487 | 8.113 | 1.00 | 113.43 | A | C |
| ATOM | 137 | O | LYS | A | 143 | 23.772 | 21.224 | 7.604 | 1.00 | 112.42 | A | O |
| ATOM | 138 | N | PHE | A | 144 | 24.347 | 19.269 | 8.566 | 1.00 | 112.92 | A | N |
| ATOM | 139 | CA | PHE | A | 144 | 23.014 | 18.687 | 8.512 | 1.00 | 111.42 | A | C |
| ATOM | 140 | CB | PHE | A | 144 | 22.961 | 17.481 | 9.448 | 1.00 | 109.06 | A | C |
| ATOM | 141 | CG | PHE | A | 144 | 23.264 | 17.829 | 10.872 | 1.00 | 107.42 | A | C |
| ATOM | 142 | CD1 | PHE | A | 144 | 22.254 | 17.858 | 11.824 | 1.00 | 107.19 | A | C |
| ATOM | 143 | CD2 | PHE | A | 144 | 24.543 | 18.232 | 11.240 | 1.00 | 104.89 | A | C |
| ATOM | 144 | CE1 | PHE | A | 144 | 22.510 | 18.291 | 13.115 | 1.00 | 106.53 | A | C |
| ATOM | 145 | CE2 | PHE | A | 144 | 24.806 | 18.667 | 12.527 | 1.00 | 104.75 | A | C |
| ATOM | 146 | CZ | PHE | A | 144 | 23.786 | 18.699 | 13.465 | 1.00 | 106.91 | A | C |
| ATOM | 147 | C | PHE | A | 144 | 21.989 | 19.730 | 8.955 | 1.00 | 110.35 | A | C |
| ATOM | 148 | O | PHE | A | 144 | 21.012 | 19.989 | 8.255 | 1.00 | 109.93 | A | O |
| ATOM | 149 | N | GLY | A | 145 | 22.226 | 20.327 | 10.120 | 1.00 | 109.25 | A | N |
| ATOM | 150 | CA | GLY | A | 145 | 21.317 | 21.328 | 10.646 | 1.00 | 109.11 | A | C |
| ATOM | 151 | C | GLY | A | 145 | 21.840 | 21.997 | 11.902 | 1.00 | 109.43 | A | C |
| ATOM | 152 | O | GLY | A | 145 | 22.520 | 21.370 | 12.717 | 1.00 | 108.80 | A | O |
| ATOM | 153 | N | ASN | A | 146 | 21.509 | 23.274 | 12.061 | 1.00 | 108.86 | A | N |
| ATOM | 154 | CA | ASN | A | 146 | 21.953 | 24.055 | 13.208 | 1.00 | 104.91 | A | C |
| ATOM | 155 | CB | ASN | A | 146 | 22.130 | 25.518 | 12.798 | 1.00 | 105.52 | A | C |
| ATOM | 156 | CG | ASN | A | 146 | 22.632 | 25.669 | 11.377 | 1.00 | 106.13 | A | C |
| ATOM | 157 | OD1 | ASN | A | 146 | 23.696 | 25.161 | 11.023 | 1.00 | 106.74 | A | O |
| ATOM | 158 | ND2 | ASN | A | 146 | 21.864 | 26.370 | 10.552 | 1.00 | 105.37 | A | N |
| ATOM | 159 | C | ASN | A | 146 | 20.965 | 23.986 | 14.366 | 1.00 | 102.25 | A | C |
| ATOM | 160 | O | ASN | A | 146 | 19.814 | 23.581 | 14.198 | 1.00 | 101.20 | A | O |
| ATOM | 161 | N | VAL | A | 147 | 21.429 | 24.385 | 15.545 | 1.00 | 99.56 | A | N |
| ATOM | 162 | CA | VAL | A | 147 | 20.593 | 24.407 | 16.736 | 1.00 | 99.53 | A | C |
| ATOM | 163 | CB | VAL | A | 147 | 21.335 | 23.850 | 17.963 | 1.00 | 102.12 | A | C |
| ATOM | 164 | CG1 | VAL | A | 147 | 20.466 | 23.995 | 19.202 | 1.00 | 104.13 | A | C |
| ATOM | 165 | CG2 | VAL | A | 147 | 21.697 | 22.394 | 17.735 | 1.00 | 105.72 | A | C |
| ATOM | 166 | C | VAL | A | 147 | 20.248 | 25.865 | 17.000 | 1.00 | 96.66 | A | C |
| ATOM | 167 | O | VAL | A | 147 | 21.136 | 26.714 | 17.060 | 1.00 | 96.10 | A | O |
| ATOM | 168 | N | TYR | A | 148 | 18.961 | 26.157 | 17.149 | 1.00 | 95.42 | A | N |
| ATOM | 169 | CA | TYR | A | 148 | 18.522 | 27.526 | 17.391 | 1.00 | 94.17 | A | C |
| ATOM | 170 | CB | TYR | A | 148 | 17.627 | 28.011 | 16.243 | 1.00 | 98.41 | A | C |
| ATOM | 171 | CG | TYR | A | 148 | 18.156 | 27.733 | 14.852 | 1.00 | 102.75 | A | C |
| ATOM | 172 | CD1 | TYR | A | 148 | 17.353 | 27.112 | 13.895 | 1.00 | 104.82 | A | C |
| ATOM | 173 | CE1 | TYR | A | 148 | 17.825 | 26.858 | 12.610 | 1.00 | 106.48 | A | C |
| ATOM | 174 | CD2 | TYR | A | 148 | 19.452 | 28.096 | 14.487 | 1.00 | 103.82 | A | C |
| ATOM | 175 | CE2 | TYR | A | 148 | 19.935 | 27.846 | 13.201 | 1.00 | 105.10 | A | C |
| ATOM | 176 | CZ | TYR | A | 148 | 19.116 | 27.226 | 12.270 | 1.00 | 106.26 | A | C |
| ATOM | 177 | OH | TYR | A | 148 | 19.589 | 26.964 | 11.005 | 1.00 | 105.49 | A | O |
| ATOM | 178 | C | TYR | A | 148 | 17.738 | 27.637 | 18.692 | 1.00 | 88.98 | A | C |
| ATOM | 179 | O | TYR | A | 148 | 16.700 | 26.995 | 18.848 | 1.00 | 86.31 | A | O |
| ATOM | 180 | N | LEU | A | 149 | 18.226 | 28.449 | 19.624 | 1.00 | 85.38 | A | N |
| ATOM | 181 | CA | LEU | A | 149 | 17.513 | 28.629 | 20.880 | 1.00 | 84.60 | A | C |
| ATOM | 182 | CB | LEU | A | 149 | 18.177 | 29.713 | 21.728 | 1.00 | 79.30 | A | C |
| ATOM | 183 | CG | LEU | A | 149 | 17.530 | 29.958 | 23.093 | 1.00 | 74.32 | A | C |
| ATOM | 184 | CD1 | LEU | A | 149 | 17.948 | 28.864 | 24.068 | 1.00 | 70.70 | A | C |
| ATOM | 185 | CD2 | LEU | A | 149 | 17.951 | 31.321 | 23.612 | 1.00 | 74.22 | A | C |
| ATOM | 186 | C | LEU | A | 149 | 16.109 | 29.074 | 20.494 | 1.00 | 86.75 | A | C |
| ATOM | 187 | O | LEU | A | 149 | 15.929 | 29.733 | 19.470 | 1.00 | 88.87 | A | O |
| ATOM | 188 | N | ALA | A | 150 | 15.116 | 28.712 | 21.296 | 1.00 | 88.09 | A | N |

Figure 1D

```
ATOM    189  CA   ALA A 150      13.747  29.093  20.981  1.00  88.79      A    C
ATOM    190  CB   ALA A 150      13.295  28.388  19.708  1.00  88.44      A    C
ATOM    191  C    ALA A 150      12.763  28.810  22.106  1.00  90.35      A    C
ATOM    192  O    ALA A 150      12.983  27.935  22.943  1.00  90.99      A    O
ATOM    193  N    ARG A 151      11.670  29.564  22.106  1.00  91.73      A    N
ATOM    194  CA   ARG A 151      10.622  29.430  23.108  1.00  92.12      A    C
ATOM    195  CB   ARG A 151      10.369  30.771  23.804  1.00  90.75      A    C
ATOM    196  CG   ARG A 151      11.464  31.291  24.715  1.00  90.18      A    C
ATOM    197  CD   ARG A 151      11.110  32.710  25.145  1.00  90.72      A    C
ATOM    198  NE   ARG A 151      11.878  33.180  26.294  1.00  93.83      A    N
ATOM    199  CZ   ARG A 151      12.417  34.392  26.384  1.00  96.26      A    C
ATOM    200  NH1  ARG A 151      12.281  35.258  25.388  1.00  97.00      A    N
ATOM    201  NH2  ARG A 151      13.082  34.743  27.475  1.00  96.06      A    N
ATOM    202  C    ARG A 151       9.310  29.003  22.466  1.00  93.41      A    C
ATOM    203  O    ARG A 151       9.085  29.240  21.279  1.00  91.28      A    O
ATOM    204  N    GLU A 152       8.451  28.365  23.253  1.00  96.78      A    N
ATOM    205  CA   GLU A 152       7.134  27.983  22.767  1.00 102.06      A    C
ATOM    206  CB   GLU A 152       6.616  26.722  23.461  1.00 104.07      A    C
ATOM    207  CG   GLU A 152       5.128  26.495  23.223  1.00 108.42      A    C
ATOM    208  CD   GLU A 152       4.577  25.298  23.967  1.00 110.39      A    C
ATOM    209  OE1  GLU A 152       5.123  24.954  25.035  1.00 111.04      A    O
ATOM    210  OE2  GLU A 152       3.583  24.711  23.492  1.00 112.78      A    O
ATOM    211  C    GLU A 152       6.294  29.181  23.185  1.00 104.27      A    C
ATOM    212  O    GLU A 152       6.618  29.843  24.170  1.00 103.44      A    O
ATOM    213  N    LYS A 153       5.221  29.469  22.460  1.00 107.77      A    N
ATOM    214  CA   LYS A 153       4.407  30.627  22.800  1.00 110.31      A    C
ATOM    215  CB   LYS A 153       3.713  31.159  21.546  1.00 112.39      A    C
ATOM    216  CG   LYS A 153       4.692  31.558  20.457  1.00 115.61      A    C
ATOM    217  CD   LYS A 153       3.990  32.201  19.277  1.00 120.65      A    C
ATOM    218  CE   LYS A 153       4.954  33.071  18.491  1.00 124.59      A    C
ATOM    219  NZ   LYS A 153       4.245  34.041  17.616  1.00 128.43      A    N
ATOM    220  C    LYS A 153       3.390  30.475  23.927  1.00 110.30      A    C
ATOM    221  O    LYS A 153       3.176  31.421  24.685  1.00 110.14      A    O
ATOM    222  N    GLN A 154       2.762  29.310  24.055  1.00 109.62      A    N
ATOM    223  CA   GLN A 154       1.775  29.135  25.118  1.00 107.71      A    C
ATOM    224  CB   GLN A 154       0.840  27.959  24.817  1.00 110.66      A    C
ATOM    225  CG   GLN A 154       1.502  26.597  24.758  1.00 116.23      A    C
ATOM    226  CD   GLN A 154       0.489  25.468  24.814  1.00 118.82      A    C
ATOM    227  OE1  GLN A 154      -0.639  25.610  24.342  1.00 120.66      A    O
ATOM    228  NE2  GLN A 154       0.890  24.338  25.383  1.00 118.54      A    N
ATOM    229  C    GLN A 154       2.403  28.946  26.493  1.00 105.48      A    C
ATOM    230  O    GLN A 154       1.808  29.311  27.507  1.00 103.81      A    O
ATOM    231  N    SER A 155       3.601  28.374  26.531  1.00 103.19      A    N
ATOM    232  CA   SER A 155       4.287  28.162  27.799  1.00 100.54      A    C
ATOM    233  CB   SER A 155       4.843  26.738  27.877  1.00 102.21      A    C
ATOM    234  OG   SER A 155       5.873  26.541  26.924  1.00 102.53      A    O
ATOM    235  C    SER A 155       5.426  29.162  27.936  1.00  98.13      A    C
ATOM    236  O    SER A 155       6.034  29.281  29.000  1.00  96.44      A    O
ATOM    237  N    LYS A 156       5.707  29.882  26.854  1.00  95.92      A    N
ATOM    238  CA   LYS A 156       6.787  30.861  26.852  1.00  94.57      A    C
ATOM    239  CB   LYS A 156       6.459  32.019  27.798  1.00  93.51      A    C
ATOM    244  C    LYS A 156       8.050  30.150  27.317  1.00  95.02      A    C
ATOM    245  O    LYS A 156       9.059  30.781  27.631  1.00  95.60      A    O
ATOM    246  N    PHE A 157       7.977  28.823  27.350  1.00  93.90      A    N
ATOM    247  CA   PHE A 157       9.087  27.990  27.784  1.00  92.28      A    C
ATOM    248  CB   PHE A 157       8.686  26.515  27.729  1.00  90.68      A    C
ATOM    249  CG   PHE A 157       9.401  25.663  28.732  1.00  91.96      A    C
ATOM    250  CD1  PHE A 157       8.918  25.551  30.031  1.00  93.69      A    C
ATOM    251  CD2  PHE A 157      10.566  24.990  28.390  1.00  91.93      A    C
ATOM    252  CE1  PHE A 157       9.587  24.785  30.976  1.00  93.65      A    C
ATOM    253  CE2  PHE A 157      11.245  24.220  29.329  1.00  92.82      A    C
```

Figure 1E

```
ATOM    254  CZ  PHE A 157      10.753  24.117  30.625  1.00  93.45      A    C
ATOM    255  C   PHE A 157      10.317  28.220  26.916  1.00  92.26      A    C
ATOM    256  O   PHE A 157      10.204  28.503  25.726  1.00  92.77      A    O
ATOM    257  N   ILE A 158      11.491  28.092  27.525  1.00  91.24      A    N
ATOM    258  CA  ILE A 158      12.763  28.285  26.833  1.00  90.72      A    C
ATOM    259  CB  ILE A 158      13.770  29.003  27.763  1.00  88.82      A    C
ATOM    260  CG2 ILE A 158      13.986  28.182  29.025  1.00  89.43      A    C
ATOM    261  CG1 ILE A 158      15.085  29.264  27.027  1.00  88.63      A    C
ATOM    262  CD1 ILE A 158      15.009  30.401  26.022  1.00  84.57      A    C
ATOM    263  C   ILE A 158      13.322  26.924  26.410  1.00  91.05      A    C
ATOM    264  O   ILE A 158      13.485  26.028  27.238  1.00  92.86      A    O
ATOM    265  N   LEU A 159      13.622  26.768  25.123  1.00  89.70      A    N
ATOM    266  CA  LEU A 159      14.130  25.493  24.627  1.00  87.20      A    C
ATOM    267  CB  LEU A 159      12.956  24.603  24.211  1.00  86.64      A    C
ATOM    268  CG  LEU A 159      11.853  24.378  25.244  1.00  86.69      A    C
ATOM    269  CD1 LEU A 159      10.590  23.890  24.557  1.00  85.40      A    C
ATOM    270  CD2 LEU A 159      12.330  23.377  26.277  1.00  84.76      A    C
ATOM    271  C   LEU A 159      15.107  25.572  23.460  1.00  84.72      A    C
ATOM    272  O   LEU A 159      15.270  26.613  22.824  1.00  85.39      A    O
ATOM    273  N   ALA A 160      15.755  24.440  23.201  1.00  81.50      A    N
ATOM    274  CA  ALA A 160      16.699  24.296  22.103  1.00  77.15      A    C
ATOM    275  CB  ALA A 160      17.901  23.464  22.540  1.00  75.91      A    C
ATOM    276  C   ALA A 160      15.914  23.566  21.021  1.00  74.93      A    C
ATOM    277  O   ALA A 160      15.073  22.722  21.327  1.00  74.12      A    O
ATOM    278  N   LEU A 161      16.181  23.890  19.761  1.00  74.67      A    N
ATOM    279  CA  LEU A 161      15.468  23.265  18.654  1.00  75.02      A    C
ATOM    280  CB  LEU A 161      14.383  24.223  18.150  1.00  75.06      A    C
ATOM    281  CG  LEU A 161      13.510  23.833  16.956  1.00  75.02      A    C
ATOM    282  CD1 LEU A 161      12.142  24.475  17.106  1.00  75.75      A    C
ATOM    283  CD2 LEU A 161      14.171  24.267  15.657  1.00  76.38      A    C
ATOM    284  C   LEU A 161      16.418  22.883  17.526  1.00  76.40      A    C
ATOM    285  O   LEU A 161      17.018  23.747  16.886  1.00  76.89      A    O
ATOM    286  N   LYS A 162      16.544  21.582  17.282  1.00  78.13      A    N
ATOM    287  CA  LYS A 162      17.436  21.082  16.243  1.00  79.57      A    C
ATOM    288  CB  LYS A 162      17.920  19.673  16.599  1.00  77.96      A    C
ATOM    289  CG  LYS A 162      19.271  19.310  15.999  1.00  78.55      A    C
ATOM    290  CD  LYS A 162      19.860  18.076  16.665  1.00  82.07      A    C
ATOM    291  CE  LYS A 162      21.252  17.781  16.135  1.00  81.82      A    C
ATOM    292  NZ  LYS A 162      21.706  16.406  16.474  1.00  78.96      A    N
ATOM    293  C   LYS A 162      16.785  21.063  14.866  1.00  82.47      A    C
ATOM    294  O   LYS A 162      15.653  20.607  14.702  1.00  85.49      A    O
ATOM    295  N   VAL A 163      17.517  21.563  13.878  1.00  84.02      A    N
ATOM    296  CA  VAL A 163      17.039  21.606  12.504  1.00  86.85      A    C
ATOM    297  CB  VAL A 163      17.271  23.003  11.883  1.00  87.17      A    C
ATOM    298  CG1 VAL A 163      17.521  22.883  10.386  1.00  88.25      A    C
ATOM    299  CG2 VAL A 163      16.061  23.886  12.137  1.00  86.04      A    C
ATOM    300  C   VAL A 163      17.760  20.559  11.661  1.00  88.50      A    C
ATOM    301  O   VAL A 163      18.978  20.425  11.740  1.00  89.12      A    O
ATOM    302  N   LEU A 164      16.998  19.816  10.863  1.00  90.00      A    N
ATOM    303  CA  LEU A 164      17.564  18.785   9.997  1.00  91.35      A    C
ATOM    304  CB  LEU A 164      17.208  17.383  10.510  1.00  88.34      A    C
ATOM    305  CG  LEU A 164      17.406  16.974  11.976  1.00  87.99      A    C
ATOM    306  CD1 LEU A 164      18.884  16.918  12.304  1.00  84.24      A    C
ATOM    307  CD2 LEU A 164      16.686  17.951  12.891  1.00  88.71      A    C
ATOM    308  C   LEU A 164      16.996  18.950   8.589  1.00  94.98      A    C
ATOM    309  O   LEU A 164      15.802  18.743   8.373  1.00  96.48      A    O
ATOM    310  N   PHE A 165      17.840  19.329   7.633  1.00  98.57      A    N
ATOM    311  CA  PHE A 165      17.381  19.501   6.258  1.00 101.54      A    C
ATOM    312  CB  PHE A 165      18.355  20.380   5.464  1.00 104.88      A    C
ATOM    313  CG  PHE A 165      18.512  21.769   6.023  1.00 108.26      A    C
ATOM    314  CD1 PHE A 165      19.573  22.078   6.867  1.00 109.01      A    C
```

Figure 1F

```
ATOM    315  CD2 PHE A 165      17.583  22.763   5.730  1.00 109.20      A    C
ATOM    316  CE1 PHE A 165      19.709  23.353   7.414  1.00 110.42      A    C
ATOM    317  CE2 PHE A 165      17.709  24.043   6.272  1.00 108.75      A    C
ATOM    318  CZ  PHE A 165      18.775  24.337   7.116  1.00 109.79      A    C
ATOM    319  C   PHE A 165      17.240  18.134   5.593  1.00 101.63      A    C
ATOM    320  O   PHE A 165      18.218  17.401   5.445  1.00 101.61      A    O
ATOM    321  N   LYS A 166      16.016  17.799   5.195  1.00 101.72      A    N
ATOM    322  CA  LYS A 166      15.728  16.513   4.570  1.00 103.84      A    C
ATOM    323  CB  LYS A 166      14.256  16.449   4.155  1.00 103.58      A    C
ATOM    324  CG  LYS A 166      13.313  16.422   5.345  1.00 103.85      A    C
ATOM    325  CD  LYS A 166      12.105  15.538   5.102  1.00 103.86      A    C
ATOM    326  CE  LYS A 166      11.354  15.280   6.401  1.00 104.05      A    C
ATOM    327  NZ  LYS A 166      10.261  14.281   6.250  1.00 103.60      A    N
ATOM    328  C   LYS A 166      16.616  16.129   3.392  1.00 105.93      A    C
ATOM    329  O   LYS A 166      17.011  14.970   3.267  1.00 104.96      A    O
ATOM    330  N   ALA A 167      16.925  17.087   2.524  1.00 109.33      A    N
ATOM    331  CA  ALA A 167      17.784  16.797   1.381  1.00 112.33      A    C
ATOM    332  CB  ALA A 167      18.082  18.073   0.607  1.00 112.98      A    C
ATOM    333  C   ALA A 167      19.075  16.193   1.919  1.00 113.44      A    C
ATOM    334  O   ALA A 167      19.243  14.974   1.941  1.00 113.65      A    O
ATOM    335  N   GLN A 168      19.975  17.062   2.367  1.00 114.18      A    N
ATOM    336  CA  GLN A 168      21.256  16.648   2.925  1.00 115.44      A    C
ATOM    337  CB  GLN A 168      21.851  17.795   3.746  1.00 120.15      A    C
ATOM    338  CG  GLN A 168      21.906  19.121   3.002  1.00 125.55      A    C
ATOM    339  CD  GLN A 168      22.068  20.312   3.930  1.00 129.43      A    C
ATOM    340  OE1 GLN A 168      21.962  21.462   3.504  1.00 131.74      A    O
ATOM    341  NE2 GLN A 168      22.320  20.042   5.205  1.00 129.67      A    N
ATOM    342  C   GLN A 168      21.058  15.428   3.821  1.00 113.54      A    C
ATOM    343  O   GLN A 168      21.986  14.651   4.044  1.00 112.20      A    O
ATOM    344  N   LEU A 169      19.839  15.269   4.329  1.00 111.68      A    N
ATOM    345  CA  LEU A 169      19.503  14.155   5.206  1.00 111.81      A    C
ATOM    346  CB  LEU A 169      18.168  14.420   5.906  1.00 110.14      A    C
ATOM    350  C   LEU A 169      19.432  12.824   4.464  1.00 112.82      A    C
ATOM    351  O   LEU A 169      20.195  11.905   4.761  1.00 112.78      A    O
ATOM    352  N   GLU A 170      18.516  12.714   3.505  1.00 114.18      A    N
ATOM    353  CA  GLU A 170      18.387  11.471   2.755  1.00 115.81      A    C
ATOM    354  CB  GLU A 170      16.981  11.325   2.170  1.00 114.91      A    C
ATOM    355  CG  GLU A 170      16.630   9.882   1.847  1.00 113.07      A    C
ATOM    356  CD  GLU A 170      15.182   9.697   1.448  1.00 113.39      A    C
ATOM    357  OE1 GLU A 170      14.294   9.947   2.291  1.00 112.40      A    O
ATOM    358  OE2 GLU A 170      14.933   9.296   0.293  1.00 111.79      A    O
ATOM    359  C   GLU A 170      19.434  11.395   1.649  1.00 117.12      A    C
ATOM    360  O   GLU A 170      19.692  10.324   1.099  1.00 118.53      A    O
ATOM    361  N   LYS A 171      20.028  12.539   1.322  1.00 117.88      A    N
ATOM    362  CA  LYS A 171      21.085  12.589   0.320  1.00 117.42      A    C
ATOM    363  CB  LYS A 171      21.267  14.011  -0.213  1.00 116.45      A    C
ATOM    368  C   LYS A 171      22.314  12.162   1.110  1.00 117.53      A    C
ATOM    369  O   LYS A 171      23.454  12.469   0.758  1.00 115.71      A    O
ATOM    370  N   ALA A 172      22.036  11.456   2.202  1.00 118.51      A    N
ATOM    371  CA  ALA A 172      23.042  10.936   3.114  1.00 118.89      A    C
ATOM    372  CB  ALA A 172      23.190  11.867   4.311  1.00 118.79      A    C
ATOM    373  C   ALA A 172      22.584   9.557   3.578  1.00 118.84      A    C
ATOM    374  O   ALA A 172      23.232   8.926   4.412  1.00 119.39      A    O
ATOM    375  N   GLY A 173      21.457   9.103   3.032  1.00 118.85      A    N
ATOM    376  CA  GLY A 173      20.914   7.804   3.392  1.00 119.82      A    C
ATOM    377  C   GLY A 173      21.031   7.520   4.875  1.00 120.01      A    C
ATOM    378  O   GLY A 173      21.780   6.633   5.284  1.00 119.19      A    O
ATOM    379  N   VAL A 174      20.292   8.271   5.686  1.00 120.83      A    N
ATOM    380  CA  VAL A 174      20.341   8.087   7.131  1.00 121.86      A    C
ATOM    381  CB  VAL A 174      21.270   9.125   7.788  1.00 122.57      A    C
ATOM    384  C   VAL A 174      18.976   8.176   7.802  1.00 122.18      A    C
```

Figure 1G

| ATOM | 385 | O   | VAL A 174 | 18.854 | 7.927  | 9.002  | 1.00 | 122.36 | A | O |
|------|-----|-----|-----------|--------|--------|--------|------|--------|---|---|
| ATOM | 386 | N   | GLU A 175 | 17.954 | 8.527  | 7.027  | 1.00 | 121.37 | A | N |
| ATOM | 387 | CA  | GLU A 175 | 16.597 | 8.651  | 7.551  | 1.00 | 120.75 | A | C |
| ATOM | 388 | CB  | GLU A 175 | 15.588 | 8.630  | 6.396  | 1.00 | 121.34 | A | C |
| ATOM | 389 | CG  | GLU A 175 | 14.128 | 8.728  | 6.821  | 1.00 | 124.85 | A | C |
| ATOM | 390 | CD  | GLU A 175 | 13.453 | 7.373  | 6.926  | 1.00 | 127.13 | A | C |
| ATOM | 391 | OE1 | GLU A 175 | 13.987 | 6.486  | 7.625  | 1.00 | 128.98 | A | O |
| ATOM | 392 | OE2 | GLU A 175 | 12.384 | 7.194  | 6.305  | 1.00 | 127.07 | A | O |
| ATOM | 393 | C   | GLU A 175 | 16.274 | 7.545  | 8.554  | 1.00 | 120.20 | A | C |
| ATOM | 394 | O   | GLU A 175 | 15.357 | 7.679  | 9.364  | 1.00 | 119.19 | A | O |
| ATOM | 395 | N   | HIS A 176 | 17.037 | 6.457  | 8.500  | 1.00 | 120.40 | A | N |
| ATOM | 396 | CA  | HIS A 176 | 16.832 | 5.331  | 9.404  | 1.00 | 120.81 | A | C |
| ATOM | 397 | CB  | HIS A 176 | 17.754 | 4.165  | 9.020  | 1.00 | 125.34 | A | C |
| ATOM | 398 | CG  | HIS A 176 | 19.212 | 4.461  | 9.191  | 1.00 | 130.03 | A | C |
| ATOM | 399 | CD2 | HIS A 176 | 20.153 | 3.883  | 9.975  | 1.00 | 131.97 | A | C |
| ATOM | 400 | ND1 | HIS A 176 | 19.850 | 5.483  | 8.521  | 1.00 | 131.52 | A | N |
| ATOM | 401 | CE1 | HIS A 176 | 21.119 | 5.522  | 8.885  | 1.00 | 131.98 | A | C |
| ATOM | 402 | NE2 | HIS A 176 | 21.329 | 4.561  | 9.767  | 1.00 | 132.95 | A | N |
| ATOM | 403 | C   | HIS A 176 | 17.078 | 5.725  | 10.860 | 1.00 | 119.03 | A | C |
| ATOM | 404 | O   | HIS A 176 | 16.142 | 5.794  | 11.656 | 1.00 | 117.35 | A | O |
| ATOM | 405 | N   | GLN A 177 | 18.339 | 5.985  | 11.196 | 1.00 | 117.92 | A | N |
| ATOM | 406 | CA  | GLN A 177 | 18.730 | 6.368  | 12.547 | 1.00 | 117.37 | A | C |
| ATOM | 407 | CB  | GLN A 177 | 20.099 | 7.053  | 12.523 | 1.00 | 116.13 | A | C |
| ATOM | 412 | C   | GLN A 177 | 17.702 | 7.302  | 13.167 | 1.00 | 117.97 | A | C |
| ATOM | 413 | O   | GLN A 177 | 17.348 | 7.163  | 14.337 | 1.00 | 120.44 | A | O |
| ATOM | 414 | N   | LEU A 178 | 17.223 | 8.249  | 12.368 | 1.00 | 116.97 | A | N |
| ATOM | 415 | CA  | LEU A 178 | 16.235 | 9.216  | 12.823 | 1.00 | 115.33 | A | C |
| ATOM | 416 | CB  | LEU A 178 | 15.685 | 9.998  | 11.629 | 1.00 | 112.40 | A | C |
| ATOM | 417 | CG  | LEU A 178 | 15.569 | 11.515 | 11.790 | 1.00 | 110.53 | A | C |
| ATOM | 418 | CD1 | LEU A 178 | 16.951 | 12.118 | 12.009 | 1.00 | 109.48 | A | C |
| ATOM | 419 | CD2 | LEU A 178 | 14.928 | 12.110 | 10.547 | 1.00 | 110.78 | A | C |
| ATOM | 420 | C   | LEU A 178 | 15.092 | 8.514  | 13.552 | 1.00 | 115.18 | A | C |
| ATOM | 421 | O   | LEU A 178 | 14.961 | 8.628  | 14.768 | 1.00 | 115.78 | A | O |
| ATOM | 422 | N   | ARG A 179 | 14.278 | 7.777  | 12.802 | 1.00 | 112.96 | A | N |
| ATOM | 423 | CA  | ARG A 179 | 13.142 | 7.059  | 13.372 | 1.00 | 110.82 | A | C |
| ATOM | 424 | CB  | ARG A 179 | 12.510 | 6.158  | 12.306 | 1.00 | 113.18 | A | C |
| ATOM | 425 | CG  | ARG A 179 | 11.912 | 6.940  | 11.148 | 1.00 | 114.39 | A | C |
| ATOM | 426 | CD  | ARG A 179 | 11.344 | 6.043  | 10.062 | 1.00 | 113.13 | A | C |
| ATOM | 427 | NE  | ARG A 179 | 10.649 | 6.833  | 9.049  | 1.00 | 108.98 | A | N |
| ATOM | 428 | CZ  | ARG A 179 | 10.168 | 6.344  | 7.910  | 1.00 | 104.95 | A | C |
| ATOM | 429 | NH1 | ARG A 179 | 9.549  | 7.145  | 7.053  | 1.00 | 101.10 | A | N |
| ATOM | 430 | NH2 | ARG A 179 | 10.309 | 5.057  | 7.624  | 1.00 | 103.56 | A | N |
| ATOM | 431 | C   | ARG A 179 | 13.508 | 6.233  | 14.603 | 1.00 | 108.63 | A | C |
| ATOM | 432 | O   | ARG A 179 | 12.708 | 6.102  | 15.529 | 1.00 | 108.15 | A | O |
| ATOM | 433 | N   | ARG A 180 | 14.716 | 5.681  | 14.614 | 1.00 | 107.15 | A | N |
| ATOM | 434 | CA  | ARG A 180 | 15.166 | 4.875  | 15.743 | 1.00 | 107.25 | A | C |
| ATOM | 435 | CB  | ARG A 180 | 16.386 | 4.042  | 15.345 | 1.00 | 111.18 | A | C |
| ATOM | 436 | CG  | ARG A 180 | 16.097 | 2.999  | 14.282 | 1.00 | 117.87 | A | C |
| ATOM | 437 | CD  | ARG A 180 | 17.375 | 2.340  | 13.798 | 1.00 | 123.14 | A | C |
| ATOM | 438 | NE  | ARG A 180 | 17.141 | 1.505  | 12.624 | 1.00 | 126.86 | A | N |
| ATOM | 439 | CZ  | ARG A 180 | 18.104 | 0.947  | 11.898 | 1.00 | 128.62 | A | C |
| ATOM | 440 | NH1 | ARG A 180 | 17.796 | 0.203  | 10.845 | 1.00 | 127.65 | A | N |
| ATOM | 441 | NH2 | ARG A 180 | 19.377 | 1.134  | 12.222 | 1.00 | 130.30 | A | N |
| ATOM | 442 | C   | ARG A 180 | 15.518 | 5.757  | 16.937 | 1.00 | 105.77 | A | C |
| ATOM | 443 | O   | ARG A 180 | 14.850 | 5.713  | 17.970 | 1.00 | 104.05 | A | O |
| ATOM | 444 | N   | GLU A 181 | 16.568 | 6.556  | 16.784 | 1.00 | 106.19 | A | N |
| ATOM | 445 | CA  | GLU A 181 | 17.023 | 7.449  | 17.843 | 1.00 | 106.68 | A | C |
| ATOM | 446 | CB  | GLU A 181 | 18.198 | 8.291  | 17.342 | 1.00 | 109.26 | A | C |
| ATOM | 447 | CG  | GLU A 181 | 19.412 | 7.472  | 16.933 | 1.00 | 115.60 | A | C |
| ATOM | 448 | CD  | GLU A 181 | 20.500 | 8.318  | 16.303 | 1.00 | 119.11 | A | C |
| ATOM | 449 | OE1 | GLU A 181 | 20.184 | 9.097  | 15.379 | 1.00 | 119.89 | A | O |

Figure 1H

| ATOM | 450 | OE2 | GLU | A | 181 | 21.669 | 8.204 | 16.729 | 1.00 | 122.34 | A | O |
|------|-----|-----|-----|---|-----|--------|-------|--------|------|--------|---|---|
| ATOM | 451 | C | GLU | A | 181 | 15.899 | 8.362 | 18.319 | 1.00 | 105.66 | A | C |
| ATOM | 452 | O | GLU | A | 181 | 15.689 | 8.526 | 19.521 | 1.00 | 103.30 | A | O |
| ATOM | 453 | N | VAL | A | 182 | 15.180 | 8.957 | 17.374 | 1.00 | 105.89 | A | N |
| ATOM | 454 | CA | VAL | A | 182 | 14.077 | 9.843 | 17.717 | 1.00 | 105.51 | A | C |
| ATOM | 455 | CB | VAL | A | 182 | 13.305 | 10.303 | 16.464 | 1.00 | 102.41 | A | C |
| ATOM | 456 | CG1 | VAL | A | 182 | 11.964 | 10.901 | 16.865 | 1.00 | 101.98 | A | C |
| ATOM | 457 | CG2 | VAL | A | 182 | 14.125 | 11.328 | 15.702 | 1.00 | 101.95 | A | C |
| ATOM | 458 | C | VAL | A | 182 | 13.107 | 9.131 | 18.646 | 1.00 | 107.04 | A | C |
| ATOM | 459 | O | VAL | A | 182 | 12.672 | 9.692 | 19.648 | 1.00 | 105.25 | A | O |
| ATOM | 460 | N | GLU | A | 183 | 12.777 | 7.888 | 18.311 | 1.00 | 110.60 | A | N |
| ATOM | 461 | CA | GLU | A | 183 | 11.849 | 7.117 | 19.122 | 1.00 | 113.53 | A | C |
| ATOM | 462 | CB | GLU | A | 183 | 11.296 | 5.936 | 18.322 | 1.00 | 117.52 | A | C |
| ATOM | 463 | CG | GLU | A | 183 | 10.121 | 5.274 | 19.007 | 1.00 | 123.07 | A | C |
| ATOM | 464 | CD | GLU | A | 183 | 9.146 | 6.294 | 19.561 | 1.00 | 124.93 | A | C |
| ATOM | 465 | OE1 | GLU | A | 183 | 8.186 | 6.654 | 18.848 | 1.00 | 127.33 | A | O |
| ATOM | 466 | OE2 | GLU | A | 183 | 9.351 | 6.750 | 20.706 | 1.00 | 123.54 | A | O |
| ATOM | 467 | C | GLU | A | 183 | 12.474 | 6.615 | 20.418 | 1.00 | 112.55 | A | C |
| ATOM | 468 | O | GLU | A | 183 | 11.798 | 6.525 | 21.442 | 1.00 | 110.65 | A | O |
| ATOM | 469 | N | ILE | A | 184 | 13.762 | 6.288 | 20.375 | 1.00 | 112.82 | A | N |
| ATOM | 470 | CA | ILE | A | 184 | 14.454 | 5.801 | 21.564 | 1.00 | 114.40 | A | C |
| ATOM | 471 | CB | ILE | A | 184 | 15.855 | 5.243 | 21.217 | 1.00 | 112.70 | A | C |
| ATOM | 472 | CG2 | ILE | A | 184 | 16.563 | 4.785 | 22.486 | 1.00 | 113.24 | A | C |
| ATOM | 473 | CG1 | ILE | A | 184 | 15.723 | 4.077 | 20.234 | 1.00 | 109.31 | A | C |
| ATOM | 474 | CD1 | ILE | A | 184 | 17.035 | 3.388 | 19.907 | 1.00 | 105.27 | A | C |
| ATOM | 475 | C | ILE | A | 184 | 14.611 | 6.920 | 22.590 | 1.00 | 115.99 | A | C |
| ATOM | 476 | O | ILE | A | 184 | 14.585 | 6.674 | 23.796 | 1.00 | 115.91 | A | O |
| ATOM | 477 | N | GLN | A | 185 | 14.772 | 8.148 | 22.108 | 1.00 | 117.10 | A | N |
| ATOM | 478 | CA | GLN | A | 185 | 14.929 | 9.289 | 22.999 | 1.00 | 117.42 | A | C |
| ATOM | 479 | CB | GLN | A | 185 | 15.741 | 10.391 | 22.319 | 1.00 | 118.18 | A | C |
| ATOM | 480 | CG | GLN | A | 185 | 16.473 | 11.298 | 23.297 | 1.00 | 119.65 | A | C |
| ATOM | 481 | CD | GLN | A | 185 | 17.301 | 12.358 | 22.601 | 1.00 | 120.49 | A | C |
| ATOM | 482 | OE1 | GLN | A | 185 | 18.076 | 13.075 | 23.237 | 1.00 | 120.60 | A | O |
| ATOM | 483 | NE2 | GLN | A | 185 | 17.137 | 12.468 | 21.289 | 1.00 | 121.39 | A | N |
| ATOM | 484 | C | GLN | A | 185 | 13.553 | 9.815 | 23.391 | 1.00 | 116.72 | A | C |
| ATOM | 485 | O | GLN | A | 185 | 13.345 | 10.244 | 24.525 | 1.00 | 115.14 | A | O |
| ATOM | 486 | N | SER | A | 186 | 12.619 | 9.784 | 22.443 | 1.00 | 115.77 | A | N |
| ATOM | 487 | CA | SER | A | 186 | 11.256 | 10.230 | 22.702 | 1.00 | 114.36 | A | C |
| ATOM | 488 | CB | SER | A | 186 | 10.460 | 10.326 | 21.399 | 1.00 | 115.38 | A | C |
| ATOM | 489 | OG | SER | A | 186 | 9.102 | 10.639 | 21.657 | 1.00 | 118.46 | A | O |
| ATOM | 490 | C | SER | A | 186 | 10.623 | 9.190 | 23.612 | 1.00 | 112.50 | A | C |
| ATOM | 491 | O | SER | A | 186 | 9.688 | 8.489 | 23.223 | 1.00 | 112.76 | A | O |
| ATOM | 492 | N | HIS | A | 187 | 11.159 | 9.094 | 24.824 | 1.00 | 110.43 | A | N |
| ATOM | 493 | CA | HIS | A | 187 | 10.694 | 8.140 | 25.820 | 1.00 | 109.09 | A | C |
| ATOM | 494 | CB | HIS | A | 187 | 10.635 | 6.733 | 25.220 | 1.00 | 109.59 | A | C |
| ATOM | 495 | CG | HIS | A | 187 | 9.376 | 5.991 | 25.540 | 1.00 | 111.95 | A | C |
| ATOM | 496 | CD2 | HIS | A | 187 | 9.171 | 4.817 | 26.182 | 1.00 | 112.80 | A | C |
| ATOM | 497 | ND1 | HIS | A | 187 | 8.130 | 6.447 | 25.168 | 1.00 | 112.91 | A | N |
| ATOM | 498 | CE1 | HIS | A | 187 | 7.211 | 5.585 | 25.566 | 1.00 | 113.02 | A | C |
| ATOM | 499 | NE2 | HIS | A | 187 | 7.816 | 4.587 | 26.184 | 1.00 | 113.92 | A | N |
| ATOM | 500 | C | HIS | A | 187 | 11.714 | 8.163 | 26.949 | 1.00 | 107.62 | A | C |
| ATOM | 501 | O | HIS | A | 187 | 11.394 | 8.511 | 28.086 | 1.00 | 110.36 | A | O |
| ATOM | 502 | N | LEU | A | 188 | 12.946 | 7.793 | 26.608 | 1.00 | 104.43 | A | N |
| ATOM | 503 | CA | LEU | A | 188 | 14.060 | 7.756 | 27.550 | 1.00 | 100.63 | A | C |
| ATOM | 504 | CB | LEU | A | 188 | 15.382 | 7.788 | 26.779 | 1.00 | 98.13 | A | C |
| ATOM | 505 | CG | LEU | A | 188 | 16.639 | 7.244 | 27.459 | 1.00 | 96.18 | A | C |
| ATOM | 506 | CD1 | LEU | A | 188 | 16.426 | 5.788 | 27.850 | 1.00 | 94.54 | A | C |
| ATOM | 507 | CD2 | LEU | A | 188 | 17.818 | 7.370 | 26.506 | 1.00 | 96.27 | A | C |
| ATOM | 508 | C | LEU | A | 188 | 13.961 | 8.957 | 28.484 | 1.00 | 99.02 | A | C |
| ATOM | 509 | O | LEU | A | 188 | 14.381 | 10.063 | 28.143 | 1.00 | 99.73 | A | O |
| ATOM | 510 | N | ARG | A | 189 | 13.400 | 8.725 | 29.665 | 1.00 | 96.00 | A | N |

Figure 1I

```
ATOM    511  CA   ARG A 189      13.199   9.780  30.650  1.00   92.28      A  C
ATOM    512  CB   ARG A 189      11.752   9.707  31.151  1.00   93.53      A  C
ATOM    513  CG   ARG A 189      11.181  10.992  31.728  1.00   99.54      A  C
ATOM    514  CD   ARG A 189       9.692  11.072  31.406  1.00  106.53      A  C
ATOM    515  NE   ARG A 189       9.007  12.161  32.095  1.00  112.84      A  N
ATOM    516  CZ   ARG A 189       7.751  12.525  31.849  1.00  115.31      A  C
ATOM    517  NH1  ARG A 189       7.042  11.889  30.924  1.00  115.96      A  N
ATOM    518  NH2  ARG A 189       7.200  13.521  32.529  1.00  117.03      A  N
ATOM    519  C    ARG A 189      14.183   9.650  31.812  1.00   87.52      A  C
ATOM    520  O    ARG A 189      13.991   8.836  32.717  1.00   86.75      A  O
ATOM    521  N    HIS A 190      15.237  10.460  31.776  1.00   81.53      A  N
ATOM    522  CA   HIS A 190      16.266  10.447  32.812  1.00   77.41      A  C
ATOM    523  CB   HIS A 190      17.364   9.448  32.437  1.00   79.03      A  C
ATOM    524  CG   HIS A 190      18.377   9.227  33.516  1.00   81.08      A  C
ATOM    525  CD2  HIS A 190      19.573   9.817  33.748  1.00   81.13      A  C
ATOM    526  ND1  HIS A 190      18.191   8.323  34.539  1.00   80.28      A  N
ATOM    527  CE1  HIS A 190      19.229   8.365  35.356  1.00   79.22      A  C
ATOM    528  NE2  HIS A 190      20.082   9.263  34.898  1.00   80.19      A  N
ATOM    529  C    HIS A 190      16.869  11.847  32.963  1.00   74.62      A  C
ATOM    530  O    HIS A 190      16.960  12.599  31.992  1.00   73.28      A  O
ATOM    531  N    PRO A 191      17.289  12.212  34.186  1.00   73.43      A  N
ATOM    532  CD   PRO A 191      17.178  11.421  35.424  1.00   72.98      A  C
ATOM    533  CA   PRO A 191      17.885  13.524  34.469  1.00   73.07      A  C
ATOM    534  CB   PRO A 191      18.084  13.491  35.986  1.00   73.23      A  C
ATOM    535  CG   PRO A 191      18.256  12.030  36.275  1.00   74.76      A  C
ATOM    536  C    PRO A 191      19.176  13.863  33.719  1.00   72.34      A  C
ATOM    537  O    PRO A 191      19.333  14.983  33.233  1.00   71.62      A  O
ATOM    538  N    ASN A 192      20.098  12.909  33.623  1.00   71.67      A  N
ATOM    539  CA   ASN A 192      21.362  13.160  32.934  1.00   69.74      A  C
ATOM    540  CB   ASN A 192      22.492  12.373  33.604  1.00   66.25      A  C
ATOM    541  CG   ASN A 192      22.459  12.480  35.120  1.00   63.30      A  C
ATOM    542  OD1  ASN A 192      21.757  11.723  35.790  1.00   60.29      A  O
ATOM    543  ND2  ASN A 192      23.211  13.430  35.666  1.00   63.08      A  N
ATOM    544  C    ASN A 192      21.301  12.827  31.441  1.00   68.30      A  C
ATOM    545  O    ASN A 192      22.330  12.717  30.774  1.00   69.72      A  O
ATOM    546  N    ILE A 193      20.083  12.671  30.930  1.00   64.40      A  N
ATOM    547  CA   ILE A 193      19.847  12.375  29.521  1.00   60.95      A  C
ATOM    548  CB   ILE A 193      19.162  11.001  29.333  1.00   58.46      A  C
ATOM    549  CG2  ILE A 193      18.485  10.930  27.965  1.00   54.49      A  C
ATOM    550  CG1  ILE A 193      20.193   9.883  29.503  1.00   58.79      A  C
ATOM    551  CD1  ILE A 193      19.627   8.487  29.347  1.00   58.61      A  C
ATOM    552  C    ILE A 193      18.930  13.461  28.980  1.00   62.13      A  C
ATOM    553  O    ILE A 193      17.788  13.591  29.420  1.00   64.50      A  O
ATOM    554  N    LEU A 194      19.434  14.245  28.033  1.00   62.31      A  N
ATOM    555  CA   LEU A 194      18.647  15.322  27.449  1.00   63.77      A  C
ATOM    556  CB   LEU A 194      19.384  15.941  26.262  1.00   57.37      A  C
ATOM    557  CG   LEU A 194      18.800  17.255  25.743  1.00   51.42      A  C
ATOM    558  CD1  LEU A 194      19.649  18.415  26.242  1.00   43.33      A  C
ATOM    559  CD2  LEU A 194      18.776  17.243  24.229  1.00   53.35      A  C
ATOM    560  C    LEU A 194      17.304  14.776  26.979  1.00   66.99      A  C
ATOM    561  O    LEU A 194      17.249  13.778  26.260  1.00   66.89      A  O
ATOM    562  N    ARG A 195      16.223  15.430  27.386  1.00   69.52      A  N
ATOM    563  CA   ARG A 195      14.890  14.992  26.999  1.00   75.05      A  C
ATOM    564  CB   ARG A 195      13.846  15.659  27.893  1.00   80.25      A  C
ATOM    565  CG   ARG A 195      12.658  14.770  28.184  1.00   86.65      A  C
ATOM    566  CD   ARG A 195      11.599  15.493  28.980  1.00   89.95      A  C
ATOM    567  NE   ARG A 195      10.312  14.819  28.863  1.00   94.47      A  N
ATOM    568  CZ   ARG A 195       9.140  15.407  29.071  1.00   96.89      A  C
ATOM    569  NH1  ARG A 195       8.018  14.713  28.940  1.00   97.23      A  N
ATOM    570  NH2  ARG A 195       9.089  16.690  29.402  1.00   99.86      A  N
ATOM    571  C    ARG A 195      14.632  15.329  25.528  1.00   75.32      A  C
```

Figure 1J

```
ATOM    572  O    ARG A 195      15.397  16.076  24.919  1.00  72.66      A    O
ATOM    573  N    LEU A 196      13.558  14.782  24.961  1.00  79.34      A    N
ATOM    574  CA   LEU A 196      13.231  15.018  23.554  1.00  84.04      A    C
ATOM    575  CB   LEU A 196      13.534  13.754  22.742  1.00  88.38      A    C
ATOM    576  CG   LEU A 196      13.309  13.793  21.228  1.00  89.46      A    C
ATOM    577  CD1  LEU A 196      13.868  15.081  20.645  1.00  89.95      A    C
ATOM    578  CD2  LEU A 196      13.969  12.582  20.592  1.00  92.11      A    C
ATOM    579  C    LEU A 196      11.780  15.451  23.326  1.00  85.72      A    C
ATOM    580  O    LEU A 196      11.100  14.953  22.430  1.00  86.70      A    O
ATOM    581  N    TYR A 197      11.331  16.401  24.139  1.00  86.16      A    N
ATOM    582  CA   TYR A 197       9.976  16.946  24.090  1.00  86.47      A    C
ATOM    583  CB   TYR A 197      10.037  18.463  24.278  1.00  83.34      A    C
ATOM    584  CG   TYR A 197      10.640  18.880  25.600  1.00  82.62      A    C
ATOM    585  CD1  TYR A 197      11.781  19.679  25.646  1.00  83.09      A    C
ATOM    586  CE1  TYR A 197      12.348  20.051  26.861  1.00  83.11      A    C
ATOM    587  CD2  TYR A 197      10.077  18.464  26.807  1.00  83.87      A    C
ATOM    588  CE2  TYR A 197      10.638  18.834  28.027  1.00  85.48      A    C
ATOM    589  CZ   TYR A 197      11.772  19.625  28.045  1.00  83.57      A    C
ATOM    590  OH   TYR A 197      12.335  19.983  29.247  1.00  80.52      A    O
ATOM    591  C    TYR A 197       9.080  16.630  22.890  1.00  88.41      A    C
ATOM    592  O    TYR A 197       7.969  16.134  23.074  1.00  90.29      A    O
ATOM    593  N    GLY A 198       9.533  16.914  21.670  1.00  90.68      A    N
ATOM    594  CA   GLY A 198       8.675  16.648  20.525  1.00  92.01      A    C
ATOM    595  C    GLY A 198       9.297  16.310  19.182  1.00  91.88      A    C
ATOM    596  O    GLY A 198      10.497  16.056  19.079  1.00  92.62      A    O
ATOM    597  N    TYR A 199       8.460  16.315  18.146  1.00  91.47      A    N
ATOM    598  CA   TYR A 199       8.884  15.995  16.784  1.00  92.91      A    C
ATOM    599  CB   TYR A 199       9.073  14.467  16.656  1.00  94.40      A    C
ATOM    600  CG   TYR A 199       9.186  13.880  15.247  1.00  98.95      A    C
ATOM    601  CD1  TYR A 199       9.171  12.496  15.053  1.00 101.21      A    C
ATOM    602  CE1  TYR A 199       9.259  11.940  13.770  1.00 103.34      A    C
ATOM    603  CD2  TYR A 199       9.296  14.692  14.116  1.00 102.24      A    C
ATOM    604  CE2  TYR A 199       9.383  14.147  12.834  1.00 104.38      A    C
ATOM    605  CZ   TYR A 199       9.365  12.775  12.667  1.00 103.79      A    C
ATOM    606  OH   TYR A 199       9.453  12.251  11.396  1.00 102.20      A    O
ATOM    607  C    TYR A 199       7.860  16.494  15.760  1.00  94.83      A    C
ATOM    608  O    TYR A 199       6.657  16.287  15.914  1.00  97.00      A    O
ATOM    609  N    PHE A 200       8.354  17.166  14.724  1.00  96.16      A    N
ATOM    610  CA   PHE A 200       7.515  17.662  13.637  1.00  99.75      A    C
ATOM    611  CB   PHE A 200       6.739  18.921  14.047  1.00 101.18      A    C
ATOM    612  CG   PHE A 200       7.603  20.083  14.448  1.00 101.76      A    C
ATOM    613  CD1  PHE A 200       8.280  20.081  15.663  1.00 100.54      A    C
ATOM    614  CD2  PHE A 200       7.699  21.204  13.629  1.00 101.45      A    C
ATOM    615  CE1  PHE A 200       9.035  21.183  16.059  1.00  98.76      A    C
ATOM    616  CE2  PHE A 200       8.451  22.309  14.016  1.00  98.84      A    C
ATOM    617  CZ   PHE A 200       9.119  22.299  15.234  1.00  98.18      A    C
ATOM    618  C    PHE A 200       8.396  17.948  12.425  1.00 102.64      A    C
ATOM    619  O    PHE A 200       9.603  18.143  12.565  1.00 105.53      A    O
ATOM    620  N    HIS A 201       7.796  17.965  11.238  1.00 105.71      A    N
ATOM    621  CA   HIS A 201       8.556  18.197  10.012  1.00 109.97      A    C
ATOM    622  CB   HIS A 201       9.073  16.858   9.478  1.00 115.72      A    C
ATOM    623  CG   HIS A 201       8.001  15.826   9.299  1.00 122.37      A    C
ATOM    624  CD2  HIS A 201       7.729  14.695   9.992  1.00 124.07      A    C
ATOM    625  ND1  HIS A 201       7.032  15.917   8.323  1.00 125.11      A    N
ATOM    626  CE1  HIS A 201       6.209  14.889   8.423  1.00 126.58      A    C
ATOM    627  NE2  HIS A 201       6.610  14.132   9.429  1.00 126.42      A    N
ATOM    628  C    HIS A 201       7.783  18.908   8.905  1.00 110.12      A    C
ATOM    629  O    HIS A 201       6.665  18.517   8.571  1.00 109.61      A    O
ATOM    630  N    ASP A 202       8.383  19.949   8.334  1.00 112.18      A    N
ATOM    631  CA   ASP A 202       7.745  20.677   7.242  1.00 115.14      A    C
ATOM    632  CB   ASP A 202       8.037  22.185   7.322  1.00 115.18      A    C
```

Figure 1K

```
ATOM    633  CG  ASP A 202       9.496  22.527   7.047  1.00 115.61      A    C
ATOM    634  OD1 ASP A 202      10.117  21.880   6.177  1.00 115.07      A    O
ATOM    635  OD2 ASP A 202      10.018  23.462   7.690  1.00 116.37      A    O
ATOM    636  C   ASP A 202       8.282  20.113   5.932  1.00 116.67      A    C
ATOM    637  O   ASP A 202       9.098  19.190   5.937  1.00 117.19      A    O
ATOM    638  N   ALA A 203       7.829  20.670   4.815  1.00 116.52      A    N
ATOM    639  CA  ALA A 203       8.270  20.214   3.503  1.00 115.43      A    C
ATOM    640  CB  ALA A 203       7.798  21.185   2.430  1.00 114.36      A    C
ATOM    641  C   ALA A 203       9.789  20.062   3.439  1.00 116.09      A    C
ATOM    642  O   ALA A 203      10.304  18.965   3.217  1.00 114.35      A    O
ATOM    643  N   THR A 204      10.500  21.167   3.644  1.00 117.33      A    N
ATOM    644  CA  THR A 204      11.960  21.169   3.595  1.00 116.73      A    C
ATOM    645  CB  THR A 204      12.515  22.613   3.622  1.00 116.90      A    C
ATOM    646  OG1 THR A 204      11.976  23.355   2.521  1.00 117.88      A    O
ATOM    647  CG2 THR A 204      14.036  22.605   3.521  1.00 115.80      A    C
ATOM    648  C   THR A 204      12.620  20.382   4.725  1.00 115.79      A    C
ATOM    649  O   THR A 204      12.906  19.193   4.585  1.00 115.16      A    O
ATOM    650  N   ARG A 205      12.863  21.057   5.843  1.00 114.12      A    N
ATOM    651  CA  ARG A 205      13.514  20.445   6.995  1.00 112.83      A    C
ATOM    652  CB  ARG A 205      14.253  21.521   7.803  1.00 114.63      A    C
ATOM    653  CG  ARG A 205      13.529  22.867   7.902  1.00 120.69      A    C
ATOM    654  CD  ARG A 205      13.746  23.713   6.647  1.00 125.29      A    C
ATOM    655  NE  ARG A 205      13.063  25.007   6.690  1.00 132.52      A    N
ATOM    656  CZ  ARG A 205      13.315  25.969   7.573  1.00 136.85      A    C
ATOM    657  NH1 ARG A 205      14.240  25.796   8.508  1.00 139.64      A    N
ATOM    658  NH2 ARG A 205      12.644  27.113   7.518  1.00 139.70      A    N
ATOM    659  C   ARG A 205      12.594  19.664   7.928  1.00 110.90      A    C
ATOM    660  O   ARG A 205      11.419  19.443   7.635  1.00 110.68      A    O
ATOM    661  N   VAL A 206      13.167  19.233   9.048  1.00 108.69      A    N
ATOM    662  CA  VAL A 206      12.451  18.497  10.083  1.00 104.24      A    C
ATOM    663  CB  VAL A 206      12.845  16.998  10.109  1.00 102.24      A    C
ATOM    664  CG1 VAL A 206      13.162  16.523   8.710  1.00 103.73      A    C
ATOM    665  CG2 VAL A 206      14.027  16.773  11.030  1.00  98.51      A    C
ATOM    666  C   VAL A 206      12.914  19.158  11.374  1.00 102.88      A    C
ATOM    667  O   VAL A 206      13.982  19.768  11.403  1.00 103.16      A    O
ATOM    668  N   TYR A 207      12.132  19.048  12.441  1.00 101.75      A    N
ATOM    669  CA  TYR A 207      12.535  19.681  13.687  1.00 100.09      A    C
ATOM    670  CB  TYR A 207      11.733  20.962  13.921  1.00 101.19      A    C
ATOM    671  CG  TYR A 207      11.733  21.931  12.761  1.00 101.88      A    C
ATOM    672  CD1 TYR A 207      10.804  21.812  11.727  1.00 101.47      A    C
ATOM    673  CE1 TYR A 207      10.789  22.712  10.666  1.00 104.18      A    C
ATOM    674  CD2 TYR A 207      12.654  22.977  12.703  1.00 104.04      A    C
ATOM    675  CE2 TYR A 207      12.649  23.882  11.645  1.00 106.21      A    C
ATOM    676  CZ  TYR A 207      11.713  23.744  10.632  1.00 106.59      A    C
ATOM    677  OH  TYR A 207      11.699  24.638   9.587  1.00 113.08      A    O
ATOM    678  C   TYR A 207      12.429  18.813  14.929  1.00  98.20      A    C
ATOM    679  O   TYR A 207      11.399  18.191  15.194  1.00  97.21      A    O
ATOM    680  N   LEU A 208      13.515  18.795  15.691  1.00  96.15      A    N
ATOM    681  CA  LEU A 208      13.583  18.046  16.932  1.00  93.59      A    C
ATOM    682  CB  LEU A 208      14.911  17.286  17.029  1.00  94.10      A    C
ATOM    683  CG  LEU A 208      15.261  16.275  15.931  1.00  94.01      A    C
ATOM    684  CD1 LEU A 208      16.726  15.882  16.050  1.00  95.81      A    C
ATOM    685  CD2 LEU A 208      14.367  15.052  16.044  1.00  91.99      A    C
ATOM    686  C   LEU A 208      13.492  19.070  18.059  1.00  91.52      A    C
ATOM    687  O   LEU A 208      14.293  20.002  18.125  1.00  92.03      A    O
ATOM    688  N   ILE A 209      12.495  18.917  18.922  1.00  87.28      A    N
ATOM    689  CA  ILE A 209      12.325  19.823  20.050  1.00  82.44      A    C
ATOM    690  CB  ILE A 209      10.841  20.067  20.351  1.00  81.18      A    C
ATOM    691  CG2 ILE A 209      10.699  20.947  21.583  1.00  83.06      A    C
ATOM    692  CG1 ILE A 209      10.173  20.722  19.142  1.00  79.11      A    C
ATOM    693  CD1 ILE A 209       8.681  20.878  19.285  1.00  77.41      A    C
```

Figure 1L

| ATOM | 694 | C   | ILE | A | 209 | 12.974 | 19.141 | 21.242 | 1.00 | 80.66 | A | C |
|------|-----|-----|-----|---|-----|--------|--------|--------|------|-------|---|---|
| ATOM | 695 | O   | ILE | A | 209 | 12.519 | 18.086 | 21.679 | 1.00 | 83.60 | A | O |
| ATOM | 696 | N   | LEU | A | 210 | 14.032 | 19.742 | 21.772 | 1.00 | 78.81 | A | N |
| ATOM | 697 | CA  | LEU | A | 210 | 14.735 | 19.130 | 22.889 | 1.00 | 76.80 | A | C |
| ATOM | 698 | CB  | LEU | A | 210 | 16.107 | 18.644 | 22.434 | 1.00 | 76.48 | A | C |
| ATOM | 699 | CG  | LEU | A | 210 | 16.200 | 17.966 | 21.071 | 1.00 | 74.49 | A | C |
| ATOM | 700 | CD1 | LEU | A | 210 | 16.408 | 19.001 | 19.978 | 1.00 | 73.14 | A | C |
| ATOM | 701 | CD2 | LEU | A | 210 | 17.359 | 17.014 | 21.091 | 1.00 | 74.20 | A | C |
| ATOM | 702 | C   | LEU | A | 210 | 14.932 | 20.012 | 24.104 | 1.00 | 74.81 | A | C |
| ATOM | 703 | O   | LEU | A | 210 | 14.777 | 21.233 | 24.045 | 1.00 | 74.93 | A | O |
| ATOM | 704 | N   | GLU | A | 211 | 15.279 | 19.365 | 25.212 | 1.00 | 72.58 | A | N |
| ATOM | 705 | CA  | GLU | A | 211 | 15.545 | 20.067 | 26.453 | 1.00 | 72.94 | A | C |
| ATOM | 706 | CB  | GLU | A | 211 | 15.865 | 19.069 | 27.573 | 1.00 | 76.08 | A | C |
| ATOM | 707 | CG  | GLU | A | 211 | 17.052 | 19.455 | 28.445 | 1.00 | 80.00 | A | C |
| ATOM | 708 | CD  | GLU | A | 211 | 17.078 | 18.715 | 29.767 | 1.00 | 78.72 | A | C |
| ATOM | 709 | OE1 | GLU | A | 211 | 16.820 | 17.494 | 29.778 | 1.00 | 79.83 | A | O |
| ATOM | 710 | OE2 | GLU | A | 211 | 17.365 | 19.358 | 30.798 | 1.00 | 73.80 | A | O |
| ATOM | 711 | C   | GLU | A | 211 | 16.738 | 20.972 | 26.188 | 1.00 | 72.77 | A | C |
| ATOM | 712 | O   | GLU | A | 211 | 17.553 | 20.696 | 25.311 | 1.00 | 70.47 | A | O |
| ATOM | 713 | N   | TYR | A | 212 | 16.834 | 22.054 | 26.948 | 1.00 | 74.66 | A | N |
| ATOM | 714 | CA  | TYR | A | 212 | 17.917 | 23.010 | 26.783 | 1.00 | 76.39 | A | C |
| ATOM | 715 | CB  | TYR | A | 212 | 17.323 | 24.416 | 26.665 | 1.00 | 78.44 | A | C |
| ATOM | 716 | CG  | TYR | A | 212 | 18.323 | 25.532 | 26.813 | 1.00 | 80.65 | A | C |
| ATOM | 717 | CD1 | TYR | A | 212 | 19.355 | 25.703 | 25.892 | 1.00 | 78.59 | A | C |
| ATOM | 718 | CE1 | TYR | A | 212 | 20.280 | 26.733 | 26.033 | 1.00 | 78.55 | A | C |
| ATOM | 719 | CD2 | TYR | A | 212 | 18.240 | 26.420 | 27.882 | 1.00 | 81.53 | A | C |
| ATOM | 720 | CE2 | TYR | A | 212 | 19.156 | 27.450 | 28.034 | 1.00 | 79.55 | A | C |
| ATOM | 721 | CZ  | TYR | A | 212 | 20.173 | 27.602 | 27.108 | 1.00 | 78.83 | A | C |
| ATOM | 722 | OH  | TYR | A | 212 | 21.078 | 28.627 | 27.262 | 1.00 | 78.92 | A | O |
| ATOM | 723 | C   | TYR | A | 212 | 18.926 | 22.950 | 27.931 | 1.00 | 76.64 | A | C |
| ATOM | 724 | O   | TYR | A | 212 | 18.547 | 22.798 | 29.092 | 1.00 | 76.15 | A | O |
| ATOM | 725 | N   | ALA | A | 213 | 20.210 | 23.062 | 27.594 | 1.00 | 76.47 | A | N |
| ATOM | 726 | CA  | ALA | A | 213 | 21.290 | 23.036 | 28.582 | 1.00 | 77.42 | A | C |
| ATOM | 727 | CB  | ALA | A | 213 | 22.148 | 21.789 | 28.393 | 1.00 | 77.65 | A | C |
| ATOM | 728 | C   | ALA | A | 213 | 22.145 | 24.297 | 28.422 | 1.00 | 78.28 | A | C |
| ATOM | 729 | O   | ALA | A | 213 | 22.960 | 24.392 | 27.506 | 1.00 | 75.08 | A | O |
| ATOM | 730 | N   | PRO | A | 214 | 21.968 | 25.275 | 29.326 | 1.00 | 80.20 | A | N |
| ATOM | 731 | CD  | PRO | A | 214 | 20.990 | 25.179 | 30.425 | 1.00 | 80.42 | A | C |
| ATOM | 732 | CA  | PRO | A | 214 | 22.661 | 26.570 | 29.371 | 1.00 | 80.88 | A | C |
| ATOM | 733 | CB  | PRO | A | 214 | 21.876 | 27.333 | 30.436 | 1.00 | 80.64 | A | C |
| ATOM | 734 | CG  | PRO | A | 214 | 21.465 | 26.252 | 31.374 | 1.00 | 80.40 | A | C |
| ATOM | 735 | C   | PRO | A | 214 | 24.173 | 26.633 | 29.624 | 1.00 | 80.54 | A | C |
| ATOM | 736 | O   | PRO | A | 214 | 24.775 | 27.696 | 29.469 | 1.00 | 82.40 | A | O |
| ATOM | 737 | N   | LEU | A | 215 | 24.795 | 25.523 | 30.008 | 1.00 | 77.95 | A | N |
| ATOM | 738 | CA  | LEU | A | 215 | 26.232 | 25.545 | 30.275 | 1.00 | 74.18 | A | C |
| ATOM | 739 | CB  | LEU | A | 215 | 26.538 | 24.798 | 31.572 | 1.00 | 76.09 | A | C |
| ATOM | 740 | CG  | LEU | A | 215 | 26.427 | 25.661 | 32.833 | 1.00 | 79.15 | A | C |
| ATOM | 741 | CD1 | LEU | A | 215 | 26.323 | 24.772 | 34.053 | 1.00 | 80.09 | A | C |
| ATOM | 742 | CD2 | LEU | A | 215 | 27.631 | 26.591 | 32.933 | 1.00 | 81.98 | A | C |
| ATOM | 743 | C   | LEU | A | 215 | 27.106 | 25.011 | 29.149 | 1.00 | 72.14 | A | C |
| ATOM | 744 | O   | LEU | A | 215 | 28.332 | 24.979 | 29.268 | 1.00 | 71.05 | A | O |
| ATOM | 745 | N   | GLY | A | 216 | 26.476 | 24.592 | 28.057 | 1.00 | 70.26 | A | N |
| ATOM | 746 | CA  | GLY | A | 216 | 27.227 | 24.091 | 26.921 | 1.00 | 67.90 | A | C |
| ATOM | 747 | C   | GLY | A | 216 | 27.677 | 22.647 | 27.022 | 1.00 | 65.44 | A | C |
| ATOM | 748 | O   | GLY | A | 216 | 27.056 | 21.834 | 27.705 | 1.00 | 64.26 | A | O |
| ATOM | 749 | N   | THR | A | 217 | 28.766 | 22.327 | 26.334 | 1.00 | 62.90 | A | N |
| ATOM | 750 | CA  | THR | A | 217 | 29.296 | 20.971 | 26.341 | 1.00 | 62.07 | A | C |
| ATOM | 751 | CB  | THR | A | 217 | 29.828 | 20.586 | 24.955 | 1.00 | 58.21 | A | C |
| ATOM | 752 | OG1 | THR | A | 217 | 30.927 | 21.440 | 24.614 | 1.00 | 56.12 | A | O |
| ATOM | 753 | CG2 | THR | A | 217 | 28.733 | 20.736 | 23.909 | 1.00 | 55.88 | A | C |
| ATOM | 754 | C   | THR | A | 217 | 30.431 | 20.819 | 27.343 | 1.00 | 64.73 | A | C |

Figure 1M

```
ATOM    755  O    THR A 217      31.143  21.779  27.637  1.00  65.23      A    O
ATOM    756  N    VAL A 218      30.600  19.607  27.863  1.00  65.76      A    N
ATOM    757  CA   VAL A 218      31.666  19.344  28.819  1.00  65.75      A    C
ATOM    758  CB   VAL A 218      31.628  17.886  29.333  1.00  62.46      A    C
ATOM    759  CG1  VAL A 218      32.718  17.673  30.378  1.00  59.39      A    C
ATOM    760  CG2  VAL A 218      30.264  17.578  29.926  1.00  61.71      A    C
ATOM    761  C    VAL A 218      32.997  19.582  28.114  1.00  68.91      A    C
ATOM    762  O    VAL A 218      33.993  19.933  28.744  1.00  70.76      A    O
ATOM    763  N    TYR A 219      32.999  19.394  26.797  1.00  70.27      A    N
ATOM    764  CA   TYR A 219      34.198  19.588  25.994  1.00  71.74      A    C
ATOM    765  CB   TYR A 219      33.912  19.288  24.519  1.00  70.23      A    C
ATOM    766  CG   TYR A 219      35.098  19.539  23.614  1.00  70.80      A    C
ATOM    767  CD1  TYR A 219      36.367  19.078  23.960  1.00  72.10      A    C
ATOM    768  CE1  TYR A 219      37.465  19.303  23.138  1.00  74.02      A    C
ATOM    769  CD2  TYR A 219      34.955  20.233  22.413  1.00  72.83      A    C
ATOM    770  CE2  TYR A 219      36.050  20.462  21.580  1.00  74.82      A    C
ATOM    771  CZ   TYR A 219      37.300  19.994  21.951  1.00  76.33      A    C
ATOM    772  OH   TYR A 219      38.385  20.218  21.138  1.00  76.92      A    O
ATOM    773  C    TYR A 219      34.749  21.002  26.118  1.00  74.36      A    C
ATOM    774  O    TYR A 219      35.940  21.190  26.367  1.00  74.47      A    O
ATOM    775  N    ARG A 220      33.885  21.996  25.942  1.00  77.38      A    N
ATOM    776  CA   ARG A 220      34.326  23.380  26.029  1.00  81.83      A    C
ATOM    777  CB   ARG A 220      33.210  24.341  25.626  1.00  86.64      A    C
ATOM    778  CG   ARG A 220      33.751  25.720  25.309  1.00  92.65      A    C
ATOM    779  CD   ARG A 220      32.695  26.804  25.317  1.00  97.88      A    C
ATOM    780  NE   ARG A 220      33.266  28.069  24.864  1.00  98.55      A    N
ATOM    781  CZ   ARG A 220      32.647  29.242  24.926  1.00  95.81      A    C
ATOM    782  NH1  ARG A 220      31.422  29.325  25.427  1.00  94.05      A    N
ATOM    783  NH2  ARG A 220      33.255  30.333  24.485  1.00  93.24      A    N
ATOM    784  C    ARG A 220      34.804  23.727  27.431  1.00  82.37      A    C
ATOM    785  O    ARG A 220      35.895  24.265  27.604  1.00  83.73      A    O
ATOM    786  N    GLU A 221      33.984  23.425  28.431  1.00  83.07      A    N
ATOM    787  CA   GLU A 221      34.351  23.707  29.813  1.00  85.35      A    C
ATOM    788  CB   GLU A 221      33.195  23.360  30.753  1.00  87.33      A    C
ATOM    789  CG   GLU A 221      33.535  23.482  32.231  1.00  90.73      A    C
ATOM    790  CD   GLU A 221      33.298  24.871  32.790  1.00  92.50      A    C
ATOM    791  OE1  GLU A 221      32.207  25.430  32.551  1.00  95.78      A    O
ATOM    792  OE2  GLU A 221      34.196  25.402  33.478  1.00  90.48      A    O
ATOM    793  C    GLU A 221      35.582  22.884  30.181  1.00  85.57      A    C
ATOM    794  O    GLU A 221      36.188  23.089  31.233  1.00  86.94      A    O
ATOM    795  N    LEU A 222      35.941  21.947  29.309  1.00  85.47      A    N
ATOM    796  CA   LEU A 222      37.107  21.101  29.535  1.00  85.07      A    C
ATOM    797  CB   LEU A 222      36.867  19.694  28.969  1.00  86.86      A    C
ATOM    798  CG   LEU A 222      37.979  18.651  29.129  1.00  89.01      A    C
ATOM    799  CD1  LEU A 222      38.431  18.588  30.578  1.00  90.45      A    C
ATOM    800  CD2  LEU A 222      37.475  17.292  28.662  1.00  89.40      A    C
ATOM    801  C    LEU A 222      38.328  21.726  28.874  1.00  84.81      A    C
ATOM    802  O    LEU A 222      39.425  21.706  29.431  1.00  84.04      A    O
ATOM    803  N    GLN A 223      38.133  22.290  27.686  1.00  87.70      A    N
ATOM    804  CA   GLN A 223      39.229  22.919  26.962  1.00  92.05      A    C
ATOM    805  CB   GLN A 223      38.860  23.117  25.484  1.00  95.24      A    C
ATOM    806  CG   GLN A 223      37.703  24.068  25.205  1.00  99.72      A    C
ATOM    807  CD   GLN A 223      37.346  24.120  23.727  1.00 100.63      A    C
ATOM    808  OE1  GLN A 223      36.403  24.804  23.324  1.00 101.42      A    O
ATOM    809  NE2  GLN A 223      38.101  23.392  22.911  1.00 100.32      A    N
ATOM    810  C    GLN A 223      39.634  24.247  27.593  1.00  92.42      A    C
ATOM    811  O    GLN A 223      40.729  24.751  27.346  1.00  93.09      A    O
ATOM    812  N    LYS A 224      38.751  24.807  28.415  1.00  93.18      A    N
ATOM    813  CA   LYS A 224      39.027  26.072  29.091  1.00  93.04      A    C
ATOM    814  CB   LYS A 224      37.717  26.775  29.463  1.00  95.71      A    C
ATOM    815  CG   LYS A 224      36.700  26.896  28.331  1.00  98.55      A    C
```

Figure 1N

```
ATOM    816  CD  LYS A 224      37.159  27.860  27.244  1.00  98.21      A    C
ATOM    817  CE  LYS A 224      36.455  27.596  25.913  1.00  97.94      A    C
ATOM    818  NZ  LYS A 224      36.265  28.846  25.120  1.00  93.95      A    N
ATOM    819  C   LYS A 224      39.804  25.764  30.366  1.00  90.14      A    C
ATOM    820  O   LYS A 224      40.856  26.347  30.636  1.00  90.33      A    O
ATOM    821  N   LEU A 225      39.260  24.833  31.141  1.00  85.73      A    N
ATOM    822  CA  LEU A 225      39.847  24.413  32.405  1.00  82.95      A    C
ATOM    823  CB  LEU A 225      38.767  23.768  33.278  1.00  79.91      A    C
ATOM    824  CG  LEU A 225      38.272  24.583  34.478  1.00  79.40      A    C
ATOM    825  CD1 LEU A 225      37.987  26.023  34.074  1.00  80.68      A    C
ATOM    826  CD2 LEU A 225      37.030  23.923  35.048  1.00  77.55      A    C
ATOM    827  C   LEU A 225      41.029  23.460  32.248  1.00  83.25      A    C
ATOM    828  O   LEU A 225      41.665  23.091  33.234  1.00  84.26      A    O
ATOM    829  N   SER A 226      41.316  23.061  31.013  1.00  83.25      A    N
ATOM    830  CA  SER A 226      42.435  22.165  30.733  1.00  81.93      A    C
ATOM    831  CB  SER A 226      43.710  22.715  31.385  1.00  83.49      A    C
ATOM    832  OG  SER A 226      44.755  22.856  30.440  1.00  86.13      A    O
ATOM    833  C   SER A 226      42.175  20.738  31.221  1.00  80.46      A    C
ATOM    834  O   SER A 226      42.008  19.819  30.418  1.00  80.71      A    O
ATOM    835  N   LYS A 227      42.143  20.561  32.538  1.00  78.84      A    N
ATOM    836  CA  LYS A 227      41.907  19.253  33.143  1.00  79.61      A    C
ATOM    837  CB  LYS A 227      43.227  18.659  33.646  1.00  78.81      A    C
ATOM    838  CG  LYS A 227      43.068  17.407  34.499  1.00  83.08      A    C
ATOM    839  CD  LYS A 227      44.237  17.252  35.455  1.00  83.38      A    C
ATOM    840  CE  LYS A 227      43.894  16.305  36.593  1.00  83.21      A    C
ATOM    841  NZ  LYS A 227      44.864  16.411  37.717  1.00  82.39      A    N
ATOM    842  C   LYS A 227      40.930  19.373  34.310  1.00  80.74      A    C
ATOM    843  O   LYS A 227      40.794  20.441  34.907  1.00  82.85      A    O
ATOM    844  N   PHE A 228      40.256  18.272  34.630  1.00  81.37      A    N
ATOM    845  CA  PHE A 228      39.298  18.246  35.731  1.00  81.27      A    C
ATOM    846  CB  PHE A 228      38.068  17.400  35.370  1.00  77.46      A    C
ATOM    847  CG  PHE A 228      37.222  17.973  34.265  1.00  73.67      A    C
ATOM    848  CD1 PHE A 228      37.273  19.327  33.951  1.00  70.30      A    C
ATOM    849  CD2 PHE A 228      36.345  17.154  33.556  1.00  71.19      A    C
ATOM    850  CE1 PHE A 228      36.463  19.860  32.950  1.00  68.60      A    C
ATOM    851  CE2 PHE A 228      35.530  17.676  32.555  1.00  67.99      A    C
ATOM    852  CZ  PHE A 228      35.589  19.032  32.251  1.00  67.14      A    C
ATOM    853  C   PHE A 228      39.920  17.658  36.993  1.00  84.23      A    C
ATOM    854  O   PHE A 228      40.832  16.835  36.917  1.00  85.49      A    O
ATOM    855  N   ASP A 229      39.424  18.086  38.152  1.00  87.03      A    N
ATOM    856  CA  ASP A 229      39.912  17.561  39.422  1.00  87.98      A    C
ATOM    857  CB  ASP A 229      39.641  18.543  40.569  1.00  92.20      A    C
ATOM    858  CG  ASP A 229      38.162  18.813  40.773  1.00  94.47      A    C
ATOM    859  OD1 ASP A 229      37.538  19.438  39.889  1.00  93.40      A    O
ATOM    860  OD2 ASP A 229      37.620  18.395  41.817  1.00  97.35      A    O
ATOM    861  C   ASP A 229      39.149  16.262  39.659  1.00  85.99      A    C
ATOM    862  O   ASP A 229      38.124  16.021  39.022  1.00  82.28      A    O
ATOM    863  N   GLU A 230      39.637  15.428  40.571  1.00  87.00      A    N
ATOM    864  CA  GLU A 230      38.981  14.155  40.844  1.00  90.39      A    C
ATOM    865  CB  GLU A 230      39.850  13.295  41.768  1.00  93.88      A    C
ATOM    866  CG  GLU A 230      40.984  14.025  42.463  1.00  99.69      A    C
ATOM    867  CD  GLU A 230      42.343  13.474  42.067  1.00 102.31      A    C
ATOM    868  OE1 GLU A 230      42.465  12.238  41.938  1.00 101.27      A    O
ATOM    869  OE2 GLU A 230      43.288  14.271  41.890  1.00 104.60      A    O
ATOM    870  C   GLU A 230      37.562  14.242  41.406  1.00  91.31      A    C
ATOM    871  O   GLU A 230      36.814  13.267  41.349  1.00  90.26      A    O
ATOM    872  N   GLN A 231      37.185  15.400  41.941  1.00  93.98      A    N
ATOM    873  CA  GLN A 231      35.841  15.573  42.492  1.00  95.14      A    C
ATOM    874  CB  GLN A 231      35.803  16.742  43.479  1.00  97.54      A    C
ATOM    875  CG  GLN A 231      36.579  16.516  44.765  1.00  99.92      A    C
ATOM    876  CD  GLN A 231      38.025  16.144  44.519  1.00 101.11      A    C
```

Figure 10

```
ATOM    877  OE1 GLN A 231      38.341  14.989  44.231  1.00 105.38      A    O
ATOM    878  NE2 GLN A 231      38.913  17.125  44.619  1.00  98.87      A    N
ATOM    879  C   GLN A 231      34.852  15.839  41.365  1.00  94.23      A    C
ATOM    880  O   GLN A 231      33.724  15.350  41.378  1.00  92.43      A    O
ATOM    881  N   ARG A 232      35.281  16.630  40.392  1.00  93.32      A    N
ATOM    882  CA  ARG A 232      34.432  16.950  39.258  1.00  91.45      A    C
ATOM    883  CB  ARG A 232      35.032  18.111  38.467  1.00  92.28      A    C
ATOM    884  CG  ARG A 232      34.190  18.540  37.289  1.00  95.39      A    C
ATOM    885  CD  ARG A 232      34.513  19.955  36.871  1.00  96.89      A    C
ATOM    886  NE  ARG A 232      33.645  20.375  35.779  1.00 101.97      A    N
ATOM    887  CZ  ARG A 232      33.613  21.600  35.271  1.00 104.47      A    C
ATOM    888  NH1 ARG A 232      34.405  22.550  35.753  1.00 104.97      A    N
ATOM    889  NH2 ARG A 232      32.778  21.874  34.281  1.00 104.96      A    N
ATOM    890  C   ARG A 232      34.314  15.719  38.372  1.00  90.04      A    C
ATOM    891  O   ARG A 232      33.221  15.348  37.940  1.00  88.50      A    O
ATOM    892  N   THR A 233      35.452  15.086  38.117  1.00  89.90      A    N
ATOM    893  CA  THR A 233      35.500  13.893  37.286  1.00  88.96      A    C
ATOM    894  CB  THR A 233      36.953  13.425  37.069  1.00  88.59      A    C
ATOM    895  OG1 THR A 233      37.739  14.512  36.565  1.00  86.45      A    O
ATOM    896  CG2 THR A 233      36.996  12.273  36.075  1.00  86.30      A    C
ATOM    897  C   THR A 233      34.711  12.742  37.903  1.00  88.42      A    C
ATOM    898  O   THR A 233      33.755  12.248  37.308  1.00  87.03      A    O
ATOM    899  N   ALA A 234      35.112  12.322  39.099  1.00  88.51      A    N
ATOM    900  CA  ALA A 234      34.454  11.213  39.780  1.00  86.27      A    C
ATOM    901  CB  ALA A 234      35.125  10.952  41.125  1.00  87.18      A    C
ATOM    902  C   ALA A 234      32.947  11.377  39.966  1.00  85.58      A    C
ATOM    903  O   ALA A 234      32.250  10.394  40.214  1.00  85.70      A    O
ATOM    904  N   THR A 235      32.437  12.602  39.858  1.00  84.56      A    N
ATOM    905  CA  THR A 235      31.000  12.811  40.007  1.00  84.21      A    C
ATOM    906  CB  THR A 235      30.665  14.102  40.776  1.00  83.98      A    C
ATOM    907  OG1 THR A 235      29.245  14.184  40.961  1.00  86.69      A    O
ATOM    908  CG2 THR A 235      31.138  15.322  40.009  1.00  82.48      A    C
ATOM    909  C   THR A 235      30.349  12.872  38.633  1.00  82.82      A    C
ATOM    910  O   THR A 235      29.142  12.685  38.500  1.00  80.06      A    O
ATOM    911  N   TYR A 236      31.150  13.162  37.612  1.00  82.22      A    N
ATOM    912  CA  TYR A 236      30.633  13.185  36.253  1.00  80.40      A    C
ATOM    913  CB  TYR A 236      31.614  13.868  35.298  1.00  81.31      A    C
ATOM    914  CG  TYR A 236      31.411  15.368  35.185  1.00  82.36      A    C
ATOM    915  CD1 TYR A 236      30.368  16.011  35.861  1.00  82.98      A    C
ATOM    916  CE1 TYR A 236      30.168  17.386  35.740  1.00  85.13      A    C
ATOM    917  CD2 TYR A 236      32.248  16.143  34.385  1.00  84.39      A    C
ATOM    918  CE2 TYR A 236      32.055  17.517  34.257  1.00  87.07      A    C
ATOM    919  CZ  TYR A 236      31.016  18.131  34.936  1.00  88.40      A    C
ATOM    920  OH  TYR A 236      30.829  19.489  34.810  1.00  90.84      A    O
ATOM    921  C   TYR A 236      30.470  11.713  35.923  1.00  77.82      A    C
ATOM    922  O   TYR A 236      29.543  11.318  35.216  1.00  73.41      A    O
ATOM    923  N   ILE A 237      31.394  10.908  36.441  1.00  78.17      A    N
ATOM    924  CA  ILE A 237      31.314   9.466  36.290  1.00  78.47      A    C
ATOM    925  CB  ILE A 237      32.637   8.772  36.634  1.00  76.30      A    C
ATOM    926  CG2 ILE A 237      32.514   7.278  36.376  1.00  71.32      A    C
ATOM    927  CG1 ILE A 237      33.767   9.361  35.784  1.00  73.49      A    C
ATOM    928  CD1 ILE A 237      33.516   9.309  34.286  1.00  76.49      A    C
ATOM    929  C   ILE A 237      30.286   9.240  37.387  1.00  82.65      A    C
ATOM    930  O   ILE A 237      30.469   9.690  38.515  1.00  82.70      A    O
ATOM    931  N   THR A 238      29.214   8.547  37.032  1.00  85.03      A    N
ATOM    932  CA  THR A 238      28.043   8.315  37.875  1.00  85.40      A    C
ATOM    933  CB  THR A 238      28.188   8.852  39.328  1.00  88.03      A    C
ATOM    934  OG1 THR A 238      27.275   8.152  40.182  1.00  92.44      A    O
ATOM    935  CG2 THR A 238      27.871  10.342  39.402  1.00  91.64      A    C
ATOM    936  C   THR A 238      27.264   9.297  37.012  1.00  83.02      A    C
ATOM    937  O   THR A 238      27.866   9.857  36.102  1.00  82.96      A    O
```

Figure 1P

| ATOM | 938 | N   | GLU | A | 239 | 25.990 | 9.567  | 37.263 | 1.00 | 79.97 | A | N |
|------|-----|-----|-----|---|-----|--------|--------|--------|------|-------|---|---|
| ATOM | 939 | CA  | GLU | A | 239 | 25.282 | 10.461 | 36.344 | 1.00 | 78.88 | A | C |
| ATOM | 940 | CB  | GLU | A | 239 | 25.994 | 11.817 | 36.183 | 1.00 | 77.01 | A | C |
| ATOM | 941 | CG  | GLU | A | 239 | 25.859 | 12.792 | 37.350 | 1.00 | 76.68 | A | C |
| ATOM | 942 | CD  | GLU | A | 239 | 25.890 | 14.250 | 36.896 | 1.00 | 73.09 | A | C |
| ATOM | 943 | OE1 | GLU | A | 239 | 26.064 | 15.146 | 37.750 | 1.00 | 69.24 | A | O |
| ATOM | 944 | OE2 | GLU | A | 239 | 25.729 | 14.501 | 35.684 | 1.00 | 70.34 | A | O |
| ATOM | 945 | C   | GLU | A | 239 | 25.381 | 9.688  | 35.025 | 1.00 | 78.47 | A | C |
| ATOM | 946 | O   | GLU | A | 239 | 24.427 | 9.041  | 34.598 | 1.00 | 79.87 | A | O |
| ATOM | 947 | N   | LEU | A | 240 | 26.554 | 9.760  | 34.396 | 1.00 | 77.02 | A | N |
| ATOM | 948 | CA  | LEU | A | 240 | 26.830 | 9.038  | 33.160 | 1.00 | 74.70 | A | C |
| ATOM | 949 | CB  | LEU | A | 240 | 28.308 | 9.162  | 32.776 | 1.00 | 70.36 | A | C |
| ATOM | 950 | CG  | LEU | A | 240 | 28.768 | 10.233 | 31.791 | 1.00 | 64.42 | A | C |
| ATOM | 951 | CD1 | LEU | A | 240 | 30.251 | 10.045 | 31.516 | 1.00 | 58.25 | A | C |
| ATOM | 952 | CD2 | LEU | A | 240 | 27.975 | 10.121 | 30.500 | 1.00 | 59.32 | A | C |
| ATOM | 953 | C   | LEU | A | 240 | 26.524 | 7.568  | 33.398 | 1.00 | 73.98 | A | C |
| ATOM | 954 | O   | LEU | A | 240 | 25.578 | 7.022  | 32.838 | 1.00 | 74.52 | A | O |
| ATOM | 955 | N   | ALA | A | 241 | 27.333 | 6.938  | 34.245 | 1.00 | 72.15 | A | N |
| ATOM | 956 | CA  | ALA | A | 241 | 27.175 | 5.526  | 34.568 | 1.00 | 70.75 | A | C |
| ATOM | 957 | CB  | ALA | A | 241 | 28.177 | 5.122  | 35.641 | 1.00 | 67.24 | A | C |
| ATOM | 958 | C   | ALA | A | 241 | 25.761 | 5.172  | 35.018 | 1.00 | 72.13 | A | C |
| ATOM | 959 | O   | ALA | A | 241 | 25.379 | 4.003  | 35.002 | 1.00 | 73.99 | A | O |
| ATOM | 960 | N   | ASN | A | 242 | 24.985 | 6.174  | 35.421 | 1.00 | 72.05 | A | N |
| ATOM | 961 | CA  | ASN | A | 242 | 23.620 | 5.923  | 35.864 | 1.00 | 70.46 | A | C |
| ATOM | 962 | CB  | ASN | A | 242 | 23.271 | 6.817  | 37.055 | 1.00 | 73.99 | A | C |
| ATOM | 963 | CG  | ASN | A | 242 | 21.859 | 6.590  | 37.554 | 1.00 | 79.17 | A | C |
| ATOM | 964 | OD1 | ASN | A | 242 | 21.334 | 5.478  | 37.486 | 1.00 | 83.57 | A | O |
| ATOM | 965 | ND2 | ASN | A | 242 | 21.239 | 7.644  | 38.072 | 1.00 | 80.38 | A | N |
| ATOM | 966 | C   | ASN | A | 242 | 22.609 | 6.119  | 34.740 | 1.00 | 67.08 | A | C |
| ATOM | 967 | O   | ASN | A | 242 | 21.574 | 5.453  | 34.705 | 1.00 | 63.26 | A | O |
| ATOM | 968 | N   | ALA | A | 243 | 22.904 | 7.037  | 33.825 | 1.00 | 64.69 | A | N |
| ATOM | 969 | CA  | ALA | A | 243 | 22.020 | 7.275  | 32.691 | 1.00 | 65.11 | A | C |
| ATOM | 970 | CB  | ALA | A | 243 | 22.338 | 8.609  | 32.042 | 1.00 | 60.99 | A | C |
| ATOM | 971 | C   | ALA | A | 243 | 22.339 | 6.142  | 31.735 | 1.00 | 69.67 | A | C |
| ATOM | 972 | O   | ALA | A | 243 | 21.557 | 5.800  | 30.848 | 1.00 | 71.13 | A | O |
| ATOM | 973 | N   | LEU | A | 244 | 23.516 | 5.567  | 31.949 | 1.00 | 73.41 | A | N |
| ATOM | 974 | CA  | LEU | A | 244 | 24.027 | 4.466  | 31.152 | 1.00 | 74.63 | A | C |
| ATOM | 975 | CB  | LEU | A | 244 | 25.539 | 4.365  | 31.359 | 1.00 | 73.56 | A | C |
| ATOM | 976 | CG  | LEU | A | 244 | 26.467 | 4.485  | 30.147 | 1.00 | 70.75 | A | C |
| ATOM | 977 | CD1 | LEU | A | 244 | 25.703 | 4.959  | 28.920 | 1.00 | 71.94 | A | C |
| ATOM | 978 | CD2 | LEU | A | 244 | 27.593 | 5.453  | 30.490 | 1.00 | 66.59 | A | C |
| ATOM | 979 | C   | LEU | A | 244 | 23.343 | 3.177  | 31.585 | 1.00 | 74.67 | A | C |
| ATOM | 980 | O   | LEU | A | 244 | 22.914 | 2.379  | 30.752 | 1.00 | 76.93 | A | O |
| ATOM | 981 | N   | SER | A | 245 | 23.250 | 2.982  | 32.896 | 1.00 | 73.64 | A | N |
| ATOM | 982 | CA  | SER | A | 245 | 22.605 | 1.802  | 33.449 | 1.00 | 75.44 | A | C |
| ATOM | 983 | CB  | SER | A | 245 | 22.765 | 1.773  | 34.969 | 1.00 | 75.61 | A | C |
| ATOM | 984 | OG  | SER | A | 245 | 22.575 | 0.463  | 35.474 | 1.00 | 79.33 | A | O |
| ATOM | 985 | C   | SER | A | 245 | 21.131 | 1.878  | 33.083 | 1.00 | 76.58 | A | C |
| ATOM | 986 | O   | SER | A | 245 | 20.578 | 0.948  | 32.494 | 1.00 | 76.07 | A | O |
| ATOM | 987 | N   | TYR | A | 246 | 20.502 | 2.996  | 33.439 | 1.00 | 76.96 | A | N |
| ATOM | 988 | CA  | TYR | A | 246 | 19.096 | 3.211  | 33.127 | 1.00 | 78.83 | A | C |
| ATOM | 989 | CB  | TYR | A | 246 | 18.680 | 4.642  | 33.473 | 1.00 | 75.97 | A | C |
| ATOM | 990 | CG  | TYR | A | 246 | 17.390 | 5.068  | 32.809 | 1.00 | 79.29 | A | C |
| ATOM | 991 | CD1 | TYR | A | 246 | 16.154 | 4.647  | 33.299 | 1.00 | 79.17 | A | C |
| ATOM | 992 | CE1 | TYR | A | 246 | 14.966 | 4.997  | 32.656 | 1.00 | 81.13 | A | C |
| ATOM | 993 | CD2 | TYR | A | 246 | 17.409 | 5.854  | 31.660 | 1.00 | 81.72 | A | C |
| ATOM | 994 | CE2 | TYR | A | 246 | 16.231 | 6.209  | 31.011 | 1.00 | 80.64 | A | C |
| ATOM | 995 | CZ  | TYR | A | 246 | 15.015 | 5.778  | 31.511 | 1.00 | 80.96 | A | C |
| ATOM | 996 | OH  | TYR | A | 246 | 13.856 | 6.120  | 30.853 | 1.00 | 76.16 | A | O |
| ATOM | 997 | C   | TYR | A | 246 | 18.922 | 2.971  | 31.635 | 1.00 | 81.66 | A | C |
| ATOM | 998 | O   | TYR | A | 246 | 17.874 | 2.509  | 31.186 | 1.00 | 82.82 | A | O |

Figure 1Q

```
ATOM    999  N   CYS A 247      19.959   3.299  30.871  1.00  84.18      A    N
ATOM   1000  CA  CYS A 247      19.934   3.096  29.430  1.00  86.69      A    C
ATOM   1001  CB  CYS A 247      21.069   3.866  28.752  1.00  85.41      A    C
ATOM   1002  SG  CYS A 247      20.539   5.359  27.886  1.00  89.36      A    S
ATOM   1003  C   CYS A 247      20.081   1.610  29.139  1.00  87.79      A    C
ATOM   1004  O   CYS A 247      19.401   1.070  28.268  1.00  85.88      A    O
ATOM   1005  N   HIS A 248      20.974   0.956  29.877  1.00  91.06      A    N
ATOM   1006  CA  HIS A 248      21.208  -0.472  29.706  1.00  93.69      A    C
ATOM   1007  CB  HIS A 248      22.320  -0.964  30.643  1.00  95.80      A    C
ATOM   1008  CG  HIS A 248      23.705  -0.612  30.192  1.00  96.43      A    C
ATOM   1009  CD2 HIS A 248      24.886  -0.625  30.854  1.00  94.27      A    C
ATOM   1010  ND1 HIS A 248      23.996  -0.244  28.896  1.00  95.60      A    N
ATOM   1011  CE1 HIS A 248      25.297  -0.046  28.779  1.00  93.15      A    C
ATOM   1012  NE2 HIS A 248      25.861  -0.271  29.952  1.00  92.81      A    N
ATOM   1013  C   HIS A 248      19.942  -1.281  29.972  1.00  93.26      A    C
ATOM   1014  O   HIS A 248      19.685  -2.276  29.295  1.00  93.78      A    O
ATOM   1015  N   SER A 249      19.155  -0.854  30.957  1.00  91.12      A    N
ATOM   1016  CA  SER A 249      17.924  -1.555  31.312  1.00  88.77      A    C
ATOM   1017  CB  SER A 249      17.309  -0.957  32.578  1.00  85.88      A    C
ATOM   1018  OG  SER A 249      16.590   0.229  32.290  1.00  82.36      A    O
ATOM   1019  C   SER A 249      16.898  -1.492  30.191  1.00  88.21      A    C
ATOM   1020  O   SER A 249      16.431  -2.521  29.703  1.00  90.86      A    O
ATOM   1021  N   LYS A 250      16.543  -0.276  29.789  1.00  86.52      A    N
ATOM   1022  CA  LYS A 250      15.567  -0.084  28.726  1.00  86.28      A    C
ATOM   1023  CB  LYS A 250      15.301   1.409  28.521  1.00  86.17      A    C
ATOM   1028  C   LYS A 250      16.040  -0.707  27.415  1.00  86.56      A    C
ATOM   1029  O   LYS A 250      15.423  -0.510  26.368  1.00  84.67      A    O
ATOM   1030  N   ARG A 251      17.135  -1.459  27.480  1.00  88.16      A    N
ATOM   1031  CA  ARG A 251      17.698  -2.118  26.305  1.00  89.43      A    C
ATOM   1032  CB  ARG A 251      16.636  -2.986  25.620  1.00  90.20      A    C
ATOM   1039  C   ARG A 251      18.251  -1.109  25.307  1.00  89.95      A    C
ATOM   1040  O   ARG A 251      18.017  -1.220  24.104  1.00  90.39      A    O
ATOM   1041  N   VAL A 252      18.991  -0.126  25.810  1.00  90.42      A    N
ATOM   1042  CA  VAL A 252      19.574   0.899  24.954  1.00  91.68      A    C
ATOM   1043  CB  VAL A 252      18.933   2.283  25.210  1.00  88.89      A    C
ATOM   1044  CG1 VAL A 252      19.637   3.345  24.372  1.00  88.48      A    C
ATOM   1045  CG2 VAL A 252      17.452   2.244  24.869  1.00  86.55      A    C
ATOM   1046  C   VAL A 252      21.078   1.036  25.145  1.00  95.55      A    C
ATOM   1047  O   VAL A 252      21.540   1.589  26.143  1.00  97.78      A    O
ATOM   1048  N   ILE A 253      21.839   0.527  24.181  1.00  97.48      A    N
ATOM   1049  CA  ILE A 253      23.292   0.620  24.226  1.00  96.69      A    C
ATOM   1050  CB  ILE A 253      23.974  -0.616  23.587  1.00  95.60      A    C
ATOM   1051  CG2 ILE A 253      25.486  -0.449  23.627  1.00  96.66      A    C
ATOM   1052  CG1 ILE A 253      23.570  -1.896  24.328  1.00  92.70      A    C
ATOM   1053  CD1 ILE A 253      22.235  -2.475  23.897  1.00  90.25      A    C
ATOM   1054  C   ILE A 253      23.674   1.861  23.421  1.00  97.77      A    C
ATOM   1055  O   ILE A 253      23.788   1.801  22.197  1.00  98.28      A    O
ATOM   1056  N   HIS A 254      23.857   2.983  24.112  1.00  97.86      A    N
ATOM   1057  CA  HIS A 254      24.210   4.241  23.459  1.00  97.97      A    C
ATOM   1058  CB  HIS A 254      23.833   5.421  24.358  1.00  99.21      A    C
ATOM   1059  CG  HIS A 254      22.892   6.392  23.715  1.00 105.22      A    C
ATOM   1060  CD2 HIS A 254      21.629   6.755  24.041  1.00 107.77      A    C
ATOM   1061  ND1 HIS A 254      23.224   7.116  22.592  1.00 108.31      A    N
ATOM   1062  CE1 HIS A 254      22.204   7.886  22.252  1.00 110.97      A    C
ATOM   1063  NE2 HIS A 254      21.225   7.686  23.114  1.00 111.77      A    N
ATOM   1064  C   HIS A 254      25.693   4.315  23.114  1.00  96.74      A    C
ATOM   1065  O   HIS A 254      26.154   3.641  22.191  1.00  95.57      A    O
ATOM   1066  N   ARG A 255      26.422   5.149  23.854  1.00  94.48      A    N
ATOM   1067  CA  ARG A 255      27.862   5.346  23.682  1.00  94.14      A    C
ATOM   1068  CB  ARG A 255      28.522   4.112  23.052  1.00  91.58      A    C
ATOM   1075  C   ARG A 255      28.253   6.587  22.885  1.00  95.07      A    C
```

Figure 1R

```
ATOM   1076  O    ARG A 255      27.500   7.561  22.814  1.00  91.67      A    O
ATOM   1077  N    ASP A 256      29.437   6.521  22.277  1.00  97.41      A    N
ATOM   1078  CA   ASP A 256      30.020   7.626  21.522  1.00  94.96      A    C
ATOM   1079  CB   ASP A 256      29.500   7.707  20.087  1.00  97.08      A    C
ATOM   1080  CG   ASP A 256      30.518   8.346  19.143  1.00  98.93      A    C
ATOM   1081  OD1  ASP A 256      31.440   9.039  19.629  1.00  95.83      A    O
ATOM   1082  OD2  ASP A 256      30.399   8.156  17.915  1.00 101.47      A    O
ATOM   1083  C    ASP A 256      29.718   8.911  22.262  1.00  92.06      A    C
ATOM   1084  O    ASP A 256      29.588   9.987  21.675  1.00  88.97      A    O
ATOM   1085  N    ILE A 257      29.564   8.756  23.571  1.00  89.62      A    N
ATOM   1086  CA   ILE A 257      29.340   9.865  24.467  1.00  85.97      A    C
ATOM   1087  CB   ILE A 257      28.961   9.383  25.880  1.00  81.37      A    C
ATOM   1088  CG2  ILE A 257      27.495   8.971  25.926  1.00  81.99      A    C
ATOM   1089  CG1  ILE A 257      29.873   8.214  26.271  1.00  77.22      A    C
ATOM   1090  CD1  ILE A 257      30.242   8.157  27.734  1.00  73.68      A    C
ATOM   1091  C    ILE A 257      30.768  10.371  24.508  1.00  87.10      A    C
ATOM   1092  O    ILE A 257      31.689   9.632  24.161  1.00  91.22      A    O
ATOM   1093  N    LYS A 258      30.954  11.615  24.919  1.00  83.96      A    N
ATOM   1094  CA   LYS A 258      32.279  12.208  25.015  1.00  78.70      A    C
ATOM   1095  CB   LYS A 258      33.169  11.812  23.818  1.00  73.98      A    C
ATOM   1096  CG   LYS A 258      32.542  11.903  22.430  1.00  72.21      A    C
ATOM   1097  CD   LYS A 258      33.399  11.130  21.423  1.00  72.30      A    C
ATOM   1098  CE   LYS A 258      33.288  11.680  20.007  1.00  69.20      A    C
ATOM   1099  NZ   LYS A 258      34.457  11.286  19.164  1.00  70.94      A    N
ATOM   1100  C    LYS A 258      32.119  13.711  25.095  1.00  77.42      A    C
ATOM   1101  O    LYS A 258      31.096  14.253  24.680  1.00  75.43      A    O
ATOM   1102  N    PRO A 259      33.127  14.406  25.642  1.00  77.43      A    N
ATOM   1103  CD   PRO A 259      34.496  13.904  25.867  1.00  77.13      A    C
ATOM   1104  CA   PRO A 259      33.086  15.861  25.780  1.00  77.33      A    C
ATOM   1105  CB   PRO A 259      34.551  16.244  25.631  1.00  77.11      A    C
ATOM   1106  CG   PRO A 259      35.225  15.137  26.373  1.00  77.96      A    C
ATOM   1107  C    PRO A 259      32.181  16.552  24.762  1.00  76.08      A    C
ATOM   1108  O    PRO A 259      31.202  17.201  25.128  1.00  77.45      A    O
ATOM   1109  N    GLU A 260      32.500  16.376  23.485  1.00  74.03      A    N
ATOM   1110  CA   GLU A 260      31.749  16.992  22.396  1.00  73.63      A    C
ATOM   1111  CB   GLU A 260      32.343  16.561  21.050  1.00  76.31      A    C
ATOM   1112  CG   GLU A 260      33.860  16.651  20.984  1.00  80.27      A    C
ATOM   1113  CD   GLU A 260      34.533  15.298  21.126  1.00  82.34      A    C
ATOM   1114  OE1  GLU A 260      35.646  15.240  21.688  1.00  81.73      A    O
ATOM   1115  OE2  GLU A 260      33.955  14.293  20.663  1.00  85.70      A    O
ATOM   1116  C    GLU A 260      30.241  16.733  22.376  1.00  71.66      A    C
ATOM   1117  O    GLU A 260      29.480  17.571  21.897  1.00  73.66      A    O
ATOM   1118  N    ASN A 261      29.802  15.587  22.889  1.00  67.69      A    N
ATOM   1119  CA   ASN A 261      28.376  15.261  22.872  1.00  65.95      A    C
ATOM   1120  CB   ASN A 261      28.164  13.921  22.159  1.00  67.65      A    C
ATOM   1121  CG   ASN A 261      28.806  13.885  20.783  1.00  70.09      A    C
ATOM   1122  OD1  ASN A 261      28.497  14.706  19.919  1.00  72.78      A    O
ATOM   1123  ND2  ASN A 261      29.707  12.931  20.575  1.00  70.72      A    N
ATOM   1124  C    ASN A 261      27.702  15.227  24.244  1.00  64.57      A    C
ATOM   1125  O    ASN A 261      26.623  14.654  24.399  1.00  64.11      A    O
ATOM   1126  N    LEU A 262      28.332  15.845  25.236  1.00  63.53      A    N
ATOM   1127  CA   LEU A 262      27.771  15.875  26.582  1.00  64.28      A    C
ATOM   1128  CB   LEU A 262      28.715  15.170  27.556  1.00  62.90      A    C
ATOM   1129  CG   LEU A 262      28.917  13.670  27.318  1.00  59.58      A    C
ATOM   1130  CD1  LEU A 262      30.129  13.197  28.097  1.00  55.63      A    C
ATOM   1131  CD2  LEU A 262      27.671  12.897  27.730  1.00  57.08      A    C
ATOM   1132  C    LEU A 262      27.513  17.311  27.038  1.00  64.94      A    C
ATOM   1133  O    LEU A 262      28.437  18.118  27.142  1.00  65.55      A    O
ATOM   1134  N    LEU A 263      26.250  17.622  27.310  1.00  63.24      A    N
ATOM   1135  CA   LEU A 263      25.871  18.962  27.737  1.00  62.23      A    C
ATOM   1136  CB   LEU A 263      24.546  19.358  27.079  1.00  63.99      A    C
```

Figure 1S

| ATOM | 1137 | CG  | LEU | A | 263 | 24.519 | 19.344 | 25.546 | 1.00 | 62.68 | A | C |
|------|------|-----|-----|---|-----|--------|--------|--------|------|-------|---|---|
| ATOM | 1138 | CD1 | LEU | A | 263 | 23.095 | 19.572 | 25.066 | 1.00 | 63.40 | A | C |
| ATOM | 1139 | CD2 | LEU | A | 263 | 25.454 | 20.415 | 24.992 | 1.00 | 59.47 | A | C |
| ATOM | 1140 | C   | LEU | A | 263 | 25.755 | 19.088 | 29.252 | 1.00 | 61.46 | A | C |
| ATOM | 1141 | O   | LEU | A | 263 | 25.645 | 18.092 | 29.965 | 1.00 | 60.18 | A | O |
| ATOM | 1142 | N   | LEU | A | 264 | 25.782 | 20.326 | 29.734 | 1.00 | 62.60 | A | N |
| ATOM | 1143 | CA  | LEU | A | 264 | 25.683 | 20.599 | 31.162 | 1.00 | 66.05 | A | C |
| ATOM | 1144 | CB  | LEU | A | 264 | 26.950 | 21.311 | 31.643 | 1.00 | 62.69 | A | C |
| ATOM | 1145 | CG  | LEU | A | 264 | 28.259 | 20.571 | 31.349 | 1.00 | 62.68 | A | C |
| ATOM | 1146 | CD1 | LEU | A | 264 | 29.441 | 21.501 | 31.555 | 1.00 | 61.04 | A | C |
| ATOM | 1147 | CD2 | LEU | A | 264 | 28.368 | 19.345 | 32.241 | 1.00 | 63.10 | A | C |
| ATOM | 1148 | C   | LEU | A | 264 | 24.459 | 21.464 | 31.446 | 1.00 | 71.25 | A | C |
| ATOM | 1149 | O   | LEU | A | 264 | 24.304 | 22.544 | 30.875 | 1.00 | 72.79 | A | O |
| ATOM | 1150 | N   | GLY | A | 265 | 23.592 | 20.981 | 32.330 | 1.00 | 74.49 | A | N |
| ATOM | 1151 | CA  | GLY | A | 265 | 22.386 | 21.716 | 32.668 | 1.00 | 77.02 | A | C |
| ATOM | 1152 | C   | GLY | A | 265 | 22.623 | 22.958 | 33.509 | 1.00 | 80.14 | A | C |
| ATOM | 1153 | O   | GLY | A | 265 | 23.671 | 23.597 | 33.411 | 1.00 | 79.51 | A | O |
| ATOM | 1154 | N   | SER | A | 266 | 21.641 | 23.297 | 34.339 | 1.00 | 82.00 | A | N |
| ATOM | 1155 | CA  | SER | A | 266 | 21.729 | 24.471 | 35.201 | 1.00 | 84.92 | A | C |
| ATOM | 1156 | CB  | SER | A | 266 | 20.334 | 24.871 | 35.689 | 1.00 | 84.90 | A | C |
| ATOM | 1157 | OG  | SER | A | 266 | 19.472 | 25.160 | 34.601 | 1.00 | 90.15 | A | O |
| ATOM | 1158 | C   | SER | A | 266 | 22.638 | 24.228 | 36.401 | 1.00 | 87.00 | A | C |
| ATOM | 1159 | O   | SER | A | 266 | 23.466 | 25.072 | 36.742 | 1.00 | 90.66 | A | O |
| ATOM | 1160 | N   | ALA | A | 267 | 22.482 | 23.074 | 37.040 | 1.00 | 86.96 | A | N |
| ATOM | 1161 | CA  | ALA | A | 267 | 23.293 | 22.736 | 38.204 | 1.00 | 87.35 | A | C |
| ATOM | 1162 | CB  | ALA | A | 267 | 22.523 | 21.792 | 39.115 | 1.00 | 88.52 | A | C |
| ATOM | 1163 | C   | ALA | A | 267 | 24.612 | 22.095 | 37.792 | 1.00 | 87.15 | A | C |
| ATOM | 1164 | O   | ALA | A | 267 | 25.231 | 21.376 | 38.573 | 1.00 | 87.84 | A | O |
| ATOM | 1165 | N   | GLY | A | 268 | 25.047 | 22.360 | 36.566 | 1.00 | 85.80 | A | N |
| ATOM | 1166 | CA  | GLY | A | 268 | 26.287 | 21.769 | 36.101 | 1.00 | 83.82 | A | C |
| ATOM | 1167 | C   | GLY | A | 268 | 26.122 | 20.267 | 35.969 | 1.00 | 82.41 | A | C |
| ATOM | 1168 | O   | GLY | A | 268 | 27.097 | 19.533 | 35.810 | 1.00 | 82.61 | A | O |
| ATOM | 1169 | N   | GLU | A | 269 | 24.875 | 19.810 | 36.045 | 1.00 | 80.23 | A | N |
| ATOM | 1170 | CA  | GLU | A | 269 | 24.567 | 18.390 | 35.923 | 1.00 | 81.12 | A | C |
| ATOM | 1171 | CB  | GLU | A | 269 | 23.108 | 18.123 | 36.315 | 1.00 | 84.16 | A | C |
| ATOM | 1172 | CG  | GLU | A | 269 | 22.304 | 19.373 | 36.648 | 1.00 | 88.34 | A | C |
| ATOM | 1173 | CD  | GLU | A | 269 | 21.110 | 19.568 | 35.731 | 1.00 | 89.21 | A | C |
| ATOM | 1174 | OE1 | GLU | A | 269 | 20.270 | 18.649 | 35.639 | 1.00 | 91.10 | A | O |
| ATOM | 1175 | OE2 | GLU | A | 269 | 21.008 | 20.645 | 35.106 | 1.00 | 85.80 | A | O |
| ATOM | 1176 | C   | GLU | A | 269 | 24.807 | 17.936 | 34.489 | 1.00 | 81.41 | A | C |
| ATOM | 1177 | O   | GLU | A | 269 | 24.502 | 18.662 | 33.544 | 1.00 | 81.45 | A | O |
| ATOM | 1178 | N   | LEU | A | 270 | 25.363 | 16.739 | 34.329 | 1.00 | 82.53 | A | N |
| ATOM | 1179 | CA  | LEU | A | 270 | 25.636 | 16.204 | 33.002 | 1.00 | 85.63 | A | C |
| ATOM | 1180 | CB  | LEU | A | 270 | 26.484 | 14.932 | 33.097 | 1.00 | 87.10 | A | C |
| ATOM | 1181 | CG  | LEU | A | 270 | 27.981 | 15.088 | 32.820 | 1.00 | 86.77 | A | C |
| ATOM | 1182 | CD1 | LEU | A | 270 | 28.715 | 13.802 | 33.169 | 1.00 | 86.80 | A | C |
| ATOM | 1183 | CD2 | LEU | A | 270 | 28.181 | 15.433 | 31.353 | 1.00 | 86.46 | A | C |
| ATOM | 1184 | C   | LEU | A | 270 | 24.355 | 15.898 | 32.244 | 1.00 | 86.17 | A | C |
| ATOM | 1185 | O   | LEU | A | 270 | 23.266 | 15.881 | 32.814 | 1.00 | 89.09 | A | O |
| ATOM | 1186 | N   | LYS | A | 271 | 24.506 | 15.663 | 30.947 | 1.00 | 84.70 | A | N |
| ATOM | 1187 | CA  | LYS | A | 271 | 23.392 | 15.341 | 30.067 | 1.00 | 85.02 | A | C |
| ATOM | 1188 | CB  | LYS | A | 271 | 22.634 | 16.605 | 29.646 | 1.00 | 80.67 | A | C |
| ATOM | 1189 | CG  | LYS | A | 271 | 21.963 | 17.402 | 30.755 | 1.00 | 78.60 | A | C |
| ATOM | 1190 | CD  | LYS | A | 271 | 20.652 | 16.785 | 31.212 | 1.00 | 78.50 | A | C |
| ATOM | 1191 | CE  | LYS | A | 271 | 19.659 | 17.870 | 31.620 | 1.00 | 78.81 | A | C |
| ATOM | 1192 | NZ  | LYS | A | 271 | 19.404 | 17.896 | 33.089 | 1.00 | 85.61 | A | N |
| ATOM | 1193 | C   | LYS | A | 271 | 24.014 | 14.727 | 28.822 | 1.00 | 89.00 | A | C |
| ATOM | 1194 | O   | LYS | A | 271 | 25.011 | 15.242 | 28.315 | 1.00 | 89.64 | A | O |
| ATOM | 1195 | N   | ILE | A | 272 | 23.446 | 13.628 | 28.335 | 1.00 | 94.42 | A | N |
| ATOM | 1196 | CA  | ILE | A | 272 | 23.964 | 13.009 | 27.120 | 1.00 | 98.28 | A | C |
| ATOM | 1197 | CB  | ILE | A | 272 | 24.049 | 11.454 | 27.220 | 1.00 | 96.97 | A | C |

Figure 1T

```
ATOM   1198  CG2 ILE A 272      24.325  11.037  28.657  1.00  96.63      A    C
ATOM   1199  CG1 ILE A 272      22.753  10.809  26.724  1.00  94.52      A    C
ATOM   1200  CD1 ILE A 272      22.980   9.676  25.736  1.00  90.80      A    C
ATOM   1201  C   ILE A 272      23.012  13.390  25.991  1.00  99.75      A    C
ATOM   1202  O   ILE A 272      21.837  13.675  26.228  1.00  98.91      A    O
ATOM   1203  N   ALA A 273      23.527  13.409  24.768  1.00 100.92      A    N
ATOM   1204  CA  ALA A 273      22.720  13.759  23.607  1.00 101.66      A    C
ATOM   1205  CB  ALA A 273      22.537  15.265  23.542  1.00 100.28      A    C
ATOM   1206  C   ALA A 273      23.399  13.250  22.342  1.00 103.46      A    C
ATOM   1207  O   ALA A 273      24.553  13.583  22.072  1.00 103.70      A    O
ATOM   1208  N   ASP A 274      22.675  12.454  21.560  1.00 104.59      A    N
ATOM   1209  CA  ASP A 274      23.232  11.880  20.341  1.00 103.89      A    C
ATOM   1210  CB  ASP A 274      23.296  10.358  20.480  1.00  97.97      A    C
ATOM   1211  CG  ASP A 274      24.596   9.886  21.093  1.00  95.56      A    C
ATOM   1212  OD1 ASP A 274      25.621   9.898  20.379  1.00  95.42      A    O
ATOM   1213  OD2 ASP A 274      24.598   9.508  22.283  1.00  93.78      A    O
ATOM   1214  C   ASP A 274      22.557  12.232  19.016  1.00 106.91      A    C
ATOM   1215  O   ASP A 274      22.713  13.339  18.501  1.00 108.26      A    O
ATOM   1216  N   PHE A 275      21.800  11.273  18.484  1.00 108.56      A    N
ATOM   1217  CA  PHE A 275      21.117  11.401  17.198  1.00 108.63      A    C
ATOM   1218  CB  PHE A 275      19.749  12.104  17.338  1.00 108.66      A    C
ATOM   1219  CG  PHE A 275      19.718  13.212  18.348  1.00 111.57      A    C
ATOM   1220  CD1 PHE A 275      19.592  12.937  19.707  1.00 112.94      A    C
ATOM   1221  CD2 PHE A 275      19.814  14.534  17.938  1.00 111.92      A    C
ATOM   1222  CE1 PHE A 275      19.569  13.967  20.640  1.00 112.27      A    C
ATOM   1223  CE2 PHE A 275      19.792  15.566  18.863  1.00 112.32      A    C
ATOM   1224  CZ  PHE A 275      19.668  15.280  20.216  1.00 112.23      A    C
ATOM   1225  C   PHE A 275      21.995  12.082  16.145  1.00 107.62      A    C
ATOM   1226  O   PHE A 275      21.513  12.791  15.260  1.00 106.19      A    O
ATOM   1227  N   GLY A 276      23.298  11.826  16.269  1.00 107.26      A    N
ATOM   1228  CA  GLY A 276      24.313  12.343  15.361  1.00 105.49      A    C
ATOM   1229  C   GLY A 276      24.299  13.802  14.948  1.00 106.32      A    C
ATOM   1230  O   GLY A 276      23.305  14.294  14.413  1.00 103.73      A    O
ATOM   1231  N   TRP A 277      25.411  14.498  15.185  1.00 109.28      A    N
ATOM   1232  CA  TRP A 277      25.510  15.901  14.801  1.00 113.03      A    C
ATOM   1233  CB  TRP A 277      24.597  16.764  15.687  1.00 116.38      A    C
ATOM   1234  CG  TRP A 277      25.106  17.152  17.047  1.00 119.83      A    C
ATOM   1235  CD2 TRP A 277      24.380  17.069  18.279  1.00 120.48      A    C
ATOM   1236  CE2 TRP A 277      25.176  17.672  19.278  1.00 120.99      A    C
ATOM   1237  CE3 TRP A 277      23.128  16.553  18.634  1.00 119.93      A    C
ATOM   1238  CD1 TRP A 277      26.286  17.773  17.341  1.00 120.79      A    C
ATOM   1239  NE1 TRP A 277      26.335  18.092  18.681  1.00 119.88      A    N
ATOM   1240  CZ2 TRP A 277      24.761  17.767  20.609  1.00 122.14      A    C
ATOM   1241  CZ3 TRP A 277      22.716  16.648  19.955  1.00 121.05      A    C
ATOM   1242  CH2 TRP A 277      23.530  17.253  20.926  1.00 123.58      A    C
ATOM   1243  C   TRP A 277      26.919  16.495  14.761  1.00 113.86      A    C
ATOM   1244  O   TRP A 277      27.898  15.860  15.158  1.00 112.61      A    O
ATOM   1245  N   SER A 278      26.993  17.729  14.268  1.00 114.18      A    N
ATOM   1246  CA  SER A 278      28.243  18.469  14.134  1.00 111.58      A    C
ATOM   1247  CB  SER A 278      28.062  19.590  13.105  1.00 108.42      A    C
ATOM   1248  OG  SER A 278      29.254  20.333  12.917  1.00 102.59      A    O
ATOM   1249  C   SER A 278      28.682  19.056  15.473  1.00 111.28      A    C
ATOM   1250  O   SER A 278      29.069  20.222  15.557  1.00 109.28      A    O
ATOM   1251  N   CYS A 290      42.402  12.691  15.198  1.00 109.15      A    N
ATOM   1252  CA  CYS A 290      41.980  11.295  15.190  1.00 109.38      A    C
ATOM   1253  CB  CYS A 290      43.138  10.393  15.619  1.00 112.00      A    C
ATOM   1254  SG  CYS A 290      44.588  10.476  14.546  1.00 116.21      A    S
ATOM   1255  C   CYS A 290      40.807  11.096  16.141  1.00 107.53      A    C
ATOM   1256  O   CYS A 290      40.578   9.993  16.637  1.00 107.57      A    O
ATOM   1257  N   GLY A 291      40.067  12.174  16.384  1.00 105.63      A    N
ATOM   1258  CA  GLY A 291      38.930  12.122  17.287  1.00 103.04      A    C
```

Figure 1U

```
ATOM   1259  C   GLY A 291      37.801  11.188  16.893  1.00  99.11      A    C
ATOM   1260  O   GLY A 291      36.746  11.190  17.529  1.00  99.15      A    O
ATOM   1261  N   THR A 292      38.009  10.392  15.848  1.00  95.20      A    N
ATOM   1262  CA  THR A 292      36.992   9.450  15.391  1.00  89.55      A    C
ATOM   1263  CB  THR A 292      37.013   9.291  13.855  1.00  87.32      A    C
ATOM   1264  OG1 THR A 292      38.240   8.668  13.456  1.00  87.47      A    O
ATOM   1265  CG2 THR A 292      36.892  10.648  13.173  1.00  84.15      A    C
ATOM   1266  C   THR A 292      37.218   8.075  16.020  1.00  86.28      A    C
ATOM   1267  O   THR A 292      36.278   7.445  16.502  1.00  86.04      A    O
ATOM   1268  N   LEU A 293      38.466   7.615  16.013  1.00  80.57      A    N
ATOM   1269  CA  LEU A 293      38.811   6.314  16.587  1.00  72.64      A    C
ATOM   1270  CB  LEU A 293      40.112   5.777  15.977  1.00  70.14      A    C
ATOM   1271  CG  LEU A 293      40.152   5.118  14.599  1.00  72.57      A    C
ATOM   1272  CD1 LEU A 293      41.548   4.554  14.355  1.00  69.12      A    C
ATOM   1273  CD2 LEU A 293      39.122   4.009  14.537  1.00  73.26      A    C
ATOM   1274  C   LEU A 293      38.997   6.370  18.102  1.00  70.44      A    C
ATOM   1275  O   LEU A 293      38.763   5.387  18.802  1.00  70.20      A    O
ATOM   1276  N   ASP A 294      39.419   7.530  18.593  1.00  70.63      A    N
ATOM   1277  CA  ASP A 294      39.703   7.749  20.010  1.00  68.26      A    C
ATOM   1278  CB  ASP A 294      39.928   9.241  20.268  1.00  65.94      A    C
ATOM   1279  CG  ASP A 294      41.374   9.648  20.079  1.00  66.75      A    C
ATOM   1280  OD1 ASP A 294      41.778   9.924  18.930  1.00  66.44      A    O
ATOM   1281  OD2 ASP A 294      42.110   9.675  21.087  1.00  70.87      A    O
ATOM   1282  C   ASP A 294      38.797   7.199  21.112  1.00  66.91      A    C
ATOM   1283  O   ASP A 294      39.234   7.104  22.257  1.00  62.67      A    O
ATOM   1284  N   TYR A 295      37.553   6.847  20.809  1.00  69.98      A    N
ATOM   1285  CA  TYR A 295      36.680   6.318  21.855  1.00  72.30      A    C
ATOM   1286  CB  TYR A 295      35.536   7.296  22.146  1.00  73.70      A    C
ATOM   1287  CG  TYR A 295      35.936   8.450  23.044  1.00  73.37      A    C
ATOM   1288  CD1 TYR A 295      36.924   9.354  22.654  1.00  75.69      A    C
ATOM   1289  CE1 TYR A 295      37.302  10.411  23.483  1.00  75.51      A    C
ATOM   1290  CD2 TYR A 295      35.334   8.630  24.291  1.00  69.24      A    C
ATOM   1291  CE2 TYR A 295      35.705   9.683  25.127  1.00  70.87      A    C
ATOM   1292  CZ  TYR A 295      36.688  10.568  24.717  1.00  74.03      A    C
ATOM   1293  OH  TYR A 295      37.052  11.609  25.537  1.00  77.13      A    O
ATOM   1294  C   TYR A 295      36.121   4.938  21.542  1.00  71.27      A    C
ATOM   1295  O   TYR A 295      35.519   4.290  22.401  1.00  70.55      A    O
ATOM   1296  N   LEU A 296      36.330   4.489  20.310  1.00  66.62      A    N
ATOM   1297  CA  LEU A 296      35.858   3.179  19.890  1.00  62.00      A    C
ATOM   1298  CB  LEU A 296      36.080   2.995  18.390  1.00  59.67      A    C
ATOM   1299  CG  LEU A 296      35.424   4.017  17.464  1.00  57.94      A    C
ATOM   1300  CD1 LEU A 296      35.794   3.706  16.025  1.00  59.45      A    C
ATOM   1301  CD2 LEU A 296      33.916   3.985  17.651  1.00  58.03      A    C
ATOM   1302  C   LEU A 296      36.620   2.097  20.642  1.00  62.36      A    C
ATOM   1303  O   LEU A 296      37.834   2.193  20.818  1.00  60.84      A    O
ATOM   1304  N   PRO A 297      35.916   1.056  21.109  1.00  62.57      A    N
ATOM   1305  CD  PRO A 297      34.467   0.797  21.025  1.00  62.94      A    C
ATOM   1306  CA  PRO A 297      36.594  -0.019  21.834  1.00  59.56      A    C
ATOM   1307  CB  PRO A 297      35.439  -0.769  22.480  1.00  59.60      A    C
ATOM   1308  CG  PRO A 297      34.374  -0.662  21.432  1.00  58.84      A    C
ATOM   1309  C   PRO A 297      37.355  -0.881  20.834  1.00  59.80      A    C
ATOM   1310  O   PRO A 297      37.229  -0.692  19.624  1.00  60.49      A    O
ATOM   1311  N   PRO A 298      38.163  -1.833  21.322  1.00  60.93      A    N
ATOM   1312  CD  PRO A 298      38.693  -1.987  22.689  1.00  61.40      A    C
ATOM   1313  CA  PRO A 298      38.904  -2.677  20.383  1.00  60.77      A    C
ATOM   1314  CB  PRO A 298      39.782  -3.522  21.302  1.00  58.81      A    C
ATOM   1315  CG  PRO A 298      40.061  -2.586  22.433  1.00  58.46      A    C
ATOM   1316  C   PRO A 298      38.008  -3.534  19.488  1.00  63.91      A    C
ATOM   1317  O   PRO A 298      38.336  -3.769  18.325  1.00  61.30      A    O
ATOM   1318  N   GLU A 299      36.873  -3.983  20.019  1.00  68.47      A    N
ATOM   1319  CA  GLU A 299      35.975  -4.835  19.245  1.00  72.05      A    C
```

Figure 1V

```
ATOM   1320  CB   GLU A 299      34.887   -5.459   20.138  1.00   75.53      A    C
ATOM   1321  CG   GLU A 299      33.970   -4.502   20.885  1.00   79.40      A    C
ATOM   1322  CD   GLU A 299      34.429   -4.256   22.306  1.00   81.50      A    C
ATOM   1323  OE1  GLU A 299      33.574   -4.247   23.217  1.00   83.14      A    O
ATOM   1324  OE2  GLU A 299      35.646   -4.067   22.511  1.00   81.72      A    O
ATOM   1325  C    GLU A 299      35.324   -4.219   18.008  1.00   72.43      A    C
ATOM   1326  O    GLU A 299      35.037   -4.939   17.053  1.00   72.29      A    O
ATOM   1327  N    MET A 300      35.082   -2.909   17.999  1.00   75.36      A    N
ATOM   1328  CA   MET A 300      34.468   -2.308   16.815  1.00   79.51      A    C
ATOM   1329  CB   MET A 300      33.671   -1.044   17.152  1.00   86.80      A    C
ATOM   1330  CG   MET A 300      32.578   -0.759   16.111  1.00   98.28      A    C
ATOM   1331  SD   MET A 300      32.363    0.967   15.636  1.00  110.98      A    S
ATOM   1332  CE   MET A 300      33.232    0.986   14.045  1.00  106.30      A    C
ATOM   1333  C    MET A 300      35.500   -1.958   15.751  1.00   77.49      A    C
ATOM   1334  O    MET A 300      35.314   -2.271   14.577  1.00   80.56      A    O
ATOM   1335  N    ILE A 301      36.583   -1.300   16.151  1.00   73.12      A    N
ATOM   1336  CA   ILE A 301      37.615   -0.934   15.190  1.00   73.24      A    C
ATOM   1337  CB   ILE A 301      38.836   -0.274   15.870  1.00   73.32      A    C
ATOM   1338  CG2  ILE A 301      38.367    0.738   16.899  1.00   73.00      A    C
ATOM   1339  CG1  ILE A 301      39.714   -1.336   16.536  1.00   74.96      A    C
ATOM   1340  CD1  ILE A 301      41.045   -0.806   17.027  1.00   71.37      A    C
ATOM   1341  C    ILE A 301      38.074   -2.212   14.503  1.00   73.93      A    C
ATOM   1342  O    ILE A 301      38.520   -2.191   13.356  1.00   71.39      A    O
ATOM   1343  N    GLU A 302      37.948   -3.322   15.225  1.00   76.64      A    N
ATOM   1344  CA   GLU A 302      38.341   -4.634   14.729  1.00   77.44      A    C
ATOM   1345  CB   GLU A 302      38.755   -5.527   15.904  1.00   75.82      A    C
ATOM   1346  CG   GLU A 302      40.258   -5.565   16.138  1.00   77.10      A    C
ATOM   1347  CD   GLU A 302      40.630   -6.124   17.495  1.00   77.22      A    C
ATOM   1348  OE1  GLU A 302      40.044   -7.148   17.899  1.00   75.06      A    O
ATOM   1349  OE2  GLU A 302      41.517   -5.542   18.154  1.00   76.89      A    O
ATOM   1350  C    GLU A 302      37.255   -5.320   13.901  1.00   78.88      A    C
ATOM   1351  O    GLU A 302      37.541   -6.254   13.154  1.00   77.29      A    O
ATOM   1352  N    GLY A 303      36.014   -4.858   14.033  1.00   82.09      A    N
ATOM   1353  CA   GLY A 303      34.920   -5.435   13.267  1.00   81.95      A    C
ATOM   1354  C    GLY A 303      34.081   -6.461   14.005  1.00   82.32      A    C
ATOM   1355  O    GLY A 303      32.934   -6.720   13.633  1.00   83.26      A    O
ATOM   1356  N    ARG A 304      34.654   -7.046   15.050  1.00   82.72      A    N
ATOM   1357  CA   ARG A 304      33.971   -8.056   15.853  1.00   82.93      A    C
ATOM   1358  CB   ARG A 304      34.820   -8.398   17.079  1.00   84.98      A    C
ATOM   1359  CG   ARG A 304      36.199   -8.944   16.743  1.00   91.84      A    C
ATOM   1360  CD   ARG A 304      37.177   -8.724   17.885  1.00  100.66      A    C
ATOM   1361  NE   ARG A 304      38.418   -9.470   17.699  1.00  111.07      A    N
ATOM   1362  CZ   ARG A 304      39.408   -9.504   18.585  1.00  114.58      A    C
ATOM   1363  NH1  ARG A 304      40.500  -10.212   18.333  1.00  116.75      A    N
ATOM   1364  NH2  ARG A 304      39.313   -8.820   19.718  1.00  113.67      A    N
ATOM   1365  C    ARG A 304      32.581   -7.611   16.301  1.00   81.93      A    C
ATOM   1366  O    ARG A 304      32.138   -6.506   15.990  1.00   78.99      A    O
ATOM   1367  N    MET A 305      31.901   -8.480   17.044  1.00   82.97      A    N
ATOM   1368  CA   MET A 305      30.558   -8.190   17.530  1.00   85.52      A    C
ATOM   1369  CB   MET A 305      29.726   -9.476   17.560  1.00   86.07      A    C
ATOM   1373  C    MET A 305      30.555   -7.547   18.915  1.00   88.79      A    C
ATOM   1374  O    MET A 305      30.855   -8.195   19.918  1.00   86.40      A    O
ATOM   1375  N    HIS A 306      30.211   -6.264   18.953  1.00   94.28      A    N
ATOM   1376  CA   HIS A 306      30.143   -5.495   20.193  1.00   99.57      A    C
ATOM   1377  CB   HIS A 306      30.321   -4.011   19.887  1.00  103.72      A    C
ATOM   1378  CG   HIS A 306      29.182   -3.428   19.108  1.00  107.47      A    C
ATOM   1379  CD2  HIS A 306      28.265   -2.488   19.436  1.00  108.68      A    C
ATOM   1380  ND1  HIS A 306      28.860   -3.852   17.837  1.00  108.46      A    N
ATOM   1381  CE1  HIS A 306      27.791   -3.198   17.415  1.00  107.45      A    C
ATOM   1382  NE2  HIS A 306      27.411   -2.366   18.366  1.00  108.27      A    N
ATOM   1383  C    HIS A 306      28.753   -5.697   20.784  1.00  101.39      A    C
```

Figure 1W

| ATOM | 1384 | O   | HIS | A | 306 | 27.893 | -6.295 | 20.138 | 1.00 | 103.87 | A | O |
|------|------|-----|-----|---|-----|--------|--------|--------|------|--------|---|---|
| ATOM | 1385 | N   | ASP | A | 307 | 28.536 | -5.192 | 21.998 | 1.00 | 101.02 | A | N |
| ATOM | 1386 | CA  | ASP | A | 307 | 27.233 | -5.291 | 22.652 | 1.00 | 98.62  | A | C |
| ATOM | 1387 | CB  | ASP | A | 307 | 26.618 | -6.677 | 22.436 | 1.00 | 107.40 | A | C |
| ATOM | 1388 | CG  | ASP | A | 307 | 25.143 | -6.610 | 22.088 | 1.00 | 113.35 | A | C |
| ATOM | 1389 | OD1 | ASP | A | 307 | 24.815 | -6.166 | 20.966 | 1.00 | 113.31 | A | O |
| ATOM | 1390 | OD2 | ASP | A | 307 | 24.312 | -6.995 | 22.936 | 1.00 | 116.92 | A | O |
| ATOM | 1391 | C   | ASP | A | 307 | 27.226 | -4.991 | 24.147 | 1.00 | 92.83  | A | C |
| ATOM | 1392 | O   | ASP | A | 307 | 27.757 | -5.762 | 24.947 | 1.00 | 89.55  | A | O |
| ATOM | 1393 | N   | GLU | A | 308 | 26.621 | -3.864 | 24.512 | 1.00 | 87.84  | A | N |
| ATOM | 1394 | CA  | GLU | A | 308 | 26.485 | -3.470 | 25.912 | 1.00 | 84.64  | A | C |
| ATOM | 1395 | CB  | GLU | A | 308 | 25.673 | -4.546 | 26.645 | 1.00 | 84.79  | A | C |
| ATOM | 1396 | CG  | GLU | A | 308 | 25.769 | -4.523 | 28.160 | 1.00 | 85.31  | A | C |
| ATOM | 1397 | CD  | GLU | A | 308 | 26.179 | -5.874 | 28.723 | 1.00 | 86.21  | A | C |
| ATOM | 1398 | OE1 | GLU | A | 308 | 25.559 | -6.895 | 28.351 | 1.00 | 86.01  | A | O |
| ATOM | 1399 | OE2 | GLU | A | 308 | 27.123 | -5.917 | 29.539 | 1.00 | 87.12  | A | O |
| ATOM | 1400 | C   | GLU | A | 308 | 27.770 | -3.179 | 26.686 | 1.00 | 82.84  | A | C |
| ATOM | 1401 | O   | GLU | A | 308 | 27.778 | -2.328 | 27.576 | 1.00 | 81.84  | A | O |
| ATOM | 1402 | N   | LYS | A | 309 | 28.853 | -3.875 | 26.359 | 1.00 | 81.92  | A | N |
| ATOM | 1403 | CA  | LYS | A | 309 | 30.112 | -3.669 | 27.068 | 1.00 | 79.59  | A | C |
| ATOM | 1404 | CB  | LYS | A | 309 | 30.992 | -4.918 | 26.963 | 1.00 | 80.41  | A | C |
| ATOM | 1405 | CG  | LYS | A | 309 | 30.671 | -5.953 | 28.028 | 1.00 | 83.88  | A | C |
| ATOM | 1406 | CD  | LYS | A | 309 | 30.609 | -5.281 | 29.397 | 1.00 | 88.76  | A | C |
| ATOM | 1407 | CE  | LYS | A | 309 | 30.083 | -6.206 | 30.485 | 1.00 | 91.71  | A | C |
| ATOM | 1408 | NZ  | LYS | A | 309 | 31.157 | -6.822 | 31.309 | 1.00 | 90.42  | A | N |
| ATOM | 1409 | C   | LYS | A | 309 | 30.913 | -2.450 | 26.645 | 1.00 | 76.97  | A | C |
| ATOM | 1410 | O   | LYS | A | 309 | 31.588 | -1.829 | 27.465 | 1.00 | 77.18  | A | O |
| ATOM | 1411 | N   | VAL | A | 310 | 30.836 | -2.105 | 25.367 | 1.00 | 74.98  | A | N |
| ATOM | 1412 | CA  | VAL | A | 310 | 31.567 | -0.959 | 24.846 | 1.00 | 74.68  | A | C |
| ATOM | 1413 | CB  | VAL | A | 310 | 31.032 | -0.548 | 23.463 | 1.00 | 74.56  | A | C |
| ATOM | 1414 | CG1 | VAL | A | 310 | 31.131 | -1.719 | 22.502 | 1.00 | 74.14  | A | C |
| ATOM | 1415 | CG2 | VAL | A | 310 | 29.594 | -0.076 | 23.585 | 1.00 | 75.32  | A | C |
| ATOM | 1416 | C   | VAL | A | 310 | 31.505 | 0.259  | 25.765 | 1.00 | 75.81  | A | C |
| ATOM | 1417 | O   | VAL | A | 310 | 32.489 | 0.985  | 25.904 | 1.00 | 78.46  | A | O |
| ATOM | 1418 | N   | ASP | A | 311 | 30.354 | 0.476  | 26.395 | 1.00 | 75.34  | A | N |
| ATOM | 1419 | CA  | ASP | A | 311 | 30.177 | 1.625  | 27.278 | 1.00 | 73.08  | A | C |
| ATOM | 1420 | CB  | ASP | A | 311 | 28.745 | 1.669  | 27.812 | 1.00 | 80.08  | A | C |
| ATOM | 1421 | CG  | ASP | A | 311 | 27.734 | 1.958  | 26.722 | 1.00 | 85.72  | A | C |
| ATOM | 1422 | OD1 | ASP | A | 311 | 28.044 | 2.778  | 25.832 | 1.00 | 89.31  | A | O |
| ATOM | 1423 | OD2 | ASP | A | 311 | 26.631 | 1.376  | 26.754 | 1.00 | 89.18  | A | O |
| ATOM | 1424 | C   | ASP | A | 311 | 31.163 | 1.703  | 28.437 | 1.00 | 67.57  | A | C |
| ATOM | 1425 | O   | ASP | A | 311 | 31.651 | 2.783  | 28.762 | 1.00 | 63.00  | A | O |
| ATOM | 1426 | N   | LEU | A | 312 | 31.451 | 0.571  | 29.070 | 1.00 | 65.08  | A | N |
| ATOM | 1427 | CA  | LEU | A | 312 | 32.404 | 0.565  | 30.174 | 1.00 | 63.29  | A | C |
| ATOM | 1428 | CB  | LEU | A | 312 | 32.509 | -0.833 | 30.789 | 1.00 | 63.28  | A | C |
| ATOM | 1429 | CG  | LEU | A | 312 | 31.480 | -1.177 | 31.872 | 1.00 | 61.20  | A | C |
| ATOM | 1430 | CD1 | LEU | A | 312 | 31.879 | -0.520 | 33.184 | 1.00 | 62.60  | A | C |
| ATOM | 1431 | CD2 | LEU | A | 312 | 30.098 | -0.721 | 31.439 | 1.00 | 60.06  | A | C |
| ATOM | 1432 | C   | LEU | A | 312 | 33.763 | 1.014  | 29.652 | 1.00 | 63.07  | A | C |
| ATOM | 1433 | O   | LEU | A | 312 | 34.557 | 1.608  | 30.383 | 1.00 | 65.54  | A | O |
| ATOM | 1434 | N   | TRP | A | 313 | 34.018 | 0.728  | 28.379 | 1.00 | 62.33  | A | N |
| ATOM | 1435 | CA  | TRP | A | 313 | 35.268 | 1.114  | 27.737 | 1.00 | 64.42  | A | C |
| ATOM | 1436 | CB  | TRP | A | 313 | 35.447 | 0.339  | 26.426 | 1.00 | 68.18  | A | C |
| ATOM | 1437 | CG  | TRP | A | 313 | 36.593 | 0.816  | 25.578 | 1.00 | 70.13  | A | C |
| ATOM | 1438 | CD2 | TRP | A | 313 | 37.915 | 0.266  | 25.530 | 1.00 | 69.22  | A | C |
| ATOM | 1439 | CE2 | TRP | A | 313 | 38.658 | 1.039  | 24.609 | 1.00 | 69.11  | A | C |
| ATOM | 1440 | CE3 | TRP | A | 313 | 38.545 | -0.807 | 26.174 | 1.00 | 69.93  | A | C |
| ATOM | 1441 | CD1 | TRP | A | 313 | 36.587 | 1.872  | 24.711 | 1.00 | 71.92  | A | C |
| ATOM | 1442 | NE1 | TRP | A | 313 | 37.825 | 2.012  | 24.124 | 1.00 | 70.63  | A | N |
| ATOM | 1443 | CZ2 | TRP | A | 313 | 40.001 | 0.775  | 24.320 | 1.00 | 67.64  | A | C |
| ATOM | 1444 | CZ3 | TRP | A | 313 | 39.884 | -1.069 | 25.884 | 1.00 | 67.83  | A | C |

Figure 1X

| ATOM | 1445 | CH2 | TRP | A | 313 | 40.594 | -0.280 | 24.964 | 1.00 | 63.35 | A | C |
|---|---|---|---|---|---|---|---|---|---|---|---|---|
| ATOM | 1446 | C | TRP | A | 313 | 35.237 | 2.613 | 27.470 | 1.00 | 65.74 | A | C |
| ATOM | 1447 | O | TRP | A | 313 | 36.124 | 3.350 | 27.903 | 1.00 | 64.60 | A | O |
| ATOM | 1448 | N | SER | A | 314 | 34.211 | 3.058 | 26.752 | 1.00 | 67.32 | A | N |
| ATOM | 1449 | CA | SER | A | 314 | 34.057 | 4.472 | 26.449 | 1.00 | 66.80 | A | C |
| ATOM | 1450 | CB | SER | A | 314 | 32.686 | 4.728 | 25.825 | 1.00 | 69.36 | A | C |
| ATOM | 1451 | OG | SER | A | 314 | 32.582 | 4.074 | 24.574 | 1.00 | 76.05 | A | O |
| ATOM | 1452 | C | SER | A | 314 | 34.185 | 5.225 | 27.764 | 1.00 | 64.67 | A | C |
| ATOM | 1453 | O | SER | A | 314 | 35.058 | 6.077 | 27.926 | 1.00 | 61.27 | A | O |
| ATOM | 1454 | N | LEU | A | 315 | 33.312 | 4.888 | 28.706 | 1.00 | 64.39 | A | N |
| ATOM | 1455 | CA | LEU | A | 315 | 33.324 | 5.503 | 30.025 | 1.00 | 62.14 | A | C |
| ATOM | 1456 | CB | LEU | A | 315 | 32.335 | 4.777 | 30.941 | 1.00 | 61.30 | A | C |
| ATOM | 1457 | CG | LEU | A | 315 | 32.143 | 5.295 | 32.367 | 1.00 | 61.14 | A | C |
| ATOM | 1458 | CD1 | LEU | A | 315 | 31.630 | 6.726 | 32.338 | 1.00 | 62.79 | A | C |
| ATOM | 1459 | CD2 | LEU | A | 315 | 31.161 | 4.396 | 33.100 | 1.00 | 59.71 | A | C |
| ATOM | 1460 | C | LEU | A | 315 | 34.731 | 5.425 | 30.613 | 1.00 | 60.98 | A | C |
| ATOM | 1461 | O | LEU | A | 315 | 35.088 | 6.198 | 31.499 | 1.00 | 60.23 | A | O |
| ATOM | 1462 | N | GLY | A | 316 | 35.527 | 4.485 | 30.111 | 1.00 | 60.42 | A | N |
| ATOM | 1463 | CA | GLY | A | 316 | 36.885 | 4.326 | 30.599 | 1.00 | 60.05 | A | C |
| ATOM | 1464 | C | GLY | A | 316 | 37.805 | 5.387 | 30.036 | 1.00 | 60.12 | A | C |
| ATOM | 1465 | O | GLY | A | 316 | 38.661 | 5.923 | 30.740 | 1.00 | 60.16 | A | O |
| ATOM | 1466 | N | VAL | A | 317 | 37.625 | 5.692 | 28.757 | 1.00 | 58.47 | A | N |
| ATOM | 1467 | CA | VAL | A | 317 | 38.433 | 6.698 | 28.089 | 1.00 | 58.01 | A | C |
| ATOM | 1468 | CB | VAL | A | 317 | 38.157 | 6.709 | 26.584 | 1.00 | 56.62 | A | C |
| ATOM | 1469 | CG1 | VAL | A | 317 | 39.250 | 7.475 | 25.864 | 1.00 | 56.39 | A | C |
| ATOM | 1470 | CG2 | VAL | A | 317 | 38.052 | 5.293 | 26.067 | 1.00 | 53.04 | A | C |
| ATOM | 1471 | C | VAL | A | 317 | 38.078 | 8.069 | 28.639 | 1.00 | 59.78 | A | C |
| ATOM | 1472 | O | VAL | A | 317 | 38.946 | 8.914 | 28.853 | 1.00 | 61.19 | A | O |
| ATOM | 1473 | N | LEU | A | 318 | 36.785 | 8.278 | 28.852 | 1.00 | 59.83 | A | N |
| ATOM | 1474 | CA | LEU | A | 318 | 36.278 | 9.536 | 29.374 | 1.00 | 60.59 | A | C |
| ATOM | 1475 | CB | LEU | A | 318 | 34.758 | 9.439 | 29.540 | 1.00 | 64.41 | A | C |
| ATOM | 1476 | CG | LEU | A | 318 | 33.926 | 10.717 | 29.419 | 1.00 | 65.10 | A | C |
| ATOM | 1477 | CD1 | LEU | A | 318 | 34.502 | 11.605 | 28.326 | 1.00 | 63.64 | A | C |
| ATOM | 1478 | CD2 | LEU | A | 318 | 32.481 | 10.353 | 29.108 | 1.00 | 64.53 | A | C |
| ATOM | 1479 | C | LEU | A | 318 | 36.948 | 9.827 | 30.714 | 1.00 | 60.86 | A | C |
| ATOM | 1480 | O | LEU | A | 318 | 37.613 | 10.853 | 30.882 | 1.00 | 62.50 | A | O |
| ATOM | 1481 | N | CYS | A | 319 | 36.780 | 8.902 | 31.656 | 1.00 | 61.28 | A | N |
| ATOM | 1482 | CA | CYS | A | 319 | 37.357 | 9.034 | 32.988 | 1.00 | 63.73 | A | C |
| ATOM | 1483 | CB | CYS | A | 319 | 37.259 | 7.702 | 33.740 | 1.00 | 68.60 | A | C |
| ATOM | 1484 | SG | CYS | A | 319 | 37.322 | 7.844 | 35.544 | 1.00 | 74.58 | A | S |
| ATOM | 1485 | C | CYS | A | 319 | 38.816 | 9.462 | 32.877 | 1.00 | 62.69 | A | C |
| ATOM | 1486 | O | CYS | A | 319 | 39.316 | 10.220 | 33.708 | 1.00 | 62.36 | A | O |
| ATOM | 1487 | N | TYR | A | 320 | 39.490 | 8.976 | 31.838 | 1.00 | 64.27 | A | N |
| ATOM | 1488 | CA | TYR | A | 320 | 40.890 | 9.310 | 31.597 | 1.00 | 68.69 | A | C |
| ATOM | 1489 | CB | TYR | A | 320 | 41.480 | 8.427 | 30.495 | 1.00 | 70.97 | A | C |
| ATOM | 1490 | CG | TYR | A | 320 | 42.957 | 8.662 | 30.253 | 1.00 | 71.15 | A | C |
| ATOM | 1491 | CD1 | TYR | A | 320 | 43.921 | 7.933 | 30.947 | 1.00 | 67.85 | A | C |
| ATOM | 1492 | CE1 | TYR | A | 320 | 45.281 | 8.163 | 30.748 | 1.00 | 66.84 | A | C |
| ATOM | 1493 | CD2 | TYR | A | 320 | 43.392 | 9.632 | 29.350 | 1.00 | 73.18 | A | C |
| ATOM | 1494 | CE2 | TYR | A | 320 | 44.751 | 9.870 | 29.145 | 1.00 | 73.75 | A | C |
| ATOM | 1495 | CZ | TYR | A | 320 | 45.688 | 9.132 | 29.848 | 1.00 | 69.70 | A | C |
| ATOM | 1496 | OH | TYR | A | 320 | 47.032 | 9.364 | 29.657 | 1.00 | 62.02 | A | O |
| ATOM | 1497 | C | TYR | A | 320 | 41.015 | 10.764 | 31.162 | 1.00 | 69.87 | A | C |
| ATOM | 1498 | O | TYR | A | 320 | 41.527 | 11.605 | 31.901 | 1.00 | 71.42 | A | O |
| ATOM | 1499 | N | GLU | A | 321 | 40.547 | 11.042 | 29.948 | 1.00 | 70.58 | A | N |
| ATOM | 1500 | CA | GLU | A | 321 | 40.601 | 12.384 | 29.376 | 1.00 | 70.66 | A | C |
| ATOM | 1501 | CB | GLU | A | 321 | 39.588 | 12.519 | 28.238 | 1.00 | 72.38 | A | C |
| ATOM | 1502 | CG | GLU | A | 321 | 40.199 | 12.946 | 26.915 | 1.00 | 80.40 | A | C |
| ATOM | 1503 | CD | GLU | A | 321 | 39.308 | 13.900 | 26.145 | 1.00 | 84.47 | A | C |
| ATOM | 1504 | OE1 | GLU | A | 321 | 38.095 | 13.630 | 26.041 | 1.00 | 88.10 | A | O |
| ATOM | 1505 | OE2 | GLU | A | 321 | 39.821 | 14.921 | 25.640 | 1.00 | 86.17 | A | O |

Figure 1Y

```
ATOM  1506  C    GLU A 321      40.324  13.460  30.418  1.00  71.15      A    C
ATOM  1507  O    GLU A 321      41.074  14.430  30.537  1.00  69.71      A    O
ATOM  1508  N    PHE A 322      39.243  13.288  31.170  1.00  70.29      A    N
ATOM  1509  CA   PHE A 322      38.877  14.253  32.198  1.00  68.50      A    C
ATOM  1510  CB   PHE A 322      37.722  13.725  33.056  1.00  59.21      A    C
ATOM  1511  CG   PHE A 322      36.389  13.705  32.360  1.00  51.02      A    C
ATOM  1512  CD1  PHE A 322      36.146  14.513  31.253  1.00  46.80      A    C
ATOM  1513  CD2  PHE A 322      35.355  12.910  32.847  1.00  49.96      A    C
ATOM  1514  CE1  PHE A 322      34.893  14.531  30.646  1.00  47.66      A    C
ATOM  1515  CE2  PHE A 322      34.098  12.923  32.247  1.00  48.76      A    C
ATOM  1516  CZ   PHE A 322      33.868  13.735  31.144  1.00  49.16      A    C
ATOM  1517  C    PHE A 322      40.038  14.597  33.125  1.00  71.37      A    C
ATOM  1518  O    PHE A 322      40.192  15.747  33.535  1.00  74.60      A    O
ATOM  1519  N    LEU A 323      40.852  13.599  33.452  1.00  72.30      A    N
ATOM  1520  CA   LEU A 323      41.970  13.794  34.368  1.00  71.37      A    C
ATOM  1521  CB   LEU A 323      42.111  12.562  35.270  1.00  71.27      A    C
ATOM  1522  CG   LEU A 323      40.842  12.093  35.992  1.00  69.94      A    C
ATOM  1523  CD1  LEU A 323      41.061  10.710  36.591  1.00  72.65      A    C
ATOM  1524  CD2  LEU A 323      40.467  13.097  37.072  1.00  70.46      A    C
ATOM  1525  C    LEU A 323      43.322  14.102  33.726  1.00  70.63      A    C
ATOM  1526  O    LEU A 323      44.339  14.115  34.417  1.00  72.87      A    O
ATOM  1527  N    VAL A 324      43.350  14.355  32.421  1.00  69.48      A    N
ATOM  1528  CA   VAL A 324      44.620  14.643  31.758  1.00  69.28      A    C
ATOM  1529  CB   VAL A 324      45.261  13.352  31.201  1.00  67.56      A    C
ATOM  1530  CG1  VAL A 324      46.655  13.648  30.668  1.00  68.29      A    C
ATOM  1531  CG2  VAL A 324      45.331  12.296  32.289  1.00  65.20      A    C
ATOM  1532  C    VAL A 324      44.492  15.652  30.621  1.00  72.55      A    C
ATOM  1533  O    VAL A 324      45.468  16.304  30.245  1.00  73.88      A    O
ATOM  1534  N    GLY A 325      43.288  15.781  30.073  1.00  72.69      A    N
ATOM  1535  CA   GLY A 325      43.076  16.719  28.987  1.00  73.78      A    C
ATOM  1536  C    GLY A 325      43.001  16.049  27.629  1.00  74.19      A    C
ATOM  1537  O    GLY A 325      42.417  16.595  26.692  1.00  80.44      A    O
ATOM  1538  N    LYS A 326      43.589  14.864  27.516  1.00  69.35      A    N
ATOM  1539  CA   LYS A 326      43.575  14.131  26.255  1.00  65.10      A    C
ATOM  1540  CB   LYS A 326      44.900  14.330  25.515  1.00  64.07      A    C
ATOM  1541  CG   LYS A 326      46.136  13.996  26.333  1.00  64.20      A    C
ATOM  1542  CD   LYS A 326      47.407  14.299  25.549  1.00  66.30      A    C
ATOM  1543  CE   LYS A 326      48.658  13.904  26.320  1.00  68.72      A    C
ATOM  1544  NZ   LYS A 326      48.688  14.456  27.701  1.00  70.08      A    N
ATOM  1545  C    LYS A 326      43.316  12.642  26.471  1.00  63.47      A    C
ATOM  1546  O    LYS A 326      43.547  12.112  27.560  1.00  59.38      A    O
ATOM  1547  N    PRO A 327      42.816  11.951  25.432  1.00  61.80      A    N
ATOM  1548  CD   PRO A 327      42.361  12.523  24.153  1.00  59.30      A    C
ATOM  1549  CA   PRO A 327      42.516  10.514  25.490  1.00  61.39      A    C
ATOM  1550  CB   PRO A 327      41.880  10.238  24.128  1.00  60.42      A    C
ATOM  1551  CG   PRO A 327      41.277  11.557  23.754  1.00  56.17      A    C
ATOM  1552  C    PRO A 327      43.781   9.682  25.711  1.00  61.60      A    C
ATOM  1553  O    PRO A 327      44.891  10.167  25.502  1.00  61.65      A    O
ATOM  1554  N    PRO A 328      43.629   8.417  26.135  1.00  62.94      A    N
ATOM  1555  CD   PRO A 328      42.400   7.768  26.627  1.00  62.32      A    C
ATOM  1556  CA   PRO A 328      44.793   7.557  26.371  1.00  66.12      A    C
ATOM  1557  CB   PRO A 328      44.232   6.478  27.288  1.00  66.21      A    C
ATOM  1558  CG   PRO A 328      42.838   6.326  26.778  1.00  64.07      A    C
ATOM  1559  C    PRO A 328      45.459   6.955  25.131  1.00  69.10      A    C
ATOM  1560  O    PRO A 328      46.579   6.448  25.215  1.00  69.99      A    O
ATOM  1561  N    PHE A 329      44.785   7.009  23.986  1.00  70.96      A    N
ATOM  1562  CA   PHE A 329      45.341   6.428  22.767  1.00  73.93      A    C
ATOM  1563  CB   PHE A 329      44.436   5.291  22.295  1.00  73.09      A    C
ATOM  1564  CG   PHE A 329      43.981   4.393  23.407  1.00  67.14      A    C
ATOM  1565  CD1  PHE A 329      44.893   3.607  24.103  1.00  62.52      A    C
ATOM  1566  CD2  PHE A 329      42.647   4.372  23.795  1.00  66.77      A    C
```

Figure 1Z

```
ATOM  1567  CE1  PHE A 329      44.482   2.814  25.171  1.00  61.94      A    C
ATOM  1568  CE2  PHE A 329      42.227   3.582  24.862  1.00  63.91      A    C
ATOM  1569  CZ   PHE A 329      43.147   2.803  25.552  1.00  64.00      A    C
ATOM  1570  C    PHE A 329      45.550   7.440  21.647  1.00  77.92      A    C
ATOM  1571  O    PHE A 329      45.856   7.070  20.512  1.00  80.68      A    O
ATOM  1572  N    GLU A 330      45.381   8.718  21.970  1.00  81.78      A    N
ATOM  1573  CA   GLU A 330      45.576   9.784  20.996  1.00  84.46      A    C
ATOM  1574  CB   GLU A 330      45.333  11.144  21.658  1.00  85.13      A    C
ATOM  1575  CG   GLU A 330      45.868  12.340  20.885  1.00  87.63      A    C
ATOM  1576  CD   GLU A 330      45.631  13.651  21.611  1.00  88.70      A    C
ATOM  1577  OE1  GLU A 330      44.505  14.182  21.525  1.00  91.66      A    O
ATOM  1578  OE2  GLU A 330      46.567  14.148  22.273  1.00  88.30      A    O
ATOM  1579  C    GLU A 330      47.003   9.700  20.466  1.00  86.04      A    C
ATOM  1580  O    GLU A 330      47.937   9.454  21.230  1.00  82.26      A    O
ATOM  1581  N    ALA A 331      47.174   9.900  19.162  1.00  89.59      A    N
ATOM  1582  CA   ALA A 331      48.504   9.825  18.571  1.00  93.10      A    C
ATOM  1583  CB   ALA A 331      48.970   8.376  18.544  1.00  93.91      A    C
ATOM  1584  C    ALA A 331      48.625  10.425  17.175  1.00  95.06      A    C
ATOM  1585  O    ALA A 331      47.699  11.053  16.658  1.00  92.91      A    O
ATOM  1586  N    ASN A 332      49.794  10.211  16.580  1.00  99.10      A    N
ATOM  1587  CA   ASN A 332      50.116  10.699  15.248  1.00 102.47      A    C
ATOM  1588  CB   ASN A 332      51.632  10.860  15.120  1.00 103.56      A    C
ATOM  1589  CG   ASN A 332      52.385   9.625  15.579  1.00 105.59      A    C
ATOM  1590  OD1  ASN A 332      52.379   9.285  16.763  1.00 104.67      A    O
ATOM  1591  ND2  ASN A 332      53.033   8.942  14.641  1.00 106.76      A    N
ATOM  1592  C    ASN A 332      49.614   9.751  14.164  1.00 104.90      A    C
ATOM  1593  O    ASN A 332      50.368   8.909  13.684  1.00 105.73      A    O
ATOM  1594  N    THR A 333      48.341   9.905  13.798  1.00 105.87      A    N
ATOM  1595  CA   THR A 333      47.664   9.110  12.765  1.00 106.12      A    C
ATOM  1596  CB   THR A 333      48.645   8.594  11.674  1.00 109.36      A    C
ATOM  1597  OG1  THR A 333      47.951   8.495  10.425  1.00 113.09      A    O
ATOM  1598  CG2  THR A 333      49.186   7.211  12.034  1.00 110.86      A    C
ATOM  1599  C    THR A 333      46.877   7.920  13.312  1.00 102.49      A    C
ATOM  1600  O    THR A 333      47.179   7.397  14.384  1.00 103.44      A    O
ATOM  1601  N    TYR A 334      45.866   7.505  12.552  1.00  97.46      A    N
ATOM  1602  CA   TYR A 334      45.000   6.388  12.920  1.00  93.45      A    C
ATOM  1603  CB   TYR A 334      43.896   6.210  11.879  1.00  94.80      A    C
ATOM  1604  CG   TYR A 334      42.917   7.354  11.769  1.00  98.46      A    C
ATOM  1605  CD1  TYR A 334      42.078   7.690  12.830  1.00 101.64      A    C
ATOM  1606  CE1  TYR A 334      41.142   8.715  12.709  1.00 106.33      A    C
ATOM  1607  CD2  TYR A 334      42.801   8.075  10.583  1.00 101.48      A    C
ATOM  1608  CE2  TYR A 334      41.871   9.100  10.451  1.00 104.51      A    C
ATOM  1609  CZ   TYR A 334      41.043   9.413  11.515  1.00 106.06      A    C
ATOM  1610  OH   TYR A 334      40.108  10.413  11.378  1.00 106.62      A    O
ATOM  1611  C    TYR A 334      45.732   5.057  13.069  1.00  91.47      A    C
ATOM  1612  O    TYR A 334      45.391   4.264  13.945  1.00  92.73      A    O
ATOM  1613  N    GLN A 335      46.705   4.797  12.198  1.00  89.49      A    N
ATOM  1614  CA   GLN A 335      47.471   3.552  12.261  1.00  89.06      A    C
ATOM  1615  CB   GLN A 335      48.719   3.643  11.383  1.00  90.33      A    C
ATOM  1616  CG   GLN A 335      48.424   3.760   9.891  1.00  92.09      A    C
ATOM  1617  CD   GLN A 335      47.509   4.926   9.558  1.00  93.60      A    C
ATOM  1618  OE1  GLN A 335      46.292   4.844   9.722  1.00  91.71      A    O
ATOM  1619  NE2  GLN A 335      48.096   6.023   9.094  1.00  97.59      A    N
ATOM  1620  C    GLN A 335      47.848   3.354  13.718  1.00  88.56      A    C
ATOM  1621  O    GLN A 335      47.610   2.289  14.294  1.00  90.18      A    O
ATOM  1622  N    GLU A 336      48.440   4.389  14.310  1.00  85.02      A    N
ATOM  1623  CA   GLU A 336      48.770   4.364  15.729  1.00  81.44      A    C
ATOM  1624  CB   GLU A 336      49.471   5.657  16.148  1.00  81.66      A    C
ATOM  1625  CG   GLU A 336      50.907   5.813  15.668  1.00  87.82      A    C
ATOM  1626  CD   GLU A 336      51.869   4.874  16.371  1.00  94.22      A    C
ATOM  1627  OE1  GLU A 336      52.146   3.781  15.833  1.00  97.25      A    O
```

Figure 1AA

```
ATOM   1628  OE2 GLU A 336      52.340   5.228  17.473  1.00  97.60      A   O
ATOM   1629  C   GLU A 336      47.347   4.347  16.276  1.00  79.60      A   C
ATOM   1630  O   GLU A 336      46.460   3.832  15.613  1.00  84.36      A   O
ATOM   1631  N   THR A 337      47.099   4.920  17.446  1.00  73.12      A   N
ATOM   1632  CA  THR A 337      45.734   4.926  17.976  1.00  70.19      A   C
ATOM   1633  CB  THR A 337      44.820   5.847  17.135  1.00  68.05      A   C
ATOM   1634  OG1 THR A 337      45.557   7.006  16.728  1.00  66.16      A   O
ATOM   1635  CG2 THR A 337      43.613   6.295  17.951  1.00  66.43      A   C
ATOM   1636  C   THR A 337      45.184   3.497  17.940  1.00  70.77      A   C
ATOM   1637  O   THR A 337      45.052   2.860  18.979  1.00  71.10      A   O
ATOM   1638  N   TYR A 338      44.854   3.002  16.747  1.00  70.08      A   N
ATOM   1639  CA  TYR A 338      44.366   1.634  16.592  1.00  66.84      A   C
ATOM   1640  CB  TYR A 338      44.287   1.245  15.109  1.00  72.87      A   C
ATOM   1641  CG  TYR A 338      43.705  -0.135  14.853  1.00  81.75      A   C
ATOM   1642  CD1 TYR A 338      42.515  -0.288  14.145  1.00  85.69      A   C
ATOM   1643  CE1 TYR A 338      41.954  -1.547  13.934  1.00  85.27      A   C
ATOM   1644  CD2 TYR A 338      44.327  -1.285  15.342  1.00  84.66      A   C
ATOM   1645  CE2 TYR A 338      43.774  -2.549  15.137  1.00  87.13      A   C
ATOM   1646  CZ  TYR A 338      42.587  -2.668  14.433  1.00  86.38      A   C
ATOM   1647  OH  TYR A 338      42.017  -3.903  14.243  1.00  86.81      A   O
ATOM   1648  C   TYR A 338      45.412   0.771  17.278  1.00  62.62      A   C
ATOM   1649  O   TYR A 338      45.110   0.008  18.196  1.00  64.08      A   O
ATOM   1650  N   LYS A 339      46.650   0.915  16.819  1.00  55.79      A   N
ATOM   1651  CA  LYS A 339      47.769   0.173  17.371  1.00  50.23      A   C
ATOM   1652  CB  LYS A 339      49.086   0.816  16.929  1.00  48.02      A   C
ATOM   1653  CG  LYS A 339      50.331   0.108  17.446  1.00  49.73      A   C
ATOM   1654  CD  LYS A 339      51.586   0.544  16.686  1.00  52.62      A   C
ATOM   1655  CE  LYS A 339      51.542   0.052  15.242  1.00  55.54      A   C
ATOM   1656  NZ  LYS A 339      52.769   0.372  14.451  1.00  58.93      A   N
ATOM   1657  C   LYS A 339      47.685   0.137  18.893  1.00  49.93      A   C
ATOM   1658  O   LYS A 339      47.578  -0.935  19.488  1.00  47.91      A   O
ATOM   1659  N   ARG A 340      47.708   1.311  19.517  1.00  52.40      A   N
ATOM   1660  CA  ARG A 340      47.646   1.408  20.972  1.00  54.39      A   C
ATOM   1661  CB  ARG A 340      48.125   2.789  21.424  1.00  60.69      A   C
ATOM   1662  CG  ARG A 340      49.573   3.076  21.055  1.00  74.59      A   C
ATOM   1663  CD  ARG A 340      49.972   4.494  21.407  1.00  86.78      A   C
ATOM   1664  NE  ARG A 340      51.129   4.927  20.628  1.00  99.96      A   N
ATOM   1665  CZ  ARG A 340      51.521   6.191  20.511  1.00 105.56      A   C
ATOM   1666  NH1 ARG A 340      50.850   7.156  21.126  1.00 107.00      A   N
ATOM   1667  NH2 ARG A 340      52.576   6.493  19.767  1.00 108.09      A   N
ATOM   1668  C   ARG A 340      46.260   1.123  21.549  1.00  51.73      A   C
ATOM   1669  O   ARG A 340      46.131   0.835  22.738  1.00  50.86      A   O
ATOM   1670  N   ILE A 341      45.225   1.209  20.718  1.00  50.26      A   N
ATOM   1671  CA  ILE A 341      43.870   0.930  21.182  1.00  50.94      A   C
ATOM   1672  CB  ILE A 341      42.792   1.497  20.220  1.00  52.17      A   C
ATOM   1673  CG2 ILE A 341      41.492   0.716  20.379  1.00  52.54      A   C
ATOM   1674  CG1 ILE A 341      42.549   2.983  20.506  1.00  50.97      A   C
ATOM   1675  CD1 ILE A 341      41.540   3.637  19.572  1.00  44.72      A   C
ATOM   1676  C   ILE A 341      43.688  -0.580  21.271  1.00  51.79      A   C
ATOM   1677  O   ILE A 341      43.248  -1.104  22.292  1.00  49.99      A   O
ATOM   1678  N   SER A 342      44.034  -1.272  20.190  1.00  55.69      A   N
ATOM   1679  CA  SER A 342      43.911  -2.723  20.133  1.00  59.70      A   C
ATOM   1680  CB  SER A 342      44.051  -3.210  18.688  1.00  56.71      A   C
ATOM   1681  OG  SER A 342      45.312  -2.858  18.148  1.00  56.64      A   O
ATOM   1682  C   SER A 342      44.947  -3.412  21.015  1.00  63.35      A   C
ATOM   1683  O   SER A 342      44.754  -4.555  21.426  1.00  64.45      A   O
ATOM   1684  N   ARG A 343      46.050  -2.724  21.297  1.00  66.96      A   N
ATOM   1685  CA  ARG A 343      47.089  -3.293  22.149  1.00  69.51      A   C
ATOM   1686  CB  ARG A 343      48.484  -3.021  21.576  1.00  75.49      A   C
ATOM   1687  CG  ARG A 343      48.938  -3.987  20.491  1.00  81.68      A   C
ATOM   1688  CD  ARG A 343      50.448  -3.918  20.325  1.00  85.52      A   C
```

Figure 1BB

```
ATOM   1689  NE   ARG A 343      50.859  -3.974  18.925  1.00  87.10      A  N
ATOM   1690  CZ   ARG A 343      51.889  -3.300  18.422  1.00  89.22      A  C
ATOM   1691  NH1  ARG A 343      52.193  -3.411  17.135  1.00  91.00      A  N
ATOM   1692  NH2  ARG A 343      52.612  -2.508  19.203  1.00  89.19      A  N
ATOM   1693  C    ARG A 343      46.987  -2.686  23.541  1.00  69.20      A  C
ATOM   1694  O    ARG A 343      47.829  -2.943  24.402  1.00  71.36      A  O
ATOM   1695  N    VAL A 344      45.954  -1.875  23.747  1.00  69.00      A  N
ATOM   1696  CA   VAL A 344      45.726  -1.225  25.030  1.00  68.61      A  C
ATOM   1697  CB   VAL A 344      45.112  -2.216  26.046  1.00  67.63      A  C
ATOM   1698  CG1  VAL A 344      44.741  -1.492  27.328  1.00  68.26      A  C
ATOM   1699  CG2  VAL A 344      43.887  -2.884  25.442  1.00  69.64      A  C
ATOM   1700  C    VAL A 344      47.045  -0.680  25.575  1.00  70.76      A  C
ATOM   1701  O    VAL A 344      47.479  -1.036  26.672  1.00  69.87      A  O
ATOM   1702  N    GLU A 345      47.680   0.184  24.790  1.00  72.52      A  N
ATOM   1703  CA   GLU A 345      48.954   0.778  25.176  1.00  77.62      A  C
ATOM   1704  CB   GLU A 345      49.910   0.796  23.977  1.00  77.44      A  C
ATOM   1705  CG   GLU A 345      49.795  -0.435  23.087  1.00  73.64      A  C
ATOM   1706  CD   GLU A 345      51.064  -0.740  22.314  1.00  71.14      A  C
ATOM   1707  OE1  GLU A 345      51.631   0.178  21.687  1.00  67.47      A  O
ATOM   1708  OE2  GLU A 345      51.493  -1.912  22.331  1.00  68.43      A  O
ATOM   1709  C    GLU A 345      48.739   2.197  25.694  1.00  81.79      A  C
ATOM   1710  O    GLU A 345      48.894   3.170  24.955  1.00  82.61      A  O
ATOM   1711  N    PHE A 346      48.378   2.304  26.969  1.00  88.75      A  N
ATOM   1712  CA   PHE A 346      48.131   3.599  27.592  1.00  96.38      A  C
ATOM   1713  CB   PHE A 346      46.624   3.792  27.801  1.00  99.32      A  C
ATOM   1714  CG   PHE A 346      46.040   2.923  28.883  1.00 101.61      A  C
ATOM   1715  CD1  PHE A 346      46.016   3.357  30.205  1.00 100.34      A  C
ATOM   1716  CD2  PHE A 346      45.508   1.674  28.581  1.00 103.01      A  C
ATOM   1717  CE1  PHE A 346      45.475   2.561  31.211  1.00 104.40      A  C
ATOM   1718  CE2  PHE A 346      44.964   0.868  29.581  1.00 103.77      A  C
ATOM   1719  CZ   PHE A 346      44.945   1.315  30.898  1.00 104.44      A  C
ATOM   1720  C    PHE A 346      48.865   3.706  28.928  1.00  99.33      A  C
ATOM   1721  O    PHE A 346      49.012   2.714  29.642  1.00  99.78      A  O
ATOM   1722  N    THR A 347      49.323   4.911  29.260  1.00 100.36      A  N
ATOM   1723  CA   THR A 347      50.039   5.144  30.512  1.00 103.94      A  C
ATOM   1724  CB   THR A 347      51.564   5.201  30.267  1.00 105.34      A  C
ATOM   1725  OG1  THR A 347      52.249   5.229  31.524  1.00 106.68      A  O
ATOM   1726  CG2  THR A 347      51.934   6.429  29.456  1.00 105.74      A  C
ATOM   1727  C    THR A 347      49.559   6.437  31.189  1.00 103.53      A  C
ATOM   1728  O    THR A 347      49.003   7.316  30.531  1.00 103.60      A  O
ATOM   1729  N    PHE A 348      49.782   6.547  32.499  1.00 103.30      A  N
ATOM   1730  CA   PHE A 348      49.332   7.702  33.289  1.00 102.41      A  C
ATOM   1731  CB   PHE A 348      48.846   7.236  34.661  1.00 101.42      A  C
ATOM   1732  CG   PHE A 348      47.704   6.281  34.611  1.00  97.86      A  C
ATOM   1733  CD1  PHE A 348      46.432   6.714  34.262  1.00  97.29      A  C
ATOM   1734  CD2  PHE A 348      47.898   4.942  34.924  1.00  98.42      A  C
ATOM   1735  CE1  PHE A 348      45.369   5.826  34.229  1.00  96.46      A  C
ATOM   1736  CE2  PHE A 348      46.844   4.045  34.894  1.00  98.86      A  C
ATOM   1737  CZ   PHE A 348      45.577   4.485  34.545  1.00  96.44      A  C
ATOM   1738  C    PHE A 348      50.317   8.835  33.550  1.00 102.01      A  C
ATOM   1739  O    PHE A 348      51.436   8.600  34.002  1.00 103.96      A  O
ATOM   1740  N    PRO A 349      49.893  10.089  33.317  1.00 100.57      A  N
ATOM   1741  CD   PRO A 349      48.539  10.559  32.976  1.00  99.87      A  C
ATOM   1742  CA   PRO A 349      50.788  11.222  33.561  1.00  99.02      A  C
ATOM   1743  CB   PRO A 349      49.932  12.427  33.181  1.00  96.96      A  C
ATOM   1744  CG   PRO A 349      48.551  11.969  33.518  1.00  97.63      A  C
ATOM   1745  C    PRO A 349      51.160  11.203  35.043  1.00  99.44      A  C
ATOM   1746  O    PRO A 349      50.388  10.727  35.875  1.00  98.79      A  O
ATOM   1747  N    ASP A 350      52.336  11.723  35.366  1.00  99.90      A  N
ATOM   1748  CA   ASP A 350      52.841  11.733  36.733  1.00  99.38      A  C
ATOM   1749  CB   ASP A 350      54.246  12.343  36.734  1.00 103.18      A  C
```

Figure 1CC

| ATOM | 1750 | CG | ASP | A | 350 | 55.134 | 11.767 | 37.818 | 1.00 | 107.14 | A | C |
|---|---|---|---|---|---|---|---|---|---|---|---|---|
| ATOM | 1751 | OD1 | ASP | A | 350 | 55.163 | 10.527 | 37.963 | 1.00 | 110.05 | A | O |
| ATOM | 1752 | OD2 | ASP | A | 350 | 55.810 | 12.549 | 38.519 | 1.00 | 107.17 | A | O |
| ATOM | 1753 | C | ASP | A | 350 | 51.985 | 12.431 | 37.797 | 1.00 | 97.22 | A | C |
| ATOM | 1754 | O | ASP | A | 350 | 52.241 | 13.589 | 38.127 | 1.00 | 96.30 | A | O |
| ATOM | 1755 | N | PHE | A | 351 | 50.978 | 11.729 | 38.326 | 1.00 | 94.00 | A | N |
| ATOM | 1756 | CA | PHE | A | 351 | 50.116 | 12.264 | 39.390 | 1.00 | 91.51 | A | C |
| ATOM | 1757 | CB | PHE | A | 351 | 49.916 | 13.783 | 39.234 | 1.00 | 90.18 | A | C |
| ATOM | 1758 | CG | PHE | A | 351 | 49.014 | 14.176 | 38.099 | 1.00 | 88.37 | A | C |
| ATOM | 1759 | CD1 | PHE | A | 351 | 47.636 | 14.014 | 38.198 | 1.00 | 87.54 | A | C |
| ATOM | 1760 | CD2 | PHE | A | 351 | 49.541 | 14.716 | 36.931 | 1.00 | 89.42 | A | C |
| ATOM | 1761 | CE1 | PHE | A | 351 | 46.796 | 14.382 | 37.154 | 1.00 | 88.78 | A | C |
| ATOM | 1762 | CE2 | PHE | A | 351 | 48.708 | 15.089 | 35.879 | 1.00 | 89.04 | A | C |
| ATOM | 1763 | CZ | PHE | A | 351 | 47.332 | 14.921 | 35.992 | 1.00 | 89.27 | A | C |
| ATOM | 1764 | C | PHE | A | 351 | 48.749 | 11.597 | 39.565 | 1.00 | 90.32 | A | C |
| ATOM | 1765 | O | PHE | A | 351 | 48.100 | 11.783 | 40.596 | 1.00 | 92.13 | A | O |
| ATOM | 1766 | N | VAL | A | 352 | 48.303 | 10.830 | 38.576 | 1.00 | 87.82 | A | N |
| ATOM | 1767 | CA | VAL | A | 352 | 47.002 | 10.171 | 38.675 | 1.00 | 87.40 | A | C |
| ATOM | 1768 | CB | VAL | A | 352 | 46.738 | 9.251 | 37.463 | 1.00 | 85.41 | A | C |
| ATOM | 1769 | CG1 | VAL | A | 352 | 45.338 | 8.650 | 37.555 | 1.00 | 81.11 | A | C |
| ATOM | 1770 | CG2 | VAL | A | 352 | 46.887 | 10.043 | 36.177 | 1.00 | 86.93 | A | C |
| ATOM | 1771 | C | VAL | A | 352 | 46.880 | 9.346 | 39.952 | 1.00 | 87.82 | A | C |
| ATOM | 1772 | O | VAL | A | 352 | 47.753 | 8.539 | 40.271 | 1.00 | 88.33 | A | O |
| ATOM | 1773 | N | THR | A | 353 | 45.789 | 9.559 | 40.680 | 1.00 | 88.01 | A | N |
| ATOM | 1774 | CA | THR | A | 353 | 45.544 | 8.841 | 41.924 | 1.00 | 89.73 | A | C |
| ATOM | 1775 | CB | THR | A | 353 | 44.197 | 9.252 | 42.551 | 1.00 | 93.08 | A | C |
| ATOM | 1776 | OG1 | THR | A | 353 | 43.845 | 8.323 | 43.584 | 1.00 | 97.32 | A | O |
| ATOM | 1777 | CG2 | THR | A | 353 | 43.107 | 9.276 | 41.495 | 1.00 | 94.79 | A | C |
| ATOM | 1778 | C | THR | A | 353 | 45.528 | 7.335 | 41.704 | 1.00 | 87.39 | A | C |
| ATOM | 1779 | O | THR | A | 353 | 44.955 | 6.848 | 40.729 | 1.00 | 83.88 | A | O |
| ATOM | 1780 | N | GLU | A | 354 | 46.167 | 6.601 | 42.610 | 1.00 | 87.16 | A | N |
| ATOM | 1781 | CA | GLU | A | 354 | 46.197 | 5.148 | 42.516 | 1.00 | 87.36 | A | C |
| ATOM | 1782 | CB | GLU | A | 354 | 46.901 | 4.545 | 43.740 | 1.00 | 91.80 | A | C |
| ATOM | 1783 | CG | GLU | A | 354 | 46.642 | 3.054 | 43.963 | 1.00 | 100.66 | A | C |
| ATOM | 1784 | CD | GLU | A | 354 | 47.563 | 2.448 | 45.010 | 1.00 | 105.03 | A | C |
| ATOM | 1785 | OE1 | GLU | A | 354 | 47.932 | 3.162 | 45.966 | 1.00 | 107.78 | A | O |
| ATOM | 1786 | OE2 | GLU | A | 354 | 47.909 | 1.253 | 44.883 | 1.00 | 107.92 | A | O |
| ATOM | 1787 | C | GLU | A | 354 | 44.756 | 4.660 | 42.433 | 1.00 | 85.09 | A | C |
| ATOM | 1788 | O | GLU | A | 354 | 44.497 | 3.511 | 42.084 | 1.00 | 88.33 | A | O |
| ATOM | 1789 | N | GLY | A | 355 | 43.822 | 5.549 | 42.752 | 1.00 | 81.49 | A | N |
| ATOM | 1790 | CA | GLY | A | 355 | 42.415 | 5.201 | 42.699 | 1.00 | 79.11 | A | C |
| ATOM | 1791 | C | GLY | A | 355 | 41.890 | 5.262 | 41.279 | 1.00 | 79.21 | A | C |
| ATOM | 1792 | O | GLY | A | 355 | 41.165 | 4.373 | 40.836 | 1.00 | 79.18 | A | O |
| ATOM | 1793 | N | ALA | A | 356 | 42.251 | 6.319 | 40.560 | 1.00 | 79.61 | A | N |
| ATOM | 1794 | CA | ALA | A | 356 | 41.813 | 6.469 | 39.179 | 1.00 | 80.14 | A | C |
| ATOM | 1795 | CB | ALA | A | 356 | 42.093 | 7.881 | 38.690 | 1.00 | 80.26 | A | C |
| ATOM | 1796 | C | ALA | A | 356 | 42.568 | 5.459 | 38.327 | 1.00 | 81.05 | A | C |
| ATOM | 1797 | O | ALA | A | 356 | 42.001 | 4.837 | 37.427 | 1.00 | 80.61 | A | O |
| ATOM | 1798 | N | ARG | A | 357 | 43.853 | 5.301 | 38.629 | 1.00 | 81.02 | A | N |
| ATOM | 1799 | CA | ARG | A | 357 | 44.719 | 4.375 | 37.913 | 1.00 | 80.85 | A | C |
| ATOM | 1800 | CB | ARG | A | 357 | 46.097 | 4.331 | 38.583 | 1.00 | 81.00 | A | C |
| ATOM | 1801 | CG | ARG | A | 357 | 46.998 | 5.502 | 38.213 | 1.00 | 84.22 | A | C |
| ATOM | 1802 | CD | ARG | A | 357 | 48.106 | 5.720 | 39.235 | 1.00 | 84.92 | A | C |
| ATOM | 1803 | NE | ARG | A | 357 | 49.194 | 6.523 | 38.683 | 1.00 | 85.32 | A | N |
| ATOM | 1804 | CZ | ARG | A | 357 | 50.012 | 6.105 | 37.721 | 1.00 | 85.13 | A | C |
| ATOM | 1805 | NH1 | ARG | A | 357 | 49.868 | 4.890 | 37.210 | 1.00 | 83.70 | A | N |
| ATOM | 1806 | NH2 | ARG | A | 357 | 50.970 | 6.901 | 37.264 | 1.00 | 82.39 | A | N |
| ATOM | 1807 | C | ARG | A | 357 | 44.139 | 2.968 | 37.816 | 1.00 | 80.46 | A | C |
| ATOM | 1808 | O | ARG | A | 357 | 44.192 | 2.345 | 36.756 | 1.00 | 81.00 | A | O |
| ATOM | 1809 | N | ASP | A | 358 | 43.581 | 2.467 | 38.912 | 1.00 | 80.63 | A | N |
| ATOM | 1810 | CA | ASP | A | 358 | 43.009 | 1.127 | 38.902 | 1.00 | 85.31 | A | C |

Figure 1DD

```
ATOM  1811  CB   ASP A 358      43.140    0.483   40.284   1.00   90.08   A        C
ATOM  1812  CG   ASP A 358      42.324    1.195   41.338   1.00   95.10   A        C
ATOM  1813  OD1  ASP A 358      42.327    2.440   41.349   1.00   97.84   A        O
ATOM  1814  OD2  ASP A 358      41.685    0.509   42.162   1.00   99.78   A        O
ATOM  1815  C    ASP A 358      41.548    1.147   38.470   1.00   85.66   A        C
ATOM  1816  O    ASP A 358      41.017    0.135   38.014   1.00   84.97   A        O
ATOM  1817  N    LEU A 359      40.902    2.299   38.613   1.00   85.76   A        N
ATOM  1818  CA   LEU A 359      39.506    2.430   38.225   1.00   88.71   A        C
ATOM  1819  CB   LEU A 359      38.917    3.726   38.794   1.00   88.21   A        C
ATOM  1820  CG   LEU A 359      37.480    4.117   38.421   1.00   87.42   A        C
ATOM  1821  CD1  LEU A 359      37.485    4.978   37.167   1.00   87.71   A        C
ATOM  1822  CD2  LEU A 359      36.627    2.866   38.233   1.00   84.26   A        C
ATOM  1823  C    LEU A 359      39.376    2.415   36.709   1.00   89.80   A        C
ATOM  1824  O    LEU A 359      38.428    1.853   36.165   1.00   93.70   A        O
ATOM  1825  N    ILE A 360      40.335    3.030   36.027   1.00   89.63   A        N
ATOM  1826  CA   ILE A 360      40.305    3.081   34.574   1.00   89.46   A        C
ATOM  1827  CB   ILE A 360      41.064    4.312   34.050   1.00   88.57   A        C
ATOM  1828  CG2  ILE A 360      42.506    4.259   34.503   1.00   85.73   A        C
ATOM  1829  CG1  ILE A 360      40.983    4.362   32.526   1.00   87.34   A        C
ATOM  1830  CD1  ILE A 360      41.597    5.600   31.931   1.00   86.28   A        C
ATOM  1831  C    ILE A 360      40.912    1.824   33.965   1.00   88.13   A        C
ATOM  1832  O    ILE A 360      40.408    1.301   32.971   1.00   87.68   A        O
ATOM  1833  N    SER A 361      41.993    1.341   34.566   1.00   84.60   A        N
ATOM  1834  CA   SER A 361      42.656    0.143   34.074   1.00   80.91   A        C
ATOM  1835  CB   SER A 361      43.913   -0.139   34.894   1.00   79.16   A        C
ATOM  1836  OG   SER A 361      45.067   -0.042   34.078   1.00   75.11   A        O
ATOM  1837  C    SER A 361      41.706   -1.042   34.146   1.00   79.71   A        C
ATOM  1838  O    SER A 361      41.827   -1.999   33.380   1.00   80.94   A        O
ATOM  1839  N    ARG A 362      40.760   -0.965   35.075   1.00   75.83   A        N
ATOM  1840  CA   ARG A 362      39.768   -2.014   35.246   1.00   74.19   A        C
ATOM  1841  CB   ARG A 362      39.096   -1.889   36.616   1.00   74.56   A        C
ATOM  1842  CG   ARG A 362      38.181   -3.051   36.956   1.00   79.80   A        C
ATOM  1843  CD   ARG A 362      38.828   -3.986   37.963   1.00   84.13   A        C
ATOM  1844  NE   ARG A 362      38.581   -3.550   39.335   1.00   85.30   A        N
ATOM  1845  CZ   ARG A 362      37.395   -3.616   39.932   1.00   86.23   A        C
ATOM  1846  NH1  ARG A 362      36.348   -4.101   39.278   1.00   86.36   A        N
ATOM  1847  NH2  ARG A 362      37.253   -3.201   41.183   1.00   84.60   A        N
ATOM  1848  C    ARG A 362      38.721   -1.855   34.143   1.00   72.90   A        C
ATOM  1849  O    ARG A 362      38.140   -2.833   33.678   1.00   72.79   A        O
ATOM  1850  N    LEU A 363      38.490   -0.612   33.728   1.00   71.80   A        N
ATOM  1851  CA   LEU A 363      37.515   -0.315   32.681   1.00   70.72   A        C
ATOM  1852  CB   LEU A 363      37.079    1.151   32.762   1.00   64.76   A        C
ATOM  1853  CG   LEU A 363      36.158    1.555   33.915   1.00   60.12   A        C
ATOM  1854  CD1  LEU A 363      36.021    3.069   33.978   1.00   56.35   A        C
ATOM  1855  CD2  LEU A 363      34.803    0.907   33.716   1.00   52.11   A        C
ATOM  1856  C    LEU A 363      38.068   -0.590   31.290   1.00   72.44   A        C
ATOM  1857  O    LEU A 363      37.393   -1.184   30.446   1.00   70.48   A        O
ATOM  1858  N    LEU A 364      39.300   -0.151   31.060   1.00   76.73   A        N
ATOM  1859  CA   LEU A 364      39.949   -0.324   29.770   1.00   81.33   A        C
ATOM  1860  CB   LEU A 364      40.978    0.790   29.556   1.00   84.37   A        C
ATOM  1861  CG   LEU A 364      40.379    2.192   29.398   1.00   85.33   A        C
ATOM  1862  CD1  LEU A 364      41.489    3.202   29.169   1.00   86.20   A        C
ATOM  1863  CD2  LEU A 364      39.401    2.209   28.230   1.00   81.47   A        C
ATOM  1864  C    LEU A 364      40.608   -1.686   29.585   1.00   80.71   A        C
ATOM  1865  O    LEU A 364      41.825   -1.825   29.714   1.00   79.90   A        O
ATOM  1866  N    LYS A 365      39.792   -2.688   29.280   1.00   79.64   A        N
ATOM  1867  CA   LYS A 365      40.287   -4.036   29.052   1.00   78.35   A        C
ATOM  1868  CB   LYS A 365      39.772   -4.986   30.136   1.00   77.82   A        C
ATOM  1869  CG   LYS A 365      40.702   -5.055   31.338   1.00   80.03   A        C
ATOM  1870  CD   LYS A 365      40.021   -5.574   32.591   1.00   83.87   A        C
ATOM  1871  CE   LYS A 365      40.989   -5.516   33.764   1.00   86.11   A        C
```

Figure 1EE

```
ATOM   1872  NZ   LYS A 365      40.345  -5.793  35.075  1.00  85.44      A    N
ATOM   1873  C    LYS A 365      39.875  -4.519  27.670  1.00  80.50      A    C
ATOM   1874  O    LYS A 365      38.705  -4.445  27.292  1.00  78.83      A    O
ATOM   1875  N    HIS A 366      40.859  -5.000  26.918  1.00  83.28      A    N
ATOM   1876  CA   HIS A 366      40.636  -5.495  25.567  1.00  84.31      A    C
ATOM   1877  CB   HIS A 366      41.879  -6.235  25.068  1.00  87.07      A    C
ATOM   1878  CG   HIS A 366      41.815  -6.617  23.622  1.00  92.58      A    C
ATOM   1879  CD2  HIS A 366      40.986  -7.455  22.956  1.00  95.01      A    C
ATOM   1880  ND1  HIS A 366      42.674  -6.097  22.677  1.00  97.09      A    N
ATOM   1881  CE1  HIS A 366      42.377  -6.599  21.492  1.00  98.44      A    C
ATOM   1882  NE2  HIS A 366      41.356  -7.425  21.633  1.00  97.38      A    N
ATOM   1883  C    HIS A 366      39.435  -6.428  25.520  1.00  83.89      A    C
ATOM   1884  O    HIS A 366      38.633  -6.373  24.590  1.00  80.13      A    O
ATOM   1885  N    ASN A 367      39.312  -7.279  26.532  1.00  87.01      A    N
ATOM   1886  CA   ASN A 367      38.213  -8.231  26.594  1.00  90.31      A    C
ATOM   1887  CB   ASN A 367      38.675  -9.499  27.316  1.00  94.38      A    C
ATOM   1888  CG   ASN A 367      38.396 -10.755  26.516  1.00  99.40      A    C
ATOM   1889  OD1  ASN A 367      38.540 -10.766  25.293  1.00  98.07      A    O
ATOM   1890  ND2  ASN A 367      38.009 -11.825  27.202  1.00 102.68      A    N
ATOM   1891  C    ASN A 367      36.992  -7.637  27.293  1.00  89.33      A    C
ATOM   1892  O    ASN A 367      37.070  -7.216  28.447  1.00  88.68      A    O
ATOM   1893  N    PRO A 368      35.844  -7.593  26.593  1.00  89.38      A    N
ATOM   1894  CD   PRO A 368      35.626  -8.089  25.224  1.00  86.96      A    C
ATOM   1895  CA   PRO A 368      34.602  -7.046  27.148  1.00  91.53      A    C
ATOM   1896  CB   PRO A 368      33.591  -7.269  26.023  1.00  89.15      A    C
ATOM   1897  CG   PRO A 368      34.438  -7.278  24.785  1.00  86.98      A    C
ATOM   1898  C    PRO A 368      34.213  -7.803  28.410  1.00  94.64      A    C
ATOM   1899  O    PRO A 368      33.976  -7.214  29.464  1.00  96.41      A    O
ATOM   1900  N    SER A 369      34.156  -9.123  28.273  1.00  97.36      A    N
ATOM   1901  CA   SER A 369      33.805 -10.018  29.364  1.00 101.06      A    C
ATOM   1902  CB   SER A 369      34.152 -11.457  28.974  1.00 102.60      A    C
ATOM   1903  OG   SER A 369      34.268 -12.285  30.117  1.00 108.96      A    O
ATOM   1904  C    SER A 369      34.500  -9.667  30.676  1.00 102.42      A    C
ATOM   1905  O    SER A 369      33.939  -9.873  31.751  1.00 103.45      A    O
ATOM   1906  N    GLN A 370      35.716  -9.134  30.589  1.00 103.21      A    N
ATOM   1907  CA   GLN A 370      36.474  -8.780  31.787  1.00 103.35      A    C
ATOM   1908  CB   GLN A 370      37.979  -8.864  31.513  1.00 101.24      A    C
ATOM   1909  CG   GLN A 370      38.497 -10.257  31.195  1.00  99.41      A    C
ATOM   1910  CD   GLN A 370      40.014 -10.335  31.243  1.00  99.54      A    C
ATOM   1911  OE1  GLN A 370      40.629 -11.136  30.539  1.00 103.93      A    O
ATOM   1912  NE2  GLN A 370      40.623  -9.509  32.087  1.00  98.34      A    N
ATOM   1913  C    GLN A 370      36.159  -7.396  32.345  1.00 103.55      A    C
ATOM   1914  O    GLN A 370      36.649  -7.032  33.415  1.00 104.91      A    O
ATOM   1915  N    ARG A 371      35.349  -6.626  31.628  1.00 101.46      A    N
ATOM   1916  CA   ARG A 371      34.998  -5.280  32.067  1.00  97.63      A    C
ATOM   1917  CB   ARG A 371      34.549  -4.438  30.870  1.00  95.62      A    C
ATOM   1924  C    ARG A 371      33.906  -5.273  33.135  1.00  95.93      A    C
ATOM   1925  O    ARG A 371      32.894  -5.962  33.008  1.00  95.32      A    O
ATOM   1926  N    PRO A 372      34.099  -4.479  34.202  1.00  94.85      A    N
ATOM   1927  CD   PRO A 372      35.209  -3.530  34.394  1.00  95.12      A    C
ATOM   1928  CA   PRO A 372      33.135  -4.374  35.300  1.00  95.00      A    C
ATOM   1929  CB   PRO A 372      33.820  -3.413  36.268  1.00  95.57      A    C
ATOM   1930  CG   PRO A 372      34.610  -2.533  35.357  1.00  96.16      A    C
ATOM   1931  C    PRO A 372      31.777  -3.861  34.832  1.00  94.75      A    C
ATOM   1932  O    PRO A 372      31.646  -3.352  33.719  1.00  97.12      A    O
ATOM   1933  N    MET A 373      30.771  -3.998  35.687  1.00  92.10      A    N
ATOM   1934  CA   MET A 373      29.426  -3.554  35.349  1.00  92.05      A    C
ATOM   1935  CB   MET A 373      28.412  -4.660  35.656  1.00  93.38      A    C
ATOM   1936  CG   MET A 373      27.438  -4.948  34.519  1.00  96.77      A    C
ATOM   1937  SD   MET A 373      26.501  -3.495  34.006  1.00 102.02      A    S
ATOM   1938  CE   MET A 373      25.407  -4.195  32.770  1.00  92.68      A    C
```

Figure 1FF

```
ATOM   1939  C   MET A 373      29.048  -2.286  36.106  1.00  91.70      A  C
ATOM   1940  O   MET A 373      29.842  -1.739  36.871  1.00  91.12      A  O
ATOM   1941  N   LEU A 374      27.821  -1.834  35.876  1.00  91.98      A  N
ATOM   1942  CA  LEU A 374      27.265  -0.637  36.492  1.00  93.17      A  C
ATOM   1943  CB  LEU A 374      25.747  -0.640  36.281  1.00  92.14      A  C
ATOM   1944  CG  LEU A 374      25.059  -2.007  36.417  1.00  89.07      A  C
ATOM   1945  CD1 LEU A 374      24.547  -2.208  37.832  1.00  86.18      A  C
ATOM   1946  CD2 LEU A 374      23.901  -2.092  35.441  1.00  86.52      A  C
ATOM   1947  C   LEU A 374      27.592  -0.434  37.973  1.00  95.60      A  C
ATOM   1948  O   LEU A 374      28.374   0.450  38.327  1.00  95.97      A  O
ATOM   1949  N   ARG A 375      26.994  -1.257  38.828  1.00  95.21      A  N
ATOM   1950  CA  ARG A 375      27.182  -1.170  40.274  1.00  92.13      A  C
ATOM   1951  CB  ARG A 375      26.447  -2.323  40.960  1.00  90.79      A  C
ATOM   1958  C   ARG A 375      28.634  -1.153  40.740  1.00  91.00      A  C
ATOM   1959  O   ARG A 375      28.958  -0.527  41.751  1.00  90.97      A  O
ATOM   1960  N   GLU A 376      29.506  -1.843  40.012  1.00  90.15      A  N
ATOM   1961  CA  GLU A 376      30.917  -1.898  40.378  1.00  90.23      A  C
ATOM   1962  CB  GLU A 376      31.700  -2.709  39.342  1.00  89.46      A  C
ATOM   1967  C   GLU A 376      31.510  -0.497  40.493  1.00  90.92      A  C
ATOM   1968  O   GLU A 376      31.945  -0.083  41.567  1.00  90.38      A  O
ATOM   1969  N   VAL A 377      31.521   0.228  39.380  1.00  93.10      A  N
ATOM   1970  CA  VAL A 377      32.061   1.582  39.350  1.00  94.36      A  C
ATOM   1971  CB  VAL A 377      32.093   2.133  37.910  1.00  94.04      A  C
ATOM   1974  C   VAL A 377      31.235   2.529  40.214  1.00  95.21      A  C
ATOM   1975  O   VAL A 377      31.769   3.463  40.810  1.00  96.50      A  O
ATOM   1976  N   LEU A 378      29.932   2.279  40.276  1.00  95.05      A  N
ATOM   1977  CA  LEU A 378      29.021   3.102  41.061  1.00  94.61      A  C
ATOM   1978  CB  LEU A 378      27.578   2.819  40.633  1.00  88.14      A  C
ATOM   1979  CG  LEU A 378      26.811   3.947  39.934  1.00  83.74      A  C
ATOM   1980  CD1 LEU A 378      27.761   4.860  39.169  1.00  80.09      A  C
ATOM   1981  CD2 LEU A 378      25.771   3.336  39.005  1.00  82.05      A  C
ATOM   1982  C   LEU A 378      29.177   2.876  42.562  1.00  96.93      A  C
ATOM   1983  O   LEU A 378      28.501   3.515  43.369  1.00  97.72      A  O
ATOM   1984  N   GLU A 379      30.074   1.965  42.928  1.00  97.82      A  N
ATOM   1985  CA  GLU A 379      30.339   1.649  44.329  1.00  96.52      A  C
ATOM   1986  CB  GLU A 379      29.540   0.415  44.754  1.00  96.06      A  C
ATOM   1991  C   GLU A 379      31.832   1.386  44.516  1.00  94.69      A  C
ATOM   1992  O   GLU A 379      32.254   0.782  45.503  1.00  97.69      A  O
ATOM   1993  N   HIS A 380      32.619   1.850  43.551  1.00  91.51      A  N
ATOM   1994  CA  HIS A 380      34.068   1.685  43.558  1.00  91.22      A  C
ATOM   1995  CB  HIS A 380      34.604   1.930  42.141  1.00  90.28      A  C
ATOM   1996  CG  HIS A 380      36.098   1.952  42.046  1.00  87.98      A  C
ATOM   1997  CD2 HIS A 380      36.970   1.060  41.521  1.00  86.19      A  C
ATOM   1998  ND1 HIS A 380      36.858   2.990  42.537  1.00  87.48      A  N
ATOM   1999  CE1 HIS A 380      38.137   2.737  42.318  1.00  85.91      A  C
ATOM   2000  NE2 HIS A 380      38.232   1.573  41.704  1.00  86.00      A  N
ATOM   2001  C   HIS A 380      34.739   2.625  44.563  1.00  91.71      A  C
ATOM   2002  O   HIS A 380      34.252   3.724  44.819  1.00  89.07      A  O
ATOM   2003  N   PRO A 381      35.867   2.197  45.154  1.00  93.36      A  N
ATOM   2004  CD  PRO A 381      36.509   0.881  44.999  1.00  93.32      A  C
ATOM   2005  CA  PRO A 381      36.596   3.009  46.134  1.00  95.25      A  C
ATOM   2006  CB  PRO A 381      37.728   2.081  46.579  1.00  94.28      A  C
ATOM   2007  CG  PRO A 381      37.925   1.181  45.397  1.00  92.08      A  C
ATOM   2008  C   PRO A 381      37.108   4.370  45.657  1.00  96.97      A  C
ATOM   2009  O   PRO A 381      37.861   5.030  46.372  1.00  97.79      A  O
ATOM   2010  N   TRP A 382      36.712   4.792  44.458  1.00  98.24      A  N
ATOM   2011  CA  TRP A 382      37.143   6.093  43.956  1.00 100.14      A  C
ATOM   2012  CB  TRP A 382      37.956   5.959  42.669  1.00 102.98      A  C
ATOM   2013  CG  TRP A 382      38.809   7.168  42.412  1.00 106.14      A  C
ATOM   2014  CD2 TRP A 382      38.634   8.143  41.376  1.00 106.96      A  C
ATOM   2015  CE2 TRP A 382      39.646   9.116  41.541  1.00 108.81      A  C
```

Figure 1GG

```
ATOM  2016  CE3  TRP A 382      37.715   8.294  40.329  1.00  105.08    A    C
ATOM  2017  CD1  TRP A 382      39.892   7.574  43.139  1.00  108.44    A    C
ATOM  2018  NE1  TRP A 382      40.401   8.745  42.622  1.00  110.49    A    N
ATOM  2019  CZ2  TRP A 382      39.770  10.220  40.692  1.00  107.72    A    C
ATOM  2020  CZ3  TRP A 382      37.839   9.394  39.483  1.00  106.37    A    C
ATOM  2021  CH2  TRP A 382      38.858  10.344  39.674  1.00  106.62    A    C
ATOM  2022  C    TRP A 382      35.932   6.987  43.715  1.00  100.57    A    C
ATOM  2023  O    TRP A 382      35.994   8.195  43.951  1.00   98.78    A    O
ATOM  2024  N    ILE A 383      34.838   6.403  43.231  1.00  101.81    A    N
ATOM  2025  CA   ILE A 383      33.617   7.176  43.022  1.00  104.81    A    C
ATOM  2026  CB   ILE A 383      32.452   6.309  42.481  1.00  106.59    A    C
ATOM  2027  CG2  ILE A 383      32.459   4.942  43.139  1.00  104.66    A    C
ATOM  2028  CG1  ILE A 383      31.119   7.022  42.733  1.00  108.98    A    C
ATOM  2029  CD1  ILE A 383      29.893   6.146  42.554  1.00  109.51    A    C
ATOM  2030  C    ILE A 383      33.261   7.648  44.422  1.00  106.17    A    C
ATOM  2031  O    ILE A 383      32.991   8.828  44.651  1.00  106.49    A    O
ATOM  2032  N    THR A 384      33.273   6.699  45.353  1.00  108.25    A    N
ATOM  2033  CA   THR A 384      32.996   6.970  46.754  1.00  109.45    A    C
ATOM  2034  CB   THR A 384      32.741   5.660  47.537  1.00  110.60    A    C
ATOM  2035  OG1  THR A 384      33.891   4.809  47.441  1.00  110.98    A    O
ATOM  2036  CG2  THR A 384      31.530   4.927  46.971  1.00  109.33    A    C
ATOM  2037  C    THR A 384      34.254   7.649  47.285  1.00  109.77    A    C
ATOM  2038  O    THR A 384      35.353   7.115  47.142  1.00  109.57    A    O
ATOM  2039  N    ALA A 385      34.071   8.826  47.882  1.00  110.37    A    N
ATOM  2040  CA   ALA A 385      35.141   9.666  48.432  1.00  112.53    A    C
ATOM  2041  CB   ALA A 385      36.474   8.913  48.501  1.00  111.99    A    C
ATOM  2042  C    ALA A 385      35.258  10.860  47.491  1.00  113.04    A    C
ATOM  2043  O    ALA A 385      34.446  11.783  47.559  1.00  115.94    A    O
ATOM  2044  N    ASN A 386      36.253  10.840  46.609  1.00  111.79    A    N
ATOM  2045  CA   ASN A 386      36.425  11.929  45.654  1.00  109.04    A    C
ATOM  2046  CB   ASN A 386      37.598  11.647  44.710  1.00  104.45    A    C
ATOM  2047  CG   ASN A 386      38.936  11.658  45.417  1.00  104.48    A    C
ATOM  2048  OD1  ASN A 386      39.279  12.618  46.106  1.00  103.93    A    O
ATOM  2049  ND2  ASN A 386      39.706  10.590  45.243  1.00  106.22    A    N
ATOM  2050  C    ASN A 386      35.150  12.066  44.830  1.00  109.99    A    C
ATOM  2051  O    ASN A 386      34.628  11.076  44.316  1.00  110.65    A    O
ATOM  2052  N    SER A 387      34.648  13.292  44.719  1.00  110.34    A    N
ATOM  2053  CA   SER A 387      33.439  13.571  43.949  1.00  111.41    A    C
ATOM  2054  CB   SER A 387      33.621  13.116  42.504  1.00  111.26    A    C
ATOM  2056  C    SER A 387      32.181  12.927  44.517  1.00  112.05    A    C
ATOM  2057  O    SER A 387      32.088  11.703  44.628  1.00  112.03    A    O
ATOM  2058  N    SER A 388      31.212  13.774  44.852  1.00  112.96    A    N
ATOM  2059  CA   SER A 388      29.931  13.357  45.414  1.00  114.75    A    C
ATOM  2060  CB   SER A 388      28.847  14.367  45.031  1.00  112.67    A    C
ATOM  2061  OG   SER A 388      27.597  14.013  45.596  1.00  114.44    A    O
ATOM  2062  C    SER A 388      29.466  11.958  45.018  1.00  117.30    A    C
ATOM  2063  O    SER A 388      29.737  11.482  43.914  1.00  115.65    A    O
ATOM  2064  N    LYS A 389      28.746  11.319  45.935  1.00  121.30    A    N
ATOM  2065  CA   LYS A 389      28.216   9.975  45.736  1.00  125.05    A    C
ATOM  2066  CB   LYS A 389      27.800   9.389  47.089  1.00  122.77    A    C
ATOM  2071  C    LYS A 389      27.020   9.990  44.778  1.00  128.15    A    C
ATOM  2072  O    LYS A 389      26.569  11.057  44.358  1.00  129.66    A    O
ATOM  2073  N    PRO A 390      26.492   8.803  44.420  1.00  128.94    A    N
ATOM  2074  CD   PRO A 390      26.918   7.463  44.867  1.00  128.63    A    C
ATOM  2075  CA   PRO A 390      25.347   8.695  43.509  1.00  128.53    A    C
ATOM  2076  CB   PRO A 390      24.858   7.274  43.754  1.00  126.83    A    C
ATOM  2077  CG   PRO A 390      26.134   6.539  43.951  1.00  126.18    A    C
ATOM  2078  C    PRO A 390      24.257   9.734  43.757  1.00  129.34    A    C
ATOM  2079  O    PRO A 390      24.289  10.765  43.051  1.00  129.66    A    O
TER   2081       PRO A 390                                              A
ATOM  2082  C1   216 B   1      27.070  23.338  20.180  1.00   93.97    B    C
```

Figure 1HH

```
ATOM   2083  C2   216 B   1      25.733  23.364  20.566  1.00   93.18      B    C
ATOM   2084  C3   216 B   1      24.767  22.820  19.732  1.00   92.55      B    C
ATOM   2085  C4   216 B   1      25.128  22.260  18.505  1.00   92.63      B    C
ATOM   2086  C55  216 B   1      26.469  22.237  18.117  1.00   94.07      B    C
ATOM   2087  C6   216 B   1      27.443  22.780  18.955  1.00   94.54      B    C
ATOM   2088  C7   216 B   1      24.625  25.148  24.180  1.00   95.50      B    C
ATOM   2089  C9   216 B   1      25.796  25.550  23.500  1.00   96.00      B    C
ATOM   2090  N    216 B   1      26.152  24.948  22.310  1.00   93.73      B    N
ATOM   2091  C14  216 B   1      25.370  23.950  21.770  1.00   92.76      B    C
ATOM   2092  N2   216 B   1      24.229  23.566  22.443  1.00   92.60      B    N
ATOM   2093  C17  216 B   1      23.838  24.138  23.634  1.00   94.87      B    C
ATOM   2094  C8   216 B   1      21.062  20.844  23.065  1.00  100.05      B    C
ATOM   2095  C10  216 B   1      22.140  21.767  23.054  1.00   97.29      B    C
ATOM   2096  C12  216 B   1      21.776  22.769  23.932  1.00   94.91      B    C
ATOM   2097  N4   216 B   1      20.479  22.633  24.356  1.00   91.80      B    N
ATOM   2098  N3   216 B   1      19.999  21.500  23.741  1.00   95.15      B    N
ATOM   2099  C15  216 B   1      21.052  19.595  22.496  1.00  104.55      B    C
ATOM   2100  C11  216 B   1      24.268  25.768  25.380  1.00   95.89      B    C
ATOM   2101  C13  216 B   1      25.069  26.790  25.909  1.00   96.79      B    C
ATOM   2102  C16  216 B   1      26.233  27.189  25.238  1.00   98.64      B    C
ATOM   2103  C5   216 B   1      26.594  26.568  24.035  1.00   98.25      B    C
ATOM   2104  N6   216 B   1      22.682  23.749  24.277  1.00   96.61      B    N
ATOM   2105  C18  216 B   1      20.263  19.429  21.331  1.00  105.53      B    C
ATOM   2106  C19  216 B   1      19.797  18.949  22.583  1.00  107.33      B    C
TER    2107       216 B   1                                                B
END
```

Figure 2A

| Atom | Type | Resid | # | X | Y | Z | Occ | B | Mol | |
|------|------|-------|---|---|---|---|-----|---|-----|---|
| ATOM | 1 | CB | ASN A 120 | -25.184 | 17.387 | 17.980 | 1.00 | 134.47 | A | C |
| ATOM | 5 | C | ASN A 120 | -23.201 | 15.983 | 17.367 | 1.00 | 139.87 | A | C |
| ATOM | 6 | O | ASN A 120 | -22.523 | 17.000 | 17.516 | 1.00 | 141.64 | A | O |
| ATOM | 7 | N | ASN A 120 | -25.010 | 15.048 | 18.805 | 1.00 | 137.11 | A | N |
| ATOM | 8 | CA | ASN A 120 | -24.696 | 15.967 | 17.672 | 1.00 | 139.34 | A | C |
| ATOM | 9 | N | GLU A 121 | -22.716 | 14.819 | 16.953 | 1.00 | 143.53 | A | N |
| ATOM | 10 | CA | GLU A 121 | -21.332 | 14.556 | 16.564 | 1.00 | 145.36 | A | C |
| ATOM | 11 | CB | GLU A 121 | -21.265 | 14.440 | 15.038 | 1.00 | 148.03 | A | C |
| ATOM | 16 | C | GLU A 121 | -20.142 | 15.404 | 17.024 | 1.00 | 145.17 | A | C |
| ATOM | 17 | O | GLU A 121 | -19.788 | 15.422 | 18.205 | 1.00 | 147.49 | A | O |
| ATOM | 18 | N | GLU A 122 | -19.531 | 16.080 | 16.049 | 1.00 | 142.16 | A | N |
| ATOM | 19 | CA | GLU A 122 | -18.316 | 16.885 | 16.203 | 1.00 | 138.66 | A | C |
| ATOM | 20 | CB | GLU A 122 | -18.059 | 17.310 | 17.653 | 1.00 | 138.41 | A | C |
| ATOM | 25 | C | GLU A 122 | -17.328 | 15.809 | 15.806 | 1.00 | 133.45 | A | C |
| ATOM | 26 | O | GLU A 122 | -16.478 | 16.014 | 14.931 | 1.00 | 134.51 | A | O |
| ATOM | 27 | N | SER A 123 | -17.484 | 14.650 | 16.454 | 1.00 | 128.27 | A | N |
| ATOM | 28 | CA | SER A 123 | -16.674 | 13.471 | 16.172 | 1.00 | 122.12 | A | C |
| ATOM | 29 | CB | SER A 123 | -17.429 | 12.213 | 16.618 | 1.00 | 120.57 | A | C |
| ATOM | 31 | C | SER A 123 | -16.496 | 13.499 | 14.650 | 1.00 | 117.73 | A | C |
| ATOM | 32 | O | SER A 123 | -17.391 | 13.117 | 13.887 | 1.00 | 116.68 | A | O |
| ATOM | 33 | N | LYS A 124 | -15.333 | 13.978 | 14.226 | 1.00 | 114.78 | A | N |
| ATOM | 34 | CA | LYS A 124 | -15.039 | 14.147 | 12.816 | 1.00 | 111.29 | A | C |
| ATOM | 35 | CB | LYS A 124 | -14.153 | 15.380 | 12.657 | 1.00 | 108.44 | A | C |
| ATOM | 40 | C | LYS A 124 | -14.407 | 12.972 | 12.072 | 1.00 | 110.56 | A | C |
| ATOM | 41 | O | LYS A 124 | -13.623 | 13.184 | 11.154 | 1.00 | 111.66 | A | O |
| ATOM | 42 | N | LYS A 125 | -14.775 | 11.744 | 12.416 | 1.00 | 110.30 | A | N |
| ATOM | 43 | CA | LYS A 125 | -14.185 | 10.568 | 11.772 | 1.00 | 109.56 | A | C |
| ATOM | 44 | CB | LYS A 125 | -14.239 | 9.399 | 12.764 | 1.00 | 106.61 | A | C |
| ATOM | 49 | C | LYS A 125 | -14.699 | 10.084 | 10.383 | 1.00 | 109.28 | A | C |
| ATOM | 50 | O | LYS A 125 | -14.010 | 9.317 | 9.715 | 1.00 | 113.16 | A | O |
| ATOM | 51 | N | ARG A 126 | -15.874 | 10.547 | 9.949 | 1.00 | 104.45 | A | N |
| ATOM | 52 | CA | ARG A 126 | -16.553 | 10.151 | 8.683 | 1.00 | 98.84 | A | C |
| ATOM | 53 | CB | ARG A 126 | -17.682 | 11.156 | 8.404 | 1.00 | 94.42 | A | C |
| ATOM | 60 | C | ARG A 126 | -15.854 | 9.859 | 7.330 | 1.00 | 94.87 | A | C |
| ATOM | 61 | O | ARG A 126 | -14.821 | 9.181 | 7.258 | 1.00 | 93.08 | A | O |
| ATOM | 62 | N | GLN A 127 | -16.510 | 10.340 | 6.263 | 1.00 | 93.82 | A | N |
| ATOM | 63 | CA | GLN A 127 | -16.082 | 10.229 | 4.852 | 1.00 | 91.47 | A | C |
| ATOM | 64 | CB | GLN A 127 | -16.553 | 8.893 | 4.254 | 1.00 | 89.98 | A | C |
| ATOM | 69 | C | GLN A 127 | -16.709 | 11.418 | 4.074 | 1.00 | 89.31 | A | C |
| ATOM | 70 | O | GLN A 127 | -17.539 | 11.248 | 3.172 | 1.00 | 89.46 | A | O |
| ATOM | 71 | N | TRP A 128 | -16.281 | 12.619 | 4.455 | 1.00 | 87.24 | A | N |
| ATOM | 72 | CA | TRP A 128 | -16.748 | 13.901 | 3.927 | 1.00 | 83.92 | A | C |
| ATOM | 73 | CB | TRP A 128 | -15.728 | 14.968 | 4.300 | 1.00 | 86.41 | A | C |
| ATOM | 74 | CG | TRP A 128 | -15.199 | 14.741 | 5.655 | 1.00 | 92.37 | A | C |
| ATOM | 75 | CD2 | TRP A 128 | -15.930 | 14.831 | 6.882 | 1.00 | 94.67 | A | C |
| ATOM | 76 | CE2 | TRP A 128 | -15.048 | 14.464 | 7.922 | 1.00 | 96.00 | A | C |
| ATOM | 77 | CE3 | TRP A 128 | -17.243 | 15.185 | 7.202 | 1.00 | 93.59 | A | C |
| ATOM | 78 | CD1 | TRP A 128 | -13.940 | 14.338 | 5.986 | 1.00 | 95.29 | A | C |
| ATOM | 79 | NE1 | TRP A 128 | -13.841 | 14.168 | 7.350 | 1.00 | 97.00 | A | N |
| ATOM | 80 | CZ2 | TRP A 128 | -15.438 | 14.440 | 9.263 | 1.00 | 95.88 | A | C |
| ATOM | 81 | CZ3 | TRP A 128 | -17.631 | 15.159 | 8.532 | 1.00 | 94.85 | A | C |
| ATOM | 82 | CH2 | TRP A 128 | -16.729 | 14.788 | 9.550 | 1.00 | 95.78 | A | C |
| ATOM | 83 | C | TRP A 128 | -17.141 | 14.102 | 2.466 | 1.00 | 81.09 | A | C |
| ATOM | 84 | O | TRP A 128 | -16.633 | 13.447 | 1.552 | 1.00 | 79.39 | A | O |
| ATOM | 85 | N | ALA A 129 | -18.053 | 15.058 | 2.290 | 1.00 | 78.26 | A | N |
| ATOM | 86 | CA | ALA A 129 | -18.587 | 15.477 | 1.001 | 1.00 | 76.01 | A | C |
| ATOM | 87 | CB | ALA A 129 | -19.874 | 14.727 | 0.693 | 1.00 | 74.48 | A | C |
| ATOM | 88 | C | ALA A 129 | -18.881 | 16.966 | 1.165 | 1.00 | 75.27 | A | C |

Figure 2B

| ATOM | 89 | O | ALA | A | 129 | -19.232 | 17.405 | 2.265 | 1.00 | 74.01 | A | O |
| --- | --- | --- | --- | --- | --- | --- | --- | --- | --- | --- | --- | --- |
| ATOM | 90 | N | LEU | A | 130 | -18.741 | 17.746 | 0.093 | 1.00 | 74.72 | A | N |
| ATOM | 91 | CA | LEU | A | 130 | -19.016 | 19.172 | 0.187 | 1.00 | 72.32 | A | C |
| ATOM | 92 | CB | LEU | A | 130 | -18.910 | 19.849 | -1.180 | 1.00 | 66.69 | A | C |
| ATOM | 93 | CG | LEU | A | 130 | -19.205 | 21.360 | -1.201 | 1.00 | 62.03 | A | C |
| ATOM | 94 | CD1 | LEU | A | 130 | -18.330 | 22.068 | -0.158 | 1.00 | 57.90 | A | C |
| ATOM | 95 | CD2 | LEU | A | 130 | -18.931 | 21.938 | -2.593 | 1.00 | 59.55 | A | C |
| ATOM | 96 | C | LEU | A | 130 | -20.420 | 19.347 | 0.738 | 1.00 | 74.13 | A | C |
| ATOM | 97 | O | LEU | A | 130 | -20.712 | 20.325 | 1.429 | 1.00 | 74.05 | A | O |
| ATOM | 98 | N | GLU | A | 131 | -21.288 | 18.384 | 0.448 | 1.00 | 75.10 | A | N |
| ATOM | 99 | CA | GLU | A | 131 | -22.663 | 18.463 | 0.924 | 1.00 | 75.77 | A | C |
| ATOM | 100 | CB | GLU | A | 131 | -23.483 | 17.255 | 0.468 | 1.00 | 79.06 | A | C |
| ATOM | 101 | CG | GLU | A | 131 | -24.975 | 17.453 | 0.710 | 1.00 | 87.95 | A | C |
| ATOM | 102 | CD | GLU | A | 131 | -25.740 | 16.155 | 0.902 | 1.00 | 93.25 | A | C |
| ATOM | 103 | OE1 | GLU | A | 131 | -25.653 | 15.270 | 0.024 | 1.00 | 95.69 | A | O |
| ATOM | 104 | OE2 | GLU | A | 131 | -26.440 | 16.025 | 1.935 | 1.00 | 96.56 | A | O |
| ATOM | 105 | C | GLU | A | 131 | -22.760 | 18.557 | 2.441 | 1.00 | 74.18 | A | C |
| ATOM | 106 | O | GLU | A | 131 | -23.487 | 19.400 | 2.950 | 1.00 | 76.86 | A | O |
| ATOM | 107 | N | ASP | A | 132 | -22.032 | 17.692 | 3.151 | 1.00 | 72.20 | A | N |
| ATOM | 108 | CA | ASP | A | 132 | -22.050 | 17.650 | 4.626 | 1.00 | 69.11 | A | C |
| ATOM | 109 | CB | ASP | A | 132 | -21.021 | 16.633 | 5.150 | 1.00 | 67.71 | A | C |
| ATOM | 110 | CG | ASP | A | 132 | -21.232 | 15.235 | 4.592 | 1.00 | 67.05 | A | C |
| ATOM | 111 | OD1 | ASP | A | 132 | -21.251 | 15.100 | 3.358 | 1.00 | 70.79 | A | O |
| ATOM | 112 | OD2 | ASP | A | 132 | -21.373 | 14.270 | 5.377 | 1.00 | 62.87 | A | O |
| ATOM | 113 | C | ASP | A | 132 | -21.808 | 18.969 | 5.372 | 1.00 | 66.16 | A | C |
| ATOM | 114 | O | ASP | A | 132 | -21.774 | 18.970 | 6.597 | 1.00 | 60.94 | A | O |
| ATOM | 115 | N | PHE | A | 133 | -21.655 | 20.084 | 4.660 | 1.00 | 65.23 | A | N |
| ATOM | 116 | CA | PHE | A | 133 | -21.363 | 21.355 | 5.327 | 1.00 | 60.63 | A | C |
| ATOM | 117 | CB | PHE | A | 133 | -19.865 | 21.676 | 5.187 | 1.00 | 59.10 | A | C |
| ATOM | 118 | CG | PHE | A | 133 | -18.953 | 20.607 | 5.730 | 1.00 | 54.10 | A | C |
| ATOM | 119 | CD1 | PHE | A | 133 | -18.756 | 19.431 | 5.029 | 1.00 | 49.91 | A | C |
| ATOM | 120 | CD2 | PHE | A | 133 | -18.299 | 20.789 | 6.951 | 1.00 | 54.44 | A | C |
| ATOM | 121 | CE1 | PHE | A | 133 | -17.925 | 18.447 | 5.519 | 1.00 | 49.64 | A | C |
| ATOM | 122 | CE2 | PHE | A | 133 | -17.462 | 19.820 | 7.462 | 1.00 | 54.13 | A | C |
| ATOM | 123 | CZ | PHE | A | 133 | -17.267 | 18.635 | 6.746 | 1.00 | 51.78 | A | C |
| ATOM | 124 | C | PHE | A | 133 | -22.140 | 22.575 | 4.878 | 1.00 | 58.23 | A | C |
| ATOM | 125 | O | PHE | A | 133 | -22.522 | 22.675 | 3.729 | 1.00 | 58.00 | A | O |
| ATOM | 126 | N | GLU | A | 134 | -22.347 | 23.507 | 5.805 | 1.00 | 57.00 | A | N |
| ATOM | 127 | CA | GLU | A | 134 | -23.036 | 24.774 | 5.531 | 1.00 | 57.26 | A | C |
| ATOM | 128 | CB | GLU | A | 134 | -24.039 | 25.086 | 6.639 | 1.00 | 49.36 | A | C |
| ATOM | 133 | C | GLU | A | 134 | -21.945 | 25.848 | 5.491 | 1.00 | 59.26 | A | C |
| ATOM | 134 | O | GLU | A | 134 | -21.188 | 26.020 | 6.446 | 1.00 | 60.67 | A | O |
| ATOM | 135 | N | ILE | A | 135 | -21.845 | 26.570 | 4.390 | 1.00 | 60.17 | A | N |
| ATOM | 136 | CA | ILE | A | 135 | -20.783 | 27.548 | 4.292 | 1.00 | 62.37 | A | C |
| ATOM | 137 | CB | ILE | A | 135 | -20.202 | 27.605 | 2.854 | 1.00 | 59.94 | A | C |
| ATOM | 138 | CG2 | ILE | A | 135 | -19.541 | 26.277 | 2.509 | 1.00 | 56.04 | A | C |
| ATOM | 139 | CG1 | ILE | A | 135 | -21.319 | 27.926 | 1.862 | 1.00 | 61.70 | A | C |
| ATOM | 140 | CD1 | ILE | A | 135 | -20.858 | 28.594 | 0.569 | 1.00 | 60.25 | A | C |
| ATOM | 141 | C | ILE | A | 135 | -21.167 | 28.953 | 4.706 | 1.00 | 66.13 | A | C |
| ATOM | 142 | O | ILE | A | 135 | -22.229 | 29.456 | 4.331 | 1.00 | 68.81 | A | O |
| ATOM | 143 | N | GLY | A | 136 | -20.282 | 29.580 | 5.478 | 1.00 | 68.37 | A | N |
| ATOM | 144 | CA | GLY | A | 136 | -20.495 | 30.944 | 5.922 | 1.00 | 67.99 | A | C |
| ATOM | 145 | C | GLY | A | 136 | -19.749 | 31.913 | 5.018 | 1.00 | 66.99 | A | C |
| ATOM | 146 | O | GLY | A | 136 | -19.551 | 31.619 | 3.842 | 1.00 | 68.95 | A | O |
| ATOM | 147 | N | ARG | A | 137 | -19.338 | 33.058 | 5.562 | 1.00 | 65.08 | A | N |
| ATOM | 148 | CA | ARG | A | 137 | -18.611 | 34.075 | 4.799 | 1.00 | 64.58 | A | C |
| ATOM | 149 | CB | ARG | A | 137 | -18.516 | 35.369 | 5.612 | 1.00 | 64.24 | A | C |
| ATOM | 150 | CG | ARG | A | 137 | -17.245 | 35.491 | 6.489 | 1.00 | 61.36 | A | C |
| ATOM | 151 | CD | ARG | A | 137 | -17.508 | 36.256 | 7.792 | 1.00 | 62.13 | A | C |
| ATOM | 152 | NE | ARG | A | 137 | -16.265 | 36.433 | 8.541 | 1.00 | 72.52 | A | N |
| ATOM | 153 | CZ | ARG | A | 137 | -16.173 | 36.502 | 9.868 | 1.00 | 75.05 | A | C |

Figure 2C

```
ATOM    154  NH1 ARG A 137     -14.986  36.664  10.449  1.00  74.71      A  N
ATOM    155  NH2 ARG A 137     -17.257  36.399  10.617  1.00  75.04      A  N
ATOM    156  C   ARG A 137     -17.204  33.593   4.514  1.00  65.94      A  C
ATOM    157  O   ARG A 137     -16.818  32.513   4.942  1.00  66.67      A  O
ATOM    158  N   PRO A 138     -16.429  34.369   3.749  1.00  68.43      A  N
ATOM    159  CD  PRO A 138     -16.934  35.337   2.762  1.00  71.71      A  C
ATOM    160  CA  PRO A 138     -15.040  33.996   3.430  1.00  68.44      A  C
ATOM    161  CB  PRO A 138     -14.818  34.626   2.059  1.00  68.50      A  C
ATOM    162  CG  PRO A 138     -15.651  35.852   2.132  1.00  72.38      A  C
ATOM    163  C   PRO A 138     -14.102  34.582   4.501  1.00  69.30      A  C
ATOM    164  O   PRO A 138     -13.894  35.807   4.568  1.00  71.18      A  O
ATOM    165  N   LEU A 139     -13.551  33.709   5.341  1.00  68.08      A  N
ATOM    166  CA  LEU A 139     -12.676  34.149   6.402  1.00  66.00      A  C
ATOM    167  CB  LEU A 139     -12.226  32.962   7.246  1.00  60.44      A  C
ATOM    168  CG  LEU A 139     -13.366  32.246   7.995  1.00  56.97      A  C
ATOM    169  CD1 LEU A 139     -12.791  31.129   8.881  1.00  58.44      A  C
ATOM    170  CD2 LEU A 139     -14.150  33.250   8.856  1.00  55.72      A  C
ATOM    171  C   LEU A 139     -11.474  34.937   5.917  1.00  69.54      A  C
ATOM    172  O   LEU A 139     -10.885  35.680   6.701  1.00  70.82      A  O
ATOM    173  N   GLY A 140     -11.121  34.803   4.639  1.00  72.38      A  N
ATOM    174  CA  GLY A 140      -9.987  35.548   4.116  1.00  76.78      A  C
ATOM    175  C   GLY A 140      -9.433  35.075   2.780  1.00  80.16      A  C
ATOM    176  O   GLY A 140      -9.590  33.904   2.426  1.00  80.45      A  O
ATOM    177  N   LYS A 141      -8.772  35.974   2.046  1.00  82.86      A  N
ATOM    178  CA  LYS A 141      -8.198  35.639   0.742  1.00  88.14      A  C
ATOM    179  CB  LYS A 141      -7.649  36.899   0.067  1.00  84.53      A  C
ATOM    184  C   LYS A 141      -7.094  34.569   0.788  1.00  92.85      A  C
ATOM    185  O   LYS A 141      -6.452  34.360   1.820  1.00  95.88      A  O
ATOM    186  N   GLY A 142      -6.873  33.899  -0.341  1.00  96.31      A  N
ATOM    187  CA  GLY A 142      -5.851  32.867  -0.391  1.00  99.27      A  C
ATOM    188  C   GLY A 142      -5.416  32.479  -1.793  1.00 102.36      A  C
ATOM    189  O   GLY A 142      -4.659  31.516  -1.950  1.00 101.58      A  O
ATOM    190  N   LYS A 143      -5.896  33.232  -2.790  1.00 105.52      A  N
ATOM    191  CA  LYS A 143      -5.597  33.040  -4.222  1.00 106.84      A  C
ATOM    192  CB  LYS A 143      -4.193  33.581  -4.553  1.00 108.45      A  C
ATOM    193  CG  LYS A 143      -3.903  33.731  -6.047  1.00 109.75      A  C
ATOM    194  CD  LYS A 143      -2.518  34.328  -6.297  1.00 110.63      A  C
ATOM    195  CE  LYS A 143      -2.229  34.527  -7.790  1.00 112.22      A  C
ATOM    196  NZ  LYS A 143      -3.041  35.612  -8.427  1.00 111.69      A  N
ATOM    197  C   LYS A 143      -5.733  31.587  -4.696  1.00 106.80      A  C
ATOM    198  O   LYS A 143      -6.361  31.317  -5.727  1.00 106.21      A  O
ATOM    199  N   PHE A 144      -5.123  30.665  -3.950  1.00 106.27      A  N
ATOM    200  CA  PHE A 144      -5.194  29.236  -4.236  1.00 101.88      A  C
ATOM    201  CB  PHE A 144      -4.263  28.461  -3.301  1.00 102.76      A  C
ATOM    202  CG  PHE A 144      -2.980  28.022  -3.944  1.00 105.27      A  C
ATOM    203  CD1 PHE A 144      -1.924  27.560  -3.166  1.00 106.66      A  C
ATOM    204  CD2 PHE A 144      -2.830  28.044  -5.326  1.00 104.58      A  C
ATOM    205  CE1 PHE A 144      -0.739  27.126  -3.754  1.00 104.82      A  C
ATOM    206  CE2 PHE A 144      -1.650  27.611  -5.925  1.00 103.14      A  C
ATOM    207  CZ  PHE A 144      -0.603  27.151  -5.136  1.00 103.53      A  C
ATOM    208  C   PHE A 144      -6.630  28.858  -3.931  1.00  98.80      A  C
ATOM    209  O   PHE A 144      -7.278  28.125  -4.680  1.00  97.75      A  O
ATOM    210  N   GLY A 145      -7.116  29.388  -2.815  1.00  95.65      A  N
ATOM    211  CA  GLY A 145      -8.471  29.122  -2.392  1.00  91.96      A  C
ATOM    212  C   GLY A 145      -8.787  29.798  -1.075  1.00  89.29      A  C
ATOM    213  O   GLY A 145      -7.974  29.774  -0.141  1.00  90.14      A  O
ATOM    214  N   ASN A 146      -9.968  30.411  -1.009  1.00  85.63      A  N
ATOM    215  CA  ASN A 146     -10.423  31.091   0.195  1.00  80.37      A  C
ATOM    216  CB  ASN A 146     -11.774  31.761  -0.031  1.00  77.72      A  C
ATOM    217  CG  ASN A 146     -11.845  32.497  -1.333  1.00  75.55      A  C
ATOM    218  OD1 ASN A 146     -10.953  33.272  -1.662  1.00  73.48      A  O
```

Figure 2D

```
ATOM    219  ND2 ASN A 146     -12.915  32.271  -2.085  1.00  74.52      A    N
ATOM    220  C   ASN A 146     -10.615  30.074   1.295  1.00  79.12      A    C
ATOM    221  O   ASN A 146     -10.521  28.861   1.079  1.00  78.35      A    O
ATOM    222  N   VAL A 147     -10.884  30.582   2.487  1.00  77.60      A    N
ATOM    223  CA  VAL A 147     -11.155  29.724   3.620  1.00  77.24      A    C
ATOM    224  CB  VAL A 147     -10.133  29.889   4.739  1.00  77.88      A    C
ATOM    225  CG1 VAL A 147     -10.391  28.840   5.832  1.00  78.34      A    C
ATOM    226  CG2 VAL A 147      -8.735  29.750   4.183  1.00  82.13      A    C
ATOM    227  C   VAL A 147     -12.487  30.241   4.082  1.00  76.51      A    C
ATOM    228  O   VAL A 147     -12.604  31.405   4.447  1.00  76.88      A    O
ATOM    229  N   TYR A 148     -13.501  29.388   4.035  1.00  77.03      A    N
ATOM    230  CA  TYR A 148     -14.830  29.816   4.442  1.00  76.02      A    C
ATOM    231  CB  TYR A 148     -15.890  29.344   3.448  1.00  77.00      A    C
ATOM    232  CG  TYR A 148     -15.725  29.863   2.049  1.00  75.64      A    C
ATOM    233  CD1 TYR A 148     -14.756  29.327   1.196  1.00  73.17      A    C
ATOM    234  CE1 TYR A 148     -14.617  29.782  -0.098  1.00  72.40      A    C
ATOM    235  CD2 TYR A 148     -16.548  30.876   1.571  1.00  74.33      A    C
ATOM    236  CE2 TYR A 148     -16.415  31.339   0.280  1.00  75.51      A    C
ATOM    237  CZ  TYR A 148     -15.449  30.787  -0.553  1.00  74.23      A    C
ATOM    238  OH  TYR A 148     -15.342  31.240  -1.846  1.00  74.52      A    O
ATOM    239  C   TYR A 148     -15.240  29.316   5.801  1.00  73.10      A    C
ATOM    240  O   TYR A 148     -14.793  28.257   6.242  1.00  73.57      A    O
ATOM    241  N   LEU A 149     -16.097  30.093   6.458  1.00  69.73      A    N
ATOM    242  CA  LEU A 149     -16.628  29.695   7.744  1.00  69.52      A    C
ATOM    243  CB  LEU A 149     -17.522  30.779   8.314  1.00  70.25      A    C
ATOM    244  CG  LEU A 149     -17.076  31.433   9.620  1.00  69.99      A    C
ATOM    245  CD1 LEU A 149     -18.310  32.028  10.272  1.00  72.54      A    C
ATOM    246  CD2 LEU A 149     -16.421  30.433  10.556  1.00  67.04      A    C
ATOM    247  C   LEU A 149     -17.479  28.507   7.363  1.00  69.47      A    C
ATOM    248  O   LEU A 149     -18.012  28.457   6.254  1.00  68.87      A    O
ATOM    249  N   ALA A 150     -17.616  27.544   8.255  1.00  68.72      A    N
ATOM    250  CA  ALA A 150     -18.419  26.387   7.909  1.00  64.76      A    C
ATOM    251  CB  ALA A 150     -17.606  25.449   7.014  1.00  65.19      A    C
ATOM    252  C   ALA A 150     -18.955  25.633   9.108  1.00  63.39      A    C
ATOM    253  O   ALA A 150     -18.427  25.723  10.217  1.00  60.48      A    O
ATOM    254  N   ARG A 151     -20.003  24.864   8.858  1.00  64.44      A    N
ATOM    255  CA  ARG A 151     -20.647  24.078   9.906  1.00  65.91      A    C
ATOM    256  CB  ARG A 151     -21.959  24.743  10.324  1.00  66.85      A    C
ATOM    257  CG  ARG A 151     -22.059  25.117  11.786  1.00  65.08      A    C
ATOM    258  CD  ARG A 151     -23.363  25.889  12.056  1.00  63.90      A    C
ATOM    259  NE  ARG A 151     -23.338  26.527  13.367  1.00  64.48      A    N
ATOM    260  CZ  ARG A 151     -23.704  27.784  13.589  1.00  64.89      A    C
ATOM    261  NH1 ARG A 151     -24.126  28.540  12.592  1.00  63.05      A    N
ATOM    262  NH2 ARG A 151     -23.627  28.286  14.817  1.00  65.98      A    N
ATOM    263  C   ARG A 151     -20.967  22.684   9.420  1.00  65.57      A    C
ATOM    264  O   ARG A 151     -21.399  22.506   8.281  1.00  63.56      A    O
ATOM    265  N   GLU A 152     -20.745  21.683  10.260  1.00  67.29      A    N
ATOM    266  CA  GLU A 152     -21.124  20.341   9.843  1.00  70.72      A    C
ATOM    267  CB  GLU A 152     -20.341  19.246  10.573  1.00  74.84      A    C
ATOM    268  CG  GLU A 152     -20.963  17.885  10.243  1.00  84.84      A    C
ATOM    269  CD  GLU A 152     -20.157  16.696  10.704  1.00  91.77      A    C
ATOM    270  OE1 GLU A 152     -19.836  16.611  11.911  1.00  96.51      A    O
ATOM    271  OE2 GLU A 152     -19.859  15.833   9.853  1.00  96.32      A    O
ATOM    272  C   GLU A 152     -22.623  20.202  10.159  1.00  70.47      A    C
ATOM    273  O   GLU A 152     -23.034  20.229  11.329  1.00  70.01      A    O
ATOM    274  N   ALA A 153     -23.434  20.059   9.112  1.00  69.74      A    N
ATOM    275  CA  ALA A 153     -24.886  19.934   9.274  1.00  68.06      A    C
ATOM    276  CB  ALA A 153     -25.517  19.440   7.962  1.00  67.15      A    C
ATOM    277  C   ALA A 153     -25.338  19.047  10.453  1.00  65.26      A    C
ATOM    278  O   ALA A 153     -26.289  19.377  11.142  1.00  64.34      A    O
ATOM    279  N   ALA A 154     -24.646  17.938  10.684  1.00  62.32      A    N
```

Figure 2E

```
ATOM    280  CA  ALA A 154     -24.982  17.005  11.758  1.00  59.92      A    C
ATOM    281  CB  ALA A 154     -24.254  15.694  11.537  1.00  56.94      A    C
ATOM    282  C   ALA A 154     -24.634  17.542  13.138  1.00  60.87      A    C
ATOM    283  O   ALA A 154     -25.507  17.822  13.962  1.00  61.89      A    O
ATOM    284  N   SER A 155     -23.339  17.682  13.383  1.00  61.32      A    N
ATOM    285  CA  SER A 155     -22.850  18.171  14.664  1.00  61.35      A    C
ATOM    286  CB  SER A 155     -21.357  17.879  14.777  1.00  64.23      A    C
ATOM    287  OG  SER A 155     -20.645  18.518  13.729  1.00  63.27      A    O
ATOM    288  C   SER A 155     -23.072  19.651  14.896  1.00  59.60      A    C
ATOM    289  O   SER A 155     -22.881  20.124  16.001  1.00  59.22      A    O
ATOM    290  N   ALA A 156     -23.465  20.376  13.856  1.00  58.53      A    N
ATOM    291  CA  ALA A 156     -23.663  21.822  13.943  1.00  60.56      A    C
ATOM    292  CB  ALA A 156     -24.820  22.150  14.872  1.00  58.68      A    C
ATOM    293  C   ALA A 156     -22.373  22.469  14.453  1.00  63.19      A    C
ATOM    294  O   ALA A 156     -22.373  23.612  14.916  1.00  63.12      A    O
ATOM    295  N   PHE A 157     -21.278  21.714  14.360  1.00  65.85      A    N
ATOM    296  CA  PHE A 157     -19.947  22.161  14.800  1.00  63.55      A    C
ATOM    297  CB  PHE A 157     -18.977  20.978  14.870  1.00  61.20      A    C
ATOM    298  CG  PHE A 157     -17.677  21.309  15.528  1.00  61.88      A    C
ATOM    299  CD1 PHE A 157     -17.651  21.769  16.845  1.00  65.01      A    C
ATOM    300  CD2 PHE A 157     -16.478  21.165  14.849  1.00  61.24      A    C
ATOM    301  CE1 PHE A 157     -16.447  22.086  17.479  1.00  65.15      A    C
ATOM    302  CE2 PHE A 157     -15.263  21.479  15.478  1.00  63.94      A    C
ATOM    303  CZ  PHE A 157     -15.253  21.942  16.796  1.00  65.83      A    C
ATOM    304  C   PHE A 157     -19.367  23.200  13.859  1.00  62.39      A    C
ATOM    305  O   PHE A 157     -19.182  22.933  12.670  1.00  62.00      A    O
ATOM    306  N   ILE A 158     -19.073  24.380  14.399  1.00  61.09      A    N
ATOM    307  CA  ILE A 158     -18.518  25.481  13.605  1.00  59.33      A    C
ATOM    308  CB  ILE A 158     -18.603  26.789  14.406  1.00  59.98      A    C
ATOM    309  CG2 ILE A 158     -18.432  26.460  15.904  1.00  61.02      A    C
ATOM    310  CG1 ILE A 158     -17.545  27.793  13.944  1.00  61.79      A    C
ATOM    311  CD1 ILE A 158     -17.545  28.077  12.462  1.00  61.05      A    C
ATOM    312  C   ILE A 158     -17.074  25.153  13.244  1.00  59.03      A    C
ATOM    313  O   ILE A 158     -16.275  24.828  14.108  1.00  60.97      A    O
ATOM    314  N   LEU A 159     -16.762  25.230  11.955  1.00  56.83      A    N
ATOM    315  CA  LEU A 159     -15.431  24.917  11.453  1.00  54.91      A    C
ATOM    316  CB  LEU A 159     -15.437  23.487  10.922  1.00  55.64      A    C
ATOM    317  CG  LEU A 159     -15.477  22.455  12.044  1.00  56.96      A    C
ATOM    318  CD1 LEU A 159     -15.798  21.058  11.503  1.00  59.38      A    C
ATOM    319  CD2 LEU A 159     -14.126  22.503  12.755  1.00  54.02      A    C
ATOM    320  C   LEU A 159     -14.908  25.859  10.367  1.00  53.75      A    C
ATOM    321  O   LEU A 159     -15.453  26.926  10.142  1.00  50.62      A    O
ATOM    322  N   ALA A 160     -13.834  25.450   9.704  1.00  54.03      A    N
ATOM    323  CA  ALA A 160     -13.255  26.239   8.635  1.00  55.56      A    C
ATOM    324  CB  ALA A 160     -11.939  26.887   9.080  1.00  55.30      A    C
ATOM    325  C   ALA A 160     -13.019  25.309   7.460  1.00  57.12      A    C
ATOM    326  O   ALA A 160     -12.603  24.174   7.634  1.00  61.53      A    O
ATOM    327  N   LEU A 161     -13.282  25.782   6.257  1.00  55.41      A    N
ATOM    328  CA  LEU A 161     -13.110  24.922   5.106  1.00  55.58      A    C
ATOM    329  CB  LEU A 161     -14.489  24.635   4.498  1.00  55.19      A    C
ATOM    330  CG  LEU A 161     -14.672  23.619   3.364  1.00  53.85      A    C
ATOM    331  CD1 LEU A 161     -16.142  23.133   3.258  1.00  51.55      A    C
ATOM    332  CD2 LEU A 161     -14.258  24.308   2.069  1.00  55.87      A    C
ATOM    333  C   LEU A 161     -12.149  25.589   4.116  1.00  58.99      A    C
ATOM    334  O   LEU A 161     -12.431  26.650   3.540  1.00  60.39      A    O
ATOM    335  N   LYS A 162     -10.976  24.987   3.969  1.00  57.69      A    N
ATOM    336  CA  LYS A 162      -9.991  25.532   3.071  1.00  55.73      A    C
ATOM    337  CB  LYS A 162      -8.593  25.159   3.519  1.00  49.05      A    C
ATOM    342  C   LYS A 162     -10.269  24.949   1.711  1.00  59.22      A    C
ATOM    343  O   LYS A 162     -10.331  23.731   1.550  1.00  59.62      A    O
ATOM    344  N   VAL A 163     -10.484  25.835   0.749  1.00  63.45      A    N
```

Figure 2F

| ATOM | 345 | CA | VAL | A | 163 | -10.734 | 25.455 | -0.625 | 1.00 | 67.46 | A | C |
|---|---|---|---|---|---|---|---|---|---|---|---|---|
| ATOM | 346 | CB | VAL | A | 163 | -11.755 | 26.413 | -1.284 | 1.00 | 67.92 | A | C |
| ATOM | 347 | CG1 | VAL | A | 163 | -11.318 | 26.733 | -2.710 | 1.00 | 70.55 | A | C |
| ATOM | 348 | CG2 | VAL | A | 163 | -13.153 | 25.789 | -1.284 | 1.00 | 66.29 | A | C |
| ATOM | 349 | C | VAL | A | 163 | -9.398 | 25.564 | -1.358 | 1.00 | 70.60 | A | C |
| ATOM | 350 | O | VAL | A | 163 | -8.682 | 26.560 | -1.221 | 1.00 | 69.61 | A | O |
| ATOM | 351 | N | LEU | A | 164 | -9.058 | 24.528 | -2.117 | 1.00 | 74.32 | A | N |
| ATOM | 352 | CA | LEU | A | 164 | -7.821 | 24.499 | -2.901 | 1.00 | 76.23 | A | C |
| ATOM | 353 | CB | LEU | A | 164 | -6.860 | 23.440 | -2.362 | 1.00 | 72.97 | A | C |
| ATOM | 354 | CG | LEU | A | 164 | -6.278 | 23.613 | -0.960 | 1.00 | 68.75 | A | C |
| ATOM | 355 | CD1 | LEU | A | 164 | -5.484 | 24.907 | -0.909 | 1.00 | 66.02 | A | C |
| ATOM | 356 | CD2 | LEU | A | 164 | -7.395 | 23.609 | 0.072 | 1.00 | 70.05 | A | C |
| ATOM | 357 | C | LEU | A | 164 | -8.195 | 24.132 | -4.324 | 1.00 | 80.27 | A | C |
| ATOM | 358 | O | LEU | A | 164 | -8.792 | 23.082 | -4.545 | 1.00 | 81.88 | A | O |
| ATOM | 359 | N | PHE | A | 165 | -7.851 | 24.976 | -5.294 | 1.00 | 82.77 | A | N |
| ATOM | 360 | CA | PHE | A | 165 | -8.195 | 24.674 | -6.686 | 1.00 | 84.62 | A | C |
| ATOM | 361 | CB | PHE | A | 165 | -8.334 | 25.961 | -7.495 | 1.00 | 85.97 | A | C |
| ATOM | 362 | CG | PHE | A | 165 | -9.628 | 26.671 | -7.264 | 1.00 | 89.67 | A | C |
| ATOM | 363 | CD1 | PHE | A | 165 | -9.940 | 27.189 | -6.011 | 1.00 | 90.31 | A | C |
| ATOM | 364 | CD2 | PHE | A | 165 | -10.555 | 26.799 | -8.288 | 1.00 | 92.81 | A | C |
| ATOM | 365 | CE1 | PHE | A | 165 | -11.160 | 27.824 | -5.787 | 1.00 | 91.32 | A | C |
| ATOM | 366 | CE2 | PHE | A | 165 | -11.778 | 27.433 | -8.072 | 1.00 | 93.88 | A | C |
| ATOM | 367 | CZ | PHE | A | 165 | -12.082 | 27.943 | -6.824 | 1.00 | 92.30 | A | C |
| ATOM | 368 | C | PHE | A | 165 | -7.245 | 23.724 | -7.397 | 1.00 | 86.65 | A | C |
| ATOM | 369 | O | PHE | A | 165 | -6.030 | 23.762 | -7.192 | 1.00 | 87.81 | A | O |
| ATOM | 370 | N | LYS | A | 166 | -7.814 | 22.859 | -8.230 | 1.00 | 89.07 | A | N |
| ATOM | 371 | CA | LYS | A | 166 | -7.024 | 21.901 | -8.996 | 1.00 | 90.60 | A | C |
| ATOM | 372 | CB | LYS | A | 166 | -7.940 | 21.010 | -9.842 | 1.00 | 89.27 | A | C |
| ATOM | 377 | C | LYS | A | 166 | -6.100 | 22.691 | -9.911 | 1.00 | 92.14 | A | C |
| ATOM | 378 | O | LYS | A | 166 | -4.884 | 22.521 | -9.883 | 1.00 | 91.22 | A | O |
| ATOM | 379 | N | ALA | A | 167 | -6.701 | 23.567 | -10.710 | 1.00 | 94.87 | A | N |
| ATOM | 380 | CA | ALA | A | 167 | -5.964 | 24.402 | -11.647 | 1.00 | 96.69 | A | C |
| ATOM | 381 | CB | ALA | A | 167 | -6.861 | 25.536 | -12.153 | 1.00 | 96.62 | A | C |
| ATOM | 382 | C | ALA | A | 167 | -4.704 | 24.972 | -10.999 | 1.00 | 97.46 | A | C |
| ATOM | 383 | O | ALA | A | 167 | -3.583 | 24.644 | -11.398 | 1.00 | 98.79 | A | O |
| ATOM | 384 | N | GLN | A | 168 | -4.888 | 25.825 | -10.000 | 1.00 | 97.12 | A | N |
| ATOM | 385 | CA | GLN | A | 168 | -3.758 | 26.421 | -9.318 | 1.00 | 97.80 | A | C |
| ATOM | 386 | CB | GLN | A | 168 | -4.243 | 27.185 | -8.096 | 1.00 | 101.53 | A | C |
| ATOM | 387 | CG | GLN | A | 168 | -5.454 | 28.057 | -8.365 | 1.00 | 106.90 | A | C |
| ATOM | 388 | CD | GLN | A | 168 | -5.200 | 29.094 | -9.433 | 1.00 | 110.01 | A | C |
| ATOM | 389 | OE1 | GLN | A | 168 | -4.892 | 28.762 | -10.580 | 1.00 | 112.17 | A | O |
| ATOM | 390 | NE2 | GLN | A | 168 | -5.330 | 30.364 | -9.063 | 1.00 | 110.01 | A | N |
| ATOM | 391 | C | GLN | A | 168 | -2.792 | 25.326 | -8.891 | 1.00 | 96.74 | A | C |
| ATOM | 392 | O | GLN | A | 168 | -1.612 | 25.355 | -9.235 | 1.00 | 94.27 | A | O |
| ATOM | 393 | N | LEU | A | 169 | -3.303 | 24.356 | -8.142 | 1.00 | 97.32 | A | N |
| ATOM | 394 | CA | LEU | A | 169 | -2.480 | 23.249 | -7.666 | 1.00 | 98.86 | A | C |
| ATOM | 395 | CB | LEU | A | 169 | -3.353 | 22.190 | -6.981 | 1.00 | 97.16 | A | C |
| ATOM | 399 | C | LEU | A | 169 | -1.713 | 22.621 | -8.828 | 1.00 | 100.16 | A | C |
| ATOM | 400 | O | LEU | A | 169 | -0.561 | 22.213 | -8.672 | 1.00 | 102.12 | A | O |
| ATOM | 401 | N | GLU | A | 170 | -2.356 | 22.558 | -9.993 | 1.00 | 100.84 | A | N |
| ATOM | 402 | CA | GLU | A | 170 | -1.747 | 21.984 | -11.193 | 1.00 | 100.44 | A | C |
| ATOM | 403 | CB | GLU | A | 170 | -2.824 | 21.698 | -12.245 | 1.00 | 98.56 | A | C |
| ATOM | 408 | C | GLU | A | 170 | -0.690 | 22.918 | -11.789 | 1.00 | 100.25 | A | C |
| ATOM | 409 | O | GLU | A | 170 | 0.458 | 22.517 | -11.993 | 1.00 | 99.86 | A | O |
| ATOM | 410 | N | LYS | A | 171 | -1.088 | 24.160 | -12.064 | 1.00 | 99.04 | A | N |
| ATOM | 411 | CA | LYS | A | 171 | -0.190 | 25.164 | -12.635 | 1.00 | 96.37 | A | C |
| ATOM | 412 | CB | LYS | A | 171 | -0.980 | 26.426 | -13.018 | 1.00 | 94.50 | A | C |
| ATOM | 417 | C | LYS | A | 171 | 0.925 | 25.538 | -11.660 | 1.00 | 94.44 | A | C |
| ATOM | 418 | O | LYS | A | 171 | 1.276 | 26.715 | -11.523 | 1.00 | 94.15 | A | O |
| ATOM | 419 | N | ALA | A | 172 | 1.473 | 24.530 | -10.985 | 1.00 | 91.81 | A | N |
| ATOM | 420 | CA | ALA | A | 172 | 2.537 | 24.738 | -10.021 | 1.00 | 90.59 | A | C |

Figure 2G

```
ATOM    421  CB  ALA A 172       2.193  25.887  -9.087  1.00  90.72      A    C
ATOM    422  C   ALA A 172       2.752  23.473  -9.215  1.00  89.71      A    C
ATOM    423  O   ALA A 172       2.423  23.427  -8.023  1.00  89.62      A    O
ATOM    424  N   GLY A 173       3.297  22.454  -9.867  1.00  88.62      A    N
ATOM    425  CA  GLY A 173       3.564  21.205  -9.188  1.00  87.20      A    C
ATOM    426  C   GLY A 173       3.749  21.429  -7.702  1.00  86.57      A    C
ATOM    427  O   GLY A 173       4.781  21.941  -7.254  1.00  85.87      A    O
ATOM    428  N   VAL A 174       2.711  21.084  -6.946  1.00  86.85      A    N
ATOM    429  CA  VAL A 174       2.711  21.217  -5.492  1.00  86.05      A    C
ATOM    430  CB  VAL A 174       2.037  22.538  -5.028  1.00  86.56      A    C
ATOM    433  C   VAL A 174       1.922  20.043  -4.939  1.00  84.87      A    C
ATOM    434  O   VAL A 174       2.130  19.638  -3.802  1.00  84.57      A    O
ATOM    435  N   GLU A 175       1.010  19.508  -5.753  1.00  83.91      A    N
ATOM    436  CA  GLU A 175       0.204  18.362  -5.353  1.00  85.21      A    C
ATOM    437  CB  GLU A 175      -0.301  17.609  -6.592  1.00  85.17      A    C
ATOM    442  C   GLU A 175       1.101  17.452  -4.515  1.00  86.96      A    C
ATOM    443  O   GLU A 175       0.641  16.760  -3.607  1.00  88.04      A    O
ATOM    444  N   HIS A 176       2.391  17.474  -4.833  1.00  89.02      A    N
ATOM    445  CA  HIS A 176       3.378  16.684  -4.114  1.00  91.29      A    C
ATOM    446  CB  HIS A 176       4.710  16.652  -4.889  1.00  89.92      A    C
ATOM    452  C   HIS A 176       3.576  17.340  -2.750  1.00  93.41      A    C
ATOM    453  O   HIS A 176       3.376  16.703  -1.710  1.00  94.69      A    O
ATOM    454  N   GLN A 177       3.980  18.613  -2.756  1.00  93.26      A    N
ATOM    455  CA  GLN A 177       4.179  19.366  -1.505  1.00  90.02      A    C
ATOM    456  CB  GLN A 177       4.295  20.874  -1.778  1.00  85.72      A    C
ATOM    461  C   GLN A 177       2.941  19.098  -0.657  1.00  87.75      A    C
ATOM    462  O   GLN A 177       3.039  18.804   0.539  1.00  87.33      A    O
ATOM    463  N   LEU A 178       1.777  19.188  -1.303  1.00  86.24      A    N
ATOM    464  CA  LEU A 178       0.507  18.936  -0.646  1.00  82.79      A    C
ATOM    465  CB  LEU A 178      -0.642  19.222  -1.613  1.00  79.26      A    C
ATOM    466  CG  LEU A 178      -1.783  20.087  -1.067  1.00  72.68      A    C
ATOM    467  CD1 LEU A 178      -2.424  20.859  -2.195  1.00  69.47      A    C
ATOM    468  CD2 LEU A 178      -2.791  19.212  -0.345  1.00  71.05      A    C
ATOM    469  C   LEU A 178       0.561  17.466  -0.253  1.00  84.70      A    C
ATOM    470  O   LEU A 178       1.632  16.871  -0.301  1.00  83.02      A    O
ATOM    471  N   ARG A 179      -0.562  16.866   0.119  1.00  86.50      A    N
ATOM    472  CA  ARG A 179      -0.526  15.466   0.540  1.00  91.77      A    C
ATOM    473  CB  ARG A 179      -0.078  14.552  -0.603  1.00  96.19      A    C
ATOM    474  CG  ARG A 179      -1.166  14.101  -1.553  1.00 106.72      A    C
ATOM    475  CD  ARG A 179      -0.796  12.738  -2.136  1.00 116.36      A    C
ATOM    476  NE  ARG A 179      -1.691  12.311  -3.209  1.00 123.85      A    N
ATOM    477  CZ  ARG A 179      -1.775  12.908  -4.395  1.00 125.37      A    C
ATOM    478  NH1 ARG A 179      -2.619  12.451  -5.317  1.00 123.70      A    N
ATOM    479  NH2 ARG A 179      -1.013  13.963  -4.661  1.00 127.09      A    N
ATOM    480  C   ARG A 179       0.491  15.352   1.675  1.00  93.28      A    C
ATOM    481  O   ARG A 179       0.129  15.168   2.833  1.00  95.60      A    O
ATOM    482  N   ARG A 180       1.765  15.453   1.314  1.00  93.39      A    N
ATOM    483  CA  ARG A 180       2.876  15.399   2.251  1.00  95.31      A    C
ATOM    484  CB  ARG A 180       4.103  16.072   1.616  1.00  96.64      A    C
ATOM    485  CG  ARG A 180       5.456  15.712   2.231  1.00  98.53      A    C
ATOM    486  CD  ARG A 180       5.951  14.312   1.815  1.00  98.96      A    C
ATOM    487  NE  ARG A 180       6.277  14.194   0.390  1.00  99.36      A    N
ATOM    488  CZ  ARG A 180       7.159  14.955  -0.255  1.00  99.72      A    C
ATOM    489  NH1 ARG A 180       7.382  14.762  -1.549  1.00  97.63      A    N
ATOM    490  NH2 ARG A 180       7.816  15.914   0.385  1.00 100.37      A    N
ATOM    491  C   ARG A 180       2.471  16.130   3.537  1.00  96.04      A    C
ATOM    492  O   ARG A 180       2.382  15.515   4.609  1.00  94.73      A    O
ATOM    493  N   GLU A 181       2.207  17.434   3.428  1.00  96.50      A    N
ATOM    494  CA  GLU A 181       1.800  18.221   4.596  1.00  95.99      A    C
ATOM    495  CB  GLU A 181       1.555  19.690   4.227  1.00 100.69      A    C
ATOM    496  CG  GLU A 181       2.649  20.359   3.414  1.00 107.20      A    C
```

Figure 2H

```
ATOM  497  CD   GLU A 181     2.598  21.883   3.494  1.00  109.29    A  C
ATOM  498  OE1  GLU A 181     1.486  22.457   3.504  1.00  109.80    A  O
ATOM  499  OE2  GLU A 181     3.679  22.509   3.536  1.00  111.33    A  O
ATOM  500  C    GLU A 181     0.505  17.635   5.158  1.00   93.01    A  C
ATOM  501  O    GLU A 181     0.386  17.389   6.361  1.00   90.72    A  O
ATOM  502  N    VAL A 182    -0.462  17.424   4.271  1.00   90.73    A  N
ATOM  503  CA   VAL A 182    -1.750  16.860   4.647  1.00   88.08    A  C
ATOM  504  CB   VAL A 182    -2.503  16.303   3.417  1.00   85.35    A  C
ATOM  505  CG1  VAL A 182    -3.623  15.388   3.870  1.00   84.70    A  C
ATOM  506  CG2  VAL A 182    -3.067  17.449   2.583  1.00   81.53    A  C
ATOM  507  C    VAL A 182    -1.577  15.734   5.652  1.00   87.40    A  C
ATOM  508  O    VAL A 182    -1.852  15.902   6.837  1.00   85.59    A  O
ATOM  509  N    GLU A 183    -1.115  14.585   5.167  1.00   87.45    A  N
ATOM  510  CA   GLU A 183    -0.906  13.422   6.018  1.00   86.73    A  C
ATOM  511  CB   GLU A 183    -0.107  12.355   5.271  1.00   89.56    A  C
ATOM  512  CG   GLU A 183     0.112  11.102   6.091  1.00   93.22    A  C
ATOM  513  CD   GLU A 183    -1.197  10.475   6.526  1.00   94.60    A  C
ATOM  514  OE1  GLU A 183    -1.869   9.856   5.676  1.00   94.65    A  O
ATOM  515  OE2  GLU A 183    -1.559  10.617   7.717  1.00   96.69    A  O
ATOM  516  C    GLU A 183    -0.196  13.779   7.320  1.00   86.17    A  C
ATOM  517  O    GLU A 183    -0.573  13.279   8.372  1.00   86.48    A  O
ATOM  518  N    ILE A 184     0.832  14.628   7.247  1.00   86.63    A  N
ATOM  519  CA   ILE A 184     1.565  15.057   8.445  1.00   88.15    A  C
ATOM  520  CB   ILE A 184     2.702  16.032   8.093  1.00   87.30    A  C
ATOM  521  CG2  ILE A 184     3.432  16.454   9.360  1.00   86.63    A  C
ATOM  522  CG1  ILE A 184     3.667  15.376   7.108  1.00   84.31    A  C
ATOM  523  CD1  ILE A 184     4.786  16.281   6.654  1.00   81.32    A  C
ATOM  524  C    ILE A 184     0.596  15.776   9.389  1.00   90.70    A  C
ATOM  525  O    ILE A 184     0.433  15.397  10.545  1.00   87.30    A  O
ATOM  526  N    GLN A 185    -0.046  16.826   8.887  1.00   93.30    A  N
ATOM  527  CA   GLN A 185    -1.014  17.566   9.682  1.00   95.37    A  C
ATOM  528  CB   GLN A 185    -1.590  18.722   8.862  1.00   97.61    A  C
ATOM  529  CG   GLN A 185    -0.547  19.770   8.538  1.00  103.35    A  C
ATOM  530  CD   GLN A 185    -0.039  20.441   9.793  1.00  106.52    A  C
ATOM  531  OE1  GLN A 185     1.035  21.042   9.795  1.00  107.64    A  O
ATOM  532  NE2  GLN A 185    -0.821  20.360  10.871  1.00  107.24    A  N
ATOM  533  C    GLN A 185    -2.115  16.589  10.066  1.00   94.94    A  C
ATOM  534  O    GLN A 185    -2.561  16.564  11.217  1.00   95.32    A  O
ATOM  535  N    SER A 186    -2.541  15.796   9.082  1.00   97.07    A  N
ATOM  536  CA   SER A 186    -3.571  14.777   9.248  1.00   97.57    A  C
ATOM  537  CB   SER A 186    -3.864  14.104   7.900  1.00   97.40    A  C
ATOM  538  OG   SER A 186    -4.753  13.010   8.050  1.00   99.43    A  O
ATOM  539  C    SER A 186    -3.028  13.751  10.230  1.00   97.37    A  C
ATOM  540  O    SER A 186    -2.768  12.603   9.867  1.00   97.45    A  O
ATOM  541  N    HIS A 187    -2.859  14.193  11.472  1.00   96.71    A  N
ATOM  542  CA   HIS A 187    -2.319  13.385  12.558  1.00   96.67    A  C
ATOM  543  CB   HIS A 187    -1.038  12.674  12.100  1.00   99.07    A  C
ATOM  544  CG   HIS A 187    -1.015  11.207  12.404  1.00  104.64    A  C
ATOM  545  CD2  HIS A 187    -0.018  10.401  12.845  1.00  106.54    A  C
ATOM  546  ND1  HIS A 187    -2.114  10.392  12.227  1.00  106.15    A  N
ATOM  547  CE1  HIS A 187    -1.796   9.150  12.547  1.00  106.73    A  C
ATOM  548  NE2  HIS A 187    -0.530   9.127  12.925  1.00  106.81    A  N
ATOM  549  C    HIS A 187    -1.985  14.390  13.658  1.00   95.21    A  C
ATOM  550  O    HIS A 187    -2.706  14.512  14.653  1.00   96.74    A  O
ATOM  551  N    LEU A 188    -0.891  15.116  13.455  1.00   89.19    A  N
ATOM  552  CA   LEU A 188    -0.432  16.130  14.392  1.00   82.17    A  C
ATOM  553  CB   LEU A 188     0.147  17.321  13.619  1.00   79.40    A  C
ATOM  554  CG   LEU A 188     1.560  17.775  14.014  1.00   75.97    A  C
ATOM  555  CD1  LEU A 188     2.523  16.635  13.805  1.00   72.51    A  C
ATOM  556  CD2  LEU A 188     1.976  18.971  13.176  1.00   76.13    A  C
ATOM  557  C    LEU A 188    -1.562  16.613  15.292  1.00   77.90    A  C
```

Figure 2I

```
ATOM    558  O   LEU A 188      -2.454  17.325  14.838  1.00  78.03      A    O
ATOM    559  N   ARG A 189      -1.531  16.210  16.556  1.00  72.06      A    N
ATOM    560  CA  ARG A 189      -2.549  16.611  17.521  1.00  67.92      A    C
ATOM    561  CB  ARG A 189      -3.229  15.367  18.103  1.00  73.90      A    C
ATOM    562  CG  ARG A 189      -4.597  15.566  18.786  1.00  78.66      A    C
ATOM    563  CD  ARG A 189      -5.498  14.400  18.364  1.00  85.49      A    C
ATOM    564  NE  ARG A 189      -6.684  14.185  19.194  1.00  91.19      A    N
ATOM    565  CZ  ARG A 189      -7.548  13.186  19.005  1.00  91.51      A    C
ATOM    566  NH1 ARG A 189      -7.357  12.321  18.012  1.00  93.38      A    N
ATOM    567  NH2 ARG A 189      -8.588  13.032  19.815  1.00  87.51      A    N
ATOM    568  C   ARG A 189      -1.858  17.406  18.624  1.00  60.47      A    C
ATOM    569  O   ARG A 189      -1.084  16.863  19.421  1.00  59.30      A    O
ATOM    570  N   HIS A 190      -2.111  18.704  18.656  1.00  54.86      A    N
ATOM    571  CA  HIS A 190      -1.497  19.541  19.671  1.00  50.95      A    C
ATOM    572  CB  HIS A 190      -0.066  19.933  19.252  1.00  51.83      A    C
ATOM    573  CG  HIS A 190       0.678  20.679  20.313  1.00  56.16      A    C
ATOM    574  CD2 HIS A 190       0.602  21.973  20.712  1.00  58.65      A    C
ATOM    575  ND1 HIS A 190       1.554  20.064  21.181  1.00  59.30      A    N
ATOM    576  CE1 HIS A 190       1.981  20.946  22.074  1.00  59.95      A    C
ATOM    577  NE2 HIS A 190       1.415  22.114  21.810  1.00  57.34      A    N
ATOM    578  C   HIS A 190      -2.326  20.795  19.907  1.00  49.69      A    C
ATOM    579  O   HIS A 190      -2.845  21.390  18.970  1.00  47.67      A    O
ATOM    580  N   PRO A 191      -2.435  21.228  21.169  1.00  47.55      A    N
ATOM    581  CD  PRO A 191      -1.833  20.635  22.376  1.00  47.91      A    C
ATOM    582  CA  PRO A 191      -3.215  22.429  21.492  1.00  45.35      A    C
ATOM    583  CB  PRO A 191      -3.045  22.579  23.008  1.00  42.47      A    C
ATOM    584  CG  PRO A 191      -1.783  21.809  23.316  1.00  46.75      A    C
ATOM    585  C   PRO A 191      -2.785  23.673  20.738  1.00  44.79      A    C
ATOM    586  O   PRO A 191      -3.617  24.499  20.376  1.00  48.53      A    O
ATOM    587  N   ASN A 192      -1.490  23.814  20.493  1.00  45.28      A    N
ATOM    588  CA  ASN A 192      -1.010  24.981  19.788  1.00  42.05      A    C
ATOM    589  CB  ASN A 192       0.196  25.557  20.519  1.00  46.05      A    C
ATOM    590  CG  ASN A 192      -0.169  26.091  21.909  1.00  49.31      A    C
ATOM    591  OD1 ASN A 192       0.510  25.815  22.906  1.00  51.60      A    O
ATOM    592  ND2 ASN A 192      -1.236  26.862  21.975  1.00  49.16      A    N
ATOM    593  C   ASN A 192      -0.727  24.753  18.301  1.00  40.78      A    C
ATOM    594  O   ASN A 192       0.022  25.531  17.664  1.00  39.75      A    O
ATOM    595  N   ILE A 193      -1.357  23.716  17.738  1.00  39.81      A    N
ATOM    596  CA  ILE A 193      -1.218  23.429  16.306  1.00  38.68      A    C
ATOM    597  CB  ILE A 193      -0.504  22.106  16.073  1.00  37.03      A    C
ATOM    598  CG2 ILE A 193      -0.627  21.684  14.631  1.00  35.39      A    C
ATOM    599  CG1 ILE A 193       0.979  22.295  16.403  1.00  36.80      A    C
ATOM    600  CD1 ILE A 193       1.856  21.084  16.162  1.00  40.43      A    C
ATOM    601  C   ILE A 193      -2.610  23.417  15.628  1.00  39.73      A    C
ATOM    602  O   ILE A 193      -3.563  22.815  16.147  1.00  41.98      A    O
ATOM    603  N   LEU A 194      -2.763  24.070  14.484  1.00  40.12      A    N
ATOM    604  CA  LEU A 194      -4.083  24.056  13.925  1.00  45.02      A    C
ATOM    605  CB  LEU A 194      -4.251  25.138  12.850  1.00  40.58      A    C
ATOM    606  CG  LEU A 194      -5.744  25.360  12.537  1.00  36.62      A    C
ATOM    607  CD1 LEU A 194      -6.365  26.215  13.662  1.00  34.79      A    C
ATOM    608  CD2 LEU A 194      -5.921  26.063  11.181  1.00  37.83      A    C
ATOM    609  C   LEU A 194      -4.408  22.661  13.373  1.00  50.26      A    C
ATOM    610  O   LEU A 194      -3.865  22.234  12.335  1.00  52.67      A    O
ATOM    611  N   ARG A 195      -5.308  21.968  14.070  1.00  52.68      A    N
ATOM    612  CA  ARG A 195      -5.708  20.623  13.695  1.00  55.93      A    C
ATOM    613  CB  ARG A 195      -6.722  20.079  14.711  1.00  62.40      A    C
ATOM    614  CG  ARG A 195      -7.098  18.616  14.480  1.00  74.73      A    C
ATOM    615  CD  ARG A 195      -7.982  18.045  15.599  1.00  83.65      A    C
ATOM    616  NE  ARG A 195      -8.294  16.628  15.376  1.00  87.43      A    N
ATOM    617  CZ  ARG A 195      -9.033  15.878  16.190  1.00  88.90      A    C
ATOM    618  NH1 ARG A 195      -9.253  14.598  15.899  1.00  89.95      A    N
```

Figure 2J

| ATOM | 619 | NH2 | ARG | A | 195 | -9.552 | 16.408 | 17.294 | 1.00 | 87.25 | A | N |
|------|-----|-----|-----|---|-----|--------|--------|--------|------|-------|---|---|
| ATOM | 620 | C | ARG | A | 195 | -6.291 | 20.522 | 12.294 | 1.00 | 55.88 | A | C |
| ATOM | 621 | O | ARG | A | 195 | -6.790 | 21.490 | 11.757 | 1.00 | 50.34 | A | O |
| ATOM | 622 | N | LEU | A | 196 | -6.209 | 19.336 | 11.698 | 1.00 | 58.92 | A | N |
| ATOM | 623 | CA | LEU | A | 196 | -6.758 | 19.109 | 10.358 | 1.00 | 60.64 | A | C |
| ATOM | 624 | CB | LEU | A | 196 | -5.641 | 18.794 | 9.361 | 1.00 | 62.65 | A | C |
| ATOM | 625 | CG | LEU | A | 196 | -6.067 | 18.246 | 7.987 | 1.00 | 63.74 | A | C |
| ATOM | 626 | CD1 | LEU | A | 196 | -7.235 | 19.049 | 7.422 | 1.00 | 65.54 | A | C |
| ATOM | 627 | CD2 | LEU | A | 196 | -4.889 | 18.300 | 7.034 | 1.00 | 65.02 | A | C |
| ATOM | 628 | C | LEU | A | 196 | -7.767 | 17.960 | 10.375 | 1.00 | 60.32 | A | C |
| ATOM | 629 | O | LEU | A | 196 | -7.497 | 16.895 | 9.856 | 1.00 | 63.33 | A | O |
| ATOM | 630 | N | TYR | A | 197 | -8.937 | 18.196 | 10.954 | 1.00 | 57.84 | A | N |
| ATOM | 631 | CA | TYR | A | 197 | -9.969 | 17.172 | 11.056 | 1.00 | 55.75 | A | C |
| ATOM | 632 | CB | TYR | A | 197 | -11.332 | 17.813 | 11.335 | 1.00 | 53.02 | A | C |
| ATOM | 633 | CG | TYR | A | 197 | -11.358 | 18.736 | 12.512 | 1.00 | 50.75 | A | C |
| ATOM | 634 | CD1 | TYR | A | 197 | -11.619 | 20.084 | 12.337 | 1.00 | 52.00 | A | C |
| ATOM | 635 | CE1 | TYR | A | 197 | -11.645 | 20.952 | 13.408 | 1.00 | 53.28 | A | C |
| ATOM | 636 | CD2 | TYR | A | 197 | -11.126 | 18.266 | 13.803 | 1.00 | 50.67 | A | C |
| ATOM | 637 | CE2 | TYR | A | 197 | -11.158 | 19.132 | 14.890 | 1.00 | 54.83 | A | C |
| ATOM | 638 | CZ | TYR | A | 197 | -11.417 | 20.484 | 14.679 | 1.00 | 55.28 | A | C |
| ATOM | 639 | OH | TYR | A | 197 | -11.440 | 21.388 | 15.718 | 1.00 | 56.06 | A | O |
| ATOM | 640 | C | TYR | A | 197 | -10.111 | 16.253 | 9.833 | 1.00 | 56.90 | A | C |
| ATOM | 641 | O | TYR | A | 197 | -10.370 | 15.057 | 9.978 | 1.00 | 58.41 | A | O |
| ATOM | 642 | N | GLY | A | 198 | -9.973 | 16.793 | 8.633 | 1.00 | 56.06 | A | N |
| ATOM | 643 | CA | GLY | A | 198 | -10.142 | 15.925 | 7.489 | 1.00 | 55.27 | A | C |
| ATOM | 644 | C | GLY | A | 198 | -9.947 | 16.587 | 6.159 | 1.00 | 56.71 | A | C |
| ATOM | 645 | O | GLY | A | 198 | -9.712 | 17.782 | 6.072 | 1.00 | 56.62 | A | O |
| ATOM | 646 | N | TYR | A | 199 | -10.065 | 15.791 | 5.111 | 1.00 | 60.94 | A | N |
| ATOM | 647 | CA | TYR | A | 199 | -9.866 | 16.275 | 3.756 | 1.00 | 65.84 | A | C |
| ATOM | 648 | CB | TYR | A | 199 | -8.364 | 16.186 | 3.412 | 1.00 | 74.72 | A | C |
| ATOM | 649 | CG | TYR | A | 199 | -7.996 | 15.390 | 2.163 | 1.00 | 83.56 | A | C |
| ATOM | 650 | CD1 | TYR | A | 199 | -7.325 | 14.158 | 2.253 | 1.00 | 82.92 | A | C |
| ATOM | 651 | CE1 | TYR | A | 199 | -6.942 | 13.454 | 1.088 | 1.00 | 83.87 | A | C |
| ATOM | 652 | CD2 | TYR | A | 199 | -8.281 | 15.894 | 0.880 | 1.00 | 87.81 | A | C |
| ATOM | 653 | CE2 | TYR | A | 199 | -7.909 | 15.201 | -0.278 | 1.00 | 86.53 | A | C |
| ATOM | 654 | CZ | TYR | A | 199 | -7.243 | 13.990 | -0.171 | 1.00 | 84.97 | A | C |
| ATOM | 655 | OH | TYR | A | 199 | -6.885 | 13.333 | -1.326 | 1.00 | 81.59 | A | O |
| ATOM | 656 | C | TYR | A | 199 | -10.686 | 15.465 | 2.767 | 1.00 | 65.66 | A | C |
| ATOM | 657 | O | TYR | A | 199 | -10.855 | 14.241 | 2.921 | 1.00 | 63.27 | A | O |
| ATOM | 658 | N | PHE | A | 200 | -11.204 | 16.163 | 1.760 | 1.00 | 66.20 | A | N |
| ATOM | 659 | CA | PHE | A | 200 | -11.977 | 15.527 | 0.698 | 1.00 | 69.20 | A | C |
| ATOM | 660 | CB | PHE | A | 200 | -13.464 | 15.395 | 1.064 | 1.00 | 66.91 | A | C |
| ATOM | 661 | CG | PHE | A | 200 | -14.151 | 16.694 | 1.335 | 1.00 | 62.69 | A | C |
| ATOM | 662 | CD1 | PHE | A | 200 | -14.056 | 17.293 | 2.585 | 1.00 | 58.08 | A | C |
| ATOM | 663 | CD2 | PHE | A | 200 | -14.959 | 17.282 | 0.363 | 1.00 | 62.80 | A | C |
| ATOM | 664 | CE1 | PHE | A | 200 | -14.761 | 18.446 | 2.864 | 1.00 | 56.62 | A | C |
| ATOM | 665 | CE2 | PHE | A | 200 | -15.673 | 18.442 | 0.637 | 1.00 | 60.26 | A | C |
| ATOM | 666 | CZ | PHE | A | 200 | -15.577 | 19.026 | 1.892 | 1.00 | 57.41 | A | C |
| ATOM | 667 | C | PHE | A | 200 | -11.810 | 16.314 | -0.588 | 1.00 | 69.75 | A | C |
| ATOM | 668 | O | PHE | A | 200 | -11.216 | 17.381 | -0.580 | 1.00 | 69.79 | A | O |
| ATOM | 669 | N | HIS | A | 201 | -12.319 | 15.790 | -1.697 | 1.00 | 73.90 | A | N |
| ATOM | 670 | CA | HIS | A | 201 | -12.149 | 16.489 | -2.960 | 1.00 | 81.60 | A | C |
| ATOM | 671 | CB | HIS | A | 201 | -10.754 | 16.210 | -3.512 | 1.00 | 86.89 | A | C |
| ATOM | 672 | CG | HIS | A | 201 | -10.470 | 14.753 | -3.714 | 1.00 | 91.24 | A | C |
| ATOM | 673 | CD2 | HIS | A | 201 | -9.564 | 13.930 | -3.131 | 1.00 | 92.97 | A | C |
| ATOM | 674 | ND1 | HIS | A | 201 | -11.183 | 13.971 | -4.597 | 1.00 | 91.80 | A | N |
| ATOM | 675 | CE1 | HIS | A | 201 | -10.730 | 12.731 | -4.549 | 1.00 | 94.28 | A | C |
| ATOM | 676 | NE2 | HIS | A | 201 | -9.747 | 12.679 | -3.667 | 1.00 | 94.89 | A | N |
| ATOM | 677 | C | HIS | A | 201 | -13.149 | 16.124 | -4.030 | 1.00 | 84.24 | A | C |
| ATOM | 678 | O | HIS | A | 201 | -13.518 | 14.966 | -4.175 | 1.00 | 85.37 | A | O |
| ATOM | 679 | N | ASP | A | 202 | -13.586 | 17.123 | -4.783 | 1.00 | 86.70 | A | N |

Figure 2K

```
ATOM    680  CA  ASP A 202     -14.492  16.871  -5.887  1.00  89.01      A  C
ATOM    681  CB  ASP A 202     -15.638  17.891  -5.918  1.00  90.40      A  C
ATOM    682  CG  ASP A 202     -15.156  19.316  -6.030  1.00  90.77      A  C
ATOM    683  OD1 ASP A 202     -14.206  19.561  -6.794  1.00  93.69      A  O
ATOM    684  OD2 ASP A 202     -15.742  20.196  -5.365  1.00  91.09      A  O
ATOM    685  C   ASP A 202     -13.614  16.988  -7.135  1.00  90.09      A  C
ATOM    686  O   ASP A 202     -12.388  17.068  -7.024  1.00  89.07      A  O
ATOM    687  N   ALA A 203     -14.226  16.998  -8.312  1.00  91.58      A  N
ATOM    688  CA  ALA A 203     -13.472  17.098  -9.556  1.00  92.91      A  C
ATOM    689  CB  ALA A 203     -14.426  17.079 -10.742  1.00  92.83      A  C
ATOM    690  C   ALA A 203     -12.594  18.345  -9.616  1.00  94.23      A  C
ATOM    691  O   ALA A 203     -11.363  18.261  -9.575  1.00  95.32      A  O
ATOM    692  N   THR A 204     -13.240  19.502  -9.706  1.00  95.48      A  N
ATOM    693  CA  THR A 204     -12.549  20.785  -9.799  1.00  95.58      A  C
ATOM    694  CB  THR A 204     -13.535  21.902 -10.195  1.00  95.40      A  C
ATOM    695  OG1 THR A 204     -12.928  23.177  -9.955  1.00  98.51      A  O
ATOM    696  CG2 THR A 204     -14.819  21.795  -9.391  1.00  94.84      A  C
ATOM    697  C   THR A 204     -11.749  21.289  -8.586  1.00  93.13      A  C
ATOM    698  O   THR A 204     -10.637  21.794  -8.746  1.00  94.45      A  O
ATOM    699  N   ARG A 205     -12.300  21.158  -7.385  1.00  88.53      A  N
ATOM    700  CA  ARG A 205     -11.625  21.662  -6.187  1.00  81.26      A  C
ATOM    701  CB  ARG A 205     -12.401  22.864  -5.646  1.00  82.44      A  C
ATOM    702  CG  ARG A 205     -13.898  22.665  -5.707  1.00  85.01      A  C
ATOM    703  CD  ARG A 205     -14.642  23.956  -5.501  1.00  88.56      A  C
ATOM    704  NE  ARG A 205     -16.049  23.808  -5.850  1.00  91.44      A  N
ATOM    705  CZ  ARG A 205     -16.966  24.755  -5.672  1.00  93.46      A  C
ATOM    706  NH1 ARG A 205     -16.619  25.926  -5.143  1.00  93.93      A  N
ATOM    707  NH2 ARG A 205     -18.228  24.533  -6.028  1.00  92.05      A  N
ATOM    708  C   ARG A 205     -11.415  20.657  -5.067  1.00  76.60      A  C
ATOM    709  O   ARG A 205     -12.091  19.629  -5.001  1.00  76.13      A  O
ATOM    710  N   VAL A 206     -10.462  20.969  -4.193  1.00  71.44      A  N
ATOM    711  CA  VAL A 206     -10.138  20.127  -3.046  1.00  67.56      A  C
ATOM    712  CB  VAL A 206      -8.638  19.789  -3.023  1.00  63.79      A  C
ATOM    713  CG1 VAL A 206      -7.941  20.550  -4.112  1.00  61.96      A  C
ATOM    714  CG2 VAL A 206      -8.036  20.096  -1.669  1.00  58.59      A  C
ATOM    715  C   VAL A 206     -10.534  20.858  -1.770  1.00  67.52      A  C
ATOM    716  O   VAL A 206     -10.688  22.070  -1.785  1.00  68.61      A  O
ATOM    717  N   TYR A 207     -10.710  20.120  -0.674  1.00  68.01      A  N
ATOM    718  CA  TYR A 207     -11.113  20.731   0.586  1.00  66.54      A  C
ATOM    719  CB  TYR A 207     -12.617  20.595   0.788  1.00  66.72      A  C
ATOM    720  CG  TYR A 207     -13.428  21.030  -0.394  1.00  72.29      A  C
ATOM    721  CD1 TYR A 207     -13.700  20.145  -1.441  1.00  72.58      A  C
ATOM    722  CE1 TYR A 207     -14.478  20.527  -2.515  1.00  75.07      A  C
ATOM    723  CD2 TYR A 207     -13.952  22.316  -0.463  1.00  76.04      A  C
ATOM    724  CE2 TYR A 207     -14.734  22.711  -1.539  1.00  77.50      A  C
ATOM    725  CZ  TYR A 207     -14.995  21.806  -2.557  1.00  76.66      A  C
ATOM    726  OH  TYR A 207     -15.808  22.169  -3.598  1.00  82.13      A  O
ATOM    727  C   TYR A 207     -10.440  20.235   1.855  1.00  67.58      A  C
ATOM    728  O   TYR A 207     -10.345  19.022   2.128  1.00  67.06      A  O
ATOM    729  N   LEU A 208     -10.007  21.203   2.651  1.00  67.63      A  N
ATOM    730  CA  LEU A 208      -9.385  20.926   3.923  1.00  67.84      A  C
ATOM    731  CB  LEU A 208      -8.108  21.747   4.074  1.00  70.80      A  C
ATOM    732  CG  LEU A 208      -6.930  21.460   3.129  1.00  73.43      A  C
ATOM    733  CD1 LEU A 208      -5.944  22.616   3.225  1.00  74.66      A  C
ATOM    734  CD2 LEU A 208      -6.264  20.115   3.469  1.00  68.68      A  C
ATOM    735  C   LEU A 208     -10.381  21.309   5.008  1.00  65.82      A  C
ATOM    736  O   LEU A 208     -10.803  22.464   5.106  1.00  66.83      A  O
ATOM    737  N   ILE A 209     -10.786  20.328   5.802  1.00  62.12      A  N
ATOM    738  CA  ILE A 209     -11.690  20.582   6.896  1.00  57.67      A  C
ATOM    739  CB  ILE A 209     -12.392  19.319   7.336  1.00  57.85      A  C
ATOM    740  CG2 ILE A 209     -13.350  19.636   8.484  1.00  59.56      A  C
```

Figure 2L

| ATOM | 741 | CG1 | ILE | A | 209 | -13.144 | 18.716 | 6.165 | 1.00 | 58.82 | A | C |
|---|---|---|---|---|---|---|---|---|---|---|---|---|
| ATOM | 742 | CD1 | ILE | A | 209 | -13.902 | 17.497 | 6.543 | 1.00 | 59.20 | A | C |
| ATOM | 743 | C | ILE | A | 209 | -10.776 | 20.999 | 8.013 | 1.00 | 54.58 | A | C |
| ATOM | 744 | O | ILE | A | 209 | -9.939 | 20.207 | 8.430 | 1.00 | 55.70 | A | O |
| ATOM | 745 | N | LEU | A | 210 | -10.938 | 22.211 | 8.527 | 1.00 | 49.77 | A | N |
| ATOM | 746 | CA | LEU | A | 210 | -10.039 | 22.668 | 9.576 | 1.00 | 47.70 | A | C |
| ATOM | 747 | CB | LEU | A | 210 | -9.002 | 23.627 | 8.972 | 1.00 | 49.91 | A | C |
| ATOM | 748 | CG | LEU | A | 210 | -7.898 | 23.099 | 8.039 | 1.00 | 49.59 | A | C |
| ATOM | 749 | CD1 | LEU | A | 210 | -8.214 | 23.467 | 6.603 | 1.00 | 51.49 | A | C |
| ATOM | 750 | CD2 | LEU | A | 210 | -6.548 | 23.722 | 8.440 | 1.00 | 48.94 | A | C |
| ATOM | 751 | C | LEU | A | 210 | -10.601 | 23.326 | 10.843 | 1.00 | 46.77 | A | C |
| ATOM | 752 | O | LEU | A | 210 | -11.682 | 23.947 | 10.839 | 1.00 | 47.63 | A | O |
| ATOM | 753 | N | GLU | A | 211 | -9.828 | 23.192 | 11.923 | 1.00 | 43.80 | A | N |
| ATOM | 754 | CA | GLU | A | 211 | -10.157 | 23.810 | 13.191 | 1.00 | 41.15 | A | C |
| ATOM | 755 | CB | GLU | A | 211 | -8.994 | 23.661 | 14.160 | 1.00 | 46.41 | A | C |
| ATOM | 756 | CG | GLU | A | 211 | -9.065 | 24.461 | 15.447 | 1.00 | 49.38 | A | C |
| ATOM | 757 | CD | GLU | A | 211 | -7.943 | 24.064 | 16.419 | 1.00 | 50.81 | A | C |
| ATOM | 758 | OE1 | GLU | A | 211 | -7.009 | 23.367 | 15.983 | 1.00 | 53.42 | A | O |
| ATOM | 759 | OE2 | GLU | A | 211 | -7.972 | 24.447 | 17.601 | 1.00 | 50.30 | A | O |
| ATOM | 760 | C | GLU | A | 211 | -10.389 | 25.281 | 12.879 | 1.00 | 40.72 | A | C |
| ATOM | 761 | O | GLU | A | 211 | -9.761 | 25.841 | 11.998 | 1.00 | 42.48 | A | O |
| ATOM | 762 | N | TYR | A | 212 | -11.312 | 25.906 | 13.589 | 1.00 | 40.45 | A | N |
| ATOM | 763 | CA | TYR | A | 212 | -11.611 | 27.296 | 13.346 | 1.00 | 36.06 | A | C |
| ATOM | 764 | CB | TYR | A | 212 | -13.125 | 27.543 | 13.286 | 1.00 | 33.34 | A | C |
| ATOM | 765 | CG | TYR | A | 212 | -13.426 | 29.011 | 13.240 | 1.00 | 34.48 | A | C |
| ATOM | 766 | CD1 | TYR | A | 212 | -12.992 | 29.777 | 12.177 | 1.00 | 40.29 | A | C |
| ATOM | 767 | CE1 | TYR | A | 212 | -13.160 | 31.135 | 12.149 | 1.00 | 42.24 | A | C |
| ATOM | 768 | CD2 | TYR | A | 212 | -14.054 | 29.648 | 14.285 | 1.00 | 36.96 | A | C |
| ATOM | 769 | CE2 | TYR | A | 212 | -14.234 | 31.031 | 14.270 | 1.00 | 40.03 | A | C |
| ATOM | 770 | CZ | TYR | A | 212 | -13.777 | 31.762 | 13.198 | 1.00 | 39.86 | A | C |
| ATOM | 771 | OH | TYR | A | 212 | -13.901 | 33.143 | 13.153 | 1.00 | 42.95 | A | O |
| ATOM | 772 | C | TYR | A | 212 | -11.032 | 28.088 | 14.491 | 1.00 | 37.10 | A | C |
| ATOM | 773 | O | TYR | A | 212 | -11.235 | 27.744 | 15.678 | 1.00 | 37.85 | A | O |
| ATOM | 774 | N | ALA | A | 213 | -10.304 | 29.139 | 14.121 | 1.00 | 36.19 | A | N |
| ATOM | 775 | CA | ALA | A | 213 | -9.681 | 29.998 | 15.089 | 1.00 | 37.02 | A | C |
| ATOM | 776 | CB | ALA | A | 213 | -8.188 | 30.053 | 14.855 | 1.00 | 37.96 | A | C |
| ATOM | 777 | C | ALA | A | 213 | -10.322 | 31.372 | 14.933 | 1.00 | 40.53 | A | C |
| ATOM | 778 | O | ALA | A | 213 | -10.062 | 32.103 | 13.960 | 1.00 | 38.10 | A | O |
| ATOM | 779 | N | PRO | A | 214 | -11.182 | 31.729 | 15.904 | 1.00 | 45.35 | A | N |
| ATOM | 780 | CD | PRO | A | 214 | -11.658 | 30.789 | 16.933 | 1.00 | 46.36 | A | C |
| ATOM | 781 | CA | PRO | A | 214 | -11.936 | 32.974 | 15.993 | 1.00 | 44.49 | A | C |
| ATOM | 782 | CB | PRO | A | 214 | -12.975 | 32.669 | 17.062 | 1.00 | 46.90 | A | C |
| ATOM | 783 | CG | PRO | A | 214 | -12.278 | 31.717 | 17.932 | 1.00 | 44.61 | A | C |
| ATOM | 784 | C | PRO | A | 214 | -11.246 | 34.286 | 16.258 | 1.00 | 45.02 | A | C |
| ATOM | 785 | O | PRO | A | 214 | -11.831 | 35.334 | 15.974 | 1.00 | 48.98 | A | O |
| ATOM | 786 | N | LEU | A | 215 | -10.030 | 34.285 | 16.778 | 1.00 | 44.72 | A | N |
| ATOM | 787 | CA | LEU | A | 215 | -9.431 | 35.586 | 17.059 | 1.00 | 45.19 | A | C |
| ATOM | 788 | CB | LEU | A | 215 | -8.744 | 35.568 | 18.425 | 1.00 | 45.00 | A | C |
| ATOM | 789 | CG | LEU | A | 215 | -9.851 | 35.667 | 19.482 | 1.00 | 45.94 | A | C |
| ATOM | 790 | CD1 | LEU | A | 215 | -9.318 | 35.460 | 20.905 | 1.00 | 50.35 | A | C |
| ATOM | 791 | CD2 | LEU | A | 215 | -10.491 | 37.031 | 19.349 | 1.00 | 45.10 | A | C |
| ATOM | 792 | C | LEU | A | 215 | -8.522 | 36.094 | 15.972 | 1.00 | 46.43 | A | C |
| ATOM | 793 | O | LEU | A | 215 | -7.909 | 37.171 | 16.097 | 1.00 | 47.38 | A | O |
| ATOM | 794 | N | GLY | A | 216 | -8.460 | 35.318 | 14.894 | 1.00 | 45.89 | A | N |
| ATOM | 795 | CA | GLY | A | 216 | -7.667 | 35.714 | 13.742 | 1.00 | 44.64 | A | C |
| ATOM | 796 | C | GLY | A | 216 | -6.149 | 35.565 | 13.809 | 1.00 | 44.96 | A | C |
| ATOM | 797 | O | GLY | A | 216 | -5.570 | 34.830 | 14.634 | 1.00 | 45.47 | A | O |
| ATOM | 798 | N | THR | A | 217 | -5.501 | 36.307 | 12.933 | 1.00 | 44.73 | A | N |
| ATOM | 799 | CA | THR | A | 217 | -4.064 | 36.248 | 12.802 | 1.00 | 46.75 | A | C |
| ATOM | 800 | CB | THR | A | 217 | -3.734 | 36.445 | 11.329 | 1.00 | 47.56 | A | C |
| ATOM | 801 | OG1 | THR | A | 217 | -2.913 | 35.359 | 10.901 | 1.00 | 53.23 | A | O |

Figure 2M

```
ATOM    802  CG2 THR A 217      -3.052  37.766  11.103  1.00  49.62      A    C
ATOM    803  C   THR A 217      -3.168  37.148  13.690  1.00  46.71      A    C
ATOM    804  O   THR A 217      -3.446  38.317  13.920  1.00  48.33      A    O
ATOM    805  N   VAL A 218      -2.097  36.571  14.205  1.00  46.45      A    N
ATOM    806  CA  VAL A 218      -1.166  37.332  15.029  1.00  47.22      A    C
ATOM    807  CB  VAL A 218      -0.012  36.441  15.519  1.00  47.68      A    C
ATOM    808  CG1 VAL A 218       1.239  37.266  15.791  1.00  47.53      A    C
ATOM    809  CG2 VAL A 218      -0.454  35.741  16.776  1.00  47.53      A    C
ATOM    810  C   VAL A 218      -0.632  38.500  14.216  1.00  46.92      A    C
ATOM    811  O   VAL A 218      -0.361  39.565  14.748  1.00  46.99      A    O
ATOM    812  N   TYR A 219      -0.517  38.297  12.909  1.00  48.89      A    N
ATOM    813  CA  TYR A 219      -0.049  39.348  12.034  1.00  48.66      A    C
ATOM    814  CB  TYR A 219      -0.204  38.949  10.579  1.00  49.72      A    C
ATOM    815  CG  TYR A 219       0.161  40.052   9.603  1.00  57.49      A    C
ATOM    816  CD1 TYR A 219       1.450  40.591   9.575  1.00  61.63      A    C
ATOM    817  CE1 TYR A 219       1.821  41.532   8.618  1.00  61.98      A    C
ATOM    818  CD2 TYR A 219      -0.758  40.503   8.655  1.00  60.63      A    C
ATOM    819  CE2 TYR A 219      -0.399  41.444   7.697  1.00  63.54      A    C
ATOM    820  CZ  TYR A 219       0.896  41.946   7.679  1.00  63.29      A    C
ATOM    821  OH  TYR A 219       1.276  42.812   6.677  1.00  63.78      A    O
ATOM    822  C   TYR A 219      -0.904  40.573  12.295  1.00  49.45      A    C
ATOM    823  O   TYR A 219      -0.376  41.685  12.440  1.00  50.30      A    O
ATOM    824  N   ARG A 220      -2.223  40.347  12.346  1.00  49.53      A    N
ATOM    825  CA  ARG A 220      -3.201  41.398  12.582  1.00  53.27      A    C
ATOM    826  CB  ARG A 220      -4.612  40.900  12.257  1.00  56.83      A    C
ATOM    827  CG  ARG A 220      -4.851  40.670  10.766  1.00  69.43      A    C
ATOM    828  CD  ARG A 220      -4.982  41.985  10.008  1.00  75.60      A    C
ATOM    829  NE  ARG A 220      -4.866  41.820   8.559  1.00  83.49      A    N
ATOM    830  CZ  ARG A 220      -5.621  41.003   7.828  1.00  88.43      A    C
ATOM    831  NH1 ARG A 220      -5.437  40.928   6.516  1.00  90.26      A    N
ATOM    832  NH2 ARG A 220      -6.555  40.254   8.402  1.00  91.97      A    N
ATOM    833  C   ARG A 220      -3.180  41.974  13.994  1.00  56.03      A    C
ATOM    834  O   ARG A 220      -3.171  43.187  14.153  1.00  59.37      A    O
ATOM    835  N   GLU A 221      -3.170  41.134  15.020  1.00  58.09      A    N
ATOM    836  CA  GLU A 221      -3.147  41.683  16.364  1.00  60.51      A    C
ATOM    837  CB  GLU A 221      -3.063  40.581  17.414  1.00  57.61      A    C
ATOM    838  CG  GLU A 221      -4.395  40.306  18.102  1.00  59.70      A    C
ATOM    839  CD  GLU A 221      -4.847  41.450  19.023  1.00  62.45      A    C
ATOM    840  OE1 GLU A 221      -4.826  42.626  18.575  1.00  65.90      A    O
ATOM    841  OE2 GLU A 221      -5.233  41.172  20.196  1.00  60.04      A    O
ATOM    842  C   GLU A 221      -1.938  42.581  16.452  1.00  63.48      A    C
ATOM    843  O   GLU A 221      -2.017  43.738  16.879  1.00  64.26      A    O
ATOM    844  N   LEU A 222      -0.820  42.033  15.995  1.00  67.70      A    N
ATOM    845  CA  LEU A 222       0.460  42.722  15.987  1.00  67.87      A    C
ATOM    846  CB  LEU A 222       1.515  41.885  15.244  1.00  67.58      A    C
ATOM    847  CG  LEU A 222       2.946  42.415  15.346  1.00  65.18      A    C
ATOM    848  CD1 LEU A 222       3.175  42.970  16.758  1.00  64.68      A    C
ATOM    849  CD2 LEU A 222       3.942  41.303  15.025  1.00  62.50      A    C
ATOM    850  C   LEU A 222       0.340  44.094  15.357  1.00  67.72      A    C
ATOM    851  O   LEU A 222       0.791  45.075  15.944  1.00  69.85      A    O
ATOM    852  N   GLN A 223      -0.260  44.186  14.179  1.00  66.51      A    N
ATOM    853  CA  GLN A 223      -0.408  45.502  13.571  1.00  67.39      A    C
ATOM    854  CB  GLN A 223      -0.768  45.376  12.086  1.00  66.06      A    C
ATOM    855  CG  GLN A 223      -2.046  44.668  11.795  1.00  67.20      A    C
ATOM    856  CD  GLN A 223      -2.305  44.601  10.305  1.00  68.41      A    C
ATOM    857  OE1 GLN A 223      -3.366  44.139   9.854  1.00  70.58      A    O
ATOM    858  NE2 GLN A 223      -1.335  45.063   9.527  1.00  67.38      A    N
ATOM    859  C   GLN A 223      -1.426  46.412  14.305  1.00  67.84      A    C
ATOM    860  O   GLN A 223      -1.327  47.636  14.240  1.00  67.50      A    O
ATOM    861  N   LYS A 224      -2.385  45.818  15.017  1.00  69.61      A    N
ATOM    862  CA  LYS A 224      -3.366  46.597  15.764  1.00  70.41      A    C
```

Figure 2N

| ATOM | 863 | CB  | LYS A 224 | -4.636  | 45.767 | 16.050 | 1.00 | 70.62 | A | C |
|------|-----|-----|-----------|---------|--------|--------|------|-------|---|---|
| ATOM | 864 | CG  | LYS A 224 | -5.663  | 45.788 | 14.895 | 1.00 | 68.80 | A | C |
| ATOM | 865 | CD  | LYS A 224 | -6.855  | 44.854 | 15.124 | 1.00 | 68.86 | A | C |
| ATOM | 866 | CE  | LYS A 224 | -7.685  | 45.273 | 16.327 | 1.00 | 69.95 | A | C |
| ATOM | 867 | NZ  | LYS A 224 | -8.809  | 44.344 | 16.620 | 1.00 | 68.17 | A | N |
| ATOM | 868 | C   | LYS A 224 | -2.743  | 47.109 | 17.063 | 1.00 | 70.17 | A | C |
| ATOM | 869 | O   | LYS A 224 | -2.878  | 48.285 | 17.392 | 1.00 | 73.67 | A | O |
| ATOM | 870 | N   | LEU A 225 | -2.056  | 46.249 | 17.806 | 1.00 | 66.47 | A | N |
| ATOM | 871 | CA  | LEU A 225 | -1.416  | 46.710 | 19.038 | 1.00 | 61.45 | A | C |
| ATOM | 872 | CB  | LEU A 225 | -1.322  | 45.570 | 20.060 | 1.00 | 58.57 | A | C |
| ATOM | 873 | CG  | LEU A 225 | -2.506  | 45.483 | 21.039 | 1.00 | 57.64 | A | C |
| ATOM | 874 | CD1 | LEU A 225 | -3.781  | 45.256 | 20.257 | 1.00 | 58.81 | A | C |
| ATOM | 875 | CD2 | LEU A 225 | -2.295  | 44.364 | 22.056 | 1.00 | 55.79 | A | C |
| ATOM | 876 | C   | LEU A 225 | -0.020  | 47.312 | 18.799 | 1.00 | 60.75 | A | C |
| ATOM | 877 | O   | LEU A 225 | 0.642   | 47.729 | 19.731 | 1.00 | 60.05 | A | O |
| ATOM | 878 | N   | SER A 226 | 0.409   | 47.369 | 17.545 | 1.00 | 61.40 | A | N |
| ATOM | 879 | CA  | SER A 226 | 1.724   | 47.895 | 17.189 | 1.00 | 62.37 | A | C |
| ATOM | 880 | CB  | SER A 226 | 1.899   | 49.318 | 17.733 | 1.00 | 65.25 | A | C |
| ATOM | 881 | OG  | SER A 226 | 2.870   | 50.050 | 16.986 | 1.00 | 66.92 | A | O |
| ATOM | 882 | C   | SER A 226 | 2.870   | 47.005 | 17.708 | 1.00 | 62.22 | A | C |
| ATOM | 883 | O   | SER A 226 | 3.716   | 46.520 | 16.941 | 1.00 | 62.39 | A | O |
| ATOM | 884 | N   | LYS A 227 | 2.874   | 46.786 | 19.016 | 1.00 | 59.86 | A | N |
| ATOM | 885 | CA  | LYS A 227 | 3.905   | 45.986 | 19.655 | 1.00 | 58.85 | A | C |
| ATOM | 886 | CB  | LYS A 227 | 4.986   | 46.933 | 20.203 | 1.00 | 60.81 | A | C |
| ATOM | 887 | CG  | LYS A 227 | 5.810   | 46.364 | 21.313 | 1.00 | 70.18 | A | C |
| ATOM | 888 | CD  | LYS A 227 | 6.349   | 47.457 | 22.246 | 1.00 | 74.56 | A | C |
| ATOM | 889 | CE  | LYS A 227 | 6.895   | 46.838 | 23.554 | 1.00 | 75.22 | A | C |
| ATOM | 890 | NZ  | LYS A 227 | 6.781   | 47.751 | 24.730 | 1.00 | 75.08 | A | N |
| ATOM | 891 | C   | LYS A 227 | 3.257   | 45.208 | 20.784 | 1.00 | 59.37 | A | C |
| ATOM | 892 | O   | LYS A 227 | 2.288   | 45.683 | 21.339 | 1.00 | 63.91 | A | O |
| ATOM | 893 | N   | PHE A 228 | 3.763   | 44.021 | 21.121 | 1.00 | 57.55 | A | N |
| ATOM | 894 | CA  | PHE A 228 | 3.198   | 43.247 | 22.237 | 1.00 | 54.42 | A | C |
| ATOM | 895 | CB  | PHE A 228 | 3.139   | 41.748 | 21.931 | 1.00 | 46.81 | A | C |
| ATOM | 896 | CG  | PHE A 228 | 2.318   | 41.393 | 20.732 | 1.00 | 38.81 | A | C |
| ATOM | 897 | CD1 | PHE A 228 | 1.317   | 42.233 | 20.282 | 1.00 | 35.93 | A | C |
| ATOM | 898 | CD2 | PHE A 228 | 2.512   | 40.173 | 20.095 | 1.00 | 36.88 | A | C |
| ATOM | 899 | CE1 | PHE A 228 | 0.518   | 41.880 | 19.227 | 1.00 | 37.85 | A | C |
| ATOM | 900 | CE2 | PHE A 228 | 1.721   | 39.791 | 19.039 | 1.00 | 34.85 | A | C |
| ATOM | 901 | CZ  | PHE A 228 | 0.709   | 40.658 | 18.596 | 1.00 | 38.71 | A | C |
| ATOM | 902 | C   | PHE A 228 | 4.047   | 43.401 | 23.497 | 1.00 | 56.35 | A | C |
| ATOM | 903 | O   | PHE A 228 | 5.280   | 43.424 | 23.422 | 1.00 | 56.01 | A | O |
| ATOM | 904 | N   | ASP A 229 | 3.389   | 43.474 | 24.650 | 1.00 | 60.32 | A | N |
| ATOM | 905 | CA  | ASP A 229 | 4.087   | 43.595 | 25.932 | 1.00 | 62.60 | A | C |
| ATOM | 906 | CB  | ASP A 229 | 3.100   | 43.752 | 27.096 | 1.00 | 66.99 | A | C |
| ATOM | 907 | CG  | ASP A 229 | 2.098   | 42.606 | 27.160 | 1.00 | 69.72 | A | C |
| ATOM | 908 | OD1 | ASP A 229 | 1.103   | 42.651 | 26.392 | 1.00 | 69.32 | A | O |
| ATOM | 909 | OD2 | ASP A 229 | 2.317   | 41.660 | 27.950 | 1.00 | 70.81 | A | O |
| ATOM | 910 | C   | ASP A 229 | 4.842   | 42.307 | 26.147 | 1.00 | 61.76 | A | C |
| ATOM | 911 | O   | ASP A 229 | 4.682   | 41.356 | 25.396 | 1.00 | 60.08 | A | O |
| ATOM | 912 | N   | GLU A 230 | 5.622   | 42.274 | 27.214 | 1.00 | 62.08 | A | N |
| ATOM | 913 | CA  | GLU A 230 | 6.427   | 41.128 | 27.560 | 1.00 | 65.64 | A | C |
| ATOM | 914 | CB  | GLU A 230 | 7.422   | 41.553 | 28.619 | 1.00 | 68.09 | A | C |
| ATOM | 915 | CG  | GLU A 230 | 8.259   | 42.727 | 28.153 | 1.00 | 76.32 | A | C |
| ATOM | 916 | CD  | GLU A 230 | 9.484   | 42.918 | 29.002 | 1.00 | 80.67 | A | C |
| ATOM | 917 | OE1 | GLU A 230 | 10.125  | 41.895 | 29.343 | 1.00 | 82.99 | A | O |
| ATOM | 918 | OE2 | GLU A 230 | 9.804   | 44.084 | 29.310 | 1.00 | 80.88 | A | O |
| ATOM | 919 | C   | GLU A 230 | 5.663   | 39.892 | 28.017 | 1.00 | 69.18 | A | C |
| ATOM | 920 | O   | GLU A 230 | 6.123   | 38.759 | 27.826 | 1.00 | 69.91 | A | O |
| ATOM | 921 | N   | GLN A 231 | 4.503   | 40.101 | 28.628 | 1.00 | 73.90 | A | N |
| ATOM | 922 | CA  | GLN A 231 | 3.685   | 38.988 | 29.097 | 1.00 | 75.17 | A | C |
| ATOM | 923 | CB  | GLN A 231 | 2.467   | 39.520 | 29.863 | 1.00 | 79.55 | A | C |

Figure 20

```
ATOM    924  CG  GLN A 231       2.798  40.367  31.089  1.00  89.47      A    C
ATOM    925  CD  GLN A 231       1.549  40.957  31.744  1.00  96.98      A    C
ATOM    926  OE1 GLN A 231       1.576  41.407  32.898  1.00 100.89      A    O
ATOM    927  NE2 GLN A 231       0.447  40.965  31.002  1.00  99.51      A    N
ATOM    928  C   GLN A 231       3.219  38.166  27.890  1.00  72.65      A    C
ATOM    929  O   GLN A 231       3.584  36.998  27.727  1.00  72.45      A    O
ATOM    930  N   ARG A 232       2.429  38.803  27.035  1.00  68.15      A    N
ATOM    931  CA  ARG A 232       1.879  38.170  25.846  1.00  63.38      A    C
ATOM    932  CB  ARG A 232       1.044  39.207  25.107  1.00  63.50      A    C
ATOM    933  CG  ARG A 232       0.215  38.677  23.969  1.00  65.53      A    C
ATOM    934  CD  ARG A 232      -0.748  39.766  23.568  1.00  67.35      A    C
ATOM    935  NE  ARG A 232      -1.432  39.509  22.304  1.00  70.97      A    N
ATOM    936  CZ  ARG A 232      -2.307  40.354  21.777  1.00  72.33      A    C
ATOM    937  NH1 ARG A 232      -2.586  41.485  22.418  1.00  69.71      A    N
ATOM    938  NH2 ARG A 232      -2.884  40.079  20.613  1.00  73.23      A    N
ATOM    939  C   ARG A 232       2.921  37.540  24.902  1.00  60.23      A    C
ATOM    940  O   ARG A 232       2.745  36.416  24.414  1.00  58.38      A    O
ATOM    941  N   THR A 233       4.004  38.272  24.648  1.00  55.56      A    N
ATOM    942  CA  THR A 233       5.070  37.794  23.781  1.00  48.72      A    C
ATOM    943  CB  THR A 233       6.149  38.859  23.610  1.00  39.44      A    C
ATOM    944  OG1 THR A 233       7.351  38.260  23.119  1.00  35.31      A    O
ATOM    945  CG2 THR A 233       6.443  39.475  24.921  1.00  38.09      A    C
ATOM    946  C   THR A 233       5.716  36.561  24.366  1.00  51.20      A    C
ATOM    947  O   THR A 233       5.943  35.583  23.669  1.00  52.51      A    O
ATOM    948  N   ALA A 234       5.989  36.605  25.665  1.00  53.14      A    N
ATOM    949  CA  ALA A 234       6.638  35.496  26.349  1.00  49.87      A    C
ATOM    950  CB  ALA A 234       7.074  35.921  27.742  1.00  52.72      A    C
ATOM    951  C   ALA A 234       5.779  34.260  26.445  1.00  48.45      A    C
ATOM    952  O   ALA A 234       6.292  33.154  26.392  1.00  47.78      A    O
ATOM    953  N   THR A 235       4.472  34.419  26.610  1.00  49.37      A    N
ATOM    954  CA  THR A 235       3.659  33.218  26.686  1.00  51.73      A    C
ATOM    955  CB  THR A 235       2.315  33.447  27.481  1.00  51.82      A    C
ATOM    956  OG1 THR A 235       1.261  32.688  26.884  1.00  58.83      A    O
ATOM    957  CG2 THR A 235       1.947  34.912  27.554  1.00  48.59      A    C
ATOM    958  C   THR A 235       3.460  32.688  25.271  1.00  52.58      A    C
ATOM    959  O   THR A 235       3.381  31.475  25.070  1.00  52.21      A    O
ATOM    960  N   TYR A 236       3.427  33.587  24.283  1.00  54.10      A    N
ATOM    961  CA  TYR A 236       3.297  33.143  22.883  1.00  53.71      A    C
ATOM    962  CB  TYR A 236       3.162  34.328  21.906  1.00  53.73      A    C
ATOM    963  CG  TYR A 236       1.750  34.812  21.663  1.00  61.66      A    C
ATOM    964  CD1 TYR A 236       0.652  34.070  22.074  1.00  66.38      A    C
ATOM    965  CE1 TYR A 236      -0.653  34.525  21.874  1.00  70.18      A    C
ATOM    966  CD2 TYR A 236       1.513  36.023  21.035  1.00  66.15      A    C
ATOM    967  CE2 TYR A 236       0.210  36.494  20.827  1.00  69.63      A    C
ATOM    968  CZ  TYR A 236      -0.871  35.739  21.252  1.00  70.75      A    C
ATOM    969  OH  TYR A 236      -2.164  36.202  21.067  1.00  69.03      A    O
ATOM    970  C   TYR A 236       4.554  32.342  22.518  1.00  52.18      A    C
ATOM    971  O   TYR A 236       4.488  31.341  21.792  1.00  51.78      A    O
ATOM    972  N   ILE A 237       5.695  32.779  23.041  1.00  50.58      A    N
ATOM    973  CA  ILE A 237       6.941  32.104  22.770  1.00  45.21      A    C
ATOM    974  CB  ILE A 237       8.137  32.957  23.271  1.00  41.69      A    C
ATOM    975  CG2 ILE A 237       9.415  32.140  23.281  1.00  39.89      A    C
ATOM    976  CG1 ILE A 237       8.312  34.160  22.349  1.00  38.56      A    C
ATOM    977  CD1 ILE A 237       8.430  33.772  20.858  1.00  35.28      A    C
ATOM    978  C   ILE A 237       6.951  30.698  23.381  1.00  45.03      A    C
ATOM    979  O   ILE A 237       7.433  29.749  22.767  1.00  43.50      A    O
ATOM    980  N   THR A 238       6.401  30.550  24.582  1.00  45.32      A    N
ATOM    981  CA  THR A 238       6.362  29.226  25.196  1.00  49.64      A    C
ATOM    982  CB  THR A 238       6.024  29.329  26.683  1.00  52.31      A    C
ATOM    983  OG1 THR A 238       5.180  28.233  27.077  1.00  57.19      A    O
ATOM    984  CG2 THR A 238       5.352  30.650  26.964  1.00  51.31      A    C
```

Figure 2P

```
ATOM    985  C   THR A 238       5.359  28.304  24.490  1.00  50.52      A  C
ATOM    986  O   THR A 238       5.621  27.115  24.297  1.00  48.52      A  O
ATOM    987  N   GLU A 239       4.216  28.857  24.092  1.00  53.64      A  N
ATOM    988  CA  GLU A 239       3.205  28.074  23.399  1.00  56.73      A  C
ATOM    989  CB  GLU A 239       1.983  28.929  23.068  1.00  57.03      A  C
ATOM    990  CG  GLU A 239       1.204  29.373  24.280  1.00  58.12      A  C
ATOM    991  CD  GLU A 239      -0.106  30.015  23.931  1.00  55.27      A  C
ATOM    992  OE1 GLU A 239      -0.843  30.341  24.877  1.00  54.36      A  O
ATOM    993  OE2 GLU A 239      -0.400  30.198  22.729  1.00  52.64      A  O
ATOM    994  C   GLU A 239       3.800  27.574  22.111  1.00  57.95      A  C
ATOM    995  O   GLU A 239       3.616  26.425  21.726  1.00  60.77      A  O
ATOM    996  N   LEU A 240       4.528  28.471  21.457  1.00  57.89      A  N
ATOM    997  CA  LEU A 240       5.166  28.180  20.183  1.00  57.54      A  C
ATOM    998  CB  LEU A 240       5.773  29.470  19.648  1.00  56.34      A  C
ATOM    999  CG  LEU A 240       5.551  29.768  18.179  1.00  56.65      A  C
ATOM   1000  CD1 LEU A 240       4.307  29.072  17.672  1.00  55.80      A  C
ATOM   1001  CD2 LEU A 240       5.459  31.276  18.027  1.00  56.33      A  C
ATOM   1002  C   LEU A 240       6.236  27.097  20.305  1.00  57.23      A  C
ATOM   1003  O   LEU A 240       6.254  26.125  19.536  1.00  56.19      A  O
ATOM   1004  N   ALA A 241       7.122  27.269  21.280  1.00  57.00      A  N
ATOM   1005  CA  ALA A 241       8.192  26.307  21.509  1.00  57.21      A  C
ATOM   1006  CB  ALA A 241       9.040  26.743  22.700  1.00  56.49      A  C
ATOM   1007  C   ALA A 241       7.641  24.889  21.734  1.00  57.20      A  C
ATOM   1008  O   ALA A 241       8.243  23.909  21.303  1.00  58.21      A  O
ATOM   1009  N   ASN A 242       6.493  24.779  22.397  1.00  56.93      A  N
ATOM   1010  CA  ASN A 242       5.917  23.465  22.633  1.00  56.45      A  C
ATOM   1011  CB  ASN A 242       4.750  23.561  23.614  1.00  61.22      A  C
ATOM   1012  CG  ASN A 242       5.190  23.981  25.002  1.00  65.81      A  C
ATOM   1013  OD1 ASN A 242       4.386  24.011  25.931  1.00  69.34      A  O
ATOM   1014  ND2 ASN A 242       6.477  24.311  25.152  1.00  67.04      A  N
ATOM   1015  C   ASN A 242       5.436  22.858  21.314  1.00  54.08      A  C
ATOM   1016  O   ASN A 242       5.776  21.713  20.980  1.00  51.81      A  O
ATOM   1017  N   ALA A 243       4.646  23.630  20.573  1.00  50.33      A  N
ATOM   1018  CA  ALA A 243       4.121  23.154  19.302  1.00  48.11      A  C
ATOM   1019  CB  ALA A 243       3.379  24.285  18.548  1.00  47.57      A  C
ATOM   1020  C   ALA A 243       5.311  22.686  18.496  1.00  46.61      A  C
ATOM   1021  O   ALA A 243       5.252  21.705  17.783  1.00  45.43      A  O
ATOM   1022  N   LEU A 244       6.395  23.429  18.616  1.00  48.76      A  N
ATOM   1023  CA  LEU A 244       7.617  23.081  17.930  1.00  51.97      A  C
ATOM   1024  CB  LEU A 244       8.608  24.233  18.065  1.00  47.46      A  C
ATOM   1025  CG  LEU A 244       8.958  25.044  16.820  1.00  43.86      A  C
ATOM   1026  CD1 LEU A 244       8.169  24.584  15.577  1.00  41.27      A  C
ATOM   1027  CD2 LEU A 244       8.723  26.506  17.148  1.00  40.03      A  C
ATOM   1028  C   LEU A 244       8.178  21.791  18.571  1.00  57.31      A  C
ATOM   1029  O   LEU A 244       8.430  20.781  17.877  1.00  58.25      A  O
ATOM   1030  N   SER A 245       8.337  21.817  19.897  1.00  59.32      A  N
ATOM   1031  CA  SER A 245       8.868  20.662  20.600  1.00  58.93      A  C
ATOM   1032  CB  SER A 245       8.845  20.870  22.095  1.00  58.15      A  C
ATOM   1033  OG  SER A 245       9.385  19.715  22.705  1.00  63.44      A  O
ATOM   1034  C   SER A 245       8.098  19.400  20.262  1.00  60.89      A  C
ATOM   1035  O   SER A 245       8.697  18.345  20.051  1.00  58.79      A  O
ATOM   1036  N   TYR A 246       6.771  19.507  20.219  1.00  65.62      A  N
ATOM   1037  CA  TYR A 246       5.937  18.372  19.852  1.00  69.78      A  C
ATOM   1038  CB  TYR A 246       4.451  18.676  20.080  1.00  67.46      A  C
ATOM   1039  CG  TYR A 246       3.526  17.734  19.329  1.00  68.67      A  C
ATOM   1040  CD1 TYR A 246       2.973  16.611  19.949  1.00  70.54      A  C
ATOM   1041  CE1 TYR A 246       2.177  15.706  19.227  1.00  71.87      A  C
ATOM   1042  CD2 TYR A 246       3.259  17.934  17.972  1.00  70.37      A  C
ATOM   1043  CE2 TYR A 246       2.476  17.049  17.247  1.00  71.97      A  C
ATOM   1044  CZ  TYR A 246       1.936  15.932  17.877  1.00  72.29      A  C
ATOM   1045  OH  TYR A 246       1.179  15.051  17.133  1.00  70.95      A  O
```

Figure 2Q

| | | | | | | | | | | |
|---|---|---|---|---|---|---|---|---|---|---|
| ATOM | 1046 | C | TYR | A | 246 | 6.175 | 18.075 | 18.362 | 1.00 | 73.83 | A | C |
| ATOM | 1047 | O | TYR | A | 246 | 5.937 | 16.953 | 17.895 | 1.00 | 77.90 | A | O |
| ATOM | 1048 | N | CYS | A | 247 | 6.635 | 19.067 | 17.605 | 1.00 | 73.82 | A | N |
| ATOM | 1049 | CA | CYS | A | 247 | 6.871 | 18.826 | 16.193 | 1.00 | 73.88 | A | C |
| ATOM | 1050 | CB | CYS | A | 247 | 6.821 | 20.133 | 15.400 | 1.00 | 71.94 | A | C |
| ATOM | 1051 | SG | CYS | A | 247 | 5.157 | 20.515 | 14.790 | 1.00 | 74.34 | A | S |
| ATOM | 1052 | C | CYS | A | 247 | 8.196 | 18.118 | 15.971 | 1.00 | 76.59 | A | C |
| ATOM | 1053 | O | CYS | A | 247 | 8.332 | 17.311 | 15.054 | 1.00 | 77.68 | A | O |
| ATOM | 1054 | N | HIS | A | 248 | 9.170 | 18.417 | 16.821 | 1.00 | 79.02 | A | N |
| ATOM | 1055 | CA | HIS | A | 248 | 10.472 | 17.794 | 16.713 | 1.00 | 82.34 | A | C |
| ATOM | 1056 | CB | HIS | A | 248 | 11.474 | 18.501 | 17.637 | 1.00 | 83.92 | A | C |
| ATOM | 1057 | CG | HIS | A | 248 | 12.012 | 19.784 | 17.080 | 1.00 | 87.69 | A | C |
| ATOM | 1058 | CD2 | HIS | A | 248 | 13.201 | 20.406 | 17.264 | 1.00 | 88.71 | A | C |
| ATOM | 1059 | ND1 | HIS | A | 248 | 11.285 | 20.592 | 16.231 | 1.00 | 88.91 | A | N |
| ATOM | 1060 | CE1 | HIS | A | 248 | 12.004 | 21.655 | 15.915 | 1.00 | 88.73 | A | C |
| ATOM | 1061 | NE2 | HIS | A | 248 | 13.170 | 21.566 | 16.528 | 1.00 | 88.38 | A | N |
| ATOM | 1062 | C | HIS | A | 248 | 10.378 | 16.298 | 17.052 | 1.00 | 84.20 | A | C |
| ATOM | 1063 | O | HIS | A | 248 | 10.631 | 15.457 | 16.191 | 1.00 | 85.73 | A | O |
| ATOM | 1064 | N | SER | A | 249 | 10.003 | 15.968 | 18.290 | 1.00 | 84.96 | A | N |
| ATOM | 1065 | CA | SER | A | 249 | 9.904 | 14.565 | 18.713 | 1.00 | 86.31 | A | C |
| ATOM | 1066 | CB | SER | A | 249 | 9.087 | 14.440 | 20.000 | 1.00 | 85.00 | A | C |
| ATOM | 1067 | OG | SER | A | 249 | 7.723 | 14.705 | 19.746 | 1.00 | 84.45 | A | O |
| ATOM | 1068 | C | SER | A | 249 | 9.262 | 13.678 | 17.651 | 1.00 | 87.78 | A | C |
| ATOM | 1069 | O | SER | A | 249 | 9.759 | 12.590 | 17.346 | 1.00 | 87.49 | A | O |
| ATOM | 1070 | N | LYS | A | 250 | 8.153 | 14.153 | 17.098 | 1.00 | 89.35 | A | N |
| ATOM | 1071 | CA | LYS | A | 250 | 7.422 | 13.427 | 16.074 | 1.00 | 91.23 | A | C |
| ATOM | 1072 | CB | LYS | A | 250 | 5.997 | 13.989 | 16.040 | 1.00 | 93.29 | A | C |
| ATOM | 1073 | CG | LYS | A | 250 | 5.180 | 13.766 | 14.786 | 1.00 | 101.85 | A | C |
| ATOM | 1074 | CD | LYS | A | 250 | 5.425 | 14.865 | 13.746 | 1.00 | 108.05 | A | C |
| ATOM | 1075 | CE | LYS | A | 250 | 5.897 | 16.189 | 14.372 | 1.00 | 109.23 | A | C |
| ATOM | 1076 | NZ | LYS | A | 250 | 5.059 | 16.669 | 15.508 | 1.00 | 111.44 | A | N |
| ATOM | 1077 | C | LYS | A | 250 | 8.159 | 13.532 | 14.727 | 1.00 | 91.14 | A | C |
| ATOM | 1078 | O | LYS | A | 250 | 7.638 | 13.186 | 13.664 | 1.00 | 90.16 | A | O |
| ATOM | 1079 | N | ARG | A | 251 | 9.405 | 13.986 | 14.813 | 1.00 | 91.81 | A | N |
| ATOM | 1080 | CA | ARG | A | 251 | 10.300 | 14.162 | 13.672 | 1.00 | 92.21 | A | C |
| ATOM | 1081 | CB | ARG | A | 251 | 10.901 | 12.816 | 13.245 | 1.00 | 98.53 | A | C |
| ATOM | 1082 | CG | ARG | A | 251 | 12.150 | 12.454 | 14.052 | 1.00 | 108.16 | A | C |
| ATOM | 1083 | CD | ARG | A | 251 | 12.892 | 11.236 | 13.510 | 1.00 | 114.93 | A | C |
| ATOM | 1084 | NE | ARG | A | 251 | 14.198 | 11.105 | 14.158 | 1.00 | 121.78 | A | N |
| ATOM | 1085 | CZ | ARG | A | 251 | 15.045 | 10.097 | 13.966 | 1.00 | 124.87 | A | C |
| ATOM | 1086 | NH1 | ARG | A | 251 | 14.731 | 9.110 | 13.136 | 1.00 | 127.26 | A | N |
| ATOM | 1087 | NH2 | ARG | A | 251 | 16.213 | 10.081 | 14.601 | 1.00 | 125.17 | A | N |
| ATOM | 1088 | C | ARG | A | 251 | 9.762 | 14.900 | 12.456 | 1.00 | 88.57 | A | C |
| ATOM | 1089 | O | ARG | A | 251 | 9.643 | 14.345 | 11.369 | 1.00 | 87.62 | A | O |
| ATOM | 1090 | N | VAL | A | 252 | 9.462 | 16.174 | 12.663 | 1.00 | 86.18 | A | N |
| ATOM | 1091 | CA | VAL | A | 252 | 8.974 | 17.052 | 11.611 | 1.00 | 84.70 | A | C |
| ATOM | 1092 | CB | VAL | A | 252 | 7.431 | 17.182 | 11.635 | 1.00 | 82.24 | A | C |
| ATOM | 1093 | CG1 | VAL | A | 252 | 6.995 | 18.381 | 10.816 | 1.00 | 80.36 | A | C |
| ATOM | 1094 | CG2 | VAL | A | 252 | 6.797 | 15.922 | 11.072 | 1.00 | 79.35 | A | C |
| ATOM | 1095 | C | VAL | A | 252 | 9.605 | 18.402 | 11.908 | 1.00 | 85.34 | A | C |
| ATOM | 1096 | O | VAL | A | 252 | 9.631 | 18.836 | 13.057 | 1.00 | 87.00 | A | O |
| ATOM | 1097 | N | ILE | A | 253 | 10.149 | 19.046 | 10.886 | 1.00 | 85.65 | A | N |
| ATOM | 1098 | CA | ILE | A | 253 | 10.770 | 20.343 | 11.078 | 1.00 | 87.22 | A | C |
| ATOM | 1099 | CB | ILE | A | 253 | 12.216 | 20.371 | 10.588 | 1.00 | 89.79 | A | C |
| ATOM | 1100 | CG2 | ILE | A | 253 | 12.711 | 21.797 | 10.591 | 1.00 | 91.38 | A | C |
| ATOM | 1101 | CG1 | ILE | A | 253 | 13.106 | 19.505 | 11.485 | 1.00 | 91.78 | A | C |
| ATOM | 1102 | CD1 | ILE | A | 253 | 12.836 | 18.010 | 11.380 | 1.00 | 91.55 | A | C |
| ATOM | 1103 | C | ILE | A | 253 | 9.998 | 21.393 | 10.312 | 1.00 | 87.67 | A | C |
| ATOM | 1104 | O | ILE | A | 253 | 9.975 | 21.378 | 9.080 | 1.00 | 87.82 | A | O |
| ATOM | 1105 | N | HIS | A | 254 | 9.368 | 22.306 | 11.049 | 1.00 | 86.39 | A | N |
| ATOM | 1106 | CA | HIS | A | 254 | 8.571 | 23.363 | 10.442 | 1.00 | 85.51 | A | C |

Figure 2R

```
ATOM   1107  CB   HIS A 254       7.451  23.827  11.389  1.00  80.51      A  C
ATOM   1108  CG   HIS A 254       6.110  23.251  11.063  1.00  82.33      A  C
ATOM   1109  CD2  HIS A 254       5.222  22.573  11.825  1.00  84.09      A  C
ATOM   1110  ND1  HIS A 254       5.557  23.323   9.801  1.00  84.07      A  N
ATOM   1111  CE1  HIS A 254       4.386  22.711   9.800  1.00  86.17      A  C
ATOM   1112  NE2  HIS A 254       4.160  22.246  11.016  1.00  86.48      A  N
ATOM   1113  C    HIS A 254       9.400  24.566  10.062  1.00  86.59      A  C
ATOM   1114  O    HIS A 254      10.525  24.455   9.543  1.00  86.38      A  O
ATOM   1115  N    ARG A 255       8.803  25.714  10.366  1.00  88.55      A  N
ATOM   1116  CA   ARG A 255       9.338  27.037  10.116  1.00  87.88      A  C
ATOM   1117  CB   ARG A 255      10.523  26.987   9.138  1.00  88.00      A  C
ATOM   1124  C    ARG A 255       8.156  27.794   9.504  1.00  87.48      A  C
ATOM   1125  O    ARG A 255       6.991  27.403   9.685  1.00  83.80      A  O
ATOM   1126  N    ASP A 256       8.454  28.865   8.773  1.00  85.49      A  N
ATOM   1127  CA   ASP A 256       7.415  29.674   8.163  1.00  79.91      A  C
ATOM   1128  CB   ASP A 256       6.572  28.839   7.200  1.00  77.83      A  C
ATOM   1132  C    ASP A 256       6.516  30.226   9.261  1.00  76.92      A  C
ATOM   1133  O    ASP A 256       5.643  31.036   8.969  1.00  80.83      A  O
ATOM   1134  N    ILE A 257       6.731  29.796  10.508  1.00  68.19      A  N
ATOM   1135  CA   ILE A 257       5.915  30.247  11.625  1.00  57.62      A  C
ATOM   1136  CB   ILE A 257       6.280  29.551  12.973  1.00  53.48      A  C
ATOM   1137  CG2  ILE A 257       5.820  28.118  12.979  1.00  54.94      A  C
ATOM   1138  CG1  ILE A 257       7.770  29.661  13.232  1.00  49.61      A  C
ATOM   1139  CD1  ILE A 257       8.119  30.548  14.383  1.00  43.70      A  C
ATOM   1140  C    ILE A 257       5.959  31.744  11.878  1.00  54.17      A  C
ATOM   1141  O    ILE A 257       6.230  32.175  12.982  1.00  55.38      A  O
ATOM   1142  N    LYS A 258       5.680  32.531  10.856  1.00  49.16      A  N
ATOM   1143  CA   LYS A 258       5.649  33.971  10.991  1.00  46.30      A  C
ATOM   1144  CB   LYS A 258       6.128  34.630   9.691  1.00  47.36      A  C
ATOM   1145  CG   LYS A 258       5.575  33.995   8.448  1.00  48.03      A  C
ATOM   1146  CD   LYS A 258       6.122  34.644   7.196  1.00  47.79      A  C
ATOM   1147  CE   LYS A 258       7.598  34.477   7.051  1.00  48.62      A  C
ATOM   1148  NZ   LYS A 258       7.892  34.598   5.596  1.00  58.33      A  N
ATOM   1149  C    LYS A 258       4.229  34.420  11.333  1.00  45.88      A  C
ATOM   1150  O    LYS A 258       3.285  33.653  11.212  1.00  46.55      A  O
ATOM   1151  N    PRO A 259       4.068  35.677  11.761  1.00  45.68      A  N
ATOM   1152  CD   PRO A 259       5.118  36.704  11.817  1.00  46.78      A  C
ATOM   1153  CA   PRO A 259       2.775  36.253  12.132  1.00  45.43      A  C
ATOM   1154  CB   PRO A 259       3.077  37.740  12.180  1.00  46.00      A  C
ATOM   1155  CG   PRO A 259       4.473  37.754  12.674  1.00  46.05      A  C
ATOM   1156  C    PRO A 259       1.624  35.921  11.172  1.00  44.45      A  C
ATOM   1157  O    PRO A 259       0.495  35.659  11.581  1.00  41.11      A  O
ATOM   1158  N    GLU A 260       1.944  35.955   9.889  1.00  46.37      A  N
ATOM   1159  CA   GLU A 260       1.007  35.685   8.833  1.00  46.16      A  C
ATOM   1160  CB   GLU A 260       1.756  35.684   7.497  1.00  46.91      A  C
ATOM   1161  CG   GLU A 260       2.573  36.965   7.163  1.00  47.60      A  C
ATOM   1162  CD   GLU A 260       3.594  37.349   8.231  1.00  51.56      A  C
ATOM   1163  OE1  GLU A 260       3.944  38.549   8.333  1.00  49.95      A  O
ATOM   1164  OE2  GLU A 260       4.061  36.465   8.972  1.00  56.64      A  O
ATOM   1165  C    GLU A 260       0.387  34.310   9.057  1.00  48.99      A  C
ATOM   1166  O    GLU A 260      -0.809  34.113   8.877  1.00  51.12      A  O
ATOM   1167  N    ASN A 261       1.210  33.360   9.483  1.00  52.67      A  N
ATOM   1168  CA   ASN A 261       0.745  31.985   9.648  1.00  52.53      A  C
ATOM   1169  CB   ASN A 261       1.806  31.011   9.092  1.00  53.47      A  C
ATOM   1170  CG   ASN A 261       2.308  31.417   7.710  1.00  53.07      A  C
ATOM   1171  OD1  ASN A 261       1.526  31.794   6.832  1.00  50.76      A  O
ATOM   1172  ND2  ASN A 261       3.620  31.334   7.513  1.00  52.27      A  N
ATOM   1173  C    ASN A 261       0.351  31.562  11.042  1.00  49.79      A  C
ATOM   1174  O    ASN A 261       0.018  30.403  11.261  1.00  52.25      A  O
ATOM   1175  N    LEU A 262       0.392  32.495  11.984  1.00  46.23      A  N
ATOM   1176  CA   LEU A 262       0.016  32.171  13.339  1.00  42.90      A  C
```

Figure 2S

```
ATOM   1177  CB   LEU A 262       1.026  32.782  14.319  1.00  42.14      A    C
ATOM   1178  CG   LEU A 262       2.503  32.370  14.139  1.00  38.18      A    C
ATOM   1179  CD1  LEU A 262       3.305  33.014  15.238  1.00  34.58      A    C
ATOM   1180  CD2  LEU A 262       2.675  30.845  14.216  1.00  33.80      A    C
ATOM   1181  C    LEU A 262      -1.402  32.693  13.598  1.00  40.82      A    C
ATOM   1182  O    LEU A 262      -1.691  33.875  13.350  1.00  41.46      A    O
ATOM   1183  N    LEU A 263      -2.300  31.825  14.061  1.00  39.36      A    N
ATOM   1184  CA   LEU A 263      -3.669  32.261  14.325  1.00  43.05      A    C
ATOM   1185  CB   LEU A 263      -4.648  31.375  13.568  1.00  43.53      A    C
ATOM   1186  CG   LEU A 263      -4.681  31.451  12.040  1.00  43.00      A    C
ATOM   1187  CD1  LEU A 263      -5.699  30.417  11.435  1.00  38.01      A    C
ATOM   1188  CD2  LEU A 263      -5.106  32.848  11.703  1.00  46.40      A    C
ATOM   1189  C    LEU A 263      -4.012  32.254  15.815  1.00  45.66      A    C
ATOM   1190  O    LEU A 263      -3.360  31.589  16.620  1.00  47.95      A    O
ATOM   1191  N    LEU A 264      -5.039  32.993  16.203  1.00  48.56      A    N
ATOM   1192  CA   LEU A 264      -5.377  33.026  17.618  1.00  50.80      A    C
ATOM   1193  CB   LEU A 264      -5.425  34.490  18.074  1.00  52.52      A    C
ATOM   1194  CG   LEU A 264      -4.151  35.277  17.752  1.00  53.11      A    C
ATOM   1195  CD1  LEU A 264      -4.343  36.772  17.933  1.00  54.84      A    C
ATOM   1196  CD2  LEU A 264      -3.033  34.768  18.639  1.00  56.84      A    C
ATOM   1197  C    LEU A 264      -6.684  32.277  17.971  1.00  52.77      A    C
ATOM   1198  O    LEU A 264      -7.637  32.220  17.184  1.00  54.59      A    O
ATOM   1199  N    GLY A 265      -6.704  31.691  19.163  1.00  54.07      A    N
ATOM   1200  CA   GLY A 265      -7.877  30.952  19.615  1.00  55.88      A    C
ATOM   1201  C    GLY A 265      -8.780  31.761  20.540  1.00  57.02      A    C
ATOM   1202  O    GLY A 265      -8.523  32.942  20.799  1.00  56.82      A    O
ATOM   1203  N    SER A 266      -9.844  31.111  21.015  1.00  59.39      A    N
ATOM   1204  CA   SER A 266     -10.832  31.695  21.922  1.00  62.78      A    C
ATOM   1205  CB   SER A 266     -11.621  30.585  22.623  1.00  65.55      A    C
ATOM   1206  OG   SER A 266     -12.199  29.660  21.715  1.00  65.97      A    O
ATOM   1207  C    SER A 266     -10.128  32.531  22.980  1.00  65.41      A    C
ATOM   1208  O    SER A 266     -10.269  33.749  23.022  1.00  70.21      A    O
ATOM   1209  N    ALA A 267      -9.365  31.861  23.830  1.00  64.66      A    N
ATOM   1210  CA   ALA A 267      -8.630  32.512  24.895  1.00  63.74      A    C
ATOM   1211  CB   ALA A 267      -8.088  31.470  25.837  1.00  62.31      A    C
ATOM   1212  C    ALA A 267      -7.486  33.368  24.371  1.00  65.69      A    C
ATOM   1213  O    ALA A 267      -6.794  34.031  25.137  1.00  65.00      A    O
ATOM   1214  N    GLY A 268      -7.272  33.352  23.065  1.00  66.78      A    N
ATOM   1215  CA   GLY A 268      -6.187  34.142  22.517  1.00  62.93      A    C
ATOM   1216  C    GLY A 268      -4.927  33.308  22.483  1.00  61.09      A    C
ATOM   1217  O    GLY A 268      -3.819  33.834  22.564  1.00  61.62      A    O
ATOM   1218  N    GLU A 269      -5.128  32.000  22.354  1.00  58.70      A    N
ATOM   1219  CA   GLU A 269      -4.063  31.012  22.315  1.00  58.24      A    C
ATOM   1220  CB   GLU A 269      -4.595  29.676  22.828  1.00  60.49      A    C
ATOM   1221  CG   GLU A 269      -6.118  29.559  22.749  1.00  65.14      A    C
ATOM   1222  CD   GLU A 269      -6.584  28.250  22.140  1.00  69.20      A    C
ATOM   1223  OE1  GLU A 269      -6.008  27.183  22.467  1.00  72.44      A    O
ATOM   1224  OE2  GLU A 269      -7.542  28.295  21.335  1.00  69.75      A    O
ATOM   1225  C    GLU A 269      -3.511  30.839  20.907  1.00  57.55      A    C
ATOM   1226  O    GLU A 269      -4.253  30.880  19.912  1.00  56.54      A    O
ATOM   1227  N    LEU A 270      -2.207  30.607  20.831  1.00  58.50      A    N
ATOM   1228  CA   LEU A 270      -1.546  30.455  19.552  1.00  59.98      A    C
ATOM   1229  CB   LEU A 270      -0.040  30.479  19.754  1.00  59.88      A    C
ATOM   1230  CG   LEU A 270       0.700  30.847  18.479  1.00  63.72      A    C
ATOM   1231  CD1  LEU A 270       0.101  32.116  17.920  1.00  64.75      A    C
ATOM   1232  CD2  LEU A 270       2.170  31.034  18.771  1.00  67.97      A    C
ATOM   1233  C    LEU A 270      -1.936  29.216  18.762  1.00  60.16      A    C
ATOM   1234  O    LEU A 270      -2.085  28.137  19.317  1.00  61.13      A    O
ATOM   1235  N    LYS A 271      -2.101  29.388  17.454  1.00  59.79      A    N
ATOM   1236  CA   LYS A 271      -2.457  28.289  16.567  1.00  58.46      A    C
ATOM   1237  CB   LYS A 271      -3.904  28.357  16.097  1.00  59.31      A    C
```

Figure 2T

```
ATOM   1238  CG  LYS A 271      -4.954  28.195  17.164  1.00  59.77      A    C
ATOM   1239  CD  LYS A 271      -4.790  26.905  17.947  1.00  59.69      A    C
ATOM   1240  CE  LYS A 271      -6.085  26.568  18.646  1.00  61.18      A    C
ATOM   1241  NZ  LYS A 271      -5.924  25.504  19.648  1.00  62.99      A    N
ATOM   1242  C   LYS A 271      -1.601  28.395  15.350  1.00  58.99      A    C
ATOM   1243  O   LYS A 271      -1.895  29.206  14.455  1.00  57.96      A    O
ATOM   1244  N   ILE A 272      -0.538  27.588  15.315  1.00  61.86      A    N
ATOM   1245  CA  ILE A 272       0.370  27.566  14.168  1.00  63.81      A    C
ATOM   1246  CB  ILE A 272       1.548  26.626  14.403  1.00  62.25      A    C
ATOM   1247  CG2 ILE A 272       2.270  26.379  13.098  1.00  60.79      A    C
ATOM   1248  CG1 ILE A 272       2.456  27.210  15.478  1.00  62.05      A    C
ATOM   1249  CD1 ILE A 272       3.719  26.415  15.715  1.00  65.85      A    C
ATOM   1250  C   ILE A 272      -0.392  27.055  12.971  1.00  65.96      A    C
ATOM   1251  O   ILE A 272      -0.974  25.991  13.026  1.00  66.85      A    O
ATOM   1252  N   ALA A 273      -0.391  27.810  11.887  1.00  70.98      A    N
ATOM   1253  CA  ALA A 273      -1.112  27.382  10.697  1.00  77.37      A    C
ATOM   1254  CB  ALA A 273      -2.418  28.155  10.586  1.00  78.27      A    C
ATOM   1255  C   ALA A 273      -0.298  27.532   9.412  1.00  81.17      A    C
ATOM   1256  O   ALA A 273       0.183  28.616   9.087  1.00  84.58      A    O
ATOM   1257  N   ASP A 274      -0.143  26.437   8.678  1.00  83.86      A    N
ATOM   1258  CA  ASP A 274       0.610  26.469   7.426  1.00  83.78      A    C
ATOM   1259  CB  ASP A 274       2.111  26.677   7.696  1.00  79.07      A    C
ATOM   1260  CG  ASP A 274       2.715  25.574   8.562  1.00  77.63      A    C
ATOM   1261  OD1 ASP A 274       1.972  24.687   9.037  1.00  76.25      A    O
ATOM   1262  OD2 ASP A 274       3.945  25.595   8.777  1.00  77.42      A    O
ATOM   1263  C   ASP A 274       0.426  25.200   6.618  1.00  84.86      A    C
ATOM   1264  O   ASP A 274       1.206  24.265   6.756  1.00  85.25      A    O
ATOM   1265  N   PHE A 275      -0.616  25.144   5.795  1.00  87.85      A    N
ATOM   1266  CA  PHE A 275      -0.815  23.970   4.958  1.00  90.71      A    C
ATOM   1267  CB  PHE A 275      -2.124  23.261   5.272  1.00  94.31      A    C
ATOM   1268  CG  PHE A 275      -2.318  22.948   6.711  1.00 100.68      A    C
ATOM   1269  CD1 PHE A 275      -1.290  23.141   7.642  1.00 103.29      A    C
ATOM   1270  CD2 PHE A 275      -3.547  22.463   7.148  1.00 102.78      A    C
ATOM   1271  CE1 PHE A 275      -1.486  22.859   8.984  1.00 105.17      A    C
ATOM   1272  CE2 PHE A 275      -3.760  22.173   8.488  1.00 105.64      A    C
ATOM   1273  CZ  PHE A 275      -2.730  22.370   9.419  1.00 106.34      A    C
ATOM   1274  C   PHE A 275      -0.886  24.411   3.515  1.00  91.32      A    C
ATOM   1275  O   PHE A 275       0.131  24.575   2.828  1.00  91.62      A    O
ATOM   1276  N   GLY A 276      -2.126  24.605   3.083  1.00  92.25      A    N
ATOM   1277  CA  GLY A 276      -2.393  25.008   1.733  1.00  93.34      A    C
ATOM   1278  C   GLY A 276      -2.707  26.472   1.581  1.00  94.14      A    C
ATOM   1279  O   GLY A 276      -3.841  26.829   1.249  1.00  95.97      A    O
ATOM   1280  N   TRP A 277      -1.725  27.329   1.853  1.00  93.73      A    N
ATOM   1281  CA  TRP A 277      -1.924  28.760   1.647  1.00  92.60      A    C
ATOM   1282  CB  TRP A 277      -3.332  29.226   2.099  1.00  90.63      A    C
ATOM   1283  CG  TRP A 277      -3.685  29.027   3.534  1.00  86.21      A    C
ATOM   1284  CD2 TRP A 277      -3.579  30.004   4.587  1.00  82.11      A    C
ATOM   1285  CE2 TRP A 277      -4.076  29.404   5.764  1.00  80.84      A    C
ATOM   1286  CE3 TRP A 277      -3.113  31.325   4.645  1.00  78.55      A    C
ATOM   1287  CD1 TRP A 277      -4.222  27.902   4.104  1.00  84.13      A    C
ATOM   1288  NE1 TRP A 277      -4.462  28.124   5.446  1.00  82.59      A    N
ATOM   1289  CZ2 TRP A 277      -4.119  30.083   6.987  1.00  79.73      A    C
ATOM   1290  CZ3 TRP A 277      -3.154  32.000   5.856  1.00  74.73      A    C
ATOM   1291  CH2 TRP A 277      -3.654  31.379   7.013  1.00  76.97      A    C
ATOM   1292  C   TRP A 277      -0.865  29.733   2.164  1.00  93.14      A    C
ATOM   1293  O   TRP A 277       0.103  29.365   2.861  1.00  93.04      A    O
ATOM   1294  N   SER A 278      -1.072  30.985   1.762  1.00  92.88      A    N
ATOM   1295  CA  SER A 278      -0.195  32.108   2.064  1.00  91.95      A    C
ATOM   1296  CB  SER A 278       0.897  32.176   0.980  1.00  91.93      A    C
ATOM   1297  OG  SER A 278       1.876  33.166   1.240  1.00  89.50      A    O
ATOM   1298  C   SER A 278      -1.139  33.316   1.974  1.00  91.22      A    C
```

Figure 2U

| ATOM | 1299 | O | SER | A | 278 | -1.893 | 33.583 | 2.904 | 1.00 | 90.97 | A | O |
|---|---|---|---|---|---|---|---|---|---|---|---|---|
| ATOM | 1300 | N | VAL | A | 279 | -1.090 | 34.018 | 0.842 | 1.00 | 89.97 | A | N |
| ATOM | 1301 | CA | VAL | A | 279 | -1.952 | 35.175 | 0.550 | 1.00 | 88.55 | A | C |
| ATOM | 1302 | CB | VAL | A | 279 | -2.774 | 34.937 | -0.743 | 1.00 | 86.75 | A | C |
| ATOM | 1305 | C | VAL | A | 279 | -2.949 | 35.525 | 1.651 | 1.00 | 87.15 | A | C |
| ATOM | 1306 | O | VAL | A | 279 | -4.098 | 35.049 | 1.506 | 1.00 | 85.02 | A | O |
| TER | 1308 | | VAL | A | 279 | | | | | | A | |
| ATOM | 1309 | CB | THR | A | 287 | 8.902 | 46.475 | -4.662 | 1.00 | 124.67 | A | C |
| ATOM | 1312 | C | THR | A | 287 | 8.560 | 46.308 | -2.217 | 1.00 | 128.38 | A | C |
| ATOM | 1313 | O | THR | A | 287 | 7.713 | 47.203 | -2.114 | 1.00 | 130.20 | A | O |
| ATOM | 1314 | N | THR | A | 287 | 7.395 | 44.710 | -3.726 | 1.00 | 126.64 | A | N |
| ATOM | 1315 | CA | THR | A | 287 | 8.644 | 45.496 | -3.501 | 1.00 | 127.54 | A | C |
| ATOM | 1316 | N | THR | A | 288 | 9.433 | 45.989 | -1.256 | 1.00 | 127.57 | A | N |
| ATOM | 1317 | CA | THR | A | 288 | 9.525 | 46.673 | 0.045 | 1.00 | 125.37 | A | C |
| ATOM | 1318 | CB | THR | A | 288 | 8.306 | 47.562 | 0.349 | 1.00 | 123.59 | A | C |
| ATOM | 1321 | C | THR | A | 288 | 9.619 | 45.660 | 1.167 | 1.00 | 125.68 | A | C |
| ATOM | 1322 | O | THR | A | 288 | 10.696 | 45.428 | 1.726 | 1.00 | 126.39 | A | O |
| ATOM | 1323 | N | LEU | A | 289 | 8.475 | 45.068 | 1.503 | 1.00 | 124.65 | A | N |
| ATOM | 1324 | CA | LEU | A | 289 | 8.416 | 44.074 | 2.557 | 1.00 | 123.06 | A | C |
| ATOM | 1325 | CB | LEU | A | 289 | 6.983 | 43.547 | 2.709 | 1.00 | 122.14 | A | C |
| ATOM | 1329 | C | LEU | A | 289 | 9.358 | 42.940 | 2.170 | 1.00 | 122.75 | A | C |
| ATOM | 1330 | O | LEU | A | 289 | 9.005 | 42.068 | 1.352 | 1.00 | 123.30 | A | O |
| ATOM | 1331 | N | CYS | A | 290 | 10.574 | 42.966 | 2.705 | 1.00 | 119.67 | A | N |
| ATOM | 1332 | CA | CYS | A | 290 | 11.512 | 41.891 | 2.402 | 1.00 | 115.54 | A | C |
| ATOM | 1333 | CB | CYS | A | 290 | 12.953 | 42.318 | 2.719 | 1.00 | 112.99 | A | C |
| ATOM | 1335 | C | CYS | A | 290 | 11.051 | 40.785 | 3.348 | 1.00 | 114.21 | A | C |
| ATOM | 1336 | O | CYS | A | 290 | 11.859 | 40.046 | 3.921 | 1.00 | 115.43 | A | O |
| ATOM | 1337 | N | GLY | A | 291 | 9.728 | 40.725 | 3.526 | 1.00 | 111.20 | A | N |
| ATOM | 1338 | CA | GLY | A | 291 | 9.104 | 39.740 | 4.395 | 1.00 | 104.53 | A | C |
| ATOM | 1339 | C | GLY | A | 291 | 9.331 | 38.314 | 3.935 | 1.00 | 98.52 | A | C |
| ATOM | 1340 | O | GLY | A | 291 | 8.916 | 37.358 | 4.585 | 1.00 | 97.34 | A | O |
| ATOM | 1341 | N | THR | A | 292 | 9.994 | 38.184 | 2.796 | 1.00 | 92.23 | A | N |
| ATOM | 1342 | CA | THR | A | 292 | 10.307 | 36.887 | 2.238 | 1.00 | 84.71 | A | C |
| ATOM | 1343 | CB | THR | A | 292 | 10.598 | 37.013 | 0.723 | 1.00 | 83.69 | A | C |
| ATOM | 1344 | OG1 | THR | A | 292 | 9.611 | 37.858 | 0.111 | 1.00 | 81.22 | A | O |
| ATOM | 1345 | CG2 | THR | A | 292 | 10.542 | 35.656 | 0.059 | 1.00 | 83.67 | A | C |
| ATOM | 1346 | C | THR | A | 292 | 11.541 | 36.363 | 2.989 | 1.00 | 80.47 | A | C |
| ATOM | 1347 | O | THR | A | 292 | 11.489 | 35.303 | 3.610 | 1.00 | 81.07 | A | O |
| ATOM | 1348 | N | LEU | A | 293 | 12.634 | 37.130 | 2.952 | 1.00 | 73.33 | A | N |
| ATOM | 1349 | CA | LEU | A | 293 | 13.883 | 36.764 | 3.620 | 1.00 | 65.30 | A | C |
| ATOM | 1350 | CB | LEU | A | 293 | 15.039 | 37.602 | 3.067 | 1.00 | 61.91 | A | C |
| ATOM | 1351 | CG | LEU | A | 293 | 15.664 | 37.180 | 1.739 | 1.00 | 55.12 | A | C |
| ATOM | 1352 | CD1 | LEU | A | 293 | 16.630 | 38.261 | 1.297 | 1.00 | 49.15 | A | C |
| ATOM | 1353 | CD2 | LEU | A | 293 | 16.371 | 35.817 | 1.885 | 1.00 | 52.96 | A | C |
| ATOM | 1354 | C | LEU | A | 293 | 13.860 | 36.926 | 5.135 | 1.00 | 60.26 | A | C |
| ATOM | 1355 | O | LEU | A | 293 | 14.522 | 36.177 | 5.849 | 1.00 | 59.00 | A | O |
| ATOM | 1356 | N | ASP | A | 294 | 13.092 | 37.914 | 5.596 | 1.00 | 55.84 | A | N |
| ATOM | 1357 | CA | ASP | A | 294 | 12.938 | 38.275 | 7.008 | 1.00 | 51.34 | A | C |
| ATOM | 1358 | CB | ASP | A | 294 | 11.655 | 39.083 | 7.205 | 1.00 | 52.57 | A | C |
| ATOM | 1359 | CG | ASP | A | 294 | 11.801 | 40.560 | 6.801 | 1.00 | 53.26 | A | C |
| ATOM | 1360 | OD1 | ASP | A | 294 | 10.792 | 41.103 | 6.320 | 1.00 | 59.26 | A | O |
| ATOM | 1361 | OD2 | ASP | A | 294 | 12.891 | 41.181 | 6.975 | 1.00 | 49.59 | A | O |
| ATOM | 1362 | C | ASP | A | 294 | 12.944 | 37.180 | 8.035 | 1.00 | 49.15 | A | C |
| ATOM | 1363 | O | ASP | A | 294 | 13.298 | 37.424 | 9.172 | 1.00 | 49.68 | A | O |
| ATOM | 1364 | N | TYR | A | 295 | 12.554 | 35.970 | 7.661 | 1.00 | 47.93 | A | N |
| ATOM | 1365 | CA | TYR | A | 295 | 12.495 | 34.882 | 8.635 | 1.00 | 52.63 | A | C |
| ATOM | 1366 | CB | TYR | A | 295 | 11.056 | 34.404 | 8.745 | 1.00 | 56.24 | A | C |
| ATOM | 1367 | CG | TYR | A | 295 | 10.266 | 35.306 | 9.619 | 1.00 | 59.44 | A | C |
| ATOM | 1368 | CD1 | TYR | A | 295 | 9.640 | 36.451 | 9.116 | 1.00 | 57.70 | A | C |
| ATOM | 1369 | CE1 | TYR | A | 295 | 9.064 | 37.384 | 9.976 | 1.00 | 54.11 | A | C |
| ATOM | 1370 | CD2 | TYR | A | 295 | 10.278 | 35.107 | 10.989 | 1.00 | 57.71 | A | C |

Figure 2V

```
ATOM   1371  CE2 TYR A 295       9.714  36.023  11.842  1.00  57.14      A  C
ATOM   1372  CZ  TYR A 295       9.122  37.155  11.338  1.00  55.50      A  C
ATOM   1373  OH  TYR A 295       8.667  38.053  12.257  1.00  60.87      A  O
ATOM   1374  C   TYR A 295      13.407  33.697   8.379  1.00  53.01      A  C
ATOM   1375  O   TYR A 295      13.602  32.840   9.235  1.00  51.62      A  O
ATOM   1376  N   LEU A 296      13.954  33.647   7.181  1.00  52.76      A  N
ATOM   1377  CA  LEU A 296      14.853  32.576   6.814  1.00  48.84      A  C
ATOM   1378  CB  LEU A 296      15.127  32.653   5.299  1.00  45.66      A  C
ATOM   1379  CG  LEU A 296      13.837  32.796   4.467  1.00  41.77      A  C
ATOM   1380  CD1 LEU A 296      14.119  33.232   3.065  1.00  40.15      A  C
ATOM   1381  CD2 LEU A 296      13.103  31.499   4.454  1.00  40.24      A  C
ATOM   1382  C   LEU A 296      16.156  32.709   7.623  1.00  50.65      A  C
ATOM   1383  O   LEU A 296      16.654  33.805   7.881  1.00  51.36      A  O
ATOM   1384  N   PRO A 297      16.694  31.581   8.081  1.00  52.09      A  N
ATOM   1385  CD  PRO A 297      16.169  30.206   8.008  1.00  52.91      A  C
ATOM   1386  CA  PRO A 297      17.933  31.621   8.842  1.00  51.42      A  C
ATOM   1387  CB  PRO A 297      17.842  30.354   9.669  1.00  50.56      A  C
ATOM   1388  CG  PRO A 297      17.243  29.400   8.714  1.00  51.03      A  C
ATOM   1389  C   PRO A 297      19.085  31.579   7.827  1.00  51.79      A  C
ATOM   1390  O   PRO A 297      18.866  31.307   6.643  1.00  55.81      A  O
ATOM   1391  N   PRO A 298      20.322  31.855   8.277  1.00  49.60      A  N
ATOM   1392  CD  PRO A 298      20.638  32.489   9.575  1.00  49.41      A  C
ATOM   1393  CA  PRO A 298      21.503  31.848   7.408  1.00  45.21      A  C
ATOM   1394  CB  PRO A 298      22.627  32.179   8.376  1.00  48.70      A  C
ATOM   1395  CG  PRO A 298      21.977  33.191   9.279  1.00  49.09      A  C
ATOM   1396  C   PRO A 298      21.748  30.554   6.655  1.00  43.50      A  C
ATOM   1397  O   PRO A 298      22.004  30.563   5.448  1.00  42.56      A  O
ATOM   1398  N   GLU A 299      21.647  29.431   7.346  1.00  45.68      A  N
ATOM   1399  CA  GLU A 299      21.910  28.176   6.670  1.00  46.73      A  C
ATOM   1400  CB  GLU A 299      21.779  26.953   7.622  1.00  48.19      A  C
ATOM   1401  CG  GLU A 299      20.524  26.826   8.530  1.00  50.95      A  C
ATOM   1402  CD  GLU A 299      20.552  27.746   9.741  1.00  51.89      A  C
ATOM   1403  OE1 GLU A 299      19.995  27.375  10.822  1.00  50.56      A  O
ATOM   1404  OE2 GLU A 299      21.124  28.858   9.613  1.00  58.09      A  O
ATOM   1405  C   GLU A 299      21.033  28.020   5.443  1.00  47.16      A  C
ATOM   1406  O   GLU A 299      21.500  27.545   4.408  1.00  44.66      A  O
ATOM   1407  N   MET A 300      19.778  28.480   5.556  1.00  54.37      A  N
ATOM   1408  CA  MET A 300      18.784  28.372   4.484  1.00  58.02      A  C
ATOM   1409  CB  MET A 300      17.357  28.512   5.059  1.00  62.93      A  C
ATOM   1410  CG  MET A 300      16.270  27.601   4.428  1.00  72.31      A  C
ATOM   1411  SD  MET A 300      16.158  27.571   2.583  1.00  91.50      A  S
ATOM   1412  CE  MET A 300      14.937  28.875   2.150  1.00  85.83      A  C
ATOM   1413  C   MET A 300      18.977  29.357   3.348  1.00  55.93      A  C
ATOM   1414  O   MET A 300      18.908  28.972   2.199  1.00  57.54      A  O
ATOM   1415  N   ILE A 301      19.213  30.626   3.633  1.00  54.65      A  N
ATOM   1416  CA  ILE A 301      19.395  31.530   2.509  1.00  54.46      A  C
ATOM   1417  CB  ILE A 301      19.475  33.026   2.944  1.00  55.81      A  C
ATOM   1418  CG2 ILE A 301      18.381  33.320   3.953  1.00  53.39      A  C
ATOM   1419  CG1 ILE A 301      20.841  33.354   3.567  1.00  58.05      A  C
ATOM   1420  CD1 ILE A 301      21.027  34.860   3.983  1.00  51.64      A  C
ATOM   1421  C   ILE A 301      20.658  31.128   1.730  1.00  54.61      A  C
ATOM   1422  O   ILE A 301      20.595  30.881   0.527  1.00  52.31      A  O
ATOM   1423  N   GLU A 302      21.787  31.016   2.429  1.00  56.63      A  N
ATOM   1424  CA  GLU A 302      23.052  30.668   1.786  1.00  57.94      A  C
ATOM   1425  CB  GLU A 302      24.180  30.625   2.829  1.00  54.31      A  C
ATOM   1426  CG  GLU A 302      24.405  31.956   3.523  1.00  53.21      A  C
ATOM   1427  CD  GLU A 302      25.199  31.808   4.783  1.00  52.91      A  C
ATOM   1428  OE1 GLU A 302      25.106  30.724   5.389  1.00  55.63      A  O
ATOM   1429  OE2 GLU A 302      25.910  32.765   5.182  1.00  50.07      A  O
ATOM   1430  C   GLU A 302      23.035  29.364   0.963  1.00  60.56      A  C
ATOM   1431  O   GLU A 302      23.969  29.103   0.203  1.00  60.47      A  O
```

Figure 2W

```
ATOM   1432  N    GLY A 303      21.979  28.566   1.093  1.00  62.46      A    N
ATOM   1433  CA   GLY A 303      21.891  27.333   0.329  1.00  61.40      A    C
ATOM   1434  C    GLY A 303      22.625  26.172   0.972  1.00  64.14      A    C
ATOM   1435  O    GLY A 303      23.032  25.222   0.296  1.00  62.37      A    O
ATOM   1436  N    ARG A 304      22.810  26.249   2.284  1.00  70.43      A    N
ATOM   1437  CA   ARG A 304      23.486  25.192   3.015  1.00  77.34      A    C
ATOM   1438  CB   ARG A 304      24.338  25.773   4.132  1.00  79.09      A    C
ATOM   1439  CG   ARG A 304      25.454  26.649   3.646  1.00  83.43      A    C
ATOM   1440  CD   ARG A 304      26.136  27.354   4.810  1.00  90.93      A    C
ATOM   1441  NE   ARG A 304      26.587  26.396   5.815  1.00 102.58      A    N
ATOM   1442  CZ   ARG A 304      27.305  25.301   5.548  1.00 109.08      A    C
ATOM   1443  NH1  ARG A 304      27.665  25.009   4.295  1.00 112.50      A    N
ATOM   1444  NH2  ARG A 304      27.669  24.494   6.539  1.00 109.83      A    N
ATOM   1445  C    ARG A 304      22.480  24.221   3.612  1.00  80.67      A    C
ATOM   1446  O    ARG A 304      21.263  24.393   3.507  1.00  80.30      A    O
ATOM   1447  N    MET A 305      23.013  23.196   4.254  1.00  86.43      A    N
ATOM   1448  CA   MET A 305      22.202  22.170   4.874  1.00  91.44      A    C
ATOM   1449  CB   MET A 305      23.096  20.999   5.309  1.00  95.15      A    C
ATOM   1450  CG   MET A 305      24.057  20.457   4.224  1.00  97.75      A    C
ATOM   1451  SD   MET A 305      25.346  21.624   3.627  1.00 102.71      A    S
ATOM   1452  CE   MET A 305      26.139  22.130   5.187  1.00 100.89      A    C
ATOM   1453  C    MET A 305      21.489  22.770   6.081  1.00  92.74      A    C
ATOM   1454  O    MET A 305      22.124  23.361   6.959  1.00  93.86      A    O
ATOM   1455  N    HIS A 306      20.168  22.626   6.116  1.00  93.31      A    N
ATOM   1456  CA   HIS A 306      19.374  23.147   7.223  1.00  95.45      A    C
ATOM   1457  CB   HIS A 306      18.358  24.155   6.711  1.00  95.53      A    C
ATOM   1458  CG   HIS A 306      17.228  23.519   5.971  1.00  96.27      A    C
ATOM   1459  CD2  HIS A 306      15.996  23.139   6.385  1.00  98.19      A    C
ATOM   1460  ND1  HIS A 306      17.343  23.091   4.668  1.00  95.71      A    N
ATOM   1461  CE1  HIS A 306      16.233  22.470   4.312  1.00  97.93      A    C
ATOM   1462  NE2  HIS A 306      15.400  22.484   5.336  1.00  98.85      A    N
ATOM   1463  C    HIS A 306      18.615  21.976   7.842  1.00  95.21      A    C
ATOM   1464  O    HIS A 306      18.352  20.989   7.151  1.00  94.72      A    O
ATOM   1465  N    ASP A 307      18.249  22.093   9.120  1.00  92.49      A    N
ATOM   1466  CA   ASP A 307      17.506  21.034   9.802  1.00  87.25      A    C
ATOM   1467  CB   ASP A 307      18.232  19.691   9.627  1.00  94.22      A    C
ATOM   1468  CG   ASP A 307      17.519  18.745   8.651  1.00  99.85      A    C
ATOM   1469  OD1  ASP A 307      17.353  19.109   7.461  1.00 100.61      A    O
ATOM   1470  OD2  ASP A 307      17.131  17.627   9.077  1.00 100.81      A    O
ATOM   1471  C    ASP A 307      17.248  21.246  11.299  1.00  79.95      A    C
ATOM   1472  O    ASP A 307      18.188  21.392  12.079  1.00  78.41      A    O
ATOM   1473  N    GLU A 308      15.975  21.248  11.684  1.00  73.99      A    N
ATOM   1474  CA   GLU A 308      15.562  21.361  13.093  1.00  71.73      A    C
ATOM   1475  CB   GLU A 308      16.127  20.183  13.883  1.00  73.55      A    C
ATOM   1476  CG   GLU A 308      16.432  20.492  15.336  1.00  75.72      A    C
ATOM   1477  CD   GLU A 308      17.307  19.418  15.962  1.00  79.42      A    C
ATOM   1478  OE1  GLU A 308      18.439  19.216  15.452  1.00  79.54      A    O
ATOM   1479  OE2  GLU A 308      16.859  18.778  16.950  1.00  82.63      A    O
ATOM   1480  C    GLU A 308      15.872  22.640  13.857  1.00  68.99      A    C
ATOM   1481  O    GLU A 308      14.969  23.249  14.427  1.00  69.09      A    O
ATOM   1482  N    LYS A 309      17.140  23.035  13.901  1.00  64.55      A    N
ATOM   1483  CA   LYS A 309      17.515  24.250  14.615  1.00  58.23      A    C
ATOM   1484  CB   LYS A 309      19.043  24.348  14.714  1.00  52.75      A    C
ATOM   1489  C    LYS A 309      16.909  25.523  13.970  1.00  56.91      A    C
ATOM   1490  O    LYS A 309      16.575  26.486  14.682  1.00  58.52      A    O
ATOM   1491  N    VAL A 310      16.738  25.525  12.646  1.00  53.69      A    N
ATOM   1492  CA   VAL A 310      16.158  26.685  11.949  1.00  48.49      A    C
ATOM   1493  CB   VAL A 310      15.499  26.343  10.536  1.00  46.10      A    C
ATOM   1494  CG1  VAL A 310      16.524  25.843   9.534  1.00  43.14      A    C
ATOM   1495  CG2  VAL A 310      14.411  25.345  10.698  1.00  42.09      A    C
ATOM   1496  C    VAL A 310      15.050  27.286  12.809  1.00  48.19      A    C
```

Figure 2X

| ATOM | 1497 | O | VAL | A | 310 | 14.985 | 28.518 | 12.967 | 1.00 | 51.28 | A | O |
| --- | --- | --- | --- | --- | --- | --- | --- | --- | --- | --- | --- | --- |
| ATOM | 1498 | N | ASP | A | 311 | 14.213 | 26.407 | 13.380 | 1.00 | 44.88 | A | N |
| ATOM | 1499 | CA | ASP | A | 311 | 13.090 | 26.823 | 14.208 | 1.00 | 43.50 | A | C |
| ATOM | 1500 | CB | ASP | A | 311 | 12.294 | 25.628 | 14.747 | 1.00 | 41.71 | A | C |
| ATOM | 1501 | CG | ASP | A | 311 | 11.649 | 24.827 | 13.656 | 1.00 | 46.32 | A | C |
| ATOM | 1502 | OD1 | ASP | A | 311 | 11.171 | 25.430 | 12.680 | 1.00 | 51.41 | A | O |
| ATOM | 1503 | OD2 | ASP | A | 311 | 11.615 | 23.588 | 13.761 | 1.00 | 48.43 | A | O |
| ATOM | 1504 | C | ASP | A | 311 | 13.477 | 27.698 | 15.356 | 1.00 | 42.81 | A | C |
| ATOM | 1505 | O | ASP | A | 311 | 12.797 | 28.692 | 15.635 | 1.00 | 43.46 | A | O |
| ATOM | 1506 | N | LEU | A | 312 | 14.558 | 27.362 | 16.041 | 1.00 | 42.27 | A | N |
| ATOM | 1507 | CA | LEU | A | 312 | 14.957 | 28.195 | 17.175 | 1.00 | 45.36 | A | C |
| ATOM | 1508 | CB | LEU | A | 312 | 16.176 | 27.582 | 17.879 | 1.00 | 45.36 | A | C |
| ATOM | 1509 | CG | LEU | A | 312 | 15.953 | 26.289 | 18.689 | 1.00 | 46.26 | A | C |
| ATOM | 1510 | CD1 | LEU | A | 312 | 15.003 | 26.507 | 19.841 | 1.00 | 41.67 | A | C |
| ATOM | 1511 | CD2 | LEU | A | 312 | 15.421 | 25.208 | 17.776 | 1.00 | 49.22 | A | C |
| ATOM | 1512 | C | LEU | A | 312 | 15.273 | 29.612 | 16.696 | 1.00 | 44.80 | A | C |
| ATOM | 1513 | O | LEU | A | 312 | 15.150 | 30.587 | 17.439 | 1.00 | 45.76 | A | O |
| ATOM | 1514 | N | TRP | A | 313 | 15.688 | 29.704 | 15.437 | 1.00 | 42.21 | A | N |
| ATOM | 1515 | CA | TRP | A | 313 | 16.046 | 30.969 | 14.833 | 1.00 | 42.63 | A | C |
| ATOM | 1516 | CB | TRP | A | 313 | 17.001 | 30.721 | 13.644 | 1.00 | 44.56 | A | C |
| ATOM | 1517 | CG | TRP | A | 313 | 17.161 | 31.879 | 12.719 | 1.00 | 47.92 | A | C |
| ATOM | 1518 | CD2 | TRP | A | 313 | 18.274 | 32.768 | 12.648 | 1.00 | 47.41 | A | C |
| ATOM | 1519 | CE2 | TRP | A | 313 | 17.938 | 33.795 | 11.724 | 1.00 | 47.97 | A | C |
| ATOM | 1520 | CE3 | TRP | A | 313 | 19.525 | 32.809 | 13.277 | 1.00 | 46.27 | A | C |
| ATOM | 1521 | CD1 | TRP | A | 313 | 16.218 | 32.374 | 11.847 | 1.00 | 50.55 | A | C |
| ATOM | 1522 | NE1 | TRP | A | 313 | 16.682 | 33.527 | 11.250 | 1.00 | 51.40 | A | N |
| ATOM | 1523 | CZ2 | TRP | A | 313 | 18.809 | 34.844 | 11.421 | 1.00 | 45.76 | A | C |
| ATOM | 1524 | CZ3 | TRP | A | 313 | 20.397 | 33.864 | 12.968 | 1.00 | 44.53 | A | C |
| ATOM | 1525 | CH2 | TRP | A | 313 | 20.031 | 34.861 | 12.052 | 1.00 | 41.13 | A | C |
| ATOM | 1526 | C | TRP | A | 313 | 14.756 | 31.661 | 14.400 | 1.00 | 43.51 | A | C |
| ATOM | 1527 | O | TRP | A | 313 | 14.536 | 32.855 | 14.687 | 1.00 | 43.28 | A | O |
| ATOM | 1528 | N | SER | A | 314 | 13.918 | 30.926 | 13.678 | 1.00 | 43.63 | A | N |
| ATOM | 1529 | CA | SER | A | 314 | 12.653 | 31.492 | 13.266 | 1.00 | 42.23 | A | C |
| ATOM | 1530 | CB | SER | A | 314 | 11.762 | 30.401 | 12.676 | 1.00 | 39.93 | A | C |
| ATOM | 1532 | C | SER | A | 314 | 12.098 | 32.028 | 14.596 | 1.00 | 43.25 | A | C |
| ATOM | 1533 | O | SER | A | 314 | 11.754 | 33.201 | 14.724 | 1.00 | 44.96 | A | O |
| ATOM | 1534 | N | LEU | A | 315 | 12.086 | 31.164 | 15.604 | 1.00 | 43.95 | A | N |
| ATOM | 1535 | CA | LEU | A | 315 | 11.622 | 31.521 | 16.941 | 1.00 | 44.48 | A | C |
| ATOM | 1536 | CB | LEU | A | 315 | 11.814 | 30.338 | 17.875 | 1.00 | 45.33 | A | C |
| ATOM | 1537 | CG | LEU | A | 315 | 11.311 | 30.565 | 19.281 | 1.00 | 46.97 | A | C |
| ATOM | 1538 | CD1 | LEU | A | 315 | 9.762 | 30.689 | 19.245 | 1.00 | 49.48 | A | C |
| ATOM | 1539 | CD2 | LEU | A | 315 | 11.730 | 29.407 | 20.158 | 1.00 | 46.51 | A | C |
| ATOM | 1540 | C | LEU | A | 315 | 12.368 | 32.715 | 17.506 | 1.00 | 43.75 | A | C |
| ATOM | 1541 | O | LEU | A | 315 | 11.860 | 33.436 | 18.365 | 1.00 | 42.92 | A | O |
| ATOM | 1542 | N | GLY | A | 316 | 13.598 | 32.919 | 17.053 | 1.00 | 44.78 | A | N |
| ATOM | 1543 | CA | GLY | A | 316 | 14.365 | 34.056 | 17.548 | 1.00 | 43.88 | A | C |
| ATOM | 1544 | C | GLY | A | 316 | 13.841 | 35.351 | 16.948 | 1.00 | 42.75 | A | C |
| ATOM | 1545 | O | GLY | A | 316 | 13.710 | 36.333 | 17.636 | 1.00 | 39.41 | A | O |
| ATOM | 1546 | N | VAL | A | 317 | 13.539 | 35.333 | 15.657 | 1.00 | 43.37 | A | N |
| ATOM | 1547 | CA | VAL | A | 317 | 13.029 | 36.494 | 14.955 | 1.00 | 42.78 | A | C |
| ATOM | 1548 | CB | VAL | A | 317 | 12.904 | 36.199 | 13.470 | 1.00 | 43.24 | A | C |
| ATOM | 1549 | CG1 | VAL | A | 317 | 12.360 | 37.433 | 12.735 | 1.00 | 47.79 | A | C |
| ATOM | 1550 | CG2 | VAL | A | 317 | 14.286 | 35.790 | 12.927 | 1.00 | 43.06 | A | C |
| ATOM | 1551 | C | VAL | A | 317 | 11.683 | 36.957 | 15.463 | 1.00 | 41.53 | A | C |
| ATOM | 1552 | O | VAL | A | 317 | 11.486 | 38.127 | 15.783 | 1.00 | 41.06 | A | O |
| ATOM | 1553 | N | LEU | A | 318 | 10.766 | 36.008 | 15.538 | 1.00 | 43.09 | A | N |
| ATOM | 1554 | CA | LEU | A | 318 | 9.420 | 36.227 | 16.015 | 1.00 | 42.15 | A | C |
| ATOM | 1555 | CB | LEU | A | 318 | 8.716 | 34.880 | 16.201 | 1.00 | 41.81 | A | C |
| ATOM | 1556 | CG | LEU | A | 318 | 7.192 | 34.743 | 16.136 | 1.00 | 46.38 | A | C |
| ATOM | 1557 | CD1 | LEU | A | 318 | 6.631 | 35.404 | 14.897 | 1.00 | 49.07 | A | C |
| ATOM | 1558 | CD2 | LEU | A | 318 | 6.844 | 33.282 | 16.052 | 1.00 | 53.42 | A | C |

Figure 2Y

```
ATOM   1559  C    LEU A 318       9.490  36.915  17.347  1.00  43.57           A  C
ATOM   1560  O    LEU A 318       8.894  37.989  17.529  1.00  46.60           A  O
ATOM   1561  N    CYS A 319      10.241  36.302  18.273  1.00  45.52           A  N
ATOM   1562  CA   CYS A 319      10.320  36.837  19.624  1.00  46.48           A  C
ATOM   1563  CB   CYS A 319      11.230  36.034  20.557  1.00  52.09           A  C
ATOM   1564  SG   CYS A 319      11.390  36.845  22.199  1.00  49.92           A  S
ATOM   1565  C    CYS A 319      10.756  38.247  19.651  1.00  44.95           A  C
ATOM   1566  O    CYS A 319      10.481  38.948  20.615  1.00  46.16           A  O
ATOM   1567  N    TYR A 320      11.433  38.667  18.601  1.00  45.60           A  N
ATOM   1568  CA   TYR A 320      11.886  40.040  18.508  1.00  48.02           A  C
ATOM   1569  CB   TYR A 320      13.195  40.102  17.703  1.00  47.08           A  C
ATOM   1570  CG   TYR A 320      13.715  41.493  17.426  1.00  47.28           A  C
ATOM   1571  CD1  TYR A 320      14.818  41.982  18.109  1.00  50.06           A  C
ATOM   1572  CE1  TYR A 320      15.361  43.269  17.820  1.00  48.55           A  C
ATOM   1573  CD2  TYR A 320      13.141  42.293  16.453  1.00  49.51           A  C
ATOM   1574  CE2  TYR A 320      13.649  43.541  16.158  1.00  52.16           A  C
ATOM   1575  CZ   TYR A 320      14.766  44.031  16.847  1.00  49.70           A  C
ATOM   1576  OH   TYR A 320      15.279  45.280  16.572  1.00  47.87           A  O
ATOM   1577  C    TYR A 320      10.802  40.866  17.799  1.00  50.46           A  C
ATOM   1578  O    TYR A 320      10.639  42.063  18.088  1.00  51.59           A  O
ATOM   1579  N    GLU A 321      10.078  40.272  16.851  1.00  51.34           A  N
ATOM   1580  CA   GLU A 321       9.060  41.101  16.218  1.00  49.68           A  C
ATOM   1581  CB   GLU A 321       8.449  40.497  14.939  1.00  45.86           A  C
ATOM   1582  CG   GLU A 321       7.975  41.633  14.061  1.00  48.37           A  C
ATOM   1583  CD   GLU A 321       7.146  41.271  12.831  1.00  48.80           A  C
ATOM   1584  OE1  GLU A 321       7.310  40.171  12.273  1.00  52.55           A  O
ATOM   1585  OE2  GLU A 321       6.332  42.142  12.400  1.00  44.17           A  O
ATOM   1586  C    GLU A 321       7.966  41.401  17.235  1.00  50.20           A  C
ATOM   1587  O    GLU A 321       7.422  42.494  17.262  1.00  50.39           A  O
ATOM   1588  N    PHE A 322       7.679  40.452  18.114  1.00  49.87           A  N
ATOM   1589  CA   PHE A 322       6.640  40.697  19.098  1.00  48.27           A  C
ATOM   1590  CB   PHE A 322       6.386  39.455  19.944  1.00  47.20           A  C
ATOM   1591  CG   PHE A 322       5.825  38.290  19.185  1.00  42.45           A  C
ATOM   1592  CD1  PHE A 322       5.092  38.478  18.033  1.00  43.75           A  C
ATOM   1593  CD2  PHE A 322       5.974  36.993  19.681  1.00  41.47           A  C
ATOM   1594  CE1  PHE A 322       4.507  37.394  17.381  1.00  43.73           A  C
ATOM   1595  CE2  PHE A 322       5.400  35.929  19.041  1.00  42.73           A  C
ATOM   1596  CZ   PHE A 322       4.657  36.132  17.881  1.00  44.76           A  C
ATOM   1597  C    PHE A 322       6.948  41.874  20.022  1.00  49.87           A  C
ATOM   1598  O    PHE A 322       6.068  42.681  20.305  1.00  52.23           A  O
ATOM   1599  N    LEU A 323       8.185  41.985  20.498  1.00  52.69           A  N
ATOM   1600  CA   LEU A 323       8.516  43.088  21.395  1.00  53.90           A  C
ATOM   1601  CB   LEU A 323       9.729  42.741  22.264  1.00  54.60           A  C
ATOM   1602  CG   LEU A 323       9.630  41.472  23.105  1.00  54.07           A  C
ATOM   1603  CD1  LEU A 323      11.012  41.085  23.581  1.00  53.78           A  C
ATOM   1604  CD2  LEU A 323       8.671  41.679  24.263  1.00  53.68           A  C
ATOM   1605  C    LEU A 323       8.798  44.398  20.701  1.00  54.78           A  C
ATOM   1606  O    LEU A 323       8.643  45.465  21.295  1.00  58.12           A  O
ATOM   1607  N    VAL A 324       9.212  44.349  19.446  1.00  52.85           A  N
ATOM   1608  CA   VAL A 324       9.543  45.589  18.767  1.00  52.29           A  C
ATOM   1609  CB   VAL A 324      10.964  45.468  18.170  1.00  52.85           A  C
ATOM   1610  CG1  VAL A 324      11.359  46.753  17.441  1.00  53.29           A  C
ATOM   1611  CG2  VAL A 324      11.935  45.145  19.293  1.00  50.68           A  C
ATOM   1612  C    VAL A 324       8.547  46.067  17.711  1.00  50.93           A  C
ATOM   1613  O    VAL A 324       8.436  47.261  17.433  1.00  53.71           A  O
ATOM   1614  N    GLY A 325       7.818  45.140  17.118  1.00  48.42           A  N
ATOM   1615  CA   GLY A 325       6.848  45.553  16.130  1.00  45.98           A  C
ATOM   1616  C    GLY A 325       7.285  45.390  14.700  1.00  43.81           A  C
ATOM   1617  O    GLY A 325       6.481  45.599  13.802  1.00  42.72           A  O
ATOM   1618  N    LYS A 326       8.558  45.069  14.487  1.00  42.03           A  N
ATOM   1619  CA   LYS A 326       9.094  44.806  13.142  1.00  41.76           A  C
```

Figure 2Z

```
ATOM   1620  CB  LYS A 326       9.651  46.070  12.497  1.00  42.96      A  C
ATOM   1621  CG  LYS A 326      10.778  46.689  13.239  1.00  47.50      A  C
ATOM   1622  CD  LYS A 326      11.188  47.981  12.555  1.00  55.73      A  C
ATOM   1623  CE  LYS A 326      11.892  48.899  13.534  1.00  60.78      A  C
ATOM   1624  NZ  LYS A 326      11.073  49.010  14.787  1.00  63.79      A  N
ATOM   1625  C   LYS A 326      10.192  43.751  13.265  1.00  38.50      A  C
ATOM   1626  O   LYS A 326      10.749  43.544  14.329  1.00  32.33      A  O
ATOM   1627  N   PRO A 327      10.498  43.050  12.179  1.00  39.05      A  N
ATOM   1628  CD  PRO A 327       9.943  43.127  10.822  1.00  41.94      A  C
ATOM   1629  CA  PRO A 327      11.542  42.027  12.280  1.00  37.98      A  C
ATOM   1630  CB  PRO A 327      11.396  41.278  10.952  1.00  37.99      A  C
ATOM   1631  CG  PRO A 327      10.934  42.350  10.017  1.00  41.14      A  C
ATOM   1632  C   PRO A 327      12.929  42.639  12.538  1.00  34.88      A  C
ATOM   1633  O   PRO A 327      13.106  43.863  12.486  1.00  34.41      A  O
ATOM   1634  N   PRO A 328      13.927  41.816  12.840  1.00  34.23      A  N
ATOM   1635  CD  PRO A 328      13.878  40.507  13.502  1.00  34.09      A  C
ATOM   1636  CA  PRO A 328      15.228  42.483  13.086  1.00  38.10      A  C
ATOM   1637  CB  PRO A 328      15.828  41.670  14.233  1.00  34.71      A  C
ATOM   1638  CG  PRO A 328      15.377  40.315  13.924  1.00  31.90      A  C
ATOM   1639  C   PRO A 328      16.227  42.646  11.947  1.00  41.07      A  C
ATOM   1640  O   PRO A 328      17.333  43.118  12.170  1.00  45.00      A  O
ATOM   1641  N   PHE A 329      15.857  42.269  10.736  1.00  42.48      A  N
ATOM   1642  CA  PHE A 329      16.770  42.386   9.627  1.00  45.31      A  C
ATOM   1643  CB  PHE A 329      17.246  40.995   9.234  1.00  44.49      A  C
ATOM   1644  CG  PHE A 329      17.897  40.263  10.367  1.00  40.05      A  C
ATOM   1645  CD1 PHE A 329      19.085  40.755  10.926  1.00  40.92      A  C
ATOM   1646  CD2 PHE A 329      17.317  39.115  10.899  1.00  37.91      A  C
ATOM   1647  CE1 PHE A 329      19.696  40.128  11.983  1.00  35.39      A  C
ATOM   1648  CE2 PHE A 329      17.910  38.463  11.972  1.00  36.46      A  C
ATOM   1649  CZ  PHE A 329      19.115  38.970  12.524  1.00  34.95      A  C
ATOM   1650  C   PHE A 329      16.024  43.051   8.505  1.00  51.35      A  C
ATOM   1651  O   PHE A 329      16.442  43.051   7.332  1.00  56.54      A  O
ATOM   1652  N   GLU A 330      14.879  43.596   8.880  1.00  54.02      A  N
ATOM   1653  CA  GLU A 330      14.040  44.274   7.940  1.00  54.79      A  C
ATOM   1654  CB  GLU A 330      12.834  44.850   8.657  1.00  52.31      A  C
ATOM   1655  CG  GLU A 330      11.917  45.674   7.800  1.00  56.24      A  C
ATOM   1656  CD  GLU A 330      10.619  45.942   8.505  1.00  56.77      A  C
ATOM   1657  OE1 GLU A 330       9.731  45.079   8.466  1.00  60.81      A  O
ATOM   1658  OE2 GLU A 330      10.493  47.002   9.125  1.00  57.86      A  O
ATOM   1659  C   GLU A 330      14.882  45.365   7.289  1.00  57.36      A  C
ATOM   1660  O   GLU A 330      15.721  46.019   7.931  1.00  56.39      A  O
ATOM   1661  N   ALA A 331      14.667  45.527   5.992  1.00  59.09      A  N
ATOM   1662  CA  ALA A 331      15.403  46.509   5.261  1.00  59.33      A  C
ATOM   1663  CB  ALA A 331      16.790  46.018   5.043  1.00  54.89      A  C
ATOM   1664  C   ALA A 331      14.778  46.866   3.934  1.00  60.87      A  C
ATOM   1665  O   ALA A 331      13.780  46.306   3.502  1.00  60.55      A  O
ATOM   1666  N   ASN A 332      15.399  47.843   3.306  1.00  64.05      A  N
ATOM   1667  CA  ASN A 332      15.010  48.315   2.003  1.00  68.05      A  C
ATOM   1668  CB  ASN A 332      15.644  49.676   1.801  1.00  71.14      A  C
ATOM   1669  CG  ASN A 332      17.081  49.715   2.331  1.00  75.03      A  C
ATOM   1670  OD1 ASN A 332      17.315  49.557   3.538  1.00  77.13      A  O
ATOM   1671  ND2 ASN A 332      18.049  49.899   1.429  1.00  75.69      A  N
ATOM   1672  C   ASN A 332      15.704  47.305   1.111  1.00  69.58      A  C
ATOM   1673  O   ASN A 332      16.928  47.155   1.195  1.00  74.45      A  O
ATOM   1674  N   THR A 333      14.955  46.586   0.289  1.00  66.05      A  N
ATOM   1675  CA  THR A 333      15.586  45.629  -0.628  1.00  63.54      A  C
ATOM   1676  CB  THR A 333      16.722  46.326  -1.451  1.00  66.50      A  C
ATOM   1677  OG1 THR A 333      16.644  45.906  -2.826  1.00  71.94      A  O
ATOM   1678  CG2 THR A 333      18.139  45.978  -0.857  1.00  61.77      A  C
ATOM   1679  C   THR A 333      16.162  44.334  -0.022  1.00  58.06      A  C
ATOM   1680  O   THR A 333      16.716  44.332   1.060  1.00  58.56      A  O
```

Figure 2AA

```
ATOM   1681  N    TYR A 334      16.014  43.249  -0.768  1.00  53.45      A    N
ATOM   1682  CA   TYR A 334      16.477  41.920  -0.406  1.00  49.63      A    C
ATOM   1683  CB   TYR A 334      16.264  40.966  -1.593  1.00  52.96      A    C
ATOM   1684  CG   TYR A 334      14.836  40.528  -1.784  1.00  54.85      A    C
ATOM   1685  CD1  TYR A 334      14.140  39.950  -0.739  1.00  57.72      A    C
ATOM   1686  CE1  TYR A 334      12.819  39.600  -0.868  1.00  61.56      A    C
ATOM   1687  CD2  TYR A 334      14.171  40.743  -2.984  1.00  56.03      A    C
ATOM   1688  CE2  TYR A 334      12.845  40.396  -3.130  1.00  59.10      A    C
ATOM   1689  CZ   TYR A 334      12.169  39.822  -2.059  1.00  61.28      A    C
ATOM   1690  OH   TYR A 334      10.853  39.466  -2.152  1.00  64.44      A    O
ATOM   1691  C    TYR A 334      17.934  41.838  -0.012  1.00  49.32      A    C
ATOM   1692  O    TYR A 334      18.285  41.178   0.960  1.00  49.44      A    O
ATOM   1693  N    GLN A 335      18.778  42.485  -0.814  1.00  53.49      A    N
ATOM   1694  CA   GLN A 335      20.212  42.477  -0.615  1.00  56.61      A    C
ATOM   1695  CB   GLN A 335      20.888  43.394  -1.642  1.00  55.70      A    C
ATOM   1696  CG   GLN A 335      20.613  42.924  -3.101  1.00  59.93      A    C
ATOM   1697  CD   GLN A 335      19.150  43.151  -3.571  1.00  64.38      A    C
ATOM   1698  OE1  GLN A 335      18.664  42.485  -4.482  1.00  61.98      A    O
ATOM   1699  NE2  GLN A 335      18.469  44.111  -2.952  1.00  71.58      A    N
ATOM   1700  C    GLN A 335      20.540  42.838   0.824  1.00  58.91      A    C
ATOM   1701  O    GLN A 335      21.295  42.103   1.489  1.00  63.07      A    O
ATOM   1702  N    GLU A 336      20.009  43.963   1.304  1.00  59.80      A    N
ATOM   1703  CA   GLU A 336      20.201  44.304   2.709  1.00  60.35      A    C
ATOM   1704  CB   GLU A 336      19.948  45.781   2.969  1.00  62.45      A    C
ATOM   1705  CG   GLU A 336      20.866  46.680   2.204  1.00  66.41      A    C
ATOM   1706  CD   GLU A 336      22.055  47.122   3.026  1.00  68.37      A    C
ATOM   1707  OE1  GLU A 336      23.050  47.589   2.410  1.00  68.20      A    O
ATOM   1708  OE2  GLU A 336      21.976  47.008   4.278  1.00  66.72      A    O
ATOM   1709  C    GLU2A 336      19.065  43.470   3.273  1.00  62.28      A    C
ATOM   1710  O    GLU A 336      17.970  43.480   2.745  1.00  71.79      A    O
ATOM   1711  N    THR A 337      19.337  42.743   4.328  1.00  57.60      A    N
ATOM   1712  CA   THR A 337      18.394  41.826   4.968  1.00  53.08      A    C
ATOM   1713  CB   THR A 337      17.070  41.538   4.217  1.00  53.42      A    C
ATOM   1714  OG1  THR A 337      16.310  42.732   4.037  1.00  54.38      A    O
ATOM   1715  CG2  THR A 337      16.238  40.552   5.035  1.00  49.58      A    C
ATOM   1716  C    THR A 337      19.200  40.584   4.825  1.00  52.01      A    C
ATOM   1717  O    THR A 337      19.513  39.927   5.800  1.00  51.26      A    O
ATOM   1718  N    TYR A 338      19.541  40.258   3.586  1.00  52.12      A    N
ATOM   1719  CA   TYR A 338      20.373  39.099   3.391  1.00  53.73      A    C
ATOM   1720  CB   TYR A 338      20.768  38.888   1.926  1.00  59.18      A    C
ATOM   1721  CG   TYR A 338      21.750  37.736   1.791  1.00  67.20      A    C
ATOM   1722  CD1  TYR A 338      21.356  36.502   1.276  1.00  68.39      A    C
ATOM   1723  CE1  TYR A 338      22.242  35.414   1.264  1.00  72.03      A    C
ATOM   1724  CD2  TYR A 338      23.054  37.858   2.282  1.00  71.64      A    C
ATOM   1725  CE2  TYR A 338      23.938  36.790   2.279  1.00  73.51      A    C
ATOM   1726  CZ   TYR A 338      23.533  35.573   1.775  1.00  74.22      A    C
ATOM   1727  OH   TYR A 338      24.424  34.522   1.801  1.00  77.08      A    O
ATOM   1728  C    TYR A 338      21.601  39.462   4.209  1.00  49.60      A    C
ATOM   1729  O    TYR A 338      21.908  38.820   5.211  1.00  50.06      A    O
ATOM   1730  N    LYS A 339      22.261  40.525   3.769  1.00  45.49      A    N
ATOM   1731  CA   LYS A 339      23.438  41.071   4.405  1.00  42.43      A    C
ATOM   1732  CB   LYS A 339      23.623  42.514   3.935  1.00  40.27      A    C
ATOM   1733  CG   LYS A 339      24.843  43.238   4.417  1.00  37.89      A    C
ATOM   1734  CD   LYS A 339      24.953  44.600   3.729  1.00  34.82      A    C
ATOM   1735  CE   LYS A 339      25.325  44.390   2.285  1.00  39.67      A    C
ATOM   1736  NZ   LYS A 339      25.557  45.631   1.502  1.00  45.46      A    N
ATOM   1737  C    LYS A 339      23.356  41.022   5.925  1.00  42.54      A    C
ATOM   1738  O    LYS A 339      24.273  40.494   6.594  1.00  46.81      A    O
ATOM   1739  N    ARG A 340      22.273  41.544   6.492  1.00  40.62      A    N
ATOM   1740  CA   ARG A 340      22.185  41.545   7.950  1.00  41.64      A    C
ATOM   1741  CB   ARG A 340      21.273  42.667   8.428  1.00  44.31      A    C
```

Figure 2BB

```
ATOM   1742  CG  ARG A 340      21.825  44.023   8.003  1.00  59.83      A    C
ATOM   1743  CD  ARG A 340      21.007  45.198   8.504  1.00  71.33      A    C
ATOM   1744  NE  ARG A 340      21.131  46.337   7.602  1.00  81.01      A    N
ATOM   1745  CZ  ARG A 340      20.285  47.361   7.564  1.00  82.71      A    C
ATOM   1746  NH1 ARG A 340      19.249  47.403   8.387  1.00  83.78      A    N
ATOM   1747  NH2 ARG A 340      20.457  48.324   6.665  1.00  83.76      A    N
ATOM   1748  C   ARG A 340      21.799  40.219   8.568  1.00  42.70      A    C
ATOM   1749  O   ARG A 340      22.165  39.955   9.701  1.00  47.43      A    O
ATOM   1750  N   ILE A 341      21.086  39.372   7.837  1.00  41.92      A    N
ATOM   1751  CA  ILE A 341      20.730  38.080   8.386  1.00  44.37      A    C
ATOM   1752  CB  ILE A 341      19.685  37.327   7.517  1.00  42.19      A    C
ATOM   1753  CG2 ILE A 341      19.687  35.822   7.893  1.00  44.11      A    C
ATOM   1754  CG1 ILE A 341      18.293  37.931   7.704  1.00  41.50      A    C
ATOM   1755  CD1 ILE A 341      17.288  37.477   6.660  1.00  37.46      A    C
ATOM   1756  C   ILE A 341      21.979  37.197   8.462  1.00  46.30      A    C
ATOM   1757  O   ILE A 341      22.308  36.659   9.510  1.00  47.05      A    O
ATOM   1758  N   SER A 342      22.660  37.062   7.330  1.00  47.68      A    N
ATOM   1759  CA  SER A 342      23.846  36.223   7.231  1.00  49.44      A    C
ATOM   1760  CB  SER A 342      24.315  36.104   5.780  1.00  45.11      A    C
ATOM   1761  OG  SER A 342      24.567  37.382   5.260  1.00  42.19      A    O
ATOM   1762  C   SER A 342      24.939  36.804   8.056  1.00  53.85      A    C
ATOM   1763  O   SER A 342      25.622  36.095   8.788  1.00  59.98      A    O
ATOM   1764  N   ARG A 343      25.095  38.112   7.951  1.00  55.58      A    N
ATOM   1765  CA  ARG A 343      26.127  38.789   8.719  1.00  58.12      A    C
ATOM   1766  CB  ARG A 343      26.437  40.138   8.032  1.00  64.50      A    C
ATOM   1767  CG  ARG A 343      27.536  40.999   8.622  1.00  72.73      A    C
ATOM   1768  CD  ARG A 343      27.028  41.824   9.822  1.00  79.05      A    C
ATOM   1769  NE  ARG A 343      27.247  43.257   9.634  1.00  85.87      A    N
ATOM   1770  CZ  ARG A 343      26.433  44.066   8.965  1.00  89.63      A    C
ATOM   1771  NH1 ARG A 343      25.324  43.594   8.417  1.00  95.09      A    N
ATOM   1772  NH2 ARG A 343      26.743  45.345   8.824  1.00  90.56      A    N
ATOM   1773  C   ARG A 343      25.639  38.933  10.173  1.00  54.47      A    C
ATOM   1774  O   ARG A 343      26.391  39.339  11.051  1.00  51.77      A    O
ATOM   1775  N   VAL A 344      24.387  38.549  10.415  1.00  52.67      A    N
ATOM   1776  CA  VAL A 344      23.758  38.620  11.749  1.00  51.62      A    C
ATOM   1777  CB  VAL A 344      24.395  37.612  12.721  1.00  49.15      A    C
ATOM   1778  CG1 VAL A 344      23.754  37.699  14.069  1.00  45.07      A    C
ATOM   1779  CG2 VAL A 344      24.202  36.205  12.197  1.00  48.33      A    C
ATOM   1780  C   VAL A 344      23.788  40.018  12.364  1.00  53.23      A    C
ATOM   1781  O   VAL A 344      24.050  40.206  13.543  1.00  50.74      A    O
ATOM   1782  N   GLU A 345      23.482  40.999  11.535  1.00  60.88      A    N
ATOM   1783  CA  GLU A 345      23.472  42.393  11.935  1.00  68.32      A    C
ATOM   1784  CB  GLU A 345      23.777  43.260  10.714  1.00  78.90      A    C
ATOM   1785  CG  GLU A 345      23.642  44.752  10.934  1.00  92.11      A    C
ATOM   1786  CD  GLU A 345      24.680  45.289  11.890  1.00  99.48      A    C
ATOM   1787  OE1 GLU A 345      25.890  45.068  11.645  1.00 104.34      A    O
ATOM   1788  OE2 GLU A 345      24.289  45.933  12.885  1.00 101.82      A    O
ATOM   1789  C   GLU A 345      22.130  42.797  12.520  1.00  67.83      A    C
ATOM   1790  O   GLU A 345      21.117  42.776  11.831  1.00  70.02      A    O
ATOM   1791  N   PHE A 346      22.109  43.173  13.787  1.00  66.14      A    N
ATOM   1792  CA  PHE A 346      20.849  43.578  14.386  1.00  64.32      A    C
ATOM   1793  CB  PHE A 346      19.891  42.378  14.499  1.00  59.52      A    C
ATOM   1794  CG  PHE A 346      20.120  41.563  15.705  1.00  56.13      A    C
ATOM   1795  CD1 PHE A 346      19.465  41.868  16.894  1.00  53.68      A    C
ATOM   1796  CD2 PHE A 346      21.067  40.539  15.694  1.00  57.97      A    C
ATOM   1797  CE1 PHE A 346      19.750  41.180  18.040  1.00  57.61      A    C
ATOM   1798  CE2 PHE A 346      21.365  39.833  16.860  1.00  56.32      A    C
ATOM   1799  CZ  PHE A 346      20.712  40.152  18.029  1.00  57.24      A    C
ATOM   1800  C   PHE A 346      21.032  44.201  15.754  1.00  63.96      A    C
ATOM   1801  O   PHE A 346      21.812  43.709  16.582  1.00  59.78      A    O
ATOM   1802  N   THR A 347      20.278  45.274  15.978  1.00  65.98      A    N
```

Figure 2CC

```
ATOM  1803  CA   THR A 347    20.299  46.003  17.244  1.00   64.66   A  C
ATOM  1804  CB   THR A 347    20.868  47.406  17.067  1.00   62.47   A  C
ATOM  1805  OG1  THR A 347    20.680  48.121  18.286  1.00   65.60   A  O
ATOM  1806  CG2  THR A 347    20.173  48.133  15.957  1.00   62.43   A  C
ATOM  1807  C    THR A 347    18.922  46.131  17.915  1.00   63.95   A  C
ATOM  1808  O    THR A 347    17.870  46.037  17.275  1.00   64.61   A  O
ATOM  1809  N    PHE A 348    18.939  46.352  19.216  1.00   62.36   A  N
ATOM  1810  CA   PHE A 348    17.710  46.483  19.965  1.00   64.90   A  C
ATOM  1811  CB   PHE A 348    17.887  45.863  21.338  1.00   61.18   A  C
ATOM  1812  CG   PHE A 348    18.075  44.379  21.314  1.00   56.76   A  C
ATOM  1813  CD1  PHE A 348    16.972  43.523  21.251  1.00   52.77   A  C
ATOM  1814  CD2  PHE A 348    19.359  43.831  21.375  1.00   55.34   A  C
ATOM  1815  CE1  PHE A 348    17.143  42.132  21.257  1.00   51.15   A  C
ATOM  1816  CE2  PHE A 348    19.544  42.456  21.379  1.00   53.54   A  C
ATOM  1817  CZ   PHE A 348    18.427  41.598  21.322  1.00   50.44   A  C
ATOM  1818  C    PHE A 348    17.302  47.937  20.115  1.00   68.31   A  C
ATOM  1819  O    PHE A 348    18.102  48.833  19.895  1.00   69.63   A  O
ATOM  1820  N    PRO A 349    16.030  48.190  20.453  1.00   70.74   A  N
ATOM  1821  CD   PRO A 349    14.873  47.300  20.257  1.00   72.47   A  C
ATOM  1822  CA   PRO A 349    15.585  49.571  20.620  1.00   71.83   A  C
ATOM  1823  CB   PRO A 349    14.171  49.531  20.070  1.00   73.51   A  C
ATOM  1824  CG   PRO A 349    13.705  48.213  20.529  1.00   72.22   A  C
ATOM  1825  C    PRO A 349    15.657  49.955  22.098  1.00   72.44   A  C
ATOM  1826  O    PRO A 349    15.801  49.091  22.982  1.00   69.14   A  O
ATOM  1827  N    ASP A 350    15.544  51.250  22.361  1.00   73.44   A  N
ATOM  1828  CA   ASP A 350    15.662  51.763  23.718  1.00   73.24   A  C
ATOM  1829  CB   ASP A 350    15.812  53.282  23.668  1.00   75.54   A  C
ATOM  1830  CG   ASP A 350    17.090  53.760  24.346  1.00   78.07   A  C
ATOM  1831  OD1  ASP A 350    18.190  53.328  23.930  1.00   76.23   A  O
ATOM  1832  OD2  ASP A 350    16.988  54.565  25.303  1.00   81.48   A  O
ATOM  1833  C    ASP A 350    14.556  51.392  24.691  1.00   72.27   A  C
ATOM  1834  O    ASP A 350    13.751  52.250  25.060  1.00   71.86   A  O
ATOM  1835  N    PHE A 351    14.526  50.122  25.109  1.00   71.33   A  N
ATOM  1836  CA   PHE A 351    13.519  49.642  26.061  1.00   69.65   A  C
ATOM  1837  CB   PHE A 351    12.143  50.251  25.759  1.00   66.71   A  C
ATOM  1838  CG   PHE A 351    11.472  49.659  24.562  1.00   64.49   A  C
ATOM  1839  CD1  PHE A 351    11.069  48.323  24.561  1.00   60.72   A  C
ATOM  1840  CD2  PHE A 351    11.275  50.423  23.411  1.00   64.89   A  C
ATOM  1841  CE1  PHE A 351    10.486  47.752  23.436  1.00   58.87   A  C
ATOM  1842  CE2  PHE A 351    10.693  49.862  22.280  1.00   64.08   A  C
ATOM  1843  CZ   PHE A 351    10.300  48.520  22.297  1.00   60.81   A  C
ATOM  1844  C    PHE A 351    13.344  48.124  26.176  1.00   68.28   A  C
ATOM  1845  O    PHE A 351    12.577  47.670  27.023  1.00   70.46   A  O
ATOM  1846  N    VAL A 352    14.002  47.331  25.335  1.00   68.23   A  N
ATOM  1847  CA   VAL A 352    13.830  45.882  25.446  1.00   69.78   A  C
ATOM  1848  CB   VAL A 352    14.328  45.117  24.179  1.00   71.24   A  C
ATOM  1849  CG1  VAL A 352    14.250  43.615  24.392  1.00   65.45   A  C
ATOM  1850  CG2  VAL A 352    13.478  45.494  22.984  1.00   72.78   A  C
ATOM  1851  C    VAL A 352    14.575  45.394  26.665  1.00   69.39   A  C
ATOM  1852  O    VAL A 352    15.731  45.712  26.863  1.00   68.69   A  O
ATOM  1853  N    THR A 353    13.881  44.628  27.489  1.00   70.86   A  N
ATOM  1854  CA   THR A 353    14.434  44.086  28.724  1.00   74.68   A  C
ATOM  1855  CB   THR A 353    13.355  43.284  29.475  1.00   78.59   A  C
ATOM  1856  OG1  THR A 353    13.953  42.564  30.556  1.00   86.89   A  O
ATOM  1857  CG2  THR A 353    12.699  42.282  28.543  1.00   79.25   A  C
ATOM  1858  C    THR A 353    15.656  43.189  28.518  1.00   75.55   A  C
ATOM  1859  O    THR A 353    15.677  42.327  27.636  1.00   75.77   A  O
ATOM  1860  N    GLU A 354    16.670  43.395  29.350  1.00   77.78   A  N
ATOM  1861  CA   GLU A 354    17.895  42.604  29.274  1.00   80.45   A  C
ATOM  1862  CB   GLU A 354    18.818  42.930  30.451  1.00   91.48   A  C
ATOM  1863  CG   GLU A 354    20.124  42.141  30.434  1.00  106.92   A  C
```

Figure 2DD

```
ATOM   1864  CD   GLU A 354      21.064  42.525  31.568  1.00 114.99      A    C
ATOM   1865  OE1  GLU A 354      20.639  42.450  32.748  1.00 119.30      A    O
ATOM   1866  OE2  GLU A 354      22.228  42.897  31.276  1.00 121.09      A    O
ATOM   1867  C    GLU A 354      17.612  41.112  29.262  1.00  75.57      A    C
ATOM   1868  O    GLU A 354      18.393  40.336  28.717  1.00  74.11      A    O
ATOM   1869  N    GLY A 355      16.505  40.712  29.878  1.00  71.66      A    N
ATOM   1870  CA   GLY A 355      16.149  39.306  29.894  1.00  70.66      A    C
ATOM   1871  C    GLY A 355      15.754  38.889  28.486  1.00  70.30      A    C
ATOM   1872  O    GLY A 355      15.973  37.749  28.062  1.00  68.56      A    O
ATOM   1873  N    ALA A 356      15.166  39.832  27.757  1.00  69.83      A    N
ATOM   1874  CA   ALA A 356      14.737  39.595  26.383  1.00  68.17      A    C
ATOM   1875  CB   ALA A 356      13.674  40.626  25.979  1.00  66.92      A    C
ATOM   1876  C    ALA A 356      15.958  39.704  25.472  1.00  66.14      A    C
ATOM   1877  O    ALA A 356      16.214  38.826  24.626  1.00  65.31      A    O
ATOM   1878  N    ARG A 357      16.707  40.786  25.669  1.00  63.92      A    N
ATOM   1879  CA   ARG A 357      17.916  41.031  24.901  1.00  60.47      A    C
ATOM   1880  CB   ARG A 357      18.691  42.225  25.462  1.00  56.64      A    C
ATOM   1881  CG   ARG A 357      18.229  43.572  24.905  1.00  56.72      A    C
ATOM   1882  CD   ARG A 357      18.268  44.633  25.975  1.00  58.20      A    C
ATOM   1883  NE   ARG A 357      18.121  45.992  25.457  1.00  58.90      A    N
ATOM   1884  CZ   ARG A 357      19.023  46.610  24.707  1.00  58.38      A    C
ATOM   1885  NH1  ARG A 357      20.155  45.996  24.363  1.00  54.85      A    N
ATOM   1886  NH2  ARG A 357      18.803  47.852  24.324  1.00  60.08      A    N
ATOM   1887  C    ARG A 357      18.809  39.812  24.874  1.00  60.05      A    C
ATOM   1888  O    ARG A 357      19.537  39.611  23.910  1.00  61.51      A    O
ATOM   1889  N    ASP A 358      18.744  38.970  25.896  1.00  59.94      A    N
ATOM   1890  CA   ASP A 358      19.616  37.807  25.883  1.00  59.69      A    C
ATOM   1891  CB   ASP A 358      20.252  37.591  27.272  1.00  66.38      A    C
ATOM   1892  CG   ASP A 358      19.624  36.456  28.034  1.00  70.14      A    C
ATOM   1893  OD1  ASP A 358      18.521  36.658  28.562  1.00  75.97      A    O
ATOM   1894  OD2  ASP A 358      20.228  35.368  28.097  1.00  71.29      A    O
ATOM   1895  C    ASP A 358      18.993  36.521  25.390  1.00  54.49      A    C
ATOM   1896  O    ASP A 358      19.696  35.648  24.915  1.00  55.10      A    O
ATOM   1897  N    LEU A 359      17.678  36.389  25.487  1.00  48.98      A    N
ATOM   1898  CA   LEU A 359      17.047  35.159  25.019  1.00  44.69      A    C
ATOM   1899  CB   LEU A 359      15.664  35.043  25.614  1.00  40.23      A    C
ATOM   1900  CG   LEU A 359      14.667  33.987  25.170  1.00  38.66      A    C
ATOM   1901  CD1  LEU A 359      13.946  34.472  23.932  1.00  44.87      A    C
ATOM   1902  CD2  LEU A 359      15.359  32.661  24.958  1.00  37.22      A    C
ATOM   1903  C    LEU A 359      17.010  35.126  23.493  1.00  47.42      A    C
ATOM   1904  O    LEU A 359      17.125  34.061  22.881  1.00  48.65      A    O
ATOM   1905  N    ILE A 360      16.884  36.288  22.861  1.00  50.50      A    N
ATOM   1906  CA   ILE A 360      16.884  36.295  21.406  1.00  53.67      A    C
ATOM   1907  CB   ILE A 360      16.177  37.561  20.797  1.00  54.43      A    C
ATOM   1908  CG2  ILE A 360      16.640  38.828  21.468  1.00  52.55      A    C
ATOM   1909  CG1  ILE A 360      16.445  37.605  19.294  1.00  57.63      A    C
ATOM   1910  CD1  ILE A 360      15.853  38.768  18.621  1.00  58.08      A    C
ATOM   1911  C    ILE A 360      18.326  36.169  20.899  1.00  53.44      A    C
ATOM   1912  O    ILE A 360      18.574  35.529  19.863  1.00  52.69      A    O
ATOM   1913  N    SER A 361      19.268  36.763  21.634  1.00  51.55      A    N
ATOM   1914  CA   SER A 361      20.688  36.657  21.283  1.00  50.87      A    C
ATOM   1915  CB   SER A 361      21.572  37.393  22.299  1.00  50.55      A    C
ATOM   1916  OG   SER A 361      21.607  38.799  22.099  1.00  53.11      A    O
ATOM   1917  C    SER A 361      21.063  35.175  21.318  1.00  52.18      A    C
ATOM   1918  O    SER A 361      21.862  34.705  20.519  1.00  53.10      A    O
ATOM   1919  N    ARG A 362      20.476  34.447  22.263  1.00  54.11      A    N
ATOM   1920  CA   ARG A 362      20.756  33.026  22.424  1.00  53.69      A    C
ATOM   1921  CB   ARG A 362      20.276  32.544  23.796  1.00  56.55      A    C
ATOM   1922  CG   ARG A 362      20.914  31.236  24.258  1.00  63.22      A    C
ATOM   1923  CD   ARG A 362      21.909  31.472  25.401  1.00  67.36      A    C
ATOM   1924  NE   ARG A 362      21.305  31.247  26.706  1.00  68.28      A    N
```

Figure 2EE

| ATOM | 1925 | CZ | ARG A 362 | 20.885 | 30.055 | 27.131 | 1.00 | 73.30 | A | C |
|---|---|---|---|---|---|---|---|---|---|---|
| ATOM | 1926 | NH1 | ARG A 362 | 21.014 | 28.985 | 26.344 | 1.00 | 72.26 | A | N |
| ATOM | 1927 | NH2 | ARG A 362 | 20.327 | 29.928 | 28.336 | 1.00 | 73.66 | A | N |
| ATOM | 1928 | C | ARG A 362 | 20.047 | 32.239 | 21.333 | 1.00 | 50.70 | A | C |
| ATOM | 1929 | O | ARG A 362 | 20.303 | 31.035 | 21.125 | 1.00 | 47.88 | A | O |
| ATOM | 1930 | N | LEU A 363 | 19.167 | 32.939 | 20.620 | 1.00 | 50.12 | A | N |
| ATOM | 1931 | CA | LEU A 363 | 18.386 | 32.318 | 19.574 | 1.00 | 51.08 | A | C |
| ATOM | 1932 | CB | LEU A 363 | 16.936 | 32.796 | 19.667 | 1.00 | 47.96 | A | C |
| ATOM | 1933 | CG | LEU A 363 | 15.851 | 31.795 | 20.098 | 1.00 | 46.52 | A | C |
| ATOM | 1934 | CD1 | LEU A 363 | 16.434 | 30.476 | 20.607 | 1.00 | 46.57 | A | C |
| ATOM | 1935 | CD2 | LEU A 363 | 14.998 | 32.484 | 21.179 | 1.00 | 49.24 | A | C |
| ATOM | 1936 | C | LEU A 363 | 18.926 | 32.591 | 18.192 | 1.00 | 52.62 | A | C |
| ATOM | 1937 | O | LEU A 363 | 18.890 | 31.721 | 17.320 | 1.00 | 54.75 | A | O |
| ATOM | 1938 | N | LEU A 364 | 19.423 | 33.794 | 17.968 | 1.00 | 54.42 | A | N |
| ATOM | 1939 | CA | LEU A 364 | 19.925 | 34.086 | 16.640 | 1.00 | 55.77 | A | C |
| ATOM | 1940 | CB | LEU A 364 | 19.277 | 35.364 | 16.082 | 1.00 | 60.93 | A | C |
| ATOM | 1941 | CG | LEU A 364 | 19.712 | 36.773 | 16.483 | 1.00 | 69.73 | A | C |
| ATOM | 1942 | CD1 | LEU A 364 | 20.045 | 36.818 | 17.971 | 1.00 | 75.26 | A | C |
| ATOM | 1943 | CD2 | LEU A 364 | 20.929 | 37.190 | 15.635 | 1.00 | 74.05 | A | C |
| ATOM | 1944 | C | LEU A 364 | 21.427 | 34.149 | 16.649 | 1.00 | 54.58 | A | C |
| ATOM | 1945 | O | LEU A 364 | 22.049 | 35.110 | 17.096 | 1.00 | 52.94 | A | O |
| ATOM | 1946 | N | LYS A 365 | 22.007 | 33.058 | 16.182 | 1.00 | 57.89 | A | N |
| ATOM | 1947 | CA | LYS A 365 | 23.437 | 32.927 | 16.111 | 1.00 | 62.63 | A | C |
| ATOM | 1948 | CB | LYS A 365 | 23.924 | 31.962 | 17.194 | 1.00 | 63.77 | A | C |
| ATOM | 1949 | CG | LYS A 365 | 25.334 | 32.209 | 17.714 | 1.00 | 69.14 | A | C |
| ATOM | 1950 | CD | LYS A 365 | 25.457 | 33.528 | 18.492 | 1.00 | 66.34 | A | C |
| ATOM | 1951 | CE | LYS A 365 | 26.492 | 34.486 | 17.845 | 1.00 | 62.60 | A | C |
| ATOM | 1952 | NZ | LYS A 365 | 26.101 | 34.919 | 16.473 | 1.00 | 56.98 | A | N |
| ATOM | 1953 | C | LYS A 365 | 23.626 | 32.321 | 14.742 | 1.00 | 65.11 | A | C |
| ATOM | 1954 | O | LYS A 365 | 22.800 | 31.510 | 14.304 | 1.00 | 66.58 | A | O |
| ATOM | 1955 | N | HIS A 366 | 24.701 | 32.711 | 14.065 | 1.00 | 65.84 | A | N |
| ATOM | 1956 | CA | HIS A 366 | 24.958 | 32.193 | 12.743 | 1.00 | 65.65 | A | C |
| ATOM | 1957 | CB | HIS A 366 | 26.218 | 32.816 | 12.151 | 1.00 | 66.16 | A | C |
| ATOM | 1958 | CG | HIS A 366 | 26.375 | 32.539 | 10.698 | 1.00 | 69.15 | A | C |
| ATOM | 1959 | CD2 | HIS A 366 | 26.706 | 31.408 | 10.039 | 1.00 | 74.25 | A | C |
| ATOM | 1960 | ND1 | HIS A 366 | 26.052 | 33.462 | 9.732 | 1.00 | 70.33 | A | N |
| ATOM | 1961 | CE1 | HIS A 366 | 26.174 | 32.911 | 8.536 | 1.00 | 74.91 | A | C |
| ATOM | 1962 | NE2 | HIS A 366 | 26.571 | 31.664 | 8.694 | 1.00 | 77.28 | A | N |
| ATOM | 1963 | C | HIS A 366 | 25.110 | 30.684 | 12.761 | 1.00 | 65.51 | A | C |
| ATOM | 1964 | O | HIS A 366 | 24.558 | 29.992 | 11.920 | 1.00 | 64.76 | A | O |
| ATOM | 1965 | N | ASN A 367 | 25.873 | 30.180 | 13.722 | 1.00 | 66.30 | A | N |
| ATOM | 1966 | CA | ASN A 367 | 26.096 | 28.744 | 13.840 | 1.00 | 69.53 | A | C |
| ATOM | 1967 | CB | ASN A 367 | 27.179 | 28.479 | 14.882 | 1.00 | 75.65 | A | C |
| ATOM | 1968 | CG | ASN A 367 | 27.971 | 27.225 | 14.589 | 1.00 | 81.83 | A | C |
| ATOM | 1969 | OD1 | ASN A 367 | 27.413 | 26.165 | 14.308 | 1.00 | 84.39 | A | O |
| ATOM | 1970 | ND2 | ASN A 367 | 29.288 | 27.343 | 14.651 | 1.00 | 85.71 | A | N |
| ATOM | 1971 | C | ASN A 367 | 24.800 | 28.058 | 14.267 | 1.00 | 67.75 | A | C |
| ATOM | 1972 | O | ASN A 367 | 24.232 | 28.370 | 15.322 | 1.00 | 69.67 | A | O |
| ATOM | 1973 | N | PRO A 368 | 24.311 | 27.108 | 13.466 | 1.00 | 63.97 | A | N |
| ATOM | 1974 | CD | PRO A 368 | 24.661 | 26.693 | 12.101 | 1.00 | 61.89 | A | C |
| ATOM | 1975 | CA | PRO A 368 | 23.070 | 26.476 | 13.899 | 1.00 | 63.31 | A | C |
| ATOM | 1976 | CB | PRO A 368 | 22.766 | 25.512 | 12.770 | 1.00 | 62.08 | A | C |
| ATOM | 1977 | CG | PRO A 368 | 23.334 | 26.200 | 11.582 | 1.00 | 61.98 | A | C |
| ATOM | 1978 | C | PRO A 368 | 23.216 | 25.777 | 15.231 | 1.00 | 65.26 | A | C |
| ATOM | 1979 | O | PRO A 368 | 22.326 | 25.858 | 16.085 | 1.00 | 65.63 | A | O |
| ATOM | 1980 | N | SER A 369 | 24.360 | 25.119 | 15.412 | 1.00 | 69.07 | A | N |
| ATOM | 1981 | CA | SER A 369 | 24.642 | 24.364 | 16.628 | 1.00 | 72.93 | A | C |
| ATOM | 1982 | CB | SER A 369 | 25.905 | 23.514 | 16.429 | 1.00 | 71.59 | A | C |
| ATOM | 1983 | OG | SER A 369 | 27.080 | 24.313 | 16.352 | 1.00 | 69.95 | A | O |
| ATOM | 1984 | C | SER A 369 | 24.777 | 25.172 | 17.913 | 1.00 | 75.91 | A | C |
| ATOM | 1985 | O | SER A 369 | 24.603 | 24.627 | 18.994 | 1.00 | 76.83 | A | O |

Figure 2FF

| ATOM | 1986 | N | GLN | A | 370 | 25.093 | 26.457 | 17.819 | 1.00 | 79.58 | A | N |
|---|---|---|---|---|---|---|---|---|---|---|---|---|
| ATOM | 1987 | CA | GLN | A | 370 | 25.236 | 27.262 | 19.030 | 1.00 | 83.65 | A | C |
| ATOM | 1988 | CB | GLN | A | 370 | 26.092 | 28.504 | 18.769 | 1.00 | 83.13 | A | C |
| ATOM | 1989 | CG | GLN | A | 370 | 27.481 | 28.207 | 18.248 | 1.00 | 84.40 | A | C |
| ATOM | 1990 | CD | GLN | A | 370 | 28.374 | 29.443 | 18.204 | 1.00 | 87.42 | A | C |
| ATOM | 1991 | OE1 | GLN | A | 370 | 29.500 | 29.384 | 17.713 | 1.00 | 88.83 | A | O |
| ATOM | 1992 | NE2 | GLN | A | 370 | 27.876 | 30.566 | 18.723 | 1.00 | 90.21 | A | N |
| ATOM | 1993 | C | GLN | A | 370 | 23.871 | 27.688 | 19.556 | 1.00 | 86.94 | A | C |
| ATOM | 1994 | O | GLN | A | 370 | 23.770 | 28.400 | 20.558 | 1.00 | 88.37 | A | O |
| ATOM | 1995 | N | ARG | A | 371 | 22.816 | 27.245 | 18.881 | 1.00 | 89.17 | A | N |
| ATOM | 1996 | CA | ARG | A | 371 | 21.467 | 27.598 | 19.289 | 1.00 | 90.00 | A | C |
| ATOM | 1997 | CB | ARG | A | 371 | 20.567 | 27.766 | 18.057 | 1.00 | 96.17 | A | C |
| ATOM | 1998 | CG | ARG | A | 371 | 21.001 | 28.915 | 17.144 | 1.00 | 104.80 | A | C |
| ATOM | 1999 | CD | ARG | A | 371 | 21.284 | 30.211 | 17.937 | 1.00 | 117.05 | A | C |
| ATOM | 2000 | NE | ARG | A | 371 | 22.424 | 30.091 | 18.860 | 1.00 | 126.19 | A | N |
| ATOM | 2001 | CZ | ARG | A | 371 | 22.842 | 31.044 | 19.698 | 1.00 | 129.40 | A | C |
| ATOM | 2002 | NH1 | ARG | A | 371 | 23.887 | 30.826 | 20.491 | 1.00 | 128.85 | A | N |
| ATOM | 2003 | NH2 | ARG | A | 371 | 22.232 | 32.223 | 19.739 | 1.00 | 133.12 | A | N |
| ATOM | 2004 | C | ARG | A | 371 | 20.893 | 26.580 | 20.250 | 1.00 | 85.05 | A | C |
| ATOM | 2005 | O | ARG | A | 371 | 21.011 | 25.382 | 20.029 | 1.00 | 84.80 | A | O |
| ATOM | 2006 | N | PRO | A | 372 | 20.255 | 27.053 | 21.330 | 1.00 | 80.33 | A | N |
| ATOM | 2007 | CD | PRO | A | 372 | 19.881 | 28.462 | 21.520 | 1.00 | 75.06 | A | C |
| ATOM | 2008 | CA | PRO | A | 372 | 19.649 | 26.220 | 22.366 | 1.00 | 79.44 | A | C |
| ATOM | 2009 | CB | PRO | A | 372 | 19.058 | 27.245 | 23.319 | 1.00 | 77.16 | A | C |
| ATOM | 2010 | CG | PRO | A | 372 | 18.699 | 28.358 | 22.424 | 1.00 | 73.68 | A | C |
| ATOM | 2011 | C | PRO | A | 372 | 18.610 | 25.270 | 21.824 | 1.00 | 80.27 | A | C |
| ATOM | 2012 | O | PRO | A | 372 | 18.210 | 25.385 | 20.678 | 1.00 | 83.31 | A | O |
| ATOM | 2013 | N | MET | A | 373 | 18.182 | 24.310 | 22.635 | 1.00 | 80.21 | A | N |
| ATOM | 2014 | CA | MET | A | 373 | 17.157 | 23.380 | 22.174 | 1.00 | 81.35 | A | C |
| ATOM | 2015 | CB | MET | A | 373 | 17.511 | 21.933 | 22.522 | 1.00 | 78.96 | A | C |
| ATOM | 2016 | CG | MET | A | 373 | 17.143 | 20.896 | 21.441 | 1.00 | 75.32 | A | C |
| ATOM | 2017 | SD | MET | A | 373 | 15.388 | 20.761 | 20.867 | 1.00 | 74.22 | A | S |
| ATOM | 2018 | CE | MET | A | 373 | 15.640 | 20.042 | 19.288 | 1.00 | 71.60 | A | C |
| ATOM | 2019 | C | MET | A | 373 | 15.885 | 23.770 | 22.895 | 1.00 | 85.20 | A | C |
| ATOM | 2020 | O | MET | A | 373 | 15.888 | 24.661 | 23.735 | 1.00 | 84.12 | A | O |
| ATOM | 2021 | N | LEU | A | 374 | 14.800 | 23.107 | 22.532 | 1.00 | 91.43 | A | N |
| ATOM | 2022 | CA | LEU | A | 374 | 13.487 | 23.304 | 23.130 | 1.00 | 96.00 | A | C |
| ATOM | 2023 | CB | LEU | A | 374 | 12.717 | 21.969 | 23.018 | 1.00 | 97.56 | A | C |
| ATOM | 2024 | CG | LEU | A | 374 | 13.518 | 20.663 | 23.254 | 1.00 | 95.49 | A | C |
| ATOM | 2025 | CD1 | LEU | A | 374 | 13.623 | 20.352 | 24.740 | 1.00 | 93.11 | A | C |
| ATOM | 2026 | CD2 | LEU | A | 374 | 12.846 | 19.499 | 22.524 | 1.00 | 91.99 | A | C |
| ATOM | 2027 | C | LEU | A | 374 | 13.466 | 23.801 | 24.594 | 1.00 | 97.88 | A | C |
| ATOM | 2028 | O | LEU | A | 374 | 13.000 | 24.906 | 24.889 | 1.00 | 97.21 | A | O |
| ATOM | 2029 | N | ARG | A | 375 | 13.984 | 22.977 | 25.497 | 1.00 | 99.22 | A | N |
| ATOM | 2030 | CA | ARG | A | 375 | 13.984 | 23.271 | 26.920 | 1.00 | 100.59 | A | C |
| ATOM | 2031 | CB | ARG | A | 375 | 14.547 | 22.078 | 27.687 | 1.00 | 104.56 | A | C |
| ATOM | 2032 | CG | ARG | A | 375 | 14.435 | 22.217 | 29.197 | 1.00 | 109.85 | A | C |
| ATOM | 2033 | CD | ARG | A | 375 | 15.234 | 21.156 | 29.932 | 1.00 | 116.44 | A | C |
| ATOM | 2034 | NE | ARG | A | 375 | 16.669 | 21.440 | 29.943 | 1.00 | 123.68 | A | N |
| ATOM | 2035 | CZ | ARG | A | 375 | 17.482 | 21.308 | 28.896 | 1.00 | 128.43 | A | C |
| ATOM | 2036 | NH1 | ARG | A | 375 | 18.772 | 21.597 | 29.021 | 1.00 | 130.54 | A | N |
| ATOM | 2037 | NH2 | ARG | A | 375 | 17.017 | 20.881 | 27.728 | 1.00 | 132.85 | A | N |
| ATOM | 2038 | C | ARG | A | 375 | 14.682 | 24.534 | 27.405 | 1.00 | 99.40 | A | C |
| ATOM | 2039 | O | ARG | A | 375 | 14.218 | 25.176 | 28.348 | 1.00 | 100.55 | A | O |
| ATOM | 2040 | N | GLU | A | 376 | 15.793 | 24.900 | 26.786 | 1.00 | 98.02 | A | N |
| ATOM | 2041 | CA | GLU | A | 376 | 16.512 | 26.074 | 27.244 | 1.00 | 96.90 | A | C |
| ATOM | 2042 | CB | GLU | A | 376 | 17.725 | 26.338 | 26.357 | 1.00 | 105.25 | A | C |
| ATOM | 2043 | CG | GLU | A | 376 | 18.591 | 27.489 | 26.851 | 1.00 | 114.81 | A | C |
| ATOM | 2044 | CD | GLU | A | 376 | 18.996 | 27.319 | 28.306 | 1.00 | 118.52 | A | C |
| ATOM | 2045 | OE1 | GLU | A | 376 | 19.576 | 26.257 | 28.630 | 1.00 | 121.73 | A | O |
| ATOM | 2046 | OE2 | GLU | A | 376 | 18.735 | 28.238 | 29.122 | 1.00 | 116.75 | A | O |

Figure 2GG

| ATOM | 2047 | C   | GLU | A | 376 | 15.647 | 27.322 | 27.322 | 1.00 | 91.62  | A | C |
|------|------|-----|-----|---|-----|--------|--------|--------|------|--------|---|---|
| ATOM | 2048 | O   | GLU | A | 376 | 15.672 | 28.028 | 28.333 | 1.00 | 88.64  | A | O |
| ATOM | 2049 | N   | VAL | A | 377 | 14.886 | 27.595 | 26.261 | 1.00 | 87.66  | A | N |
| ATOM | 2050 | CA  | VAL | A | 377 | 14.022 | 28.772 | 26.238 | 1.00 | 84.36  | A | C |
| ATOM | 2051 | CB  | VAL | A | 377 | 13.475 | 29.065 | 24.832 | 1.00 | 84.47  | A | C |
| ATOM | 2052 | CG1 | VAL | A | 377 | 14.597 | 29.568 | 23.933 | 1.00 | 84.90  | A | C |
| ATOM | 2053 | CG2 | VAL | A | 377 | 12.823 | 27.814 | 24.254 | 1.00 | 82.93  | A | C |
| ATOM | 2054 | C   | VAL | A | 377 | 12.848 | 28.582 | 27.169 | 1.00 | 81.88  | A | C |
| ATOM | 2055 | O   | VAL | A | 377 | 12.446 | 29.509 | 27.873 | 1.00 | 82.61  | A | O |
| ATOM | 2056 | N   | LEU | A | 378 | 12.302 | 27.372 | 27.165 | 1.00 | 76.97  | A | N |
| ATOM | 2057 | CA  | LEU | A | 378 | 11.182 | 27.040 | 28.030 | 1.00 | 72.85  | A | C |
| ATOM | 2058 | CB  | LEU | A | 378 | 10.752 | 25.592 | 27.767 | 1.00 | 63.89  | A | C |
| ATOM | 2059 | CG  | LEU | A | 378 | 9.440  | 25.385 | 27.011 | 1.00 | 57.48  | A | C |
| ATOM | 2060 | CD1 | LEU | A | 378 | 9.049  | 26.658 | 26.300 | 1.00 | 57.13  | A | C |
| ATOM | 2061 | CD2 | LEU | A | 378 | 9.575  | 24.233 | 26.050 | 1.00 | 52.29  | A | C |
| ATOM | 2062 | C   | LEU | A | 378 | 11.535 | 27.248 | 29.511 | 1.00 | 74.24  | A | C |
| ATOM | 2063 | O   | LEU | A | 378 | 10.659 | 27.509 | 30.327 | 1.00 | 74.43  | A | O |
| ATOM | 2064 | N   | GLU | A | 379 | 12.818 | 27.143 | 29.847 | 1.00 | 74.45  | A | N |
| ATOM | 2065 | CA  | GLU | A | 379 | 13.284 | 27.328 | 31.224 | 1.00 | 75.07  | A | C |
| ATOM | 2066 | CB  | GLU | A | 379 | 14.192 | 26.158 | 31.629 | 1.00 | 81.37  | A | C |
| ATOM | 2067 | CG  | GLU | A | 379 | 14.548 | 26.085 | 33.124 | 1.00 | 94.68  | A | C |
| ATOM | 2068 | CD  | GLU | A | 379 | 15.900 | 26.731 | 33.504 | 1.00 | 99.79  | A | C |
| ATOM | 2069 | OE1 | GLU | A | 379 | 16.238 | 26.727 | 34.712 | 1.00 | 103.20 | A | O |
| ATOM | 2070 | OE2 | GLU | A | 379 | 16.622 | 27.233 | 32.614 | 1.00 | 101.24 | A | O |
| ATOM | 2071 | C   | GLU | A | 379 | 14.051 | 28.644 | 31.352 | 1.00 | 72.61  | A | C |
| ATOM | 2072 | O   | GLU | A | 379 | 14.693 | 28.919 | 32.363 | 1.00 | 74.67  | A | O |
| ATOM | 2073 | N   | HIS | A | 380 | 13.989 | 29.471 | 30.323 | 1.00 | 69.17  | A | N |
| ATOM | 2074 | CA  | HIS | A | 380 | 14.711 | 30.713 | 30.374 | 1.00 | 67.78  | A | C |
| ATOM | 2075 | CB  | HIS | A | 380 | 14.722 | 31.379 | 29.000 | 1.00 | 65.12  | A | C |
| ATOM | 2076 | CG  | HIS | A | 380 | 15.578 | 32.602 | 28.937 | 1.00 | 64.64  | A | C |
| ATOM | 2077 | CD2 | HIS | A | 380 | 16.680 | 32.882 | 28.200 | 1.00 | 64.84  | A | C |
| ATOM | 2078 | ND1 | HIS | A | 380 | 15.342 | 33.714 | 29.715 | 1.00 | 62.16  | A | N |
| ATOM | 2079 | CE1 | HIS | A | 380 | 16.261 | 34.629 | 29.459 | 1.00 | 64.59  | A | C |
| ATOM | 2080 | NE2 | HIS | A | 380 | 17.084 | 34.149 | 28.543 | 1.00 | 65.94  | A | N |
| ATOM | 2081 | C   | HIS | A | 380 | 14.145 | 31.676 | 31.405 | 1.00 | 67.54  | A | C |
| ATOM | 2082 | O   | HIS | A | 380 | 12.937 | 31.857 | 31.506 | 1.00 | 65.56  | A | O |
| ATOM | 2083 | N   | PRO | A | 381 | 15.032 | 32.319 | 32.179 | 1.00 | 70.03  | A | N |
| ATOM | 2084 | CD  | PRO | A | 381 | 16.502 | 32.201 | 32.078 | 1.00 | 73.09  | A | C |
| ATOM | 2085 | CA  | PRO | A | 381 | 14.673 | 33.281 | 33.216 | 1.00 | 72.41  | A | C |
| ATOM | 2086 | CB  | PRO | A | 381 | 16.015 | 33.936 | 33.548 | 1.00 | 74.53  | A | C |
| ATOM | 2087 | CG  | PRO | A | 381 | 16.980 | 32.810 | 33.384 | 1.00 | 73.59  | A | C |
| ATOM | 2088 | C   | PRO | A | 381 | 13.657 | 34.300 | 32.726 | 1.00 | 72.56  | A | C |
| ATOM | 2089 | O   | PRO | A | 381 | 13.031 | 35.001 | 33.525 | 1.00 | 76.18  | A | O |
| ATOM | 2090 | N   | TRP | A | 382 | 13.490 | 34.394 | 31.415 | 1.00 | 68.97  | A | N |
| ATOM | 2091 | CA  | TRP | A | 382 | 12.552 | 35.365 | 30.889 | 1.00 | 66.42  | A | C |
| ATOM | 2092 | CB  | TRP | A | 382 | 13.142 | 36.048 | 29.667 | 1.00 | 67.04  | A | C |
| ATOM | 2093 | CG  | TRP | A | 382 | 12.521 | 37.359 | 29.372 | 1.00 | 68.56  | A | C |
| ATOM | 2094 | CD2 | TRP | A | 382 | 11.639 | 37.662 | 28.285 | 1.00 | 68.32  | A | C |
| ATOM | 2095 | CE2 | TRP | A | 382 | 11.306 | 39.029 | 28.387 | 1.00 | 70.67  | A | C |
| ATOM | 2096 | CE3 | TRP | A | 382 | 11.100 | 36.910 | 27.235 | 1.00 | 65.32  | A | C |
| ATOM | 2097 | CD1 | TRP | A | 382 | 12.680 | 38.512 | 30.073 | 1.00 | 70.66  | A | C |
| ATOM | 2098 | NE1 | TRP | A | 382 | 11.953 | 39.528 | 29.486 | 1.00 | 70.62  | A | N |
| ATOM | 2099 | CZ2 | TRP | A | 382 | 10.457 | 39.661 | 27.477 | 1.00 | 71.40  | A | C |
| ATOM | 2100 | CZ3 | TRP | A | 382 | 10.262 | 37.536 | 26.335 | 1.00 | 65.56  | A | C |
| ATOM | 2101 | CH2 | TRP | A | 382 | 9.948  | 38.899 | 26.460 | 1.00 | 69.28  | A | C |
| ATOM | 2102 | C   | TRP | A | 382 | 11.204 | 34.744 | 30.539 | 1.00 | 65.66  | A | C |
| ATOM | 2103 | O   | TRP | A | 382 | 10.167 | 35.335 | 30.796 | 1.00 | 64.09  | A | O |
| ATOM | 2104 | N   | ILE | A | 383 | 11.210 | 33.558 | 29.946 | 1.00 | 65.21  | A | N |
| ATOM | 2105 | CA  | ILE | A | 383 | 9.951  | 32.923 | 29.615 | 1.00 | 64.53  | A | C |
| ATOM | 2106 | CB  | ILE | A | 383 | 10.157 | 31.575 | 28.918 | 1.00 | 62.96  | A | C |
| ATOM | 2107 | CG2 | ILE | A | 383 | 8.874  | 30.765 | 28.959 | 1.00 | 66.81  | A | C |

Figure 2HH

```
ATOM   2108  CG1 ILE A 383      10.571  31.806  27.466  1.00  62.65      A   C
ATOM   2109  CD1 ILE A 383      11.983  32.338  27.293  1.00  58.44      A   C
ATOM   2110  C   ILE A 383       9.232  32.724  30.934  1.00  65.61      A   C
ATOM   2111  O   ILE A 383       8.033  32.952  31.044  1.00  67.02      A   O
ATOM   2112  N   THR A 384       9.991  32.313  31.941  1.00  68.02      A   N
ATOM   2113  CA  THR A 384       9.447  32.106  33.281  1.00  71.46      A   C
ATOM   2114  CB  THR A 384      10.246  31.031  34.022  1.00  73.46      A   C
ATOM   2115  OG1 THR A 384      11.582  31.499  34.253  1.00  78.58      A   O
ATOM   2116  CG2 THR A 384      10.307  29.766  33.186  1.00  70.85      A   C
ATOM   2117  C   THR A 384       9.533  33.424  34.056  1.00  72.04      A   C
ATOM   2118  O   THR A 384      10.630  33.889  34.369  1.00  74.73      A   O
ATOM   2119  N   ALA A 385       8.372  34.012  34.338  1.00  71.40      A   N
ATOM   2120  CA  ALA A 385       8.234  35.290  35.061  1.00  75.23      A   C
ATOM   2121  CB  ALA A 385       9.553  36.065  35.094  1.00  75.05      A   C
ATOM   2122  C   ALA A 385       7.183  36.106  34.323  1.00  76.36      A   C
ATOM   2123  O   ALA A 385       5.980  35.988  34.578  1.00  77.74      A   O
ATOM   2124  N   ASN A 386       7.647  36.961  33.422  1.00  75.64      A   N
ATOM   2125  CA  ASN A 386       6.735  37.734  32.605  1.00  72.43      A   C
ATOM   2126  CB  ASN A 386       7.493  38.806  31.843  1.00  69.05      A   C
ATOM   2127  CG  ASN A 386       8.911  38.429  31.631  1.00  69.63      A   C
ATOM   2128  OD1 ASN A 386       9.189  37.395  31.048  1.00  71.83      A   O
ATOM   2129  ND2 ASN A 386       9.831  39.248  32.125  1.00  70.84      A   N
ATOM   2130  C   ASN A 386       6.341  36.607  31.694  1.00  71.63      A   C
ATOM   2131  O   ASN A 386       7.178  36.079  30.992  1.00  69.35      A   O
ATOM   2132  N   SER A 387       5.082  36.206  31.769  1.00  74.69      A   N
ATOM   2133  CA  SER A 387       4.556  35.104  30.986  1.00  79.07      A   C
ATOM   2134  CB  SER A 387       5.466  33.886  31.104  1.00  74.02      A   C
ATOM   2135  OG  SER A 387       5.008  32.832  30.277  1.00  69.72      A   O
ATOM   2136  C   SER A 387       3.187  34.765  31.566  1.00  85.99      A   C
ATOM   2137  O   SER A 387       2.884  35.145  32.698  1.00  89.72      A   O
ATOM   2138  N   SER A 388       2.371  34.050  30.794  1.00  90.29      A   N
ATOM   2139  CA  SER A 388       1.022  33.671  31.224  1.00  90.60      A   C
ATOM   2140  CB  SER A 388       1.092  32.519  32.240  1.00  89.06      A   C
ATOM   2141  OG  SER A 388       1.645  31.345  31.669  1.00  81.60      A   O
ATOM   2142  C   SER A 388       0.256  34.858  31.838  1.00  92.18      A   C
ATOM   2143  O   SER A 388       0.179  35.934  31.189  1.00  90.40      A   O
TER    2145      SER A 388                                               A
ATOM   2146  C1  071 B   1      -6.880  35.378   7.060  1.00  61.02      B   C
ATOM   2147  C2  071 B   1      -7.767  34.356   7.351  1.00  62.09      B   C
ATOM   2148  C3  071 B   1      -7.918  33.307   6.448  1.00  59.96      B   C
ATOM   2149  C4  071 B   1      -7.161  33.271   5.241  1.00  57.29      B   C
ATOM   2150  C55 071 B   1      -6.268  34.293   4.960  1.00  58.62      B   C
ATOM   2151  C6  071 B   1      -6.126  35.353   5.872  1.00  59.65      B   C
ATOM   2152  C7  071 B   1     -10.003  34.352  10.885  1.00  64.92      B   C
ATOM   2153  C9  071 B   1      -9.793  35.555  10.174  1.00  67.16      B   C
ATOM   2154  N   071 B   1      -9.061  35.542   9.004  1.00  66.96      B   N
ATOM   2155  C14 071 B   1      -8.492  34.368   8.544  1.00  64.43      B   C
ATOM   2156  N2  071 B   1      -8.670  33.200   9.262  1.00  64.57      B   N
ATOM   2157  C17 071 B   1      -9.422  33.180  10.418  1.00  63.54      B   C
ATOM   2158  C8  071 B   1      -8.630  28.910   9.243  1.00  57.82      B   C
ATOM   2159  S1  071 B   1      -8.634  30.449   9.248  1.00  57.42      B   S
ATOM   2160  C12 071 B   1      -9.315  30.765  10.618  1.00  58.31      B   C
ATOM   2161  N4  071 B   1      -9.625  29.584  11.252  1.00  56.40      B   N
ATOM   2162  C18 071 B   1      -9.223  28.493  10.450  1.00  55.53      B   C
ATOM   2163  C15 071 B   1      -8.151  28.099   8.245  1.00  61.33      B   C
ATOM   2164  C11 071 B   1     -10.716  34.365  12.100  1.00  61.72      B   C
ATOM   2165  C13 071 B   1     -11.201  35.572  12.616  1.00  60.76      B   C
ATOM   2166  C16 071 B   1     -10.985  36.771  11.917  1.00  61.57      B   C
ATOM   2167  C5  071 B   1     -10.282  36.763  10.692  1.00  65.67      B   C
ATOM   2168  N6  071 B   1      -9.582  32.016  11.141  1.00  61.24      B   N
TER    2169      071 B   1                                               B   END
```

Figure 3A

| Atom | Type | Resid | # | X | Y | Z | Occ | B | Mol | |
|---|---|---|---|---|---|---|---|---|---|---|
| ATOM | 1 | CB | TRP A | 128 | -15.553 | 14.572 | 4.229 | 1.00 | 77.31 | A | C |
| ATOM | 2 | CG | TRP A | 128 | -15.362 | 14.455 | 5.718 | 1.00 | 85.23 | A | C |
| ATOM | 3 | CD2 | TRP A | 128 | -16.385 | 14.507 | 6.723 | 1.00 | 86.59 | A | C |
| ATOM | 4 | CE2 | TRP A | 128 | -15.760 | 14.275 | 7.970 | 1.00 | 87.74 | A | C |
| ATOM | 5 | CE3 | TRP A | 128 | -17.769 | 14.722 | 6.691 | 1.00 | 86.90 | A | C |
| ATOM | 6 | CD1 | TRP A | 128 | -14.192 | 14.211 | 6.382 | 1.00 | 90.48 | A | C |
| ATOM | 7 | NE1 | TRP A | 128 | -14.424 | 14.097 | 7.734 | 1.00 | 89.69 | A | N |
| ATOM | 8 | CZ2 | TRP A | 128 | -16.474 | 14.251 | 9.172 | 1.00 | 88.40 | A | C |
| ATOM | 9 | CZ3 | TRP A | 128 | -18.478 | 14.698 | 7.890 | 1.00 | 89.69 | A | C |
| ATOM | 10 | CH2 | TRP A | 128 | -17.828 | 14.464 | 9.111 | 1.00 | 89.34 | A | C |
| ATOM | 11 | C | TRP A | 128 | -17.013 | 14.056 | 2.258 | 1.00 | 83.98 | A | C |
| ATOM | 12 | O | TRP A | 128 | -16.503 | 13.454 | 1.297 | 1.00 | 83.56 | A | O |
| ATOM | 13 | N | TRP A | 128 | -16.342 | 12.243 | 3.830 | 1.00 | 76.50 | A | N |
| ATOM | 14 | CA | TRP A | 128 | -16.696 | 13.688 | 3.702 | 1.00 | 79.54 | A | C |
| ATOM | 15 | N | ALA A | 129 | -17.890 | 15.040 | 2.123 | 1.00 | 88.41 | A | N |
| ATOM | 16 | CA | ALA A | 129 | -18.304 | 15.541 | 0.825 | 1.00 | 92.73 | A | C |
| ATOM | 17 | CB | ALA A | 129 | -19.405 | 14.659 | 0.238 | 1.00 | 93.48 | A | C |
| ATOM | 18 | C | ALA A | 129 | -18.814 | 16.960 | 1.078 | 1.00 | 95.42 | A | C |
| ATOM | 19 | O | ALA A | 129 | -19.115 | 17.318 | 2.226 | 1.00 | 95.13 | A | O |
| ATOM | 20 | N | LEU A | 130 | -18.907 | 17.764 | 0.021 | 1.00 | 96.54 | A | N |
| ATOM | 21 | CA | LEU A | 130 | -19.351 | 19.145 | 0.154 | 1.00 | 94.67 | A | C |
| ATOM | 22 | CB | LEU A | 130 | -19.346 | 19.821 | -1.206 | 1.00 | 91.24 | A | C |
| ATOM | 23 | CG | LEU A | 130 | -19.491 | 21.323 | -1.047 | 1.00 | 91.28 | A | C |
| ATOM | 24 | CD1 | LEU A | 130 | -18.266 | 21.860 | -0.324 | 1.00 | 87.66 | A | C |
| ATOM | 25 | CD2 | LEU A | 130 | -19.649 | 21.967 | -2.402 | 1.00 | 97.34 | A | C |
| ATOM | 26 | C | LEU A | 130 | -20.733 | 19.299 | 0.786 | 1.00 | 94.87 | A | C |
| ATOM | 27 | O | LEU A | 130 | -20.943 | 20.168 | 1.632 | 1.00 | 95.15 | A | O |
| ATOM | 28 | N | GLU A | 131 | -21.666 | 18.450 | 0.366 | 1.00 | 94.46 | A | N |
| ATOM | 29 | CA | GLU A | 131 | -23.043 | 18.462 | 0.865 | 1.00 | 96.62 | A | C |
| ATOM | 30 | CB | GLU A | 131 | -23.795 | 17.239 | 0.323 | 1.00 | 102.53 | A | C |
| ATOM | 31 | CG | GLU A | 131 | -25.288 | 17.184 | 0.689 | 1.00 | 112.45 | A | C |
| ATOM | 32 | CD | GLU A | 131 | -25.929 | 15.787 | 0.495 | 1.00 | 116.42 | A | C |
| ATOM | 33 | OE1 | GLU A | 131 | -25.774 | 15.179 | -0.597 | 1.00 | 113.92 | A | O |
| ATOM | 34 | OE2 | GLU A | 131 | -26.602 | 15.304 | 1.445 | 1.00 | 120.54 | A | O |
| ATOM | 35 | C | GLU A | 131 | -23.153 | 18.478 | 2.393 | 1.00 | 94.79 | A | C |
| ATOM | 36 | O | GLU A | 131 | -24.053 | 19.108 | 2.948 | 1.00 | 97.60 | A | O |
| ATOM | 37 | N | ASP A | 132 | -22.238 | 17.777 | 3.059 | 1.00 | 90.89 | A | N |
| ATOM | 38 | CA | ASP A | 132 | -22.232 | 17.679 | 4.520 | 1.00 | 87.25 | A | C |
| ATOM | 39 | CB | ASP A | 132 | -21.206 | 16.630 | 4.997 | 1.00 | 87.32 | A | C |
| ATOM | 40 | CG | ASP A | 132 | -21.388 | 15.264 | 4.350 | 1.00 | 85.90 | A | C |
| ATOM | 41 | OD1 | ASP A | 132 | -20.601 | 14.921 | 3.450 | 1.00 | 85.52 | A | O |
| ATOM | 42 | OD2 | ASP A | 132 | -22.307 | 14.527 | 4.744 | 1.00 | 84.66 | A | O |
| ATOM | 43 | C | ASP A | 132 | -21.931 | 19.001 | 5.245 | 1.00 | 86.25 | A | C |
| ATOM | 44 | O | ASP A | 132 | -21.973 | 19.055 | 6.481 | 1.00 | 80.94 | A | O |
| ATOM | 45 | N | PHE A | 133 | -21.627 | 20.063 | 4.498 | 1.00 | 86.93 | A | N |
| ATOM | 46 | CA | PHE A | 133 | -21.306 | 21.339 | 5.137 | 1.00 | 86.09 | A | C |
| ATOM | 47 | CB | PHE A | 133 | -19.805 | 21.626 | 5.025 | 1.00 | 80.07 | A | C |
| ATOM | 48 | CG | PHE A | 133 | -18.928 | 20.483 | 5.436 | 1.00 | 78.44 | A | C |
| ATOM | 49 | CD1 | PHE A | 133 | -18.638 | 19.459 | 4.549 | 1.00 | 82.03 | A | C |
| ATOM | 50 | CD2 | PHE A | 133 | -18.382 | 20.433 | 6.711 | 1.00 | 77.09 | A | C |
| ATOM | 51 | CE1 | PHE A | 133 | -17.815 | 18.403 | 4.926 | 1.00 | 84.91 | A | C |
| ATOM | 52 | CE2 | PHE A | 133 | -17.555 | 19.379 | 7.098 | 1.00 | 79.24 | A | C |
| ATOM | 53 | CZ | PHE A | 133 | -17.272 | 18.363 | 6.203 | 1.00 | 83.43 | A | C |
| ATOM | 54 | C | PHE A | 133 | -22.057 | 22.559 | 4.609 | 1.00 | 89.60 | A | C |
| ATOM | 55 | O | PHE A | 133 | -22.246 | 22.717 | 3.399 | 1.00 | 95.80 | A | O |
| ATOM | 56 | N | GLU A | 134 | -22.482 | 23.420 | 5.533 | 1.00 | 87.87 | A | N |
| ATOM | 57 | CA | GLU A | 134 | -23.159 | 24.677 | 5.193 | 1.00 | 85.28 | A | C |
| ATOM | 58 | CB | GLU A | 134 | -24.174 | 25.050 | 6.281 | 1.00 | 79.70 | A | C |

Figure 3B

```
ATOM     63  C   GLU A 134     -21.995  25.677   5.184  1.00  87.50      A    C
ATOM     64  O   GLU A 134     -21.261  25.787   6.180  1.00  86.82      A    O
ATOM     65  N   ILE A 135     -21.796  26.396   4.085  1.00  90.97      A    N
ATOM     66  CA  ILE A 135     -20.655  27.302   4.056  1.00  96.38      A    C
ATOM     67  CB  ILE A 135     -19.878  27.109   2.757  1.00  95.44      A    C
ATOM     68  CG2 ILE A 135     -19.649  25.639   2.516  1.00  92.77      A    C
ATOM     69  CG1 ILE A 135     -20.682  27.643   1.582  1.00  95.02      A    C
ATOM     70  CD1 ILE A 135     -19.855  27.735   0.306  1.00  93.84      A    C
ATOM     71  C   ILE A 135     -20.973  28.791   4.266  1.00  99.65      A    C
ATOM     72  O   ILE A 135     -21.885  29.334   3.627  1.00 102.52      A    O
ATOM     73  N   GLY A 136     -20.201  29.448   5.144  1.00 100.02      A    N
ATOM     74  CA  GLY A 136     -20.429  30.857   5.454  1.00  99.30      A    C
ATOM     75  C   GLY A 136     -19.492  31.933   4.915  1.00  97.66      A    C
ATOM     76  O   GLY A 136     -19.006  31.864   3.784  1.00  98.59      A    O
ATOM     77  N   ARG A 137     -19.267  32.957   5.733  1.00  95.67      A    N
ATOM     78  CA  ARG A 137     -18.395  34.085   5.383  1.00  93.46      A    C
ATOM     79  CB  ARG A 137     -18.061  34.869   6.670  1.00  94.85      A    C
ATOM     80  CG  ARG A 137     -17.295  36.188   6.516  1.00  90.17      A    C
ATOM     81  CD  ARG A 137     -17.134  36.844   7.872  1.00  92.55      A    C
ATOM     82  NE  ARG A 137     -16.090  36.208   8.670  1.00  97.19      A    N
ATOM     83  CZ  ARG A 137     -15.990  36.314   9.991  1.00  97.06      A    C
ATOM     84  NH1 ARG A 137     -15.005  35.718  10.645  1.00  94.41      A    N
ATOM     85  NH2 ARG A 137     -16.895  37.004  10.662  1.00 100.09      A    N
ATOM     86  C   ARG A 137     -17.112  33.590   4.705  1.00  91.91      A    C
ATOM     87  O   ARG A 137     -16.668  32.476   4.950  1.00  88.62      A    O
ATOM     88  N   PRO A 138     -16.512  34.405   3.832  1.00  93.60      A    N
ATOM     89  CD  PRO A 138     -17.074  35.619   3.227  1.00  96.09      A    C
ATOM     90  CA  PRO A 138     -15.281  34.023   3.140  1.00  97.65      A    C
ATOM     91  CB  PRO A 138     -15.388  34.774   1.832  1.00  99.93      A    C
ATOM     92  CG  PRO A 138     -15.942  36.068   2.297  1.00 100.66      A    C
ATOM     93  C   PRO A 138     -14.035  34.438   3.914  1.00  99.90      A    C
ATOM     94  O   PRO A 138     -13.309  35.332   3.481  1.00 104.10      A    O
ATOM     95  N   LEU A 139     -13.802  33.778   5.048  1.00 101.15      A    N
ATOM     96  CA  LEU A 139     -12.655  34.038   5.913  1.00 105.20      A    C
ATOM     97  CB  LEU A 139     -12.274  32.755   6.640  1.00  90.42      A    C
ATOM     98  CG  LEU A 139     -13.329  32.241   7.607  1.00  77.92      A    C
ATOM     99  CD1 LEU A 139     -12.993  30.849   8.042  1.00  78.13      A    C
ATOM    100  CD2 LEU A 139     -13.391  33.148   8.800  1.00  77.06      A    C
ATOM    101  C   LEU A 139     -11.427  34.610   5.192  1.00 117.43      A    C
ATOM    102  O   LEU A 139     -10.771  33.943   4.380  1.00 119.91      A    O
ATOM    103  N   GLY A 140     -11.062  35.868   5.389  1.00 128.58      A    N
ATOM    104  CA  GLY A 140      -9.894  36.337   4.633  1.00 138.05      A    C
ATOM    105  C   GLY A 140      -9.817  35.762   3.200  1.00 142.86      A    C
ATOM    106  O   GLY A 140     -10.852  35.654   2.533  1.00 145.31      A    O
ATOM    107  N   LYS A 141      -8.629  35.369   2.721  1.00 144.54      A    N
ATOM    108  CA  LYS A 141      -8.513  34.822   1.354  1.00 143.46      A    C
ATOM    109  CB  LYS A 141      -8.718  35.945   0.326  1.00 144.47      A    C
ATOM    114  C   LYS A 141      -7.226  34.054   0.994  1.00 141.14      A    C
ATOM    115  O   LYS A 141      -6.356  33.838   1.838  1.00 140.51      A    O
ATOM    116  N   GLY A 142      -7.120  33.651  -0.275  1.00 137.64      A    N
ATOM    117  CA  GLY A 142      -5.952  32.911  -0.725  1.00 134.77      A    C
ATOM    118  C   GLY A 142      -5.729  32.865  -2.233  1.00 134.01      A    C
ATOM    119  O   GLY A 142      -6.670  33.036  -3.025  1.00 131.68      A    O
ATOM    120  N   LYS A 143      -4.468  32.611  -2.610  1.00 133.98      A    N
ATOM    121  CA  LYS A 143      -3.993  32.538  -4.004  1.00 130.27      A    C
ATOM    122  CB  LYS A 143      -2.463  32.412  -4.017  1.00 130.74      A    C
ATOM    127  C   LYS A 143      -4.587  31.391  -4.816  1.00 127.42      A    C
ATOM    128  O   LYS A 143      -5.442  31.603  -5.685  1.00 125.93      A    O
ATOM    129  N   PHE A 144      -4.097  30.182  -4.545  1.00 126.26      A    N
ATOM    130  CA  PHE A 144      -4.584  28.975  -5.222  1.00 123.04      A    C
ATOM    131  CB  PHE A 144      -3.415  27.997  -5.491  1.00 127.84      A    C
```

Figure 3C

| ATOM | 132 | CG | PHE | A | 144 | -2.572 | 27.697 | -4.273 | 1.00 | 134.57 | A | C |
|------|-----|-----|-----|---|-----|--------|--------|--------|------|--------|---|---|
| ATOM | 133 | CD1 | PHE | A | 144 | -1.190 | 27.485 | -4.400 | 1.00 | 135.67 | A | C |
| ATOM | 134 | CD2 | PHE | A | 144 | -3.156 | 27.605 | -2.996 | 1.00 | 139.76 | A | C |
| ATOM | 135 | CE1 | PHE | A | 144 | -0.396 | 27.182 | -3.264 | 1.00 | 135.40 | A | C |
| ATOM | 136 | CE2 | PHE | A | 144 | -2.379 | 27.304 | -1.860 | 1.00 | 141.38 | A | C |
| ATOM | 137 | CZ | PHE | A | 144 | -0.996 | 27.090 | -1.991 | 1.00 | 138.23 | A | C |
| ATOM | 138 | C | PHE | A | 144 | -5.684 | 28.294 | -4.385 | 1.00 | 117.70 | A | C |
| ATOM | 139 | O | PHE | A | 144 | -5.995 | 27.115 | -4.599 | 1.00 | 115.14 | A | O |
| ATOM | 140 | N | GLY | A | 145 | -6.255 | 29.059 | -3.444 | 1.00 | 112.93 | A | N |
| ATOM | 141 | CA | GLY | A | 145 | -7.316 | 28.567 | -2.572 | 1.00 | 107.72 | A | C |
| ATOM | 142 | C | GLY | A | 145 | -7.953 | 29.592 | -1.629 | 1.00 | 101.63 | A | C |
| ATOM | 143 | O | GLY | A | 145 | -7.306 | 30.555 | -1.224 | 1.00 | 100.71 | A | O |
| ATOM | 144 | N | ASN | A | 146 | -9.226 | 29.374 | -1.280 | 1.00 | 94.19 | A | N |
| ATOM | 145 | CA | ASN | A | 146 | -10.003 | 30.245 | -0.375 | 1.00 | 82.32 | A | C |
| ATOM | 146 | CB | ASN | A | 146 | -11.299 | 30.687 | -1.069 | 1.00 | 86.43 | A | C |
| ATOM | 147 | CG | ASN | A | 146 | -11.220 | 32.083 | -1.645 | 1.00 | 91.63 | A | C |
| ATOM | 148 | OD1 | ASN | A | 146 | -10.125 | 32.626 | -1.863 | 1.00 | 93.69 | A | O |
| ATOM | 149 | ND2 | ASN | A | 146 | -12.386 | 32.676 | -1.914 | 1.00 | 96.13 | A | N |
| ATOM | 150 | C | ASN | A | 146 | -10.382 | 29.469 | 0.894 | 1.00 | 72.23 | A | C |
| ATOM | 151 | O | ASN | A | 146 | -10.322 | 28.236 | 0.906 | 1.00 | 65.89 | A | O |
| ATOM | 152 | N | VAL | A | 147 | -10.753 | 30.160 | 1.968 | 1.00 | 62.79 | A | N |
| ATOM | 153 | CA | VAL | A | 147 | -11.184 | 29.414 | 3.143 | 1.00 | 54.74 | A | C |
| ATOM | 154 | CB | VAL | A | 147 | -10.122 | 29.358 | 4.229 | 1.00 | 48.60 | A | C |
| ATOM | 155 | CG1 | VAL | A | 147 | -10.666 | 28.666 | 5.444 | 1.00 | 48.86 | A | C |
| ATOM | 156 | CG2 | VAL | A | 147 | -8.973 | 28.590 | 3.755 | 1.00 | 50.37 | A | C |
| ATOM | 157 | C | VAL | A | 147 | -12.456 | 30.000 | 3.735 | 1.00 | 53.07 | A | C |
| ATOM | 158 | O | VAL | A | 147 | -12.420 | 31.047 | 4.389 | 1.00 | 52.63 | A | O |
| ATOM | 159 | N | TYR | A | 148 | -13.580 | 29.323 | 3.490 | 1.00 | 50.14 | A | N |
| ATOM | 160 | CA | TYR | A | 148 | -14.876 | 29.758 | 3.994 | 1.00 | 45.39 | A | C |
| ATOM | 161 | CB | TYR | A | 148 | -15.956 | 29.274 | 3.013 | 1.00 | 51.26 | A | C |
| ATOM | 162 | CG | TYR | A | 148 | -15.534 | 29.573 | 1.586 | 1.00 | 56.30 | A | C |
| ATOM | 163 | CD1 | TYR | A | 148 | -14.369 | 29.035 | 1.087 | 1.00 | 58.16 | A | C |
| ATOM | 164 | CE1 | TYR | A | 148 | -13.854 | 29.423 | -0.127 | 1.00 | 60.14 | A | C |
| ATOM | 165 | CD2 | TYR | A | 148 | -16.205 | 30.515 | 0.794 | 1.00 | 56.63 | A | C |
| ATOM | 166 | CE2 | TYR | A | 148 | -15.681 | 30.916 | -0.477 | 1.00 | 54.78 | A | C |
| ATOM | 167 | CZ | TYR | A | 148 | -14.492 | 30.354 | -0.898 | 1.00 | 57.89 | A | C |
| ATOM | 168 | OH | TYR | A | 148 | -13.863 | 30.729 | -2.040 | 1.00 | 58.06 | A | O |
| ATOM | 169 | C | TYR | A | 148 | -15.087 | 29.231 | 5.407 | 1.00 | 41.28 | A | C |
| ATOM | 170 | O | TYR | A | 148 | -14.439 | 28.268 | 5.803 | 1.00 | 38.71 | A | O |
| ATOM | 171 | N | LEU | A | 149 | -15.893 | 29.938 | 6.195 | 1.00 | 36.58 | A | N |
| ATOM | 172 | CA | LEU | A | 149 | -16.256 | 29.515 | 7.528 | 1.00 | 39.96 | A | C |
| ATOM | 173 | CB | LEU | A | 149 | -16.644 | 30.738 | 8.324 | 1.00 | 42.23 | A | C |
| ATOM | 174 | CG | LEU | A | 149 | -17.285 | 30.533 | 9.681 | 1.00 | 45.82 | A | C |
| ATOM | 175 | CD1 | LEU | A | 149 | -16.286 | 30.075 | 10.747 | 1.00 | 39.65 | A | C |
| ATOM | 176 | CD2 | LEU | A | 149 | -17.898 | 31.875 | 10.031 | 1.00 | 45.90 | A | C |
| ATOM | 177 | C | LEU | A | 149 | -17.463 | 28.606 | 7.286 | 1.00 | 40.87 | A | C |
| ATOM | 178 | O | LEU | A | 149 | -18.378 | 28.990 | 6.552 | 1.00 | 38.84 | A | O |
| ATOM | 179 | N | ALA | A | 150 | -17.469 | 27.408 | 7.875 | 1.00 | 44.73 | A | N |
| ATOM | 180 | CA | ALA | A | 150 | -18.574 | 26.476 | 7.642 | 1.00 | 48.40 | A | C |
| ATOM | 181 | CB | ALA | A | 150 | -18.204 | 25.507 | 6.541 | 1.00 | 42.43 | A | C |
| ATOM | 182 | C | ALA | A | 150 | -19.051 | 25.703 | 8.857 | 1.00 | 53.67 | A | C |
| ATOM | 183 | O | ALA | A | 150 | -18.529 | 25.872 | 9.954 | 1.00 | 52.06 | A | O |
| ATOM | 184 | N | ARG | A | 151 | -20.041 | 24.838 | 8.628 | 1.00 | 61.27 | A | N |
| ATOM | 185 | CA | ARG | A | 151 | -20.666 | 24.026 | 9.680 | 1.00 | 69.32 | A | C |
| ATOM | 186 | CB | ARG | A | 151 | -21.959 | 24.699 | 10.147 | 1.00 | 71.06 | A | C |
| ATOM | 187 | CG | ARG | A | 151 | -22.129 | 24.876 | 11.654 | 1.00 | 70.20 | A | C |
| ATOM | 188 | CD | ARG | A | 151 | -23.262 | 25.869 | 11.928 | 1.00 | 66.99 | A | C |
| ATOM | 189 | NE | ARG | A | 151 | -23.290 | 26.411 | 13.282 | 1.00 | 61.89 | A | N |
| ATOM | 190 | CZ | ARG | A | 151 | -23.707 | 27.640 | 13.563 | 1.00 | 58.11 | A | C |
| ATOM | 191 | NH1 | ARG | A | 151 | -24.123 | 28.439 | 12.583 | 1.00 | 51.52 | A | N |
| ATOM | 192 | NH2 | ARG | A | 151 | -23.707 | 28.071 | 14.817 | 1.00 | 54.97 | A | N |

Figure 3D

| ATOM | 193 | C | ARG | A | 151 | -21.030 | 22.657 | 9.147 | 1.00 | 71.14 | A | C |
|---|---|---|---|---|---|---|---|---|---|---|---|---|
| ATOM | 194 | O | ARG | A | 151 | -21.553 | 22.553 | 8.047 | 1.00 | 64.70 | A | O |
| ATOM | 195 | N | GLU | A | 152 | -20.752 | 21.607 | 9.907 | 1.00 | 77.25 | A | N |
| ATOM | 196 | CA | GLU | A | 152 | -21.140 | 20.284 | 9.457 | 1.00 | 87.55 | A | C |
| ATOM | 197 | CB | GLU | A | 152 | -20.449 | 19.190 | 10.249 | 1.00 | 90.69 | A | C |
| ATOM | 198 | CG | GLU | A | 152 | -21.090 | 17.841 | 9.964 | 1.00 | 99.83 | A | C |
| ATOM | 199 | CD | GLU | A | 152 | -20.453 | 16.699 | 10.716 | 1.00 | 106.11 | A | C |
| ATOM | 200 | OE1 | GLU | A | 152 | -20.148 | 16.882 | 11.915 | 1.00 | 111.30 | A | O |
| ATOM | 201 | OE2 | GLU | A | 152 | -20.273 | 15.619 | 10.110 | 1.00 | 106.43 | A | O |
| ATOM | 202 | C | GLU | A | 152 | -22.625 | 20.221 | 9.749 | 1.00 | 92.09 | A | C |
| ATOM | 203 | O | GLU | A | 152 | -23.037 | 20.574 | 10.848 | 1.00 | 96.88 | A | O |
| ATOM | 204 | N | ALA | A | 153 | -23.430 | 19.765 | 8.792 | 1.00 | 93.64 | A | N |
| ATOM | 205 | CA | ALA | A | 153 | -24.885 | 19.710 | 8.985 | 1.00 | 92.55 | A | C |
| ATOM | 206 | CB | ALA | A | 153 | -25.576 | 19.383 | 7.653 | 1.00 | 92.47 | A | C |
| ATOM | 207 | C | ALA | A | 153 | -25.382 | 18.762 | 10.092 | 1.00 | 91.12 | A | C |
| ATOM | 208 | O | ALA | A | 153 | -26.504 | 18.906 | 10.587 | 1.00 | 88.22 | A | O |
| ATOM | 209 | N | ALA | A | 154 | -24.555 | 17.799 | 10.481 | 1.00 | 91.50 | A | N |
| ATOM | 210 | CA | ALA | A | 154 | -24.943 | 16.869 | 11.531 | 1.00 | 90.00 | A | C |
| ATOM | 211 | CB | ALA | A | 154 | -24.027 | 15.644 | 11.521 | 1.00 | 87.30 | A | C |
| ATOM | 212 | C | ALA | A | 154 | -24.869 | 17.569 | 12.881 | 1.00 | 88.61 | A | C |
| ATOM | 213 | O | ALA | A | 154 | -25.869 | 18.109 | 13.362 | 1.00 | 90.52 | A | O |
| ATOM | 214 | N | SER | A | 155 | -23.668 | 17.577 | 13.463 | 1.00 | 85.98 | A | N |
| ATOM | 215 | CA | SER | A | 155 | -23.387 | 18.173 | 14.778 | 1.00 | 84.79 | A | C |
| ATOM | 216 | CB | SER | A | 155 | -22.013 | 17.665 | 15.282 | 1.00 | 83.43 | A | C |
| ATOM | 217 | OG | SER | A | 155 | -20.963 | 17.879 | 14.340 | 1.00 | 83.48 | A | O |
| ATOM | 218 | C | SER | A | 155 | -23.458 | 19.707 | 14.929 | 1.00 | 83.11 | A | C |
| ATOM | 219 | O | SER | A | 155 | -23.015 | 20.254 | 15.937 | 1.00 | 81.27 | A | O |
| ATOM | 220 | N | ALA | A | 156 | -24.026 | 20.396 | 13.947 | 1.00 | 80.52 | A | N |
| ATOM | 221 | CA | ALA | A | 156 | -24.138 | 21.854 | 14.002 | 1.00 | 78.57 | A | C |
| ATOM | 222 | CB | ALA | A | 156 | -25.276 | 22.257 | 14.909 | 1.00 | 75.82 | A | C |
| ATOM | 223 | C | ALA | A | 156 | -22.835 | 22.466 | 14.490 | 1.00 | 79.48 | A | C |
| ATOM | 224 | O | ALA | A | 156 | -22.786 | 23.622 | 14.913 | 1.00 | 80.86 | A | O |
| ATOM | 225 | N | PHE | A | 157 | -21.784 | 21.656 | 14.413 | 1.00 | 78.71 | A | N |
| ATOM | 226 | CA | PHE | A | 157 | -20.433 | 22.034 | 14.805 | 1.00 | 75.49 | A | C |
| ATOM | 227 | CB | PHE | A | 157 | -19.525 | 20.804 | 14.770 | 1.00 | 73.43 | A | C |
| ATOM | 228 | CG | PHE | A | 157 | -18.165 | 21.050 | 15.320 | 1.00 | 69.44 | A | C |
| ATOM | 229 | CD1 | PHE | A | 157 | -18.017 | 21.685 | 16.544 | 1.00 | 71.28 | A | C |
| ATOM | 230 | CD2 | PHE | A | 157 | -17.033 | 20.626 | 14.636 | 1.00 | 67.24 | A | C |
| ATOM | 231 | CE1 | PHE | A | 157 | -16.771 | 21.895 | 17.082 | 1.00 | 73.58 | A | C |
| ATOM | 232 | CE2 | PHE | A | 157 | -15.779 | 20.831 | 15.167 | 1.00 | 69.72 | A | C |
| ATOM | 233 | CZ | PHE | A | 157 | -15.646 | 21.469 | 16.395 | 1.00 | 73.86 | A | C |
| ATOM | 234 | C | PHE | A | 157 | -19.894 | 23.092 | 13.844 | 1.00 | 72.57 | A | C |
| ATOM | 235 | O | PHE | A | 157 | -20.233 | 23.100 | 12.662 | 1.00 | 70.95 | A | O |
| ATOM | 236 | N | ILE | A | 158 | -19.044 | 23.976 | 14.343 | 1.00 | 67.81 | A | N |
| ATOM | 237 | CA | ILE | A | 158 | -18.512 | 25.017 | 13.496 | 1.00 | 64.30 | A | C |
| ATOM | 238 | CB | ILE | A | 158 | -18.729 | 26.390 | 14.159 | 1.00 | 63.36 | A | C |
| ATOM | 239 | CG2 | ILE | A | 158 | -18.436 | 26.294 | 15.642 | 1.00 | 68.60 | A | C |
| ATOM | 240 | CG1 | ILE | A | 158 | -17.877 | 27.452 | 13.472 | 1.00 | 67.69 | A | C |
| ATOM | 241 | CD1 | ILE | A | 158 | -18.128 | 27.587 | 11.992 | 1.00 | 67.96 | A | C |
| ATOM | 242 | C | ILE | A | 158 | -17.044 | 24.750 | 13.198 | 1.00 | 64.51 | A | C |
| ATOM | 243 | O | ILE | A | 158 | -16.295 | 24.321 | 14.078 | 1.00 | 61.45 | A | O |
| ATOM | 244 | N | LEU | A | 159 | -16.657 | 24.995 | 11.943 | 1.00 | 65.49 | A | N |
| ATOM | 245 | CA | LEU | A | 159 | -15.298 | 24.767 | 11.461 | 1.00 | 65.08 | A | C |
| ATOM | 246 | CB | LEU | A | 159 | -15.196 | 23.392 | 10.826 | 1.00 | 66.01 | A | C |
| ATOM | 247 | CG | LEU | A | 159 | -15.364 | 22.251 | 11.802 | 1.00 | 65.69 | A | C |
| ATOM | 248 | CD1 | LEU | A | 159 | -15.351 | 20.936 | 11.040 | 1.00 | 65.16 | A | C |
| ATOM | 249 | CD2 | LEU | A | 159 | -14.242 | 22.339 | 12.842 | 1.00 | 67.69 | A | C |
| ATOM | 250 | C | LEU | A | 159 | -14.799 | 25.748 | 10.430 | 1.00 | 63.07 | A | C |
| ATOM | 251 | O | LEU | A | 159 | -15.473 | 26.715 | 10.078 | 1.00 | 60.37 | A | O |
| ATOM | 252 | N | ALA | A | 160 | -13.603 | 25.436 | 9.938 | 1.00 | 63.97 | A | N |
| ATOM | 253 | CA | ALA | A | 160 | -12.902 | 26.198 | 8.912 | 1.00 | 63.42 | A | C |

Figure 3E

| ATOM | 254 | CB | ALA A 160 | -11.591 | 26.758 | 9.464 | 1.00 | 62.98 | A | C |
|---|---|---|---|---|---|---|---|---|---|---|
| ATOM | 255 | C | ALA A 160 | -12.624 | 25.183 | 7.812 | 1.00 | 63.12 | A | C |
| ATOM | 256 | O | ALA A 160 | -11.940 | 24.194 | 8.041 | 1.00 | 59.21 | A | O |
| ATOM | 257 | N | LEU A 161 | -13.164 | 25.430 | 6.627 | 1.00 | 64.59 | A | N |
| ATOM | 258 | CA | LEU A 161 | -13.008 | 24.528 | 5.502 | 1.00 | 69.26 | A | C |
| ATOM | 259 | CB | LEU A 161 | -14.414 | 24.146 | 5.032 | 1.00 | 72.36 | A | C |
| ATOM | 260 | CG | LEU A 161 | -14.776 | 23.257 | 3.853 | 1.00 | 77.16 | A | C |
| ATOM | 261 | CD1 | LEU A 161 | -16.180 | 22.727 | 4.025 | 1.00 | 78.53 | A | C |
| ATOM | 262 | CD2 | LEU A 161 | -14.679 | 24.055 | 2.579 | 1.00 | 77.95 | A | C |
| ATOM | 263 | C | LEU A 161 | -12.192 | 25.255 | 4.427 | 1.00 | 71.39 | A | C |
| ATOM | 264 | O | LEU A 161 | -12.598 | 26.314 | 3.941 | 1.00 | 70.83 | A | O |
| ATOM | 265 | N | LYS A 162 | -11.033 | 24.661 | 4.116 | 1.00 | 73.87 | A | N |
| ATOM | 266 | CA | LYS A 162 | -10.090 | 25.201 | 3.145 | 1.00 | 78.58 | A | C |
| ATOM | 267 | CB | LYS A 162 | -8.659 | 24.991 | 3.596 | 1.00 | 80.39 | A | C |
| ATOM | 268 | CG | LYS A 162 | -7.669 | 25.678 | 2.688 | 1.00 | 84.40 | A | C |
| ATOM | 269 | CD | LYS A 162 | -6.211 | 25.555 | 3.169 | 1.00 | 90.20 | A | C |
| ATOM | 270 | CE | LYS A 162 | -5.834 | 26.419 | 4.390 | 1.00 | 95.76 | A | C |
| ATOM | 271 | NZ | LYS A 162 | -4.372 | 26.291 | 4.740 | 1.00 | 97.90 | A | N |
| ATOM | 272 | C | LYS A 162 | -10.249 | 24.543 | 1.821 | 1.00 | 81.19 | A | C |
| ATOM | 273 | O | LYS A 162 | -10.113 | 23.334 | 1.727 | 1.00 | 78.25 | A | O |
| ATOM | 274 | N | VAL A 163 | -10.516 | 25.363 | 0.806 | 1.00 | 87.52 | A | N |
| ATOM | 275 | CA | VAL A 163 | -10.730 | 24.940 | -0.579 | 1.00 | 93.77 | A | C |
| ATOM | 276 | CB | VAL A 163 | -11.807 | 25.806 | -1.248 | 1.00 | 91.82 | A | C |
| ATOM | 277 | CG1 | VAL A 163 | -11.176 | 26.736 | -2.246 | 1.00 | 92.36 | A | C |
| ATOM | 278 | CG2 | VAL A 163 | -12.849 | 24.956 | -1.896 | 1.00 | 90.93 | A | C |
| ATOM | 279 | C | VAL A 163 | -9.446 | 25.129 | -1.371 | 1.00 | 101.54 | A | C |
| ATOM | 280 | O | VAL A 163 | -8.678 | 26.057 | -1.104 | 1.00 | 104.47 | A | O |
| ATOM | 281 | N | LEU A 164 | -9.214 | 24.244 | -2.337 | 1.00 | 109.10 | A | N |
| ATOM | 282 | CA | LEU A 164 | -8.037 | 24.317 | -3.203 | 1.00 | 112.72 | A | C |
| ATOM | 283 | CB | LEU A 164 | -6.902 | 23.446 | -2.677 | 1.00 | 113.10 | A | C |
| ATOM | 284 | CG | LEU A 164 | -5.964 | 24.163 | -1.731 | 1.00 | 112.48 | A | C |
| ATOM | 285 | CD1 | LEU A 164 | -5.660 | 25.539 | -2.272 | 1.00 | 113.22 | A | C |
| ATOM | 286 | CD2 | LEU A 164 | -6.601 | 24.272 | -0.394 | 1.00 | 111.32 | A | C |
| ATOM | 287 | C | LEU A 164 | -8.356 | 23.923 | -4.644 | 1.00 | 114.09 | A | C |
| ATOM | 288 | O | LEU A 164 | -8.312 | 22.735 | -4.997 | 1.00 | 111.80 | A | O |
| ATOM | 289 | N | PHE A 165 | -8.689 | 24.936 | -5.457 | 1.00 | 116.34 | A | N |
| ATOM | 290 | CA | PHE A 165 | -9.018 | 24.744 | -6.868 | 1.00 | 117.46 | A | C |
| ATOM | 291 | CB | PHE A 165 | -9.114 | 26.102 | -7.607 | 1.00 | 118.05 | A | C |
| ATOM | 292 | CG | PHE A 165 | -10.289 | 26.985 | -7.160 | 1.00 | 123.74 | A | C |
| ATOM | 293 | CD1 | PHE A 165 | -10.154 | 27.887 | -6.094 | 1.00 | 126.01 | A | C |
| ATOM | 294 | CD2 | PHE A 165 | -11.531 | 26.923 | -7.817 | 1.00 | 126.36 | A | C |
| ATOM | 295 | CE1 | PHE A 165 | -11.236 | 28.716 | -5.688 | 1.00 | 126.54 | A | C |
| ATOM | 296 | CE2 | PHE A 165 | -12.624 | 27.749 | -7.421 | 1.00 | 126.31 | A | C |
| ATOM | 297 | CZ | PHE A 165 | -12.467 | 28.644 | -6.353 | 1.00 | 125.83 | A | C |
| ATOM | 298 | C | PHE A 165 | -7.843 | 23.915 | -7.351 | 1.00 | 118.07 | A | C |
| ATOM | 299 | O | PHE A 165 | -6.698 | 24.251 | -7.089 | 1.00 | 112.70 | A | O |
| ATOM | 300 | N | LYS A 166 | -8.123 | 22.798 | -8.000 | 1.00 | 124.06 | A | N |
| ATOM | 301 | CA | LYS A 166 | -7.047 | 21.937 | -8.455 | 1.00 | 132.23 | A | C |
| ATOM | 302 | CB | LYS A 166 | -7.591 | 20.559 | -8.854 | 1.00 | 134.10 | A | C |
| ATOM | 307 | C | LYS A 166 | -6.330 | 22.590 | -9.617 | 1.00 | 138.16 | A | C |
| ATOM | 308 | O | LYS A 166 | -5.134 | 22.367 | -9.817 | 1.00 | 138.17 | A | O |
| ATOM | 309 | N | ALA A 167 | -7.072 | 23.393 | -10.381 | 1.00 | 144.68 | A | N |
| ATOM | 310 | CA | ALA A 167 | -6.494 | 24.116 | -11.515 | 1.00 | 148.10 | A | C |
| ATOM | 311 | CB | ALA A 167 | -7.546 | 25.077 | -12.140 | 1.00 | 148.09 | A | C |
| ATOM | 312 | C | ALA A 167 | -5.268 | 24.896 | -10.989 | 1.00 | 148.80 | A | C |
| ATOM | 313 | O | ALA A 167 | -4.144 | 24.418 | -11.115 | 1.00 | 151.89 | A | O |
| ATOM | 314 | N | GLN A 168 | -5.529 | 26.551 | -10.435 | 1.00 | 149.06 | A | N |
| ATOM | 315 | CA | GLN A 168 | -4.377 | 27.128 | -9.778 | 1.00 | 146.35 | A | C |
| ATOM | 316 | CB | GLN A 168 | -4.832 | 27.918 | -8.559 | 1.00 | 147.48 | A | C |
| ATOM | 317 | CG | GLN A 168 | -5.811 | 29.044 | -8.878 | 1.00 | 153.35 | A | C |
| ATOM | 318 | CD | GLN A 168 | -5.212 | 30.126 | -9.754 | 1.00 | 158.45 | A | C |

Figure 3F

| ATOM | 319 | OE1 | GLN | A | 168 | -4.099 | 30.594 | -9.513 | 1.00 | 163.83 | A | O |
|---|---|---|---|---|---|---|---|---|---|---|---|---|
| ATOM | 320 | NE2 | GLN | A | 168 | -5.951 | 30.526 | -10.784 | 1.00 | 158.04 | A | N |
| ATOM | 321 | C | GLN | A | 168 | -3.434 | 26.006 | -9.361 | 1.00 | 144.67 | A | C |
| ATOM | 322 | O | GLN | A | 168 | -2.270 | 25.976 | -9.761 | 1.00 | 144.23 | A | O |
| ATOM | 323 | N | LEU | A | 169 | -3.953 | 24.703 | -8.703 | 1.00 | 140.59 | A | N |
| ATOM | 324 | CA | LEU | A | 169 | -3.195 | 23.639 | -8.058 | 1.00 | 140.61 | A | C |
| ATOM | 325 | CB | LEU | A | 169 | -4.076 | 22.810 | -7.119 | 1.00 | 138.01 | A | C |
| ATOM | 329 | C | LEU | A | 169 | -2.795 | 22.784 | -9.229 | 1.00 | 142.44 | A | C |
| ATOM | 330 | O | LEU | A | 169 | -3.020 | 21.574 | -9.223 | 1.00 | 142.01 | A | O |
| ATOM | 331 | N | GLU | A | 170 | -2.242 | 23.445 | -10.249 | 1.00 | 146.41 | A | N |
| ATOM | 332 | CA | GLU | A | 170 | -1.791 | 22.805 | -11.507 | 1.00 | 148.77 | A | C |
| ATOM | 333 | CB | GLU | A | 170 | -2.991 | 22.156 | -12.222 | 1.00 | 152.02 | A | C |
| ATOM | 338 | C | GLU | A | 170 | -1.043 | 23.760 | -12.491 | 1.00 | 147.17 | A | C |
| ATOM | 339 | O | GLU | A | 170 | -0.359 | 23.297 | -13.420 | 1.00 | 144.27 | A | O |
| ATOM | 340 | N | LYS | A | 171 | -1.207 | 25.074 | -12.283 | 1.00 | 145.29 | A | N |
| ATOM | 341 | CA | LYS | A | 171 | -0.536 | 26.118 | -13.067 | 1.00 | 139.63 | A | C |
| ATOM | 342 | CB | LYS | A | 171 | -1.378 | 27.404 | -13.073 | 1.00 | 134.52 | A | C |
| ATOM | 347 | C | LYS | A | 171 | 0.818 | 26.336 | -12.341 | 1.00 | 137.12 | A | C |
| ATOM | 348 | O | LYS | A | 171 | 1.598 | 27.254 | -12.655 | 1.00 | 136.48 | A | O |
| ATOM | 349 | N | ALA | A | 172 | 1.048 | 25.457 | -11.358 | 1.00 | 133.18 | A | N |
| ATOM | 350 | CA | ALA | A | 172 | 2.249 | 25.373 | -10.521 | 1.00 | 126.97 | A | C |
| ATOM | 351 | CB | ALA | A | 172 | 2.014 | 26.019 | -9.160 | 1.00 | 123.45 | A | C |
| ATOM | 352 | C | ALA | A | 172 | 2.475 | 23.860 | -10.357 | 1.00 | 123.95 | A | C |
| ATOM | 353 | O | ALA | A | 172 | 2.155 | 23.081 | -11.271 | 1.00 | 127.57 | A | O |
| ATOM | 354 | N | GLY | A | 173 | 2.993 | 23.425 | -9.208 | 1.00 | 117.34 | A | N |
| ATOM | 355 | CA | GLY | A | 173 | 3.227 | 21.999 | -9.052 | 1.00 | 111.94 | A | C |
| ATOM | 356 | C | GLY | A | 173 | 3.560 | 21.494 | -7.664 | 1.00 | 110.26 | A | C |
| ATOM | 357 | O | GLY | A | 173 | 4.728 | 21.545 | -7.251 | 1.00 | 110.13 | A | O |
| ATOM | 358 | N | VAL | A | 174 | 2.524 | 21.003 | -6.964 | 1.00 | 107.18 | A | N |
| ATOM | 359 | CA | VAL | A | 174 | 2.616 | 20.427 | -5.608 | 1.00 | 100.57 | A | C |
| ATOM | 360 | CB | VAL | A | 174 | 2.339 | 21.487 | -4.512 | 1.00 | 98.60 | A | C |
| ATOM | 363 | C | VAL | A | 174 | 1.575 | 19.312 | -5.498 | 1.00 | 96.48 | A | C |
| ATOM | 364 | O | VAL | A | 174 | 0.580 | 19.306 | -6.216 | 1.00 | 94.14 | A | O |
| ATOM | 365 | N | GLU | A | 175 | 1.811 | 18.355 | -4.620 | 1.00 | 94.91 | A | N |
| ATOM | 366 | CA | GLU | A | 175 | 0.872 | 17.253 | -4.461 | 1.00 | 96.03 | A | C |
| ATOM | 367 | CB | GLU | A | 175 | 0.801 | 16.388 | -5.743 | 1.00 | 93.20 | A | C |
| ATOM | 368 | CG | GLU | A | 175 | 0.852 | 14.844 | -5.524 | 1.00 | 85.82 | A | C |
| ATOM | 369 | CD | GLU | A | 175 | 2.214 | 14.182 | -5.862 | 1.00 | 83.39 | A | C |
| ATOM | 370 | OE1 | GLU | A | 175 | 2.386 | 13.712 | -7.012 | 1.00 | 81.36 | A | O |
| ATOM | 371 | OE2 | GLU | A | 175 | 3.108 | 14.128 | -4.979 | 1.00 | 78.96 | A | O |
| ATOM | 372 | C | GLU | A | 175 | 1.303 | 16.405 | -3.279 | 1.00 | 99.54 | A | C |
| ATOM | 373 | O | GLU | A | 175 | 2.322 | 16.677 | -2.654 | 1.00 | 99.67 | A | O |
| ATOM | 374 | N | HIS | A | 176 | 3.605 | 17.574 | -5.870 | 1.00 | 103.10 | A | N |
| ATOM | 375 | CA | HIS | A | 176 | 4.828 | 17.421 | -5.105 | 1.00 | 105.22 | A | C |
| ATOM | 376 | CB | HIS | A | 176 | 5.880 | 18.435 | -5.617 | 1.00 | 107.53 | A | C |
| ATOM | 377 | CG | HIS | A | 176 | 7.058 | 18.655 | -4.702 | 1.00 | 110.66 | A | C |
| ATOM | 378 | CD2 | HIS | A | 176 | 8.246 | 18.008 | -4.603 | 1.00 | 110.65 | A | C |
| ATOM | 379 | ND1 | HIS | A | 176 | 7.137 | 19.724 | -3.830 | 1.00 | 111.34 | A | N |
| ATOM | 380 | CE1 | HIS | A | 176 | 8.322 | 19.732 | -3.244 | 1.00 | 112.37 | A | C |
| ATOM | 381 | NE2 | HIS | A | 176 | 9.014 | 18.702 | -3.697 | 1.00 | 110.61 | A | N |
| ATOM | 382 | C | HIS | A | 176 | 4.570 | 17.591 | -3.612 | 1.00 | 105.67 | A | C |
| ATOM | 383 | O | HIS | A | 176 | 4.687 | 16.617 | -2.846 | 1.00 | 105.54 | A | O |
| ATOM | 384 | N | GLN | A | 177 | 4.170 | 18.810 | -3.226 | 1.00 | 103.45 | A | N |
| ATOM | 385 | CA | GLN | A | 177 | 3.965 | 19.201 | -1.817 | 1.00 | 98.22 | A | C |
| ATOM | 386 | CB | GLN | A | 177 | 4.079 | 20.727 | -1.718 | 1.00 | 90.87 | A | C |
| ATOM | 387 | CG | GLN | A | 177 | 5.315 | 21.208 | -0.987 | 1.00 | 85.76 | A | C |
| ATOM | 388 | CD | GLN | A | 177 | 5.450 | 22.737 | -1.009 | 1.00 | 84.63 | A | C |
| ATOM | 389 | OE1 | GLN | A | 177 | 6.001 | 23.317 | -1.959 | 1.00 | 83.32 | A | O |
| ATOM | 390 | NE2 | GLN | A | 177 | 4.933 | 23.397 | 0.039 | 1.00 | 81.24 | A | N |
| ATOM | 391 | C | GLN | A | 177 | 2.738 | 18.744 | -1.007 | 1.00 | 99.24 | A | C |
| ATOM | 392 | O | GLN | A | 177 | 2.879 | 18.222 | 0.117 | 1.00 | 100.33 | A | O |

Figure 3G

| ATOM | 393 | N   | LEU | A | 178 |  1.550 | 18.962 | -1.576 | 1.00 | 100.36 | A | N |
|------|-----|-----|-----|---|-----|--------|--------|--------|------|--------|---|---|
| ATOM | 394 | CA  | LEU | A | 178 |  0.288 | 18.621 | -0.929 | 1.00 | 101.59 | A | C |
| ATOM | 395 | CB  | LEU | A | 178 | -0.794 | 18.333 | -1.972 | 1.00 |  95.71 | A | C |
| ATOM | 399 | C   | LEU | A | 178 |  0.454 | 17.435 |  0.002 | 1.00 | 105.74 | A | C |
| ATOM | 400 | O   | LEU | A | 178 |  1.006 | 17.601 |  1.095 | 1.00 | 110.45 | A | O |
| ATOM | 401 | N   | ARG | A | 179 | -0.010 | 16.260 | -0.452 | 1.00 | 108.52 | A | N |
| ATOM | 402 | CA  | ARG | A | 179 |  0.014 | 14.980 |  0.270 | 1.00 | 109.52 | A | C |
| ATOM | 403 | CB  | ARG | A | 179 |  0.315 | 13.821 | -0.693 | 1.00 | 109.92 | A | C |
| ATOM | 410 | C   | ARG | A | 179 |  1.005 | 14.971 |  1.434 | 1.00 | 109.11 | A | C |
| ATOM | 411 | O   | ARG | A | 179 |  0.763 | 14.311 |  2.451 | 1.00 | 108.59 | A | O |
| ATOM | 412 | N   | ARG | A | 180 |  2.101 | 15.720 |  1.287 | 1.00 | 107.22 | A | N |
| ATOM | 413 | CA  | ARG | A | 180 |  3.126 | 15.819 |  2.326 | 1.00 | 103.65 | A | C |
| ATOM | 414 | CB  | ARG | A | 180 |  4.364 | 16.525 |  1.766 | 1.00 | 103.61 | A | C |
| ATOM | 421 | C   | ARG | A | 180 |  2.646 | 16.535 |  3.608 | 1.00 | 101.41 | A | C |
| ATOM | 422 | O   | ARG | A | 180 |  2.510 | 15.892 |  4.662 | 1.00 |  99.47 | A | O |
| ATOM | 423 | N   | GLU | A | 181 |  2.401 | 17.851 |  3.523 | 1.00 |  98.19 | A | N |
| ATOM | 424 | CA  | GLU | A | 181 |  1.923 | 18.628 |  4.682 | 1.00 |  92.21 | A | C |
| ATOM | 425 | CB  | GLU | A | 181 |  1.782 | 20.124 |  4.318 | 1.00 |  94.86 | A | C |
| ATOM | 426 | CG  | GLU | A | 181 |  3.110 | 20.893 |  4.187 | 1.00 |  95.88 | A | C |
| ATOM | 427 | CD  | GLU | A | 181 |  2.942 | 22.375 |  3.812 | 1.00 |  94.20 | A | C |
| ATOM | 428 | OE1 | GLU | A | 181 |  2.215 | 22.663 |  2.838 | 1.00 | 100.44 | A | O |
| ATOM | 429 | OE2 | GLU | A | 181 |  3.555 | 23.245 |  4.481 | 1.00 |  88.32 | A | O |
| ATOM | 430 | C   | GLU | A | 181 |  0.568 | 18.087 |  5.190 | 1.00 |  88.24 | A | C |
| ATOM | 431 | O   | GLU | A | 181 |  0.229 | 18.208 |  6.372 | 1.00 |  83.36 | A | O |
| ATOM | 432 | N   | VAL | A | 182 | -0.190 | 17.483 |  4.276 | 1.00 |  85.49 | A | N |
| ATOM | 433 | CA  | VAL | A | 182 | -1.497 | 16.912 |  4.564 | 1.00 |  82.64 | A | C |
| ATOM | 434 | CB  | VAL | A | 182 | -2.231 | 16.613 |  3.256 | 1.00 |  74.74 | A | C |
| ATOM | 435 | CG1 | VAL | A | 182 | -3.502 | 15.859 |  3.541 | 1.00 |  71.90 | A | C |
| ATOM | 436 | CG2 | VAL | A | 182 | -2.534 | 17.918 |  2.535 | 1.00 |  71.31 | A | C |
| ATOM | 437 | C   | VAL | A | 182 | -1.433 | 15.638 |  5.407 | 1.00 |  87.09 | A | C |
| ATOM | 438 | O   | VAL | A | 182 | -2.295 | 15.396 |  6.251 | 1.00 |  86.81 | A | O |
| ATOM | 439 | N   | GLU | A | 183 | -0.415 | 14.819 |  5.184 | 1.00 |  93.45 | A | N |
| ATOM | 440 | CA  | GLU | A | 183 | -0.285 | 13.587 |  5.952 | 1.00 | 102.25 | A | C |
| ATOM | 441 | CB  | GLU | A | 183 |  0.435 | 12.513 |  5.120 | 1.00 | 108.73 | A | C |
| ATOM | 442 | CG  | GLU | A | 183 |  0.415 | 11.138 |  5.762 | 1.00 | 120.23 | A | C |
| ATOM | 443 | CD  | GLU | A | 183 | -0.957 | 10.785 |  6.314 | 1.00 | 126.97 | A | C |
| ATOM | 444 | OE1 | GLU | A | 183 | -1.866 | 10.456 |  5.519 | 1.00 | 127.18 | A | O |
| ATOM | 445 | OE2 | GLU | A | 183 | -1.130 | 10.856 |  7.551 | 1.00 | 133.27 | A | O |
| ATOM | 446 | C   | GLU | A | 183 |  0.453 | 13.834 |  7.268 | 1.00 | 104.36 | A | C |
| ATOM | 447 | O   | GLU | A | 183 |  0.495 | 12.967 |  8.142 | 1.00 | 102.11 | A | O |
| ATOM | 448 | N   | ILE | A | 184 |  1.029 | 15.024 |  7.403 | 1.00 | 109.43 | A | N |
| ATOM | 449 | CA  | ILE | A | 184 |  1.751 | 15.391 |  8.619 | 1.00 | 116.61 | A | C |
| ATOM | 450 | CB  | ILE | A | 184 |  2.991 | 16.227 |  8.308 | 1.00 | 118.69 | A | C |
| ATOM | 451 | CG2 | ILE | A | 184 |  3.907 | 16.264 |  9.528 | 1.00 | 121.87 | A | C |
| ATOM | 452 | CG1 | ILE | A | 184 |  3.736 | 15.614 |  7.130 | 1.00 | 117.81 | A | C |
| ATOM | 453 | CD1 | ILE | A | 184 |  4.783 | 16.522 |  6.549 | 1.00 | 118.04 | A | C |
| ATOM | 454 | C   | ILE | A | 184 |  0.860 | 16.193 |  9.582 | 1.00 | 119.29 | A | C |
| ATOM | 455 | O   | ILE | A | 184 |  1.062 | 16.152 | 10.800 | 1.00 | 122.94 | A | O |
| ATOM | 456 | N   | GLN | A | 185 | -0.100 | 16.948 |  9.040 | 1.00 | 119.04 | A | N |
| ATOM | 457 | CA  | GLN | A | 185 | -1.030 | 17.701 |  9.886 | 1.00 | 118.41 | A | C |
| ATOM | 458 | CB  | GLN | A | 185 | -1.702 | 18.856 |  9.116 | 1.00 | 120.00 | A | C |
| ATOM | 459 | CG  | GLN | A | 185 | -0.816 | 20.098 |  8.887 | 1.00 | 120.95 | A | C |
| ATOM | 460 | CD  | GLN | A | 185 | -0.143 | 20.632 | 10.165 | 1.00 | 120.15 | A | C |
| ATOM | 461 | OE1 | GLN | A | 185 |  1.007 | 20.289 | 10.469 | 1.00 | 118.86 | A | O |
| ATOM | 462 | NE2 | GLN | A | 185 | -0.863 | 21.466 | 10.914 | 1.00 | 115.74 | A | N |
| ATOM | 463 | C   | GLN | A | 185 | -2.058 | 16.654 | 10.286 | 1.00 | 116.11 | A | C |
| ATOM | 464 | O   | GLN | A | 185 | -2.359 | 16.486 | 11.468 | 1.00 | 114.96 | A | O |
| ATOM | 465 | N   | SER | A | 186 | -2.563 | 15.933 |  9.286 | 1.00 | 113.50 | A | N |
| ATOM | 466 | CA  | SER | A | 186 | -3.532 | 14.873 |  9.523 | 1.00 | 110.46 | A | C |
| ATOM | 467 | CB  | SER | A | 186 | -3.906 | 14.172 |  8.213 | 1.00 | 111.00 | A | C |
| ATOM | 468 | OG  | SER | A | 186 | -4.950 | 13.238 |  8.426 | 1.00 | 110.96 | A | O |

Figure 3H

```
ATOM    469  C   SER A 186      -2.844  13.891  10.453  1.00 106.61      A    C
ATOM    470  O   SER A 186      -2.120  13.007   9.995  1.00 107.58      A    O
ATOM    471  N   HIS A 187      -3.069  14.078  11.752  1.00 101.61      A    N
ATOM    472  CA  HIS A 187      -2.492  13.255  12.805  1.00  98.17      A    C
ATOM    473  CB  HIS A 187      -1.271  12.486  12.303  1.00 103.48      A    C
ATOM    474  CG  HIS A 187      -1.247  11.048  12.722  1.00 108.31      A    C
ATOM    475  CD2 HIS A 187      -0.297  10.319  13.354  1.00 109.64      A    C
ATOM    476  ND1 HIS A 187      -2.289  10.182  12.466  1.00 107.48      A    N
ATOM    477  CE1 HIS A 187      -1.981   8.981  12.921  1.00 108.29      A    C
ATOM    478  NE2 HIS A 187      -0.779   9.037  13.464  1.00 109.59      A    N
ATOM    479  C   HIS A 187      -2.047  14.194  13.907  1.00  92.88      A    C
ATOM    480  O   HIS A 187      -2.533  14.126  15.029  1.00  91.44      A    O
ATOM    481  N   LEU A 188      -1.116  15.075  13.564  1.00  87.30      A    N
ATOM    482  CA  LEU A 188      -0.567  16.053  14.498  1.00  84.14      A    C
ATOM    483  CB  LEU A 188       0.083  17.188  13.693  1.00  81.14      A    C
ATOM    484  CG  LEU A 188       1.507  17.631  14.055  1.00  75.81      A    C
ATOM    485  CD1 LEU A 188       2.199  16.528  14.810  1.00  70.84      A    C
ATOM    486  CD2 LEU A 188       2.279  18.022  12.779  1.00  69.30      A    C
ATOM    487  C   LEU A 188      -1.620  16.601  15.477  1.00  82.49      A    C
ATOM    488  O   LEU A 188      -2.338  17.567  15.181  1.00  83.36      A    O
ATOM    489  N   ARG A 189      -1.695  15.973  16.648  1.00  77.92      A    N
ATOM    490  CA  ARG A 189      -2.654  16.349  17.689  1.00  72.19      A    C
ATOM    491  CB  ARG A 189      -3.210  15.068  18.347  1.00  74.40      A    C
ATOM    492  CG  ARG A 189      -4.556  15.170  19.105  1.00  80.93      A    C
ATOM    493  CD  ARG A 189      -5.455  13.963  18.715  1.00  88.55      A    C
ATOM    494  NE  ARG A 189      -6.619  13.737  19.585  1.00  95.81      A    N
ATOM    495  CZ  ARG A 189      -7.545  12.794  19.382  1.00  92.81      A    C
ATOM    496  NH1 ARG A 189      -7.449  11.989  18.331  1.00  93.22      A    N
ATOM    497  NH2 ARG A 189      -8.557  12.642  20.236  1.00  84.15      A    N
ATOM    498  C   ARG A 189      -1.955  17.215  18.733  1.00  64.94      A    C
ATOM    499  O   ARG A 189      -1.105  16.732  19.472  1.00  65.95      A    O
ATOM    500  N   HIS A 190      -2.303  18.493  18.798  1.00  56.75      A    N
ATOM    501  CA  HIS A 190      -1.669  19.363  19.776  1.00  51.00      A    C
ATOM    502  CB  HIS A 190      -0.226  19.675  19.377  1.00  47.39      A    C
ATOM    503  CG  HIS A 190       0.529  20.451  20.410  1.00  47.75      A    C
ATOM    504  CD2 HIS A 190       0.895  21.753  20.458  1.00  47.13      A    C
ATOM    505  ND1 HIS A 190       0.959  19.892  21.591  1.00  49.87      A    N
ATOM    506  CE1 HIS A 190       1.556  20.815  22.325  1.00  44.35      A    C
ATOM    507  NE2 HIS A 190       1.531  21.955  21.661  1.00  45.59      A    N
ATOM    508  C   HIS A 190      -2.407  20.673  19.937  1.00  48.28      A    C
ATOM    509  O   HIS A 190      -2.917  21.246  18.955  1.00  39.14      A    O
ATOM    510  N   PRO A 191      -2.479  21.167  21.193  1.00  50.04      A    N
ATOM    511  CD  PRO A 191      -2.036  20.502  22.430  1.00  47.47      A    C
ATOM    512  CA  PRO A 191      -3.153  22.430  21.511  1.00  51.00      A    C
ATOM    513  CB  PRO A 191      -2.829  22.643  23.003  1.00  46.77      A    C
ATOM    514  CG  PRO A 191      -1.719  21.679  23.298  1.00  44.44      A    C
ATOM    515  C   PRO A 191      -2.725  23.609  20.627  1.00  52.63      A    C
ATOM    516  O   PRO A 191      -3.565  24.260  20.006  1.00  55.11      A    O
ATOM    517  N   ASN A 192      -1.427  23.866  20.544  1.00  54.13      A    N
ATOM    518  CA  ASN A 192      -0.950  24.974  19.744  1.00  49.74      A    C
ATOM    519  CB  ASN A 192       0.274  25.581  20.421  1.00  51.26      A    C
ATOM    520  CG  ASN A 192       0.054  25.825  21.912  1.00  54.13      A    C
ATOM    521  OD1 ASN A 192       0.530  25.068  22.753  1.00  58.83      A    O
ATOM    522  ND2 ASN A 192      -0.671  26.879  22.239  1.00  54.81      A    N
ATOM    523  C   ASN A 192      -0.684  24.687  18.256  1.00  49.04      A    C
ATOM    524  O   ASN A 192      -0.033  25.486  17.573  1.00  46.63      A    O
ATOM    525  N   ILE A 193      -1.189  23.550  17.764  1.00  48.31      A    N
ATOM    526  CA  ILE A 193      -1.083  23.186  16.333  1.00  47.23      A    C
ATOM    527  CB  ILE A 193      -0.493  21.771  16.044  1.00  49.41      A    C
ATOM    528  CG2 ILE A 193      -0.437  21.568  14.533  1.00  47.50      A    C
ATOM    529  CG1 ILE A 193       0.887  21.588  16.673  1.00  53.44      A    C
```

Figure 3I

```
ATOM   530  CD1 ILE A 193       2.006  22.283  15.958  1.00  57.72      A   C
ATOM   531  C   ILE A 193      -2.521  23.117  15.809  1.00  46.37      A   C
ATOM   532  O   ILE A 193      -3.357  22.365  16.352  1.00  42.34      A   O
ATOM   533  N   LEU A 194      -2.810  23.888  14.763  1.00  49.54      A   N
ATOM   534  CA  LEU A 194      -4.151  23.889  14.194  1.00  58.82      A   C
ATOM   535  CB  LEU A 194      -4.191  24.777  12.953  1.00  56.73      A   C
ATOM   536  CG  LEU A 194      -5.567  25.074  12.369  1.00  55.12      A   C
ATOM   537  CD1 LEU A 194      -6.392  25.823  13.380  1.00  57.56      A   C
ATOM   538  CD2 LEU A 194      -5.417  25.879  11.098  1.00  58.91      A   C
ATOM   539  C   LEU A 194      -4.406  22.439  13.821  1.00  66.41      A   C
ATOM   540  O   LEU A 194      -3.541  21.815  13.221  1.00  76.54      A   O
ATOM   541  N   ARG A 195      -5.557  21.884  14.185  1.00  68.19      A   N
ATOM   542  CA  ARG A 195      -5.809  20.492  13.860  1.00  72.63      A   C
ATOM   543  CB  ARG A 195      -6.848  19.912  14.807  1.00  81.50      A   C
ATOM   544  CG  ARG A 195      -6.952  18.417  14.648  1.00  96.26      A   C
ATOM   545  CD  ARG A 195      -7.761  17.718  15.712  1.00 108.70      A   C
ATOM   546  NE  ARG A 195      -7.847  16.298  15.371  1.00 121.99      A   N
ATOM   547  CZ  ARG A 195      -8.425  15.366  16.124  1.00 128.81      A   C
ATOM   548  NH1 ARG A 195      -8.444  14.092  15.713  1.00 132.70      A   N
ATOM   549  NH2 ARG A 195      -8.984  15.707  17.286  1.00 130.96      A   N
ATOM   550  C   ARG A 195      -6.245  20.312  12.412  1.00  70.38      A   C
ATOM   551  O   ARG A 195      -6.578  21.291  11.760  1.00  64.84      A   O
ATOM   552  N   LEU A 196      -6.241  19.074  11.904  1.00  71.48      A   N
ATOM   553  CA  LEU A 196      -6.629  18.826  10.507  1.00  71.75      A   C
ATOM   554  CB  LEU A 196      -5.409  18.386   9.702  1.00  75.54      A   C
ATOM   555  CG  LEU A 196      -5.634  18.158   8.208  1.00  75.85      A   C
ATOM   556  CD1 LEU A 196      -6.218  19.402   7.563  1.00  76.37      A   C
ATOM   557  CD2 LEU A 196      -4.318  17.769   7.578  1.00  78.11      A   C
ATOM   558  C   LEU A 196      -7.791  17.859  10.221  1.00  71.19      A   C
ATOM   559  O   LEU A 196      -7.793  17.143   9.224  1.00  69.85      A   O
ATOM   560  N   TYR A 197      -8.784  17.871  11.098  1.00  71.20      A   N
ATOM   561  CA  TYR A 197      -9.997  17.061  11.005  1.00  69.07      A   C
ATOM   562  CB  TYR A 197     -11.197  18.007  11.082  1.00  69.72      A   C
ATOM   563  CG  TYR A 197     -11.300  18.786  12.375  1.00  67.85      A   C
ATOM   564  CD1 TYR A 197     -11.219  20.175  12.383  1.00  66.00      A   C
ATOM   565  CE1 TYR A 197     -11.330  20.891  13.559  1.00  74.03      A   C
ATOM   566  CD2 TYR A 197     -11.491  18.131  13.580  1.00  71.26      A   C
ATOM   567  CE2 TYR A 197     -11.602  18.834  14.765  1.00  80.65      A   C
ATOM   568  CZ  TYR A 197     -11.520  20.217  14.760  1.00  81.54      A   C
ATOM   569  OH  TYR A 197     -11.610  20.912  15.964  1.00  90.21      A   O
ATOM   570  C   TYR A 197     -10.226  16.050   9.853  1.00  68.26      A   C
ATOM   571  O   TYR A 197     -10.343  14.848  10.101  1.00  67.94      A   O
ATOM   572  N   GLY A 198     -10.324  16.510   8.608  1.00  67.62      A   N
ATOM   573  CA  GLY A 198     -10.572  15.569   7.527  1.00  66.61      A   C
ATOM   574  C   GLY A 198     -10.196  16.095   6.163  1.00  66.51      A   C
ATOM   575  O   GLY A 198     -10.111  17.302   5.960  1.00  64.63      A   O
ATOM   576  N   TYR A 199     -10.007  15.175   5.220  1.00  68.42      A   N
ATOM   577  CA  TYR A 199      -9.586  15.486   3.847  1.00  70.71      A   C
ATOM   578  CB  TYR A 199      -8.153  14.942   3.650  1.00  75.76      A   C
ATOM   579  CG  TYR A 199      -7.744  14.594   2.227  1.00  83.90      A   C
ATOM   580  CD1 TYR A 199      -6.839  13.549   1.975  1.00  86.31      A   C
ATOM   581  CE1 TYR A 199      -6.422  13.248   0.648  1.00  83.56      A   C
ATOM   582  CD2 TYR A 199      -8.227  15.329   1.127  1.00  85.70      A   C
ATOM   583  CE2 TYR A 199      -7.818  15.038  -0.196  1.00  84.50      A   C
ATOM   584  CZ  TYR A 199      -6.919  14.004  -0.426  1.00  82.85      A   C
ATOM   585  OH  TYR A 199      -6.513  13.762  -1.718  1.00  80.99      A   O
ATOM   586  C   TYR A 199     -10.511  14.880   2.791  1.00  68.57      A   C
ATOM   587  O   TYR A 199     -10.775  13.678   2.819  1.00  68.21      A   O
ATOM   588  N   PHE A 200     -10.997  15.702   1.861  1.00  64.46      A   N
ATOM   589  CA  PHE A 200     -11.849  15.190   0.774  1.00  61.99      A   C
ATOM   590  CB  PHE A 200     -13.325  15.086   1.212  1.00  63.35      A   C
```

Figure 3J

| ATOM | 591 | CG | PHE | A | 200 | -13.998 | 16.409 | 1.500 | 1.00 | 58.91 | A | C |
| --- | --- | --- | --- | --- | --- | --- | --- | --- | --- | --- | --- | --- |
| ATOM | 592 | CD1 | PHE | A | 200 | -13.882 | 17.000 | 2.743 | 1.00 | 53.59 | A | C |
| ATOM | 593 | CD2 | PHE | A | 200 | -14.792 | 17.022 | 0.537 | 1.00 | 55.17 | A | C |
| ATOM | 594 | CE1 | PHE | A | 200 | -14.551 | 18.173 | 3.022 | 1.00 | 53.96 | A | C |
| ATOM | 595 | CE2 | PHE | A | 200 | -15.459 | 18.187 | 0.811 | 1.00 | 51.28 | A | C |
| ATOM | 596 | CZ | PHE | A | 200 | -15.341 | 18.766 | 2.053 | 1.00 | 48.79 | A | C |
| ATOM | 597 | C | PHE | A | 200 | -11.723 | 16.049 | -0.480 | 1.00 | 57.46 | A | C |
| ATOM | 598 | O | PHE | A | 200 | -11.415 | 17.228 | -0.381 | 1.00 | 51.28 | A | O |
| ATOM | 599 | N | HIS | A | 201 | -11.971 | 15.477 | -1.652 | 1.00 | 59.81 | A | N |
| ATOM | 600 | CA | HIS | A | 201 | -11.818 | 16.242 | -2.883 | 1.00 | 67.84 | A | C |
| ATOM | 601 | CB | HIS | A | 201 | -10.482 | 15.898 | -3.521 | 1.00 | 80.86 | A | C |
| ATOM | 602 | CG | HIS | A | 201 | -10.218 | 14.421 | -3.590 | 1.00 | 95.43 | A | C |
| ATOM | 603 | CD2 | HIS | A | 201 | -9.457 | 13.614 | -2.805 | 1.00 | 100.35 | A | C |
| ATOM | 604 | ND1 | HIS | A | 201 | -10.819 | 13.594 | -4.519 | 1.00 | 101.77 | A | N |
| ATOM | 605 | CE1 | HIS | A | 201 | -10.442 | 12.344 | -4.304 | 1.00 | 105.34 | A | C |
| ATOM | 606 | NE2 | HIS | A | 201 | -9.616 | 12.328 | -3.269 | 1.00 | 104.92 | A | N |
| ATOM | 607 | C | HIS | A | 201 | -12.890 | 15.978 | -3.892 | 1.00 | 65.62 | A | C |
| ATOM | 608 | O | HIS | A | 201 | -13.284 | 14.842 | -4.080 | 1.00 | 64.82 | A | O |
| ATOM | 609 | N | ASP | A | 202 | -13.356 | 17.023 | -4.562 | 1.00 | 67.53 | A | N |
| ATOM | 610 | CA | ASP | A | 202 | -14.373 | 16.836 | -5.591 | 1.00 | 69.70 | A | C |
| ATOM | 611 | CB | ASP | A | 202 | -15.385 | 18.021 | -5.649 | 1.00 | 74.35 | A | C |
| ATOM | 612 | CG | ASP | A | 202 | -14.779 | 19.341 | -6.152 | 1.00 | 74.67 | A | C |
| ATOM | 613 | OD1 | ASP | A | 202 | -14.185 | 19.345 | -7.241 | 1.00 | 71.87 | A | O |
| ATOM | 614 | OD2 | ASP | A | 202 | -14.923 | 20.385 | -5.473 | 1.00 | 74.10 | A | O |
| ATOM | 615 | C | ASP | A | 202 | -13.624 | 16.670 | -6.898 | 1.00 | 70.98 | A | C |
| ATOM | 616 | O | ASP | A | 202 | -12.529 | 16.114 | -6.910 | 1.00 | 70.70 | A | O |
| ATOM | 617 | N | ALA | A | 203 | -14.199 | 17.132 | -7.996 | 1.00 | 70.67 | A | N |
| ATOM | 618 | CA | ALA | A | 203 | -13.534 | 17.024 | -9.285 | 1.00 | 74.56 | A | C |
| ATOM | 619 | CB | ALA | A | 203 | -14.577 | 17.043 | -10.392 | 1.00 | 78.53 | A | C |
| ATOM | 620 | C | ALA | A | 203 | -12.554 | 18.186 | -9.471 | 1.00 | 76.27 | A | C |
| ATOM | 621 | O | ALA | A | 203 | -11.330 | 18.020 | -9.449 | 1.00 | 71.67 | A | O |
| ATOM | 622 | N | THR | A | 204 | -13.135 | 19.365 | -9.648 | 1.00 | 81.65 | A | N |
| ATOM | 623 | CA | THR | A | 204 | -12.421 | 20.623 | -9.849 | 1.00 | 89.51 | A | C |
| ATOM | 624 | CB | THR | A | 204 | -13.469 | 21.760 | -10.179 | 1.00 | 92.73 | A | C |
| ATOM | 625 | OG1 | THR | A | 204 | -13.139 | 22.965 | -9.473 | 1.00 | 98.44 | A | O |
| ATOM | 626 | CG2 | THR | A | 204 | -14.885 | 21.323 | -9.788 | 1.00 | 93.07 | A | C |
| ATOM | 627 | C | THR | A | 204 | -11.486 | 21.090 | -8.702 | 1.00 | 90.46 | A | C |
| ATOM | 628 | O | THR | A | 204 | -10.288 | 21.344 | -8.926 | 1.00 | 92.45 | A | O |
| ATOM | 629 | N | ARG | A | 205 | -12.047 | 21.182 | -7.490 | 1.00 | 89.13 | A | N |
| ATOM | 630 | CA | ARG | A | 205 | -11.359 | 21.660 | -6.286 | 1.00 | 85.22 | A | C |
| ATOM | 631 | CB | ARG | A | 205 | -12.221 | 22.763 | -5.672 | 1.00 | 93.07 | A | C |
| ATOM | 632 | CG | ARG | A | 205 | -13.662 | 22.770 | -6.219 | 1.00 | 104.05 | A | C |
| ATOM | 633 | CD | ARG | A | 205 | -14.509 | 23.907 | -5.644 | 1.00 | 114.67 | A | C |
| ATOM | 634 | NE | ARG | A | 205 | -15.771 | 24.116 | -6.366 | 1.00 | 120.94 | A | N |
| ATOM | 635 | CZ | ARG | A | 205 | -16.715 | 24.996 | -6.013 | 1.00 | 125.05 | A | C |
| ATOM | 636 | NH1 | ARG | A | 205 | -16.552 | 25.763 | -4.934 | 1.00 | 129.67 | A | N |
| ATOM | 637 | NH2 | ARG | A | 205 | -17.823 | 25.121 | -6.745 | 1.00 | 122.18 | A | N |
| ATOM | 638 | C | ARG | A | 205 | -11.071 | 20.593 | -5.229 | 1.00 | 79.83 | A | C |
| ATOM | 639 | O | ARG | A | 205 | -11.513 | 19.456 | -5.357 | 1.00 | 70.49 | A | O |
| ATOM | 640 | N | VAL | A | 206 | -10.308 | 20.955 | -4.198 | 1.00 | 82.29 | A | N |
| ATOM | 641 | CA | VAL | A | 206 | -10.025 | 20.019 | -3.104 | 1.00 | 88.98 | A | C |
| ATOM | 642 | CB | VAL | A | 206 | -8.509 | 19.649 | -2.982 | 1.00 | 93.12 | A | C |
| ATOM | 643 | CG1 | VAL | A | 206 | -7.866 | 19.645 | -4.353 | 1.00 | 98.17 | A | C |
| ATOM | 644 | CG2 | VAL | A | 206 | -7.805 | 20.566 | -2.022 | 1.00 | 94.89 | A | C |
| ATOM | 645 | C | VAL | A | 206 | -10.540 | 20.619 | -1.781 | 1.00 | 87.37 | A | C |
| ATOM | 646 | O | VAL | A | 206 | -10.858 | 21.809 | -1.711 | 1.00 | 87.88 | A | O |
| ATOM | 647 | N | TYR | A | 207 | -10.627 | 19.804 | -0.736 | 1.00 | 85.04 | A | N |
| ATOM | 648 | CA | TYR | A | 207 | -11.160 | 20.287 | 0.523 | 1.00 | 81.96 | A | C |
| ATOM | 649 | CB | TYR | A | 207 | -12.623 | 19.899 | 0.603 | 1.00 | 77.56 | A | C |
| ATOM | 650 | CG | TYR | A | 207 | -13.419 | 20.439 | -0.544 | 1.00 | 74.00 | A | C |
| ATOM | 651 | CD1 | TYR | A | 207 | -14.086 | 19.590 | -1.416 | 1.00 | 71.96 | A | C |

Figure 3K

| ATOM | 652 | CE1 | TYR A 207 | -14.806 | 20.085 | -2.488 | 1.00 | 77.80 | A | C |
| ATOM | 653 | CD2 | TYR A 207 | -13.492 | 21.805 | -0.771 | 1.00 | 76.62 | A | C |
| ATOM | 654 | CE2 | TYR A 207 | -14.209 | 22.315 | -1.842 | 1.00 | 83.65 | A | C |
| ATOM | 655 | CZ | TYR A 207 | -14.861 | 21.452 | -2.699 | 1.00 | 84.30 | A | C |
| ATOM | 656 | OH | TYR A 207 | -15.545 | 21.960 | -3.780 | 1.00 | 94.32 | A | O |
| ATOM | 657 | C | TYR A 207 | -10.445 | 19.843 | 1.789 | 1.00 | 84.31 | A | C |
| ATOM | 658 | O | TYR A 207 | -10.427 | 18.654 | 2.148 | 1.00 | 84.87 | A | O |
| ATOM | 659 | N | LEU A 208 | -9.866 | 20.827 | 2.467 | 1.00 | 85.26 | A | N |
| ATOM | 660 | CA | LEU A 208 | -9.154 | 20.605 | 3.711 | 1.00 | 88.23 | A | C |
| ATOM | 661 | CB | LEU A 208 | -7.856 | 21.419 | 3.728 | 1.00 | 91.53 | A | C |
| ATOM | 662 | CG | LEU A 208 | -6.614 | 20.869 | 3.023 | 1.00 | 91.59 | A | C |
| ATOM | 663 | CD1 | LEU A 208 | -5.543 | 21.939 | 2.902 | 1.00 | 93.02 | A | C |
| ATOM | 664 | CD2 | LEU A 208 | -6.081 | 19.710 | 3.800 | 1.00 | 95.04 | A | C |
| ATOM | 665 | C | LEU A 208 | -10.047 | 21.035 | 4.877 | 1.00 | 86.49 | A | C |
| ATOM | 666 | O | LEU A 208 | -10.451 | 22.200 | 4.952 | 1.00 | 88.88 | A | O |
| ATOM | 667 | N | ILE A 209 | -10.367 | 20.092 | 5.765 | 1.00 | 79.00 | A | N |
| ATOM | 668 | CA | ILE A 209 | -11.189 | 20.375 | 6.934 | 1.00 | 67.40 | A | C |
| ATOM | 669 | CB | ILE A 209 | -12.081 | 19.162 | 7.322 | 1.00 | 65.42 | A | C |
| ATOM | 670 | CG2 | ILE A 209 | -12.945 | 19.503 | 8.521 | 1.00 | 68.14 | A | C |
| ATOM | 671 | CG1 | ILE A 209 | -13.012 | 18.784 | 6.181 | 1.00 | 66.25 | A | C |
| ATOM | 672 | CD1 | ILE A 209 | -14.057 | 17.742 | 6.577 | 1.00 | 58.82 | A | C |
| ATOM | 673 | C | ILE A 209 | -10.233 | 20.633 | 8.090 | 1.00 | 61.72 | A | C |
| ATOM | 674 | O | ILE A 209 | -9.473 | 19.750 | 8.443 | 1.00 | 63.43 | A | O |
| ATOM | 675 | N | LEU A 210 | -10.254 | 21.821 | 8.686 | 1.00 | 53.29 | A | N |
| ATOM | 676 | CA | LEU A 210 | -9.357 | 22.083 | 9.807 | 1.00 | 43.66 | A | C |
| ATOM | 677 | CB | LEU A 210 | -8.173 | 22.942 | 9.380 | 1.00 | 51.28 | A | C |
| ATOM | 678 | CG | LEU A 210 | -7.483 | 22.794 | 8.036 | 1.00 | 53.50 | A | C |
| ATOM | 679 | CD1 | LEU A 210 | -8.439 | 23.312 | 6.985 | 1.00 | 54.60 | A | C |
| ATOM | 680 | CD2 | LEU A 210 | -6.166 | 23.592 | 8.016 | 1.00 | 53.47 | A | C |
| ATOM | 681 | C | LEU A 210 | -10.012 | 22.797 | 10.968 | 1.00 | 39.82 | A | C |
| ATOM | 682 | O | LEU A 210 | -11.121 | 23.297 | 10.861 | 1.00 | 40.71 | A | O |
| ATOM | 683 | N | GLU A 211 | -9.286 | 22.852 | 12.077 | 1.00 | 38.14 | A | N |
| ATOM | 684 | CA | GLU A 211 | -9.716 | 23.551 | 13.277 | 1.00 | 35.96 | A | C |
| ATOM | 685 | CB | GLU A 211 | -8.543 | 23.628 | 14.274 | 1.00 | 32.26 | A | C |
| ATOM | 686 | CG | GLU A 211 | -8.902 | 23.950 | 15.735 | 1.00 | 33.26 | A | C |
| ATOM | 687 | CD | GLU A 211 | -7.725 | 23.765 | 16.715 | 1.00 | 33.19 | A | C |
| ATOM | 688 | OE1 | GLU A 211 | -6.927 | 22.822 | 16.527 | 1.00 | 33.06 | A | O |
| ATOM | 689 | OE2 | GLU A 211 | -7.601 | 24.545 | 17.688 | 1.00 | 36.20 | A | O |
| ATOM | 690 | C | GLU A 211 | -10.072 | 24.947 | 12.771 | 1.00 | 35.87 | A | C |
| ATOM | 691 | O | GLU A 211 | -9.721 | 25.315 | 11.648 | 1.00 | 30.07 | A | O |
| ATOM | 692 | N | TYR A 212 | -10.792 | 25.714 | 13.578 | 1.00 | 37.47 | A | N |
| ATOM | 693 | CA | TYR A 212 | -11.163 | 27.077 | 13.211 | 1.00 | 38.73 | A | C |
| ATOM | 694 | CB | TYR A 212 | -12.691 | 27.185 | 12.995 | 1.00 | 42.94 | A | C |
| ATOM | 695 | CG | TYR A 212 | -13.252 | 28.595 | 13.146 | 1.00 | 45.80 | A | C |
| ATOM | 696 | CD1 | TYR A 212 | -12.874 | 29.628 | 12.282 | 1.00 | 47.17 | A | C |
| ATOM | 697 | CE1 | TYR A 212 | -13.312 | 30.937 | 12.495 | 1.00 | 46.25 | A | C |
| ATOM | 698 | CD2 | TYR A 212 | -14.092 | 28.908 | 14.216 | 1.00 | 45.65 | A | C |
| ATOM | 699 | CE2 | TYR A 212 | -14.530 | 30.204 | 14.439 | 1.00 | 46.16 | A | C |
| ATOM | 700 | CZ | TYR A 212 | -14.137 | 31.220 | 13.587 | 1.00 | 45.98 | A | C |
| ATOM | 701 | OH | TYR A 212 | -14.529 | 32.516 | 13.887 | 1.00 | 43.32 | A | O |
| ATOM | 702 | C | TYR A 212 | -10.708 | 27.955 | 14.369 | 1.00 | 35.32 | A | C |
| ATOM | 703 | O | TYR A 212 | -10.797 | 27.559 | 15.525 | 1.00 | 28.60 | A | O |
| ATOM | 704 | N | ALA A 213 | -10.197 | 29.133 | 14.059 | 1.00 | 36.72 | A | N |
| ATOM | 705 | CA | ALA A 213 | -9.743 | 30.031 | 15.106 | 1.00 | 37.52 | A | C |
| ATOM | 706 | CB | ALA A 213 | -8.250 | 30.212 | 15.022 | 1.00 | 42.50 | A | C |
| ATOM | 707 | C | ALA A 213 | -10.440 | 31.368 | 14.984 | 1.00 | 39.83 | A | C |
| ATOM | 708 | O | ALA A 213 | -10.195 | 32.134 | 14.057 | 1.00 | 34.00 | A | O |
| ATOM | 709 | N | PRO A 214 | -11.309 | 31.677 | 15.945 | 1.00 | 46.72 | A | N |
| ATOM | 710 | CD | PRO A 214 | -11.495 | 30.880 | 17.169 | 1.00 | 50.90 | A | C |
| ATOM | 711 | CA | PRO A 214 | -12.097 | 32.912 | 16.012 | 1.00 | 46.86 | A | C |
| ATOM | 712 | CB | PRO A 214 | -13.024 | 32.647 | 17.185 | 1.00 | 50.42 | A | C |

Figure 3L

| ATOM | 713 | CG | PRO | A | 214 | -12.114 | 31.885 | 18.110 | 1.00 | 51.64 | A | C |
|---|---|---|---|---|---|---|---|---|---|---|---|---|
| ATOM | 714 | C | PRO | A | 214 | -11.338 | 34.225 | 16.196 | 1.00 | 43.43 | A | C |
| ATOM | 715 | O | PRO | A | 214 | -11.694 | 35.250 | 15.607 | 1.00 | 40.84 | A | O |
| ATOM | 716 | N | LEU | A | 215 | -10.295 | 34.207 | 17.009 | 1.00 | 38.39 | A | N |
| ATOM | 717 | CA | LEU | A | 215 | -9.584 | 35.433 | 17.265 | 1.00 | 37.94 | A | C |
| ATOM | 718 | CB | LEU | A | 215 | -8.760 | 35.261 | 18.520 | 1.00 | 44.50 | A | C |
| ATOM | 719 | CG | LEU | A | 215 | -9.598 | 35.763 | 19.680 | 1.00 | 48.05 | A | C |
| ATOM | 720 | CD1 | LEU | A | 215 | -8.962 | 35.366 | 20.993 | 1.00 | 56.16 | A | C |
| ATOM | 721 | CD2 | LEU | A | 215 | -9.736 | 37.287 | 19.544 | 1.00 | 47.41 | A | C |
| ATOM | 722 | C | LEU | A | 215 | -8.749 | 36.047 | 16.161 | 1.00 | 38.31 | A | C |
| ATOM | 723 | O | LEU | A | 215 | -8.123 | 37.084 | 16.363 | 1.00 | 43.75 | A | O |
| ATOM | 724 | N | GLY | A | 216 | -8.748 | 35.436 | 14.990 | 1.00 | 38.55 | A | N |
| ATOM | 725 | CA | GLY | A | 216 | -7.960 | 35.994 | 13.902 | 1.00 | 48.83 | A | C |
| ATOM | 726 | C | GLY | A | 216 | -6.483 | 35.611 | 13.916 | 1.00 | 51.10 | A | C |
| ATOM | 727 | O | GLY | A | 216 | -6.014 | 34.856 | 14.784 | 1.00 | 48.91 | A | O |
| ATOM | 728 | N | THR | A | 217 | -5.731 | 36.142 | 12.959 | 1.00 | 49.53 | A | N |
| ATOM | 729 | CA | THR | A | 217 | -4.320 | 35.812 | 12.883 | 1.00 | 44.63 | A | C |
| ATOM | 730 | CB | THR | A | 217 | -3.917 | 35.773 | 11.417 | 1.00 | 38.70 | A | C |
| ATOM | 731 | OG1 | THR | A | 217 | -2.575 | 35.315 | 11.301 | 1.00 | 44.10 | A | O |
| ATOM | 732 | CG2 | THR | A | 217 | -4.048 | 37.126 | 10.807 | 1.00 | 38.24 | A | C |
| ATOM | 733 | C | THR | A | 217 | -3.397 | 36.753 | 13.700 | 1.00 | 44.78 | A | C |
| ATOM | 734 | O | THR | A | 217 | -3.627 | 37.961 | 13.768 | 1.00 | 42.48 | A | O |
| ATOM | 735 | N | VAL | A | 218 | -2.367 | 36.186 | 14.333 | 1.00 | 46.56 | A | N |
| ATOM | 736 | CA | VAL | A | 218 | -1.401 | 36.946 | 15.146 | 1.00 | 46.39 | A | C |
| ATOM | 737 | CB | VAL | A | 218 | -0.164 | 36.066 | 15.514 | 1.00 | 44.78 | A | C |
| ATOM | 738 | CG1 | VAL | A | 218 | 1.071 | 36.935 | 15.664 | 1.00 | 44.70 | A | C |
| ATOM | 739 | CG2 | VAL | A | 218 | -0.417 | 35.318 | 16.818 | 1.00 | 44.46 | A | C |
| ATOM | 740 | C | VAL | A | 218 | -0.906 | 38.220 | 14.453 | 1.00 | 44.26 | A | C |
| ATOM | 741 | O | VAL | A | 218 | -0.460 | 39.177 | 15.100 | 1.00 | 39.89 | A | O |
| ATOM | 742 | N | TYR | A | 219 | -0.983 | 38.206 | 13.130 | 1.00 | 44.17 | A | N |
| ATOM | 743 | CA | TYR | A | 219 | -0.558 | 39.329 | 12.327 | 1.00 | 48.66 | A | C |
| ATOM | 744 | CB | TYR | A | 219 | -0.650 | 38.959 | 10.846 | 1.00 | 51.43 | A | C |
| ATOM | 745 | CG | TYR | A | 219 | -0.229 | 40.036 | 9.865 | 1.00 | 58.02 | A | C |
| ATOM | 746 | CD1 | TYR | A | 219 | 1.071 | 40.553 | 9.861 | 1.00 | 63.18 | A | C |
| ATOM | 747 | CE1 | TYR | A | 219 | 1.476 | 41.499 | 8.895 | 1.00 | 65.99 | A | C |
| ATOM | 748 | CD2 | TYR | A | 219 | -1.117 | 40.492 | 8.892 | 1.00 | 61.04 | A | C |
| ATOM | 749 | CE2 | TYR | A | 219 | -0.728 | 41.432 | 7.929 | 1.00 | 67.96 | A | C |
| ATOM | 750 | CZ | TYR | A | 219 | 0.565 | 41.931 | 7.931 | 1.00 | 67.88 | A | C |
| ATOM | 751 | OH | TYR | A | 219 | 0.919 | 42.846 | 6.959 | 1.00 | 62.74 | A | O |
| ATOM | 752 | C | TYR | A | 219 | -1.488 | 40.475 | 12.652 | 1.00 | 51.83 | A | C |
| ATOM | 753 | O | TYR | A | 219 | -1.091 | 41.438 | 13.297 | 1.00 | 50.71 | A | O |
| ATOM | 754 | N | ARG | A | 220 | -2.739 | 40.352 | 12.222 | 1.00 | 59.10 | A | N |
| ATOM | 755 | CA | ARG | A | 220 | -3.742 | 41.396 | 12.451 | 1.00 | 63.20 | A | C |
| ATOM | 756 | CB | ARG | A | 220 | -5.161 | 40.893 | 12.078 | 1.00 | 66.35 | A | C |
| ATOM | 757 | CG | ARG | A | 220 | -5.298 | 40.216 | 10.682 | 1.00 | 66.02 | A | C |
| ATOM | 758 | CD | ARG | A | 220 | -6.625 | 39.399 | 10.587 | 1.00 | 64.68 | A | C |
| ATOM | 759 | NE | ARG | A | 220 | -6.675 | 38.338 | 9.554 | 1.00 | 56.48 | A | N |
| ATOM | 760 | CZ | ARG | A | 220 | -6.460 | 38.513 | 8.243 | 1.00 | 52.81 | A | C |
| ATOM | 761 | NH1 | ARG | A | 220 | -6.542 | 37.488 | 7.393 | 1.00 | 38.03 | A | N |
| ATOM | 762 | NH2 | ARG | A | 220 | -6.138 | 39.714 | 7.780 | 1.00 | 53.07 | A | N |
| ATOM | 763 | C | ARG | A | 220 | -3.709 | 41.848 | 13.915 | 1.00 | 61.93 | A | C |
| ATOM | 764 | O | ARG | A | 220 | -4.010 | 43.001 | 14.219 | 1.00 | 59.82 | A | O |
| ATOM | 765 | N | GLU | A | 221 | -3.327 | 40.947 | 14.816 | 1.00 | 61.29 | A | N |
| ATOM | 766 | CA | GLU | A | 221 | -3.280 | 41.295 | 16.227 | 1.00 | 62.35 | A | C |
| ATOM | 767 | CB | GLU | A | 221 | -3.250 | 40.042 | 17.108 | 1.00 | 68.29 | A | C |
| ATOM | 768 | CG | GLU | A | 221 | -3.221 | 40.361 | 18.597 | 1.00 | 78.85 | A | C |
| ATOM | 769 | CD | GLU | A | 221 | -4.473 | 41.087 | 19.054 | 1.00 | 84.92 | A | C |
| ATOM | 770 | OE1 | GLU | A | 221 | -5.038 | 41.842 | 18.240 | 1.00 | 92.38 | A | O |
| ATOM | 771 | OE2 | GLU | A | 221 | -4.895 | 40.915 | 20.219 | 1.00 | 84.44 | A | O |
| ATOM | 772 | C | GLU | A | 221 | -2.066 | 42.146 | 16.536 | 1.00 | 59.60 | A | C |
| ATOM | 773 | O | GLU | A | 221 | -2.089 | 42.962 | 17.456 | 1.00 | 56.87 | A | O |

Figure 3M

| ATOM | 774 | N | LEU | A | 222 | -1.010 | 41.956 | 15.756 | 1.00 | 57.41 | A | N |
| ATOM | 775 | CA | LEU | A | 222 | 0.238 | 42.683 | 15.954 | 1.00 | 55.11 | A | C |
| ATOM | 776 | CB | LEU | A | 222 | 1.406 | 41.857 | 15.413 | 1.00 | 57.36 | A | C |
| ATOM | 777 | CG | LEU | A | 222 | 2.816 | 42.453 | 15.339 | 1.00 | 58.26 | A | C |
| ATOM | 778 | CD1 | LEU | A | 222 | 3.193 | 43.149 | 16.621 | 1.00 | 58.09 | A | C |
| ATOM | 779 | CD2 | LEU | A | 222 | 3.793 | 41.320 | 15.035 | 1.00 | 60.99 | A | C |
| ATOM | 780 | C | LEU | A | 222 | 0.274 | 44.078 | 15.358 | 1.00 | 52.81 | A | C |
| ATOM | 781 | O | LEU | A | 222 | 1.032 | 44.927 | 15.807 | 1.00 | 54.33 | A | O |
| ATOM | 782 | N | GLN | A | 223 | -0.522 | 44.329 | 14.336 | 1.00 | 53.36 | A | N |
| ATOM | 783 | CA | GLN | A | 223 | -0.521 | 45.667 | 13.778 | 1.00 | 56.35 | A | C |
| ATOM | 784 | CB | GLN | A | 223 | -0.848 | 45.633 | 12.293 | 1.00 | 60.52 | A | C |
| ATOM | 785 | CG | GLN | A | 223 | -2.030 | 44.818 | 11.973 | 1.00 | 62.89 | A | C |
| ATOM | 786 | CD | GLN | A | 223 | -1.956 | 44.324 | 10.575 | 1.00 | 69.02 | A | C |
| ATOM | 787 | OE1 | GLN | A | 223 | -2.749 | 43.471 | 10.162 | 1.00 | 76.87 | A | O |
| ATOM | 788 | NE2 | GLN | A | 223 | -0.996 | 44.854 | 9.813 | 1.00 | 68.83 | A | N |
| ATOM | 789 | C | GLN | A | 223 | -1.513 | 46.554 | 14.524 | 1.00 | 53.22 | A | C |
| ATOM | 790 | O | GLN | A | 223 | -1.449 | 47.780 | 14.435 | 1.00 | 51.68 | A | O |
| ATOM | 791 | N | LYS | A | 224 | -2.431 | 45.949 | 15.269 | 1.00 | 52.10 | A | N |
| ATOM | 792 | CA | LYS | A | 224 | -3.372 | 46.765 | 16.002 | 1.00 | 54.36 | A | C |
| ATOM | 793 | CB | LYS | A | 224 | -4.656 | 45.990 | 16.309 | 1.00 | 57.97 | A | C |
| ATOM | 794 | CG | LYS | A | 224 | -5.782 | 46.375 | 15.337 | 1.00 | 64.10 | A | C |
| ATOM | 795 | CD | LYS | A | 224 | -6.925 | 45.346 | 15.242 | 1.00 | 69.79 | A | C |
| ATOM | 796 | CE | LYS | A | 224 | -7.985 | 45.478 | 16.341 | 1.00 | 76.21 | A | C |
| ATOM | 797 | NZ | LYS | A | 224 | -9.076 | 44.471 | 16.158 | 1.00 | 70.29 | A | N |
| ATOM | 798 | C | LYS | A | 224 | -2.713 | 47.308 | 17.258 | 1.00 | 51.88 | A | C |
| ATOM | 799 | O | LYS | A | 224 | -2.807 | 48.513 | 17.529 | 1.00 | 53.76 | A | O |
| ATOM | 800 | N | LEU | A | 225 | -2.009 | 46.461 | 18.006 | 1.00 | 43.94 | A | N |
| ATOM | 801 | CA | LEU | A | 225 | -1.350 | 46.945 | 19.219 | 1.00 | 42.30 | A | C |
| ATOM | 802 | CB | LEU | A | 225 | -1.356 | 45.869 | 20.289 | 1.00 | 45.89 | A | C |
| ATOM | 803 | CG | LEU | A | 225 | -2.669 | 45.751 | 21.040 | 1.00 | 53.53 | A | C |
| ATOM | 804 | CD1 | LEU | A | 225 | -3.776 | 45.497 | 20.043 | 1.00 | 54.36 | A | C |
| ATOM | 805 | CD2 | LEU | A | 225 | -2.593 | 44.629 | 22.063 | 1.00 | 62.84 | A | C |
| ATOM | 806 | C | LEU | A | 225 | 0.079 | 47.462 | 19.038 | 1.00 | 42.71 | A | C |
| ATOM | 807 | O | LEU | A | 225 | 0.768 | 47.715 | 20.020 | 1.00 | 41.91 | A | O |
| ATOM | 808 | N | SER | A | 226 | 0.515 | 47.630 | 17.791 | 1.00 | 41.46 | A | N |
| ATOM | 809 | CA | SER | A | 226 | 1.864 | 48.108 | 17.480 | 1.00 | 40.21 | A | C |
| ATOM | 810 | CB | SER | A | 226 | 2.152 | 49.435 | 18.192 | 1.00 | 43.40 | A | C |
| ATOM | 811 | OG | SER | A | 226 | 3.073 | 50.238 | 17.456 | 1.00 | 41.30 | A | O |
| ATOM | 812 | C | SER | A | 226 | 2.911 | 47.068 | 17.869 | 1.00 | 41.79 | A | C |
| ATOM | 813 | O | SER | A | 226 | 3.605 | 46.532 | 17.002 | 1.00 | 45.18 | A | O |
| ATOM | 814 | N | LYS | A | 227 | 3.038 | 46.789 | 19.162 | 1.00 | 42.45 | A | N |
| ATOM | 815 | CA | LYS | A | 227 | 3.988 | 45.782 | 19.622 | 1.00 | 46.59 | A | C |
| ATOM | 816 | CB | LYS | A | 227 | 5.371 | 46.404 | 19.887 | 1.00 | 50.09 | A | C |
| ATOM | 817 | CG | LYS | A | 227 | 5.591 | 46.911 | 21.306 | 1.00 | 59.10 | A | C |
| ATOM | 818 | CD | LYS | A | 227 | 6.713 | 46.143 | 22.027 | 1.00 | 59.92 | A | C |
| ATOM | 819 | CE | LYS | A | 227 | 6.881 | 46.550 | 23.500 | 1.00 | 65.32 | A | C |
| ATOM | 820 | NZ | LYS | A | 227 | 7.978 | 45.831 | 24.203 | 1.00 | 65.66 | A | N |
| ATOM | 821 | C | LYS | A | 227 | 3.441 | 45.120 | 20.884 | 1.00 | 47.16 | A | C |
| ATOM | 822 | O | LYS | A | 227 | 2.670 | 45.722 | 21.613 | 1.00 | 44.36 | A | O |
| ATOM | 823 | N | PHE | A | 228 | 3.834 | 43.881 | 21.146 | 1.00 | 52.52 | A | N |
| ATOM | 824 | CA | PHE | A | 228 | 3.340 | 43.174 | 22.325 | 1.00 | 54.36 | A | C |
| ATOM | 825 | CB | PHE | A | 228 | 3.300 | 41.663 | 22.104 | 1.00 | 51.99 | A | C |
| ATOM | 826 | CG | PHE | A | 228 | 2.668 | 41.247 | 20.828 | 1.00 | 50.48 | A | C |
| ATOM | 827 | CD1 | PHE | A | 228 | 2.041 | 42.157 | 20.016 | 1.00 | 48.97 | A | C |
| ATOM | 828 | CD2 | PHE | A | 228 | 2.722 | 39.926 | 20.434 | 1.00 | 51.71 | A | C |
| ATOM | 829 | CE1 | PHE | A | 228 | 1.488 | 41.756 | 18.836 | 1.00 | 54.43 | A | C |
| ATOM | 830 | CE2 | PHE | A | 228 | 2.169 | 39.520 | 19.252 | 1.00 | 51.46 | A | C |
| ATOM | 831 | CZ | PHE | A | 228 | 1.550 | 40.434 | 18.448 | 1.00 | 53.61 | A | C |
| ATOM | 832 | C | PHE | A | 228 | 4.146 | 43.396 | 23.588 | 1.00 | 54.18 | A | C |
| ATOM | 833 | O | PHE | A | 228 | 5.382 | 43.406 | 23.568 | 1.00 | 53.36 | A | O |
| ATOM | 834 | N | ASP | A | 229 | 3.422 | 43.544 | 24.695 | 1.00 | 56.23 | A | N |

Figure 3N

```
ATOM  835  CA   ASP A 229      4.047  43.713  25.995  1.00  58.19  A  C
ATOM  836  CB   ASP A 229      3.026  44.162  27.064  1.00  62.05  A  C
ATOM  837  CG   ASP A 229      1.848  43.211  27.197  1.00  62.68  A  C
ATOM  838  OD1  ASP A 229      0.846  43.413  26.469  1.00  58.88  A  O
ATOM  839  OD2  ASP A 229      1.928  42.264  28.020  1.00  58.91  A  O
ATOM  840  C    ASP A 229      4.690  42.382  26.388  1.00  53.12  A  C
ATOM  841  O    ASP A 229      4.406  41.332  25.810  1.00  48.18  A  O
ATOM  842  N    GLU A 230      5.557  42.440  27.380  1.00  50.98  A  N
ATOM  843  CA   GLU A 230      6.273  41.275  27.808  1.00  60.44  A  C
ATOM  844  CB   GLU A 230      7.321  41.708  28.818  1.00  67.90  A  C
ATOM  845  CG   GLU A 230      8.243  42.757  28.224  1.00  79.97  A  C
ATOM  846  CD   GLU A 230      9.421  43.059  29.103  1.00  84.27  A  C
ATOM  847  OE1  GLU A 230     10.178  42.114  29.415  1.00  86.02  A  O
ATOM  848  OE2  GLU A 230      9.582  44.244  29.475  1.00  88.59  A  O
ATOM  849  C    GLU A 230      5.386  40.164  28.326  1.00  66.70  A  C
ATOM  850  O    GLU A 230      5.821  39.017  28.467  1.00  70.84  A  O
ATOM  851  N    GLN A 231      4.131  40.489  28.605  1.00  71.78  A  N
ATOM  852  CA   GLN A 231      3.213  39.453  29.060  1.00  74.62  A  C
ATOM  853  CB   GLN A 231      1.868  40.053  29.503  1.00  79.18  A  C
ATOM  854  CG   GLN A 231      1.872  40.766  30.848  1.00  87.57  A  C
ATOM  855  CD   GLN A 231      3.040  41.713  31.007  1.00  94.32  A  C
ATOM  856  OE1  GLN A 231      4.181  41.286  31.224  1.00  99.33  A  O
ATOM  857  NE2  GLN A 231      2.768  43.009  30.892  1.00  92.95  A  N
ATOM  858  C    GLN A 231      3.002  38.609  27.810  1.00  71.80  A  C
ATOM  859  O    GLN A 231      3.678  37.599  27.584  1.00  68.85  A  O
ATOM  860  N    ARG A 232      2.074  39.073  26.985  1.00  69.31  A  N
ATOM  861  CA   ARG A 232      1.721  38.420  25.741  1.00  69.56  A  C
ATOM  862  CB   ARG A 232      1.056  39.454  24.845  1.00  76.48  A  C
ATOM  863  CG   ARG A 232      0.233  38.921  23.715  1.00  91.88  A  C
ATOM  864  CD   ARG A 232      0.172  39.986  22.631  1.00 101.76  A  C
ATOM  865  NE   ARG A 232     -1.157  40.160  22.044  1.00 107.10  A  N
ATOM  866  CZ   ARG A 232     -2.141  40.901  22.567  1.00 107.88  A  C
ATOM  867  NH1  ARG A 232     -1.972  41.563  23.713  1.00 106.99  A  N
ATOM  868  NH2  ARG A 232     -3.304  40.991  21.928  1.00 105.36  A  N
ATOM  869  C    ARG A 232      2.937  37.789  25.024  1.00  66.57  A  C
ATOM  870  O    ARG A 232      3.040  36.553  24.910  1.00  63.64  A  O
ATOM  871  N    THR A 233      3.866  38.632  24.566  1.00  63.52  A  N
ATOM  872  CA   THR A 233      5.045  38.156  23.833  1.00  61.82  A  C
ATOM  873  CB   THR A 233      6.067  39.303  23.614  1.00  61.91  A  C
ATOM  874  OG1  THR A 233      7.241  38.802  22.959  1.00  59.56  A  O
ATOM  875  CG2  THR A 233      6.447  39.902  24.912  1.00  62.29  A  C
ATOM  876  C    THR A 233      5.788  36.938  24.396  1.00  59.02  A  C
ATOM  877  O    THR A 233      6.216  36.063  23.636  1.00  55.98  A  O
ATOM  878  N    ALA A 234      5.919  36.853  25.714  1.00  56.46  A  N
ATOM  879  CA   ALA A 234      6.665  35.751  26.299  1.00  50.51  A  C
ATOM  880  CB   ALA A 234      7.219  36.171  27.625  1.00  47.88  A  C
ATOM  881  C    ALA A 234      5.934  34.433  26.439  1.00  44.56  A  C
ATOM  882  O    ALA A 234      6.534  33.373  26.295  1.00  43.41  A  O
ATOM  883  N    THR A 235      4.643  34.476  26.715  1.00  36.78  A  N
ATOM  884  CA   THR A 235      3.925  33.232  26.862  1.00  38.11  A  C
ATOM  885  CB   THR A 235      2.643  33.416  27.581  1.00  41.37  A  C
ATOM  886  OG1  THR A 235      1.852  32.249  27.370  1.00  49.66  A  O
ATOM  887  CG2  THR A 235      1.911  34.627  27.053  1.00  41.45  A  C
ATOM  888  C    THR A 235      3.617  32.592  25.522  1.00  38.38  A  C
ATOM  889  O    THR A 235      3.267  31.415  25.450  1.00  41.95  A  O
ATOM  890  N    TYR A 236      3.727  33.383  24.459  1.00  40.40  A  N
ATOM  891  CA   TYR A 236      3.499  32.880  23.102  1.00  45.47  A  C
ATOM  892  CB   TYR A 236      3.483  34.037  22.085  1.00  55.45  A  C
ATOM  893  CG   TYR A 236      2.148  34.722  21.894  1.00  66.59  A  C
ATOM  894  CD1  TYR A 236      1.115  34.559  22.818  1.00  70.13  A  C
ATOM  895  CE1  TYR A 236     -0.062  35.270  22.700  1.00  74.91  A  C
```

Figure 30

| ATOM | 896 | CD2 | TYR A 236 | 1.959 | 35.609 | 20.838 | 1.00 | 71.57 | A | C |
| --- | --- | --- | --- | --- | --- | --- | --- | --- | --- | --- |
| ATOM | 897 | CE2 | TYR A 236 | 0.792 | 36.328 | 20.708 | 1.00 | 75.91 | A | C |
| ATOM | 898 | CZ | TYR A 236 | -0.220 | 36.166 | 21.642 | 1.00 | 77.30 | A | C |
| ATOM | 899 | OH | TYR A 236 | -1.367 | 36.937 | 21.540 | 1.00 | 81.01 | A | O |
| ATOM | 900 | C | TYR A 236 | 4.632 | 31.911 | 22.735 | 1.00 | 38.50 | A | C |
| ATOM | 901 | O | TYR A 236 | 4.406 | 30.849 | 22.156 | 1.00 | 33.41 | A | O |
| ATOM | 902 | N | ILE A 237 | 5.853 | 32.301 | 23.078 | 1.00 | 35.01 | A | N |
| ATOM | 903 | CA | ILE A 237 | 7.016 | 31.491 | 22.793 | 1.00 | 31.23 | A | C |
| ATOM | 904 | CB | ILE A 237 | 8.271 | 32.259 | 23.155 | 1.00 | 19.44 | A | C |
| ATOM | 905 | CG2 | ILE A 237 | 9.479 | 31.479 | 22.761 | 1.00 | 23.51 | A | C |
| ATOM | 906 | CG1 | ILE A 237 | 8.289 | 33.554 | 22.369 | 1.00 | 14.01 | A | C |
| ATOM | 907 | CD1 | ILE A 237 | 8.265 | 33.312 | 20.885 | 1.00 | 12.88 | A | C |
| ATOM | 908 | C | ILE A 237 | 6.945 | 30.151 | 23.525 | 1.00 | 32.97 | A | C |
| ATOM | 909 | O | ILE A 237 | 7.252 | 29.103 | 22.943 | 1.00 | 31.27 | A | O |
| ATOM | 910 | N | THR A 238 | 6.524 | 30.181 | 24.789 | 1.00 | 34.53 | A | N |
| ATOM | 911 | CA | THR A 238 | 6.373 | 28.939 | 25.552 | 1.00 | 44.20 | A | C |
| ATOM | 912 | CB | THR A 238 | 5.929 | 29.221 | 27.009 | 1.00 | 49.15 | A | C |
| ATOM | 913 | OG1 | THR A 238 | 4.833 | 28.369 | 27.357 | 1.00 | 49.73 | A | O |
| ATOM | 914 | CG2 | THR A 238 | 5.510 | 30.653 | 27.155 | 1.00 | 53.69 | A | C |
| ATOM | 915 | C | THR A 238 | 5.334 | 28.039 | 24.860 | 1.00 | 47.12 | A | C |
| ATOM | 916 | O | THR A 238 | 5.526 | 26.838 | 24.738 | 1.00 | 44.22 | A | O |
| ATOM | 917 | N | GLU A 239 | 4.229 | 28.624 | 24.416 | 1.00 | 52.02 | A | N |
| ATOM | 918 | CA | GLU A 239 | 3.209 | 27.851 | 23.715 | 1.00 | 58.67 | A | C |
| ATOM | 919 | CB | GLU A 239 | 1.980 | 28.714 | 23.394 | 1.00 | 66.04 | A | C |
| ATOM | 920 | CG | GLU A 239 | 1.135 | 29.121 | 24.594 | 1.00 | 73.68 | A | C |
| ATOM | 921 | CD | GLU A 239 | -0.111 | 29.911 | 24.211 | 1.00 | 75.31 | A | C |
| ATOM | 922 | OE1 | GLU A 239 | -0.912 | 30.218 | 25.122 | 1.00 | 72.95 | A | O |
| ATOM | 923 | OE2 | GLU A 239 | -0.287 | 30.225 | 23.012 | 1.00 | 73.83 | A | O |
| ATOM | 924 | C | GLU A 239 | 3.830 | 27.400 | 22.405 | 1.00 | 57.67 | A | C |
| ATOM | 925 | O | GLU A 239 | 3.566 | 26.304 | 21.910 | 1.00 | 54.44 | A | O |
| ATOM | 926 | N | LEU A 240 | 4.661 | 28.280 | 21.854 | 1.00 | 57.74 | A | N |
| ATOM | 927 | CA | LEU A 240 | 5.349 | 28.053 | 20.582 | 1.00 | 56.95 | A | C |
| ATOM | 928 | CB | LEU A 240 | 6.003 | 29.359 | 20.121 | 1.00 | 51.97 | A | C |
| ATOM | 929 | CG | LEU A 240 | 5.994 | 29.675 | 18.636 | 1.00 | 51.90 | A | C |
| ATOM | 930 | CD1 | LEU A 240 | 4.905 | 28.941 | 17.871 | 1.00 | 57.33 | A | C |
| ATOM | 931 | CD2 | LEU A 240 | 5.789 | 31.147 | 18.551 | 1.00 | 50.91 | A | C |
| ATOM | 932 | C | LEU A 240 | 6.402 | 26.958 | 20.720 | 1.00 | 57.51 | A | C |
| ATOM | 933 | O | LEU A 240 | 6.397 | 25.961 | 19.989 | 1.00 | 55.95 | A | O |
| ATOM | 934 | N | ALA A 241 | 7.309 | 27.158 | 21.663 | 1.00 | 59.16 | A | N |
| ATOM | 935 | CA | ALA A 241 | 8.354 | 26.186 | 21.924 | 1.00 | 59.19 | A | C |
| ATOM | 936 | CB | ALA A 241 | 9.018 | 26.495 | 23.252 | 1.00 | 62.26 | A | C |
| ATOM | 937 | C | ALA A 241 | 7.753 | 24.788 | 21.953 | 1.00 | 55.24 | A | C |
| ATOM | 938 | O | ALA A 241 | 8.209 | 23.904 | 21.262 | 1.00 | 50.97 | A | O |
| ATOM | 939 | N | ASN A 242 | 6.722 | 24.598 | 22.761 | 1.00 | 54.53 | A | N |
| ATOM | 940 | CA | ASN A 242 | 6.050 | 23.304 | 22.873 | 1.00 | 54.17 | A | C |
| ATOM | 941 | CB | ASN A 242 | 4.878 | 23.405 | 23.852 | 1.00 | 57.22 | A | C |
| ATOM | 942 | CG | ASN A 242 | 5.253 | 24.087 | 25.132 | 1.00 | 56.71 | A | C |
| ATOM | 943 | OD1 | ASN A 242 | 4.387 | 24.637 | 25.820 | 1.00 | 54.75 | A | O |
| ATOM | 944 | ND2 | ASN A 242 | 6.548 | 24.055 | 25.472 | 1.00 | 57.66 | A | N |
| ATOM | 945 | C | ASN A 242 | 5.504 | 22.823 | 21.529 | 1.00 | 52.08 | A | C |
| ATOM | 946 | O | ASN A 242 | 5.962 | 21.824 | 20.977 | 1.00 | 48.09 | A | O |
| ATOM | 947 | N | ALA A 243 | 4.500 | 23.527 | 21.023 | 1.00 | 53.90 | A | N |
| ATOM | 948 | CA | ALA A 243 | 3.895 | 23.160 | 19.759 | 1.00 | 59.18 | A | C |
| ATOM | 949 | CB | ALA A 243 | 3.119 | 24.324 | 19.206 | 1.00 | 62.18 | A | C |
| ATOM | 950 | C | ALA A 243 | 5.011 | 22.788 | 18.813 | 1.00 | 60.69 | A | C |
| ATOM | 951 | O | ALA A 243 | 4.806 | 22.104 | 17.811 | 1.00 | 62.87 | A | O |
| ATOM | 952 | N | LEU A 244 | 6.201 | 23.253 | 19.166 | 1.00 | 62.13 | A | N |
| ATOM | 953 | CA | LEU A 244 | 7.414 | 23.031 | 18.393 | 1.00 | 66.20 | A | C |
| ATOM | 954 | CB | LEU A 244 | 8.313 | 24.266 | 18.569 | 1.00 | 63.08 | A | C |
| ATOM | 955 | CG | LEU A 244 | 9.123 | 24.867 | 17.429 | 1.00 | 62.33 | A | C |
| ATOM | 956 | CD1 | LEU A 244 | 8.524 | 24.562 | 16.048 | 1.00 | 62.03 | A | C |

Figure 3P

| ATOM | 957 | CD2 | LEU | A | 244 | 9.176 | 26.345 | 17.711 | 1.00 | 58.66 | A | C |
|---|---|---|---|---|---|---|---|---|---|---|---|---|
| ATOM | 958 | C | LEU | A | 244 | 8.155 | 21.732 | 18.809 | 1.00 | 69.75 | A | C |
| ATOM | 959 | O | LEU | A | 244 | 8.449 | 20.870 | 17.966 | 1.00 | 70.85 | A | O |
| ATOM | 960 | N | SER | A | 245 | 8.456 | 21.600 | 20.099 | 1.00 | 73.70 | A | N |
| ATOM | 961 | CA | SER | A | 245 | 9.147 | 20.424 | 20.611 | 1.00 | 78.27 | A | C |
| ATOM | 962 | CB | SER | A | 245 | 9.317 | 20.517 | 22.127 | 1.00 | 84.64 | A | C |
| ATOM | 963 | OG | SER | A | 245 | 9.342 | 19.224 | 22.711 | 1.00 | 94.91 | A | O |
| ATOM | 964 | C | SER | A | 245 | 8.368 | 19.176 | 20.271 | 1.00 | 80.42 | A | C |
| ATOM | 965 | O | SER | A | 245 | 8.937 | 18.212 | 19.789 | 1.00 | 78.52 | A | O |
| ATOM | 966 | N | TYR | A | 246 | 7.066 | 19.188 | 20.530 | 1.00 | 86.84 | A | N |
| ATOM | 967 | CA | TYR | A | 246 | 6.244 | 18.030 | 20.218 | 1.00 | 96.04 | A | C |
| ATOM | 968 | CB | TYR | A | 246 | 4.767 | 18.314 | 20.504 | 1.00 | 98.89 | A | C |
| ATOM | 969 | CG | TYR | A | 246 | 3.818 | 17.390 | 19.763 | 1.00 | 105.13 | A | C |
| ATOM | 970 | CD1 | TYR | A | 246 | 3.458 | 16.145 | 20.281 | 1.00 | 107.12 | A | C |
| ATOM | 971 | CE1 | TYR | A | 246 | 2.608 | 15.281 | 19.557 | 1.00 | 110.61 | A | C |
| ATOM | 972 | CD2 | TYR | A | 246 | 3.312 | 17.751 | 18.511 | 1.00 | 108.23 | A | C |
| ATOM | 973 | CE2 | TYR | A | 246 | 2.475 | 16.905 | 17.786 | 1.00 | 109.34 | A | C |
| ATOM | 974 | CZ | TYR | A | 246 | 2.122 | 15.672 | 18.305 | 1.00 | 110.30 | A | C |
| ATOM | 975 | OH | TYR | A | 246 | 1.288 | 14.846 | 17.570 | 1.00 | 106.48 | A | O |
| ATOM | 976 | C | TYR | A | 246 | 6.426 | 17.668 | 18.741 | 1.00 | 102.38 | A | C |
| ATOM | 977 | O | TYR | A | 246 | 6.118 | 16.547 | 18.333 | 1.00 | 106.46 | A | O |
| ATOM | 978 | N | CYS | A | 247 | 6.907 | 18.613 | 17.934 | 1.00 | 105.78 | A | N |
| ATOM | 979 | CA | CYS | A | 247 | 7.146 | 18.333 | 16.518 | 1.00 | 106.40 | A | C |
| ATOM | 980 | CB | CYS | A | 247 | 6.990 | 19.592 | 15.667 | 1.00 | 110.42 | A | C |
| ATOM | 981 | SG | CYS | A | 247 | 5.359 | 19.737 | 14.910 | 1.00 | 117.71 | A | S |
| ATOM | 982 | C | CYS | A | 247 | 8.554 | 17.784 | 16.384 | 1.00 | 103.70 | A | C |
| ATOM | 983 | O | CYS | A | 247 | 8.773 | 16.760 | 15.748 | 1.00 | 104.03 | A | O |
| ATOM | 984 | N | HIS | A | 248 | 9.506 | 18.466 | 17.006 | 1.00 | 100.96 | A | N |
| ATOM | 985 | CA | HIS | A | 248 | 10.896 | 18.034 | 16.984 | 1.00 | 99.23 | A | C |
| ATOM | 986 | CB | HIS | A | 248 | 11.753 | 18.969 | 17.851 | 1.00 | 99.09 | A | C |
| ATOM | 987 | CG | HIS | A | 248 | 12.319 | 20.144 | 17.114 | 1.00 | 96.77 | A | C |
| ATOM | 988 | CD2 | HIS | A | 248 | 13.578 | 20.640 | 17.064 | 1.00 | 94.31 | A | C |
| ATOM | 989 | ND1 | HIS | A | 248 | 11.550 | 20.972 | 16.327 | 1.00 | 96.50 | A | N |
| ATOM | 990 | CE1 | HIS | A | 248 | 12.311 | 21.927 | 15.825 | 1.00 | 92.48 | A | C |
| ATOM | 991 | NE2 | HIS | A | 248 | 13.545 | 21.749 | 16.255 | 1.00 | 90.90 | A | N |
| ATOM | 992 | C | HIS | A | 248 | 11.043 | 16.592 | 17.489 | 1.00 | 96.19 | A | C |
| ATOM | 993 | O | HIS | A | 248 | 12.014 | 15.920 | 17.164 | 1.00 | 99.92 | A | O |
| ATOM | 994 | N | SER | A | 249 | 10.104 | 16.115 | 18.298 | 1.00 | 90.24 | A | N |
| ATOM | 995 | CA | SER | A | 249 | 10.208 | 14.747 | 18.779 | 1.00 | 85.03 | A | C |
| ATOM | 996 | CB | SER | A | 249 | 9.295 | 14.492 | 19.979 | 1.00 | 81.64 | A | C |
| ATOM | 997 | OG | SER | A | 249 | 8.020 | 14.022 | 19.582 | 1.00 | 72.88 | A | O |
| ATOM | 998 | C | SER | A | 249 | 9.757 | 13.888 | 17.629 | 1.00 | 85.40 | A | C |
| ATOM | 999 | O | SER | A | 249 | 10.546 | 13.170 | 17.033 | 1.00 | 88.47 | A | O |
| ATOM | 1000 | N | LYS | A | 250 | 8.477 | 13.995 | 17.307 | 1.00 | 83.68 | A | N |
| ATOM | 1001 | CA | LYS | A | 250 | 7.860 | 13.240 | 16.231 | 1.00 | 83.38 | A | C |
| ATOM | 1002 | CB | LYS | A | 250 | 6.406 | 13.692 | 16.128 | 1.00 | 87.13 | A | C |
| ATOM | 1003 | CG | LYS | A | 250 | 5.656 | 13.260 | 14.913 | 1.00 | 100.15 | A | C |
| ATOM | 1004 | CD | LYS | A | 250 | 4.607 | 14.302 | 14.615 | 1.00 | 113.49 | A | C |
| ATOM | 1005 | CE | LYS | A | 250 | 5.196 | 15.727 | 14.655 | 1.00 | 119.58 | A | C |
| ATOM | 1006 | NZ | LYS | A | 250 | 5.281 | 16.284 | 16.034 | 1.00 | 118.84 | A | N |
| ATOM | 1007 | C | LYS | A | 250 | 8.597 | 13.361 | 14.883 | 1.00 | 82.38 | A | C |
| ATOM | 1008 | O | LYS | A | 250 | 8.140 | 12.858 | 13.857 | 1.00 | 81.73 | A | O |
| ATOM | 1009 | N | ARG | A | 251 | 9.749 | 14.018 | 14.893 | 1.00 | 83.73 | A | N |
| ATOM | 1010 | CA | ARG | A | 251 | 10.552 | 14.182 | 13.690 | 1.00 | 89.24 | A | C |
| ATOM | 1011 | CB | ARG | A | 251 | 11.148 | 12.837 | 13.274 | 1.00 | 99.32 | A | C |
| ATOM | 1012 | CG | ARG | A | 251 | 12.354 | 12.457 | 14.129 | 1.00 | 112.74 | A | C |
| ATOM | 1013 | CD | ARG | A | 251 | 13.181 | 11.326 | 13.532 | 1.00 | 122.34 | A | C |
| ATOM | 1014 | NE | ARG | A | 251 | 14.512 | 11.274 | 14.141 | 1.00 | 133.01 | A | N |
| ATOM | 1015 | CZ | ARG | A | 251 | 15.436 | 10.355 | 13.868 | 1.00 | 137.24 | A | C |
| ATOM | 1016 | NH1 | ARG | A | 251 | 15.186 | 9.389 | 12.987 | 1.00 | 140.46 | A | N |
| ATOM | 1017 | NH2 | ARG | A | 251 | 16.615 | 10.401 | 14.478 | 1.00 | 137.41 | A | N |

Figure 3Q

```
ATOM   1018  C    ARG A 251       9.871  14.846  12.503  1.00   88.64      A    C
ATOM   1019  O    ARG A 251       9.440  14.195  11.549  1.00   89.26      A    O
ATOM   1020  N    VAL A 252       9.813  16.171  12.595  1.00   87.34      A    N
ATOM   1021  CA   VAL A 252       9.234  17.054  11.597  1.00   90.39      A    C
ATOM   1022  CB   VAL A 252       7.684  17.004  11.624  1.00   89.80      A    C
ATOM   1023  CG1  VAL A 252       7.120  18.086  10.740  1.00   92.45      A    C
ATOM   1024  CG2  VAL A 252       7.187  15.657  11.131  1.00   88.51      A    C
ATOM   1025  C    VAL A 252       9.718  18.465  11.962  1.00   92.45      A    C
ATOM   1026  O    VAL A 252       9.587  18.896  13.108  1.00   91.52      A    O
ATOM   1027  N    ILE A 253      10.300  19.159  10.984  1.00   97.53      A    N
ATOM   1028  CA   ILE A 253      10.828  20.521  11.152  1.00  100.27      A    C
ATOM   1029  CB   ILE A 253      12.331  20.580  10.828  1.00  105.49      A    C
ATOM   1030  CG2  ILE A 253      12.770  22.012  10.764  1.00  108.25      A    C
ATOM   1031  CG1  ILE A 253      13.144  19.828  11.882  1.00  107.85      A    C
ATOM   1032  CD1  ILE A 253      12.925  18.346  11.889  1.00  108.10      A    C
ATOM   1033  C    ILE A 253      10.111  21.541  10.252  1.00   98.71      A    C
ATOM   1034  O    ILE A 253      10.229  21.513   9.027  1.00   97.73      A    O
ATOM   1035  N    HIS A 254       9.385  22.457  10.876  1.00   98.30      A    N
ATOM   1036  CA   HIS A 254       8.623  23.459  10.150  1.00  101.26      A    C
ATOM   1037  CB   HIS A 254       7.559  24.074  11.067  1.00  102.81      A    C
ATOM   1038  CG   HIS A 254       6.214  23.438  10.939  1.00  108.06      A    C
ATOM   1039  CD2  HIS A 254       5.352  22.973  11.871  1.00  108.21      A    C
ATOM   1040  ND1  HIS A 254       5.604  23.243   9.719  1.00  112.19      A    N
ATOM   1041  CE1  HIS A 254       4.422  22.684   9.904  1.00  111.89      A    C
ATOM   1042  NE2  HIS A 254       4.245  22.511  11.200  1.00  110.82      A    N
ATOM   1043  C    HIS A 254       9.457  24.569   9.555  1.00  102.47      A    C
ATOM   1044  O    HIS A 254      10.219  24.361   8.614  1.00  101.81      A    O
ATOM   1045  N    ARG A 255       9.275  25.748  10.147  1.00  106.28      A    N
ATOM   1046  CA   ARG A 255       9.904  27.020   9.783  1.00  107.89      A    C
ATOM   1047  CB   ARG A 255      11.104  26.811   8.858  1.00  109.62      A    C
ATOM   1054  C    ARG A 255       8.819  27.849   9.074  1.00  107.89      A    C
ATOM   1055  O    ARG A 255       7.612  27.559   9.222  1.00  110.05      A    O
ATOM   1056  N    ASP A 256       9.238  28.866   8.313  1.00  101.96      A    N
ATOM   1057  CA   ASP A 256       8.306  29.725   7.577  1.00   91.62      A    C
ATOM   1058  CB   ASP A 256       7.997  29.112   6.204  1.00   82.66      A    C
ATOM   1062  C    ASP A 256       7.005  29.930   8.365  1.00   87.64      A    C
ATOM   1063  O    ASP A 256       5.895  29.929   7.800  1.00   87.53      A    O
ATOM   1064  N    ILE A 257       7.153  30.049   9.682  1.00   82.63      A    N
ATOM   1065  CA   ILE A 257       6.027  30.299  10.563  1.00   69.93      A    C
ATOM   1066  CB   ILE A 257       6.165  29.535  11.874  1.00   63.21      A    C
ATOM   1067  CG2  ILE A 257       6.295  28.063  11.577  1.00   56.79      A    C
ATOM   1068  CG1  ILE A 257       7.369  30.057  12.656  1.00   55.36      A    C
ATOM   1069  CD1  ILE A 257       7.543  29.435  13.985  1.00   49.65      A    C
ATOM   1070  C    ILE A 257       6.258  31.784  10.799  1.00   67.29      A    C
ATOM   1071  O    ILE A 257       7.376  32.263  10.568  1.00   70.67      A    O
ATOM   1072  N    LYS A 258       5.223  32.510  11.209  1.00   59.09      A    N
ATOM   1073  CA   LYS A 258       5.341  33.938  11.461  1.00   56.36      A    C
ATOM   1074  CB   LYS A 258       6.088  34.635  10.321  1.00   53.62      A    C
ATOM   1075  CG   LYS A 258       5.680  34.194   8.939  1.00   53.49      A    C
ATOM   1076  CD   LYS A 258       6.664  34.694   7.895  1.00   60.51      A    C
ATOM   1077  CE   LYS A 258       6.348  34.115   6.535  1.00   64.60      A    C
ATOM   1078  NZ   LYS A 258       7.444  34.353   5.567  1.00   68.38      A    N
ATOM   1079  C    LYS A 258       3.947  34.489  11.595  1.00   53.82      A    C
ATOM   1080  O    LYS A 258       2.984  33.782  11.345  1.00   51.46      A    O
ATOM   1081  N    PRO A 259       3.822  35.754  12.010  1.00   54.35      A    N
ATOM   1082  CD   PRO A 259       4.921  36.722  12.172  1.00   58.90      A    C
ATOM   1083  CA   PRO A 259       2.536  36.417  12.190  1.00   49.47      A    C
ATOM   1084  CB   PRO A 259       2.894  37.873  11.958  1.00   56.38      A    C
ATOM   1085  CG   PRO A 259       4.206  37.974  12.653  1.00   60.81      A    C
ATOM   1086  C    PRO A 259       1.466  35.921  11.240  1.00   42.86      A    C
ATOM   1087  O    PRO A 259       0.459  35.373  11.650  1.00   37.18      A    O
```

Figure 3R

| ATOM | 1088 | N | GLU | A | 260 | 1.716 | 36.115 | 9.961 | 1.00 | 43.06 | A | N |
|---|---|---|---|---|---|---|---|---|---|---|---|---|
| ATOM | 1089 | CA | GLU | A | 260 | 0.811 | 35.712 | 8.901 | 1.00 | 46.11 | A | C |
| ATOM | 1090 | CB | GLU | A | 260 | 1.559 | 35.828 | 7.548 | 1.00 | 53.53 | A | C |
| ATOM | 1091 | CG | GLU | A | 260 | 2.165 | 37.243 | 7.176 | 1.00 | 59.82 | A | C |
| ATOM | 1092 | CD | GLU | A | 260 | 3.312 | 37.752 | 8.101 | 1.00 | 63.40 | A | C |
| ATOM | 1093 | OE1 | GLU | A | 260 | 3.721 | 38.936 | 7.949 | 1.00 | 62.02 | A | O |
| ATOM | 1094 | OE2 | GLU | A | 260 | 3.804 | 36.986 | 8.972 | 1.00 | 59.24 | A | O |
| ATOM | 1095 | C | GLU | A | 260 | 0.229 | 34.283 | 9.088 | 1.00 | 46.29 | A | C |
| ATOM | 1096 | O | GLU | A | 260 | -0.933 | 34.027 | 8.758 | 1.00 | 44.46 | A | O |
| ATOM | 1097 | N | ASN | A | 261 | 1.035 | 33.360 | 9.616 | 1.00 | 49.66 | A | N |
| ATOM | 1098 | CA | ASN | A | 261 | 0.615 | 31.964 | 9.828 | 1.00 | 53.24 | A | C |
| ATOM | 1099 | CB | ASN | A | 261 | 1.663 | 30.963 | 9.340 | 1.00 | 55.31 | A | C |
| ATOM | 1100 | CG | ASN | A | 261 | 1.799 | 30.939 | 7.866 | 1.00 | 65.18 | A | C |
| ATOM | 1101 | OD1 | ASN | A | 261 | 0.809 | 30.951 | 7.144 | 1.00 | 76.46 | A | O |
| ATOM | 1102 | ND2 | ASN | A | 261 | 3.038 | 30.881 | 7.391 | 1.00 | 68.38 | A | N |
| ATOM | 1103 | C | ASN | A | 261 | 0.334 | 31.561 | 11.263 | 1.00 | 52.11 | A | C |
| ATOM | 1104 | O | ASN | A | 261 | 0.402 | 30.374 | 11.569 | 1.00 | 50.99 | A | O |
| ATOM | 1105 | N | LEU | A | 262 | 0.049 | 32.499 | 12.155 | 1.00 | 47.05 | A | N |
| ATOM | 1106 | CA | LEU | A | 262 | -0.237 | 32.093 | 13.520 | 1.00 | 42.96 | A | C |
| ATOM | 1107 | CB | LEU | A | 262 | 0.872 | 32.576 | 14.447 | 1.00 | 40.51 | A | C |
| ATOM | 1108 | CG | LEU | A | 262 | 2.151 | 31.839 | 14.092 | 1.00 | 27.59 | A | C |
| ATOM | 1109 | CD1 | LEU | A | 262 | 3.266 | 32.178 | 15.017 | 1.00 | 28.42 | A | C |
| ATOM | 1110 | CD2 | LEU | A | 262 | 1.872 | 30.401 | 14.205 | 1.00 | 18.90 | A | C |
| ATOM | 1111 | C | LEU | A | 262 | -1.600 | 32.599 | 13.974 | 1.00 | 41.66 | A | C |
| ATOM | 1112 | O | LEU | A | 262 | -1.798 | 33.803 | 14.131 | 1.00 | 43.92 | A | O |
| ATOM | 1113 | N | LEU | A | 263 | -2.552 | 31.686 | 14.154 | 1.00 | 38.96 | A | N |
| ATOM | 1114 | CA | LEU | A | 263 | -3.890 | 32.063 | 14.596 | 1.00 | 39.47 | A | C |
| ATOM | 1115 | CB | LEU | A | 263 | -4.899 | 31.068 | 14.065 | 1.00 | 27.55 | A | C |
| ATOM | 1116 | CG | LEU | A | 263 | -4.782 | 31.047 | 12.577 | 1.00 | 18.30 | A | C |
| ATOM | 1117 | CD1 | LEU | A | 263 | -5.591 | 29.971 | 11.974 | 1.00 | 15.98 | A | C |
| ATOM | 1118 | CD2 | LEU | A | 263 | -5.234 | 32.385 | 12.141 | 1.00 | 9.45 | A | C |
| ATOM | 1119 | C | LEU | A | 263 | -3.967 | 32.084 | 16.120 | 1.00 | 48.24 | A | C |
| ATOM | 1120 | O | LEU | A | 263 | -3.011 | 31.746 | 16.832 | 1.00 | 47.09 | A | O |
| ATOM | 1121 | N | LEU | A | 264 | -5.122 | 32.466 | 16.631 | 1.00 | 55.21 | A | N |
| ATOM | 1122 | CA | LEU | A | 264 | -5.299 | 32.513 | 18.062 | 1.00 | 58.52 | A | C |
| ATOM | 1123 | CB | LEU | A | 264 | -5.291 | 33.965 | 18.508 | 1.00 | 55.51 | A | C |
| ATOM | 1124 | CG | LEU | A | 264 | -4.082 | 34.643 | 17.900 | 1.00 | 54.53 | A | C |
| ATOM | 1125 | CD1 | LEU | A | 264 | -4.480 | 35.911 | 17.209 | 1.00 | 50.27 | A | C |
| ATOM | 1126 | CD2 | LEU | A | 264 | -3.078 | 34.867 | 18.972 | 1.00 | 60.70 | A | C |
| ATOM | 1127 | C | LEU | A | 264 | -6.637 | 31.863 | 18.335 | 1.00 | 61.35 | A | C |
| ATOM | 1128 | O | LEU | A | 264 | -7.548 | 31.953 | 17.516 | 1.00 | 64.20 | A | O |
| ATOM | 1129 | N | GLY | A | 265 | -6.759 | 31.204 | 19.477 | 1.00 | 63.50 | A | N |
| ATOM | 1130 | CA | GLY | A | 265 | -8.012 | 30.550 | 19.802 | 1.00 | 64.53 | A | C |
| ATOM | 1131 | C | GLY | A | 265 | -8.998 | 31.420 | 20.557 | 1.00 | 68.14 | A | C |
| ATOM | 1132 | O | GLY | A | 265 | -8.890 | 32.650 | 20.562 | 1.00 | 65.96 | A | O |
| ATOM | 1133 | N | SER | A | 266 | -9.979 | 30.764 | 21.175 | 1.00 | 73.20 | A | N |
| ATOM | 1134 | CA | SER | A | 266 | -10.994 | 31.446 | 21.964 | 1.00 | 78.83 | A | C |
| ATOM | 1135 | CB | SER | A | 266 | -11.977 | 30.433 | 22.576 | 1.00 | 82.41 | A | C |
| ATOM | 1136 | OG | SER | A | 266 | -13.120 | 30.180 | 21.760 | 1.00 | 84.79 | A | O |
| ATOM | 1137 | C | SER | A | 266 | -10.248 | 32.143 | 23.082 | 1.00 | 78.54 | A | C |
| ATOM | 1138 | O | SER | A | 266 | -10.300 | 33.363 | 23.228 | 1.00 | 76.66 | A | O |
| ATOM | 1139 | N | ALA | A | 267 | -9.542 | 31.335 | 23.861 | 1.00 | 79.99 | A | N |
| ATOM | 1140 | CA | ALA | A | 267 | -8.769 | 31.812 | 24.990 | 1.00 | 82.59 | A | C |
| ATOM | 1141 | CB | ALA | A | 267 | -8.210 | 30.624 | 25.757 | 1.00 | 84.33 | A | C |
| ATOM | 1142 | C | ALA | A | 267 | -7.641 | 32.725 | 24.532 | 1.00 | 81.88 | A | C |
| ATOM | 1143 | O | ALA | A | 267 | -6.983 | 33.375 | 25.349 | 1.00 | 80.27 | A | O |
| ATOM | 1144 | N | GLY | A | 268 | -7.427 | 32.777 | 23.222 | 1.00 | 80.66 | A | N |
| ATOM | 1145 | CA | GLY | A | 268 | -6.364 | 33.606 | 22.683 | 1.00 | 77.38 | A | C |
| ATOM | 1146 | C | GLY | A | 268 | -5.047 | 32.855 | 22.545 | 1.00 | 77.08 | A | C |
| ATOM | 1147 | O | GLY | A | 268 | -3.991 | 33.474 | 22.420 | 1.00 | 73.27 | A | O |
| ATOM | 1148 | N | GLU | A | 269 | -5.114 | 31.521 | 22.569 | 1.00 | 78.84 | A | N |

Figure 3S

| ATOM | 1149 | CA  | GLU | A | 269 | -3.936 | 30.662 | 22.436 | 1.00 | 79.80  | A | C |
| ---- | ---- | --- | --- | - | --- | ------ | ------ | ------ | ---- | ------ | - | - |
| ATOM | 1150 | CB  | GLU | A | 269 | -4.234 | 29.253 | 22.983 | 1.00 | 83.52  | A | C |
| ATOM | 1151 | CG  | GLU | A | 269 | -5.679 | 29.002 | 23.446 | 1.00 | 89.77  | A | C |
| ATOM | 1152 | CD  | GLU | A | 269 | -6.383 | 27.856 | 22.703 | 1.00 | 90.98  | A | C |
| ATOM | 1153 | OE1 | GLU | A | 269 | -5.813 | 26.747 | 22.585 | 1.00 | 97.21  | A | O |
| ATOM | 1154 | OE2 | GLU | A | 269 | -7.526 | 28.066 | 22.246 | 1.00 | 83.35  | A | O |
| ATOM | 1155 | C   | GLU | A | 269 | -3.455 | 30.555 | 20.976 | 1.00 | 78.35  | A | C |
| ATOM | 1156 | O   | GLU | A | 269 | -4.253 | 30.594 | 20.032 | 1.00 | 79.24  | A | O |
| ATOM | 1157 | N   | LEU | A | 270 | -2.143 | 30.418 | 20.797 | 1.00 | 75.50  | A | N |
| ATOM | 1158 | CA  | LEU | A | 270 | -1.550 | 30.300 | 19.466 | 1.00 | 71.01  | A | C |
| ATOM | 1159 | CB  | LEU | A | 270 | -0.029 | 30.292 | 19.581 | 1.00 | 72.84  | A | C |
| ATOM | 1160 | CG  | LEU | A | 270 | 0.564  | 31.642 | 19.201 | 1.00 | 75.37  | A | C |
| ATOM | 1161 | CD1 | LEU | A | 270 | 1.934  | 31.817 | 19.810 | 1.00 | 75.57  | A | C |
| ATOM | 1162 | CD2 | LEU | A | 270 | 0.604  | 31.738 | 17.682 | 1.00 | 79.94  | A | C |
| ATOM | 1163 | C   | LEU | A | 270 | -2.026 | 29.049 | 18.748 | 1.00 | 64.19  | A | C |
| ATOM | 1164 | O   | LEU | A | 270 | -2.729 | 28.239 | 19.327 | 1.00 | 64.26  | A | O |
| ATOM | 1165 | N   | LYS | A | 271 | -1.647 | 28.895 | 17.487 | 1.00 | 58.39  | A | N |
| ATOM | 1166 | CA  | LYS | A | 271 | -2.045 | 27.732 | 16.699 | 1.00 | 56.02  | A | C |
| ATOM | 1167 | CB  | LYS | A | 271 | -3.547 | 27.755 | 16.375 | 1.00 | 55.68  | A | C |
| ATOM | 1168 | CG  | LYS | A | 271 | -4.519 | 27.800 | 17.541 | 1.00 | 61.54  | A | C |
| ATOM | 1169 | CD  | LYS | A | 271 | -4.765 | 26.444 | 18.181 | 1.00 | 64.50  | A | C |
| ATOM | 1170 | CE  | LYS | A | 271 | -5.611 | 26.596 | 19.436 | 1.00 | 70.91  | A | C |
| ATOM | 1171 | NZ  | LYS | A | 271 | -5.876 | 25.314 | 20.130 | 1.00 | 72.98  | A | N |
| ATOM | 1172 | C   | LYS | A | 271 | -1.288 | 27.818 | 15.382 | 1.00 | 54.45  | A | C |
| ATOM | 1173 | O   | LYS | A | 271 | -1.839 | 28.316 | 14.390 | 1.00 | 48.43  | A | O |
| ATOM | 1174 | N   | ILE | A | 272 | -0.046 | 27.338 | 15.341 | 1.00 | 57.56  | A | N |
| ATOM | 1175 | CA  | ILE | A | 272 | 0.698  | 27.440 | 14.093 | 1.00 | 64.74  | A | C |
| ATOM | 1176 | CB  | ILE | A | 272 | 2.097  | 26.823 | 14.160 | 1.00 | 71.56  | A | C |
| ATOM | 1177 | CG2 | ILE | A | 272 | 2.897  | 27.459 | 15.274 | 1.00 | 74.70  | A | C |
| ATOM | 1178 | CG1 | ILE | A | 272 | 2.005  | 25.330 | 14.373 | 1.00 | 76.49  | A | C |
| ATOM | 1179 | CD1 | ILE | A | 272 | 3.344  | 24.679 | 14.255 | 1.00 | 81.85  | A | C |
| ATOM | 1180 | C   | ILE | A | 272 | -0.064 | 26.787 | 12.975 | 1.00 | 62.89  | A | C |
| ATOM | 1181 | O   | ILE | A | 272 | -0.654 | 25.731 | 13.144 | 1.00 | 56.99  | A | O |
| ATOM | 1182 | N   | ALA | A | 273 | -0.046 | 27.443 | 11.829 | 1.00 | 68.21  | A | N |
| ATOM | 1183 | CA  | ALA | A | 273 | -0.759 | 26.965 | 10.671 | 1.00 | 72.24  | A | C |
| ATOM | 1184 | CB  | ALA | A | 273 | -2.053 | 27.749 | 10.527 | 1.00 | 70.73  | A | C |
| ATOM | 1185 | C   | ALA | A | 273 | 0.067  | 27.077 | 9.396  | 1.00 | 77.78  | A | C |
| ATOM | 1186 | O   | ALA | A | 273 | 0.658  | 28.126 | 9.119  | 1.00 | 79.02  | A | O |
| ATOM | 1187 | N   | ASP | A | 274 | 0.035  | 26.007 | 8.595  | 1.00 | 82.60  | A | N |
| ATOM | 1188 | CA  | ASP | A | 274 | 0.738  | 25.932 | 7.302  | 1.00 | 85.59  | A | C |
| ATOM | 1189 | CB  | ASP | A | 274 | 1.937  | 24.984 | 7.422  | 1.00 | 78.15  | A | C |
| ATOM | 1190 | CG  | ASP | A | 274 | 2.878  | 25.385 | 8.543  | 1.00 | 77.45  | A | C |
| ATOM | 1191 | OD1 | ASP | A | 274 | 3.659  | 26.349 | 8.361  | 1.00 | 68.37  | A | O |
| ATOM | 1192 | OD2 | ASP | A | 274 | 2.818  | 24.744 | 9.615  | 1.00 | 80.34  | A | O |
| ATOM | 1193 | C   | ASP | A | 274 | -0.232 | 25.462 | 6.182  | 1.00 | 91.38  | A | C |
| ATOM | 1194 | O   | ASP | A | 274 | -1.398 | 25.889 | 6.158  | 1.00 | 91.55  | A | O |
| ATOM | 1195 | N   | PHE | A | 275 | 0.249  | 24.619 | 5.260  | 1.00 | 99.72  | A | N |
| ATOM | 1196 | CA  | PHE | A | 275 | -0.574 | 24.081 | 4.152  | 1.00 | 113.09 | A | C |
| ATOM | 1197 | CB  | PHE | A | 275 | -2.064 | 24.106 | 4.494  | 1.00 | 115.47 | A | C |
| ATOM | 1198 | CG  | PHE | A | 275 | -2.445 | 23.138 | 5.521  | 1.00 | 125.01 | A | C |
| ATOM | 1199 | CD1 | PHE | A | 275 | -2.657 | 23.551 | 6.841  | 1.00 | 128.90 | A | C |
| ATOM | 1200 | CD2 | PHE | A | 275 | -2.563 | 21.791 | 5.192  | 1.00 | 130.01 | A | C |
| ATOM | 1201 | CE1 | PHE | A | 275 | -2.990 | 22.623 | 7.841  | 1.00 | 133.49 | A | C |
| ATOM | 1202 | CE2 | PHE | A | 275 | -2.892 | 20.848 | 6.170  | 1.00 | 135.51 | A | C |
| ATOM | 1203 | CZ  | PHE | A | 275 | -3.109 | 21.265 | 7.504  | 1.00 | 136.40 | A | C |
| ATOM | 1204 | C   | PHE | A | 275 | -0.470 | 24.716 | 2.767  | 1.00 | 119.03 | A | C |
| ATOM | 1205 | O   | PHE | A | 275 | 0.508  | 24.561 | 2.026  | 1.00 | 123.97 | A | O |
| ATOM | 1206 | N   | GLY | A | 276 | -1.570 | 25.372 | 2.416  | 1.00 | 121.77 | A | N |
| ATOM | 1207 | CA  | GLY | A | 276 | -1.722 | 26.069 | 1.154  | 1.00 | 124.74 | A | C |
| ATOM | 1208 | C   | GLY | A | 276 | -2.484 | 27.306 | 1.590  | 1.00 | 126.82 | A | C |
| ATOM | 1209 | O   | GLY | A | 276 | -2.834 | 27.411 | 2.777  | 1.00 | 129.75 | A | O |

Figure 3T

| ATOM | 1210 | N   | TRP | A | 277 | -2.738 | 28.245 | 0.679  | 1.00 | 126.79 | A | N |
|------|------|-----|-----|---|-----|--------|--------|--------|------|--------|---|---|
| ATOM | 1211 | CA  | TRP | A | 277 | -3.431 | 29.492 | 1.048  | 1.00 | 126.04 | A | C |
| ATOM | 1212 | CB  | TRP | A | 277 | -2.410 | 30.492 | 1.663  | 1.00 | 121.80 | A | C |
| ATOM | 1213 | CG  | TRP | A | 277 | -1.275 | 29.799 | 2.419  | 1.00 | 117.48 | A | C |
| ATOM | 1214 | CD2 | TRP | A | 277 | -0.278 | 28.934 | 1.841  | 1.00 | 116.82 | A | C |
| ATOM | 1215 | CE2 | TRP | A | 277 | 0.414  | 28.313 | 2.912  | 1.00 | 117.21 | A | C |
| ATOM | 1216 | CE3 | TRP | A | 277 | 0.086  | 28.609 | 0.514  | 1.00 | 115.18 | A | C |
| ATOM | 1217 | CD1 | TRP | A | 277 | -1.131 | 29.688 | 3.783  | 1.00 | 113.36 | A | C |
| ATOM | 1218 | NE1 | TRP | A | 277 | -0.125 | 28.790 | 4.083  | 1.00 | 112.49 | A | N |
| ATOM | 1219 | CZ2 | TRP | A | 277 | 1.456  | 27.380 | 2.695  | 1.00 | 119.15 | A | C |
| ATOM | 1220 | CZ3 | TRP | A | 277 | 1.121  | 27.677 | 0.295  | 1.00 | 112.92 | A | C |
| ATOM | 1221 | CH2 | TRP | A | 277 | 1.791  | 27.078 | 1.381  | 1.00 | 116.41 | A | C |
| ATOM | 1222 | C   | TRP | A | 277 | -4.122 | 30.122 | -0.172 | 1.00 | 126.26 | A | C |
| ATOM | 1223 | O   | TRP | A | 277 | -3.648 | 29.892 | -1.311 | 1.00 | 127.14 | A | O |
| TER  | 1225 |     | TRP | A | 277 |        |        |        |      |        | A |   |
| ATOM | 1226 | C   | GLY | A | 291 | 9.725  | 38.836 | 3.931  | 1.00 | 96.32  | A | C |
| ATOM | 1227 | O   | GLY | A | 291 | 9.036  | 38.133 | 4.681  | 1.00 | 96.44  | A | O |
| ATOM | 1228 | N   | GLY | A | 291 | 11.317 | 40.806 | 3.965  | 1.00 | 92.80  | A | N |
| ATOM | 1229 | CA  | GLY | A | 291 | 9.904  | 40.330 | 4.180  | 1.00 | 96.64  | A | C |
| ATOM | 1230 | N   | THR | A | 292 | 10.340 | 38.352 | 2.856  | 1.00 | 94.78  | A | N |
| ATOM | 1231 | CA  | THR | A | 292 | 10.282 | 36.936 | 2.496  | 1.00 | 89.04  | A | C |
| ATOM | 1232 | CB  | THR | A | 292 | 10.385 | 36.722 | 0.969  | 1.00 | 91.48  | A | C |
| ATOM | 1233 | OG1 | THR | A | 292 | 9.554  | 37.669 | 0.273  | 1.00 | 84.85  | A | O |
| ATOM | 1234 | CG2 | THR | A | 292 | 9.950  | 35.300 | 0.631  | 1.00 | 92.75  | A | C |
| ATOM | 1235 | C   | THR | A | 292 | 11.485 | 36.251 | 3.154  | 1.00 | 83.29  | A | C |
| ATOM | 1236 | O   | THR | A | 292 | 11.423 | 35.059 | 3.485  | 1.00 | 82.70  | A | O |
| ATOM | 1237 | N   | LEU | A | 293 | 12.567 | 37.030 | 3.310  | 1.00 | 75.14  | A | N |
| ATOM | 1238 | CA  | LEU | A | 293 | 13.825 | 36.622 | 3.944  | 1.00 | 64.63  | A | C |
| ATOM | 1239 | CB  | LEU | A | 293 | 14.973 | 37.527 | 3.494  | 1.00 | 65.46  | A | C |
| ATOM | 1240 | CG  | LEU | A | 293 | 15.444 | 37.388 | 2.060  | 1.00 | 65.92  | A | C |
| ATOM | 1241 | CD1 | LEU | A | 293 | 16.228 | 38.585 | 1.603  | 1.00 | 63.00  | A | C |
| ATOM | 1242 | CD2 | LEU | A | 293 | 16.277 | 36.146 | 1.994  | 1.00 | 67.74  | A | C |
| ATOM | 1243 | C   | LEU | A | 293 | 13.686 | 36.776 | 5.453  | 1.00 | 55.24  | A | C |
| ATOM | 1244 | O   | LEU | A | 293 | 13.953 | 35.849 | 6.203  | 1.00 | 53.79  | A | O |
| ATOM | 1245 | N   | ASP | A | 294 | 13.260 | 37.970 | 5.869  | 1.00 | 46.46  | A | N |
| ATOM | 1246 | CA  | ASP | A | 294 | 13.088 | 38.350 | 7.274  | 1.00 | 39.11  | A | C |
| ATOM | 1247 | CB  | ASP | A | 294 | 11.857 | 39.245 | 7.485  | 1.00 | 37.16  | A | C |
| ATOM | 1248 | CG  | ASP | A | 294 | 12.019 | 40.664 | 6.920  | 1.00 | 40.47  | A | C |
| ATOM | 1249 | OD1 | ASP | A | 294 | 10.994 | 41.398 | 6.895  | 1.00 | 44.84  | A | O |
| ATOM | 1250 | OD2 | ASP | A | 294 | 13.141 | 41.053 | 6.519  | 1.00 | 38.47  | A | O |
| ATOM | 1251 | C   | ASP | A | 294 | 12.971 | 37.184 | 8.209  | 1.00 | 37.03  | A | C |
| ATOM | 1252 | O   | ASP | A | 294 | 13.207 | 37.364 | 9.380  | 1.00 | 35.97  | A | O |
| ATOM | 1253 | N   | TYR | A | 295 | 12.613 | 35.999 | 7.722  | 1.00 | 35.64  | A | N |
| ATOM | 1254 | CA  | TYR | A | 295 | 12.488 | 34.852 | 8.617  | 1.00 | 40.90  | A | C |
| ATOM | 1255 | CB  | TYR | A | 295 | 11.052 | 34.345 | 8.596  | 1.00 | 42.06  | A | C |
| ATOM | 1256 | CG  | TYR | A | 295 | 10.140 | 35.320 | 9.264  | 1.00 | 48.52  | A | C |
| ATOM | 1257 | CD1 | TYR | A | 295 | 9.385  | 36.233 | 8.510  | 1.00 | 46.39  | A | C |
| ATOM | 1258 | CE1 | TYR | A | 295 | 8.691  | 37.236 | 9.129  | 1.00 | 47.97  | A | C |
| ATOM | 1259 | CD2 | TYR | A | 295 | 10.150 | 35.440 | 10.660 | 1.00 | 49.00  | A | C |
| ATOM | 1260 | CE2 | TYR | A | 295 | 9.463  | 36.439 | 11.288 | 1.00 | 48.15  | A | C |
| ATOM | 1261 | CZ  | TYR | A | 295 | 8.749  | 37.338 | 10.523 | 1.00 | 52.16  | A | C |
| ATOM | 1262 | OH  | TYR | A | 295 | 8.174  | 38.399 | 11.156 | 1.00 | 52.12  | A | O |
| ATOM | 1263 | C   | TYR | A | 295 | 13.421 | 33.658 | 8.468  | 1.00 | 42.76  | A | C |
| ATOM | 1264 | O   | TYR | A | 295 | 13.786 | 33.001 | 9.444  | 1.00 | 41.69  | A | O |
| ATOM | 1265 | N   | LEU | A | 296 | 13.793 | 33.344 | 7.248  | 1.00 | 43.93  | A | N |
| ATOM | 1266 | CA  | LEU | A | 296 | 14.650 | 32.195 | 7.059  | 1.00 | 40.96  | A | C |
| ATOM | 1267 | CB  | LEU | A | 296 | 14.939 | 32.017 | 5.563  | 1.00 | 47.98  | A | C |
| ATOM | 1268 | CG  | LEU | A | 296 | 13.740 | 32.233 | 4.618  | 1.00 | 52.97  | A | C |
| ATOM | 1269 | CD1 | LEU | A | 296 | 14.214 | 32.475 | 3.198  | 1.00 | 58.28  | A | C |
| ATOM | 1270 | CD2 | LEU | A | 296 | 12.805 | 31.049 | 4.674  | 1.00 | 58.38  | A | C |
| ATOM | 1271 | C   | LEU | A | 296 | 15.926 | 32.529 | 7.834  | 1.00 | 38.62  | A | C |

Figure 3U

| ATOM | 1272 | O | LEU | A | 296 | 16.195 | 33.698 | 8.136 | 1.00 | 38.87 | A | O |
|---|---|---|---|---|---|---|---|---|---|---|---|---|
| ATOM | 1273 | N | PRO | A | 297 | 16.708 | 31.508 | 8.199 | 1.00 | 37.70 | A | N |
| ATOM | 1274 | CD | PRO | A | 297 | 16.323 | 30.095 | 8.111 | 1.00 | 40.76 | A | C |
| ATOM | 1275 | CA | PRO | A | 297 | 17.966 | 31.643 | 8.935 | 1.00 | 41.77 | A | C |
| ATOM | 1276 | CB | PRO | A | 297 | 17.951 | 30.421 | 9.808 | 1.00 | 40.27 | A | C |
| ATOM | 1277 | CG | PRO | A | 297 | 17.478 | 29.404 | 8.824 | 1.00 | 41.45 | A | C |
| ATOM | 1278 | C | PRO | A | 297 | 19.094 | 31.594 | 7.883 | 1.00 | 42.30 | A | C |
| ATOM | 1279 | O | PRO | A | 297 | 18.831 | 31.258 | 6.717 | 1.00 | 42.54 | A | O |
| ATOM | 1280 | N | PRO | A | 298 | 20.356 | 31.910 | 8.268 | 1.00 | 42.84 | A | N |
| ATOM | 1281 | CD | PRO | A | 298 | 20.833 | 32.537 | 9.513 | 1.00 | 47.33 | A | C |
| ATOM | 1282 | CA | PRO | A | 298 | 21.441 | 31.880 | 7.285 | 1.00 | 40.17 | A | C |
| ATOM | 1283 | CB | PRO | A | 298 | 22.641 | 32.334 | 8.096 | 1.00 | 42.71 | A | C |
| ATOM | 1284 | CG | PRO | A | 298 | 22.033 | 33.320 | 9.029 | 1.00 | 41.22 | A | C |
| ATOM | 1285 | C | PRO | A | 298 | 21.673 | 30.570 | 6.567 | 1.00 | 39.59 | A | C |
| ATOM | 1286 | O | PRO | A | 298 | 21.985 | 30.568 | 5.380 | 1.00 | 35.71 | A | O |
| ATOM | 1287 | N | GLU | A | 299 | 21.513 | 29.455 | 7.262 | 1.00 | 39.73 | A | N |
| ATOM | 1288 | CA | GLU | A | 299 | 21.727 | 28.194 | 6.581 | 1.00 | 48.18 | A | C |
| ATOM | 1289 | CB | GLU | A | 299 | 21.401 | 27.005 | 7.484 | 1.00 | 52.94 | A | C |
| ATOM | 1290 | CG | GLU | A | 299 | 20.298 | 27.252 | 8.467 | 1.00 | 59.22 | A | C |
| ATOM | 1291 | CD | GLU | A | 299 | 20.832 | 27.543 | 9.845 | 1.00 | 60.28 | A | C |
| ATOM | 1292 | OE1 | GLU | A | 299 | 20.745 | 26.641 | 10.706 | 1.00 | 58.87 | A | O |
| ATOM | 1293 | OE2 | GLU | A | 299 | 21.346 | 28.664 | 10.059 | 1.00 | 60.59 | A | O |
| ATOM | 1294 | C | GLU | A | 299 | 20.936 | 28.074 | 5.286 | 1.00 | 53.50 | A | C |
| ATOM | 1295 | O | GLU | A | 299 | 21.482 | 27.645 | 4.267 | 1.00 | 54.44 | A | O |
| ATOM | 1296 | N | MET | A | 300 | 19.661 | 28.463 | 5.305 | 1.00 | 60.34 | A | N |
| ATOM | 1297 | CA | MET | A | 300 | 18.847 | 28.337 | 4.101 | 1.00 | 67.53 | A | C |
| ATOM | 1298 | CB | MET | A | 300 | 17.390 | 28.030 | 4.464 | 1.00 | 74.61 | A | C |
| ATOM | 1299 | CG | MET | A | 300 | 16.634 | 27.340 | 3.324 | 1.00 | 92.03 | A | C |
| ATOM | 1300 | SD | MET | A | 300 | 14.890 | 27.852 | 3.118 | 1.00 | 108.94 | A | S |
| ATOM | 1301 | CE | MET | A | 300 | 14.843 | 28.434 | 1.366 | 1.00 | 102.65 | A | C |
| ATOM | 1302 | C | MET | A | 300 | 18.908 | 29.531 | 3.137 | 1.00 | 68.22 | A | C |
| ATOM | 1303 | O | MET | A | 300 | 18.480 | 29.429 | 1.982 | 1.00 | 72.31 | A | O |
| ATOM | 1304 | N | ILE | A | 301 | 19.415 | 30.671 | 3.580 | 1.00 | 65.22 | A | N |
| ATOM | 1305 | CA | ILE | A | 301 | 19.499 | 31.750 | 2.629 | 1.00 | 65.47 | A | C |
| ATOM | 1306 | CB | ILE | A | 301 | 19.494 | 33.124 | 3.309 | 1.00 | 67.97 | A | C |
| ATOM | 1307 | CG2 | ILE | A | 301 | 18.537 | 33.090 | 4.473 | 1.00 | 67.42 | A | C |
| ATOM | 1308 | CG1 | ILE | A | 301 | 20.891 | 33.509 | 3.792 | 1.00 | 74.32 | A | C |
| ATOM | 1309 | CD1 | ILE | A | 301 | 20.989 | 34.937 | 4.307 | 1.00 | 75.01 | A | C |
| ATOM | 1310 | C | ILE | A | 301 | 20.812 | 31.499 | 1.906 | 1.00 | 65.29 | A | C |
| ATOM | 1311 | O | ILE | A | 301 | 20.937 | 31.753 | 0.713 | 1.00 | 60.84 | A | O |
| ATOM | 1312 | N | GLU | A | 302 | 21.783 | 30.960 | 2.643 | 1.00 | 66.82 | A | N |
| ATOM | 1313 | CA | GLU | A | 302 | 23.101 | 30.644 | 2.087 | 1.00 | 67.89 | A | C |
| ATOM | 1314 | CB | GLU | A | 302 | 24.174 | 30.609 | 3.202 | 1.00 | 68.22 | A | C |
| ATOM | 1315 | CG | GLU | A | 302 | 24.479 | 31.983 | 3.835 | 1.00 | 70.47 | A | C |
| ATOM | 1316 | CD | GLU | A | 302 | 25.273 | 31.920 | 5.150 | 1.00 | 68.65 | A | C |
| ATOM | 1317 | OE1 | GLU | A | 302 | 24.969 | 31.050 | 5.996 | 1.00 | 65.41 | A | O |
| ATOM | 1318 | OE2 | GLU | A | 302 | 26.184 | 32.760 | 5.353 | 1.00 | 71.35 | A | O |
| ATOM | 1319 | C | GLU | A | 302 | 23.049 | 29.301 | 1.347 | 1.00 | 68.13 | A | C |
| ATOM | 1320 | O | GLU | A | 302 | 24.036 | 28.875 | 0.749 | 1.00 | 64.17 | A | O |
| ATOM | 1321 | N | GLY | A | 303 | 21.891 | 28.641 | 1.393 | 1.00 | 70.39 | A | N |
| ATOM | 1322 | CA | GLY | A | 303 | 21.710 | 27.372 | 0.705 | 1.00 | 73.08 | A | C |
| ATOM | 1323 | C | GLY | A | 303 | 22.464 | 26.178 | 1.255 | 1.00 | 75.93 | A | C |
| ATOM | 1324 | O | GLY | A | 303 | 22.531 | 25.128 | 0.612 | 1.00 | 71.91 | A | O |
| ATOM | 1325 | N | ARG | A | 304 | 23.053 | 26.338 | 2.431 | 1.00 | 81.09 | A | N |
| ATOM | 1326 | CA | ARG | A | 304 | 23.775 | 25.251 | 3.064 | 1.00 | 87.87 | A | C |
| ATOM | 1327 | CB | ARG | A | 304 | 24.483 | 25.759 | 4.309 | 1.00 | 88.53 | A | C |
| ATOM | 1328 | CG | ARG | A | 304 | 25.470 | 26.878 | 4.043 | 1.00 | 94.07 | A | C |
| ATOM | 1329 | CD | ARG | A | 304 | 25.980 | 27.482 | 5.347 | 1.00 | 101.65 | A | C |
| ATOM | 1330 | NE | ARG | A | 304 | 26.288 | 26.452 | 6.332 | 1.00 | 108.61 | A | N |
| ATOM | 1331 | CZ | ARG | A | 304 | 27.083 | 25.410 | 6.100 | 1.00 | 111.93 | A | C |
| ATOM | 1332 | NH1 | ARG | A | 304 | 27.658 | 25.248 | 4.909 | 1.00 | 112.63 | A | N |

Figure 3V

```
ATOM   1333  NH2 ARG A 304      27.305  24.523   7.060  1.00 113.14      A    N
ATOM   1334  C   ARG A 304      22.706  24.246   3.458  1.00  93.23      A    C
ATOM   1335  O   ARG A 304      21.526  24.464   3.188  1.00  93.41      A    O
ATOM   1336  N   MET A 305      23.092  23.144   4.092  1.00 100.97      A    N
ATOM   1337  CA  MET A 305      22.081  22.172   4.499  1.00 107.01      A    C
ATOM   1338  CB  MET A 305      22.594  20.709   4.403  1.00 115.87      A    C
ATOM   1339  CG  MET A 305      23.798  20.321   5.263  1.00 126.37      A    C
ATOM   1340  SD  MET A 305      25.396  20.345   4.397  1.00 135.35      A    S
ATOM   1341  CE  MET A 305      26.108  21.926   5.032  1.00 138.87      A    C
ATOM   1342  C   MET A 305      21.579  22.503   5.905  1.00 104.19      A    C
ATOM   1343  O   MET A 305      22.271  22.314   6.919  1.00 101.63      A    O
ATOM   1344  N   HIS A 306      20.368  23.047   5.933  1.00 103.03      A    N
ATOM   1345  CA  HIS A 306      19.703  23.430   7.169  1.00 102.83      A    C
ATOM   1346  CB  HIS A 306      18.627  24.460   6.864  1.00 112.22      A    C
ATOM   1347  CG  HIS A 306      17.630  23.980   5.860  1.00 118.55      A    C
ATOM   1348  CD2 HIS A 306      16.413  23.408   6.020  1.00 120.69      A    C
ATOM   1349  ND1 HIS A 306      17.896  23.950   4.509  1.00 121.52      A    N
ATOM   1350  CE1 HIS A 306      16.887  23.376   3.880  1.00 123.44      A    C
ATOM   1351  NE2 HIS A 306      15.975  23.037   4.774  1.00 125.05      A    N
ATOM   1352  C   HIS A 306      19.039  22.174   7.690  1.00  97.06      A    C
ATOM   1353  O   HIS A 306      18.811  21.247   6.916  1.00  97.46      A    O
ATOM   1354  N   ASP A 307      18.711  22.143   8.978  1.00  89.60      A    N
ATOM   1355  CA  ASP A 307      18.064  20.973   9.538  1.00  83.24      A    C
ATOM   1356  CB  ASP A 307      18.902  19.701   9.264  1.00  85.61      A    C
ATOM   1357  CG  ASP A 307      18.217  18.712   8.277  1.00  88.63      A    C
ATOM   1358  OD1 ASP A 307      18.137  19.010   7.057  1.00  91.87      A    O
ATOM   1359  OD2 ASP A 307      17.759  17.626   8.723  1.00  86.12      A    O
ATOM   1360  C   ASP A 307      17.806  21.060  11.026  1.00  77.32      A    C
ATOM   1361  O   ASP A 307      18.729  20.909  11.820  1.00  70.83      A    O
ATOM   1362  N   GLU A 308      16.555  21.318  11.396  1.00  75.53      A    N
ATOM   1363  CA  GLU A 308      16.137  21.334  12.803  1.00  74.45      A    C
ATOM   1364  CB  GLU A 308      16.527  20.012  13.457  1.00  80.50      A    C
ATOM   1365  CG  GLU A 308      17.095  20.185  14.847  1.00  82.30      A    C
ATOM   1366  CD  GLU A 308      17.628  18.894  15.416  1.00  85.17      A    C
ATOM   1367  OE1 GLU A 308      18.431  18.218  14.724  1.00  86.56      A    O
ATOM   1368  OE2 GLU A 308      17.243  18.565  16.561  1.00  89.63      A    O
ATOM   1369  C   GLU A 308      16.504  22.450  13.775  1.00  66.36      A    C
ATOM   1370  O   GLU A 308      15.805  22.633  14.774  1.00  63.84      A    O
ATOM   1371  N   LYS A 309      17.607  23.151  13.544  1.00  54.88      A    N
ATOM   1372  CA  LYS A 309      17.972  24.253  14.434  1.00  45.13      A    C
ATOM   1373  CB  LYS A 309      19.483  24.538  14.371  1.00  30.83      A    C
ATOM   1378  C   LYS A 309      17.175  25.498  13.998  1.00  41.19      A    C
ATOM   1379  O   LYS A 309      16.820  26.347  14.833  1.00  33.26      A    O
ATOM   1380  N   VAL A 310      16.850  25.572  12.702  1.00  40.89      A    N
ATOM   1381  CA  VAL A 310      16.136  26.724  12.185  1.00  43.85      A    C
ATOM   1382  CB  VAL A 310      15.514  26.525  10.755  1.00  49.26      A    C
ATOM   1383  CG1 VAL A 310      16.500  25.886   9.828  1.00  51.33      A    C
ATOM   1384  CG2 VAL A 310      14.267  25.733  10.822  1.00  48.70      A    C
ATOM   1385  C   VAL A 310      15.047  27.067  13.161  1.00  43.38      A    C
ATOM   1386  O   VAL A 310      15.006  28.189  13.645  1.00  49.35      A    O
ATOM   1387  N   ASP A 311      14.201  26.104  13.507  1.00  41.66      A    N
ATOM   1388  CA  ASP A 311      13.100  26.396  14.415  1.00  42.10      A    C
ATOM   1389  CB  ASP A 311      12.473  25.118  14.941  1.00  45.22      A    C
ATOM   1390  CG  ASP A 311      11.630  24.456  13.916  1.00  42.00      A    C
ATOM   1391  OD1 ASP A 311      10.958  25.198  13.181  1.00  38.71      A    O
ATOM   1392  OD2 ASP A 311      11.633  23.217  13.833  1.00  38.86      A    O
ATOM   1393  C   ASP A 311      13.460  27.297  15.572  1.00  39.54      A    C
ATOM   1394  O   ASP A 311      12.593  27.985  16.116  1.00  32.58      A    O
ATOM   1395  N   LEU A 312      14.735  27.305  15.940  1.00  39.95      A    N
ATOM   1396  CA  LEU A 312      15.189  28.147  17.030  1.00  43.57      A    C
ATOM   1397  CB  LEU A 312      16.472  27.561  17.616  1.00  47.41      A    C
```

Figure 3W

```
ATOM   1398  CG   LEU A 312      16.319  26.628  18.811  1.00  50.01      A    C
ATOM   1399  CD1  LEU A 312      15.921  27.432  20.015  1.00  56.88      A    C
ATOM   1400  CD2  LEU A 312      15.296  25.571  18.526  1.00  54.49      A    C
ATOM   1401  C    LEU A 312      15.415  29.588  16.554  1.00  41.41      A    C
ATOM   1402  O    LEU A 312      15.236  30.539  17.315  1.00  38.14      A    O
ATOM   1403  N    TRP A 313      15.812  29.726  15.291  1.00  42.35      A    N
ATOM   1404  CA   TRP A 313      16.070  31.016  14.667  1.00  47.76      A    C
ATOM   1405  CB   TRP A 313      17.037  30.830  13.491  1.00  57.23      A    C
ATOM   1406  CG   TRP A 313      17.273  32.039  12.647  1.00  62.84      A    C
ATOM   1407  CD2  TRP A 313      18.469  32.828  12.569  1.00  63.97      A    C
ATOM   1408  CE2  TRP A 313      18.228  33.858  11.650  1.00  61.27      A    C
ATOM   1409  CE3  TRP A 313      19.716  32.765  13.188  1.00  70.04      A    C
ATOM   1410  CD1  TRP A 313      16.394  32.604  11.796  1.00  66.64      A    C
ATOM   1411  NE1  TRP A 313      16.954  33.698  11.187  1.00  64.38      A    N
ATOM   1412  CZ2  TRP A 313      19.188  34.820  11.329  1.00  60.63      A    C
ATOM   1413  CZ3  TRP A 313      20.675  33.729  12.863  1.00  70.23      A    C
ATOM   1414  CH2  TRP A 313      20.400  34.739  11.946  1.00  62.67      A    C
ATOM   1415  C    TRP A 313      14.739  31.578  14.211  1.00  46.05      A    C
ATOM   1416  O    TRP A 313      14.490  32.773  14.319  1.00  46.23      A    O
ATOM   1417  N    SER A 314      13.880  30.716  13.691  1.00  44.50      A    N
ATOM   1418  CA   SER A 314      12.562  31.160  13.292  1.00  40.25      A    C
ATOM   1419  CB   SER A 314      11.718  29.976  12.825  1.00  40.94      A    C
ATOM   1421  C    SER A 314      12.014  31.719  14.596  1.00  37.13      A    C
ATOM   1422  O    SER A 314      11.549  32.849  14.663  1.00  37.32      A    O
ATOM   1423  N    LEU A 315      12.132  30.917  15.646  1.00  32.06      A    N
ATOM   1424  CA   LEU A 315      11.692  31.258  17.009  1.00  33.25      A    C
ATOM   1425  CB   LEU A 315      11.880  30.045  17.909  1.00  36.08      A    C
ATOM   1426  CG   LEU A 315      10.984  30.133  19.126  1.00  37.55      A    C
ATOM   1427  CD1  LEU A 315       9.700  29.399  18.757  1.00  37.40      A    C
ATOM   1428  CD2  LEU A 315      11.636  29.536  20.360  1.00  38.11      A    C
ATOM   1429  C    LEU A 315      12.402  32.462  17.696  1.00  32.34      A    C
ATOM   1430  O    LEU A 315      11.916  33.038  18.678  1.00  29.15      A    O
ATOM   1431  N    GLY A 316      13.586  32.804  17.220  1.00  31.11      A    N
ATOM   1432  CA   GLY A 316      14.271  33.922  17.812  1.00  25.39      A    C
ATOM   1433  C    GLY A 316      13.645  35.116  17.161  1.00  22.09      A    C
ATOM   1434  O    GLY A 316      12.932  35.867  17.796  1.00  20.03      A    O
ATOM   1435  N    VAL A 317      13.883  35.256  15.869  1.00  22.56      A    N
ATOM   1436  CA   VAL A 317      13.360  36.384  15.165  1.00  28.75      A    C
ATOM   1437  CB   VAL A 317      13.150  36.087  13.686  1.00  32.79      A    C
ATOM   1438  CG1  VAL A 317      12.434  37.269  13.041  1.00  33.42      A    C
ATOM   1439  CG2  VAL A 317      14.478  35.864  12.993  1.00  37.69      A    C
ATOM   1440  C    VAL A 317      12.040  36.817  15.771  1.00  30.61      A    C
ATOM   1441  O    VAL A 317      11.937  37.932  16.316  1.00  30.27      A    O
ATOM   1442  N    LEU A 318      11.047  35.925  15.698  1.00  29.05      A    N
ATOM   1443  CA   LEU A 318       9.693  36.184  16.211  1.00  24.26      A    C
ATOM   1444  CB   LEU A 318       8.967  34.841  16.474  1.00  30.26      A    C
ATOM   1445  CG   LEU A 318       7.591  34.451  15.889  1.00  39.57      A    C
ATOM   1446  CD1  LEU A 318       6.988  35.636  15.191  1.00  43.99      A    C
ATOM   1447  CD2  LEU A 318       7.716  33.278  14.917  1.00  38.41      A    C
ATOM   1448  C    LEU A 318       9.736  37.037  17.492  1.00  20.55      A    C
ATOM   1449  O    LEU A 318       9.384  38.216  17.483  1.00  10.54      A    O
ATOM   1450  N    CYS A 319      10.188  36.433  18.583  1.00  25.03      A    N
ATOM   1451  CA   CYS A 319      10.288  37.108  19.868  1.00  29.70      A    C
ATOM   1452  CB   CYS A 319      11.318  36.369  20.751  1.00  38.57      A    C
ATOM   1453  SG   CYS A 319      11.544  36.901  22.509  1.00  46.56      A    S
ATOM   1454  C    CYS A 319      10.684  38.572  19.656  1.00  25.40      A    C
ATOM   1455  O    CYS A 319      10.046  39.472  20.197  1.00  23.93      A    O
ATOM   1456  N    TYR A 320      11.719  38.822  18.862  1.00  21.10      A    N
ATOM   1457  CA   TYR A 320      12.131  40.202  18.627  1.00  24.44      A    C
ATOM   1458  CB   TYR A 320      13.287  40.251  17.625  1.00  31.60      A    C
ATOM   1459  CG   TYR A 320      13.866  41.638  17.371  1.00  38.15      A    C
```

Figure 3X

```
ATOM   1460  CD1 TYR A 320      14.560  42.334  18.365  1.00  38.02      A    C
ATOM   1461  CE1 TYR A 320      15.154  43.584  18.098  1.00  38.53      A    C
ATOM   1462  CD2 TYR A 320      13.772  42.226  16.111  1.00  42.15      A    C
ATOM   1463  CE2 TYR A 320      14.361  43.472  15.837  1.00  43.63      A    C
ATOM   1464  CZ  TYR A 320      15.052  44.145  16.829  1.00  40.37      A    C
ATOM   1465  OH  TYR A 320      15.639  45.357  16.522  1.00  32.05      A    O
ATOM   1466  C   TYR A 320      10.973  41.056  18.091  1.00  24.68      A    C
ATOM   1467  O   TYR A 320      10.692  42.154  18.608  1.00  18.16      A    O
ATOM   1468  N   GLU A 321      10.298  40.541  17.060  1.00  27.62      A    N
ATOM   1469  CA  GLU A 321       9.214  41.288  16.435  1.00  33.94      A    C
ATOM   1470  CB  GLU A 321       8.771  40.691  15.111  1.00  42.38      A    C
ATOM   1471  CG  GLU A 321       7.834  41.622  14.373  1.00  55.72      A    C
ATOM   1472  CD  GLU A 321       7.233  40.995  13.137  1.00  62.86      A    C
ATOM   1473  OE1 GLU A 321       7.978  40.301  12.419  1.00  66.45      A    O
ATOM   1474  OE2 GLU A 321       6.030  41.204  12.871  1.00  69.35      A    O
ATOM   1475  C   GLU A 321       8.009  41.416  17.295  1.00  32.32      A    C
ATOM   1476  O   GLU A 321       7.174  42.260  17.022  1.00  32.55      A    O
ATOM   1477  N   PHE A 322       7.890  40.571  18.310  1.00  32.13      A    N
ATOM   1478  CA  PHE A 322       6.756  40.686  19.210  1.00  31.66      A    C
ATOM   1479  CB  PHE A 322       6.621  39.470  20.109  1.00  27.27      A    C
ATOM   1480  CG  PHE A 322       6.153  38.255  19.401  1.00  27.63      A    C
ATOM   1481  CD1 PHE A 322       5.389  38.367  18.239  1.00  23.79      A    C
ATOM   1482  CD2 PHE A 322       6.450  36.990  19.901  1.00  31.93      A    C
ATOM   1483  CE1 PHE A 322       4.927  37.250  17.583  1.00  21.66      A    C
ATOM   1484  CE2 PHE A 322       5.989  35.856  19.254  1.00  34.07      A    C
ATOM   1485  CZ  PHE A 322       5.224  35.988  18.089  1.00  30.95      A    C
ATOM   1486  C   PHE A 322       7.043  41.880  20.082  1.00  36.50      A    C
ATOM   1487  O   PHE A 322       6.160  42.696  20.344  1.00  36.31      A    O
ATOM   1488  N   LEU A 323       8.303  41.980  20.509  1.00  44.09      A    N
ATOM   1489  CA  LEU A 323       8.772  43.051  21.383  1.00  49.16      A    C
ATOM   1490  CB  LEU A 323      10.048  42.613  22.105  1.00  52.42      A    C
ATOM   1491  CG  LEU A 323       9.935  41.515  23.155  1.00  52.95      A    C
ATOM   1492  CD1 LEU A 323      11.219  41.424  23.956  1.00  54.05      A    C
ATOM   1493  CD2 LEU A 323       8.773  41.850  24.065  1.00  55.22      A    C
ATOM   1494  C   LEU A 323       9.042  44.386  20.712  1.00  50.67      A    C
ATOM   1495  O   LEU A 323       9.130  45.405  21.398  1.00  49.63      A    O
ATOM   1496  N   VAL A 324       9.187  44.393  19.387  1.00  50.72      A    N
ATOM   1497  CA  VAL A 324       9.482  45.640  18.689  1.00  51.71      A    C
ATOM   1498  CB  VAL A 324      10.920  45.663  18.164  1.00  48.45      A    C
ATOM   1499  CG1 VAL A 324      11.397  47.103  18.059  1.00  46.20      A    C
ATOM   1500  CG2 VAL A 324      11.817  44.853  19.050  1.00  51.44      A    C
ATOM   1501  C   VAL A 324       8.596  45.963  17.502  1.00  51.30      A    C
ATOM   1502  O   VAL A 324       8.847  46.922  16.772  1.00  55.61      A    O
ATOM   1503  N   GLY A 325       7.573  45.173  17.272  1.00  44.65      A    N
ATOM   1504  CA  GLY A 325       6.743  45.502  16.146  1.00  42.97      A    C
ATOM   1505  C   GLY A 325       7.394  45.291  14.789  1.00  43.64      A    C
ATOM   1506  O   GLY A 325       6.720  45.497  13.785  1.00  43.99      A    O
ATOM   1507  N   LYS A 326       8.674  44.925  14.714  1.00  44.17      A    N
ATOM   1508  CA  LYS A 326       9.277  44.649  13.396  1.00  44.93      A    C
ATOM   1509  CB  LYS A 326       9.713  45.919  12.664  1.00  50.16      A    C
ATOM   1510  CG  LYS A 326      10.860  46.622  13.296  1.00  58.50      A    C
ATOM   1511  CD  LYS A 326      11.300  47.773  12.424  1.00  69.92      A    C
ATOM   1512  CE  LYS A 326      12.146  48.769  13.210  1.00  76.56      A    C
ATOM   1513  NZ  LYS A 326      11.357  49.501  14.249  1.00  81.05      A    N
ATOM   1514  C   LYS A 326      10.448  43.678  13.461  1.00  40.86      A    C
ATOM   1515  O   LYS A 326      11.016  43.441  14.522  1.00  32.62      A    O
ATOM   1516  N   PRO A 327      10.805  43.078  12.318  1.00  42.70      A    N
ATOM   1517  CD  PRO A 327      10.062  42.972  11.050  1.00  47.67      A    C
ATOM   1518  CA  PRO A 327      11.915  42.137  12.324  1.00  44.41      A    C
ATOM   1519  CB  PRO A 327      11.818  41.474  10.945  1.00  50.93      A    C
ATOM   1520  CG  PRO A 327      10.353  41.537  10.632  1.00  50.00      A    C
```

Figure 3Y

```
ATOM   1521  C    PRO A 327      13.263  42.795  12.570  1.00  40.13           A C
ATOM   1522  O    PRO A 327      13.417  43.999  12.449  1.00  28.48           A O
ATOM   1523  N    PRO A 328      14.258  41.983  12.921  1.00  40.30           A N
ATOM   1524  CD   PRO A 328      14.062  40.530  13.104  1.00  40.51           A C
ATOM   1525  CA   PRO A 328      15.630  42.359  13.216  1.00  43.78           A C
ATOM   1526  CB   PRO A 328      16.094  41.192  14.053  1.00  42.57           A C
ATOM   1527  CG   PRO A 328      15.437  40.035  13.349  1.00  42.85           A C
ATOM   1528  C    PRO A 328      16.483  42.554  11.968  1.00  49.81           A C
ATOM   1529  O    PRO A 328      17.504  43.243  11.992  1.00  47.07           A O
ATOM   1530  N    PHE A 329      16.076  41.947  10.867  1.00  55.71           A N
ATOM   1531  CA   PHE A 329      16.855  42.107   9.663  1.00  59.76           A C
ATOM   1532  CB   PHE A 329      17.376  40.741   9.242  1.00  60.96           A C
ATOM   1533  CG   PHE A 329      18.054  40.007  10.346  1.00  61.29           A C
ATOM   1534  CD1  PHE A 329      19.341  40.322  10.716  1.00  61.25           A C
ATOM   1535  CD2  PHE A 329      17.371  39.046  11.071  1.00  67.49           A C
ATOM   1536  CE1  PHE A 329      19.938  39.693  11.798  1.00  62.91           A C
ATOM   1537  CE2  PHE A 329      17.962  38.410  12.159  1.00  68.85           A C
ATOM   1538  CZ   PHE A 329      19.245  38.737  12.520  1.00  66.33           A C
ATOM   1539  C    PHE A 329      16.041  42.795   8.558  1.00  61.32           A C
ATOM   1540  O    PHE A 329      16.449  42.857   7.397  1.00  63.12           A O
ATOM   1541  N    GLU A 330      14.880  43.321   8.928  1.00  62.98           A N
ATOM   1542  CA   GLU A 330      14.038  44.037   7.982  1.00  64.41           A C
ATOM   1543  CB   GLU A 330      12.821  44.623   8.710  1.00  68.90           A C
ATOM   1544  CG   GLU A 330      11.975  45.598   7.891  1.00  70.67           A C
ATOM   1545  CD   GLU A 330      10.776  46.124   8.666  1.00  73.43           A C
ATOM   1546  OE1  GLU A 330       9.879  45.317   8.993  1.00  74.41           A O
ATOM   1547  OE2  GLU A 330      10.735  47.340   8.953  1.00  73.94           A O
ATOM   1548  C    GLU A 330      14.901  45.152   7.389  1.00  62.88           A C
ATOM   1549  O    GLU A 330      15.841  45.632   8.040  1.00  64.68           A O
ATOM   1550  N    ALA A 331      14.591  45.552   6.158  1.00  58.49           A N
ATOM   1551  CA   ALA A 331      15.366  46.593   5.509  1.00  55.73           A C
ATOM   1552  CB   ALA A 331      16.832  46.196   5.506  1.00  52.91           A C
ATOM   1553  C    ALA A 331      14.935  46.956   4.095  1.00  57.63           A C
ATOM   1554  O    ALA A 331      14.187  46.238   3.445  1.00  53.53           A O
ATOM   1555  N    ASN A 332      15.463  48.084   3.638  1.00  67.25           A N
ATOM   1556  CA   ASN A 332      15.217  48.677   2.319  1.00  76.89           A C
ATOM   1557  CB   ASN A 332      16.027  49.977   2.217  1.00  79.62           A C
ATOM   1558  CG   ASN A 332      17.529  49.763   2.525  1.00  81.85           A C
ATOM   1559  OD1  ASN A 332      17.926  49.577   3.683  1.00  82.59           A O
ATOM   1560  ND2  ASN A 332      18.357  49.777   1.482  1.00  80.21           A N
ATOM   1561  C    ASN A 332      15.525  47.839   1.070  1.00  79.53           A C
ATOM   1562  O    ASN A 332      16.005  48.399   0.083  1.00  82.00           A O
ATOM   1563  N    THR A 333      15.252  46.533   1.095  1.00  79.64           A N
ATOM   1564  CA   THR A 333      15.540  45.650  -0.051  1.00  80.36           A C
ATOM   1565  CB   THR A 333      16.558  46.301  -1.046  1.00  83.37           A C
ATOM   1566  OG1  THR A 333      16.549  45.584  -2.285  1.00  91.78           A O
ATOM   1567  CG2  THR A 333      17.973  46.284  -0.474  1.00  76.50           A C
ATOM   1568  C    THR A 333      16.116  44.294   0.398  1.00  74.55           A C
ATOM   1569  O    THR A 333      16.563  44.139   1.533  1.00  74.67           A O
ATOM   1570  N    TYR A 334      16.117  43.314  -0.495  1.00  64.53           A N
ATOM   1571  CA   TYR A 334      16.636  42.015  -0.139  1.00  56.54           A C
ATOM   1572  CB   TYR A 334      16.362  40.997  -1.244  1.00  57.90           A C
ATOM   1573  CG   TYR A 334      14.911  40.659  -1.463  1.00  61.02           A C
ATOM   1574  CD1  TYR A 334      13.963  40.858  -0.461  1.00  65.37           A C
ATOM   1575  CE1  TYR A 334      12.614  40.552  -0.671  1.00  69.31           A C
ATOM   1576  CD2  TYR A 334      14.481  40.140  -2.678  1.00  64.19           A C
ATOM   1577  CE2  TYR A 334      13.138  39.832  -2.901  1.00  67.31           A C
ATOM   1578  CZ   TYR A 334      12.210  40.041  -1.897  1.00  69.75           A C
ATOM   1579  OH   TYR A 334      10.884  39.755  -2.132  1.00  71.23           A O
ATOM   1580  C    TYR A 334      18.130  42.024   0.164  1.00  54.62           A C
ATOM   1581  O    TYR A 334      18.588  41.231   0.974  1.00  54.28           A O
```

Figure 3Z

| ATOM | 1582 | N | GLN | A | 335 | 18.905 | 42.898 | -0.471 | 1.00 | 52.79 | A | N |
|---|---|---|---|---|---|---|---|---|---|---|---|---|
| ATOM | 1583 | CA | GLN | A | 335 | 20.337 | 42.916 | -0.200 | 1.00 | 51.08 | A | C |
| ATOM | 1584 | CB | GLN | A | 335 | 21.039 | 43.971 | -1.040 | 1.00 | 56.98 | A | C |
| ATOM | 1585 | CG | GLN | A | 335 | 21.167 | 43.616 | -2.517 | 1.00 | 72.09 | A | C |
| ATOM | 1586 | CD | GLN | A | 335 | 19.826 | 43.541 | -3.246 | 1.00 | 80.01 | A | C |
| ATOM | 1587 | OE1 | GLN | A | 335 | 19.051 | 42.619 | -3.020 | 1.00 | 86.56 | A | O |
| ATOM | 1588 | NE2 | GLN | A | 335 | 19.551 | 44.517 | -4.122 | 1.00 | 85.47 | A | N |
| ATOM | 1589 | C | GLN | A | 335 | 20.651 | 43.140 | 1.276 | 1.00 | 51.33 | A | C |
| ATOM | 1590 | O | GLN | A | 335 | 21.150 | 42.237 | 1.936 | 1.00 | 49.14 | A | O |
| ATOM | 1591 | N | GLU | A | 336 | 20.359 | 44.325 | 1.808 | 1.00 | 54.30 | A | N |
| ATOM | 1592 | CA | GLU | A | 336 | 20.637 | 44.612 | 3.228 | 1.00 | 60.67 | A | C |
| ATOM | 1593 | CB | GLU | A | 336 | 19.919 | 45.891 | 3.679 | 1.00 | 72.90 | A | C |
| ATOM | 1594 | CG | GLU | A | 336 | 20.300 | 47.180 | 2.964 | 1.00 | 86.38 | A | C |
| ATOM | 1595 | CD | GLU | A | 336 | 21.552 | 47.810 | 3.526 | 1.00 | 92.32 | A | C |
| ATOM | 1596 | OE1 | GLU | A | 336 | 22.652 | 47.482 | 3.030 | 1.00 | 91.22 | A | O |
| ATOM | 1597 | OE2 | GLU | A | 336 | 21.428 | 48.628 | 4.470 | 1.00 | 96.44 | A | O |
| ATOM | 1598 | C | GLU | A | 336 | 20.203 | 43.480 | 4.172 | 1.00 | 56.11 | A | C |
| ATOM | 1599 | O | GLU | A | 336 | 21.009 | 42.913 | 4.904 | 1.00 | 51.57 | A | O |
| ATOM | 1600 | N | THR | A | 337 | 18.905 | 43.197 | 4.172 | 1.00 | 53.26 | A | N |
| ATOM | 1601 | CA | THR | A | 337 | 18.324 | 42.148 | 4.994 | 1.00 | 49.20 | A | C |
| ATOM | 1602 | CB | THR | A | 337 | 16.943 | 41.738 | 4.444 | 1.00 | 51.40 | A | C |
| ATOM | 1603 | OG1 | THR | A | 337 | 15.973 | 42.736 | 4.792 | 1.00 | 51.20 | A | O |
| ATOM | 1604 | CG2 | THR | A | 337 | 16.520 | 40.393 | 4.990 | 1.00 | 53.69 | A | C |
| ATOM | 1605 | C | THR | A | 337 | 19.248 | 40.948 | 5.010 | 1.00 | 43.93 | A | C |
| ATOM | 1606 | O | THR | A | 337 | 19.661 | 40.508 | 6.074 | 1.00 | 37.72 | A | O |
| ATOM | 1607 | N | TYR | A | 338 | 19.564 | 40.426 | 3.821 | 1.00 | 46.03 | A | N |
| ATOM | 1608 | CA | TYR | A | 338 | 20.473 | 39.279 | 3.669 | 1.00 | 49.15 | A | C |
| ATOM | 1609 | CB | TYR | A | 338 | 20.785 | 39.003 | 2.177 | 1.00 | 57.12 | A | C |
| ATOM | 1610 | CG | TYR | A | 338 | 21.740 | 37.845 | 1.946 | 1.00 | 71.41 | A | C |
| ATOM | 1611 | CD1 | TYR | A | 338 | 21.335 | 36.706 | 1.281 | 1.00 | 78.70 | A | C |
| ATOM | 1612 | CE1 | TYR | A | 338 | 22.178 | 35.616 | 1.146 | 1.00 | 87.18 | A | C |
| ATOM | 1613 | CD2 | TYR | A | 338 | 23.026 | 37.868 | 2.464 | 1.00 | 80.24 | A | C |
| ATOM | 1614 | CE2 | TYR | A | 338 | 23.879 | 36.790 | 2.335 | 1.00 | 87.60 | A | C |
| ATOM | 1615 | CZ | TYR | A | 338 | 23.452 | 35.664 | 1.676 | 1.00 | 89.52 | A | C |
| ATOM | 1616 | OH | TYR | A | 338 | 24.301 | 34.580 | 1.548 | 1.00 | 92.35 | A | O |
| ATOM | 1617 | C | TYR | A | 338 | 21.754 | 39.679 | 4.378 | 1.00 | 47.29 | A | C |
| ATOM | 1618 | O | TYR | A | 338 | 22.162 | 39.051 | 5.360 | 1.00 | 44.58 | A | O |
| ATOM | 1619 | N | LYS | A | 339 | 22.374 | 40.727 | 3.835 | 1.00 | 47.80 | A | N |
| ATOM | 1620 | CA | LYS | A | 339 | 23.588 | 41.316 | 4.352 | 1.00 | 45.74 | A | C |
| ATOM | 1621 | CB | LYS | A | 339 | 23.667 | 42.735 | 3.790 | 1.00 | 45.18 | A | C |
| ATOM | 1622 | CG | LYS | A | 339 | 24.515 | 43.747 | 4.524 | 1.00 | 44.41 | A | C |
| ATOM | 1623 | CD | LYS | A | 339 | 24.676 | 45.039 | 3.695 | 1.00 | 47.17 | A | C |
| ATOM | 1624 | CE | LYS | A | 339 | 25.566 | 44.807 | 2.460 | 1.00 | 58.17 | A | C |
| ATOM | 1625 | NZ | LYS | A | 339 | 25.803 | 46.020 | 1.610 | 1.00 | 66.40 | A | N |
| ATOM | 1626 | C | LYS | A | 339 | 23.505 | 41.265 | 5.883 | 1.00 | 46.23 | A | C |
| ATOM | 1627 | O | LYS | A | 339 | 24.324 | 40.615 | 6.520 | 1.00 | 44.50 | A | O |
| ATOM | 1628 | N | ARG | A | 340 | 22.495 | 41.892 | 6.475 | 1.00 | 45.42 | A | N |
| ATOM | 1629 | CA | ARG | A | 340 | 22.354 | 41.851 | 7.922 | 1.00 | 50.17 | A | C |
| ATOM | 1630 | CB | ARG | A | 340 | 21.344 | 42.883 | 8.385 | 1.00 | 62.49 | A | C |
| ATOM | 1631 | CG | ARG | A | 340 | 21.797 | 44.314 | 8.194 | 1.00 | 81.35 | A | C |
| ATOM | 1632 | CD | ARG | A | 340 | 20.668 | 45.295 | 8.471 | 1.00 | 93.90 | A | C |
| ATOM | 1633 | NE | ARG | A | 340 | 20.678 | 46.395 | 7.509 | 1.00 | 101.42 | A | N |
| ATOM | 1634 | CZ | ARG | A | 340 | 19.683 | 47.257 | 7.355 | 1.00 | 102.33 | A | C |
| ATOM | 1635 | NH1 | ARG | A | 340 | 18.592 | 47.141 | 8.108 | 1.00 | 103.01 | A | N |
| ATOM | 1636 | NH2 | ARG | A | 340 | 19.783 | 48.230 | 6.454 | 1.00 | 101.86 | A | N |
| ATOM | 1637 | C | ARG | A | 340 | 21.955 | 40.490 | 8.493 | 1.00 | 48.56 | A | C |
| ATOM | 1638 | O | ARG | A | 340 | 22.301 | 40.178 | 9.624 | 1.00 | 47.39 | A | O |
| ATOM | 1639 | N | ILE | A | 341 | 21.217 | 39.674 | 7.740 | 1.00 | 47.03 | A | N |
| ATOM | 1640 | CA | ILE | A | 341 | 20.813 | 38.349 | 8.246 | 1.00 | 41.13 | A | C |
| ATOM | 1641 | CB | ILE | A | 341 | 19.807 | 37.647 | 7.280 | 1.00 | 36.36 | A | C |
| ATOM | 1642 | CG2 | ILE | A | 341 | 19.713 | 36.161 | 7.584 | 1.00 | 37.23 | A | C |

Figure 3AA

| ATOM | 1643 | CG1 | ILE | A | 341 | 18.423 | 38.264 | 7.433 | 1.00 | 31.72 | A | C |
|---|---|---|---|---|---|---|---|---|---|---|---|---|
| ATOM | 1644 | CD1 | ILE | A | 341 | 17.437 | 37.729 | 6.451 | 1.00 | 34.26 | A | C |
| ATOM | 1645 | C | ILE | A | 341 | 22.037 | 37.452 | 8.460 | 1.00 | 38.07 | A | C |
| ATOM | 1646 | O | ILE | A | 341 | 22.259 | 36.941 | 9.564 | 1.00 | 34.92 | A | O |
| ATOM | 1647 | N | SER | A | 342 | 22.835 | 37.280 | 7.409 | 1.00 | 35.66 | A | N |
| ATOM | 1648 | CA | SER | A | 342 | 24.018 | 36.447 | 7.521 | 1.00 | 36.42 | A | C |
| ATOM | 1649 | CB | SER | A | 342 | 24.490 | 35.923 | 6.160 | 1.00 | 32.59 | A | C |
| ATOM | 1650 | OG | SER | A | 342 | 25.100 | 36.931 | 5.395 | 1.00 | 37.12 | A | O |
| ATOM | 1651 | C | SER | A | 342 | 25.123 | 37.220 | 8.196 | 1.00 | 34.08 | A | C |
| ATOM | 1652 | O | SER | A | 342 | 25.889 | 36.648 | 8.949 | 1.00 | 35.28 | A | O |
| ATOM | 1653 | N | ARG | A | 343 | 25.238 | 38.512 | 7.949 | 1.00 | 33.99 | A | N |
| ATOM | 1654 | CA | ARG | A | 343 | 26.282 | 39.242 | 8.652 | 1.00 | 41.52 | A | C |
| ATOM | 1655 | CB | ARG | A | 343 | 26.559 | 40.583 | 7.912 | 1.00 | 52.78 | A | C |
| ATOM | 1656 | CG | ARG | A | 343 | 27.421 | 41.703 | 8.600 | 1.00 | 68.09 | A | C |
| ATOM | 1657 | CD | ARG | A | 343 | 26.617 | 42.590 | 9.635 | 1.00 | 79.81 | A | C |
| ATOM | 1658 | NE | ARG | A | 343 | 26.460 | 44.024 | 9.296 | 1.00 | 91.78 | A | N |
| ATOM | 1659 | CZ | ARG | A | 343 | 25.441 | 44.563 | 8.608 | 1.00 | 93.76 | A | C |
| ATOM | 1660 | NH1 | ARG | A | 343 | 24.464 | 43.798 | 8.155 | 1.00 | 97.36 | A | N |
| ATOM | 1661 | NH2 | ARG | A | 343 | 25.360 | 45.879 | 8.409 | 1.00 | 88.77 | A | N |
| ATOM | 1662 | C | ARG | A | 343 | 25.722 | 39.408 | 10.091 | 1.00 | 39.37 | A | C |
| ATOM | 1663 | O | ARG | A | 343 | 26.370 | 39.994 | 10.974 | 1.00 | 36.75 | A | O |
| ATOM | 1664 | N | VAL | A | 344 | 24.532 | 38.826 | 10.311 | 1.00 | 43.31 | A | N |
| ATOM | 1665 | CA | VAL | A | 344 | 23.802 | 38.901 | 11.586 | 1.00 | 51.93 | A | C |
| ATOM | 1666 | CB | VAL | A | 344 | 24.245 | 37.825 | 12.560 | 1.00 | 52.96 | A | C |
| ATOM | 1667 | CG1 | VAL | A | 344 | 23.684 | 38.107 | 13.949 | 1.00 | 49.07 | A | C |
| ATOM | 1668 | CG2 | VAL | A | 344 | 23.757 | 36.479 | 12.062 | 1.00 | 54.22 | A | C |
| ATOM | 1669 | C | VAL | A | 344 | 23.984 | 40.264 | 12.223 | 1.00 | 57.93 | A | C |
| ATOM | 1670 | O | VAL | A | 344 | 24.711 | 40.427 | 13.190 | 1.00 | 54.91 | A | O |
| ATOM | 1671 | N | GLU | A | 345 | 23.288 | 41.236 | 11.654 | 1.00 | 70.29 | A | N |
| ATOM | 1672 | CA | GLU | A | 345 | 23.345 | 42.632 | 12.059 | 1.00 | 84.01 | A | C |
| ATOM | 1673 | CB | GLU | A | 345 | 23.677 | 43.466 | 10.822 | 1.00 | 95.43 | A | C |
| ATOM | 1674 | CG | GLU | A | 345 | 23.425 | 44.955 | 10.921 | 1.00 | 109.36 | A | C |
| ATOM | 1675 | CD | GLU | A | 345 | 24.578 | 45.698 | 11.538 | 1.00 | 117.01 | A | C |
| ATOM | 1676 | OE1 | GLU | A | 345 | 25.686 | 45.671 | 10.969 | 1.00 | 125.79 | A | O |
| ATOM | 1677 | OE2 | GLU | A | 345 | 24.379 | 46.313 | 12.598 | 1.00 | 121.00 | A | O |
| ATOM | 1678 | C | GLU | A | 345 | 22.048 | 43.133 | 12.676 | 1.00 | 87.52 | A | C |
| ATOM | 1679 | O | GLU | A | 345 | 21.151 | 43.580 | 11.967 | 1.00 | 88.71 | A | O |
| ATOM | 1680 | N | PHE | A | 346 | 21.946 | 43.065 | 13.996 | 1.00 | 91.51 | A | N |
| ATOM | 1681 | CA | PHE | A | 346 | 20.748 | 43.546 | 14.660 | 1.00 | 94.48 | A | C |
| ATOM | 1682 | CB | PHE | A | 346 | 19.794 | 42.385 | 14.937 | 1.00 | 95.21 | A | C |
| ATOM | 1683 | CG | PHE | A | 346 | 20.224 | 41.499 | 16.045 | 1.00 | 96.87 | A | C |
| ATOM | 1684 | CD1 | PHE | A | 346 | 19.560 | 41.525 | 17.257 | 1.00 | 98.35 | A | C |
| ATOM | 1685 | CD2 | PHE | A | 346 | 21.287 | 40.632 | 15.884 | 1.00 | 97.67 | A | C |
| ATOM | 1686 | CE1 | PHE | A | 346 | 19.949 | 40.698 | 18.296 | 1.00 | 101.86 | A | C |
| ATOM | 1687 | CE2 | PHE | A | 346 | 21.688 | 39.798 | 16.922 | 1.00 | 99.76 | A | C |
| ATOM | 1688 | CZ | PHE | A | 346 | 21.017 | 39.832 | 18.129 | 1.00 | 101.79 | A | C |
| ATOM | 1689 | C | PHE | A | 346 | 21.082 | 44.315 | 15.940 | 1.00 | 95.80 | A | C |
| ATOM | 1690 | O | PHE | A | 346 | 21.971 | 43.926 | 16.698 | 1.00 | 96.22 | A | O |
| ATOM | 1691 | N | THR | A | 347 | 20.355 | 45.414 | 16.152 | 1.00 | 96.60 | A | N |
| ATOM | 1692 | CA | THR | A | 347 | 20.546 | 46.316 | 17.285 | 1.00 | 94.61 | A | C |
| ATOM | 1693 | CB | THR | A | 347 | 21.047 | 47.644 | 16.760 | 1.00 | 96.49 | A | C |
| ATOM | 1694 | OG1 | THR | A | 347 | 21.375 | 48.494 | 17.853 | 1.00 | 96.97 | A | O |
| ATOM | 1695 | CG2 | THR | A | 347 | 19.983 | 48.306 | 15.932 | 1.00 | 100.44 | A | C |
| ATOM | 1696 | C | THR | A | 347 | 19.234 | 46.555 | 18.048 | 1.00 | 91.67 | A | C |
| ATOM | 1697 | O | THR | A | 347 | 18.203 | 46.793 | 17.424 | 1.00 | 88.78 | A | O |
| ATOM | 1698 | N | PHE | A | 348 | 19.279 | 46.532 | 19.383 | 1.00 | 89.08 | A | N |
| ATOM | 1699 | CA | PHE | A | 348 | 18.078 | 46.709 | 20.224 | 1.00 | 88.94 | A | C |
| ATOM | 1700 | CB | PHE | A | 348 | 18.284 | 45.958 | 21.536 | 1.00 | 82.58 | A | C |
| ATOM | 1701 | CG | PHE | A | 348 | 18.292 | 44.479 | 21.377 | 1.00 | 79.27 | A | C |
| ATOM | 1702 | CD1 | PHE | A | 348 | 17.134 | 43.796 | 21.041 | 1.00 | 76.61 | A | C |
| ATOM | 1703 | CD2 | PHE | A | 348 | 19.455 | 43.762 | 21.531 | 1.00 | 78.96 | A | C |

Figure 3BB

| ATOM | 1704 | CE1 | PHE | A | 348 | 17.138 | 42.416 | 20.858 | 1.00 | 70.66 | A | C |
|---|---|---|---|---|---|---|---|---|---|---|---|---|
| ATOM | 1705 | CE2 | PHE | A | 348 | 19.466 | 42.384 | 21.350 | 1.00 | 74.38 | A | C |
| ATOM | 1706 | CZ | PHE | A | 348 | 18.305 | 41.716 | 21.013 | 1.00 | 68.33 | A | C |
| ATOM | 1707 | C | PHE | A | 348 | 17.549 | 48.128 | 20.547 | 1.00 | 91.65 | A | C |
| ATOM | 1708 | O | PHE | A | 348 | 18.334 | 49.044 | 20.813 | 1.00 | 91.98 | A | O |
| ATOM | 1709 | N | PRO | A | 349 | 16.200 | 48.310 | 20.564 | 1.00 | 93.26 | A | N |
| ATOM | 1710 | CD | PRO | A | 349 | 15.161 | 47.271 | 20.463 | 1.00 | 94.54 | A | C |
| ATOM | 1711 | CA | PRO | A | 349 | 15.563 | 49.597 | 20.854 | 1.00 | 92.51 | A | C |
| ATOM | 1712 | CB | PRO | A | 349 | 14.113 | 49.340 | 20.506 | 1.00 | 92.56 | A | C |
| ATOM | 1713 | CG | PRO | A | 349 | 13.936 | 47.984 | 21.010 | 1.00 | 92.05 | A | C |
| ATOM | 1714 | C | PRO | A | 349 | 15.726 | 49.914 | 22.321 | 1.00 | 91.43 | A | C |
| ATOM | 1715 | O | PRO | A | 349 | 15.877 | 49.015 | 23.142 | 1.00 | 89.95 | A | O |
| ATOM | 1716 | N | ASP | A | 350 | 15.683 | 51.190 | 22.666 | 1.00 | 89.09 | A | N |
| ATOM | 1717 | CA | ASP | A | 350 | 15.853 | 51.542 | 24.056 | 1.00 | 83.53 | A | C |
| ATOM | 1718 | CB | ASP | A | 350 | 16.356 | 52.972 | 24.174 | 1.00 | 87.10 | A | C |
| ATOM | 1719 | CG | ASP | A | 350 | 17.776 | 53.034 | 24.710 | 1.00 | 89.42 | A | C |
| ATOM | 1720 | OD1 | ASP | A | 350 | 18.661 | 52.370 | 24.121 | 1.00 | 86.26 | A | O |
| ATOM | 1721 | OD2 | ASP | A | 350 | 18.006 | 53.739 | 25.722 | 1.00 | 91.36 | A | O |
| ATOM | 1722 | C | ASP | A | 350 | 14.593 | 51.339 | 24.884 | 1.00 | 78.87 | A | C |
| ATOM | 1723 | O | ASP | A | 350 | 13.732 | 52.230 | 24.976 | 1.00 | 75.15 | A | O |
| ATOM | 1724 | N | PHE | A | 351 | 14.504 | 50.141 | 25.469 | 1.00 | 71.54 | A | N |
| ATOM | 1725 | CA | PHE | A | 351 | 13.394 | 49.724 | 26.326 | 1.00 | 65.36 | A | C |
| ATOM | 1726 | CB | PHE | A | 351 | 12.036 | 50.238 | 25.804 | 1.00 | 61.38 | A | C |
| ATOM | 1727 | CG | PHE | A | 351 | 11.420 | 49.385 | 24.715 | 1.00 | 55.02 | A | C |
| ATOM | 1728 | CD1 | PHE | A | 351 | 10.842 | 48.147 | 25.009 | 1.00 | 45.80 | A | C |
| ATOM | 1729 | CD2 | PHE | A | 351 | 11.408 | 49.830 | 23.391 | 1.00 | 52.37 | A | C |
| ATOM | 1730 | CE1 | PHE | A | 351 | 10.268 | 47.371 | 24.010 | 1.00 | 43.60 | A | C |
| ATOM | 1731 | CE2 | PHE | A | 351 | 10.834 | 49.056 | 22.380 | 1.00 | 48.80 | A | C |
| ATOM | 1732 | CZ | PHE | A | 351 | 10.262 | 47.822 | 22.696 | 1.00 | 46.46 | A | C |
| ATOM | 1733 | C | PHE | A | 351 | 13.346 | 48.206 | 26.455 | 1.00 | 62.55 | A | C |
| ATOM | 1734 | O | PHE | A | 351 | 12.797 | 47.690 | 27.426 | 1.00 | 58.07 | A | O |
| ATOM | 1735 | N | VAL | A | 352 | 13.898 | 47.479 | 25.485 | 1.00 | 63.79 | A | N |
| ATOM | 1736 | CA | VAL | A | 352 | 13.865 | 46.017 | 25.597 | 1.00 | 65.68 | A | C |
| ATOM | 1737 | CB | VAL | A | 352 | 14.364 | 45.245 | 24.290 | 1.00 | 65.27 | A | C |
| ATOM | 1738 | CG1 | VAL | A | 352 | 14.455 | 43.744 | 24.559 | 1.00 | 57.23 | A | C |
| ATOM | 1739 | CG2 | VAL | A | 352 | 13.385 | 45.451 | 23.131 | 1.00 | 63.19 | A | C |
| ATOM | 1740 | C | VAL | A | 352 | 14.697 | 45.596 | 26.805 | 1.00 | 64.30 | A | C |
| ATOM | 1741 | O | VAL | A | 352 | 15.901 | 45.860 | 26.911 | 1.00 | 65.67 | A | O |
| ATOM | 1742 | N | THR | A | 353 | 13.999 | 44.970 | 27.735 | 1.00 | 59.80 | A | N |
| ATOM | 1743 | CA | THR | A | 353 | 14.584 | 44.474 | 28.949 | 1.00 | 63.12 | A | C |
| ATOM | 1744 | CB | THR | A | 353 | 13.608 | 43.616 | 29.659 | 1.00 | 63.77 | A | C |
| ATOM | 1745 | OG1 | THR | A | 353 | 14.318 | 42.784 | 30.579 | 1.00 | 70.40 | A | O |
| ATOM | 1746 | CG2 | THR | A | 353 | 12.870 | 42.746 | 28.653 | 1.00 | 61.53 | A | C |
| ATOM | 1747 | C | THR | A | 353 | 15.791 | 43.602 | 28.685 | 1.00 | 66.61 | A | C |
| ATOM | 1748 | O | THR | A | 353 | 15.783 | 42.787 | 27.763 | 1.00 | 66.09 | A | O |
| ATOM | 1749 | N | GLU | A | 354 | 16.808 | 43.758 | 29.528 | 1.00 | 72.19 | A | N |
| ATOM | 1750 | CA | GLU | A | 354 | 18.045 | 42.981 | 29.441 | 1.00 | 76.06 | A | C |
| ATOM | 1751 | CB | GLU | A | 354 | 18.922 | 43.244 | 30.667 | 1.00 | 85.78 | A | C |
| ATOM | 1752 | CG | GLU | A | 354 | 20.031 | 42.217 | 30.868 | 1.00 | 100.57 | A | C |
| ATOM | 1753 | CD | GLU | A | 354 | 20.596 | 42.220 | 32.288 | 1.00 | 106.47 | A | C |
| ATOM | 1754 | OE1 | GLU | A | 354 | 19.817 | 41.976 | 33.245 | 1.00 | 103.80 | A | O |
| ATOM | 1755 | OE2 | GLU | A | 354 | 21.819 | 42.462 | 32.440 | 1.00 | 110.46 | A | O |
| ATOM | 1756 | C | GLU | A | 354 | 17.745 | 41.492 | 29.363 | 1.00 | 74.65 | A | C |
| ATOM | 1757 | O | GLU | A | 354 | 18.339 | 40.765 | 28.565 | 1.00 | 75.75 | A | O |
| ATOM | 1758 | N | GLY | A | 355 | 16.832 | 41.041 | 30.211 | 1.00 | 73.65 | A | N |
| ATOM | 1759 | CA | GLY | A | 355 | 16.472 | 39.640 | 30.205 | 1.00 | 73.31 | A | C |
| ATOM | 1760 | C | GLY | A | 355 | 16.115 | 39.221 | 28.798 | 1.00 | 71.62 | A | C |
| ATOM | 1761 | O | GLY | A | 355 | 16.403 | 38.102 | 28.367 | 1.00 | 67.84 | A | O |
| ATOM | 1762 | N | ALA | A | 356 | 15.482 | 40.136 | 28.077 | 1.00 | 70.44 | A | N |
| ATOM | 1763 | CA | ALA | A | 356 | 15.086 | 39.874 | 26.708 | 1.00 | 68.66 | A | C |
| ATOM | 1764 | CB | ALA | A | 356 | 14.249 | 41.029 | 26.179 | 1.00 | 68.10 | A | C |

Figure 3CC

| | | | | | | | | | | | |
|---|---|---|---|---|---|---|---|---|---|---|---|
| ATOM | 1765 | C | ALA | A | 356 | 16.338 | 39.717 | 25.867 | 1.00 | 67.16 | A | C |
| ATOM | 1766 | O | ALA | A | 356 | 16.564 | 38.678 | 25.236 | 1.00 | 65.22 | A | O |
| ATOM | 1767 | N | ARG | A | 357 | 17.153 | 40.766 | 25.884 | 1.00 | 63.55 | A | N |
| ATOM | 1768 | CA | ARG | A | 357 | 18.382 | 40.804 | 25.117 | 1.00 | 59.76 | A | C |
| ATOM | 1769 | CB | ARG | A | 357 | 19.318 | 41.871 | 25.681 | 1.00 | 53.94 | A | C |
| ATOM | 1770 | CG | ARG | A | 357 | 18.991 | 43.279 | 25.172 | 1.00 | 57.49 | A | C |
| ATOM | 1771 | CD | ARG | A | 357 | 19.006 | 44.325 | 26.293 | 1.00 | 63.69 | A | C |
| ATOM | 1772 | NE | ARG | A | 357 | 18.824 | 45.691 | 25.810 | 1.00 | 66.73 | A | N |
| ATOM | 1773 | CZ | ARG | A | 357 | 19.760 | 46.391 | 25.177 | 1.00 | 71.81 | A | C |
| ATOM | 1774 | NH1 | ARG | A | 357 | 20.959 | 45.864 | 24.938 | 1.00 | 75.34 | A | N |
| ATOM | 1775 | NH2 | ARG | A | 357 | 19.498 | 47.634 | 24.798 | 1.00 | 75.86 | A | N |
| ATOM | 1776 | C | ARG | A | 357 | 19.087 | 39.467 | 25.019 | 1.00 | 59.86 | A | C |
| ATOM | 1777 | O | ARG | A | 357 | 19.530 | 39.081 | 23.937 | 1.00 | 63.20 | A | O |
| ATOM | 1778 | N | ASP | A | 358 | 19.180 | 38.729 | 26.114 | 1.00 | 59.07 | A | N |
| ATOM | 1779 | CA | ASP | A | 358 | 19.876 | 37.464 | 25.989 | 1.00 | 54.78 | A | C |
| ATOM | 1780 | CB | ASP | A | 358 | 20.837 | 37.227 | 27.166 | 1.00 | 63.30 | A | C |
| ATOM | 1781 | CG | ASP | A | 358 | 20.185 | 37.401 | 28.503 | 1.00 | 70.77 | A | C |
| ATOM | 1782 | OD1 | ASP | A | 358 | 19.830 | 38.550 | 28.847 | 1.00 | 73.52 | A | O |
| ATOM | 1783 | OD2 | ASP | A | 358 | 20.040 | 36.380 | 29.206 | 1.00 | 77.06 | A | O |
| ATOM | 1784 | C | ASP | A | 358 | 19.038 | 36.227 | 25.735 | 1.00 | 47.71 | A | C |
| ATOM | 1785 | O | ASP | A | 358 | 19.584 | 35.129 | 25.668 | 1.00 | 42.20 | A | O |
| ATOM | 1786 | N | LEU | A | 359 | 17.724 | 36.364 | 25.597 | 1.00 | 44.23 | A | N |
| ATOM | 1787 | CA | LEU | A | 359 | 16.954 | 35.169 | 25.279 | 1.00 | 51.82 | A | C |
| ATOM | 1788 | CB | LEU | A | 359 | 15.519 | 35.203 | 25.801 | 1.00 | 50.69 | A | C |
| ATOM | 1789 | CG | LEU | A | 359 | 14.598 | 34.034 | 25.366 | 1.00 | 50.60 | A | C |
| ATOM | 1790 | CD1 | LEU | A | 359 | 14.033 | 34.280 | 23.969 | 1.00 | 45.72 | A | C |
| ATOM | 1791 | CD2 | LEU | A | 359 | 15.347 | 32.719 | 25.427 | 1.00 | 54.34 | A | C |
| ATOM | 1792 | C | LEU | A | 359 | 16.922 | 35.122 | 23.779 | 1.00 | 57.56 | A | C |
| ATOM | 1793 | O | LEU | A | 359 | 16.661 | 34.077 | 23.183 | 1.00 | 62.18 | A | O |
| ATOM | 1794 | N | ILE | A | 360 | 17.163 | 36.268 | 23.158 | 1.00 | 64.80 | A | N |
| ATOM | 1795 | CA | ILE | A | 360 | 17.183 | 36.285 | 21.715 | 1.00 | 74.60 | A | C |
| ATOM | 1796 | CB | ILE | A | 360 | 16.428 | 37.516 | 21.145 | 1.00 | 81.71 | A | C |
| ATOM | 1797 | CG2 | ILE | A | 360 | 17.003 | 38.793 | 21.701 | 1.00 | 83.67 | A | C |
| ATOM | 1798 | CG1 | ILE | A | 360 | 16.448 | 37.457 | 19.615 | 1.00 | 85.27 | A | C |
| ATOM | 1799 | CD1 | ILE | A | 360 | 15.309 | 38.191 | 18.960 | 1.00 | 82.85 | A | C |
| ATOM | 1800 | C | ILE | A | 360 | 18.642 | 36.222 | 21.269 | 1.00 | 72.26 | A | C |
| ATOM | 1801 | O | ILE | A | 360 | 18.997 | 35.401 | 20.426 | 1.00 | 71.73 | A | O |
| ATOM | 1802 | N | SER | A | 361 | 19.503 | 37.043 | 21.858 | 1.00 | 69.17 | A | N |
| ATOM | 1803 | CA | SER | A | 361 | 20.907 | 36.994 | 21.478 | 1.00 | 68.51 | A | C |
| ATOM | 1804 | CB | SER | A | 361 | 21.754 | 37.827 | 22.426 | 1.00 | 68.11 | A | C |
| ATOM | 1805 | OG | SER | A | 361 | 21.464 | 39.193 | 22.271 | 1.00 | 66.69 | A | O |
| ATOM | 1806 | C | SER | A | 361 | 21.372 | 35.553 | 21.548 | 1.00 | 66.75 | A | C |
| ATOM | 1807 | O | SER | A | 361 | 22.328 | 35.158 | 20.890 | 1.00 | 65.50 | A | O |
| ATOM | 1808 | N | ARG | A | 362 | 20.670 | 34.768 | 22.348 | 1.00 | 64.87 | A | N |
| ATOM | 1809 | CA | ARG | A | 362 | 21.019 | 33.382 | 22.548 | 1.00 | 67.02 | A | C |
| ATOM | 1810 | CB | ARG | A | 362 | 20.608 | 32.952 | 23.942 | 1.00 | 69.78 | A | C |
| ATOM | 1811 | CG | ARG | A | 362 | 21.234 | 31.680 | 24.378 | 1.00 | 80.64 | A | C |
| ATOM | 1812 | CD | ARG | A | 362 | 22.181 | 31.961 | 25.512 | 1.00 | 92.81 | A | C |
| ATOM | 1813 | NE | ARG | A | 362 | 21.630 | 31.480 | 26.766 | 1.00 | 101.50 | A | N |
| ATOM | 1814 | CZ | ARG | A | 362 | 21.330 | 30.205 | 27.002 | 1.00 | 104.13 | A | C |
| ATOM | 1815 | NH1 | ARG | A | 362 | 21.528 | 29.273 | 26.068 | 1.00 | 99.14 | A | N |
| ATOM | 1816 | NH2 | ARG | A | 362 | 20.832 | 29.862 | 28.181 | 1.00 | 106.78 | A | N |
| ATOM | 1817 | C | ARG | A | 362 | 20.342 | 32.479 | 21.558 | 1.00 | 69.90 | A | C |
| ATOM | 1818 | O | ARG | A | 362 | 20.682 | 31.307 | 21.481 | 1.00 | 70.10 | A | O |
| ATOM | 1819 | N | LEU | A | 363 | 19.383 | 33.023 | 20.807 | 1.00 | 72.86 | A | N |
| ATOM | 1820 | CA | LEU | A | 363 | 18.609 | 32.251 | 19.823 | 1.00 | 75.57 | A | C |
| ATOM | 1821 | CB | LEU | A | 363 | 17.129 | 32.554 | 19.979 | 1.00 | 68.14 | A | C |
| ATOM | 1822 | CG | LEU | A | 363 | 16.275 | 31.328 | 20.227 | 1.00 | 61.69 | A | C |
| ATOM | 1823 | CD1 | LEU | A | 363 | 16.990 | 30.310 | 21.085 | 1.00 | 55.05 | A | C |
| ATOM | 1824 | CD2 | LEU | A | 363 | 15.037 | 31.800 | 20.901 | 1.00 | 68.72 | A | C |
| ATOM | 1825 | C | LEU | A | 363 | 19.001 | 32.501 | 18.384 | 1.00 | 80.34 | A | C |

Figure 3DD

| ATOM | 1826 | O   | LEU | A | 363 | 18.773 | 31.665 | 17.503 | 1.00 | 79.68  | A | O |
|------|------|-----|-----|---|-----|--------|--------|--------|------|--------|---|---|
| ATOM | 1827 | N   | LEU | A | 364 | 19.571 | 33.675 | 18.150 | 1.00 | 86.45  | A | N |
| ATOM | 1828 | CA  | LEU | A | 364 | 20.013 | 34.037 | 16.824 | 1.00 | 90.95  | A | C |
| ATOM | 1829 | CB  | LEU | A | 364 | 19.567 | 35.478 | 16.496 | 1.00 | 94.41  | A | C |
| ATOM | 1830 | CG  | LEU | A | 364 | 20.403 | 36.708 | 16.874 | 1.00 | 99.69  | A | C |
| ATOM | 1831 | CD1 | LEU | A | 364 | 20.929 | 36.598 | 18.310 | 1.00 | 101.56 | A | C |
| ATOM | 1832 | CD2 | LEU | A | 364 | 21.566 | 36.837 | 15.895 | 1.00 | 103.54 | A | C |
| ATOM | 1833 | C   | LEU | A | 364 | 21.538 | 33.870 | 16.784 | 1.00 | 91.64  | A | C |
| ATOM | 1834 | O   | LEU | A | 364 | 22.293 | 34.712 | 17.251 | 1.00 | 89.95  | A | O |
| ATOM | 1835 | N   | LYS | A | 365 | 21.985 | 32.733 | 16.274 | 1.00 | 93.08  | A | N |
| ATOM | 1836 | CA  | LYS | A | 365 | 23.405 | 32.485 | 16.165 | 1.00 | 91.91  | A | C |
| ATOM | 1837 | CB  | LYS | A | 365 | 23.875 | 31.487 | 17.204 | 1.00 | 97.36  | A | C |
| ATOM | 1838 | CG  | LYS | A | 365 | 25.372 | 31.475 | 17.421 | 1.00 | 104.52 | A | C |
| ATOM | 1839 | CD  | LYS | A | 365 | 25.864 | 32.755 | 18.114 | 1.00 | 107.60 | A | C |
| ATOM | 1840 | CE  | LYS | A | 365 | 26.619 | 33.719 | 17.168 | 1.00 | 105.34 | A | C |
| ATOM | 1841 | NZ  | LYS | A | 365 | 25.762 | 34.449 | 16.171 | 1.00 | 105.53 | A | N |
| ATOM | 1842 | C   | LYS | A | 365 | 23.620 | 31.918 | 14.793 | 1.00 | 88.85  | A | C |
| ATOM | 1843 | O   | LYS | A | 365 | 22.881 | 31.036 | 14.347 | 1.00 | 86.15  | A | O |
| ATOM | 1844 | N   | HIS | A | 366 | 24.637 | 32.441 | 14.124 | 1.00 | 86.85  | A | N |
| ATOM | 1845 | CA  | HIS | A | 366 | 24.971 | 32.022 | 12.783 | 1.00 | 84.66  | A | C |
| ATOM | 1846 | CB  | HIS | A | 366 | 26.190 | 32.786 | 12.312 | 1.00 | 89.33  | A | C |
| ATOM | 1847 | CG  | HIS | A | 366 | 26.442 | 32.639 | 10.855 | 1.00 | 96.75  | A | C |
| ATOM | 1848 | CD2 | HIS | A | 366 | 27.074 | 31.671 | 10.155 | 1.00 | 100.67 | A | C |
| ATOM | 1849 | ND1 | HIS | A | 366 | 25.924 | 33.510 |  9.925 | 1.00 | 98.80  | A | N |
| ATOM | 1850 | CE1 | HIS | A | 366 | 26.223 | 33.083 |  8.711 | 1.00 | 101.84 | A | C |
| ATOM | 1851 | NE2 | HIS | A | 366 | 26.920 | 31.968 |  8.823 | 1.00 | 101.49 | A | N |
| ATOM | 1852 | C   | HIS | A | 366 | 25.233 | 30.519 | 12.647 | 1.00 | 81.57  | A | C |
| ATOM | 1853 | O   | HIS | A | 366 | 24.923 | 29.915 | 11.609 | 1.00 | 71.88  | A | O |
| ATOM | 1854 | N   | ASN | A | 367 | 25.798 | 29.921 | 13.697 | 1.00 | 82.68  | A | N |
| ATOM | 1855 | CA  | ASN | A | 367 | 26.132 | 28.493 | 13.705 | 1.00 | 84.38  | A | C |
| ATOM | 1856 | CB  | ASN | A | 367 | 27.448 | 28.268 | 14.452 | 1.00 | 87.91  | A | C |
| ATOM | 1857 | CG  | ASN | A | 367 | 28.091 | 26.934 | 14.105 | 1.00 | 89.90  | A | C |
| ATOM | 1858 | OD1 | ASN | A | 367 | 27.486 | 25.865 | 14.278 | 1.00 | 86.54  | A | O |
| ATOM | 1859 | ND2 | ASN | A | 367 | 29.325 | 26.990 | 13.600 | 1.00 | 92.69  | A | N |
| ATOM | 1860 | C   | ASN | A | 367 | 25.063 | 27.594 | 14.321 | 1.00 | 81.67  | A | C |
| ATOM | 1861 | O   | ASN | A | 367 | 24.855 | 27.601 | 15.532 | 1.00 | 80.79  | A | O |
| ATOM | 1862 | N   | PRO | A | 368 | 24.396 | 26.779 | 13.496 | 1.00 | 78.80  | A | N |
| ATOM | 1863 | CD  | PRO | A | 368 | 24.615 | 26.547 | 12.057 | 1.00 | 77.22  | A | C |
| ATOM | 1864 | CA  | PRO | A | 368 | 23.355 | 25.892 | 14.025 | 1.00 | 76.67  | A | C |
| ATOM | 1865 | CB  | PRO | A | 368 | 23.164 | 24.890 | 12.899 | 1.00 | 78.68  | A | C |
| ATOM | 1866 | CG  | PRO | A | 368 | 23.396 | 25.747 | 11.671 | 1.00 | 79.08  | A | C |
| ATOM | 1867 | C   | PRO | A | 368 | 23.781 | 25.238 | 15.328 | 1.00 | 72.81  | A | C |
| ATOM | 1868 | O   | PRO | A | 368 | 23.044 | 25.207 | 16.301 | 1.00 | 67.46  | A | O |
| ATOM | 1869 | N   | SER | A | 369 | 25.000 | 24.738 | 15.330 | 1.00 | 73.58  | A | N |
| ATOM | 1870 | CA  | SER | A | 369 | 25.573 | 24.079 | 16.485 | 1.00 | 75.54  | A | C |
| ATOM | 1871 | CB  | SER | A | 369 | 27.063 | 23.840 | 16.230 | 1.00 | 79.27  | A | C |
| ATOM | 1872 | OG  | SER | A | 369 | 27.817 | 23.866 | 17.438 | 1.00 | 85.06  | A | O |
| ATOM | 1873 | C   | SER | A | 369 | 25.423 | 24.812 | 17.808 | 1.00 | 76.40  | A | C |
| ATOM | 1874 | O   | SER | A | 369 | 25.452 | 24.184 | 18.872 | 1.00 | 74.15  | A | O |
| ATOM | 1875 | N   | GLN | A | 370 | 25.265 | 26.129 | 17.757 | 1.00 | 78.67  | A | N |
| ATOM | 1876 | CA  | GLN | A | 370 | 25.191 | 26.905 | 18.990 | 1.00 | 81.51  | A | C |
| ATOM | 1877 | CB  | GLN | A | 370 | 25.997 | 28.194 | 18.854 | 1.00 | 82.32  | A | C |
| ATOM | 1878 | CG  | GLN | A | 370 | 27.274 | 28.043 | 18.074 | 1.00 | 80.54  | A | C |
| ATOM | 1879 | CD  | GLN | A | 370 | 28.262 | 29.134 | 18.383 | 1.00 | 84.05  | A | C |
| ATOM | 1880 | OE1 | GLN | A | 370 | 29.203 | 29.347 | 17.629 | 1.00 | 87.57  | A | O |
| ATOM | 1881 | NE2 | GLN | A | 370 | 28.066 | 29.825 | 19.506 | 1.00 | 85.89  | A | N |
| ATOM | 1882 | C   | GLN | A | 370 | 23.815 | 27.272 | 19.474 | 1.00 | 82.51  | A | C |
| ATOM | 1883 | O   | GLN | A | 370 | 23.665 | 27.737 | 20.601 | 1.00 | 81.63  | A | O |
| ATOM | 1884 | N   | ARG | A | 371 | 22.806 | 27.082 | 18.636 | 1.00 | 83.02  | A | N |
| ATOM | 1885 | CA  | ARG | A | 371 | 21.471 | 27.452 | 19.055 | 1.00 | 83.67  | A | C |
| ATOM | 1886 | CB  | ARG | A | 371 | 20.553 | 27.653 | 17.843 | 1.00 | 92.66  | A | C |

Figure 3EE

```
ATOM   1887  CG   ARG A 371      20.868  28.945  17.070  1.00 104.82      A   C
ATOM   1888  CD   ARG A 371      21.173  30.141  18.024  1.00 119.98      A   C
ATOM   1889  NE   ARG A 371      22.255  29.858  18.987  1.00 129.96      A   N
ATOM   1890  CZ   ARG A 371      22.812  30.739  19.825  1.00 132.05      A   C
ATOM   1891  NH1  ARG A 371      23.781  30.348  20.650  1.00 132.25      A   N
ATOM   1892  NH2  ARG A 371      22.425  32.011  19.829  1.00 134.27      A   N
ATOM   1893  C    ARG A 371      20.881  26.504  20.063  1.00  76.57      A   C
ATOM   1894  O    ARG A 371      20.844  25.293  19.853  1.00  75.92      A   O
ATOM   1895  N    PRO A 372      20.417  27.062  21.189  1.00  69.45      A   N
ATOM   1896  CD   PRO A 372      20.166  28.504  21.279  1.00  65.18      A   C
ATOM   1897  CA   PRO A 372      19.807  26.383  22.327  1.00  66.81      A   C
ATOM   1898  CB   PRO A 372      19.134  27.523  23.071  1.00  62.53      A   C
ATOM   1899  CG   PRO A 372      19.971  28.678  22.731  1.00  61.51      A   C
ATOM   1900  C    PRO A 372      18.806  25.353  21.848  1.00  70.16      A   C
ATOM   1901  O    PRO A 372      18.181  25.549  20.813  1.00  76.53      A   O
ATOM   1902  N    MET A 373      18.648  24.251  22.572  1.00  70.74      A   N
ATOM   1903  CA   MET A 373      17.674  23.271  22.134  1.00  71.42      A   C
ATOM   1904  CB   MET A 373      18.095  21.850  22.538  1.00  71.25      A   C
ATOM   1905  CG   MET A 373      17.671  20.759  21.541  1.00  71.53      A   C
ATOM   1906  SD   MET A 373      15.962  20.936  20.935  1.00  77.93      A   S
ATOM   1907  CE   MET A 373      15.574  19.302  20.223  1.00  76.18      A   C
ATOM   1908  C    MET A 373      16.350  23.629  22.796  1.00  72.26      A   C
ATOM   1909  O    MET A 373      16.249  24.595  23.552  1.00  69.03      A   O
ATOM   1910  N    LEU A 374      15.337  22.842  22.479  1.00  76.21      A   N
ATOM   1911  CA   LEU A 374      13.995  22.971  23.018  1.00  83.32      A   C
ATOM   1912  CB   LEU A 374      13.292  21.593  22.874  1.00  80.59      A   C
ATOM   1913  CG   LEU A 374      14.017  20.247  23.187  1.00  73.28      A   C
ATOM   1914  CD1  LEU A 374      14.056  19.950  24.696  1.00  66.69      A   C
ATOM   1915  CD2  LEU A 374      13.300  19.098  22.458  1.00  63.53      A   C
ATOM   1916  C    LEU A 374      13.916  23.459  24.486  1.00  88.94      A   C
ATOM   1917  O    LEU A 374      13.669  24.644  24.768  1.00  86.25      A   O
ATOM   1918  N    ARG A 375      14.135  22.509  25.395  1.00  96.78      A   N
ATOM   1919  CA   ARG A 375      14.067  22.686  26.835  1.00 103.22      A   C
ATOM   1920  CB   ARG A 375      14.581  21.416  27.492  1.00 113.71      A   C
ATOM   1921  CG   ARG A 375      14.508  21.393  28.997  1.00 125.70      A   C
ATOM   1922  CD   ARG A 375      15.266  20.183  29.526  1.00 138.28      A   C
ATOM   1923  NE   ARG A 375      16.719  20.387  29.626  1.00 150.11      A   N
ATOM   1924  CZ   ARG A 375      17.550  20.632  28.608  1.00 154.89      A   C
ATOM   1925  NH1  ARG A 375      18.852  20.796  28.839  1.00 153.17      A   N
ATOM   1926  NH2  ARG A 375      17.096  20.718  27.362  1.00 161.43      A   N
ATOM   1927  C    ARG A 375      14.761  23.896  27.439  1.00 100.28      A   C
ATOM   1928  O    ARG A 375      14.596  24.163  28.632  1.00  99.03      A   O
ATOM   1929  N    GLU A 376      15.521  24.629  26.630  1.00  97.34      A   N
ATOM   1930  CA   GLU A 376      16.238  25.805  27.120  1.00  95.37      A   C
ATOM   1931  CB   GLU A 376      17.425  26.135  26.214  1.00 106.76      A   C
ATOM   1932  CG   GLU A 376      18.260  27.312  26.707  1.00 124.32      A   C
ATOM   1933  CD   GLU A 376      18.842  27.078  28.096  1.00 135.59      A   C
ATOM   1934  OE1  GLU A 376      19.604  26.093  28.259  1.00 142.83      A   O
ATOM   1935  OE2  GLU A 376      18.535  27.876  29.019  1.00 140.57      A   O
ATOM   1936  C    GLU A 376      15.349  27.028  27.242  1.00  87.29      A   C
ATOM   1937  O    GLU A 376      15.235  27.617  28.313  1.00  79.74      A   O
ATOM   1938  N    VAL A 377      14.729  27.424  26.139  1.00  83.15      A   N
ATOM   1939  CA   VAL A 377      13.855  28.578  26.186  1.00  81.49      A   C
ATOM   1940  CB   VAL A 377      13.145  28.834  24.839  1.00  79.47      A   C
ATOM   1941  CG1  VAL A 377      14.131  29.337  23.827  1.00  79.27      A   C
ATOM   1942  CG2  VAL A 377      12.484  27.571  24.348  1.00  79.59      A   C
ATOM   1943  C    VAL A 377      12.804  28.328  27.252  1.00  81.85      A   C
ATOM   1944  O    VAL A 377      12.616  29.142  28.154  1.00  86.53      A   O
ATOM   1945  N    LEU A 378      12.132  27.188  27.152  1.00  79.82      A   N
ATOM   1946  CA   LEU A 378      11.092  26.838  28.101  1.00  80.69      A   C
ATOM   1947  CB   LEU A 378      10.663  25.379  27.887  1.00  73.33      A   C
```

Figure 3FF

| ATOM | 1948 | CG | LEU | A | 378 | 9.344 | 25.072 | 27.160 | 1.00 | 65.91 | A | C |
|---|---|---|---|---|---|---|---|---|---|---|---|---|
| ATOM | 1949 | CD1 | LEU | A | 378 | 8.761 | 26.319 | 26.549 | 1.00 | 60.22 | A | C |
| ATOM | 1950 | CD2 | LEU | A | 378 | 9.584 | 24.023 | 26.098 | 1.00 | 63.01 | A | C |
| ATOM | 1951 | C | LEU | A | 378 | 11.507 | 27.080 | 29.554 | 1.00 | 84.79 | A | C |
| ATOM | 1952 | O | LEU | A | 378 | 10.662 | 27.389 | 30.387 | 1.00 | 87.16 | A | O |
| ATOM | 1953 | N | GLU | A | 379 | 12.799 | 26.969 | 29.857 | 1.00 | 85.21 | A | N |
| ATOM | 1954 | CA | GLU | A | 379 | 13.270 | 27.181 | 31.226 | 1.00 | 84.39 | A | C |
| ATOM | 1955 | CB | GLU | A | 379 | 14.168 | 26.016 | 31.671 | 1.00 | 88.12 | A | C |
| ATOM | 1956 | CG | GLU | A | 379 | 14.579 | 26.043 | 33.158 | 1.00 | 94.28 | A | C |
| ATOM | 1957 | CD | GLU | A | 379 | 15.792 | 26.944 | 33.479 | 1.00 | 98.07 | A | C |
| ATOM | 1958 | OE1 | GLU | A | 379 | 16.097 | 27.107 | 34.683 | 1.00 | 99.07 | A | O |
| ATOM | 1959 | OE2 | GLU | A | 379 | 16.446 | 27.480 | 32.551 | 1.00 | 97.87 | A | O |
| ATOM | 1960 | C | GLU | A | 379 | 14.023 | 28.502 | 31.395 | 1.00 | 82.14 | A | C |
| ATOM | 1961 | O | GLU | A | 379 | 14.283 | 28.941 | 32.523 | 1.00 | 83.12 | A | O |
| ATOM | 1962 | N | HIS | A | 380 | 14.375 | 29.146 | 30.286 | 1.00 | 77.12 | A | N |
| ATOM | 1963 | CA | HIS | A | 380 | 15.098 | 30.404 | 30.393 | 1.00 | 73.06 | A | C |
| ATOM | 1964 | CB | HIS | A | 380 | 15.177 | 31.144 | 29.051 | 1.00 | 76.12 | A | C |
| ATOM | 1965 | CG | HIS | A | 380 | 15.975 | 32.418 | 29.105 | 1.00 | 77.81 | A | C |
| ATOM | 1966 | CD2 | HIS | A | 380 | 17.204 | 32.720 | 28.624 | 1.00 | 75.81 | A | C |
| ATOM | 1967 | ND1 | HIS | A | 380 | 15.510 | 33.569 | 29.707 | 1.00 | 76.82 | A | N |
| ATOM | 1968 | CE1 | HIS | A | 380 | 16.415 | 34.523 | 29.590 | 1.00 | 73.10 | A | C |
| ATOM | 1969 | NE2 | HIS | A | 380 | 17.452 | 34.034 | 28.938 | 1.00 | 71.49 | A | N |
| ATOM | 1970 | C | HIS | A | 380 | 14.443 | 31.296 | 31.428 | 1.00 | 69.83 | A | C |
| ATOM | 1971 | O | HIS | A | 380 | 13.228 | 31.441 | 31.495 | 1.00 | 61.10 | A | O |
| ATOM | 1972 | N | PRO | A | 381 | 15.260 | 31.900 | 32.265 | 1.00 | 71.01 | A | N |
| ATOM | 1973 | CD | PRO | A | 381 | 16.730 | 31.835 | 32.294 | 1.00 | 72.91 | A | C |
| ATOM | 1974 | CA | PRO | A | 381 | 14.742 | 32.778 | 33.300 | 1.00 | 72.72 | A | C |
| ATOM | 1975 | CB | PRO | A | 381 | 16.019 | 33.295 | 33.978 | 1.00 | 77.20 | A | C |
| ATOM | 1976 | CG | PRO | A | 381 | 17.087 | 33.154 | 32.895 | 1.00 | 72.88 | A | C |
| ATOM | 1977 | C | PRO | A | 381 | 13.819 | 33.894 | 32.805 | 1.00 | 73.49 | A | C |
| ATOM | 1978 | O | PRO | A | 381 | 13.130 | 34.514 | 33.610 | 1.00 | 73.11 | A | O |
| ATOM | 1979 | N | TRP | A | 382 | 13.792 | 34.163 | 31.504 | 1.00 | 76.65 | A | N |
| ATOM | 1980 | CA | TRP | A | 382 | 12.917 | 35.226 | 31.018 | 1.00 | 78.77 | A | C |
| ATOM | 1981 | CB | TRP | A | 382 | 13.529 | 35.962 | 29.834 | 1.00 | 92.91 | A | C |
| ATOM | 1982 | CG | TRP | A | 382 | 12.896 | 37.301 | 29.605 | 1.00 | 105.61 | A | C |
| ATOM | 1983 | CD2 | TRP | A | 382 | 11.926 | 37.653 | 28.595 | 1.00 | 109.44 | A | C |
| ATOM | 1984 | CE2 | TRP | A | 382 | 11.630 | 39.022 | 28.763 | 1.00 | 112.17 | A | C |
| ATOM | 1985 | CE3 | TRP | A | 382 | 11.284 | 36.946 | 27.570 | 1.00 | 107.97 | A | C |
| ATOM | 1986 | CD1 | TRP | A | 382 | 13.130 | 38.434 | 30.318 | 1.00 | 109.46 | A | C |
| ATOM | 1987 | NE1 | TRP | A | 382 | 12.377 | 39.473 | 29.819 | 1.00 | 114.96 | A | N |
| ATOM | 1988 | CZ2 | TRP | A | 382 | 10.722 | 39.700 | 27.947 | 1.00 | 109.26 | A | C |
| ATOM | 1989 | CZ3 | TRP | A | 382 | 10.386 | 37.620 | 26.761 | 1.00 | 106.63 | A | C |
| ATOM | 1990 | CH2 | TRP | A | 382 | 10.114 | 38.985 | 26.956 | 1.00 | 107.12 | A | C |
| ATOM | 1991 | C | TRP | A | 382 | 11.560 | 34.684 | 30.610 | 1.00 | 74.34 | A | C |
| ATOM | 1992 | O | TRP | A | 382 | 10.562 | 35.384 | 30.729 | 1.00 | 75.02 | A | O |
| ATOM | 1993 | N | ILE | A | 383 | 11.522 | 33.452 | 30.108 | 1.00 | 70.82 | A | N |
| ATOM | 1994 | CA | ILE | A | 383 | 10.257 | 32.852 | 29.730 | 1.00 | 70.10 | A | C |
| ATOM | 1995 | CB | ILE | A | 383 | 10.423 | 31.458 | 29.149 | 1.00 | 71.61 | A | C |
| ATOM | 1996 | CG2 | ILE | A | 383 | 11.181 | 30.587 | 30.117 | 1.00 | 65.61 | A | C |
| ATOM | 1997 | CG1 | ILE | A | 383 | 9.034 | 30.868 | 28.874 | 1.00 | 80.47 | A | C |
| ATOM | 1998 | CD1 | ILE | A | 383 | 8.942 | 29.339 | 28.841 | 1.00 | 83.18 | A | C |
| ATOM | 1999 | C | ILE | A | 383 | 9.513 | 32.708 | 31.049 | 1.00 | 68.89 | A | C |
| ATOM | 2000 | O | ILE | A | 383 | 8.315 | 32.977 | 31.143 | 1.00 | 66.86 | A | O |
| ATOM | 2001 | N | THR | A | 384 | 10.242 | 32.276 | 32.072 | 1.00 | 66.22 | A | N |
| ATOM | 2002 | CA | THR | A | 384 | 9.666 | 32.114 | 33.398 | 1.00 | 66.21 | A | C |
| ATOM | 2003 | CB | THR | A | 384 | 10.519 | 31.172 | 34.266 | 1.00 | 64.92 | A | C |
| ATOM | 2004 | OG1 | THR | A | 384 | 11.608 | 31.912 | 34.833 | 1.00 | 75.34 | A | O |
| ATOM | 2005 | CG2 | THR | A | 384 | 11.077 | 30.025 | 33.426 | 1.00 | 50.61 | A | C |
| ATOM | 2006 | C | THR | A | 384 | 9.637 | 33.493 | 34.064 | 1.00 | 69.82 | A | C |
| ATOM | 2007 | O | THR | A | 384 | 10.675 | 34.124 | 34.228 | 1.00 | 68.66 | A | O |
| ATOM | 2008 | N | ALA | A | 385 | 8.444 | 33.944 | 34.440 | 1.00 | 76.43 | A | N |

Figure 3GG

```
ATOM   2009  CA   ALA A 385       8.217  35.243  35.084  1.00   81.12      A    C
ATOM   2010  CB   ALA A 385       9.530  35.848  35.613  1.00   80.53      A    C
ATOM   2011  C    ALA A 385       7.546  36.199  34.097  1.00   82.87      A    C
ATOM   2012  O    ALA A 385       6.316  36.291  34.066  1.00   85.34      A    O
ATOM   2013  N    ASN A 386       8.334  36.918  33.302  1.00   83.36      A    N
ATOM   2014  CA   ASN A 386       7.745  37.825  32.331  1.00   82.74      A    C
ATOM   2015  CB   ASN A 386       8.789  38.344  31.356  1.00   83.56      A    C
ATOM   2016  CG   ASN A 386       9.639  39.461  31.942  1.00   86.73      A    C
ATOM   2017  OD1  ASN A 386       9.187  40.605  32.066  1.00   84.34      A    O
ATOM   2018  ND2  ASN A 386      10.884  39.135  32.309  1.00   88.09      A    N
ATOM   2019  C    ASN A 386       6.813  36.926  31.596  1.00   82.97      A    C
ATOM   2020  O    ASN A 386       7.261  35.992  30.958  1.00   83.21      A    O
ATOM   2021  N    SER A 387       5.516  37.167  31.732  1.00   84.29      A    N
ATOM   2022  CA   SER A 387       4.522  36.347  31.047  1.00   86.33      A    C
ATOM   2023  CB   SER A 387       4.810  36.353  29.544  1.00   93.76      A    C
ATOM   2024  OG   SER A 387       4.204  35.245  28.889  1.00  103.67      A    O
ATOM   2025  C    SER A 387       4.399  34.892  31.517  1.00   82.84      A    C
ATOM   2026  O    SER A 387       5.387  34.244  31.869  1.00   79.51      A    O
ATOM   2027  N    SER A 388       3.168  34.387  31.478  1.00   79.11      A    N
ATOM   2028  CA   SER A 388       2.874  33.019  31.873  1.00   73.64      A    C
ATOM   2029  CB   SER A 388       1.376  32.750  31.755  1.00   69.41      A    C
ATOM   2030  OG   SER A 388       1.100  31.420  32.131  1.00   67.33      A    O
ATOM   2031  C    SER A 388       3.642  32.016  31.013  1.00   72.12      A    C
ATOM   2032  O    SER A 388       4.646  32.430  30.392  1.00   69.89      A    O
TER    2034       SER A 388                                                A
ATOM   2035  C1   212 B   1      -4.302  30.253   8.464  1.00   68.60      B    C
ATOM   2036  C2   212 B   1      -4.851  31.084   9.411  1.00   68.12      B    C
ATOM   2037  C3   212 B   1      -5.317  32.331   9.022  1.00   70.88      B    C
ATOM   2038  C4   212 B   1      -5.251  32.762   7.698  1.00   69.06      B    C
ATOM   2039  C55  212 B   1      -4.687  31.914   6.771  1.00   73.11      B    C
ATOM   2040  C7   212 B   1      -9.623  34.126  10.749  1.00   62.88      B    C
ATOM   2041  C9   212 B   1      -9.260  35.315  10.076  1.00   66.59      B    C
ATOM   2042  N    212 B   1      -8.544  35.273   8.892  1.00   64.04      B    N
ATOM   2043  C14  212 B   1      -8.181  34.044   8.363  1.00   58.85      B    C
ATOM   2044  N2   212 B   1      -8.569  32.905   9.061  1.00   56.27      B    N
ATOM   2045  C17  212 B   1      -9.268  32.945  10.249  1.00   57.06      B    C
ATOM   2046  C8   212 B   1      -8.861  28.850   9.398  1.00   45.58      B    C
ATOM   2047  C10  212 B   1      -8.822  30.233   9.511  1.00   44.13      B    C
ATOM   2048  C12  212 B   1      -9.224  30.505  10.802  1.00   44.58      B    C
ATOM   2049  N3   212 B   1      -9.185  28.311  10.732  1.00   39.51      B    N
ATOM   2050  N4   212 B   1      -9.375  29.358  11.605  1.00   39.86      B    N
ATOM   2051  C18  212 B   1      -5.876  34.076   7.274  1.00   63.34      B    C
ATOM   2052  C15  212 B   1      -8.677  28.167   8.191  1.00   48.92      B    C
ATOM   2053  C11  212 B   1     -10.373  34.156  11.968  1.00   64.95      B    C
ATOM   2054  C13  212 B   1     -10.752  35.364  12.523  1.00   72.34      B    C
ATOM   2055  C16  212 B   1     -10.386  36.566  11.876  1.00   75.43      B    C
ATOM   2056  C5   212 B   1      -9.633  36.546  10.648  1.00   72.28      B    C
ATOM   2057  N6   212 B   1      -9.501  31.845  11.052  1.00   51.85      B    N
ATOM   2058  N9   212 B   1      -7.358  33.964   7.215  1.00   56.80      B    N
ATOM   2059  N8   212 B   1      -4.216  30.663   7.155  1.00   73.15      B    N
TER    2060       212 B   1                                                B
END
```

Figure 4A

| Atom | Type | Resid | # | X | Y | Z | Occ | B | Mol | |
|------|------|-------|---|---|---|---|-----|---|-----|---|
| ATOM | 1 | CB | TRP A 128 | 27.817 | 61.000 | 21.182 | 1.00 | 98.41 | A | C |
| ATOM | 2 | CG | TRP A 128 | 28.380 | 61.241 | 19.859 | 1.00 | 107.87 | A | C |
| ATOM | 3 | CD2 | TRP A 128 | 27.665 | 61.221 | 18.610 | 1.00 | 111.93 | A | C |
| ATOM | 4 | CE2 | TRP A 128 | 28.595 | 61.542 | 17.590 | 1.00 | 114.01 | A | C |
| ATOM | 5 | CE3 | TRP A 128 | 26.328 | 60.967 | 18.253 | 1.00 | 112.66 | A | C |
| ATOM | 6 | CD1 | TRP A 128 | 29.678 | 61.561 | 19.563 | 1.00 | 111.45 | A | C |
| ATOM | 7 | NE1 | TRP A 128 | 29.813 | 61.742 | 18.198 | 1.00 | 115.64 | A | N |
| ATOM | 8 | CZ2 | TRP A 128 | 28.225 | 61.615 | 16.219 | 1.00 | 114.76 | A | C |
| ATOM | 9 | CZ3 | TRP A 128 | 25.961 | 61.040 | 16.893 | 1.00 | 112.93 | A | C |
| ATOM | 10 | CH2 | TRP A 128 | 26.909 | 61.362 | 15.898 | 1.00 | 113.35 | A | C |
| ATOM | 11 | C | TRP A 128 | 26.497 | 61.762 | 23.050 | 1.00 | 95.74 | A | C |
| ATOM | 12 | O | TRP A 128 | 26.902 | 62.356 | 24.039 | 1.00 | 95.36 | A | O |
| ATOM | 13 | N | TRP A 128 | 27.731 | 63.429 | 21.703 | 1.00 | 91.77 | A | N |
| ATOM | 14 | CA | TRP A 128 | 26.958 | 62.149 | 21.678 | 1.00 | 94.64 | A | C |
| ATOM | 15 | N | ALA A 129 | 25.659 | 60.735 | 23.100 | 1.00 | 97.32 | A | N |
| ATOM | 16 | CA | ALA A 129 | 25.156 | 60.205 | 24.363 | 1.00 | 98.31 | A | C |
| ATOM | 17 | CB | ALA A 129 | 23.911 | 60.985 | 24.843 | 1.00 | 96.54 | A | C |
| ATOM | 18 | C | ALA A 129 | 24.821 | 58.737 | 24.127 | 1.00 | 98.04 | A | C |
| ATOM | 19 | O | ALA A 129 | 24.471 | 58.341 | 23.009 | 1.00 | 94.27 | A | O |
| ATOM | 20 | N | LEU A 130 | 24.959 | 57.930 | 25.177 | 1.00 | 100.85 | A | N |
| ATOM | 21 | CA | LEU A 130 | 24.681 | 56.495 | 25.086 | 1.00 | 103.78 | A | C |
| ATOM | 22 | CB | LEU A 130 | 24.893 | 55.813 | 26.447 | 1.00 | 102.54 | A | C |
| ATOM | 23 | CG | LEU A 130 | 24.512 | 54.324 | 26.544 | 1.00 | 100.22 | A | C |
| ATOM | 24 | CD1 | LEU A 130 | 25.310 | 53.540 | 25.509 | 1.00 | 97.26 | A | C |
| ATOM | 25 | CD2 | LEU A 130 | 24.757 | 53.788 | 27.981 | 1.00 | 99.07 | A | C |
| ATOM | 26 | C | LEU A 130 | 23.247 | 56.283 | 24.639 | 1.00 | 105.99 | A | C |
| ATOM | 27 | O | LEU A 130 | 22.857 | 55.200 | 24.186 | 1.00 | 105.36 | A | O |
| ATOM | 28 | N | GLU A 131 | 22.462 | 57.339 | 24.778 | 1.00 | 107.82 | A | N |
| ATOM | 29 | CA | GLU A 131 | 21.078 | 57.277 | 24.410 | 1.00 | 109.20 | A | C |
| ATOM | 30 | CB | GLU A 131 | 20.341 | 58.416 | 25.035 | 1.00 | 113.38 | A | C |
| ATOM | 31 | CG | GLU A 131 | 18.893 | 58.320 | 24.735 | 1.00 | 121.43 | A | C |
| ATOM | 32 | CD | GLU A 131 | 18.300 | 59.669 | 24.441 | 1.00 | 126.00 | A | C |
| ATOM | 33 | OE1 | GLU A 131 | 18.660 | 60.636 | 25.155 | 1.00 | 130.23 | A | O |
| ATOM | 34 | OE2 | GLU A 131 | 17.473 | 59.759 | 23.503 | 1.00 | 129.08 | A | O |
| ATOM | 35 | C | GLU A 131 | 20.890 | 57.366 | 22.916 | 1.00 | 108.63 | A | C |
| ATOM | 36 | O | GLU A 131 | 19.880 | 56.900 | 22.396 | 1.00 | 108.44 | A | O |
| ATOM | 37 | N | ASP A 132 | 21.865 | 57.974 | 22.240 | 1.00 | 107.80 | A | N |
| ATOM | 38 | CA | ASP A 132 | 21.848 | 58.186 | 20.785 | 1.00 | 105.97 | A | C |
| ATOM | 39 | CB | ASP A 132 | 22.988 | 59.125 | 20.403 | 1.00 | 109.93 | A | C |
| ATOM | 40 | CG | ASP A 132 | 22.946 | 60.433 | 21.169 | 1.00 | 112.63 | A | C |
| ATOM | 41 | OD1 | ASP A 132 | 22.899 | 60.396 | 22.416 | 1.00 | 115.57 | A | O |
| ATOM | 42 | OD2 | ASP A 132 | 22.964 | 61.499 | 20.527 | 1.00 | 111.61 | A | O |
| ATOM | 43 | C | ASP A 132 | 21.943 | 56.944 | 19.913 | 1.00 | 102.68 | A | C |
| ATOM | 44 | O | ASP A 132 | 21.824 | 57.020 | 18.691 | 1.00 | 99.16 | A | O |
| ATOM | 45 | N | PHE A 133 | 22.161 | 55.801 | 20.546 | 1.00 | 102.67 | A | N |
| ATOM | 46 | CA | PHE A 133 | 22.298 | 54.550 | 19.812 | 1.00 | 103.51 | A | C |
| ATOM | 47 | CB | PHE A 133 | 23.751 | 54.136 | 19.764 | 1.00 | 102.19 | A | C |
| ATOM | 48 | CG | PHE A 133 | 24.683 | 55.252 | 19.525 | 1.00 | 100.58 | A | C |
| ATOM | 49 | CD1 | PHE A 133 | 24.942 | 56.204 | 20.519 | 1.00 | 101.82 | A | C |
| ATOM | 50 | CD2 | PHE A 133 | 25.347 | 55.329 | 18.324 | 1.00 | 101.04 | A | C |
| ATOM | 51 | CE1 | PHE A 133 | 25.866 | 57.218 | 20.310 | 1.00 | 102.23 | A | C |
| ATOM | 52 | CE2 | PHE A 133 | 26.268 | 56.329 | 18.097 | 1.00 | 101.45 | A | C |
| ATOM | 53 | CZ | PHE A 133 | 26.534 | 57.279 | 19.092 | 1.00 | 101.79 | A | C |
| ATOM | 54 | C | PHE A 133 | 21.526 | 53.357 | 20.364 | 1.00 | 104.23 | A | C |
| ATOM | 55 | O | PHE A 133 | 21.140 | 53.326 | 21.543 | 1.00 | 106.87 | A | O |
| ATOM | 56 | N | GLU A 134 | 21.346 | 52.362 | 19.493 | 1.00 | 103.16 | A | N |
| ATOM | 57 | CA | GLU A 134 | 20.662 | 51.110 | 19.828 | 1.00 | 100.36 | A | C |
| ATOM | 58 | CB | GLU A 134 | 19.634 | 50.757 | 18.741 | 1.00 | 101.25 | A | C |

Figure 4B

| ATOM | 63 | C | GLU | A | 134 | 21.758 | 50.050 | 19.899 | 1.00 | 97.35 | A | C |
| --- | --- | --- | --- | --- | --- | --- | --- | --- | --- | --- | --- | --- |
| ATOM | 64 | O | GLU | A | 134 | 22.500 | 49.835 | 18.932 | 1.00 | 96.32 | A | O |
| ATOM | 65 | N | ILE | A | 135 | 21.876 | 49.391 | 21.041 | 1.00 | 93.66 | A | N |
| ATOM | 66 | CA | ILE | A | 135 | 22.933 | 48.417 | 21.159 | 1.00 | 92.68 | A | C |
| ATOM | 67 | CB | ILE | A | 135 | 23.393 | 48.248 | 22.625 | 1.00 | 91.30 | A | C |
| ATOM | 68 | CG2 | ILE | A | 135 | 23.993 | 49.540 | 23.132 | 1.00 | 89.41 | A | C |
| ATOM | 69 | CG1 | ILE | A | 135 | 22.217 | 47.852 | 23.513 | 1.00 | 94.10 | A | C |
| ATOM | 70 | CD1 | ILE | A | 135 | 22.639 | 47.482 | 24.939 | 1.00 | 97.81 | A | C |
| ATOM | 71 | C | ILE | A | 135 | 22.532 | 47.080 | 20.598 | 1.00 | 94.15 | A | C |
| ATOM | 72 | O | ILE | A | 135 | 21.384 | 46.663 | 20.730 | 1.00 | 95.53 | A | O |
| ATOM | 73 | N | GLY | A | 136 | 23.500 | 46.427 | 19.959 | 1.00 | 94.95 | A | N |
| ATOM | 74 | CA | GLY | A | 136 | 23.295 | 45.115 | 19.373 | 1.00 | 95.53 | A | C |
| ATOM | 75 | C | GLY | A | 136 | 24.037 | 44.042 | 20.157 | 1.00 | 94.17 | A | C |
| ATOM | 76 | O | GLY | A | 136 | 24.522 | 44.289 | 21.263 | 1.00 | 93.61 | A | O |
| ATOM | 77 | N | ARG | A | 137 | 24.146 | 42.850 | 19.583 | 1.00 | 93.77 | A | N |
| ATOM | 78 | CA | ARG | A | 137 | 24.808 | 41.752 | 20.270 | 1.00 | 95.52 | A | C |
| ATOM | 79 | CB | ARG | A | 137 | 24.786 | 40.490 | 19.406 | 1.00 | 94.16 | A | C |
| ATOM | 80 | CG | ARG | A | 137 | 26.050 | 40.280 | 18.626 | 1.00 | 90.11 | A | C |
| ATOM | 81 | CD | ARG | A | 137 | 25.799 | 39.408 | 17.442 | 1.00 | 86.38 | A | C |
| ATOM | 82 | NE | ARG | A | 137 | 27.036 | 39.145 | 16.718 | 1.00 | 84.37 | A | N |
| ATOM | 83 | CZ | ARG | A | 137 | 27.175 | 39.262 | 15.399 | 1.00 | 83.10 | A | C |
| ATOM | 84 | NH1 | ARG | A | 137 | 28.346 | 38.992 | 14.828 | 1.00 | 84.17 | A | N |
| ATOM | 85 | NH2 | ARG | A | 137 | 26.149 | 39.659 | 14.653 | 1.00 | 80.96 | A | N |
| ATOM | 86 | C | ARG | A | 137 | 26.245 | 42.093 | 20.609 | 1.00 | 98.31 | A | C |
| ATOM | 87 | O | ARG | A | 137 | 26.791 | 43.097 | 20.134 | 1.00 | 97.34 | A | O |
| ATOM | 88 | N | PRO | A | 138 | 26.868 | 41.263 | 21.459 | 1.00 | 101.62 | A | N |
| ATOM | 89 | CD | PRO | A | 138 | 26.198 | 40.252 | 22.303 | 1.00 | 102.67 | A | C |
| ATOM | 90 | CA | PRO | A | 138 | 28.261 | 41.453 | 21.872 | 1.00 | 104.24 | A | C |
| ATOM | 91 | CB | PRO | A | 138 | 28.331 | 40.699 | 23.196 | 1.00 | 104.85 | A | C |
| ATOM | 92 | CG | PRO | A | 138 | 27.358 | 39.560 | 22.978 | 1.00 | 103.75 | A | C |
| ATOM | 93 | C | PRO | A | 138 | 29.179 | 40.859 | 20.806 | 1.00 | 106.04 | A | C |
| ATOM | 94 | O | PRO | A | 138 | 29.285 | 39.643 | 20.662 | 1.00 | 105.49 | A | O |
| ATOM | 95 | N | LEU | A | 139 | 29.827 | 41.732 | 20.049 | 1.00 | 108.54 | A | N |
| ATOM | 96 | CA | LEU | A | 139 | 30.718 | 41.315 | 18.975 | 1.00 | 111.07 | A | C |
| ATOM | 97 | CB | LEU | A | 139 | 31.247 | 42.533 | 18.243 | 1.00 | 110.35 | A | C |
| ATOM | 98 | CG | LEU | A | 139 | 30.100 | 43.437 | 17.834 | 1.00 | 111.80 | A | C |
| ATOM | 99 | CD1 | LEU | A | 139 | 30.658 | 44.617 | 17.076 | 1.00 | 113.69 | A | C |
| ATOM | 100 | CD2 | LEU | A | 139 | 29.105 | 42.643 | 16.994 | 1.00 | 115.59 | A | C |
| ATOM | 101 | C | LEU | A | 139 | 31.887 | 40.502 | 19.462 | 1.00 | 112.97 | A | C |
| ATOM | 102 | O | LEU | A | 139 | 32.431 | 39.679 | 18.730 | 1.00 | 113.42 | A | O |
| ATOM | 103 | N | GLY | A | 140 | 32.272 | 40.759 | 20.705 | 1.00 | 115.33 | A | N |
| ATOM | 104 | CA | GLY | A | 140 | 33.381 | 40.050 | 21.307 | 1.00 | 120.54 | A | C |
| ATOM | 105 | C | GLY | A | 140 | 33.463 | 40.286 | 22.805 | 1.00 | 124.00 | A | C |
| ATOM | 106 | O | GLY | A | 140 | 32.521 | 40.790 | 23.426 | 1.00 | 123.79 | A | O |
| ATOM | 107 | N | LYS | A | 141 | 34.604 | 39.924 | 23.384 | 1.00 | 127.61 | A | N |
| ATOM | 108 | CA | LYS | A | 141 | 34.821 | 40.087 | 24.814 | 1.00 | 129.26 | A | C |
| ATOM | 109 | CB | LYS | A | 141 | 35.178 | 38.738 | 25.448 | 1.00 | 129.77 | A | C |
| ATOM | 114 | C | LYS | A | 141 | 35.919 | 41.099 | 25.125 | 1.00 | 130.38 | A | C |
| ATOM | 115 | O | LYS | A | 141 | 36.667 | 41.535 | 24.241 | 1.00 | 130.89 | A | O |
| ATOM | 116 | N | GLY | A | 142 | 36.007 | 41.457 | 26.402 | 1.00 | 130.44 | A | N |
| ATOM | 117 | CA | GLY | A | 142 | 37.007 | 42.406 | 26.846 | 1.00 | 128.74 | A | C |
| ATOM | 118 | C | GLY | A | 142 | 37.096 | 42.475 | 28.357 | 1.00 | 126.17 | A | C |
| ATOM | 119 | O | GLY | A | 142 | 36.104 | 42.752 | 29.045 | 1.00 | 125.25 | A | O |
| ATOM | 120 | N | LYS | A | 143 | 38.282 | 42.203 | 28.884 | 1.00 | 123.43 | A | N |
| ATOM | 121 | CA | LYS | A | 143 | 38.469 | 42.280 | 30.313 | 1.00 | 120.07 | A | C |
| ATOM | 122 | CB | LYS | A | 143 | 39.916 | 41.932 | 30.664 | 1.00 | 119.32 | A | C |
| ATOM | 127 | C | LYS | A | 143 | 38.120 | 43.718 | 30.730 | 1.00 | 119.74 | A | C |
| ATOM | 128 | O | LYS | A | 143 | 37.310 | 43.930 | 31.641 | 1.00 | 116.79 | A | O |
| ATOM | 129 | N | PHE | A | 144 | 38.721 | 44.701 | 30.052 | 1.00 | 119.93 | A | N |
| ATOM | 130 | CA | PHE | A | 144 | 38.444 | 46.118 | 30.344 | 1.00 | 118.94 | A | C |
| ATOM | 131 | CB | PHE | A | 144 | 39.218 | 47.082 | 29.420 | 1.00 | 80.18 | A | C |

Figure 4C

| ATOM | 132 | CG | PHE | A | 144 | 40.737 | 47.025 | 29.540 | 1.00 | 80.18 | A | C |
|---|---|---|---|---|---|---|---|---|---|---|---|---|
| ATOM | 133 | CD1 | PHE | A | 144 | 41.378 | 46.117 | 30.396 | 1.00 | 80.18 | A | C |
| ATOM | 134 | CD2 | PHE | A | 144 | 41.532 | 47.899 | 28.762 | 1.00 | 80.18 | A | C |
| ATOM | 135 | CE1 | PHE | A | 144 | 42.793 | 46.076 | 30.478 | 1.00 | 80.18 | A | C |
| ATOM | 136 | CE2 | PHE | A | 144 | 42.945 | 47.875 | 28.828 | 1.00 | 80.18 | A | C |
| ATOM | 137 | CZ | PHE | A | 144 | 43.579 | 46.961 | 29.687 | 1.00 | 80.18 | A | C |
| ATOM | 138 | C | PHE | A | 144 | 36.962 | 46.347 | 30.068 | 1.00 | 118.20 | A | C |
| ATOM | 139 | O | PHE | A | 144 | 36.123 | 46.212 | 30.957 | 1.00 | 116.18 | A | O |
| ATOM | 140 | N | GLY | A | 145 | 36.660 | 46.680 | 28.812 | 1.00 | 118.56 | A | N |
| ATOM | 141 | CA | GLY | A | 145 | 35.291 | 46.926 | 28.399 | 1.00 | 117.56 | A | C |
| ATOM | 142 | C | GLY | A | 145 | 34.826 | 46.088 | 27.215 | 1.00 | 117.62 | A | C |
| ATOM | 143 | O | GLY | A | 145 | 35.627 | 45.432 | 26.550 | 1.00 | 116.93 | A | O |
| ATOM | 144 | N | ASN | A | 146 | 33.518 | 46.126 | 26.956 | 1.00 | 118.53 | A | N |
| ATOM | 145 | CA | ASN | A | 146 | 32.872 | 45.373 | 25.871 | 1.00 | 119.35 | A | C |
| ATOM | 146 | CB | ASN | A | 146 | 31.413 | 45.050 | 26.254 | 1.00 | 122.17 | A | C |
| ATOM | 147 | CG | ASN | A | 146 | 31.302 | 44.040 | 27.389 | 1.00 | 123.33 | A | C |
| ATOM | 148 | OD1 | ASN | A | 146 | 30.271 | 43.971 | 28.063 | 1.00 | 122.65 | A | O |
| ATOM | 149 | ND2 | ASN | A | 146 | 32.353 | 43.238 | 27.590 | 1.00 | 120.18 | A | N |
| ATOM | 150 | C | ASN | A | 146 | 32.871 | 46.096 | 24.514 | 1.00 | 116.63 | A | C |
| ATOM | 151 | O | ASN | A | 146 | 33.809 | 46.826 | 24.170 | 1.00 | 114.94 | A | O |
| ATOM | 152 | N | VAL | A | 147 | 31.792 | 45.880 | 23.763 | 1.00 | 115.02 | A | N |
| ATOM | 153 | CA | VAL | A | 147 | 31.601 | 46.468 | 22.439 | 1.00 | 113.48 | A | C |
| ATOM | 154 | CB | VAL | A | 147 | 32.899 | 46.361 | 21.596 | 1.00 | 113.14 | A | C |
| ATOM | 155 | CG1 | VAL | A | 147 | 33.378 | 44.919 | 21.566 | 1.00 | 111.53 | A | C |
| ATOM | 156 | CG2 | VAL | A | 147 | 32.663 | 46.890 | 20.183 | 1.00 | 113.50 | A | C |
| ATOM | 157 | C | VAL | A | 147 | 30.453 | 45.741 | 21.726 | 1.00 | 111.73 | A | C |
| ATOM | 158 | O | VAL | A | 147 | 30.648 | 44.712 | 21.072 | 1.00 | 113.71 | A | O |
| ATOM | 159 | N | TYR | A | 148 | 29.250 | 46.285 | 21.850 | 1.00 | 106.83 | A | N |
| ATOM | 160 | CA | TYR | A | 148 | 28.090 | 45.659 | 21.244 | 1.00 | 100.85 | A | C |
| ATOM | 161 | CB | TYR | A | 148 | 26.869 | 45.825 | 22.167 | 1.00 | 104.88 | A | C |
| ATOM | 162 | CG | TYR | A | 148 | 27.139 | 45.923 | 23.686 | 1.00 | 109.95 | A | C |
| ATOM | 163 | CD1 | TYR | A | 148 | 28.061 | 45.087 | 24.332 | 1.00 | 111.84 | A | C |
| ATOM | 164 | CE1 | TYR | A | 148 | 28.240 | 45.146 | 25.728 | 1.00 | 112.26 | A | C |
| ATOM | 165 | CD2 | TYR | A | 148 | 26.409 | 46.820 | 24.486 | 1.00 | 112.30 | A | C |
| ATOM | 166 | CE2 | TYR | A | 148 | 26.582 | 46.876 | 25.879 | 1.00 | 112.24 | A | C |
| ATOM | 167 | CZ | TYR | A | 148 | 27.497 | 46.042 | 26.485 | 1.00 | 112.79 | A | C |
| ATOM | 168 | OH | TYR | A | 148 | 27.663 | 46.114 | 27.848 | 1.00 | 116.36 | A | O |
| ATOM | 169 | C | TYR | A | 148 | 27.785 | 46.272 | 19.877 | 1.00 | 94.59 | A | C |
| ATOM | 170 | O | TYR | A | 148 | 28.151 | 47.417 | 19.614 | 1.00 | 93.90 | A | O |
| ATOM | 171 | N | LEU | A | 149 | 27.158 | 45.495 | 18.996 | 1.00 | 87.77 | A | N |
| ATOM | 172 | CA | LEU | A | 149 | 26.748 | 45.994 | 17.713 | 1.00 | 83.47 | A | C |
| ATOM | 173 | CB | LEU | A | 149 | 25.826 | 44.997 | 17.038 | 1.00 | 83.90 | A | C |
| ATOM | 174 | CG | LEU | A | 149 | 26.439 | 44.182 | 15.905 | 1.00 | 83.82 | A | C |
| ATOM | 175 | CD1 | LEU | A | 149 | 25.373 | 43.254 | 15.306 | 1.00 | 84.05 | A | C |
| ATOM | 176 | CD2 | LEU | A | 149 | 27.011 | 45.135 | 14.847 | 1.00 | 82.25 | A | C |
| ATOM | 177 | C | LEU | A | 149 | 25.984 | 47.244 | 18.124 | 1.00 | 81.35 | A | C |
| ATOM | 178 | O | LEU | A | 149 | 25.421 | 47.284 | 19.211 | 1.00 | 78.76 | A | O |
| ATOM | 179 | N | ALA | A | 150 | 25.979 | 48.272 | 17.287 | 1.00 | 81.47 | A | N |
| ATOM | 180 | CA | ALA | A | 150 | 25.272 | 49.496 | 17.641 | 1.00 | 80.57 | A | C |
| ATOM | 181 | CB | ALA | A | 150 | 26.195 | 50.435 | 18.388 | 1.00 | 75.69 | A | C |
| ATOM | 182 | C | ALA | A | 150 | 24.710 | 50.189 | 16.423 | 1.00 | 81.24 | A | C |
| ATOM | 183 | O | ALA | A | 150 | 25.145 | 49.947 | 15.301 | 1.00 | 81.10 | A | O |
| ATOM | 184 | N | ARG | A | 151 | 23.747 | 51.069 | 16.661 | 1.00 | 83.00 | A | N |
| ATOM | 185 | CA | ARG | A | 151 | 23.092 | 51.796 | 15.584 | 1.00 | 84.33 | A | C |
| ATOM | 186 | CB | ARG | A | 151 | 21.828 | 51.034 | 15.153 | 1.00 | 87.82 | A | C |
| ATOM | 187 | CG | ARG | A | 151 | 21.621 | 50.814 | 13.634 | 1.00 | 90.24 | A | C |
| ATOM | 188 | CD | ARG | A | 151 | 20.396 | 49.904 | 13.422 | 1.00 | 91.47 | A | C |
| ATOM | 189 | NE | ARG | A | 151 | 20.352 | 49.232 | 12.126 | 1.00 | 91.82 | A | N |
| ATOM | 190 | CZ | ARG | A | 151 | 19.789 | 48.041 | 11.931 | 1.00 | 92.21 | A | C |
| ATOM | 191 | NH1 | ARG | A | 151 | 19.225 | 47.396 | 12.947 | 1.00 | 92.38 | A | N |
| ATOM | 192 | NH2 | ARG | A | 151 | 19.796 | 47.491 | 10.724 | 1.00 | 90.11 | A | N |

Figure 4D

```
ATOM    193  C   ARG A 151      22.700  53.189  16.049  1.00   81.62      A  C
ATOM    194  O   ARG A 151      22.084  53.349  17.094  1.00   79.22      A  O
ATOM    195  N   GLU A 152      23.066  54.205  15.287  1.00   81.47      A  N
ATOM    196  CA  GLU A 152      22.667  55.536  15.673  1.00   85.29      A  C
ATOM    197  CB  GLU A 152      23.409  56.601  14.904  1.00   84.17      A  C
ATOM    198  CG  GLU A 152      22.686  57.927  14.979  1.00   85.29      A  C
ATOM    199  CD  GLU A 152      23.529  59.056  14.491  1.00   88.90      A  C
ATOM    200  OE1 GLU A 152      23.912  59.046  13.301  1.00   89.54      A  O
ATOM    201  OE2 GLU A 152      23.814  59.953  15.311  1.00   91.63      A  O
ATOM    202  C   GLU A 152      21.222  55.663  15.306  1.00   90.26      A  C
ATOM    203  O   GLU A 152      20.872  55.552  14.132  1.00   90.70      A  O
ATOM    204  N   ALA A 153      20.388  55.925  16.304  1.00   95.96      A  N
ATOM    205  CA  ALA A 153      18.943  56.072  16.095  1.00   99.27      A  C
ATOM    206  CB  ALA A 153      18.275  56.507  17.414  1.00  102.05      A  C
ATOM    207  C   ALA A 153      18.568  57.049  14.956  1.00   99.25      A  C
ATOM    208  O   ALA A 153      17.580  56.835  14.235  1.00   97.61      A  O
ATOM    209  N   ALA A 154      19.357  58.115  14.807  1.00   99.31      A  N
ATOM    210  CA  ALA A 154      19.114  59.107  13.769  1.00   99.12      A  C
ATOM    211  CB  ALA A 154      20.048  60.312  13.955  1.00   97.38      A  C
ATOM    212  C   ALA A 154      19.320  58.484  12.388  1.00   99.26      A  C
ATOM    213  O   ALA A 154      18.349  58.190  11.686  1.00   99.46      A  O
ATOM    214  N   SER A 155      20.580  58.255  12.021  1.00   98.40      A  N
ATOM    215  CA  SER A 155      20.937  57.692  10.713  1.00   95.21      A  C
ATOM    216  CB  SER A 155      22.409  57.983  10.434  1.00   93.37      A  C
ATOM    217  OG  SER A 155      23.209  57.532  11.513  1.00   87.72      A  O
ATOM    218  C   SER A 155      20.679  56.197  10.502  1.00   92.98      A  C
ATOM    219  O   SER A 155      20.938  55.659   9.414  1.00   88.45      A  O
ATOM    220  N   ALA A 156      20.170  55.534  11.534  1.00   93.37      A  N
ATOM    221  CA  ALA A 156      19.894  54.101  11.471  1.00   97.04      A  C
ATOM    222  CB  ALA A 156      18.713  53.822  10.558  1.00   95.44      A  C
ATOM    223  C   ALA A 156      21.131  53.393  10.952  1.00  100.00      A  C
ATOM    224  O   ALA A 156      21.075  52.243  10.516  1.00  100.16      A  O
ATOM    225  N   PHE A 157      22.249  54.109  11.016  1.00  103.68      A  N
ATOM    226  CA  PHE A 157      23.540  53.616  10.553  1.00  103.38      A  C
ATOM    227  CB  PHE A 157      24.495  54.789  10.314  1.00  106.33      A  C
ATOM    228  CG  PHE A 157      25.784  54.390   9.667  1.00  107.04      A  C
ATOM    229  CD1 PHE A 157      25.786  53.849   8.387  1.00  109.27      A  C
ATOM    230  CD2 PHE A 157      26.993  54.556  10.329  1.00  107.31      A  C
ATOM    231  CE1 PHE A 157      26.976  53.479   7.774  1.00  111.22      A  C
ATOM    232  CE2 PHE A 157      28.182  54.188   9.723  1.00  108.18      A  C
ATOM    233  CZ  PHE A 157      28.173  53.647   8.440  1.00  109.95      A  C
ATOM    234  C   PHE A 157      24.199  52.627  11.511  1.00  100.93      A  C
ATOM    235  O   PHE A 157      24.549  52.956  12.655  1.00  100.02      A  O
ATOM    236  N   ILE A 158      24.481  51.426  11.031  1.00   98.13      A  N
ATOM    237  CA  ILE A 158      25.143  50.440  11.885  1.00   95.61      A  C
ATOM    238  CB  ILE A 158      25.374  49.117  11.147  1.00   96.93      A  C
ATOM    239  CG2 ILE A 158      24.063  48.590  10.622  1.00   97.24      A  C
ATOM    240  CG1 ILE A 158      26.328  49.333   9.975  1.00   99.95      A  C
ATOM    241  CD1 ILE A 158      25.756  50.222   8.847  1.00  104.38      A  C
ATOM    242  C   ILE A 158      26.500  50.960  12.368  1.00   93.56      A  C
ATOM    243  O   ILE A 158      27.180  51.712  11.664  1.00   92.38      A  O
ATOM    244  N   LEU A 159      26.882  50.544  13.573  1.00   91.06      A  N
ATOM    245  CA  LEU A 159      28.144  50.952  14.179  1.00   89.77      A  C
ATOM    246  CB  LEU A 159      27.951  52.166  15.085  1.00   87.15      A  C
ATOM    247  CG  LEU A 159      28.254  53.516  14.464  1.00   88.71      A  C
ATOM    248  CD1 LEU A 159      29.608  53.461  13.799  1.00   87.78      A  C
ATOM    249  CD2 LEU A 159      27.183  53.858  13.451  1.00   91.23      A  C
ATOM    250  C   LEU A 159      28.764  49.860  15.018  1.00   88.92      A  C
ATOM    251  O   LEU A 159      28.498  48.674  14.833  1.00   88.85      A  O
ATOM    252  N   ALA A 160      29.592  50.298  15.956  1.00   87.59      A  N
ATOM    253  CA  ALA A 160      30.284  49.420  16.872  1.00   86.36      A  C
```

Figure 4E

| ATOM | 254 | CB | ALA A 160 | 31.523 | 48.849 | 16.205 | 1.00 | 89.32 | A | C |
|---|---|---|---|---|---|---|---|---|---|---|
| ATOM | 255 | C | ALA A 160 | 30.673 | 50.296 | 18.038 | 1.00 | 84.04 | A | C |
| ATOM | 256 | O | ALA A 160 | 31.198 | 51.388 | 17.843 | 1.00 | 84.38 | A | O |
| ATOM | 257 | N | LEU A 161 | 30.441 | 49.825 | 19.251 | 1.00 | 80.78 | A | N |
| ATOM | 258 | CA | LEU A 161 | 30.774 | 50.645 | 20.389 | 1.00 | 78.78 | A | C |
| ATOM | 259 | CB | LEU A 161 | 29.504 | 51.034 | 21.104 | 1.00 | 75.84 | A | C |
| ATOM | 260 | CG | LEU A 161 | 29.836 | 52.021 | 22.211 | 1.00 | 76.35 | A | C |
| ATOM | 261 | CD1 | LEU A 161 | 30.227 | 53.349 | 21.573 | 1.00 | 80.80 | A | C |
| ATOM | 262 | CD2 | LEU A 161 | 28.655 | 52.188 | 23.136 | 1.00 | 77.68 | A | C |
| ATOM | 263 | C | LEU A 161 | 31.736 | 50.056 | 21.409 | 1.00 | 80.92 | A | C |
| ATOM | 264 | O | LEU A 161 | 31.300 | 49.419 | 22.368 | 1.00 | 83.48 | A | O |
| ATOM | 265 | N | LYS A 162 | 33.034 | 50.294 | 21.231 | 1.00 | 82.11 | A | N |
| ATOM | 266 | CA | LYS A 162 | 34.035 | 49.779 | 22.168 | 1.00 | 84.66 | A | C |
| ATOM | 267 | CB | LYS A 162 | 35.444 | 49.853 | 21.580 | 1.00 | 80.18 | A | C |
| ATOM | 268 | CG | LYS A 162 | 36.544 | 49.324 | 22.518 | 1.00 | 80.18 | A | C |
| ATOM | 269 | CD | LYS A 162 | 37.908 | 49.217 | 21.802 | 1.00 | 80.18 | A | C |
| ATOM | 270 | CE | LYS A 162 | 37.965 | 48.049 | 20.809 | 1.00 | 80.18 | A | C |
| ATOM | 271 | NZ | LYS A 162 | 38.810 | 48.330 | 19.599 | 1.00 | 80.18 | A | N |
| ATOM | 272 | C | LYS A 162 | 34.017 | 50.550 | 23.467 | 1.00 | 88.43 | A | C |
| ATOM | 273 | O | LYS A 162 | 34.709 | 51.554 | 23.621 | 1.00 | 87.47 | A | O |
| ATOM | 274 | N | VAL A 163 | 33.208 | 50.065 | 24.397 | 1.00 | 94.72 | A | N |
| ATOM | 275 | CA | VAL A 163 | 33.068 | 50.665 | 25.721 | 1.00 | 100.48 | A | C |
| ATOM | 276 | CB | VAL A 163 | 31.637 | 50.371 | 26.310 | 1.00 | 101.33 | A | C |
| ATOM | 277 | CG1 | VAL A 163 | 31.099 | 49.035 | 25.801 | 1.00 | 101.67 | A | C |
| ATOM | 278 | CG2 | VAL A 163 | 31.687 | 50.348 | 27.816 | 1.00 | 99.58 | A | C |
| ATOM | 279 | C | VAL A 163 | 34.169 | 50.111 | 26.646 | 1.00 | 104.18 | A | C |
| ATOM | 280 | O | VAL A 163 | 34.465 | 48.917 | 26.610 | 1.00 | 107.88 | A | O |
| ATOM | 281 | N | LEU A 164 | 34.779 | 50.977 | 27.457 | 1.00 | 105.67 | A | N |
| ATOM | 282 | CA | LEU A 164 | 35.847 | 50.557 | 28.368 | 1.00 | 106.96 | A | C |
| ATOM | 283 | CB | LEU A 164 | 37.190 | 51.094 | 27.893 | 1.00 | 102.71 | A | C |
| ATOM | 284 | CG | LEU A 164 | 37.398 | 51.063 | 26.383 | 1.00 | 101.07 | A | C |
| ATOM | 285 | CD1 | LEU A 164 | 36.657 | 52.223 | 25.726 | 1.00 | 98.23 | A | C |
| ATOM | 286 | CD2 | LEU A 164 | 38.873 | 51.151 | 26.090 | 1.00 | 101.16 | A | C |
| ATOM | 287 | C | LEU A 164 | 35.596 | 51.076 | 29.771 | 1.00 | 110.46 | A | C |
| ATOM | 288 | O | LEU A 164 | 35.322 | 52.257 | 29.947 | 1.00 | 112.35 | A | O |
| ATOM | 289 | N | PHE A 165 | 35.718 | 50.202 | 30.767 | 1.00 | 114.28 | A | N |
| ATOM | 290 | CA | PHE A 165 | 35.484 | 50.580 | 32.165 | 1.00 | 116.40 | A | C |
| ATOM | 291 | CB | PHE A 165 | 35.505 | 49.333 | 33.053 | 1.00 | 117.19 | A | C |
| ATOM | 292 | CG | PHE A 165 | 34.315 | 48.428 | 32.881 | 1.00 | 117.42 | A | C |
| ATOM | 293 | CD1 | PHE A 165 | 33.984 | 47.908 | 31.633 | 1.00 | 115.85 | A | C |
| ATOM | 294 | CD2 | PHE A 165 | 33.541 | 48.063 | 33.989 | 1.00 | 120.17 | A | C |
| ATOM | 295 | CE1 | PHE A 165 | 32.900 | 47.033 | 31.488 | 1.00 | 117.35 | A | C |
| ATOM | 296 | CE2 | PHE A 165 | 32.452 | 47.188 | 33.857 | 1.00 | 119.43 | A | C |
| ATOM | 297 | CZ | PHE A 165 | 32.131 | 46.671 | 32.603 | 1.00 | 118.98 | A | C |
| ATOM | 298 | C | PHE A 165 | 36.466 | 51.608 | 32.755 | 1.00 | 117.76 | A | C |
| ATOM | 299 | O | PHE A 165 | 37.660 | 51.618 | 32.421 | 1.00 | 117.93 | A | O |
| ATOM | 300 | N | LYS A 166 | 35.956 | 52.469 | 33.638 | 1.00 | 118.50 | A | N |
| ATOM | 301 | CA | LYS A 166 | 36.799 | 53.459 | 34.289 | 1.00 | 120.27 | A | C |
| ATOM | 302 | CB | LYS A 166 | 35.956 | 54.468 | 35.076 | 1.00 | 116.78 | A | C |
| ATOM | 307 | C | LYS A 166 | 37.697 | 52.662 | 35.231 | 1.00 | 123.34 | A | C |
| ATOM | 308 | O | LYS A 166 | 38.917 | 52.816 | 35.201 | 1.00 | 122.78 | A | O |
| ATOM | 309 | N | ALA A 167 | 37.085 | 51.784 | 36.034 | 1.00 | 128.28 | A | N |
| ATOM | 310 | CA | ALA A 167 | 37.807 | 50.928 | 36.985 | 1.00 | 132.90 | A | C |
| ATOM | 311 | CB | ALA A 167 | 36.858 | 49.849 | 37.546 | 1.00 | 135.29 | A | C |
| ATOM | 312 | C | ALA A 167 | 39.031 | 50.251 | 36.366 | 1.00 | 134.37 | A | C |
| ATOM | 313 | O | ALA A 167 | 40.137 | 50.341 | 36.902 | 1.00 | 135.65 | A | O |
| ATOM | 314 | N | GLN A 168 | 38.811 | 49.552 | 35.251 | 1.00 | 135.71 | A | N |
| ATOM | 315 | CA | GLN A 168 | 39.885 | 48.850 | 34.542 | 1.00 | 135.07 | A | C |
| ATOM | 316 | CB | GLN A 168 | 39.331 | 48.070 | 33.314 | 1.00 | 135.10 | A | C |
| ATOM | 317 | CG | GLN A 168 | 38.092 | 47.160 | 33.578 | 1.00 | 132.38 | A | C |
| ATOM | 318 | CD | GLN A 168 | 38.294 | 46.133 | 34.694 | 1.00 | 129.59 | A | C |

Figure 4F

| ATOM | 319 | OE1 | GLN | A | 168 | 38.373 | 46.480 | 35.881 | 1.00 | 127.94 | A | O |
|---|---|---|---|---|---|---|---|---|---|---|---|---|
| ATOM | 320 | NE2 | GLN | A | 168 | 38.380 | 44.859 | 34.313 | 1.00 | 128.23 | A | N |
| ATOM | 321 | C | GLN | A | 168 | 40.907 | 49.904 | 34.090 | 1.00 | 134.22 | A | C |
| ATOM | 322 | O | GLN | A | 168 | 42.105 | 49.786 | 34.375 | 1.00 | 134.47 | A | O |
| ATOM | 323 | N | LEU | A | 169 | 40.423 | 50.941 | 33.409 | 1.00 | 133.42 | A | N |
| ATOM | 324 | CA | LEU | A | 169 | 41.289 | 52.014 | 32.931 | 1.00 | 133.66 | A | C |
| ATOM | 325 | CB | LEU | A | 169 | 40.458 | 53.063 | 32.196 | 1.00 | 134.97 | A | C |
| ATOM | 329 | C | LEU | A | 169 | 42.059 | 52.672 | 34.080 | 1.00 | 134.00 | A | C |
| ATOM | 330 | O | LEU | A | 169 | 43.120 | 53.258 | 33.864 | 1.00 | 134.55 | A | O |
| ATOM | 331 | N | GLU | A | 170 | 41.517 | 52.574 | 35.293 | 1.00 | 133.96 | A | N |
| ATOM | 332 | CA | GLU | A | 170 | 42.153 | 53.139 | 36.484 | 1.00 | 133.46 | A | C |
| ATOM | 333 | CB | GLU | A | 170 | 41.087 | 53.475 | 37.537 | 1.00 | 132.60 | A | C |
| ATOM | 338 | C | GLU | A | 170 | 43.186 | 52.169 | 37.086 | 1.00 | 132.63 | A | C |
| ATOM | 339 | O | GLU | A | 170 | 44.321 | 52.561 | 37.397 | 1.00 | 130.27 | A | O |
| ATOM | 340 | N | LYS | A | 171 | 42.768 | 50.906 | 37.233 | 1.00 | 132.48 | A | N |
| ATOM | 341 | CA | LYS | A | 171 | 43.588 | 49.821 | 37.792 | 1.00 | 130.46 | A | C |
| ATOM | 342 | CB | LYS | A | 171 | 42.729 | 48.553 | 38.018 | 1.00 | 127.22 | A | C |
| ATOM | 347 | C | LYS | A | 171 | 44.777 | 49.481 | 36.888 | 1.00 | 129.86 | A | C |
| ATOM | 348 | O | LYS | A | 171 | 45.270 | 48.340 | 36.897 | 1.00 | 129.89 | A | O |
| ATOM | 349 | N | ALA | A | 172 | 45.238 | 50.475 | 36.123 | 1.00 | 129.81 | A | N |
| ATOM | 350 | CA | ALA | A | 172 | 46.361 | 50.293 | 35.200 | 1.00 | 129.08 | A | C |
| ATOM | 351 | CB | ALA | A | 172 | 46.042 | 49.169 | 34.206 | 1.00 | 129.86 | A | C |
| ATOM | 352 | C | ALA | A | 172 | 46.704 | 51.564 | 34.423 | 1.00 | 127.52 | A | C |
| ATOM | 353 | O | ALA | A | 172 | 46.477 | 51.614 | 33.209 | 1.00 | 127.99 | A | O |
| ATOM | 354 | N | GLY | A | 173 | 47.255 | 52.567 | 35.112 | 1.00 | 123.87 | A | N |
| ATOM | 355 | CA | GLY | A | 173 | 47.621 | 53.816 | 34.463 | 1.00 | 119.72 | A | C |
| ATOM | 356 | C | GLY | A | 173 | 47.655 | 53.709 | 32.947 | 1.00 | 117.31 | A | C |
| ATOM | 357 | O | GLY | A | 173 | 48.707 | 53.464 | 32.355 | 1.00 | 115.16 | A | O |
| ATOM | 358 | N | VAL | A | 174 | 46.486 | 53.867 | 32.328 | 1.00 | 116.72 | A | N |
| ATOM | 359 | CA | VAL | A | 174 | 46.335 | 53.795 | 30.877 | 1.00 | 116.63 | A | C |
| ATOM | 360 | CB | VAL | A | 174 | 45.542 | 52.547 | 30.429 | 1.00 | 115.44 | A | C |
| ATOM | 363 | C | VAL | A | 174 | 45.577 | 55.010 | 30.386 | 1.00 | 117.69 | A | C |
| ATOM | 364 | O | VAL | A | 174 | 45.575 | 55.281 | 29.195 | 1.00 | 118.15 | A | O |
| ATOM | 365 | N | GLU | A | 175 | 44.920 | 55.725 | 31.303 | 1.00 | 118.79 | A | N |
| ATOM | 366 | CA | GLU | A | 175 | 44.173 | 56.937 | 30.947 | 1.00 | 118.78 | A | C |
| ATOM | 367 | CB | GLU | A | 175 | 43.721 | 57.688 | 32.211 | 1.00 | 117.30 | A | C |
| ATOM | 372 | C | GLU | A | 175 | 45.125 | 57.818 | 30.128 | 1.00 | 119.42 | A | C |
| ATOM | 373 | O | GLU | A | 175 | 44.703 | 58.596 | 29.251 | 1.00 | 117.06 | A | O |
| ATOM | 374 | N | HIS | A | 176 | 46.416 | 57.669 | 30.430 | 1.00 | 120.72 | A | N |
| ATOM | 375 | CA | HIS | A | 176 | 47.477 | 58.395 | 29.746 | 1.00 | 122.24 | A | C |
| ATOM | 376 | CB | HIS | A | 176 | 48.782 | 58.289 | 30.528 | 1.00 | 119.76 | A | C |
| ATOM | 382 | C | HIS | A | 176 | 47.653 | 57.746 | 28.394 | 1.00 | 123.74 | A | C |
| ATOM | 383 | O | HIS | A | 176 | 47.657 | 58.429 | 27.371 | 1.00 | 124.46 | A | O |
| ATOM | 384 | N | GLN | A | 177 | 47.798 | 56.421 | 28.410 | 1.00 | 126.26 | A | N |
| ATOM | 385 | CA | GLN | A | 177 | 47.963 | 55.618 | 27.188 | 1.00 | 129.43 | A | C |
| ATOM | 386 | CB | GLN | A | 177 | 47.999 | 54.122 | 27.543 | 1.00 | 129.56 | A | C |
| ATOM | 391 | C | GLN | A | 177 | 46.813 | 55.889 | 26.200 | 1.00 | 130.09 | A | C |
| ATOM | 392 | O | GLN | A | 177 | 46.995 | 55.949 | 24.970 | 1.00 | 129.63 | A | O |
| ATOM | 393 | N | LEU | A | 178 | 45.623 | 56.044 | 26.768 | 1.00 | 131.63 | A | N |
| ATOM | 394 | CA | LEU | A | 178 | 44.422 | 56.340 | 26.002 | 1.00 | 131.75 | A | C |
| ATOM | 395 | CB | LEU | A | 178 | 43.193 | 56.222 | 26.924 | 1.00 | 135.82 | A | C |
| ATOM | 396 | CG | LEU | A | 178 | 42.166 | 55.135 | 26.544 | 1.00 | 137.70 | A | C |
| ATOM | 397 | CD1 | LEU | A | 178 | 41.586 | 54.461 | 27.803 | 1.00 | 137.55 | A | C |
| ATOM | 398 | CD2 | LEU | A | 178 | 41.070 | 55.771 | 25.662 | 1.00 | 138.30 | A | C |
| ATOM | 399 | C | LEU | A | 178 | 44.595 | 57.765 | 25.476 | 1.00 | 129.35 | A | C |
| ATOM | 400 | O | LEU | A | 178 | 45.720 | 58.251 | 25.409 | 1.00 | 128.48 | A | O |
| ATOM | 401 | N | ARG | A | 179 | 43.505 | 58.437 | 25.121 | 1.00 | 127.11 | A | N |
| ATOM | 402 | CA | ARG | A | 179 | 43.596 | 59.798 | 24.603 | 1.00 | 125.92 | A | C |
| ATOM | 403 | CB | ARG | A | 179 | 44.037 | 60.781 | 25.697 | 1.00 | 128.19 | A | C |
| ATOM | 404 | CG | ARG | A | 179 | 43.034 | 61.029 | 26.812 | 1.00 | 134.75 | A | C |
| ATOM | 405 | CD | ARG | A | 179 | 43.478 | 62.247 | 27.647 | 1.00 | 142.21 | A | C |

Figure 4G

| ATOM | 406 | NE  | ARG | A | 179 | 42.556 | 62.632 | 28.744 | 1.00 | 148.31 | A | N |
| --- | --- | --- | --- | --- | --- | --- | --- | --- | --- | --- | --- | --- |
| ATOM | 407 | CZ  | ARG | A | 179 | 42.526 | 62.088 | 29.974 | 1.00 | 149.47 | A | C |
| ATOM | 408 | NH1 | ARG | A | 179 | 41.646 | 62.525 | 30.885 | 1.00 | 148.53 | A | N |
| ATOM | 409 | NH2 | ARG | A | 179 | 43.374 | 61.109 | 30.307 | 1.00 | 149.92 | A | N |
| ATOM | 410 | C   | ARG | A | 179 | 44.616 | 59.832 | 23.472 | 1.00 | 123.64 | A | C |
| ATOM | 411 | O   | ARG | A | 179 | 44.288 | 60.156 | 22.336 | 1.00 | 123.65 | A | O |
| ATOM | 412 | N   | ARG | A | 180 | 45.863 | 59.512 | 23.804 | 1.00 | 121.97 | A | N |
| ATOM | 413 | CA  | ARG | A | 180 | 46.943 | 59.494 | 22.840 | 1.00 | 122.56 | A | C |
| ATOM | 414 | CB  | ARG | A | 180 | 48.125 | 58.676 | 23.369 | 1.00 | 118.93 | A | C |
| ATOM | 421 | C   | ARG | A | 180 | 46.417 | 58.892 | 21.557 | 1.00 | 124.12 | A | C |
| ATOM | 422 | O   | ARG | A | 180 | 46.169 | 59.628 | 20.598 | 1.00 | 123.29 | A | O |
| ATOM | 423 | N   | GLU | A | 181 | 46.216 | 57.567 | 21.560 | 1.00 | 127.74 | A | N |
| ATOM | 424 | CA  | GLU | A | 181 | 45.714 | 56.824 | 20.381 | 1.00 | 130.08 | A | C |
| ATOM | 425 | CB  | GLU | A | 181 | 45.473 | 55.337 | 20.671 | 1.00 | 135.75 | A | C |
| ATOM | 426 | CG  | GLU | A | 181 | 46.404 | 54.674 | 21.699 | 1.00 | 144.19 | A | C |
| ATOM | 427 | CD  | GLU | A | 181 | 46.170 | 53.136 | 21.838 | 1.00 | 148.29 | A | C |
| ATOM | 428 | OE1 | GLU | A | 181 | 44.987 | 52.668 | 21.858 | 1.00 | 150.00 | A | O |
| ATOM | 429 | OE2 | GLU | A | 181 | 47.184 | 52.394 | 21.943 | 1.00 | 150.00 | A | O |
| ATOM | 430 | C   | GLU | A | 181 | 44.388 | 57.399 | 19.961 | 1.00 | 128.41 | A | C |
| ATOM | 431 | O   | GLU | A | 181 | 44.095 | 57.518 | 18.775 | 1.00 | 127.16 | A | O |
| ATOM | 432 | N   | VAL | A | 182 | 43.572 | 57.706 | 20.959 | 1.00 | 126.62 | A | N |
| ATOM | 433 | CA  | VAL | A | 182 | 42.279 | 58.311 | 20.715 | 1.00 | 125.12 | A | C |
| ATOM | 434 | CB  | VAL | A | 182 | 41.703 | 58.867 | 22.022 | 1.00 | 123.73 | A | C |
| ATOM | 435 | CG1 | VAL | A | 182 | 40.523 | 59.809 | 21.729 | 1.00 | 123.65 | A | C |
| ATOM | 436 | CG2 | VAL | A | 182 | 41.301 | 57.714 | 22.915 | 1.00 | 121.61 | A | C |
| ATOM | 437 | C   | VAL | A | 182 | 42.438 | 59.463 | 19.719 | 1.00 | 125.84 | A | C |
| ATOM | 438 | O   | VAL | A | 182 | 42.071 | 59.355 | 18.544 | 1.00 | 125.00 | A | O |
| ATOM | 439 | N   | GLU | A | 183 | 42.994 | 60.566 | 20.204 | 1.00 | 126.31 | A | N |
| ATOM | 440 | CA  | GLU | A | 183 | 43.210 | 61.726 | 19.372 | 1.00 | 126.61 | A | C |
| ATOM | 441 | CB  | GLU | A | 183 | 44.121 | 62.722 | 20.097 | 1.00 | 130.31 | A | C |
| ATOM | 442 | CG  | GLU | A | 183 | 44.386 | 63.969 | 19.253 | 1.00 | 138.64 | A | C |
| ATOM | 443 | CD  | GLU | A | 183 | 43.101 | 64.527 | 18.600 | 1.00 | 143.22 | A | C |
| ATOM | 444 | OE1 | GLU | A | 183 | 42.247 | 65.035 | 19.353 | 1.00 | 145.29 | A | O |
| ATOM | 445 | OE2 | GLU | A | 183 | 42.933 | 64.453 | 17.348 | 1.00 | 146.15 | A | O |
| ATOM | 446 | C   | GLU | A | 183 | 43.834 | 61.326 | 18.031 | 1.00 | 124.80 | A | C |
| ATOM | 447 | O   | GLU | A | 183 | 43.556 | 61.913 | 16.974 | 1.00 | 123.96 | A | O |
| ATOM | 448 | N   | ILE | A | 184 | 44.676 | 60.311 | 18.076 | 1.00 | 123.34 | A | N |
| ATOM | 449 | CA  | ILE | A | 184 | 45.342 | 59.856 | 16.874 | 1.00 | 123.24 | A | C |
| ATOM | 450 | CB  | ILE | A | 184 | 46.478 | 58.902 | 17.264 | 1.00 | 126.50 | A | C |
| ATOM | 451 | CG2 | ILE | A | 184 | 47.222 | 58.449 | 16.011 | 1.00 | 129.77 | A | C |
| ATOM | 452 | CG1 | ILE | A | 184 | 47.427 | 59.614 | 18.246 | 1.00 | 128.57 | A | C |
| ATOM | 453 | CD1 | ILE | A | 184 | 48.521 | 58.723 | 18.853 | 1.00 | 132.81 | A | C |
| ATOM | 454 | C   | ILE | A | 184 | 44.398 | 59.197 | 15.848 | 1.00 | 120.31 | A | C |
| ATOM | 455 | O   | ILE | A | 184 | 44.314 | 59.632 | 14.683 | 1.00 | 118.97 | A | O |
| ATOM | 456 | N   | GLN | A | 185 | 43.696 | 58.152 | 16.282 | 1.00 | 118.12 | A | N |
| ATOM | 457 | CA  | GLN | A | 185 | 42.758 | 57.438 | 15.419 | 1.00 | 115.72 | A | C |
| ATOM | 458 | CB  | GLN | A | 185 | 42.120 | 56.271 | 16.195 | 1.00 | 116.69 | A | C |
| ATOM | 459 | CG  | GLN | A | 185 | 43.135 | 55.206 | 16.702 | 1.00 | 118.90 | A | C |
| ATOM | 460 | CD  | GLN | A | 185 | 43.704 | 54.302 | 15.580 | 1.00 | 119.38 | A | C |
| ATOM | 461 | OE1 | GLN | A | 185 | 44.760 | 53.653 | 15.741 | 1.00 | 119.38 | A | O |
| ATOM | 462 | NE2 | GLN | A | 185 | 42.994 | 54.249 | 14.448 | 1.00 | 118.09 | A | N |
| ATOM | 463 | C   | GLN | A | 185 | 41.706 | 58.453 | 15.004 | 1.00 | 113.84 | A | C |
| ATOM | 464 | O   | GLN | A | 185 | 41.213 | 58.450 | 13.872 | 1.00 | 111.42 | A | O |
| ATOM | 465 | N   | SER | A | 186 | 41.394 | 59.327 | 15.959 | 1.00 | 113.54 | A | N |
| ATOM | 466 | CA  | SER | A | 186 | 40.432 | 60.421 | 15.809 | 1.00 | 112.30 | A | C |
| ATOM | 467 | CB  | SER | A | 186 | 40.239 | 61.101 | 17.184 | 1.00 | 113.52 | A | C |
| ATOM | 468 | OG  | SER | A | 186 | 39.541 | 62.334 | 17.086 | 1.00 | 117.00 | A | O |
| ATOM | 469 | C   | SER | A | 186 | 40.994 | 61.410 | 14.772 | 1.00 | 108.59 | A | C |
| ATOM | 470 | O   | SER | A | 186 | 41.341 | 62.556 | 15.086 | 1.00 | 108.18 | A | O |
| ATOM | 471 | N   | HIS | A | 187 | 41.065 | 60.961 | 13.530 | 1.00 | 103.89 | A | N |
| ATOM | 472 | CA  | HIS | A | 187 | 41.633 | 61.786 | 12.507 | 1.00 | 100.30 | A | C |

Figure 4H

```
ATOM   473  CB   HIS A 187      42.923  62.376  13.017  1.00  104.02      A    C
ATOM   474  CG   HIS A 187      43.054  63.814  12.697  1.00  111.28      A    C
ATOM   475  CD2  HIS A 187      44.022  64.505  12.052  1.00  114.31      A    C
ATOM   476  ND1  HIS A 187      42.051  64.718  12.979  1.00  114.80      A    N
ATOM   477  CE1  HIS A 187      42.394  65.908  12.516  1.00  115.35      A    C
ATOM   478  NE2  HIS A 187      43.585  65.806  11.948  1.00  117.17      A    N
ATOM   479  C    HIS A 187      41.965  60.852  11.410  1.00   97.15      A    C
ATOM   480  O    HIS A 187      41.446  60.940  10.312  1.00   93.66      A    O
ATOM   481  N    LEU A 188      42.874  59.956  11.756  1.00   97.25      A    N
ATOM   482  CA   LEU A 188      43.365  58.904  10.891  1.00   97.55      A    C
ATOM   483  CB   LEU A 188      43.815  57.739  11.755  1.00  101.27      A    C
ATOM   484  CG   LEU A 188      45.220  57.250  11.437  1.00  105.84      A    C
ATOM   485  CD1  LEU A 188      46.142  58.435  11.387  1.00  109.11      A    C
ATOM   486  CD2  LEU A 188      45.688  56.266  12.496  1.00  111.20      A    C
ATOM   487  C    LEU A 188      42.319  58.411   9.915  1.00   96.45      A    C
ATOM   488  O    LEU A 188      41.561  57.474  10.223  1.00   93.73      A    O
ATOM   489  N    ARG A 189      42.307  59.024   8.733  1.00   95.72      A    N
ATOM   490  CA   ARG A 189      41.347  58.696   7.681  1.00   95.01      A    C
ATOM   491  CB   ARG A 189      40.768  59.995   7.107  1.00   99.98      A    C
ATOM   492  CG   ARG A 189      39.330  59.921   6.538  1.00  106.69      A    C
ATOM   493  CD   ARG A 189      38.552  61.241   6.855  1.00  111.79      A    C
ATOM   494  NE   ARG A 189      37.199  61.343   6.279  1.00  113.35      A    N
ATOM   495  CZ   ARG A 189      36.336  62.332   6.552  1.00  115.46      A    C
ATOM   496  NH1  ARG A 189      36.679  63.310   7.396  1.00  115.47      A    N
ATOM   497  NH2  ARG A 189      35.126  62.350   5.987  1.00  113.81      A    N
ATOM   498  C    ARG A 189      41.943  57.842   6.563  1.00   91.35      A    C
ATOM   499  O    ARG A 189      42.630  58.332   5.663  1.00   88.64      A    O
ATOM   500  N    HIS A 190      41.668  56.549   6.623  1.00   88.85      A    N
ATOM   501  CA   HIS A 190      42.181  55.652   5.617  1.00   86.54      A    C
ATOM   502  CB   HIS A 190      43.578  55.184   5.980  1.00   91.63      A    C
ATOM   503  CG   HIS A 190      44.218  54.335   4.926  1.00   94.39      A    C
ATOM   504  CD2  HIS A 190      44.282  52.991   4.777  1.00   93.98      A    C
ATOM   505  ND1  HIS A 190      44.873  54.870   3.840  1.00   97.55      A    N
ATOM   506  CE1  HIS A 190      45.318  53.892   3.069  1.00   97.31      A    C
ATOM   507  NE2  HIS A 190      44.971  52.741   3.615  1.00   94.82      A    N
ATOM   508  C    HIS A 190      41.300  54.440   5.478  1.00   84.36      A    C
ATOM   509  O    HIS A 190      40.763  53.929   6.476  1.00   77.53      A    O
ATOM   510  N    PRO A 191      41.153  53.952   4.229  1.00   84.67      A    N
ATOM   511  CD   PRO A 191      41.714  54.513   2.988  1.00   83.01      A    C
ATOM   512  CA   PRO A 191      40.336  52.781   3.919  1.00   87.77      A    C
ATOM   513  CB   PRO A 191      40.522  52.621   2.398  1.00   84.89      A    C
ATOM   514  CG   PRO A 191      41.795  53.298   2.118  1.00   82.71      A    C
ATOM   515  C    PRO A 191      40.716  51.530   4.720  1.00   90.77      A    C
ATOM   516  O    PRO A 191      39.853  50.829   5.273  1.00   94.15      A    O
ATOM   517  N    ASN A 192      42.012  51.259   4.801  1.00   90.49      A    N
ATOM   518  CA   ASN A 192      42.491  50.089   5.535  1.00   86.62      A    C
ATOM   519  CB   ASN A 192      43.714  49.506   4.810  1.00   79.06      A    C
ATOM   520  CG   ASN A 192      43.427  49.194   3.361  1.00   69.42      A    C
ATOM   521  OD1  ASN A 192      44.104  49.684   2.469  1.00   65.15      A    O
ATOM   522  ND2  ASN A 192      42.415  48.381   3.123  1.00   64.64      A    N
ATOM   523  C    ASN A 192      42.798  50.377   7.025  1.00   86.18      A    C
ATOM   524  O    ASN A 192      43.580  49.672   7.674  1.00   86.54      A    O
ATOM   525  N    ILE A 193      42.172  51.417   7.561  1.00   85.26      A    N
ATOM   526  CA   ILE A 193      42.362  51.753   8.954  1.00   84.63      A    C
ATOM   527  CB   ILE A 193      43.082  53.049   9.124  1.00   83.29      A    C
ATOM   528  CG2  ILE A 193      43.041  53.456  10.592  1.00   83.02      A    C
ATOM   529  CG1  ILE A 193      44.501  52.894   8.603  1.00   82.02      A    C
ATOM   530  CD1  ILE A 193      45.320  54.132   8.753  1.00   84.53      A    C
ATOM   531  C    ILE A 193      41.009  51.912   9.564  1.00   87.33      A    C
ATOM   532  O    ILE A 193      40.235  52.776   9.137  1.00   88.42      A    O
ATOM   533  N    LEU A 194      40.724  51.083  10.561  1.00   89.72      A    N
```

Figure 4I

```
ATOM   534  CA   LEU A 194      39.435  51.135  11.211  1.00   94.32      A        C
ATOM   535  CB   LEU A 194      39.359  50.097  12.314  1.00   91.61      A        C
ATOM   536  CG   LEU A 194      37.933  49.841  12.780  1.00   90.30      A        C
ATOM   537  CD1  LEU A 194      37.135  49.261  11.642  1.00   88.09      A        C
ATOM   538  CD2  LEU A 194      37.943  48.895  13.964  1.00   89.26      A        C
ATOM   539  C    LEU A 194      39.273  52.522  11.790  1.00   98.98      A        C
ATOM   540  O    LEU A 194      40.005  52.900  12.709  1.00   99.57      A        O
ATOM   541  N    ARG A 195      38.317  53.274  11.239  1.00  103.51      A        N
ATOM   542  CA   ARG A 195      38.034  54.655  11.664  1.00  108.42      A        C
ATOM   543  CB   ARG A 195      37.096  55.343  10.648  1.00  110.99      A        C
ATOM   544  CG   ARG A 195      36.791  56.839  10.951  1.00  115.51      A        C
ATOM   545  CD   ARG A 195      35.895  57.528   9.886  1.00  116.54      A        C
ATOM   546  NE   ARG A 195      35.720  58.962  10.154  1.00  119.15      A        N
ATOM   547  CZ   ARG A 195      35.023  59.801   9.389  1.00  120.38      A        C
ATOM   548  NH1  ARG A 195      34.939  61.087   9.743  1.00  120.69      A        N
ATOM   549  NH2  ARG A 195      34.416  59.364   8.276  1.00  119.07      A        N
ATOM   550  C    ARG A 195      37.424  54.777  13.072  1.00  109.46      A        C
ATOM   551  O    ARG A 195      36.866  53.818  13.607  1.00  110.11      A        O
ATOM   552  N    LEU A 196      37.534  55.970  13.658  1.00  109.48      A        N
ATOM   553  CA   LEU A 196      36.994  56.239  14.986  1.00  108.61      A        C
ATOM   554  CB   LEU A 196      38.131  56.458  15.973  1.00  112.89      A        C
ATOM   555  CG   LEU A 196      37.760  57.019  17.349  1.00  116.91      A        C
ATOM   556  CD1  LEU A 196      36.516  56.329  17.942  1.00  118.75      A        C
ATOM   557  CD2  LEU A 196      38.994  56.849  18.242  1.00  119.73      A        C
ATOM   558  C    LEU A 196      36.086  57.457  14.962  1.00  106.22      A        C
ATOM   559  O    LEU A 196      36.445  58.541  15.412  1.00  103.26      A        O
ATOM   560  N    TYR A 197      34.894  57.255  14.429  1.00  106.33      A        N
ATOM   561  CA   TYR A 197      33.933  58.327  14.317  1.00  106.90      A        C
ATOM   562  CB   TYR A 197      32.519  57.760  14.192  1.00  110.15      A        C
ATOM   563  CG   TYR A 197      32.399  56.820  13.041  1.00  113.34      A        C
ATOM   564  CD1  TYR A 197      32.296  55.447  13.249  1.00  116.56      A        C
ATOM   565  CE1  TYR A 197      32.258  54.553  12.182  1.00  120.68      A        C
ATOM   566  CD2  TYR A 197      32.459  57.293  11.742  1.00  114.33      A        C
ATOM   567  CE2  TYR A 197      32.425  56.420  10.660  1.00  120.50      A        C
ATOM   568  CZ   TYR A 197      32.324  55.039  10.877  1.00  122.27      A        C
ATOM   569  OH   TYR A 197      32.296  54.153   9.796  1.00  126.22      A        O
ATOM   570  C    TYR A 197      34.012  59.296  15.478  1.00  106.04      A        C
ATOM   571  O    TYR A 197      34.231  60.485  15.268  1.00  106.77      A        O
ATOM   572  N    GLY A 198      33.863  58.809  16.700  1.00  105.93      A        N
ATOM   573  CA   GLY A 198      33.909  59.732  17.809  1.00  109.51      A        C
ATOM   574  C    GLY A 198      34.061  59.077  19.152  1.00  112.38      A        C
ATOM   575  O    GLY A 198      34.355  57.879  19.247  1.00  114.66      A        O
ATOM   576  N    TYR A 199      33.868  59.877  20.196  1.00  114.31      A        N
ATOM   577  CA   TYR A 199      33.984  59.379  21.553  1.00  115.53      A        C
ATOM   578  CB   TYR A 199      35.457  59.232  21.939  1.00  119.01      A        C
ATOM   579  CG   TYR A 199      35.834  60.032  23.165  1.00  123.04      A        C
ATOM   580  CD1  TYR A 199      36.428  61.306  23.046  1.00  123.81      A        C
ATOM   581  CE1  TYR A 199      36.743  62.070  24.194  1.00  127.39      A        C
ATOM   582  CD2  TYR A 199      35.562  59.533  24.456  1.00  124.45      A        C
ATOM   583  CE2  TYR A 199      35.868  60.284  25.608  1.00  128.90      A        C
ATOM   584  CZ   TYR A 199      36.460  61.555  25.474  1.00  129.45      A        C
ATOM   585  OH   TYR A 199      36.763  62.308  26.601  1.00  129.54      A        O
ATOM   586  C    TYR A 199      33.296  60.285  22.560  1.00  114.23      A        C
ATOM   587  O    TYR A 199      33.279  61.518  22.417  1.00  113.15      A        O
ATOM   588  N    PHE A 200      32.738  59.653  23.584  1.00  113.27      A        N
ATOM   589  CA   PHE A 200      32.084  60.369  24.658  1.00  113.90      A        C
ATOM   590  CB   PHE A 200      30.565  60.539  24.385  1.00  113.63      A        C
ATOM   591  CG   PHE A 200      29.833  59.270  23.992  1.00  113.39      A        C
ATOM   592  CD1  PHE A 200      30.095  58.630  22.780  1.00  114.27      A        C
ATOM   593  CD2  PHE A 200      28.839  58.749  24.825  1.00  114.10      A        C
ATOM   594  CE1  PHE A 200      29.379  57.496  22.402  1.00  115.44      A        C
```

Figure 4J

```
ATOM    595  CE2 PHE A 200      28.120  57.620  24.459  1.00 115.32      A    C
ATOM    596  CZ  PHE A 200      28.391  56.991  23.240  1.00 115.92      A    C
ATOM    597  C   PHE A 200      32.375  59.554  25.904  1.00 115.10      A    C
ATOM    598  O   PHE A 200      33.196  58.634  25.845  1.00 113.50      A    O
ATOM    599  N   HIS A 201      31.736  59.889  27.024  1.00 118.53      A    N
ATOM    600  CA  HIS A 201      31.965  59.158  28.278  1.00 122.57      A    C
ATOM    601  CB  HIS A 201      33.407  59.387  28.749  1.00 128.03      A    C
ATOM    602  CG  HIS A 201      33.757  60.836  28.965  1.00 134.01      A    C
ATOM    603  CD2 HIS A 201      34.488  61.700  28.213  1.00 135.47      A    C
ATOM    604  ND1 HIS A 201      33.330  61.558  30.064  1.00 134.63      A    N
ATOM    605  CE1 HIS A 201      33.785  62.798  29.978  1.00 134.21      A    C
ATOM    606  NE2 HIS A 201      34.490  62.911  28.865  1.00 134.60      A    N
ATOM    607  C   HIS A 201      31.024  59.504  29.436  1.00 121.46      A    C
ATOM    608  O   HIS A 201      30.802  60.680  29.727  1.00 121.52      A    O
ATOM    609  N   ASP A 202      30.457  58.489  30.088  1.00 120.64      A    N
ATOM    610  CA  ASP A 202      29.600  58.764  31.235  1.00 120.41      A    C
ATOM    611  CB  ASP A 202      28.317  57.883  31.260  1.00 122.35      A    C
ATOM    612  CG  ASP A 202      28.601  56.386  31.348  1.00 125.06      A    C
ATOM    613  OD1 ASP A 202      29.272  55.941  32.307  1.00 129.74      A    O
ATOM    614  OD2 ASP A 202      28.127  55.648  30.458  1.00 122.75      A    O
ATOM    615  C   ASP A 202      30.481  58.541  32.463  1.00 118.89      A    C
ATOM    616  O   ASP A 202      31.685  58.266  32.337  1.00 118.27      A    O
ATOM    617  N   ALA A 203      29.891  58.688  33.641  1.00 116.54      A    N
ATOM    618  CA  ALA A 203      30.620  58.531  34.889  1.00 112.60      A    C
ATOM    619  CB  ALA A 203      29.621  58.512  36.059  1.00 114.00      A    C
ATOM    620  C   ALA A 203      31.485  57.274  34.920  1.00 109.64      A    C
ATOM    621  O   ALA A 203      32.710  57.319  34.731  1.00 104.91      A    O
ATOM    622  N   THR A 204      30.803  56.161  35.169  1.00 109.33      A    N
ATOM    623  CA  THR A 204      31.402  54.843  35.279  1.00 110.76      A    C
ATOM    624  CB  THR A 204      30.276  53.756  35.573  1.00 111.06      A    C
ATOM    625  OG1 THR A 204      30.828  52.434  35.493  1.00 113.32      A    O
ATOM    626  CG2 THR A 204      29.113  53.868  34.587  1.00 109.92      A    C
ATOM    627  C   THR A 204      32.243  54.412  34.074  1.00 111.24      A    C
ATOM    628  O   THR A 204      33.434  54.091  34.204  1.00 111.24      A    O
ATOM    629  N   ARG A 205      31.617  54.435  32.904  1.00 110.48      A    N
ATOM    630  CA  ARG A 205      32.246  53.992  31.674  1.00 108.21      A    C
ATOM    631  CB  ARG A 205      31.377  52.866  31.085  1.00 112.04      A    C
ATOM    632  CG  ARG A 205      29.859  53.011  31.371  1.00 115.23      A    C
ATOM    633  CD  ARG A 205      29.077  51.691  31.143  1.00 120.66      A    C
ATOM    634  NE  ARG A 205      27.624  51.861  31.268  1.00 123.06      A    N
ATOM    635  CZ  ARG A 205      26.709  50.962  30.892  1.00 123.80      A    C
ATOM    636  NH1 ARG A 205      27.072  49.789  30.359  1.00 123.56      A    N
ATOM    637  NH2 ARG A 205      25.415  51.259  31.021  1.00 123.10      A    N
ATOM    638  C   ARG A 205      32.543  55.047  30.608  1.00 105.44      A    C
ATOM    639  O   ARG A 205      32.236  56.229  30.754  1.00 104.27      A    O
ATOM    640  N   VAL A 206      33.170  54.588  29.535  1.00 102.74      A    N
ATOM    641  CA  VAL A 206      33.517  55.424  28.392  1.00  99.73      A    C
ATOM    642  CB  VAL A 206      35.031  55.749  28.381  1.00  99.36      A    C
ATOM    643  CG1 VAL A 206      35.699  55.098  29.590  1.00  98.06      A    C
ATOM    644  CG2 VAL A 206      35.676  55.289  27.068  1.00  97.31      A    C
ATOM    645  C   VAL A 206      33.115  54.680  27.104  1.00  97.73      A    C
ATOM    646  O   VAL A 206      32.818  53.477  27.123  1.00  97.60      A    O
ATOM    647  N   TYR A 207      33.098  55.382  25.979  1.00  94.68      A    N
ATOM    648  CA  TYR A 207      32.690  54.725  24.755  1.00  92.15      A    C
ATOM    649  CB  TYR A 207      31.188  54.874  24.578  1.00  94.55      A    C
ATOM    650  CG  TYR A 207      30.387  54.596  25.837  1.00  95.95      A    C
ATOM    651  CD1 TYR A 207      30.229  55.574  26.831  1.00  92.90      A    C
ATOM    652  CE1 TYR A 207      29.483  55.327  27.969  1.00  94.47      A    C
ATOM    653  CD2 TYR A 207      29.777  53.358  26.023  1.00  98.62      A    C
ATOM    654  CE2 TYR A 207      29.026  53.098  27.160  1.00 100.49      A    C
ATOM    655  CZ  TYR A 207      28.881  54.090  28.131  1.00  99.10      A    C
```

Figure 4K

```
ATOM    656  OH  TYR A 207      28.111  53.842  29.247  1.00  99.87      A  O
ATOM    657  C   TYR A 207      33.390  55.178  23.495  1.00  91.09      A  C
ATOM    658  O   TYR A 207      33.609  56.369  23.246  1.00  88.43      A  O
ATOM    659  N   LEU A 208      33.724  54.182  22.697  1.00  92.14      A  N
ATOM    660  CA  LEU A 208      34.405  54.393  21.447  1.00  94.34      A  C
ATOM    661  CB  LEU A 208      35.606  53.463  21.329  1.00  96.20      A  C
ATOM    662  CG  LEU A 208      36.776  53.619  22.297  1.00  96.89      A  C
ATOM    663  CD1 LEU A 208      37.662  52.367  22.221  1.00  95.76      A  C
ATOM    664  CD2 LEU A 208      37.560  54.897  21.959  1.00  94.63      A  C
ATOM    665  C   LEU A 208      33.440  54.054  20.353  1.00  95.05      A  C
ATOM    666  O   LEU A 208      32.954  52.919  20.262  1.00  96.97      A  O
ATOM    667  N   ILE A 209      33.158  55.043  19.523  1.00  94.42      A  N
ATOM    668  CA  ILE A 209      32.263  54.839  18.401  1.00  93.86      A  C
ATOM    669  CB  ILE A 209      31.454  56.092  18.112  1.00  97.36      A  C
ATOM    670  CG2 ILE A 209      30.483  55.816  16.959  1.00  98.91      A  C
ATOM    671  CG1 ILE A 209      30.738  56.537  19.396  1.00  98.47      A  C
ATOM    672  CD1 ILE A 209      30.042  57.869  19.278  1.00 101.03      A  C
ATOM    673  C   ILE A 209      33.157  54.539  17.220  1.00  90.33      A  C
ATOM    674  O   ILE A 209      34.011  55.346  16.863  1.00  89.00      A  O
ATOM    675  N   LEU A 210      32.962  53.383  16.606  1.00  88.74      A  N
ATOM    676  CA  LEU A 210      33.826  53.020  15.502  1.00  88.57      A  C
ATOM    677  CB  LEU A 210      34.976  52.159  16.047  1.00  92.54      A  C
ATOM    678  CG  LEU A 210      35.730  52.557  17.333  1.00  92.49      A  C
ATOM    679  CD1 LEU A 210      34.958  52.088  18.567  1.00  91.36      A  C
ATOM    680  CD2 LEU A 210      37.121  51.909  17.321  1.00  93.40      A  C
ATOM    681  C   LEU A 210      33.193  52.317  14.290  1.00  86.56      A  C
ATOM    682  O   LEU A 210      32.058  51.836  14.327  1.00  86.13      A  O
ATOM    683  N   GLU A 211      33.965  52.272  13.212  1.00  84.75      A  N
ATOM    684  CA  GLU A 211      33.563  51.634  11.973  1.00  83.90      A  C
ATOM    685  CB  GLU A 211      34.683  51.781  10.945  1.00  85.78      A  C
ATOM    686  CG  GLU A 211      34.603  50.856   9.732  1.00  90.03      A  C
ATOM    687  CD  GLU A 211      35.684  51.155   8.683  1.00  89.97      A  C
ATOM    688  OE1 GLU A 211      36.839  51.473   9.062  1.00  85.49      A  O
ATOM    689  OE2 GLU A 211      35.371  51.056   7.475  1.00  88.84      A  O
ATOM    690  C   GLU A 211      33.310  50.178  12.251  1.00  83.19      A  C
ATOM    691  O   GLU A 211      34.046  49.542  12.996  1.00  83.10      A  O
ATOM    692  N   TYR A 212      32.271  49.634  11.648  1.00  82.36      A  N
ATOM    693  CA  TYR A 212      31.979  48.242  11.882  1.00  80.86      A  C
ATOM    694  CB  TYR A 212      30.469  48.069  11.986  1.00  81.34      A  C
ATOM    695  CG  TYR A 212      30.078  46.645  12.168  1.00  84.50      A  C
ATOM    696  CD1 TYR A 212      30.413  45.961  13.323  1.00  85.54      A  C
ATOM    697  CE1 TYR A 212      30.183  44.607  13.436  1.00  89.83      A  C
ATOM    698  CD2 TYR A 212      29.486  45.941  11.131  1.00  88.05      A  C
ATOM    699  CE2 TYR A 212      29.252  44.586  11.233  1.00  92.80      A  C
ATOM    700  CZ  TYR A 212      29.610  43.922  12.387  1.00  92.59      A  C
ATOM    701  OH  TYR A 212      29.443  42.559  12.470  1.00  98.40      A  O
ATOM    702  C   TYR A 212      32.578  47.347  10.784  1.00  79.51      A  C
ATOM    703  O   TYR A 212      32.398  47.612   9.592  1.00  80.50      A  O
ATOM    704  N   ALA A 213      33.303  46.302  11.202  1.00  78.31      A  N
ATOM    705  CA  ALA A 213      33.954  45.334  10.295  1.00  78.11      A  C
ATOM    706  CB  ALA A 213      35.417  45.245  10.610  1.00  76.93      A  C
ATOM    707  C   ALA A 213      33.325  43.934  10.369  1.00  77.49      A  C
ATOM    708  O   ALA A 213      33.774  43.059  11.113  1.00  75.06      A  O
ATOM    709  N   PRO A 214      32.304  43.703   9.539  1.00  79.91      A  N
ATOM    710  CD  PRO A 214      32.056  44.624   8.414  1.00  81.27      A  C
ATOM    711  CA  PRO A 214      31.492  42.494   9.381  1.00  82.31      A  C
ATOM    712  CB  PRO A 214      30.620  42.830   8.180  1.00  85.18      A  C
ATOM    713  CG  PRO A 214      31.518  43.693   7.372  1.00  84.46      A  C
ATOM    714  C   PRO A 214      32.138  41.133   9.225  1.00  82.71      A  C
ATOM    715  O   PRO A 214      31.616  40.135   9.721  1.00  81.38      A  O
ATOM    716  N   LEU A 215      33.261  41.072   8.535  1.00  85.17      A  N
```

Figure 4L

| ATOM | 717 | CA  | LEU | A | 215 | 33.876 | 39.778 | 8.320  | 1.00 | 88.45  | A | C |
|------|-----|-----|-----|---|-----|--------|--------|--------|------|--------|---|---|
| ATOM | 718 | CB  | LEU | A | 215 | 34.612 | 39.789 | 6.991  | 1.00 | 94.16  | A | C |
| ATOM | 719 | CG  | LEU | A | 215 | 33.563 | 39.723 | 5.874  | 1.00 | 98.56  | A | C |
| ATOM | 720 | CD1 | LEU | A | 215 | 34.219 | 39.842 | 4.487  | 1.00 | 101.23 | A | C |
| ATOM | 721 | CD2 | LEU | A | 215 | 32.787 | 38.392 | 6.022  | 1.00 | 102.41 | A | C |
| ATOM | 722 | C   | LEU | A | 215 | 34.757 | 39.238 | 9.424  | 1.00 | 87.82  | A | C |
| ATOM | 723 | O   | LEU | A | 215 | 35.517 | 38.293 | 9.221  | 1.00 | 84.90  | A | O |
| ATOM | 724 | N   | GLY | A | 216 | 34.621 | 39.825 | 10.606 | 1.00 | 88.96  | A | N |
| ATOM | 725 | CA  | GLY | A | 216 | 35.393 | 39.371 | 11.741 | 1.00 | 90.57  | A | C |
| ATOM | 726 | C   | GLY | A | 216 | 36.884 | 39.620 | 11.620 | 1.00 | 89.46  | A | C |
| ATOM | 727 | O   | GLY | A | 216 | 37.329 | 40.452 | 10.818 | 1.00 | 88.85  | A | O |
| ATOM | 728 | N   | THR | A | 217 | 37.647 | 38.866 | 12.414 | 1.00 | 87.40  | A | N |
| ATOM | 729 | CA  | THR | A | 217 | 39.103 | 38.973 | 12.494 | 1.00 | 83.89  | A | C |
| ATOM | 730 | CB  | THR | A | 217 | 39.553 | 38.771 | 13.985 | 1.00 | 81.48  | A | C |
| ATOM | 731 | OG1 | THR | A | 217 | 40.750 | 39.508 | 14.242 | 1.00 | 82.04  | A | O |
| ATOM | 732 | CG2 | THR | A | 217 | 39.812 | 37.318 | 14.288 | 1.00 | 80.94  | A | C |
| ATOM | 733 | C   | THR | A | 217 | 39.862 | 38.005 | 11.572 | 1.00 | 82.48  | A | C |
| ATOM | 734 | O   | THR | A | 217 | 39.467 | 36.859 | 11.393 | 1.00 | 82.47  | A | O |
| ATOM | 735 | N   | VAL | A | 218 | 40.948 | 38.485 | 10.978 | 1.00 | 82.00  | A | N |
| ATOM | 736 | CA  | VAL | A | 218 | 41.773 | 37.669 | 10.094 | 1.00 | 85.16  | A | C |
| ATOM | 737 | CB  | VAL | A | 218 | 42.983 | 38.458 | 9.570  | 1.00 | 84.81  | A | C |
| ATOM | 738 | CG1 | VAL | A | 218 | 44.141 | 37.527 | 9.284  | 1.00 | 84.29  | A | C |
| ATOM | 739 | CG2 | VAL | A | 218 | 42.599 | 39.187 | 8.314  | 1.00 | 85.91  | A | C |
| ATOM | 740 | C   | VAL | A | 218 | 42.277 | 36.478 | 10.873 | 1.00 | 86.16  | A | C |
| ATOM | 741 | O   | VAL | A | 218 | 42.370 | 35.375 | 10.351 | 1.00 | 84.77  | A | O |
| ATOM | 742 | N   | TYR | A | 219 | 42.633 | 36.732 | 12.125 | 1.00 | 89.86  | A | N |
| ATOM | 743 | CA  | TYR | A | 219 | 43.105 | 35.693 | 13.021 | 1.00 | 94.02  | A | C |
| ATOM | 744 | CB  | TYR | A | 219 | 42.934 | 36.154 | 14.472 | 1.00 | 95.00  | A | C |
| ATOM | 745 | CG  | TYR | A | 219 | 43.115 | 35.065 | 15.508 | 1.00 | 96.94  | A | C |
| ATOM | 746 | CD1 | TYR | A | 219 | 44.257 | 34.256 | 15.494 | 1.00 | 99.08  | A | C |
| ATOM | 747 | CE1 | TYR | A | 219 | 44.481 | 33.300 | 16.486 | 1.00 | 99.09  | A | C |
| ATOM | 748 | CD2 | TYR | A | 219 | 42.183 | 34.885 | 16.545 | 1.00 | 97.62  | A | C |
| ATOM | 749 | CE2 | TYR | A | 219 | 42.399 | 33.930 | 17.546 | 1.00 | 99.19  | A | C |
| ATOM | 750 | CZ  | TYR | A | 219 | 43.556 | 33.149 | 17.506 | 1.00 | 99.96  | A | C |
| ATOM | 751 | OH  | TYR | A | 219 | 43.828 | 32.253 | 18.504 | 1.00 | 100.03 | A | O |
| ATOM | 752 | C   | TYR | A | 219 | 42.182 | 34.535 | 12.755 | 1.00 | 97.03  | A | C |
| ATOM | 753 | O   | TYR | A | 219 | 42.614 | 33.436 | 12.390 | 1.00 | 97.16  | A | O |
| ATOM | 754 | N   | ARG | A | 220 | 40.895 | 34.818 | 12.938 | 1.00 | 100.19 | A | N |
| ATOM | 755 | CA  | ARG | A | 220 | 39.851 | 33.841 | 12.721 | 1.00 | 102.88 | A | C |
| ATOM | 756 | CB  | ARG | A | 220 | 38.466 | 34.472 | 12.946 | 1.00 | 106.18 | A | C |
| ATOM | 757 | CG  | ARG | A | 220 | 38.163 | 34.785 | 14.408 | 1.00 | 108.69 | A | C |
| ATOM | 758 | CD  | ARG | A | 220 | 38.242 | 33.518 | 15.227 | 1.00 | 111.32 | A | C |
| ATOM | 759 | NE  | ARG | A | 220 | 38.455 | 33.773 | 16.643 | 1.00 | 112.72 | A | N |
| ATOM | 760 | CZ  | ARG | A | 220 | 37.616 | 34.463 | 17.400 | 1.00 | 113.87 | A | C |
| ATOM | 761 | NH1 | ARG | A | 220 | 37.889 | 34.640 | 18.686 | 1.00 | 113.70 | A | N |
| ATOM | 762 | NH2 | ARG | A | 220 | 36.510 | 34.979 | 16.865 | 1.00 | 114.57 | A | N |
| ATOM | 763 | C   | ARG | A | 220 | 39.985 | 33.322 | 11.299 | 1.00 | 102.35 | A | C |
| ATOM | 764 | O   | ARG | A | 220 | 40.264 | 32.141 | 11.097 | 1.00 | 102.75 | A | O |
| ATOM | 765 | N   | GLU | A | 221 | 39.819 | 34.204 | 10.316 | 1.00 | 101.44 | A | N |
| ATOM | 766 | CA  | GLU | A | 221 | 39.924 | 33.779 | 8.924  | 1.00 | 101.27 | A | C |
| ATOM | 767 | CB  | GLU | A | 221 | 40.037 | 34.971 | 7.962  | 1.00 | 104.47 | A | C |
| ATOM | 768 | CG  | GLU | A | 221 | 38.779 | 35.195 | 7.114  | 1.00 | 108.08 | A | C |
| ATOM | 769 | CD  | GLU | A | 221 | 38.448 | 34.033 | 6.155  | 1.00 | 110.40 | A | C |
| ATOM | 770 | OE1 | GLU | A | 221 | 38.768 | 32.865 | 6.462  | 1.00 | 112.62 | A | O |
| ATOM | 771 | OE2 | GLU | A | 221 | 37.842 | 34.281 | 5.090  | 1.00 | 111.59 | A | O |
| ATOM | 772 | C   | GLU | A | 221 | 41.137 | 32.913 | 8.764  | 1.00 | 99.64  | A | C |
| ATOM | 773 | O   | GLU | A | 221 | 41.122 | 31.926 | 8.030  | 1.00 | 98.98  | A | O |
| ATOM | 774 | N   | LEU | A | 222 | 42.186 | 33.287 | 9.479  | 1.00 | 99.29  | A | N |
| ATOM | 775 | CA  | LEU | A | 222 | 43.432 | 32.565 | 9.415  | 1.00 | 101.55 | A | C |
| ATOM | 776 | CB  | LEU | A | 222 | 44.534 | 33.350 | 10.120 | 1.00 | 102.80 | A | C |
| ATOM | 777 | CG  | LEU | A | 222 | 45.916 | 32.672 | 10.091 | 1.00 | 106.84 | A | C |

Figure 4M

| ATOM | 778 | CD1 | LEU | A | 222 | 46.246 | 32.146 | 8.675 | 1.00 | 108.35 | A | C |
|---|---|---|---|---|---|---|---|---|---|---|---|---|
| ATOM | 779 | CD2 | LEU | A | 222 | 46.974 | 33.670 | 10.575 | 1.00 | 105.63 | A | C |
| ATOM | 780 | C | LEU | A | 222 | 43.347 | 31.166 | 9.990 | 1.00 | 102.22 | A | C |
| ATOM | 781 | O | LEU | A | 222 | 43.865 | 30.219 | 9.396 | 1.00 | 104.96 | A | O |
| ATOM | 782 | N | GLN | A | 223 | 42.704 | 31.017 | 11.138 | 1.00 | 101.75 | A | N |
| ATOM | 783 | CA | GLN | A | 223 | 42.608 | 29.696 | 11.723 | 1.00 | 101.94 | A | C |
| ATOM | 784 | CB | GLN | A | 223 | 42.270 | 29.813 | 13.190 | 1.00 | 105.44 | A | C |
| ATOM | 785 | CG | GLN | A | 223 | 40.964 | 30.524 | 13.423 | 1.00 | 117.72 | A | C |
| ATOM | 786 | CD | GLN | A | 223 | 40.603 | 30.588 | 14.891 | 1.00 | 123.20 | A | C |
| ATOM | 787 | OE1 | GLN | A | 223 | 39.498 | 31.012 | 15.264 | 1.00 | 126.90 | A | O |
| ATOM | 788 | NE2 | GLN | A | 223 | 41.540 | 30.162 | 15.744 | 1.00 | 125.88 | A | N |
| ATOM | 789 | C | GLN | A | 223 | 41.588 | 28.802 | 11.013 | 1.00 | 99.95 | A | C |
| ATOM | 790 | O | GLN | A | 223 | 41.614 | 27.594 | 11.196 | 1.00 | 98.20 | A | O |
| ATOM | 791 | N | LYS | A | 224 | 40.703 | 29.387 | 10.201 | 1.00 | 100.07 | A | N |
| ATOM | 792 | CA | LYS | A | 224 | 39.691 | 28.605 | 9.463 | 1.00 | 101.75 | A | C |
| ATOM | 793 | CB | LYS | A | 224 | 38.405 | 29.434 | 9.204 | 1.00 | 101.69 | A | C |
| ATOM | 794 | CG | LYS | A | 224 | 37.353 | 29.392 | 10.352 | 1.00 | 99.75 | A | C |
| ATOM | 795 | CD | LYS | A | 224 | 36.088 | 30.272 | 10.140 | 1.00 | 98.17 | A | C |
| ATOM | 796 | CE | LYS | A | 224 | 35.204 | 29.825 | 8.960 | 1.00 | 96.45 | A | C |
| ATOM | 797 | NZ | LYS | A | 224 | 33.927 | 30.620 | 8.826 | 1.00 | 92.43 | A | N |
| ATOM | 798 | C | LYS | A | 224 | 40.202 | 28.026 | 8.131 | 1.00 | 103.93 | A | C |
| ATOM | 799 | O | LYS | A | 224 | 39.833 | 26.900 | 7.767 | 1.00 | 106.49 | A | O |
| ATOM | 800 | N | LEU | A | 225 | 41.032 | 28.783 | 7.404 | 1.00 | 104.30 | A | N |
| ATOM | 801 | CA | LEU | A | 225 | 41.594 | 28.316 | 6.122 | 1.00 | 103.38 | A | C |
| ATOM | 802 | CB | LEU | A | 225 | 41.702 | 29.464 | 5.106 | 1.00 | 102.20 | A | C |
| ATOM | 803 | CG | LEU | A | 225 | 40.464 | 29.703 | 4.235 | 1.00 | 101.53 | A | C |
| ATOM | 804 | CD1 | LEU | A | 225 | 39.316 | 30.238 | 5.096 | 1.00 | 103.59 | A | C |
| ATOM | 805 | CD2 | LEU | A | 225 | 40.797 | 30.678 | 3.123 | 1.00 | 100.48 | A | C |
| ATOM | 806 | C | LEU | A | 225 | 42.964 | 27.675 | 6.304 | 1.00 | 101.97 | A | C |
| ATOM | 807 | O | LEU | A | 225 | 43.581 | 27.218 | 5.343 | 1.00 | 102.41 | A | O |
| ATOM | 808 | N | SER | A | 226 | 43.420 | 27.649 | 7.551 | 1.00 | 100.20 | A | N |
| ATOM | 809 | CA | SER | A | 226 | 44.706 | 27.069 | 7.919 | 1.00 | 98.06 | A | C |
| ATOM | 810 | CB | SER | A | 226 | 44.813 | 25.633 | 7.398 | 1.00 | 98.55 | A | C |
| ATOM | 811 | OG | SER | A | 226 | 46.098 | 25.092 | 7.672 | 1.00 | 97.22 | A | O |
| ATOM | 812 | C | SER | A | 226 | 45.894 | 27.864 | 7.408 | 1.00 | 95.51 | A | C |
| ATOM | 813 | O | SER | A | 226 | 46.874 | 28.070 | 8.118 | 1.00 | 93.79 | A | O |
| ATOM | 814 | N | LYS | A | 227 | 45.793 | 28.312 | 6.170 | 1.00 | 94.01 | A | N |
| ATOM | 815 | CA | LYS | A | 227 | 46.866 | 29.045 | 5.545 | 1.00 | 93.52 | A | C |
| ATOM | 816 | CB | LYS | A | 227 | 47.971 | 28.042 | 5.213 | 1.00 | 95.86 | A | C |
| ATOM | 817 | CG | LYS | A | 227 | 48.910 | 28.466 | 4.113 | 1.00 | 104.38 | A | C |
| ATOM | 818 | CD | LYS | A | 227 | 49.007 | 27.397 | 3.000 | 1.00 | 111.96 | A | C |
| ATOM | 819 | CE | LYS | A | 227 | 49.762 | 27.914 | 1.743 | 1.00 | 116.43 | A | C |
| ATOM | 820 | NZ | LYS | A | 227 | 49.764 | 26.966 | 0.571 | 1.00 | 117.83 | A | N |
| ATOM | 821 | C | LYS | A | 227 | 46.317 | 29.732 | 4.284 | 1.00 | 93.17 | A | C |
| ATOM | 822 | O | LYS | A | 227 | 45.631 | 29.100 | 3.472 | 1.00 | 93.00 | A | O |
| ATOM | 823 | N | PHE | A | 228 | 46.608 | 31.026 | 4.129 | 1.00 | 92.35 | A | N |
| ATOM | 824 | CA | PHE | A | 228 | 46.134 | 31.811 | 2.978 | 1.00 | 93.02 | A | C |
| ATOM | 825 | CB | PHE | A | 228 | 46.225 | 33.323 | 3.248 | 1.00 | 88.79 | A | C |
| ATOM | 826 | CG | PHE | A | 228 | 45.472 | 33.783 | 4.459 | 1.00 | 83.75 | A | C |
| ATOM | 827 | CD1 | PHE | A | 228 | 44.427 | 33.032 | 4.975 | 1.00 | 87.00 | A | C |
| ATOM | 828 | CD2 | PHE | A | 228 | 45.777 | 34.993 | 5.060 | 1.00 | 79.34 | A | C |
| ATOM | 829 | CE1 | PHE | A | 228 | 43.691 | 33.486 | 6.079 | 1.00 | 89.01 | A | C |
| ATOM | 830 | CE2 | PHE | A | 228 | 45.052 | 35.452 | 6.158 | 1.00 | 80.98 | A | C |
| ATOM | 831 | CZ | PHE | A | 228 | 44.006 | 34.700 | 6.670 | 1.00 | 85.15 | A | C |
| ATOM | 832 | C | PHE | A | 228 | 46.919 | 31.543 | 1.705 | 1.00 | 95.50 | A | C |
| ATOM | 833 | O | PHE | A | 228 | 48.123 | 31.323 | 1.758 | 1.00 | 94.62 | A | O |
| ATOM | 834 | N | ASP | A | 229 | 46.241 | 31.594 | 0.558 | 1.00 | 100.44 | A | N |
| ATOM | 835 | CA | ASP | A | 229 | 46.897 | 31.383 | -0.741 | 1.00 | 102.57 | A | C |
| ATOM | 836 | CB | ASP | A | 229 | 45.881 | 31.295 | -1.887 | 1.00 | 103.03 | A | C |
| ATOM | 837 | CG | ASP | A | 229 | 45.139 | 32.612 | -2.113 | 1.00 | 103.52 | A | C |
| ATOM | 838 | OD1 | ASP | A | 229 | 44.204 | 32.929 | -1.334 | 1.00 | 104.72 | A | O |

Figure 4N

| ATOM | 839 | OD2 | ASP | A | 229 | 45.501 | 33.337 | -3.065 | 1.00 | 103.54 | A | O |
|------|-----|-----|-----|---|-----|--------|--------|--------|------|--------|---|---|
| ATOM | 840 | C | ASP | A | 229 | 47.792 | 32.580 | -0.995 | 1.00 | 102.24 | A | C |
| ATOM | 841 | O | ASP | A | 229 | 47.902 | 33.482 | -0.159 | 1.00 | 101.16 | A | O |
| ATOM | 842 | N | GLU | A | 230 | 48.408 | 32.602 | -2.164 | 1.00 | 100.71 | A | N |
| ATOM | 843 | CA | GLU | A | 230 | 49.292 | 33.702 | -2.486 | 1.00 | 100.33 | A | C |
| ATOM | 844 | CB | GLU | A | 230 | 50.312 | 33.235 | -3.520 | 1.00 | 102.96 | A | C |
| ATOM | 845 | CG | GLU | A | 230 | 51.266 | 32.185 | -2.972 | 1.00 | 105.87 | A | C |
| ATOM | 846 | CD | GLU | A | 230 | 52.372 | 31.839 | -3.948 | 1.00 | 106.22 | A | C |
| ATOM | 847 | OE1 | GLU | A | 230 | 53.072 | 32.762 | -4.436 | 1.00 | 104.14 | A | O |
| ATOM | 848 | OE2 | GLU | A | 230 | 52.535 | 30.631 | -4.215 | 1.00 | 108.49 | A | O |
| ATOM | 849 | C | GLU | A | 230 | 48.612 | 35.000 | -2.949 | 1.00 | 98.19 | A | C |
| ATOM | 850 | O | GLU | A | 230 | 49.175 | 36.084 | -2.819 | 1.00 | 98.47 | A | O |
| ATOM | 851 | N | GLN | A | 231 | 47.407 | 34.909 | -3.489 | 1.00 | 95.67 | A | N |
| ATOM | 852 | CA | GLN | A | 231 | 46.734 | 36.116 | -3.932 | 1.00 | 92.93 | A | C |
| ATOM | 853 | CB | GLN | A | 231 | 45.496 | 35.764 | -4.697 | 1.00 | 99.07 | A | C |
| ATOM | 854 | CG | GLN | A | 231 | 45.775 | 34.877 | -5.862 | 1.00 | 111.26 | A | C |
| ATOM | 855 | CD | GLN | A | 231 | 44.493 | 34.319 | -6.451 | 1.00 | 118.61 | A | C |
| ATOM | 856 | OE1 | GLN | A | 231 | 44.469 | 33.876 | -7.608 | 1.00 | 123.69 | A | O |
| ATOM | 857 | NE2 | GLN | A | 231 | 43.413 | 34.331 | -5.655 | 1.00 | 120.75 | A | N |
| ATOM | 858 | C | GLN | A | 231 | 46.318 | 36.895 | -2.731 | 1.00 | 88.61 | A | C |
| ATOM | 859 | O | GLN | A | 231 | 46.735 | 38.021 | -2.525 | 1.00 | 87.86 | A | O |
| ATOM | 860 | N | ARG | A | 232 | 45.475 | 36.260 | -1.942 | 1.00 | 85.50 | A | N |
| ATOM | 861 | CA | ARG | A | 232 | 44.946 | 36.842 | -0.738 | 1.00 | 85.80 | A | C |
| ATOM | 862 | CB | ARG | A | 232 | 44.116 | 35.783 | -0.021 | 1.00 | 91.03 | A | C |
| ATOM | 863 | CG | ARG | A | 232 | 43.336 | 36.303 | 1.148 | 1.00 | 97.43 | A | C |
| ATOM | 864 | CD | ARG | A | 232 | 42.335 | 35.277 | 1.651 | 1.00 | 101.69 | A | C |
| ATOM | 865 | NE | ARG | A | 232 | 41.736 | 35.709 | 2.919 | 1.00 | 107.49 | A | N |
| ATOM | 866 | CZ | ARG | A | 232 | 40.738 | 35.083 | 3.546 | 1.00 | 109.73 | A | C |
| ATOM | 867 | NH1 | ARG | A | 232 | 40.200 | 33.978 | 3.016 | 1.00 | 112.75 | A | N |
| ATOM | 868 | NH2 | ARG | A | 232 | 40.297 | 35.552 | 4.718 | 1.00 | 105.91 | A | N |
| ATOM | 869 | C | ARG | A | 232 | 46.001 | 37.435 | 0.204 | 1.00 | 82.33 | A | C |
| ATOM | 870 | O | ARG | A | 232 | 45.813 | 38.528 | 0.724 | 1.00 | 79.93 | A | O |
| ATOM | 871 | N | THR | A | 233 | 47.106 | 36.732 | 0.426 | 1.00 | 79.80 | A | N |
| ATOM | 872 | CA | THR | A | 233 | 48.161 | 37.227 | 1.328 | 1.00 | 77.93 | A | C |
| ATOM | 873 | CB | THR | A | 233 | 49.192 | 36.115 | 1.648 | 1.00 | 75.42 | A | C |
| ATOM | 874 | OG1 | THR | A | 233 | 50.337 | 36.679 | 2.306 | 1.00 | 71.75 | A | O |
| ATOM | 875 | CG2 | THR | A | 233 | 49.633 | 35.440 | 0.384 | 1.00 | 74.11 | A | C |
| ATOM | 876 | C | THR | A | 233 | 48.945 | 38.450 | 0.832 | 1.00 | 78.02 | A | C |
| ATOM | 877 | O | THR | A | 233 | 49.245 | 39.371 | 1.595 | 1.00 | 76.40 | A | O |
| ATOM | 878 | N | ALA | A | 234 | 49.286 | 38.445 | -0.451 | 1.00 | 77.84 | A | N |
| ATOM | 879 | CA | ALA | A | 234 | 50.045 | 39.536 | -1.062 | 1.00 | 75.29 | A | C |
| ATOM | 880 | CB | ALA | A | 234 | 50.353 | 39.202 | -2.515 | 1.00 | 77.15 | A | C |
| ATOM | 881 | C | ALA | A | 234 | 49.256 | 40.823 | -0.993 | 1.00 | 73.65 | A | C |
| ATOM | 882 | O | ALA | A | 234 | 49.747 | 41.853 | -0.539 | 1.00 | 70.31 | A | O |
| ATOM | 883 | N | THR | A | 235 | 48.022 | 40.751 | -1.464 | 1.00 | 73.53 | A | N |
| ATOM | 884 | CA | THR | A | 235 | 47.170 | 41.907 | -1.450 | 1.00 | 74.15 | A | C |
| ATOM | 885 | CB | THR | A | 235 | 45.786 | 41.559 | -2.045 | 1.00 | 73.72 | A | C |
| ATOM | 886 | OG1 | THR | A | 235 | 44.836 | 42.565 | -1.676 | 1.00 | 78.18 | A | O |
| ATOM | 887 | CG2 | THR | A | 235 | 45.320 | 40.189 | -1.573 | 1.00 | 73.17 | A | C |
| ATOM | 888 | C | THR | A | 235 | 47.056 | 42.422 | -0.016 | 1.00 | 74.46 | A | C |
| ATOM | 889 | O | THR | A | 235 | 47.271 | 43.605 | 0.256 | 1.00 | 71.96 | A | O |
| ATOM | 890 | N | TYR | A | 236 | 46.748 | 41.530 | 0.913 | 1.00 | 75.19 | A | N |
| ATOM | 891 | CA | TYR | A | 236 | 46.615 | 41.962 | 2.289 | 1.00 | 74.89 | A | C |
| ATOM | 892 | CB | TYR | A | 236 | 46.441 | 40.755 | 3.238 | 1.00 | 80.36 | A | C |
| ATOM | 893 | CG | TYR | A | 236 | 44.997 | 40.226 | 3.398 | 1.00 | 86.01 | A | C |
| ATOM | 894 | CD1 | TYR | A | 236 | 43.895 | 40.936 | 2.890 | 1.00 | 88.47 | A | C |
| ATOM | 895 | CE1 | TYR | A | 236 | 42.578 | 40.476 | 3.074 | 1.00 | 89.70 | A | C |
| ATOM | 896 | CD2 | TYR | A | 236 | 44.736 | 39.035 | 4.098 | 1.00 | 86.66 | A | C |
| ATOM | 897 | CE2 | TYR | A | 236 | 43.420 | 38.570 | 4.290 | 1.00 | 88.13 | A | C |
| ATOM | 898 | CZ | TYR | A | 236 | 42.352 | 39.296 | 3.774 | 1.00 | 89.77 | A | C |
| ATOM | 899 | OH | TYR | A | 236 | 41.062 | 38.843 | 3.946 | 1.00 | 88.66 | A | O |

Figure 40

| ATOM | 900 | C   | TYR | A | 236 | 47.859 | 42.757 | 2.630  | 1.00 | 70.33 | A | C |
|------|-----|-----|-----|---|-----|--------|--------|--------|------|-------|---|---|
| ATOM | 901 | O   | TYR | A | 236 | 47.774 | 43.870 | 3.121  | 1.00 | 71.27 | A | O |
| ATOM | 902 | N   | ILE | A | 237 | 49.016 | 42.203 | 2.315  | 1.00 | 67.78 | A | N |
| ATOM | 903 | CA  | ILE | A | 237 | 50.263 | 42.878 | 2.618  | 1.00 | 64.43 | A | C |
| ATOM | 904 | CB  | ILE | A | 237 | 51.456 | 42.082 | 2.120  | 1.00 | 62.05 | A | C |
| ATOM | 905 | CG2 | ILE | A | 237 | 52.707 | 42.907 | 2.261  | 1.00 | 63.48 | A | C |
| ATOM | 906 | CG1 | ILE | A | 237 | 51.593 | 40.799 | 2.927  | 1.00 | 57.60 | A | C |
| ATOM | 907 | CD1 | ILE | A | 237 | 51.858 | 41.042 | 4.405  | 1.00 | 52.01 | A | C |
| ATOM | 908 | C   | ILE | A | 237 | 50.336 | 44.260 | 2.017  | 1.00 | 63.37 | A | C |
| ATOM | 909 | O   | ILE | A | 237 | 50.860 | 45.183 | 2.634  | 1.00 | 57.56 | A | O |
| ATOM | 910 | N   | THR | A | 238 | 49.824 | 44.404 | 0.802  | 1.00 | 65.31 | A | N |
| ATOM | 911 | CA  | THR | A | 238 | 49.865 | 45.706 | 0.163  | 1.00 | 68.82 | A | C |
| ATOM | 912 | CB  | THR | A | 238 | 49.598 | 45.645 | -1.386 | 1.00 | 71.04 | A | C |
| ATOM | 913 | OG1 | THR | A | 238 | 48.794 | 46.768 | -1.786 | 1.00 | 73.52 | A | O |
| ATOM | 914 | CG2 | THR | A | 238 | 48.945 | 44.348 | -1.787 | 1.00 | 70.75 | A | C |
| ATOM | 915 | C   | THR | A | 238 | 48.876 | 46.638 | 0.827  | 1.00 | 69.62 | A | C |
| ATOM | 916 | O   | THR | A | 238 | 49.217 | 47.774 | 1.145  | 1.00 | 70.51 | A | O |
| ATOM | 917 | N   | GLU | A | 239 | 47.658 | 46.169 | 1.051  | 1.00 | 68.63 | A | N |
| ATOM | 918 | CA  | GLU | A | 239 | 46.683 | 47.016 | 1.702  | 1.00 | 69.12 | A | C |
| ATOM | 919 | CB  | GLU | A | 239 | 45.440 | 46.208 | 2.069  | 1.00 | 71.32 | A | C |
| ATOM | 920 | CG  | GLU | A | 239 | 44.651 | 45.685 | 0.873  | 1.00 | 80.08 | A | C |
| ATOM | 921 | CD  | GLU | A | 239 | 43.338 | 44.991 | 1.263  | 1.00 | 82.50 | A | C |
| ATOM | 922 | OE1 | GLU | A | 239 | 42.603 | 44.552 | 0.355  | 1.00 | 83.13 | A | O |
| ATOM | 923 | OE2 | GLU | A | 239 | 43.040 | 44.881 | 2.473  | 1.00 | 84.93 | A | O |
| ATOM | 924 | C   | GLU | A | 239 | 47.328 | 47.561 | 2.975  | 1.00 | 69.14 | A | C |
| ATOM | 925 | O   | GLU | A | 239 | 47.325 | 48.772 | 3.238  | 1.00 | 69.47 | A | O |
| ATOM | 926 | N   | LEU | A | 240 | 47.910 | 46.643 | 3.743  | 1.00 | 67.54 | A | N |
| ATOM | 927 | CA  | LEU | A | 240 | 48.553 | 46.948 | 5.019  | 1.00 | 61.62 | A | C |
| ATOM | 928 | CB  | LEU | A | 240 | 49.116 | 45.657 | 5.607  | 1.00 | 60.79 | A | C |
| ATOM | 929 | CG  | LEU | A | 240 | 49.114 | 45.487 | 7.123  | 1.00 | 59.67 | A | C |
| ATOM | 930 | CD1 | LEU | A | 240 | 47.817 | 45.963 | 7.731  | 1.00 | 64.22 | A | C |
| ATOM | 931 | CD2 | LEU | A | 240 | 49.331 | 44.027 | 7.431  | 1.00 | 65.44 | A | C |
| ATOM | 932 | C   | LEU | A | 240 | 49.650 | 47.978 | 4.861  | 1.00 | 58.31 | A | C |
| ATOM | 933 | O   | LEU | A | 240 | 49.671 | 49.007 | 5.529  | 1.00 | 55.60 | A | O |
| ATOM | 934 | N   | ALA | A | 241 | 50.567 | 47.687 | 3.963  | 1.00 | 55.82 | A | N |
| ATOM | 935 | CA  | ALA | A | 241 | 51.657 | 48.587 | 3.711  | 1.00 | 54.67 | A | C |
| ATOM | 936 | CB  | ALA | A | 241 | 52.378 | 48.142 | 2.456  | 1.00 | 56.06 | A | C |
| ATOM | 937 | C   | ALA | A | 241 | 51.166 | 50.036 | 3.572  | 1.00 | 55.10 | A | C |
| ATOM | 938 | O   | ALA | A | 241 | 51.668 | 50.928 | 4.241  | 1.00 | 52.52 | A | O |
| ATOM | 939 | N   | ASN | A | 242 | 50.177 | 50.269 | 2.716  | 1.00 | 55.96 | A | N |
| ATOM | 940 | CA  | ASN | A | 242 | 49.675 | 51.622 | 2.495  | 1.00 | 52.11 | A | C |
| ATOM | 941 | CB  | ASN | A | 242 | 48.605 | 51.638 | 1.427  | 1.00 | 56.23 | A | C |
| ATOM | 942 | CG  | ASN | A | 242 | 49.133 | 51.182 | 0.097  | 1.00 | 63.76 | A | C |
| ATOM | 943 | OD1 | ASN | A | 242 | 48.426 | 51.192 | -0.895 | 1.00 | 69.76 | A | O |
| ATOM | 944 | ND2 | ASN | A | 242 | 50.388 | 50.768 | 0.070  | 1.00 | 69.13 | A | N |
| ATOM | 945 | C   | ASN | A | 242 | 49.116 | 52.180 | 3.739  | 1.00 | 46.29 | A | C |
| ATOM | 946 | O   | ASN | A | 242 | 49.445 | 53.283 | 4.131  | 1.00 | 39.64 | A | O |
| ATOM | 947 | N   | ALA | A | 243 | 48.242 | 51.411 | 4.354  | 1.00 | 47.62 | A | N |
| ATOM | 948 | CA  | ALA | A | 243 | 47.659 | 51.852 | 5.590  | 1.00 | 57.54 | A | C |
| ATOM | 949 | CB  | ALA | A | 243 | 46.981 | 50.707 | 6.296  | 1.00 | 59.78 | A | C |
| ATOM | 950 | C   | ALA | A | 243 | 48.849 | 52.311 | 6.383  | 1.00 | 63.58 | A | C |
| ATOM | 951 | O   | ALA | A | 243 | 48.797 | 53.310 | 7.082  | 1.00 | 63.45 | A | O |
| ATOM | 952 | N   | LEU | A | 244 | 49.942 | 51.578 | 6.247  | 1.00 | 72.95 | A | N |
| ATOM | 953 | CA  | LEU | A | 244 | 51.151 | 51.920 | 6.972  | 1.00 | 78.61 | A | C |
| ATOM | 954 | CB  | LEU | A | 244 | 52.116 | 50.737 | 6.938  | 1.00 | 80.04 | A | C |
| ATOM | 955 | CG  | LEU | A | 244 | 52.220 | 49.827 | 8.173  | 1.00 | 82.33 | A | C |
| ATOM | 956 | CD1 | LEU | A | 244 | 51.096 | 50.068 | 9.190  | 1.00 | 83.92 | A | C |
| ATOM | 957 | CD2 | LEU | A | 244 | 52.219 | 48.389 | 7.681  | 1.00 | 84.36 | A | C |
| ATOM | 958 | C   | LEU | A | 244 | 51.800 | 53.173 | 6.396  | 1.00 | 81.09 | A | C |
| ATOM | 959 | O   | LEU | A | 244 | 52.269 | 54.041 | 7.141  | 1.00 | 80.56 | A | O |
| ATOM | 960 | N   | SER | A | 245 | 51.807 | 53.271 | 5.069  | 1.00 | 84.23 | A | N |

Figure 4P

```
ATOM    961  CA   SER A 245      52.400  54.422   4.397  1.00  88.57      A    C
ATOM    962  CB   SER A 245      52.261  54.314   2.892  1.00  90.30      A    C
ATOM    963  OG   SER A 245      52.546  55.581   2.301  1.00  92.04      A    O
ATOM    964  C    SER A 245      51.760  55.725   4.808  1.00  90.49      A    C
ATOM    965  O    SER A 245      52.446  56.692   5.112  1.00  91.94      A    O
ATOM    966  N    TYR A 246      50.438  55.759   4.751  1.00  91.95      A    N
ATOM    967  CA   TYR A 246      49.691  56.933   5.153  1.00  92.95      A    C
ATOM    968  CB   TYR A 246      48.204  56.651   4.938  1.00  92.76      A    C
ATOM    969  CG   TYR A 246      47.252  57.519   5.722  1.00  94.43      A    C
ATOM    970  CD1  TYR A 246      46.672  58.642   5.149  1.00  94.86      A    C
ATOM    971  CE1  TYR A 246      45.803  59.459   5.892  1.00  96.16      A    C
ATOM    972  CD2  TYR A 246      46.942  57.222   7.055  1.00  95.64      A    C
ATOM    973  CE2  TYR A 246      46.079  58.028   7.807  1.00  95.23      A    C
ATOM    974  CZ   TYR A 246      45.515  59.147   7.227  1.00  95.36      A    C
ATOM    975  OH   TYR A 246      44.708  59.960   8.005  1.00  93.14      A    O
ATOM    976  C    TYR A 246      50.011  57.204   6.641  1.00  94.96      A    C
ATOM    977  O    TYR A 246      49.968  58.346   7.090  1.00  95.18      A    O
ATOM    978  N    CYS A 247      50.357  56.151   7.386  1.00  96.00      A    N
ATOM    979  CA   CYS A 247      50.689  56.256   8.810  1.00  97.84      A    C
ATOM    980  CB   CYS A 247      50.789  54.879   9.444  1.00  98.48      A    C
ATOM    981  SG   CYS A 247      49.268  54.278  10.131  1.00 105.20      A    S
ATOM    982  C    CYS A 247      51.999  56.941   9.057  1.00  99.79      A    C
ATOM    983  O    CYS A 247      52.127  57.817   9.898  1.00 100.00      A    O
ATOM    984  N    HIS A 248      52.999  56.492   8.333  1.00 103.34      A    N
ATOM    985  CA   HIS A 248      54.319  57.052   8.479  1.00 106.72      A    C
ATOM    986  CB   HIS A 248      55.290  56.277   7.581  1.00 113.25      A    C
ATOM    987  CG   HIS A 248      55.765  54.976   8.173  1.00 117.98      A    C
ATOM    988  CD2  HIS A 248      56.968  54.349   8.100  1.00 118.99      A    C
ATOM    989  ND1  HIS A 248      54.962  54.174   8.960  1.00 119.15      A    N
ATOM    990  CE1  HIS A 248      55.650  53.113   9.349  1.00 120.21      A    C
ATOM    991  NE2  HIS A 248      56.870  53.196   8.841  1.00 120.93      A    N
ATOM    992  C    HIS A 248      54.318  58.529   8.133  1.00 105.90      A    C
ATOM    993  O    HIS A 248      54.797  59.358   8.893  1.00 104.00      A    O
ATOM    994  N    SER A 249      53.766  58.850   6.977  1.00 108.07      A    N
ATOM    995  CA   SER A 249      53.702  60.231   6.523  1.00 112.32      A    C
ATOM    996  CB   SER A 249      52.757  60.352   5.314  1.00 113.30      A    C
ATOM    997  OG   SER A 249      51.419  59.958   5.623  1.00 113.57      A    O
ATOM    998  C    SER A 249      53.211  61.156   7.624  1.00 114.04      A    C
ATOM    999  O    SER A 249      53.878  62.117   8.020  1.00 115.06      A    O
ATOM   1000  N    LYS A 250      52.022  60.855   8.111  1.00 115.15      A    N
ATOM   1001  CA   LYS A 250      51.409  61.654   9.140  1.00 117.05      A    C
ATOM   1002  CB   LYS A 250      49.933  61.252   9.211  1.00 121.24      A    C
ATOM   1003  CG   LYS A 250      49.225  61.429  10.525  1.00 129.31      A    C
ATOM   1004  CD   LYS A 250      49.381  60.188  11.423  1.00 136.73      A    C
ATOM   1005  CE   LYS A 250      49.805  58.902  10.661  1.00 140.50      A    C
ATOM   1006  NZ   LYS A 250      49.033  58.595   9.407  1.00 139.90      A    N
ATOM   1007  C    LYS A 250      52.183  61.445  10.435  1.00 116.65      A    C
ATOM   1008  O    LYS A 250      51.791  61.908  11.505  1.00 115.99      A    O
ATOM   1009  N    ARG A 251      53.315  60.763  10.305  1.00 116.10      A    N
ATOM   1010  CA   ARG A 251      54.200  60.486  11.425  1.00 116.43      A    C
ATOM   1011  CB   ARG A 251      54.944  61.767  11.842  1.00 119.51      A    C
ATOM   1012  CG   ARG A 251      56.140  62.111  10.934  1.00 122.96      A    C
ATOM   1013  CD   ARG A 251      56.974  63.251  11.513  1.00 127.32      A    C
ATOM   1014  NE   ARG A 251      58.205  63.495  10.756  1.00 129.97      A    N
ATOM   1015  CZ   ARG A 251      59.050  64.499  11.001  1.00 131.96      A    C
ATOM   1016  NH1  ARG A 251      58.803  65.368  11.985  1.00 132.26      A    N
ATOM   1017  NH2  ARG A 251      60.153  64.632  10.268  1.00 132.44      A    N
ATOM   1018  C    ARG A 251      53.554  59.826  12.642  1.00 114.26      A    C
ATOM   1019  O    ARG A 251      53.264  60.466  13.653  1.00 113.40      A    O
ATOM   1020  N    VAL A 252      53.344  58.526  12.523  1.00 112.60      A    N
ATOM   1021  CA   VAL A 252      52.773  57.729  13.585  1.00 113.78      A    C
```

Figure 4Q

```
ATOM   1022  CB    VAL A 252      51.263  57.696  13.534  1.00  111.99      A    C
ATOM   1023  CG1   VAL A 252      50.753  56.444  14.230  1.00  110.43      A    C
ATOM   1024  CG2   VAL A 252      50.720  58.920  14.217  1.00  112.20      A    C
ATOM   1025  C     VAL A 252      53.265  56.345  13.329  1.00  116.92      A    C
ATOM   1026  O     VAL A 252      53.151  55.851  12.213  1.00  118.09      A    O
ATOM   1027  N     ILE A 253      53.815  55.717  14.359  1.00  121.61      A    N
ATOM   1028  CA    ILE A 253      54.336  54.362  14.214  1.00  126.11      A    C
ATOM   1029  CB    ILE A 253      55.862  54.289  14.618  1.00  127.90      A    C
ATOM   1030  CG2   ILE A 253      56.359  52.838  14.574  1.00  126.98      A    C
ATOM   1031  CG1   ILE A 253      56.723  55.139  13.657  1.00  129.64      A    C
ATOM   1032  CD1   ILE A 253      56.494  56.666  13.735  1.00  131.81      A    C
ATOM   1033  C     ILE A 253      53.508  53.379  15.054  1.00  127.68      A    C
ATOM   1034  O     ILE A 253      53.477  53.466  16.295  1.00  128.33      A    O
ATOM   1035  N     HIS A 254      52.833  52.458  14.355  1.00  128.83      A    N
ATOM   1036  CA    HIS A 254      51.982  51.430  14.978  1.00  128.27      A    C
ATOM   1037  CB    HIS A 254      50.877  50.966  13.996  1.00  127.67      A    C
ATOM   1038  CG    HIS A 254      49.529  51.552  14.280  1.00  127.76      A    C
ATOM   1039  CD2   HIS A 254      48.637  52.174  13.471  1.00  129.26      A    C
ATOM   1040  ND1   HIS A 254      48.962  51.539  15.537  1.00  128.83      A    N
ATOM   1041  CE1   HIS A 254      47.780  52.132  15.492  1.00  129.37      A    C
ATOM   1042  NE2   HIS A 254      47.558  52.526  14.250  1.00  129.06      A    N
ATOM   1043  C     HIS A 254      52.724  50.183  15.507  1.00  127.13      A    C
ATOM   1044  O     HIS A 254      53.510  50.262  16.473  1.00  127.02      A    O
ATOM   1045  N     ARG A 255      52.449  49.051  14.846  1.00  124.83      A    N
ATOM   1046  CA    ARG A 255      52.974  47.720  15.170  1.00  121.48      A    C
ATOM   1047  CB    ARG A 255      54.218  47.791  16.071  1.00  120.05      A    C
ATOM   1054  C     ARG A 255      51.827  46.988  15.894  1.00  119.17      A    C
ATOM   1055  O     ARG A 255      50.662  47.445  15.869  1.00  117.57      A    O
ATOM   1056  N     ASP A 256      52.154  45.869  16.541  1.00  116.17      A    N
ATOM   1057  CA    ASP A 256      51.148  45.065  17.232  1.00  113.90      A    C
ATOM   1058  CB    ASP A 256      50.402  45.916  18.274  1.00  111.74      A    C
ATOM   1062  C     ASP A 256      50.161  44.522  16.177  1.00  111.95      A    C
ATOM   1063  O     ASP A 256      49.281  43.708  16.490  1.00  114.67      A    O
ATOM   1064  N     ILE A 257      50.337  44.968  14.930  1.00  106.47      A    N
ATOM   1065  CA    ILE A 257      49.489  44.586  13.807  1.00  101.04      A    C
ATOM   1066  CB    ILE A 257      49.819  45.450  12.584  1.00  100.47      A    C
ATOM   1067  CG2   ILE A 257      49.460  46.887  12.875  1.00  103.75      A    C
ATOM   1068  CG1   ILE A 257      51.314  45.372  12.270  1.00  100.84      A    C
ATOM   1069  CD1   ILE A 257      51.615  44.782  10.921  1.00  100.91      A    C
ATOM   1070  C     ILE A 257      49.575  43.115  13.420  1.00   97.73      A    C
ATOM   1071  O     ILE A 257      50.102  42.761  12.369  1.00   99.79      A    O
ATOM   1072  N     LYS A 258      49.038  42.259  14.274  1.00   92.64      A    N
ATOM   1073  CA    LYS A 258      49.045  40.843  14.016  1.00   86.17      A    C
ATOM   1074  CB    LYS A 258      49.656  40.128  15.203  1.00   87.21      A    C
ATOM   1075  CG    LYS A 258      49.328  40.792  16.519  1.00   87.58      A    C
ATOM   1076  CD    LYS A 258      50.166  40.214  17.624  1.00   91.32      A    C
ATOM   1077  CE    LYS A 258      49.847  40.857  18.946  1.00   93.01      A    C
ATOM   1078  NZ    LYS A 258      50.707  40.246  19.994  1.00   99.26      A    N
ATOM   1079  C     LYS A 258      47.617  40.416  13.784  1.00   83.42      A    C
ATOM   1080  O     LYS A 258      46.683  41.187  14.001  1.00   79.92      A    O
ATOM   1081  N     PRO A 259      47.424  39.175  13.344  1.00   82.25      A    N
ATOM   1082  CD    PRO A 259      48.419  38.093  13.295  1.00   78.57      A    C
ATOM   1083  CA    PRO A 259      46.082  38.658  13.077  1.00   83.46      A    C
ATOM   1084  CB    PRO A 259      46.286  37.150  13.166  1.00   81.70      A    C
ATOM   1085  CG    PRO A 259      47.655  36.988  12.625  1.00   79.81      A    C
ATOM   1086  C     PRO A 259      44.996  39.170  14.034  1.00   84.33      A    C
ATOM   1087  O     PRO A 259      43.942  39.639  13.624  1.00   81.49      A    O
ATOM   1088  N     GLU A 260      45.283  39.083  15.318  1.00   87.71      A    N
ATOM   1089  CA    GLU A 260      44.367  39.486  16.371  1.00   89.95      A    C
ATOM   1090  CB    GLU A 260      45.042  39.290  17.736  1.00   94.80      A    C
ATOM   1091  CG    GLU A 260      45.668  37.899  17.956  1.00  102.92      A    C
```

Figure 4R

| ATOM | 1092 | CD  | GLU | A | 260 | 46.877 | 37.579 | 17.035 | 1.00 | 108.44 | A | C |
|------|------|-----|-----|---|-----|--------|--------|--------|------|--------|---|---|
| ATOM | 1093 | OE1 | GLU | A | 260 | 47.399 | 36.444 | 17.128 | 1.00 | 111.46 | A | O |
| ATOM | 1094 | OE2 | GLU | A | 260 | 47.318 | 38.435 | 16.222 | 1.00 | 110.35 | A | O |
| ATOM | 1095 | C   | GLU | A | 260 | 43.913 | 40.925 | 16.240 | 1.00 | 87.92  | A | C |
| ATOM | 1096 | O   | GLU | A | 260 | 42.758 | 41.244 | 16.513 | 1.00 | 87.60  | A | O |
| ATOM | 1097 | N   | ASN | A | 261 | 44.821 | 41.792 | 15.819 | 1.00 | 86.43  | A | N |
| ATOM | 1098 | CA  | ASN | A | 261 | 44.487 | 43.197 | 15.707 | 1.00 | 88.09  | A | C |
| ATOM | 1099 | CB  | ASN | A | 261 | 45.578 | 44.056 | 16.344 | 1.00 | 88.60  | A | C |
| ATOM | 1100 | CG  | ASN | A | 261 | 45.857 | 43.665 | 17.777 | 1.00 | 88.74  | A | C |
| ATOM | 1101 | OD1 | ASN | A | 261 | 44.938 | 43.403 | 18.545 | 1.00 | 85.96  | A | O |
| ATOM | 1102 | ND2 | ASN | A | 261 | 47.130 | 43.627 | 18.147 | 1.00 | 89.76  | A | N |
| ATOM | 1103 | C   | ASN | A | 261 | 44.222 | 43.680 | 14.297 | 1.00 | 88.99  | A | C |
| ATOM | 1104 | O   | ASN | A | 261 | 44.409 | 44.861 | 13.992 | 1.00 | 88.63  | A | O |
| ATOM | 1105 | N   | LEU | A | 262 | 43.787 | 42.776 | 13.431 | 1.00 | 88.70  | A | N |
| ATOM | 1106 | CA  | LEU | A | 262 | 43.456 | 43.155 | 12.057 | 1.00 | 87.76  | A | C |
| ATOM | 1107 | CB  | LEU | A | 262 | 44.495 | 42.561 | 11.101 | 1.00 | 80.83  | A | C |
| ATOM | 1108 | CG  | LEU | A | 262 | 45.934 | 42.996 | 11.384 | 1.00 | 71.05  | A | C |
| ATOM | 1109 | CD1 | LEU | A | 262 | 46.878 | 42.303 | 10.437 | 1.00 | 63.69  | A | C |
| ATOM | 1110 | CD2 | LEU | A | 262 | 46.040 | 44.499 | 11.242 | 1.00 | 63.59  | A | C |
| ATOM | 1111 | C   | LEU | A | 262 | 42.024 | 42.658 | 11.738 | 1.00 | 89.15  | A | C |
| ATOM | 1112 | O   | LEU | A | 262 | 41.703 | 41.492 | 11.978 | 1.00 | 93.37  | A | O |
| ATOM | 1113 | N   | LEU | A | 263 | 41.160 | 43.534 | 11.224 | 1.00 | 86.92  | A | N |
| ATOM | 1114 | CA  | LEU | A | 263 | 39.785 | 43.140 | 10.930 | 1.00 | 84.68  | A | C |
| ATOM | 1115 | CB  | LEU | A | 263 | 38.837 | 44.041 | 11.704 | 1.00 | 84.62  | A | C |
| ATOM | 1116 | CG  | LEU | A | 263 | 38.970 | 43.946 | 13.221 | 1.00 | 81.46  | A | C |
| ATOM | 1117 | CD1 | LEU | A | 263 | 38.111 | 45.008 | 13.883 | 1.00 | 81.72  | A | C |
| ATOM | 1118 | CD2 | LEU | A | 263 | 38.546 | 42.563 | 13.666 | 1.00 | 83.91  | A | C |
| ATOM | 1119 | C   | LEU | A | 263 | 39.420 | 43.139 | 9.443  | 1.00 | 85.16  | A | C |
| ATOM | 1120 | O   | LEU | A | 263 | 40.139 | 43.711 | 8.627  | 1.00 | 85.56  | A | O |
| ATOM | 1121 | N   | LEU | A | 264 | 38.298 | 42.502 | 9.101  | 1.00 | 84.94  | A | N |
| ATOM | 1122 | CA  | LEU | A | 264 | 37.868 | 42.397 | 7.714  | 1.00 | 85.38  | A | C |
| ATOM | 1123 | CB  | LEU | A | 264 | 37.654 | 40.925 | 7.363  | 1.00 | 91.08  | A | C |
| ATOM | 1124 | CG  | LEU | A | 264 | 38.914 | 40.049 | 7.504  | 1.00 | 96.47  | A | C |
| ATOM | 1125 | CD1 | LEU | A | 264 | 38.580 | 38.566 | 7.331  | 1.00 | 98.05  | A | C |
| ATOM | 1126 | CD2 | LEU | A | 264 | 39.964 | 40.491 | 6.471  | 1.00 | 99.24  | A | C |
| ATOM | 1127 | C   | LEU | A | 264 | 36.617 | 43.182 | 7.401  | 1.00 | 83.76  | A | C |
| ATOM | 1128 | O   | LEU | A | 264 | 35.687 | 43.205 | 8.193  | 1.00 | 85.03  | A | O |
| ATOM | 1129 | N   | GLY | A | 265 | 36.605 | 43.812 | 6.231  | 1.00 | 82.44  | A | N |
| ATOM | 1130 | CA  | GLY | A | 265 | 35.459 | 44.599 | 5.807  | 1.00 | 85.90  | A | C |
| ATOM | 1131 | C   | GLY | A | 265 | 34.570 | 43.892 | 4.792  | 1.00 | 88.44  | A | C |
| ATOM | 1132 | O   | GLY | A | 265 | 34.836 | 42.751 | 4.428  | 1.00 | 88.85  | A | O |
| ATOM | 1133 | N   | SER | A | 266 | 33.522 | 44.581 | 4.330  | 1.00 | 91.40  | A | N |
| ATOM | 1134 | CA  | SER | A | 266 | 32.545 | 44.042 | 3.364  | 1.00 | 92.48  | A | C |
| ATOM | 1135 | CB  | SER | A | 266 | 31.747 | 45.201 | 2.707  | 1.00 | 91.85  | A | C |
| ATOM | 1136 | OG  | SER | A | 266 | 30.959 | 45.972 | 3.620  | 1.00 | 88.12  | A | O |
| ATOM | 1137 | C   | SER | A | 266 | 33.147 | 43.162 | 2.254  | 1.00 | 93.41  | A | C |
| ATOM | 1138 | O   | SER | A | 266 | 32.752 | 42.003 | 2.039  | 1.00 | 91.15  | A | O |
| ATOM | 1139 | N   | ALA | A | 267 | 34.106 | 43.732 | 1.546  | 1.00 | 95.25  | A | N |
| ATOM | 1140 | CA  | ALA | A | 267 | 34.750 | 43.037 | 0.451  | 1.00 | 100.59 | A | C |
| ATOM | 1141 | CB  | ALA | A | 267 | 35.233 | 44.058 | -0.534 | 1.00 | 103.37 | A | C |
| ATOM | 1142 | C   | ALA | A | 267 | 35.911 | 42.116 | 0.861  | 1.00 | 103.14 | A | C |
| ATOM | 1143 | O   | ALA | A | 267 | 36.648 | 41.600 | 0.010  | 1.00 | 104.32 | A | O |
| ATOM | 1144 | N   | GLY | A | 268 | 36.076 | 41.896 | 2.159  | 1.00 | 103.71 | A | N |
| ATOM | 1145 | CA  | GLY | A | 268 | 37.171 | 41.052 | 2.601  | 1.00 | 102.54 | A | C |
| ATOM | 1146 | C   | GLY | A | 268 | 38.414 | 41.907 | 2.596  | 1.00 | 102.47 | A | C |
| ATOM | 1147 | O   | GLY | A | 268 | 39.526 | 41.424 | 2.355  | 1.00 | 103.00 | A | O |
| ATOM | 1148 | N   | GLU | A | 269 | 38.187 | 43.197 | 2.851  | 1.00 | 101.81 | A | N |
| ATOM | 1149 | CA  | GLU | A | 269 | 39.224 | 44.223 | 2.906  | 1.00 | 101.15 | A | C |
| ATOM | 1150 | CB  | GLU | A | 269 | 38.619 | 45.598 | 2.574  | 1.00 | 105.01 | A | C |
| ATOM | 1151 | CG  | GLU | A | 269 | 37.079 | 45.634 | 2.406  | 1.00 | 107.45 | A | C |
| ATOM | 1152 | CD  | GLU | A | 269 | 36.438 | 46.972 | 2.837  | 1.00 | 109.25 | A | C |

Figure 4S

```
ATOM   1153  OE1 GLU A 269      36.854  48.061   2.367  1.00 110.56      A    O
ATOM   1154  OE2 GLU A 269      35.497  46.932   3.658  1.00 110.09      A    O
ATOM   1155  C   GLU A 269      39.829  44.264   4.311  1.00  98.60      A    C
ATOM   1156  O   GLU A 269      39.190  43.825   5.271  1.00 100.18      A    O
ATOM   1157  N   LEU A 270      41.039  44.819   4.428  1.00  94.11      A    N
ATOM   1158  CA  LEU A 270      41.753  44.911   5.713  1.00  89.94      A    C
ATOM   1159  CB  LEU A 270      43.243  44.711   5.469  1.00  95.33      A    C
ATOM   1160  CG  LEU A 270      44.037  44.185   6.661  1.00 100.63      A    C
ATOM   1161  CD1 LEU A 270      43.391  42.895   7.183  1.00 104.12      A    C
ATOM   1162  CD2 LEU A 270      45.477  43.915   6.224  1.00  99.41      A    C
ATOM   1163  C   LEU A 270      41.548  46.205   6.519  1.00  84.15      A    C
ATOM   1164  O   LEU A 270      41.466  47.291   5.961  1.00  84.52      A    O
ATOM   1165  N   LYS A 271      41.482  46.082   7.838  1.00  77.12      A    N
ATOM   1166  CA  LYS A 271      41.271  47.236   8.685  1.00  73.34      A    C
ATOM   1167  CB  LYS A 271      39.816  47.318   9.131  1.00  73.45      A    C
ATOM   1168  CG  LYS A 271      38.787  47.325   8.025  1.00  75.19      A    C
ATOM   1169  CD  LYS A 271      38.711  48.665   7.362  1.00  74.17      A    C
ATOM   1170  CE  LYS A 271      37.499  48.722   6.473  1.00  76.05      A    C
ATOM   1171  NZ  LYS A 271      37.387  50.052   5.834  1.00  82.53      A    N
ATOM   1172  C   LYS A 271      42.122  47.079   9.908  1.00  73.07      A    C
ATOM   1173  O   LYS A 271      41.920  46.167  10.683  1.00  72.96      A    O
ATOM   1174  N   ILE A 272      43.104  47.945  10.137  1.00  75.11      A    N
ATOM   1175  CA  ILE A 272      43.903  47.784  11.360  1.00  76.99      A    C
ATOM   1176  CB  ILE A 272      45.307  48.400  11.233  1.00  75.36      A    C
ATOM   1177  CG2 ILE A 272      45.867  48.116   9.857  1.00  74.11      A    C
ATOM   1178  CG1 ILE A 272      45.257  49.910  11.512  1.00  74.33      A    C
ATOM   1179  CD1 ILE A 272      45.249  50.317  13.026  1.00  78.74      A    C
ATOM   1180  C   ILE A 272      43.193  48.435  12.553  1.00  81.17      A    C
ATOM   1181  O   ILE A 272      42.602  49.512  12.431  1.00  82.69      A    O
ATOM   1182  N   ALA A 273      43.253  47.787  13.709  1.00  85.70      A    N
ATOM   1183  CA  ALA A 273      42.604  48.317  14.902  1.00  90.36      A    C
ATOM   1184  CB  ALA A 273      41.333  47.527  15.184  1.00  90.04      A    C
ATOM   1185  C   ALA A 273      43.536  48.255  16.114  1.00  93.56      A    C
ATOM   1186  O   ALA A 273      43.527  47.269  16.855  1.00  94.38      A    O
ATOM   1187  N   ASP A 274      44.334  49.303  16.323  1.00  95.36      A    N
ATOM   1188  CA  ASP A 274      45.257  49.316  17.453  1.00  94.75      A    C
ATOM   1189  CB  ASP A 274      46.638  49.750  17.024  1.00  94.28      A    C
ATOM   1190  CG  ASP A 274      47.281  48.762  16.091  1.00  96.71      A    C
ATOM   1191  OD1 ASP A 274      48.441  48.991  15.678  1.00  96.24      A    O
ATOM   1192  OD2 ASP A 274      46.620  47.749  15.767  1.00  97.76      A    O
ATOM   1193  C   ASP A 274      44.817  50.211  18.561  1.00  94.31      A    C
ATOM   1194  O   ASP A 274      44.949  51.434  18.460  1.00  93.97      A    O
ATOM   1195  N   PHE A 275      44.295  49.574  19.617  1.00  80.18      A    N
ATOM   1196  CA  PHE A 275      43.788  50.239  20.853  1.00  80.18      A    C
ATOM   1197  CB  PHE A 275      42.245  50.439  20.775  1.00  80.18      A    C
ATOM   1198  CG  PHE A 275      41.758  50.973  19.439  1.00  80.18      A    C
ATOM   1199  CD1 PHE A 275      41.601  50.110  18.338  1.00  80.18      A    C
ATOM   1200  CD2 PHE A 275      41.522  52.349  19.260  1.00  80.18      A    C
ATOM   1201  CE1 PHE A 275      41.216  50.607  17.072  1.00  80.18      A    C
ATOM   1202  CE2 PHE A 275      41.135  52.862  17.996  1.00  80.18      A    C
ATOM   1203  CZ  PHE A 275      40.987  51.982  16.899  1.00  80.18      A    C
ATOM   1204  C   PHE A 275      44.145  49.478  22.193  1.00  80.19      A    C
ATOM   1205  O   PHE A 275      45.065  48.626  22.227  1.00  80.17      A    O
ATOM   1206  N   GLY A 276      43.430  49.795  23.284  1.00  80.17      A    N
ATOM   1207  CA  GLY A 276      43.683  49.135  24.567  1.00  80.19      A    C
ATOM   1208  C   GLY A 276      43.212  47.678  24.638  1.00  80.18      A    C
ATOM   1209  O   GLY A 276      44.043  46.763  24.805  1.00  80.18      A    O
ATOM   1210  N   TRP A 277      41.885  47.482  24.546  1.00  80.18      A    N
ATOM   1211  CA  TRP A 277      41.212  46.160  24.552  1.00  80.19      A    C
ATOM   1212  CB  TRP A 277      41.903  45.220  23.566  1.00  80.19      A    C
ATOM   1213  CG  TRP A 277      41.011  44.873  22.467  1.00  80.19      A    C
```

Figure 4T

| ATOM | 1214 | CD2 | TRP A 277 | 41.129 | 45.318 | 21.106 | 1.00 | 80.18 | A | C |
|---|---|---|---|---|---|---|---|---|---|---|
| ATOM | 1215 | CE2 | TRP A 277 | 39.970 | 44.862 | 20.417 | 1.00 | 80.18 | A | C |
| ATOM | 1216 | CE3 | TRP A 277 | 42.101 | 46.069 | 20.396 | 1.00 | 80.18 | A | C |
| ATOM | 1217 | CD1 | TRP A 277 | 39.830 | 44.178 | 22.554 | 1.00 | 80.18 | A | C |
| ATOM | 1218 | NE1 | TRP A 277 | 39.197 | 44.174 | 21.327 | 1.00 | 80.18 | A | N |
| ATOM | 1219 | CZ2 | TRP A 277 | 39.753 | 45.134 | 19.034 | 1.00 | 80.18 | A | C |
| ATOM | 1220 | CZ3 | TRP A 277 | 41.887 | 46.345 | 19.018 | 1.00 | 80.18 | A | C |
| ATOM | 1221 | CH2 | TRP A 277 | 40.721 | 45.875 | 18.358 | 1.00 | 80.19 | A | C |
| ATOM | 1222 | C | TRP A 277 | 40.945 | 45.341 | 25.834 | 1.00 | 80.19 | A | C |
| ATOM | 1223 | O | TRP A 277 | 40.039 | 45.667 | 26.622 | 1.00 | 80.18 | A | O |
| ATOM | 1224 | N | SER A 278 | 41.702 | 44.234 | 25.970 | 1.00 | 80.18 | A | N |
| ATOM | 1225 | CA | SER A 278 | 41.623 | 43.278 | 27.102 | 1.00 | 80.19 | A | C |
| ATOM | 1226 | CB | SER A 278 | 40.443 | 42.280 | 26.891 | 1.00 | 80.19 | A | C |
| ATOM | 1227 | OG | SER A 278 | 40.430 | 41.668 | 25.587 | 1.00 | 80.18 | A | O |
| ATOM | 1228 | C | SER A 278 | 42.939 | 42.492 | 27.344 | 1.00 | 80.18 | A | C |
| ATOM | 1229 | O | SER A 278 | 43.921 | 42.601 | 26.591 | 1.00 | 80.19 | A | O |
| ATOM | 1230 | N | LEU A 289 | 51.160 | 29.641 | 23.909 | 1.00 | 91.98 | A | N |
| ATOM | 1231 | CA | LEU A 289 | 51.175 | 30.617 | 22.828 | 1.00 | 95.69 | A | C |
| ATOM | 1232 | CB | LEU A 289 | 49.776 | 31.212 | 22.620 | 1.00 | 93.34 | A | C |
| ATOM | 1236 | C | LEU A 289 | 52.161 | 31.735 | 23.145 | 1.00 | 98.98 | A | C |
| ATOM | 1237 | O | LEU A 289 | 51.884 | 32.604 | 23.988 | 1.00 | 97.51 | A | O |
| ATOM | 1238 | N | CYS A 290 | 53.316 | 31.702 | 22.473 | 1.00 | 103.16 | A | N |
| ATOM | 1239 | CA | CYS A 290 | 54.365 | 32.716 | 22.655 | 1.00 | 104.77 | A | C |
| ATOM | 1240 | CB | CYS A 290 | 55.750 | 32.135 | 22.327 | 1.00 | 103.06 | A | C |
| ATOM | 1242 | C | CYS A 290 | 54.063 | 33.893 | 21.730 | 1.00 | 106.10 | A | C |
| ATOM | 1243 | O | CYS A 290 | 54.973 | 34.581 | 21.251 | 1.00 | 106.69 | A | O |
| ATOM | 1244 | N | GLY A 291 | 52.767 | 34.101 | 21.488 | 1.00 | 106.60 | A | N |
| ATOM | 1245 | CA | GLY A 291 | 52.301 | 35.178 | 20.630 | 1.00 | 103.83 | A | C |
| ATOM | 1246 | C | GLY A 291 | 52.674 | 36.555 | 21.142 | 1.00 | 101.87 | A | C |
| ATOM | 1247 | O | GLY A 291 | 52.645 | 37.535 | 20.388 | 1.00 | 99.74 | A | O |
| ATOM | 1248 | N | THR A 292 | 53.017 | 36.621 | 22.429 | 1.00 | 100.88 | A | N |
| ATOM | 1249 | CA | THR A 292 | 53.433 | 37.866 | 23.070 | 1.00 | 98.35 | A | C |
| ATOM | 1250 | CB | THR A 292 | 53.746 | 37.608 | 24.584 | 1.00 | 98.64 | A | C |
| ATOM | 1251 | OG1 | THR A 292 | 52.681 | 36.840 | 25.163 | 1.00 | 95.90 | A | O |
| ATOM | 1252 | CG2 | THR A 292 | 53.872 | 38.919 | 25.354 | 1.00 | 97.26 | A | C |
| ATOM | 1253 | C | THR A 292 | 54.682 | 38.418 | 22.325 | 1.00 | 95.62 | A | C |
| ATOM | 1254 | O | THR A 292 | 54.658 | 39.529 | 21.776 | 1.00 | 93.74 | A | O |
| ATOM | 1255 | N | LEU A 293 | 55.757 | 37.633 | 22.293 | 1.00 | 90.33 | A | N |
| ATOM | 1256 | CA | LEU A 293 | 56.976 | 38.032 | 21.606 | 1.00 | 84.73 | A | C |
| ATOM | 1257 | CB | LEU A 293 | 58.146 | 37.209 | 22.112 | 1.00 | 83.59 | A | C |
| ATOM | 1258 | CG | LEU A 293 | 58.623 | 37.507 | 23.519 | 1.00 | 85.32 | A | C |
| ATOM | 1259 | CD1 | LEU A 293 | 59.534 | 36.398 | 24.008 | 1.00 | 87.94 | A | C |
| ATOM | 1260 | CD2 | LEU A 293 | 59.345 | 38.832 | 23.510 | 1.00 | 83.42 | A | C |
| ATOM | 1261 | C | LEU A 293 | 56.838 | 37.804 | 20.108 | 1.00 | 81.88 | A | C |
| ATOM | 1262 | O | LEU A 293 | 57.289 | 38.604 | 19.299 | 1.00 | 81.32 | A | O |
| ATOM | 1263 | N | ASP A 294 | 56.207 | 36.696 | 19.757 | 1.00 | 79.52 | A | N |
| ATOM | 1264 | CA | ASP A 294 | 56.027 | 36.309 | 18.381 | 1.00 | 77.99 | A | C |
| ATOM | 1265 | CB | ASP A 294 | 54.721 | 35.570 | 18.228 | 1.00 | 79.09 | A | C |
| ATOM | 1266 | CG | ASP A 294 | 54.879 | 34.096 | 18.487 | 1.00 | 80.00 | A | C |
| ATOM | 1267 | OD1 | ASP A 294 | 53.849 | 33.393 | 18.606 | 1.00 | 82.79 | A | O |
| ATOM | 1268 | OD2 | ASP A 294 | 56.045 | 33.645 | 18.562 | 1.00 | 75.58 | A | O |
| ATOM | 1269 | C | ASP A 294 | 56.107 | 37.384 | 17.353 | 1.00 | 77.27 | A | C |
| ATOM | 1270 | O | ASP A 294 | 56.602 | 37.135 | 16.261 | 1.00 | 77.40 | A | O |
| ATOM | 1271 | N | TYR A 295 | 55.644 | 38.578 | 17.683 | 1.00 | 76.56 | A | N |
| ATOM | 1272 | CA | TYR A 295 | 55.688 | 39.637 | 16.701 | 1.00 | 80.01 | A | C |
| ATOM | 1273 | CB | TYR A 295 | 54.291 | 40.207 | 16.540 | 1.00 | 84.15 | A | C |
| ATOM | 1274 | CG | TYR A 295 | 53.456 | 39.290 | 15.692 | 1.00 | 89.76 | A | C |
| ATOM | 1275 | CD1 | TYR A 295 | 53.024 | 38.061 | 16.190 | 1.00 | 89.96 | A | C |
| ATOM | 1276 | CE1 | TYR A 295 | 52.383 | 37.145 | 15.365 | 1.00 | 92.84 | A | C |
| ATOM | 1277 | CD2 | TYR A 295 | 53.213 | 39.587 | 14.341 | 1.00 | 92.30 | A | C |
| ATOM | 1278 | CE2 | TYR A 295 | 52.575 | 38.679 | 13.510 | 1.00 | 93.08 | A | C |

Figure 4U

| ATOM | 1279 | CZ | TYR | A | 295 | 52.169 | 37.460 | 14.031 | 1.00 | 94.56 | A | C |
|---|---|---|---|---|---|---|---|---|---|---|---|---|
| ATOM | 1280 | OH | TYR | A | 295 | 51.583 | 36.539 | 13.210 | 1.00 | 98.62 | A | O |
| ATOM | 1281 | C | TYR | A | 295 | 56.699 | 40.753 | 16.875 | 1.00 | 80.02 | A | C |
| ATOM | 1282 | O | TYR | A | 295 | 57.086 | 41.417 | 15.911 | 1.00 | 78.60 | A | O |
| ATOM | 1283 | N | LEU | A | 296 | 57.145 | 40.945 | 18.102 | 1.00 | 82.28 | A | N |
| ATOM | 1284 | CA | LEU | A | 296 | 58.099 | 41.995 | 18.404 | 1.00 | 81.54 | A | C |
| ATOM | 1285 | CB | LEU | A | 296 | 58.348 | 42.001 | 19.917 | 1.00 | 83.52 | A | C |
| ATOM | 1286 | CG | LEU | A | 296 | 57.067 | 41.911 | 20.773 | 1.00 | 84.63 | A | C |
| ATOM | 1287 | CD1 | LEU | A | 296 | 57.382 | 41.633 | 22.243 | 1.00 | 84.58 | A | C |
| ATOM | 1288 | CD2 | LEU | A | 296 | 56.294 | 43.202 | 20.634 | 1.00 | 86.07 | A | C |
| ATOM | 1289 | C | LEU | A | 296 | 59.418 | 41.840 | 17.631 | 1.00 | 81.11 | A | C |
| ATOM | 1290 | O | LEU | A | 296 | 59.843 | 40.727 | 17.312 | 1.00 | 79.86 | A | O |
| ATOM | 1291 | N | PRO | A | 297 | 60.058 | 42.970 | 17.289 | 1.00 | 80.13 | A | N |
| ATOM | 1292 | CD | PRO | A | 297 | 59.451 | 44.308 | 17.260 | 1.00 | 80.77 | A | C |
| ATOM | 1293 | CA | PRO | A | 297 | 61.324 | 42.995 | 16.563 | 1.00 | 76.50 | A | C |
| ATOM | 1294 | CB | PRO | A | 297 | 61.190 | 44.234 | 15.710 | 1.00 | 75.65 | A | C |
| ATOM | 1295 | CG | PRO | A | 297 | 60.564 | 45.155 | 16.661 | 1.00 | 79.46 | A | C |
| ATOM | 1296 | C | PRO | A | 297 | 62.498 | 43.099 | 17.545 | 1.00 | 74.40 | A | C |
| ATOM | 1297 | O | PRO | A | 297 | 62.374 | 43.668 | 18.641 | 1.00 | 69.70 | A | O |
| ATOM | 1298 | N | PRO | A | 298 | 63.659 | 42.554 | 17.150 | 1.00 | 72.29 | A | N |
| ATOM | 1299 | CD | PRO | A | 298 | 63.953 | 41.933 | 15.841 | 1.00 | 70.95 | A | C |
| ATOM | 1300 | CA | PRO | A | 298 | 64.854 | 42.573 | 17.982 | 1.00 | 68.01 | A | C |
| ATOM | 1301 | CB | PRO | A | 298 | 65.953 | 42.233 | 16.989 | 1.00 | 70.34 | A | C |
| ATOM | 1302 | CG | PRO | A | 298 | 65.268 | 41.228 | 16.095 | 1.00 | 69.45 | A | C |
| ATOM | 1303 | C | PRO | A | 298 | 65.066 | 43.895 | 18.678 | 1.00 | 64.87 | A | C |
| ATOM | 1304 | O | PRO | A | 298 | 65.144 | 43.965 | 19.889 | 1.00 | 61.59 | A | O |
| ATOM | 1305 | N | GLU | A | 299 | 65.138 | 44.957 | 17.912 | 1.00 | 64.86 | A | N |
| ATOM | 1306 | CA | GLU | A | 299 | 65.355 | 46.241 | 18.516 | 1.00 | 68.46 | A | C |
| ATOM | 1307 | CB | GLU | A | 299 | 65.241 | 47.334 | 17.455 | 1.00 | 73.05 | A | C |
| ATOM | 1308 | CG | GLU | A | 299 | 63.995 | 47.281 | 16.542 | 1.00 | 80.25 | A | C |
| ATOM | 1309 | CD | GLU | A | 299 | 64.227 | 46.502 | 15.242 | 1.00 | 82.05 | A | C |
| ATOM | 1310 | OE1 | GLU | A | 299 | 63.593 | 46.813 | 14.204 | 1.00 | 80.07 | A | O |
| ATOM | 1311 | OE2 | GLU | A | 299 | 65.047 | 45.566 | 15.259 | 1.00 | 86.62 | A | O |
| ATOM | 1312 | C | GLU | A | 299 | 64.449 | 46.557 | 19.707 | 1.00 | 69.06 | A | C |
| ATOM | 1313 | O | GLU | A | 299 | 64.823 | 47.348 | 20.568 | 1.00 | 67.71 | A | O |
| ATOM | 1314 | N | MET | A | 300 | 63.268 | 45.953 | 19.787 | 1.00 | 72.06 | A | N |
| ATOM | 1315 | CA | MET | A | 300 | 62.408 | 46.269 | 20.924 | 1.00 | 76.56 | A | C |
| ATOM | 1316 | CB | MET | A | 300 | 60.933 | 46.348 | 20.502 | 1.00 | 83.02 | A | C |
| ATOM | 1317 | CG | MET | A | 300 | 60.053 | 47.203 | 21.469 | 1.00 | 93.18 | A | C |
| ATOM | 1318 | SD | MET | A | 300 | 58.715 | 46.384 | 22.483 | 1.00 | 103.55 | A | S |
| ATOM | 1319 | CE | MET | A | 300 | 59.475 | 46.110 | 24.098 | 1.00 | 99.95 | A | C |
| ATOM | 1320 | C | MET | A | 300 | 62.559 | 45.284 | 22.080 | 1.00 | 74.61 | A | C |
| ATOM | 1321 | O | MET | A | 300 | 62.724 | 45.682 | 23.236 | 1.00 | 73.66 | A | O |
| ATOM | 1322 | N | ILE | A | 301 | 62.497 | 44.000 | 21.777 | 1.00 | 72.18 | A | N |
| ATOM | 1323 | CA | ILE | A | 301 | 62.631 | 43.009 | 22.824 | 1.00 | 72.56 | A | C |
| ATOM | 1324 | CB | ILE | A | 301 | 62.549 | 41.624 | 22.237 | 1.00 | 71.85 | A | C |
| ATOM | 1325 | CG2 | ILE | A | 301 | 61.387 | 41.565 | 21.291 | 1.00 | 73.11 | A | C |
| ATOM | 1326 | CG1 | ILE | A | 301 | 63.821 | 41.318 | 21.449 | 1.00 | 73.91 | A | C |
| ATOM | 1327 | CD1 | ILE | A | 301 | 63.873 | 39.922 | 20.845 | 1.00 | 71.55 | A | C |
| ATOM | 1328 | C | ILE | A | 301 | 63.967 | 43.171 | 23.540 | 1.00 | 74.53 | A | C |
| ATOM | 1329 | O | ILE | A | 301 | 64.081 | 42.851 | 24.720 | 1.00 | 73.44 | A | O |
| ATOM | 1330 | N | GLU | A | 302 | 64.969 | 43.658 | 22.803 | 1.00 | 79.91 | A | N |
| ATOM | 1331 | CA | GLU | A | 302 | 66.324 | 43.892 | 23.325 | 1.00 | 86.02 | A | C |
| ATOM | 1332 | CB | GLU | A | 302 | 67.370 | 43.936 | 22.186 | 1.00 | 85.05 | A | C |
| ATOM | 1333 | CG | GLU | A | 302 | 67.502 | 42.655 | 21.334 | 1.00 | 88.94 | A | C |
| ATOM | 1334 | CD | GLU | A | 302 | 68.565 | 42.751 | 20.214 | 1.00 | 87.29 | A | C |
| ATOM | 1335 | OE1 | GLU | A | 302 | 68.589 | 43.779 | 19.496 | 1.00 | 84.07 | A | O |
| ATOM | 1336 | OE2 | GLU | A | 302 | 69.363 | 41.791 | 20.042 | 1.00 | 88.65 | A | O |
| ATOM | 1337 | C | GLU | A | 302 | 66.351 | 45.233 | 24.074 | 1.00 | 91.02 | A | C |
| ATOM | 1338 | O | GLU | A | 302 | 67.412 | 45.692 | 24.530 | 1.00 | 90.32 | A | O |
| ATOM | 1339 | N | GLY | A | 303 | 65.175 | 45.857 | 24.178 | 1.00 | 95.75 | A | N |

Figure 4V

| ATOM | 1340 | CA | GLY A 303 | 65.041 | 47.124 | 24.873 | 1.00 | 97.96 | A | C |
|---|---|---|---|---|---|---|---|---|---|---|
| ATOM | 1341 | C | GLY A 303 | 65.794 | 48.256 | 24.223 | 1.00 | 101.02 | A | C |
| ATOM | 1342 | O | GLY A 303 | 65.876 | 49.340 | 24.762 | 1.00 | 99.37 | A | O |
| ATOM | 1343 | N | ARG A 304 | 66.350 | 48.015 | 23.052 | 1.00 | 105.96 | A | N |
| ATOM | 1344 | CA | ARG A 304 | 67.096 | 49.054 | 22.371 | 1.00 | 112.23 | A | C |
| ATOM | 1345 | CB | ARG A 304 | 67.909 | 48.438 | 21.226 | 1.00 | 114.86 | A | C |
| ATOM | 1346 | CG | ARG A 304 | 68.981 | 47.440 | 21.707 | 1.00 | 120.66 | A | C |
| ATOM | 1347 | CD | ARG A 304 | 69.629 | 46.633 | 20.555 | 1.00 | 125.80 | A | C |
| ATOM | 1348 | NE | ARG A 304 | 70.172 | 47.477 | 19.490 | 1.00 | 131.93 | A | N |
| ATOM | 1349 | CZ | ARG A 304 | 71.023 | 48.482 | 19.693 | 1.00 | 137.20 | A | C |
| ATOM | 1350 | NH1 | ARG A 304 | 71.437 | 48.774 | 20.932 | 1.00 | 140.05 | A | N |
| ATOM | 1351 | NH2 | ARG A 304 | 71.451 | 49.209 | 18.660 | 1.00 | 139.00 | A | N |
| ATOM | 1352 | C | ARG A 304 | 66.141 | 50.115 | 21.849 | 1.00 | 115.07 | A | C |
| ATOM | 1353 | O | ARG A 304 | 64.948 | 50.100 | 22.166 | 1.00 | 113.97 | A | O |
| ATOM | 1354 | N | MET A 305 | 66.683 | 51.033 | 21.053 | 1.00 | 120.70 | A | N |
| ATOM | 1355 | CA | MET A 305 | 65.915 | 52.128 | 20.454 | 1.00 | 126.96 | A | C |
| ATOM | 1356 | CB | MET A 305 | 66.803 | 53.360 | 20.165 | 1.00 | 133.41 | A | C |
| ATOM | 1357 | CG | MET A 305 | 67.985 | 53.615 | 21.131 | 1.00 | 140.92 | A | C |
| ATOM | 1358 | SD | MET A 305 | 69.402 | 52.352 | 21.129 | 1.00 | 150.00 | A | S |
| ATOM | 1359 | CE | MET A 305 | 69.892 | 52.292 | 19.331 | 1.00 | 150.00 | A | C |
| ATOM | 1360 | C | MET A 305 | 65.298 | 51.670 | 19.129 | 1.00 | 127.16 | A | C |
| ATOM | 1361 | O | MET A 305 | 66.004 | 51.253 | 18.196 | 1.00 | 128.67 | A | O |
| ATOM | 1362 | N | HIS A 306 | 63.980 | 51.770 | 19.047 | 1.00 | 127.09 | A | N |
| ATOM | 1363 | CA | HIS A 306 | 63.252 | 51.379 | 17.851 | 1.00 | 126.89 | A | C |
| ATOM | 1364 | CB | HIS A 306 | 62.156 | 50.365 | 18.262 | 1.00 | 133.59 | A | C |
| ATOM | 1365 | CG | HIS A 306 | 61.138 | 50.914 | 19.233 | 1.00 | 140.10 | A | C |
| ATOM | 1366 | CD2 | HIS A 306 | 59.800 | 51.113 | 19.102 | 1.00 | 142.87 | A | C |
| ATOM | 1367 | ND1 | HIS A 306 | 61.466 | 51.373 | 20.496 | 1.00 | 141.79 | A | N |
| ATOM | 1368 | CE1 | HIS A 306 | 60.378 | 51.833 | 21.095 | 1.00 | 142.27 | A | C |
| ATOM | 1369 | NE2 | HIS A 306 | 59.353 | 51.687 | 20.271 | 1.00 | 143.92 | A | N |
| ATOM | 1370 | C | HIS A 306 | 62.637 | 52.664 | 17.243 | 1.00 | 123.55 | A | C |
| ATOM | 1371 | O | HIS A 306 | 62.684 | 53.731 | 17.877 | 1.00 | 124.15 | A | O |
| ATOM | 1372 | N | ASP A 307 | 62.106 | 52.575 | 16.018 | 1.00 | 116.91 | A | N |
| ATOM | 1373 | CA | ASP A 307 | 61.419 | 53.699 | 15.379 | 1.00 | 107.68 | A | C |
| ATOM | 1374 | CB | ASP A 307 | 62.165 | 55.023 | 15.598 | 1.00 | 108.47 | A | C |
| ATOM | 1375 | CG | ASP A 307 | 61.353 | 56.029 | 16.464 | 1.00 | 111.28 | A | C |
| ATOM | 1376 | OD1 | ASP A 307 | 61.072 | 55.750 | 17.657 | 1.00 | 110.33 | A | O |
| ATOM | 1377 | OD2 | ASP A 307 | 60.985 | 57.110 | 15.949 | 1.00 | 111.11 | A | O |
| ATOM | 1378 | C | ASP A 307 | 61.162 | 53.492 | 13.907 | 1.00 | 101.08 | A | C |
| ATOM | 1379 | O | ASP A 307 | 62.101 | 53.352 | 13.127 | 1.00 | 101.13 | A | O |
| ATOM | 1380 | N | GLU A 308 | 59.875 | 53.443 | 13.553 | 1.00 | 94.88 | A | N |
| ATOM | 1381 | CA | GLU A 308 | 59.417 | 53.286 | 12.169 | 1.00 | 90.59 | A | C |
| ATOM | 1382 | CB | GLU A 308 | 59.888 | 54.510 | 11.380 | 1.00 | 91.73 | A | C |
| ATOM | 1383 | CG | GLU A 308 | 60.630 | 54.228 | 10.101 | 1.00 | 96.57 | A | C |
| ATOM | 1384 | CD | GLU A 308 | 61.568 | 55.368 | 9.716 | 1.00 | 98.44 | A | C |
| ATOM | 1385 | OE1 | GLU A 308 | 62.544 | 55.636 | 10.454 | 1.00 | 95.55 | A | O |
| ATOM | 1386 | OE2 | GLU A 308 | 61.330 | 56.003 | 8.670 | 1.00 | 103.60 | A | O |
| ATOM | 1387 | C | GLU A 308 | 59.789 | 51.975 | 11.439 | 1.00 | 85.52 | A | C |
| ATOM | 1388 | O | GLU A 308 | 58.916 | 51.245 | 10.957 | 1.00 | 84.71 | A | O |
| ATOM | 1389 | N | LYS A 309 | 61.081 | 51.682 | 11.358 | 1.00 | 79.53 | A | N |
| ATOM | 1390 | CA | LYS A 309 | 61.539 | 50.487 | 10.694 | 1.00 | 71.62 | A | C |
| ATOM | 1391 | CB | LYS A 309 | 63.025 | 50.303 | 10.977 | 1.00 | 71.18 | A | C |
| ATOM | 1396 | C | LYS A 309 | 60.746 | 49.278 | 11.174 | 1.00 | 67.62 | A | C |
| ATOM | 1397 | O | LYS A 309 | 60.363 | 48.420 | 10.395 | 1.00 | 67.83 | A | O |
| ATOM | 1398 | N | VAL A 310 | 60.478 | 49.230 | 12.463 | 1.00 | 62.80 | A | N |
| ATOM | 1399 | CA | VAL A 310 | 59.753 | 48.119 | 13.052 | 1.00 | 62.03 | A | C |
| ATOM | 1400 | CB | VAL A 310 | 59.240 | 48.508 | 14.407 | 1.00 | 59.23 | A | C |
| ATOM | 1401 | CG1 | VAL A 310 | 60.398 | 48.910 | 15.291 | 1.00 | 61.76 | A | C |
| ATOM | 1402 | CG2 | VAL A 310 | 58.262 | 49.647 | 14.265 | 1.00 | 57.08 | A | C |
| ATOM | 1403 | C | VAL A 310 | 58.576 | 47.570 | 12.267 | 1.00 | 62.27 | A | C |
| ATOM | 1404 | O | VAL A 310 | 58.380 | 46.356 | 12.176 | 1.00 | 62.69 | A | O |

Figure 4W

```
ATOM   1405  N    ASP A 311      57.783  48.460  11.701  1.00  62.41      A    N
ATOM   1406  CA   ASP A 311      56.614  48.026  10.970  1.00  66.15      A    C
ATOM   1407  CB   ASP A 311      55.834  49.231  10.495  1.00  70.56      A    C
ATOM   1408  CG   ASP A 311      55.203  49.974  11.642  1.00  78.33      A    C
ATOM   1409  OD1  ASP A 311      54.604  49.295  12.515  1.00  81.15      A    O
ATOM   1410  OD2  ASP A 311      55.302  51.220  11.674  1.00  81.93      A    O
ATOM   1411  C    ASP A 311      56.909  47.111   9.819  1.00  65.13      A    C
ATOM   1412  O    ASP A 311      56.112  46.239   9.491  1.00  65.71      A    O
ATOM   1413  N    LEU A 312      58.061  47.302   9.203  1.00  67.42      A    N
ATOM   1414  CA   LEU A 312      58.446  46.462   8.081  1.00  70.14      A    C
ATOM   1415  CB   LEU A 312      59.689  47.050   7.398  1.00  71.43      A    C
ATOM   1416  CG   LEU A 312      59.587  48.404   6.654  1.00  70.53      A    C
ATOM   1417  CD1  LEU A 312      58.737  48.278   5.389  1.00  69.99      A    C
ATOM   1418  CD2  LEU A 312      59.011  49.466   7.578  1.00  70.24      A    C
ATOM   1419  C    LEU A 312      58.711  45.039   8.586  1.00  69.19      A    C
ATOM   1420  O    LEU A 312      58.462  44.047   7.890  1.00  68.91      A    O
ATOM   1421  N    TRP A 313      59.198  44.957   9.820  1.00  65.94      A    N
ATOM   1422  CA   TRP A 313      59.497  43.685  10.454  1.00  63.75      A    C
ATOM   1423  CB   TRP A 313      60.282  43.905  11.736  1.00  69.81      A    C
ATOM   1424  CG   TRP A 313      60.358  42.697  12.588  1.00  71.86      A    C
ATOM   1425  CD2  TRP A 313      61.434  41.767  12.636  1.00  70.53      A    C
ATOM   1426  CE2  TRP A 313      61.069  40.751  13.548  1.00  70.88      A    C
ATOM   1427  CE3  TRP A 313      62.677  41.691  11.996  1.00  68.84      A    C
ATOM   1428  CD1  TRP A 313      59.404  42.229  13.448  1.00  72.58      A    C
ATOM   1429  NE1  TRP A 313      59.824  41.057  14.032  1.00  71.89      A    N
ATOM   1430  CZ2  TRP A 313      61.902  39.673  13.832  1.00  68.34      A    C
ATOM   1431  CZ3  TRP A 313      63.503  40.623  12.280  1.00  67.31      A    C
ATOM   1432  CH2  TRP A 313      63.113  39.626  13.189  1.00  68.13      A    C
ATOM   1433  C    TRP A 313      58.205  43.016  10.787  1.00  60.84      A    C
ATOM   1434  O    TRP A 313      57.972  41.872  10.429  1.00  59.96      A    O
ATOM   1435  N    SER A 314      57.373  43.733  11.514  1.00  59.53      A    N
ATOM   1436  CA   SER A 314      56.092  43.191  11.862  1.00  63.39      A    C
ATOM   1437  CB   SER A 314      55.218  44.268  12.490  1.00  63.41      A    C
ATOM   1439  C    SER A 314      55.497  42.743  10.539  1.00  66.14      A    C
ATOM   1440  O    SER A 314      54.939  41.656  10.435  1.00  69.63      A    O
ATOM   1441  N    LEU A 315      55.646  43.580   9.518  1.00  66.11      A    N
ATOM   1442  CA   LEU A 315      55.111  43.276   8.194  1.00  66.22      A    C
ATOM   1443  CB   LEU A 315      55.370  44.438   7.238  1.00  68.82      A    C
ATOM   1444  CG   LEU A 315      54.716  44.329   5.860  1.00  73.34      A    C
ATOM   1445  CD1  LEU A 315      53.206  44.295   6.005  1.00  74.73      A    C
ATOM   1446  CD2  LEU A 315      55.127  45.506   5.003  1.00  75.61      A    C
ATOM   1447  C    LEU A 315      55.743  42.009   7.652  1.00  63.01      A    C
ATOM   1448  O    LEU A 315      55.144  41.274   6.869  1.00  61.40      A    O
ATOM   1449  N    GLY A 316      56.969  41.759   8.076  1.00  62.54      A    N
ATOM   1450  CA   GLY A 316      57.637  40.556   7.638  1.00  63.17      A    C
ATOM   1451  C    GLY A 316      56.933  39.346   8.226  1.00  62.44      A    C
ATOM   1452  O    GLY A 316      56.319  38.553   7.509  1.00  66.48      A    O
ATOM   1453  N    VAL A 317      57.005  39.205   9.543  1.00  58.54      A    N
ATOM   1454  CA   VAL A 317      56.375  38.082  10.210  1.00  57.24      A    C
ATOM   1455  CB   VAL A 317      56.160  38.386  11.688  1.00  57.91      A    C
ATOM   1456  CG1  VAL A 317      55.630  37.149  12.385  1.00  63.70      A    C
ATOM   1457  CG2  VAL A 317      57.455  38.879  12.316  1.00  54.44      A    C
ATOM   1458  C    VAL A 317      55.022  37.771   9.588  1.00  58.00      A    C
ATOM   1459  O    VAL A 317      54.786  36.681   9.072  1.00  61.25      A    O
ATOM   1460  N    LEU A 318      54.142  38.758   9.636  1.00  55.23      A    N
ATOM   1461  CA   LEU A 318      52.798  38.642   9.115  1.00  54.58      A    C
ATOM   1462  CB   LEU A 318      52.217  40.033   8.973  1.00  60.38      A    C
ATOM   1463  CG   LEU A 318      50.715  40.158   9.174  1.00  72.66      A    C
ATOM   1464  CD1  LEU A 318      50.247  39.363  10.408  1.00  74.60      A    C
ATOM   1465  CD2  LEU A 318      50.392  41.635   9.331  1.00  72.45      A    C
ATOM   1466  C    LEU A 318      52.752  37.931   7.786  1.00  51.19      A    C
```

Figure 4X

| ATOM | 1467 | O | LEU | A | 318 | 52.196 | 36.851 | 7.648 | 1.00 | 52.65 | A | O |
|---|---|---|---|---|---|---|---|---|---|---|---|---|
| ATOM | 1468 | N | CYS | A | 319 | 53.343 | 38.551 | 6.792 | 1.00 | 47.74 | A | N |
| ATOM | 1469 | CA | CYS | A | 319 | 53.348 | 37.948 | 5.496 | 1.00 | 48.42 | A | C |
| ATOM | 1470 | CB | CYS | A | 319 | 54.330 | 38.660 | 4.602 | 1.00 | 51.03 | A | C |
| ATOM | 1471 | SG | CYS | A | 319 | 54.602 | 37.776 | 3.086 | 1.00 | 61.23 | A | S |
| ATOM | 1472 | C | CYS | A | 319 | 53.744 | 36.502 | 5.615 | 1.00 | 47.44 | A | C |
| ATOM | 1473 | O | CYS | A | 319 | 53.332 | 35.670 | 4.832 | 1.00 | 45.04 | A | O |
| ATOM | 1474 | N | TYR | A | 320 | 54.554 | 36.202 | 6.605 | 1.00 | 50.53 | A | N |
| ATOM | 1475 | CA | TYR | A | 320 | 54.982 | 34.846 | 6.780 | 1.00 | 57.47 | A | C |
| ATOM | 1476 | CB | TYR | A | 320 | 56.153 | 34.787 | 7.717 | 1.00 | 59.47 | A | C |
| ATOM | 1477 | CG | TYR | A | 320 | 56.644 | 33.393 | 7.958 | 1.00 | 64.22 | A | C |
| ATOM | 1478 | CD1 | TYR | A | 320 | 57.706 | 32.886 | 7.233 | 1.00 | 65.78 | A | C |
| ATOM | 1479 | CE1 | TYR | A | 320 | 58.219 | 31.618 | 7.478 | 1.00 | 66.03 | A | C |
| ATOM | 1480 | CD2 | TYR | A | 320 | 56.081 | 32.590 | 8.941 | 1.00 | 67.36 | A | C |
| ATOM | 1481 | CE2 | TYR | A | 320 | 56.583 | 31.311 | 9.195 | 1.00 | 69.47 | A | C |
| ATOM | 1482 | CZ | TYR | A | 320 | 57.665 | 30.834 | 8.456 | 1.00 | 67.05 | A | C |
| ATOM | 1483 | OH | TYR | A | 320 | 58.235 | 29.600 | 8.717 | 1.00 | 66.22 | A | O |
| ATOM | 1484 | C | TYR | A | 320 | 53.879 | 33.997 | 7.355 | 1.00 | 62.98 | A | C |
| ATOM | 1485 | O | TYR | A | 320 | 53.491 | 33.012 | 6.756 | 1.00 | 66.11 | A | O |
| ATOM | 1486 | N | GLU | A | 321 | 53.381 | 34.360 | 8.532 | 1.00 | 65.81 | A | N |
| ATOM | 1487 | CA | GLU | A | 321 | 52.330 | 33.567 | 9.161 | 1.00 | 67.09 | A | C |
| ATOM | 1488 | CB | GLU | A | 321 | 51.771 | 34.252 | 10.419 | 1.00 | 70.57 | A | C |
| ATOM | 1489 | CG | GLU | A | 321 | 51.379 | 33.237 | 11.505 | 1.00 | 79.40 | A | C |
| ATOM | 1490 | CD | GLU | A | 321 | 50.300 | 33.690 | 12.504 | 1.00 | 82.26 | A | C |
| ATOM | 1491 | OE1 | GLU | A | 321 | 50.437 | 34.761 | 13.122 | 1.00 | 79.01 | A | O |
| ATOM | 1492 | OE2 | GLU | A | 321 | 49.312 | 32.941 | 12.694 | 1.00 | 84.31 | A | O |
| ATOM | 1493 | C | GLU | A | 321 | 51.214 | 33.380 | 8.156 | 1.00 | 66.48 | A | C |
| ATOM | 1494 | O | GLU | A | 321 | 50.558 | 32.345 | 8.108 | 1.00 | 63.93 | A | O |
| ATOM | 1495 | N | PHE | A | 322 | 51.002 | 34.393 | 7.341 | 1.00 | 65.78 | A | N |
| ATOM | 1496 | CA | PHE | A | 322 | 49.966 | 34.297 | 6.352 | 1.00 | 67.34 | A | C |
| ATOM | 1497 | CB | PHE | A | 322 | 49.973 | 35.541 | 5.479 | 1.00 | 66.67 | A | C |
| ATOM | 1498 | CG | PHE | A | 322 | 49.413 | 36.743 | 6.155 | 1.00 | 67.10 | A | C |
| ATOM | 1499 | CD1 | PHE | A | 322 | 48.448 | 36.606 | 7.145 | 1.00 | 70.05 | A | C |
| ATOM | 1500 | CD2 | PHE | A | 322 | 49.786 | 38.012 | 5.756 | 1.00 | 64.93 | A | C |
| ATOM | 1501 | CE1 | PHE | A | 322 | 47.859 | 37.714 | 7.721 | 1.00 | 71.21 | A | C |
| ATOM | 1502 | CE2 | PHE | A | 322 | 49.204 | 39.123 | 6.322 | 1.00 | 62.96 | A | C |
| ATOM | 1503 | CZ | PHE | A | 322 | 48.236 | 38.974 | 7.307 | 1.00 | 68.48 | A | C |
| ATOM | 1504 | C | PHE | A | 322 | 50.158 | 33.069 | 5.488 | 1.00 | 68.77 | A | C |
| ATOM | 1505 | O | PHE | A | 322 | 49.311 | 32.173 | 5.453 | 1.00 | 69.04 | A | O |
| ATOM | 1506 | N | LEU | A | 323 | 51.292 | 33.037 | 4.803 | 1.00 | 69.52 | A | N |
| ATOM | 1507 | CA | LEU | A | 323 | 51.625 | 31.954 | 3.893 | 1.00 | 69.64 | A | C |
| ATOM | 1508 | CB | LEU | A | 323 | 52.809 | 32.372 | 3.038 | 1.00 | 64.99 | A | C |
| ATOM | 1509 | CG | LEU | A | 323 | 52.582 | 33.609 | 2.179 | 1.00 | 60.38 | A | C |
| ATOM | 1510 | CD1 | LEU | A | 323 | 53.902 | 34.106 | 1.625 | 1.00 | 56.40 | A | C |
| ATOM | 1511 | CD2 | LEU | A | 323 | 51.629 | 33.248 | 1.068 | 1.00 | 60.63 | A | C |
| ATOM | 1512 | C | LEU | A | 323 | 51.929 | 30.610 | 4.533 | 1.00 | 70.69 | A | C |
| ATOM | 1513 | O | LEU | A | 323 | 51.982 | 29.604 | 3.835 | 1.00 | 74.73 | A | O |
| ATOM | 1514 | N | VAL | A | 324 | 52.120 | 30.582 | 5.848 | 1.00 | 70.16 | A | N |
| ATOM | 1515 | CA | VAL | A | 324 | 52.444 | 29.328 | 6.517 | 1.00 | 67.98 | A | C |
| ATOM | 1516 | CB | VAL | A | 324 | 53.796 | 29.435 | 7.238 | 1.00 | 63.48 | A | C |
| ATOM | 1517 | CG1 | VAL | A | 324 | 54.169 | 28.095 | 7.803 | 1.00 | 61.67 | A | C |
| ATOM | 1518 | CG2 | VAL | A | 324 | 54.862 | 29.906 | 6.284 | 1.00 | 54.87 | A | C |
| ATOM | 1519 | C | VAL | A | 324 | 51.401 | 28.783 | 7.505 | 1.00 | 70.07 | A | C |
| ATOM | 1520 | O | VAL | A | 324 | 51.130 | 27.584 | 7.517 | 1.00 | 72.92 | A | O |
| ATOM | 1521 | N | GLY | A | 325 | 50.822 | 29.639 | 8.338 | 1.00 | 69.11 | A | N |
| ATOM | 1522 | CA | GLY | A | 325 | 49.830 | 29.145 | 9.278 | 1.00 | 68.96 | A | C |
| ATOM | 1523 | C | GLY | A | 325 | 50.276 | 29.368 | 10.698 | 1.00 | 67.27 | A | C |
| ATOM | 1524 | O | GLY | A | 325 | 49.560 | 29.073 | 11.659 | 1.00 | 65.21 | A | O |
| ATOM | 1525 | N | LYS | A | 326 | 51.483 | 29.896 | 10.812 | 1.00 | 67.06 | A | N |
| ATOM | 1526 | CA | LYS | A | 326 | 52.052 | 30.193 | 12.097 | 1.00 | 67.54 | A | C |
| ATOM | 1527 | CB | LYS | A | 326 | 52.558 | 28.929 | 12.765 | 1.00 | 75.55 | A | C |

Figure 4Y

```
ATOM   1528  CG  LYS A 326      53.570  28.159  11.959  1.00  83.17      A  C
ATOM   1529  CD  LYS A 326      54.111  26.997  12.784  1.00  91.62      A  C
ATOM   1530  CE  LYS A 326      54.986  26.073  11.956  1.00  98.25      A  C
ATOM   1531  NZ  LYS A 326      54.178  25.426  10.888  1.00 106.04      A  N
ATOM   1532  C   LYS A 326      53.181  31.160  11.912  1.00  62.90      A  C
ATOM   1533  O   LYS A 326      53.756  31.266  10.847  1.00  57.40      A  O
ATOM   1534  N   PRO A 327      53.487  31.915  12.953  1.00  64.20      A  N
ATOM   1535  CD  PRO A 327      52.984  31.846  14.329  1.00  65.35      A  C
ATOM   1536  CA  PRO A 327      54.569  32.874  12.843  1.00  66.03      A  C
ATOM   1537  CB  PRO A 327      54.569  33.552  14.199  1.00  67.53      A  C
ATOM   1538  CG  PRO A 327      54.118  32.454  15.096  1.00  68.78      A  C
ATOM   1539  C   PRO A 327      55.834  32.118  12.575  1.00  65.27      A  C
ATOM   1540  O   PRO A 327      55.881  30.892  12.695  1.00  61.89      A  O
ATOM   1541  N   PRO A 328      56.878  32.846  12.200  1.00  66.25      A  N
ATOM   1542  CD  PRO A 328      56.768  34.246  11.772  1.00  62.51      A  C
ATOM   1543  CA  PRO A 328      58.198  32.321  11.883  1.00  71.53      A  C
ATOM   1544  CB  PRO A 328      58.740  33.371  10.943  1.00  68.37      A  C
ATOM   1545  CG  PRO A 328      58.187  34.600  11.512  1.00  65.64      A  C
ATOM   1546  C   PRO A 328      59.107  32.092  13.070  1.00  75.99      A  C
ATOM   1547  O   PRO A 328      60.180  31.497  12.952  1.00  76.72      A  O
ATOM   1548  N   PHE A 329      58.688  32.550  14.230  1.00  80.01      A  N
ATOM   1549  CA  PHE A 329      59.542  32.361  15.379  1.00  86.19      A  C
ATOM   1550  CB  PHE A 329      60.072  33.722  15.805  1.00  87.46      A  C
ATOM   1551  CG  PHE A 329      60.808  34.461  14.695  1.00  87.41      A  C
ATOM   1552  CD1 PHE A 329      61.971  33.933  14.132  1.00  86.40      A  C
ATOM   1553  CD2 PHE A 329      60.343  35.692  14.224  1.00  87.36      A  C
ATOM   1554  CE1 PHE A 329      62.656  34.623  13.124  1.00  83.92      A  C
ATOM   1555  CE2 PHE A 329      61.027  36.379  13.217  1.00  84.25      A  C
ATOM   1556  CZ  PHE A 329      62.181  35.842  12.672  1.00  81.51      A  C
ATOM   1557  C   PHE A 329      58.819  31.635  16.507  1.00  90.30      A  C
ATOM   1558  O   PHE A 329      59.247  31.631  17.660  1.00  93.36      A  O
ATOM   1559  N   GLU A 330      57.715  31.000  16.138  1.00  91.24      A  N
ATOM   1560  CA  GLU A 330      56.906  30.229  17.060  1.00  89.33      A  C
ATOM   1561  CB  GLU A 330      55.685  29.687  16.329  1.00  85.78      A  C
ATOM   1562  CG  GLU A 330      54.864  28.712  17.121  1.00  82.49      A  C
ATOM   1563  CD  GLU A 330      53.638  28.289  16.361  1.00  80.36      A  C
ATOM   1564  OE1 GLU A 330      52.826  29.170  16.019  1.00  80.43      A  O
ATOM   1565  OE2 GLU A 330      53.487  27.082  16.099  1.00  77.20      A  O
ATOM   1566  C   GLU A 330      57.718  29.075  17.621  1.00  91.13      A  C
ATOM   1567  O   GLU A 330      58.377  28.329  16.887  1.00  89.13      A  O
ATOM   1568  N   ALA A 331      57.667  28.939  18.936  1.00  94.97      A  N
ATOM   1569  CA  ALA A 331      58.388  27.875  19.602  1.00  99.70      A  C
ATOM   1570  CB  ALA A 331      59.885  28.106  19.479  1.00  98.91      A  C
ATOM   1571  C   ALA A 331      57.992  27.735  21.070  1.00 102.25      A  C
ATOM   1572  O   ALA A 331      57.314  28.595  21.644  1.00 101.05      A  O
ATOM   1573  N   ASN A 332      58.425  26.621  21.652  1.00 106.38      A  N
ATOM   1574  CA  ASN A 332      58.176  26.265  23.049  1.00 108.08      A  C
ATOM   1575  CB  ASN A 332      58.666  24.826  23.278  1.00 109.70      A  C
ATOM   1576  CG  ASN A 332      60.021  24.557  22.595  1.00 111.15      A  C
ATOM   1577  OD1 ASN A 332      60.107  24.457  21.358  1.00 108.81      A  O
ATOM   1578  ND2 ASN A 332      61.085  24.466  23.399  1.00 112.08      A  N
ATOM   1579  C   ASN A 332      58.894  27.227  24.013  1.00 108.12      A  C
ATOM   1580  O   ASN A 332      60.134  27.250  24.087  1.00 109.65      A  O
ATOM   1581  N   THR A 333      58.107  28.019  24.739  1.00 106.99      A  N
ATOM   1582  CA  THR A 333      58.610  28.989  25.725  1.00 104.58      A  C
ATOM   1583  CB  THR A 333      59.710  28.363  26.662  1.00 103.30      A  C
ATOM   1584  OG1 THR A 333      59.598  28.974  27.956  1.00 101.27      A  O
ATOM   1585  CG2 THR A 333      61.149  28.570  26.100  1.00  95.97      A  C
ATOM   1586  C   THR A 333      59.134  30.309  25.157  1.00 102.26      A  C
ATOM   1587  O   THR A 333      59.538  30.388  24.004  1.00 101.90      A  O
ATOM   1588  N   TYR A 334      59.099  31.344  25.990  1.00  99.25      A  N
```

Figure 4Z

```
ATOM 1589  CA   TYR A 334    59.567  32.673  25.628  1.00   95.68   A   C
ATOM 1590  CB   TYR A 334    59.289  33.615  26.776  1.00   96.99   A   C
ATOM 1591  CG   TYR A 334    57.857  34.008  26.906  1.00  100.15   A   C
ATOM 1592  CD1  TYR A 334    57.195  34.615  25.846  1.00  103.75   A   C
ATOM 1593  CE1  TYR A 334    55.898  35.125  25.988  1.00  109.32   A   C
ATOM 1594  CD2  TYR A 334    57.193  33.894  28.121  1.00  103.89   A   C
ATOM 1595  CE2  TYR A 334    55.890  34.400  28.283  1.00  109.09   A   C
ATOM 1596  CZ   TYR A 334    55.249  35.020  27.208  1.00  111.05   A   C
ATOM 1597  OH   TYR A 334    53.979  35.558  27.341  1.00  113.89   A   O
ATOM 1598  C    TYR A 334    61.054  32.749  25.295  1.00   94.32   A   C
ATOM 1599  O    TYR A 334    61.440  33.426  24.359  1.00   92.37   A   O
ATOM 1600  N    GLN A 335    61.878  32.075  26.092  1.00   95.70   A   N
ATOM 1601  CA   GLN A 335    63.331  32.040  25.922  1.00   96.60   A   C
ATOM 1602  CB   GLN A 335    63.927  31.002  26.863  1.00   98.70   A   C
ATOM 1603  CG   GLN A 335    63.684  31.357  28.324  1.00  104.56   A   C
ATOM 1604  CD   GLN A 335    62.197  31.547  28.662  1.00  108.41   A   C
ATOM 1605  OE1  GLN A 335    61.823  32.386  29.498  1.00  109.98   A   O
ATOM 1606  NE2  GLN A 335    61.346  30.754  28.020  1.00  112.33   A   N
ATOM 1607  C    GLN A 335    63.686  31.722  24.485  1.00   97.70   A   C
ATOM 1608  O    GLN A 335    64.270  32.558  23.793  1.00   97.45   A   O
ATOM 1609  N    GLU A 336    63.362  30.510  24.034  1.00   99.72   A   N
ATOM 1610  CA   GLU A 336    63.596  30.163  22.638  1.00  100.18   A   C
ATOM 1611  CB   GLU A 336    63.107  28.741  22.362  1.00  105.13   A   C
ATOM 1612  CG   GLU A 336    63.904  27.628  23.054  1.00  110.81   A   C
ATOM 1613  CD   GLU A 336    65.030  27.045  22.175  1.00  114.62   A   C
ATOM 1614  OE1  GLU A 336    65.814  26.217  22.687  1.00  116.38   A   O
ATOM 1615  OE2  GLU A 336    65.141  27.392  20.974  1.00  115.00   A   O
ATOM 1616  C    GLU A 336    62.682  31.197  21.971  1.00   98.85   A   C
ATOM 1617  O    GLU A 336    61.865  31.809  22.658  1.00  102.56   A   O
ATOM 1618  N    THR A 337    62.789  31.398  20.666  1.00   94.24   A   N
ATOM 1619  CA   THR A 337    61.968  32.403  19.975  1.00   92.56   A   C
ATOM 1620  CB   THR A 337    60.548  32.602  20.591  1.00   94.81   A   C
ATOM 1621  OG1  THR A 337    59.780  31.397  20.462  1.00  100.57   A   O
ATOM 1622  CG2  THR A 337    59.814  33.729  19.875  1.00   96.19   A   C
ATOM 1623  C    THR A 337    62.743  33.691  20.132  1.00   88.02   A   C
ATOM 1624  O    THR A 337    63.220  34.255  19.158  1.00   85.69   A   O
ATOM 1625  N    TYR A 338    62.869  34.166  21.363  1.00   85.47   A   N
ATOM 1626  CA   TYR A 338    63.652  35.362  21.580  1.00   81.53   A   C
ATOM 1627  CB   TYR A 338    63.960  35.548  23.062  1.00   85.45   A   C
ATOM 1628  CG   TYR A 338    64.939  36.661  23.307  1.00   92.06   A   C
ATOM 1629  CD1  TYR A 338    64.500  37.963  23.545  1.00   97.39   A   C
ATOM 1630  CE1  TYR A 338    65.404  39.034  23.669  1.00   99.84   A   C
ATOM 1631  CD2  TYR A 338    66.310  36.438  23.202  1.00   97.04   A   C
ATOM 1632  CE2  TYR A 338    67.233  37.498  23.319  1.00  102.58   A   C
ATOM 1633  CZ   TYR A 338    66.767  38.799  23.550  1.00  102.63   A   C
ATOM 1634  OH   TYR A 338    67.645  39.868  23.636  1.00  102.55   A   O
ATOM 1635  C    TYR A 338    64.905  34.910  20.879  1.00   76.58   A   C
ATOM 1636  O    TYR A 338    65.380  35.506  19.915  1.00   74.36   A   O
ATOM 1637  N    LYS A 339    65.398  33.791  21.370  1.00   73.01   A   N
ATOM 1638  CA   LYS A 339    66.577  33.209  20.826  1.00   71.11   A   C
ATOM 1639  CB   LYS A 339    66.637  31.724  21.181  1.00   75.49   A   C
ATOM 1640  CG   LYS A 339    67.863  31.003  20.620  1.00   83.83   A   C
ATOM 1641  CD   LYS A 339    68.089  29.622  21.242  1.00   93.15   A   C
ATOM 1642  CE   LYS A 339    68.414  29.728  22.745  1.00   99.04   A   C
ATOM 1643  NZ   LYS A 339    68.866  28.434  23.386  1.00  106.61   A   N
ATOM 1644  C    LYS A 339    66.469  33.390  19.345  1.00   68.72   A   C
ATOM 1645  O    LYS A 339    67.242  34.110  18.743  1.00   65.80   A   O
ATOM 1646  N    ARG A 340    65.451  32.787  18.769  1.00   69.97   A   N
ATOM 1647  CA   ARG A 340    65.298  32.847  17.337  1.00   73.20   A   C
ATOM 1648  CB   ARG A 340    64.279  31.774  16.886  1.00   81.85   A   C
ATOM 1649  CG   ARG A 340    64.711  30.290  17.207  1.00   88.83   A   C
```

Figure 4AA

```
ATOM   1650  CD   ARG A 340      63.640  29.187  16.861  1.00  93.29      A  C
ATOM   1651  NE   ARG A 340      63.974  27.848  17.395  1.00  94.45      A  N
ATOM   1652  CZ   ARG A 340      63.154  26.792  17.402  1.00  90.40      A  C
ATOM   1653  NH1  ARG A 340      61.928  26.886  16.900  1.00  91.39      A  N
ATOM   1654  NH2  ARG A 340      63.555  25.639  17.924  1.00  84.42      A  N
ATOM   1655  C    ARG A 340      64.963  34.222  16.767  1.00  69.38      A  C
ATOM   1656  O    ARG A 340      65.327  34.529  15.643  1.00  70.49      A  O
ATOM   1657  N    ILE A 341      64.305  35.074  17.528  1.00  63.88      A  N
ATOM   1658  CA   ILE A 341      63.959  36.379  16.999  1.00  60.27      A  C
ATOM   1659  CB   ILE A 341      63.019  37.123  17.936  1.00  60.92      A  C
ATOM   1660  CG2  ILE A 341      62.864  38.547  17.482  1.00  63.49      A  C
ATOM   1661  CG1  ILE A 341      61.661  36.444  17.965  1.00  62.67      A  C
ATOM   1662  CD1  ILE A 341      60.668  37.149  18.831  1.00  62.60      A  C
ATOM   1663  C    ILE A 341      65.196  37.219  16.815  1.00  59.49      A  C
ATOM   1664  O    ILE A 341      65.522  37.653  15.722  1.00  55.44      A  O
ATOM   1665  N    SER A 342      65.880  37.453  17.917  1.00  63.88      A  N
ATOM   1666  CA   SER A 342      67.085  38.253  17.907  1.00  71.06      A  C
ATOM   1667  CB   SER A 342      67.603  38.415  19.324  1.00  69.66      A  C
ATOM   1668  OG   SER A 342      67.702  37.148  19.931  1.00  71.99      A  O
ATOM   1669  C    SER A 342      68.150  37.597  17.055  1.00  76.21      A  C
ATOM   1670  O    SER A 342      68.897  38.260  16.356  1.00  81.00      A  O
ATOM   1671  N    ARG A 343      68.238  36.283  17.117  1.00  78.92      A  N
ATOM   1672  CA   ARG A 343      69.237  35.588  16.323  1.00  79.63      A  C
ATOM   1673  CB   ARG A 343      69.465  34.198  16.945  1.00  85.90      A  C
ATOM   1674  CG   ARG A 343      70.373  33.233  16.185  1.00  94.40      A  C
ATOM   1675  CD   ARG A 343      69.566  32.209  15.342  1.00 101.87      A  C
ATOM   1676  NE   ARG A 343      69.843  30.803  15.694  1.00 111.15      A  N
ATOM   1677  CZ   ARG A 343      69.131  30.061  16.553  1.00 116.33      A  C
ATOM   1678  NH1  ARG A 343      68.073  30.566  17.168  1.00 120.46      A  N
ATOM   1679  NH2  ARG A 343      69.481  28.802  16.815  1.00 119.07      A  N
ATOM   1680  C    ARG A 343      68.761  35.511  14.860  1.00  76.83      A  C
ATOM   1681  O    ARG A 343      69.547  35.244  13.956  1.00  76.06      A  O
ATOM   1682  N    VAL A 344      67.476  35.789  14.640  1.00  75.06      A  N
ATOM   1683  CA   VAL A 344      66.876  35.736  13.312  1.00  74.54      A  C
ATOM   1684  CB   VAL A 344      67.577  36.670  12.357  1.00  70.64      A  C
ATOM   1685  CG1  VAL A 344      66.862  36.686  11.046  1.00  64.52      A  C
ATOM   1686  CG2  VAL A 344      67.613  38.047  12.939  1.00  69.18      A  C
ATOM   1687  C    VAL A 344      66.962  34.318  12.783  1.00  79.63      A  C
ATOM   1688  O    VAL A 344      67.491  34.059  11.712  1.00  75.82      A  O
ATOM   1689  N    GLU A 345      66.420  33.405  13.573  1.00  88.50      A  N
ATOM   1690  CA   GLU A 345      66.393  31.979  13.285  1.00  97.17      A  C
ATOM   1691  CB   GLU A 345      66.652  31.207  14.575  1.00 103.20      A  C
ATOM   1692  CG   GLU A 345      66.495  29.715  14.442  1.00 115.88      A  C
ATOM   1693  CD   GLU A 345      67.310  29.187  13.285  1.00 124.81      A  C
ATOM   1694  OE1  GLU A 345      68.492  29.611  13.177  1.00 129.03      A  O
ATOM   1695  OE2  GLU A 345      66.774  28.361  12.493  1.00 130.44      A  O
ATOM   1696  C    GLU A 345      65.060  31.514  12.701  1.00  98.90      A  C
ATOM   1697  O    GLU A 345      64.131  31.165  13.446  1.00  97.90      A  O
ATOM   1698  N    PHE A 346      64.974  31.475  11.374  1.00 101.67      A  N
ATOM   1699  CA   PHE A 346      63.732  31.058  10.716  1.00 105.15      A  C
ATOM   1700  CB   PHE A 346      62.853  32.285  10.486  1.00 101.46      A  C
ATOM   1701  CG   PHE A 346      63.165  33.008   9.229  1.00  94.81      A  C
ATOM   1702  CD1  PHE A 346      62.542  32.654   8.039  1.00  94.94      A  C
ATOM   1703  CD2  PHE A 346      64.118  34.003   9.217  1.00  92.92      A  C
ATOM   1704  CE1  PHE A 346      62.866  33.283   6.858  1.00  95.84      A  C
ATOM   1705  CE2  PHE A 346      64.452  34.640   8.036  1.00  93.74      A  C
ATOM   1706  CZ   PHE A 346      63.827  34.281   6.852  1.00  94.47      A  C
ATOM   1707  C    PHE A 346      63.932  30.313   9.377  1.00 108.68      A  C
ATOM   1708  O    PHE A 346      64.828  30.648   8.582  1.00 108.29      A  O
ATOM   1709  N    THR A 347      63.071  29.327   9.118  1.00 112.47      A  N
ATOM   1710  CA   THR A 347      63.183  28.539   7.896  1.00 115.77      A  C
```

Figure 4BB

```
ATOM   1711  CB   THR A 347      63.741  27.124   8.205  1.00 116.22      A    C
ATOM   1712  OG1  THR A 347      64.212  26.527   6.990  1.00 115.60      A    O
ATOM   1713  CG2  THR A 347      62.647  26.237   8.853  1.00 113.91      A    C
ATOM   1714  C    THR A 347      61.860  28.394   7.139  1.00 117.77      A    C
ATOM   1715  O    THR A 347      60.768  28.532   7.729  1.00 120.13      A    O
ATOM   1716  N    PHE A 348      61.989  28.091   5.839  1.00 117.75      A    N
ATOM   1717  CA   PHE A 348      60.864  27.922   4.905  1.00 114.46      A    C
ATOM   1718  CB   PHE A 348      61.191  28.546   3.536  1.00 115.32      A    C
ATOM   1719  CG   PHE A 348      61.323  30.051   3.544  1.00 115.42      A    C
ATOM   1720  CD1  PHE A 348      60.205  30.875   3.674  1.00 113.37      A    C
ATOM   1721  CD2  PHE A 348      62.570  30.639   3.406  1.00 115.78      A    C
ATOM   1722  CE1  PHE A 348      60.332  32.264   3.668  1.00 112.89      A    C
ATOM   1723  CE2  PHE A 348      62.705  32.020   3.400  1.00 116.22      A    C
ATOM   1724  CZ   PHE A 348      61.583  32.836   3.531  1.00 114.67      A    C
ATOM   1725  C    PHE A 348      60.451  26.479   4.628  1.00 111.19      A    C
ATOM   1726  O    PHE A 348      61.301  25.601   4.457  1.00 109.14      A    O
ATOM   1727  N    PRO A 349      59.129  26.235   4.545  1.00 108.80      A    N
ATOM   1728  CD   PRO A 349      58.022  27.167   4.848  1.00 108.30      A    C
ATOM   1729  CA   PRO A 349      58.602  24.906   4.271  1.00 107.30      A    C
ATOM   1730  CB   PRO A 349      57.163  25.001   4.771  1.00 106.96      A    C
ATOM   1731  CG   PRO A 349      56.792  26.393   4.383  1.00 107.53      A    C
ATOM   1732  C    PRO A 349      58.693  24.594   2.767  1.00 105.98      A    C
ATOM   1733  O    PRO A 349      58.922  25.465   1.908  1.00 103.92      A    O
ATOM   1734  N    ASP A 350      58.497  23.325   2.467  1.00 104.94      A    N
ATOM   1735  CA   ASP A 350      58.578  22.842   1.111  1.00 103.42      A    C
ATOM   1736  CB   ASP A 350      58.632  21.319   1.132  1.00 108.05      A    C
ATOM   1737  CG   ASP A 350      59.959  20.774   0.623  1.00 110.77      A    C
ATOM   1738  OD1  ASP A 350      61.025  21.331   0.991  1.00 109.18      A    O
ATOM   1739  OD2  ASP A 350      59.929  19.778  -0.138  1.00 114.39      A    O
ATOM   1740  C    ASP A 350      57.467  23.288   0.189  1.00  99.93      A    C
ATOM   1741  O    ASP A 350      56.615  22.471  -0.186  1.00  98.20      A    O
ATOM   1742  N    PHE A 351      57.471  24.567  -0.180  1.00  94.59      A    N
ATOM   1743  CA   PHE A 351      56.461  25.042  -1.103  1.00  92.87      A    C
ATOM   1744  CB   PHE A 351      55.087  24.453  -0.777  1.00  89.57      A    C
ATOM   1745  CG   PHE A 351      54.391  25.140   0.340  1.00  90.46      A    C
ATOM   1746  CD1  PHE A 351      53.801  26.386   0.153  1.00  90.98      A    C
ATOM   1747  CD2  PHE A 351      54.350  24.556   1.592  1.00  91.77      A    C
ATOM   1748  CE1  PHE A 351      53.184  27.036   1.199  1.00  93.77      A    C
ATOM   1749  CE2  PHE A 351      53.736  25.191   2.651  1.00  95.52      A    C
ATOM   1750  CZ   PHE A 351      53.151  26.435   2.460  1.00  96.07      A    C
ATOM   1751  C    PHE A 351      56.313  26.531  -1.190  1.00  94.12      A    C
ATOM   1752  O    PHE A 351      55.638  27.027  -2.088  1.00  96.72      A    O
ATOM   1753  N    VAL A 352      56.895  27.272  -0.267  1.00  93.66      A    N
ATOM   1754  CA   VAL A 352      56.710  28.708  -0.375  1.00  92.97      A    C
ATOM   1755  CB   VAL A 352      57.179  29.459   0.852  1.00  93.04      A    C
ATOM   1756  CG1  VAL A 352      57.087  30.963   0.596  1.00  88.93      A    C
ATOM   1757  CG2  VAL A 352      56.323  29.065   2.045  1.00  92.84      A    C
ATOM   1758  C    VAL A 352      57.477  29.218  -1.554  1.00  93.26      A    C
ATOM   1759  O    VAL A 352      58.677  28.993  -1.673  1.00  92.69      A    O
ATOM   1760  N    THR A 353      56.766  29.908  -2.429  1.00  94.47      A    N
ATOM   1761  CA   THR A 353      57.373  30.452  -3.625  1.00  96.66      A    C
ATOM   1762  CB   THR A 353      56.436  31.434  -4.328  1.00  97.68      A    C
ATOM   1763  OG1  THR A 353      57.158  32.119  -5.359  1.00  99.14      A    O
ATOM   1764  CG2  THR A 353      55.866  32.433  -3.329  1.00  97.94      A    C
ATOM   1765  C    THR A 353      58.647  31.174  -3.265  1.00  97.92      A    C
ATOM   1766  O    THR A 353      58.762  31.761  -2.195  1.00  99.25      A    O
ATOM   1767  N    GLU A 354      59.613  31.126  -4.161  1.00  99.61      A    N
ATOM   1768  CA   GLU A 354      60.865  31.784  -3.902  1.00 100.44      A    C
ATOM   1769  CB   GLU A 354      61.845  31.405  -4.958  1.00 107.39      A    C
ATOM   1770  CG   GLU A 354      63.099  32.164  -4.855  1.00 117.96      A    C
ATOM   1771  CD   GLU A 354      63.979  31.818  -6.003  1.00 127.17      A    C
```

Figure 4CC

```
ATOM   1772  OE1 GLU A 354      63.474  31.906  -7.171  1.00 132.51      A    O
ATOM   1773  OE2 GLU A 354      65.155  31.451  -5.726  1.00 132.47      A    O
ATOM   1774  C   GLU A 354      60.707  33.288  -3.883  1.00  97.47      A    C
ATOM   1775  O   GLU A 354      61.472  33.985  -3.215  1.00  97.39      A    O
ATOM   1776  N   GLY A 355      59.724  33.784  -4.632  1.00  94.87      A    N
ATOM   1777  CA  GLY A 355      59.464  35.218  -4.670  1.00  92.69      A    C
ATOM   1778  C   GLY A 355      59.085  35.743  -3.296  1.00  88.92      A    C
ATOM   1779  O   GLY A 355      59.300  36.907  -2.962  1.00  86.52      A    O
ATOM   1780  N   ALA A 356      58.499  34.858  -2.503  1.00  88.39      A    N
ATOM   1781  CA  ALA A 356      58.096  35.181  -1.150  1.00  87.48      A    C
ATOM   1782  CB  ALA A 356      56.997  34.201  -0.679  1.00  91.52      A    C
ATOM   1783  C   ALA A 356      59.357  35.006  -0.321  1.00  84.55      A    C
ATOM   1784  O   ALA A 356      59.771  35.897   0.426  1.00  82.86      A    O
ATOM   1785  N   ARG A 357      59.973  33.843  -0.487  1.00  80.83      A    N
ATOM   1786  CA  ARG A 357      61.176  33.513   0.226  1.00  79.07      A    C
ATOM   1787  CB  ARG A 357      61.831  32.293  -0.401  1.00  76.36      A    C
ATOM   1788  CG  ARG A 357      61.232  31.007   0.090  1.00  74.75      A    C
ATOM   1789  CD  ARG A 357      61.470  29.896  -0.885  1.00  76.91      A    C
ATOM   1790  NE  ARG A 357      61.200  28.588  -0.295  1.00  79.47      A    N
ATOM   1791  CZ  ARG A 357      62.003  27.995   0.581  1.00  81.41      A    C
ATOM   1792  NH1 ARG A 357      63.115  28.610   0.953  1.00  81.89      A    N
ATOM   1793  NH2 ARG A 357      61.707  26.792   1.077  1.00  82.39      A    N
ATOM   1794  C   ARG A 357      62.146  34.667   0.275  1.00  80.64      A    C
ATOM   1795  O   ARG A 357      62.978  34.720   1.153  1.00  82.71      A    O
ATOM   1796  N   ASP A 358      62.052  35.611  -0.647  1.00  82.32      A    N
ATOM   1797  CA  ASP A 358      62.984  36.736  -0.606  1.00  81.54      A    C
ATOM   1798  CB  ASP A 358      63.688  36.913  -1.961  1.00  86.19      A    C
ATOM   1799  CG  ASP A 358      62.905  37.791  -2.924  1.00  87.91      A    C
ATOM   1800  OD1 ASP A 358      61.888  37.331  -3.485  1.00  90.46      A    O
ATOM   1801  OD2 ASP A 358      63.313  38.954  -3.114  1.00  88.23      A    O
ATOM   1802  C   ASP A 358      62.300  38.040  -0.200  1.00  78.10      A    C
ATOM   1803  O   ASP A 358      62.921  38.929   0.374  1.00  79.03      A    O
ATOM   1804  N   LEU A 359      61.018  38.159  -0.506  1.00  75.12      A    N
ATOM   1805  CA  LEU A 359      60.298  39.358  -0.145  1.00  72.85      A    C
ATOM   1806  CB  LEU A 359      58.847  39.274  -0.620  1.00  70.08      A    C
ATOM   1807  CG  LEU A 359      57.819  40.322  -0.175  1.00  68.28      A    C
ATOM   1808  CD1 LEU A 359      57.328  39.971   1.210  1.00  67.60      A    C
ATOM   1809  CD2 LEU A 359      58.411  41.719  -0.215  1.00  67.07      A    C
ATOM   1810  C   LEU A 359      60.360  39.423   1.355  1.00  74.04      A    C
ATOM   1811  O   LEU A 359      60.572  40.481   1.929  1.00  75.69      A    O
ATOM   1812  N   ILE A 360      60.192  38.276   1.993  1.00  75.88      A    N
ATOM   1813  CA  ILE A 360      60.240  38.237   3.438  1.00  79.14      A    C
ATOM   1814  CB  ILE A 360      59.557  36.965   3.962  1.00  79.80      A    C
ATOM   1815  CG2 ILE A 360      60.239  35.752   3.398  1.00  73.30      A    C
ATOM   1816  CG1 ILE A 360      59.562  36.966   5.492  1.00  83.77      A    C
ATOM   1817  CD1 ILE A 360      58.753  35.845   6.119  1.00  88.60      A    C
ATOM   1818  C   ILE A 360      61.693  38.330   3.941  1.00  80.74      A    C
ATOM   1819  O   ILE A 360      61.987  39.080   4.868  1.00  82.77      A    O
ATOM   1820  N   SER A 361      62.610  37.589   3.329  1.00  79.31      A    N
ATOM   1821  CA  SER A 361      64.007  37.648   3.753  1.00  77.82      A    C
ATOM   1822  CB  SER A 361      64.910  36.909   2.786  1.00  77.89      A    C
ATOM   1823  OG  SER A 361      64.693  35.527   2.875  1.00  81.50      A    O
ATOM   1824  C   SER A 361      64.410  39.082   3.726  1.00  79.23      A    C
ATOM   1825  O   SER A 361      65.306  39.496   4.449  1.00  78.87      A    O
ATOM   1826  N   ARG A 362      63.739  39.821   2.852  1.00  83.07      A    N
ATOM   1827  CA  ARG A 362      63.989  41.231   2.665  1.00  87.72      A    C
ATOM   1828  CB  ARG A 362      63.637  41.656   1.248  1.00  87.31      A    C
ATOM   1829  CG  ARG A 362      64.134  43.028   0.953  1.00  91.26      A    C
ATOM   1830  CD  ARG A 362      65.317  42.942   0.055  1.00  99.16      A    C
ATOM   1831  NE  ARG A 362      64.884  43.068  -1.327  1.00 107.85      A    N
ATOM   1832  CZ  ARG A 362      64.469  44.215  -1.866  1.00 113.06      A    C
```

Figure 4DD

```
ATOM   1833  NH1 ARG A 362      64.442  45.328  -1.125  1.00 112.65      A    N
ATOM   1834  NH2 ARG A 362      64.079  44.251  -3.145  1.00 116.84      A    N
ATOM   1835  C   ARG A 362      63.165  42.058   3.622  1.00  90.36      A    C
ATOM   1836  O   ARG A 362      63.189  43.280   3.549  1.00  93.67      A    O
ATOM   1837  N   LEU A 363      62.428  41.400   4.511  1.00  91.62      A    N
ATOM   1838  CA  LEU A 363      61.593  42.114   5.473  1.00  93.79      A    C
ATOM   1839  CB  LEU A 363      60.135  41.757   5.262  1.00  92.63      A    C
ATOM   1840  CG  LEU A 363      59.238  42.973   5.100  1.00  91.15      A    C
ATOM   1841  CD1 LEU A 363      59.961  44.079   4.361  1.00  90.29      A    C
ATOM   1842  CD2 LEU A 363      58.022  42.548   4.339  1.00  95.75      A    C
ATOM   1843  C   LEU A 363      61.973  41.849   6.915  1.00  97.98      A    C
ATOM   1844  O   LEU A 363      61.681  42.634   7.811  1.00  99.90      A    O
ATOM   1845  N   LEU A 364      62.618  40.728   7.145  1.00 102.21      A    N
ATOM   1846  CA  LEU A 364      63.041  40.434   8.482  1.00 106.04      A    C
ATOM   1847  CB  LEU A 364      62.478  39.067   8.914  1.00 108.42      A    C
ATOM   1848  CG  LEU A 364      63.110  37.739   8.461  1.00 112.73      A    C
ATOM   1849  CD1 LEU A 364      63.398  37.756   6.966  1.00 114.72      A    C
ATOM   1850  CD2 LEU A 364      64.410  37.490   9.238  1.00 114.36      A    C
ATOM   1851  C   LEU A 364      64.581  40.485   8.495  1.00 107.46      A    C
ATOM   1852  O   LEU A 364      65.258  39.661   7.868  1.00 107.13      A    O
ATOM   1853  N   LYS A 365      65.123  41.506   9.162  1.00 111.08      A    N
ATOM   1854  CA  LYS A 365      66.575  41.672   9.299  1.00 115.83      A    C
ATOM   1855  CB  LYS A 365      67.158  42.466   8.137  1.00 118.34      A    C
ATOM   1856  CG  LYS A 365      68.588  42.078   7.828  1.00 122.84      A    C
ATOM   1857  CD  LYS A 365      68.665  40.680   7.170  1.00 126.91      A    C
ATOM   1858  CE  LYS A 365      70.053  39.999   7.351  1.00 128.43      A    C
ATOM   1859  NZ  LYS A 365      70.441  39.708   8.787  1.00 126.93      A    N
ATOM   1860  C   LYS A 365      66.938  42.359  10.623  1.00 117.43      A    C
ATOM   1861  O   LYS A 365      66.311  43.361  11.024  1.00 117.04      A    O
ATOM   1862  N   HIS A 366      67.950  41.804  11.296  1.00 120.22      A    N
ATOM   1863  CA  HIS A 366      68.402  42.306  12.596  1.00 122.56      A    C
ATOM   1864  CB  HIS A 366      69.726  41.660  13.013  1.00 126.19      A    C
ATOM   1865  CG  HIS A 366      70.053  41.842  14.464  1.00 129.99      A    C
ATOM   1866  CD2 HIS A 366      70.645  42.865  15.125  1.00 132.30      A    C
ATOM   1867  ND1 HIS A 366      69.759  40.891  15.421  1.00 133.57      A    N
ATOM   1868  CE1 HIS A 366      70.158  41.317  16.609  1.00 134.32      A    C
ATOM   1869  NE2 HIS A 366      70.700  42.513  16.457  1.00 135.34      A    N
ATOM   1870  C   HIS A 366      68.592  43.802  12.555  1.00 122.17      A    C
ATOM   1871  O   HIS A 366      68.029  44.543  13.376  1.00 122.56      A    O
ATOM   1872  N   ASN A 367      69.402  44.232  11.592  1.00 120.69      A    N
ATOM   1873  CA  ASN A 367      69.678  45.640  11.406  1.00 119.19      A    C
ATOM   1874  CB  ASN A 367      70.770  45.805  10.360  1.00 119.34      A    C
ATOM   1875  CG  ASN A 367      71.582  47.057  10.578  1.00 122.59      A    C
ATOM   1876  OD1 ASN A 367      71.038  48.141  10.810  1.00 124.09      A    O
ATOM   1877  ND2 ASN A 367      72.894  46.921  10.511  1.00 125.24      A    N
ATOM   1878  C   ASN A 367      68.403  46.376  10.951  1.00 118.22      A    C
ATOM   1879  O   ASN A 367      67.942  46.172   9.831  1.00 118.01      A    O
ATOM   1880  N   PRO A 368      67.820  47.236  11.818  1.00 117.67      A    N
ATOM   1881  CD  PRO A 368      68.189  47.530  13.213  1.00 117.09      A    C
ATOM   1882  CA  PRO A 368      66.607  47.971  11.458  1.00 119.21      A    C
ATOM   1883  CB  PRO A 368      66.357  48.841  12.685  1.00 116.57      A    C
ATOM   1884  CG  PRO A 368      66.892  48.021  13.786  1.00 115.01      A    C
ATOM   1885  C   PRO A 368      66.772  48.812  10.195  1.00 123.08      A    C
ATOM   1886  O   PRO A 368      65.799  49.044   9.467  1.00 125.04      A    O
ATOM   1887  N   SER A 369      67.999  49.270   9.939  1.00 126.13      A    N
ATOM   1888  CA  SER A 369      68.292  50.112   8.768  1.00 127.05      A    C
ATOM   1889  CB  SER A 369      69.603  50.886   8.973  1.00 125.63      A    C
ATOM   1890  OG  SER A 369      70.728  50.028   8.891  1.00 124.92      A    O
ATOM   1891  C   SER A 369      68.361  49.375   7.429  1.00 127.83      A    C
ATOM   1892  O   SER A 369      68.001  49.943   6.395  1.00 129.60      A    O
ATOM   1893  N   GLN A 370      68.815  48.124   7.436  1.00 127.59      A    N
```

Figure 4EE

```
ATOM   1894  CA   GLN A 370      68.924  47.362   6.191  1.00 126.82      A    C
ATOM   1895  CB   GLN A 370      69.787  46.107   6.422  1.00 129.90      A    C
ATOM   1896  CG   GLN A 370      71.210  46.370   6.928  1.00 133.53      A    C
ATOM   1897  CD   GLN A 370      72.159  45.166   6.750  1.00 136.39      A    C
ATOM   1898  OE1  GLN A 370      73.276  45.168   7.268  1.00 138.16      A    O
ATOM   1899  NE2  GLN A 370      71.721  44.147   6.009  1.00 138.57      A    N
ATOM   1900  C    GLN A 370      67.574  46.959   5.533  1.00 125.03      A    C
ATOM   1901  O    GLN A 370      67.573  46.332   4.462  1.00 123.43      A    O
ATOM   1902  N    ARG A 371      66.441  47.334   6.152  1.00 123.37      A    N
ATOM   1903  CA   ARG A 371      65.095  46.978   5.639  1.00 119.21      A    C
ATOM   1904  CB   ARG A 371      64.126  46.665   6.810  1.00 127.12      A    C
ATOM   1905  CG   ARG A 371      64.514  45.440   7.721  1.00 134.84      A    C
ATOM   1906  CD   ARG A 371      64.668  44.070   6.962  1.00 141.58      A    C
ATOM   1907  NE   ARG A 371      65.713  44.073   5.910  1.00 145.04      A    N
ATOM   1908  CZ   ARG A 371      66.127  43.013   5.197  1.00 143.97      A    C
ATOM   1909  NH1  ARG A 371      67.078  43.168   4.275  1.00 143.01      A    N
ATOM   1910  NH2  ARG A 371      65.613  41.798   5.399  1.00 143.52      A    N
ATOM   1911  C    ARG A 371      64.451  47.992   4.674  1.00 111.56      A    C
ATOM   1912  O    ARG A 371      64.511  49.211   4.872  1.00 107.85      A    O
ATOM   1913  N    PRO A 372      63.796  47.477   3.623  1.00 107.05      A    N
ATOM   1914  CD   PRO A 372      63.295  46.095   3.515  1.00 105.70      A    C
ATOM   1915  CA   PRO A 372      63.157  48.322   2.622  1.00 104.97      A    C
ATOM   1916  CB   PRO A 372      62.465  47.314   1.715  1.00 104.32      A    C
ATOM   1917  CG   PRO A 372      62.051  46.266   2.672  1.00 103.50      A    C
ATOM   1918  C    PRO A 372      62.192  49.286   3.230  1.00 103.88      A    C
ATOM   1919  O    PRO A 372      61.743  49.108   4.357  1.00 105.02      A    O
ATOM   1920  N    MET A 373      61.883  50.327   2.480  1.00 102.54      A    N
ATOM   1921  CA   MET A 373      60.935  51.291   2.965  1.00 100.05      A    C
ATOM   1922  CB   MET A 373      61.338  52.703   2.534  1.00  97.86      A    C
ATOM   1923  CG   MET A 373      61.216  53.765   3.632  1.00  92.64      A    C
ATOM   1924  SD   MET A 373      59.518  54.116   4.143  1.00  91.01      A    S
ATOM   1925  CE   MET A 373      59.679  54.352   5.900  1.00  81.46      A    C
ATOM   1926  C    MET A 373      59.637  50.877   2.316  1.00  99.17      A    C
ATOM   1927  O    MET A 373      59.577  49.924   1.548  1.00  96.25      A    O
ATOM   1928  N    LEU A 374      58.593  51.591   2.663  1.00 100.83      A    N
ATOM   1929  CA   LEU A 374      57.284  51.358   2.118  1.00 104.81      A    C
ATOM   1930  CB   LEU A 374      56.496  52.677   2.238  1.00 108.29      A    C
ATOM   1931  CG   LEU A 374      57.255  54.012   2.020  1.00 109.79      A    C
ATOM   1932  CD1  LEU A 374      57.278  54.413   0.522  1.00 108.76      A    C
ATOM   1933  CD2  LEU A 374      56.589  55.112   2.861  1.00 107.21      A    C
ATOM   1934  C    LEU A 374      57.293  50.854   0.663  1.00 106.77      A    C
ATOM   1935  O    LEU A 374      57.089  49.671   0.399  1.00 104.15      A    O
ATOM   1936  N    ARG A 375      57.550  51.772  -0.267  1.00 111.39      A    N
ATOM   1937  CA   ARG A 375      57.545  51.508  -1.708  1.00 114.73      A    C
ATOM   1938  CB   ARG A 375      58.239  52.675  -2.451  1.00 121.24      A    C
ATOM   1939  CG   ARG A 375      58.221  52.540  -3.995  1.00 129.96      A    C
ATOM   1940  CD   ARG A 375      59.022  53.641  -4.753  1.00 136.60      A    C
ATOM   1941  NE   ARG A 375      60.448  53.336  -4.980  1.00 142.14      A    N
ATOM   1942  CZ   ARG A 375      61.406  53.443  -4.055  1.00 144.03      A    C
ATOM   1943  NH1  ARG A 375      62.674  53.140  -4.361  1.00 144.67      A    N
ATOM   1944  NH2  ARG A 375      61.098  53.860  -2.822  1.00 146.67      A    N
ATOM   1945  C    ARG A 375      58.120  50.177  -2.207  1.00 112.06      A    C
ATOM   1946  O    ARG A 375      57.495  49.479  -3.015  1.00 110.66      A    O
ATOM   1947  N    GLU A 376      59.302  49.820  -1.735  1.00 111.32      A    N
ATOM   1948  CA   GLU A 376      59.913  48.601  -2.219  1.00 111.63      A    C
ATOM   1949  CB   GLU A 376      61.149  48.258  -1.374  1.00 115.45      A    C
ATOM   1950  CG   GLU A 376      62.172  47.331  -2.100  1.00 120.42      A    C
ATOM   1951  CD   GLU A 376      62.663  47.855  -3.494  1.00 121.42      A    C
ATOM   1952  OE1  GLU A 376      63.310  48.929  -3.552  1.00 118.90      A    O
ATOM   1953  OE2  GLU A 376      62.409  47.185  -4.533  1.00 121.36      A    O
ATOM   1954  C    GLU A 376      58.943  47.417  -2.316  1.00 108.94      A    C
```

Figure 4FF

```
ATOM   1955  O    GLU A 376      58.748  46.881  -3.408  1.00 109.31      A  O
ATOM   1956  N    VAL A 377      58.315  47.018  -1.211  1.00 106.15      A  N
ATOM   1957  CA   VAL A 377      57.388  45.883  -1.259  1.00 103.77      A  C
ATOM   1958  CB   VAL A 377      56.791  45.536   0.122  1.00 104.15      A  C
ATOM   1959  CG1  VAL A 377      57.851  44.919   1.013  1.00 105.26      A  C
ATOM   1960  CG2  VAL A 377      56.189  46.785   0.757  1.00 107.73      A  C
ATOM   1961  C    VAL A 377      56.221  46.138  -2.193  1.00 101.71      A  C
ATOM   1962  O    VAL A 377      55.892  45.290  -3.032  1.00 101.04      A  O
ATOM   1963  N    LEU A 378      55.590  47.301  -2.038  1.00  99.52      A  N
ATOM   1964  CA   LEU A 378      54.459  47.663  -2.879  1.00  97.29      A  C
ATOM   1965  CB   LEU A 378      54.082  49.125  -2.667  1.00  96.55      A  C
ATOM   1966  CG   LEU A 378      52.752  49.385  -1.959  1.00  98.02      A  C
ATOM   1967  CD1  LEU A 378      52.570  48.431  -0.793  1.00  96.23      A  C
ATOM   1968  CD2  LEU A 378      52.723  50.822  -1.478  1.00 101.23      A  C
ATOM   1969  C    LEU A 378      54.868  47.440  -4.316  1.00  97.23      A  C
ATOM   1970  O    LEU A 378      54.041  47.107  -5.164  1.00  96.30      A  O
ATOM   1971  N    GLU A 379      56.168  47.603  -4.556  1.00  97.66      A  N
ATOM   1972  CA   GLU A 379      56.768  47.441  -5.871  1.00  96.85      A  C
ATOM   1973  CB   GLU A 379      57.680  48.643  -6.171  1.00 100.81      A  C
ATOM   1974  CG   GLU A 379      58.097  48.800  -7.646  1.00 106.97      A  C
ATOM   1975  CD   GLU A 379      59.523  48.320  -7.934  1.00 109.48      A  C
ATOM   1976  OE1  GLU A 379      59.916  48.340  -9.124  1.00 109.75      A  O
ATOM   1977  OE2  GLU A 379      60.241  47.931  -6.977  1.00 109.57      A  O
ATOM   1978  C    GLU A 379      57.578  46.147  -5.930  1.00  94.08      A  C
ATOM   1979  O    GLU A 379      58.433  45.972  -6.790  1.00  98.02      A  O
ATOM   1980  N    HIS A 380      57.319  45.226  -5.022  1.00  87.94      A  N
ATOM   1981  CA   HIS A 380      58.086  44.012  -5.057  1.00  82.56      A  C
ATOM   1982  CB   HIS A 380      58.115  43.358  -3.692  1.00  82.26      A  C
ATOM   1983  CG   HIS A 380      58.890  42.083  -3.666  1.00  82.11      A  C
ATOM   1984  CD2  HIS A 380      60.048  41.756  -3.049  1.00  81.03      A  C
ATOM   1985  ND1  HIS A 380      58.490  40.957  -4.355  1.00  82.96      A  N
ATOM   1986  CE1  HIS A 380      59.368  39.990  -4.161  1.00  82.13      A  C
ATOM   1987  NE2  HIS A 380      60.323  40.449  -3.371  1.00  83.50      A  N
ATOM   1988  C    HIS A 380      57.512  43.065  -6.075  1.00  81.77      A  C
ATOM   1989  O    HIS A 380      56.299  42.965  -6.227  1.00  76.43      A  O
ATOM   1990  N    PRO A 381      58.394  42.359  -6.797  1.00  85.35      A  N
ATOM   1991  CD   PRO A 381      59.862  42.517  -6.709  1.00  88.70      A  C
ATOM   1992  CA   PRO A 381      58.045  41.384  -7.836  1.00  87.28      A  C
ATOM   1993  CB   PRO A 381      59.394  40.734  -8.163  1.00  89.44      A  C
ATOM   1994  CG   PRO A 381      60.351  41.874  -8.008  1.00  89.30      A  C
ATOM   1995  C    PRO A 381      57.004  40.366  -7.385  1.00  85.70      A  C
ATOM   1996  O    PRO A 381      56.473  39.596  -8.175  1.00  85.32      A  O
ATOM   1997  N    TRP A 382      56.698  40.356  -6.110  1.00  84.08      A  N
ATOM   1998  CA   TRP A 382      55.728  39.409  -5.666  1.00  82.35      A  C
ATOM   1999  CB   TRP A 382      56.207  38.778  -4.395  1.00  86.28      A  C
ATOM   2000  CG   TRP A 382      55.528  37.506  -4.138  1.00  93.30      A  C
ATOM   2001  CD2  TRP A 382      54.759  37.165  -2.973  1.00  94.03      A  C
ATOM   2002  CE2  TRP A 382      54.346  35.816  -3.124  1.00  96.26      A  C
ATOM   2003  CE3  TRP A 382      54.381  37.865  -1.816  1.00  90.54      A  C
ATOM   2004  CD1  TRP A 382      55.545  36.386  -4.935  1.00  97.22      A  C
ATOM   2005  NE1  TRP A 382      54.836  35.364  -4.327  1.00  98.14      A  N
ATOM   2006  CZ2  TRP A 382      53.577  35.156  -2.152  1.00  95.12      A  C
ATOM   2007  CZ3  TRP A 382      53.618  37.209  -0.855  1.00  88.54      A  C
ATOM   2008  CH2  TRP A 382      53.226  35.870  -1.029  1.00  91.88      A  C
ATOM   2009  C    TRP A 382      54.403  40.100  -5.451  1.00  81.95      A  C
ATOM   2010  O    TRP A 382      53.381  39.672  -5.967  1.00  81.84      A  O
ATOM   2011  N    ILE A 383      54.420  41.178  -4.684  1.00  81.87      A  N
ATOM   2012  CA   ILE A 383      53.199  41.933  -4.427  1.00  82.97      A  C
ATOM   2013  CB   ILE A 383      53.521  43.351  -3.917  1.00  84.29      A  C
ATOM   2014  CG2  ILE A 383      52.270  44.241  -4.004  1.00  84.19      A  C
ATOM   2015  CG1  ILE A 383      54.058  43.272  -2.483  1.00  83.30      A  C
```

Figure 4GG

```
ATOM   2016  CD1  ILE A 383      55.353  42.486  -2.319  1.00   80.07      A    C
ATOM   2017  C    ILE A 383      52.465  42.061  -5.740  1.00   82.79      A    C
ATOM   2018  O    ILE A 383      51.281  41.784  -5.874  1.00   79.23      A    O
ATOM   2019  N    THR A 384      53.212  42.493  -6.724  1.00   84.74      A    N
ATOM   2020  CA   THR A 384      52.664  42.663  -8.035  1.00   87.97      A    C
ATOM   2021  CB   THR A 384      53.586  43.585  -8.817  1.00   89.41      A    C
ATOM   2022  OG1  THR A 384      54.912  43.035  -8.818  1.00   91.34      A    O
ATOM   2023  CG2  THR A 384      53.637  44.956  -8.143  1.00   89.54      A    C
ATOM   2024  C    THR A 384      52.553  41.288  -8.693  1.00   90.25      A    C
ATOM   2025  O    THR A 384      53.473  40.471  -8.589  1.00   91.06      A    O
ATOM   2026  N    ALA A 385      51.417  41.050  -9.349  1.00   93.14      A    N
ATOM   2027  CA   ALA A 385      51.109  39.799 -10.053  1.00   95.90      A    C
ATOM   2028  CB   ALA A 385      52.380  38.978 -10.303  1.00   96.67      A    C
ATOM   2029  C    ALA A 385      50.137  39.025  -9.182  1.00   97.63      A    C
ATOM   2030  O    ALA A 385      48.932  39.288  -9.213  1.00   96.06      A    O
ATOM   2031  N    ASN A 386      50.658  38.060  -8.425  1.00  100.68      A    N
ATOM   2032  CA   ASN A 386      49.819  37.302  -7.514  1.00  101.83      A    C
ATOM   2033  CB   ASN A 386      50.599  36.164  -6.830  1.00  100.85      A    C
ATOM   2034  CG   ASN A 386      52.090  36.428  -6.773  1.00  101.11      A    C
ATOM   2035  OD1  ASN A 386      52.516  37.488  -6.319  1.00  102.88      A    O
ATOM   2036  ND2  ASN A 386      52.893  35.465  -7.233  1.00   98.39      A    N
ATOM   2037  C    ASN A 386      49.468  38.399  -6.534  1.00  102.28      A    C
ATOM   2038  O    ASN A 386      50.257  38.760  -5.666  1.00  100.95      A    O
ATOM   2039  N    SER A 387      48.288  38.964  -6.732  1.00  103.93      A    N
ATOM   2040  CA   SER A 387      47.801  40.056  -5.916  1.00  105.55      A    C
ATOM   2041  CB   SER A 387      48.691  41.282  -6.108  1.00  103.48      A    C
ATOM   2042  OG   SER A 387      48.125  42.430  -5.495  1.00  104.49      A    O
ATOM   2043  C    SER A 387      46.408  40.370  -6.422  1.00  108.91      A    C
ATOM   2044  O    SER A 387      46.300  40.367  -7.667  1.00  112.21      A    O
TER    2046       SER A 387                                                A
ATOM   2047  O5'  ADN B   1      37.122  43.331  20.396  1.00  110.17      B    O
ATOM   2048  C5'  ADN B   1      36.390  42.153  20.753  1.00  112.35      B    C
ATOM   2049  C4'  ADN B   1      35.872  41.464  19.511  1.00  112.18      B    C
ATOM   2050  O4'  ADN B   1      34.847  42.283  18.886  1.00  111.86      B    O
ATOM   2051  C1'  ADN B   1      34.942  42.172  17.472  1.00  110.02      B    C
ATOM   2052  N9   ADN B   1      35.095  43.513  16.891  1.00  106.02      B    N
ATOM   2053  C4   ADN B   1      34.668  43.897  15.637  1.00  103.78      B    C
ATOM   2054  N3   ADN B   1      34.090  43.122  14.693  1.00  103.70      B    N
ATOM   2055  C2   ADN B   1      33.783  43.846  13.620  1.00  102.28      B    C
ATOM   2056  N1   ADN B   1      33.968  45.162  13.398  1.00   98.04      B    N
ATOM   2057  C6   ADN B   1      34.548  45.910  14.365  1.00   95.63      B    C
ATOM   2058  N6   ADN B   1      34.711  47.216  14.152  1.00   90.44      B    N
ATOM   2059  C5   ADN B   1      34.936  45.257  15.549  1.00   98.62      B    C
ATOM   2060  N7   ADN B   1      35.560  45.711  16.703  1.00   97.18      B    N
ATOM   2061  C8   ADN B   1      35.640  44.642  17.462  1.00  100.81      B    C
ATOM   2062  C2'  ADN B   1      36.072  41.192  17.150  1.00  112.86      B    C
ATOM   2063  O2'  ADN B   1      35.501  39.925  16.877  1.00  116.91      B    O
ATOM   2064  C3'  ADN B   1      36.916  41.256  18.426  1.00  113.20      B    C
ATOM   2065  O3'  ADN B   1      37.655  40.060  18.676  1.00  113.89      B    O
TER    2066       ADN B   1                                                B
END
```

US 7,809,541 B2

CRYSTAL STRUCTURE OF AURORA-2 PROTEIN AND BINDING POCKETS THEREOF

This application is a divisional of U.S. patent application Ser. No. 10/979,375, filed Nov. 1, 2004; Confirmation No. 4847, and issued as U.S. Pat. No. 7,361,492, which is a continuation of PCT Application No. PCT/US03/13605, filed May 1, 2003, which claims benefit of U.S. Provisional Application No. 60/377,510, filed May 1, 2002

TECHNICAL FIELD OF THE INVENTION

The present invention provides crystalline molecules or molecular complexes which comprise binding pockets of Aurora-2 or its homologues. The present invention also provides crystals comprising Aurora-2. This invention also provides methods of using the structure coordinates to solve the structure of homologous proteins or protein complexes. In addition, this invention provides methods of using the structure coordinates to design compounds, including inhibitory compounds and antibodies, that bind to Aurora-2 or homologues thereof.

BACKGROUND OF THE INVENTION

Protein kinases mediate intracellular signal transduction by causing a phosphoryl transfer from a nucleoside triphosphate to a protein acceptor involved in a signaling pathway. There are a number of kinases and pathways through which extracellular and other stimuli cause a variety of cellular responses to occur inside the cell. Examples of such stimuli include environmental and chemical stress signals (e.g., osmotic shock, heat shock, ultraviolet radiation, bacterial endotoxin, $H_2O_2$), cytokines (e.g., interleukin-1 (IL-1) and tumor necrosis factor-α (TNF-α)), growth factors (e.g., granulocyte macrophage-colony-stimulating factor (GM-CSF), and fibroblast growth factor (FGF). An extracellular stimulus may affect one or more cellular responses related to cell growth, migration, differentiation, secretion of hormones, activation of transcription factors, muscle contraction, glucose metabolism, control of protein synthesis and regulation of cell cycle.

Many disease states are associated with abnormal cellular responses triggered by protein kinase-mediated events. These diseases include autoimmune diseases, inflammatory diseases, neurological and neurodegenerative diseases, cancer, cardiovascular diseases, allergies and asthma, Alzheimer's disease and hormone-related diseases. Thus, an understanding of the structure, function, and inhibition of kinase activity could lead to useful human therapeutics.

Among medically important kinases are the serine/threonine kinases. The serine/threonine kinase family include the mammalian mitogen-activated protein (MAP) kinases. MAP kinases are activated by dual phosphorylation of threonine and tyrosine at the Thr-X-Tyr segment in the activation loop. Members of the MAP kinase family also share sequence similarity and conserved structural domains, and include the extracellular-signal regulated kinases (ERKs), Jun N-terminal kinases (JNKs) and p38 kinases. MAP kinases also phosphorylate various substrates including transcription factors, which in turn regulate the expression of specific sets of genes and mediate a specific response to the stimulus.

Another important group in the serine/threonine kinase family includes a subgroup of three closely related serine/threonine protein kinases, the Aurora kinases. The Aurora kinases play a key role in protein phosphorylation events that regulate the mitotic phase of the cell cycle. Aurora-2, for example, is up-regulated during the M phase of the cell cycle and localizes to the spindle pole during mitosis, suggesting a possible involvement in centrosomal functions. The Aurora kinases share a common structure, including a highly-conserved catalytic domain, and a very short N-terminal domain that varies in size (R. Giet and C. Prigent, *J. Cell Sci.*, 112, pp. 3591-3601 (1999)). The N-terminal domains do not share any sequence similarity. The Aurora kinases are overexpressed in various types of cancer, such as colon, breast and other solid tumors (for a review see T. M. Goepfert and B. R. Brinkley, *Curr. Top. Dev. Biol.*, 49, pp. 331-342 (2000)). Even more importantly, both the Aurora-1 and -2 genes are amplified in breast and colorectal cancers whereas the Aurora-3 gene is located in a region that is rearranged or deleted in several cancer cells. Overexpression of Aurora-2 in rodent fibroblasts induces transformation, indicating that Aurora-2 is oncogenic. Recently, Aurora-2 mRNA expression has been linked to chromosomal instability in human breast cancers (Y. Miyoshi et al., *Int. J. Cancer*, 92, pp. 370-373 (2001)).

Accordingly, there has been an interest in finding inhibitors of Aurora-1, Aurora-2 or Aurora-3 that are effective as therapeutic agents. A challenge has been to find protein kinase inhibitors that act in a selective manner for the Aurora family kinases. Since there are numerous protein kinases involved in a variety of cellular responses, non-selective inhibitors may lead to undesirable side effects. In this regard, the three-dimensional structure of the kinase would assist in the rational design of inhibitors. The determination of the amino acid residues in Aurora-2 binding pockets and the determination of the shape of those binding pockets would allow one to design selective inhibitors that bind favorably to this class of enzymes. The determination of the amino acid residues in Aurora-2 binding pockets and the determination of the shape of those binding pockets would also allow one to design inhibitors that can bind selectively to Aurora-1, Aurora-2 or Aurora-3, or any combination thereof.

Despite the fact that the genes for various Aurora-1, Aurora-2 and Aurora-3 have been isolated and the amino acid sequences of Aurora-1, Aurora-2 and Aurora-3 proteins are known, the X-ray crystal structural coordinate information of Aurora-1, Aurora-2 or Aurora-3 protein has not yet been described. Such information would be useful in identifying and designing therapeutic inhibitors of the Aurora kinases or homologues thereof.

SUMMARY OF THE INVENTION

Applicants have solved this problem by providing, for the first time, the crystal structures of Aurora-2-inhibitor complexes and the crystal structure of Aurora-2 bound to adenosine. The present invention provides crystalline molecules or molecular complexes comprising Aurora-2 binding pockets, or Aurora-2-like binding pockets that have similar three-dimensional shapes. In one embodiment, the molecules or molecular complexes are Aurora-2 proteins or homologues, or Aurora-2 protein complexes or homologues thereof. In another embodiment, the molecules or molecular complexes are Aurora-2 kinase domains or homologues thereof, or Aurora-2 kinase domain complexes or homologues thereof.

The invention also provides crystal compositions comprising Aurora-2 protein, Aurora-2 kinase domain or homologues thereof in the presence or absence of a chemical entity. The invention also provides a method of crystallizing Aurora-2 protein, Aurora-2 protein complex, or homologues thereof.

The invention further provides a computer comprising a data storage medium which comprises the structure coordinates of molecules and molecular complexes comprising all or part of the Aurora-2 binding pockets or Aurora-2-like binding pockets. Such storage medium, when read and utilized by a computer programmed with appropriate software, displays on a computer screen or similar viewing device, a three-dimensional graphical representation of a molecule or molecular complex comprising such binding pockets.

The invention provides methods for screening, designing, optimizing, evaluating and identifying compounds which bind to the molecules or molecular complexes or their binding pockets. Such compounds are potential inhibitors of Aurora-2 or its homologues. Such methods can be used to identify agonist or antagonist of Aurora-2 and its homologues.

The invention also provides a method for determining at least a portion of the three-dimensional structure of molecules or molecular complexes which contain at least some structurally similar features to Aurora-2, particularly Aurora-2 homologues. This is achieved by using at least some of the structure coordinates obtained from the Aurora-2 complexes.

BRIEF DESCRIPTION OF THE DRAWINGS

The following abbreviations are used in FIGS. 1-4:

"Atom type" refers to the element whose coordinates are measured. The first letter in the column defines the element.

"Resid" refers to the amino acid residue identity in the molecular model.

"X, Y, Z" define the atomic position of the element measured.

"B" is a thermal factor that measures movement of the atom around its atomic center.

"Occ" is an occupancy factor that refers to the fraction of the molecules in which each atom occupies the position specified by the coordinates. A value of "1" indicates that each atom has the same conformation, i.e., the same position, in the molecules.

"Mol" refers to the molecule in the asymmetric unit.

FIG. 1A to 1HH lists the atomic structure coordinates for the Aurora-2-(5-Cyclopropyl-2H-pyrazol-3-yl)-(2-phenyl-quinazolin-4-yl)-amine inhibitor complex as derived by X-ray diffraction from the crystal.

FIG. 2A to 2HH lists the atomic structure coordinates for the Aurora-2-(5-Methylthiazol-2-yl)-(2-phenyl-quinazolin-4-yl)-amine inhibitor complex as derived by X-ray diffraction from the crystal.

FIG. 3A to 3GG lists the atomic structure coordinates for the Aurora-2-(5-Methyl-2H-pyrazol-3-yl)-(2-(pyridin-3-yl-methylamino)-quinazolin-4-yl)-amine inhibitor complex as derived by X-ray diffraction from the crystal.

FIG. 4A to 4GG lists the atomic structure coordinates for the Aurora-2-adenosine complex as derived by X-ray diffraction from the crystal.

Figure 5:
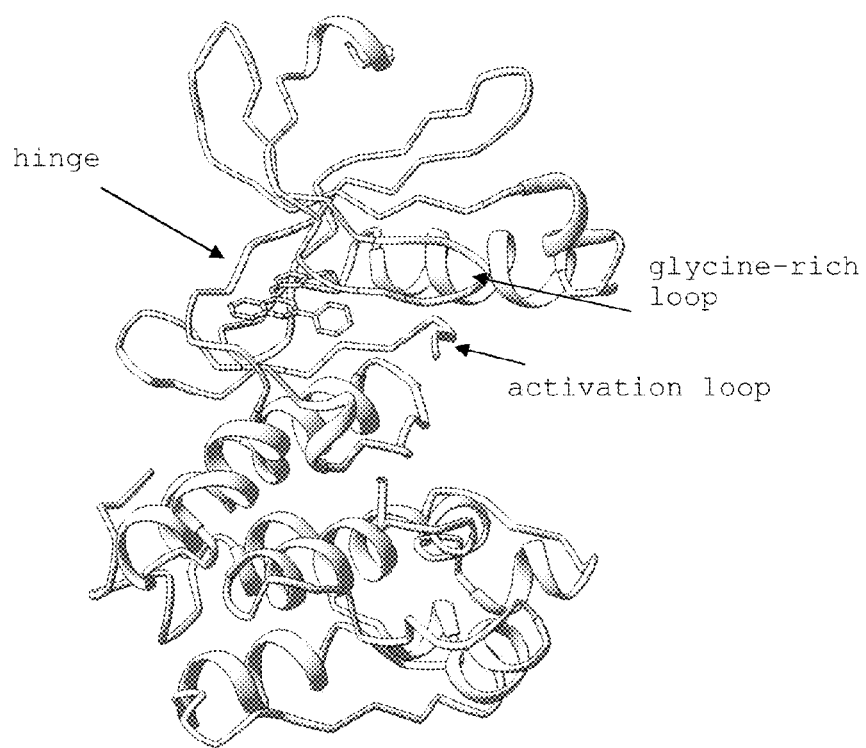

FIG. 5 depicts a ribbon diagram of the overall fold of Aurora-2-(5-Cyclopropyl-2H-pyrazol-3-yl)-(2-phenyl-quinazolin-4-yl)-amine complex. The N-terminal lobe of the Aurora-2 catalytic domain corresponds to the β-strand sub-domain and encompasses amino acid residues 127 to 215. The α-helical sub-domain corresponds to amino acid residues 216 to 390. Key features of the kinase-fold such as the hinge (approximately amino acid residues 132 to 135), glycine rich loop (approximately amino acid residues 140 to 149) and activation loop or phosphorylation lip (approximately amino acid residues 272 to 289) are indicated. In each of the Aurora-2 crystal structures some of the amino acid residues at the N-terminus (~107-126), C-terminus (~391-403) and activation loop (~279-289) were disordered. They exhibited only weak electron density and could not be fitted.

Figure 6:
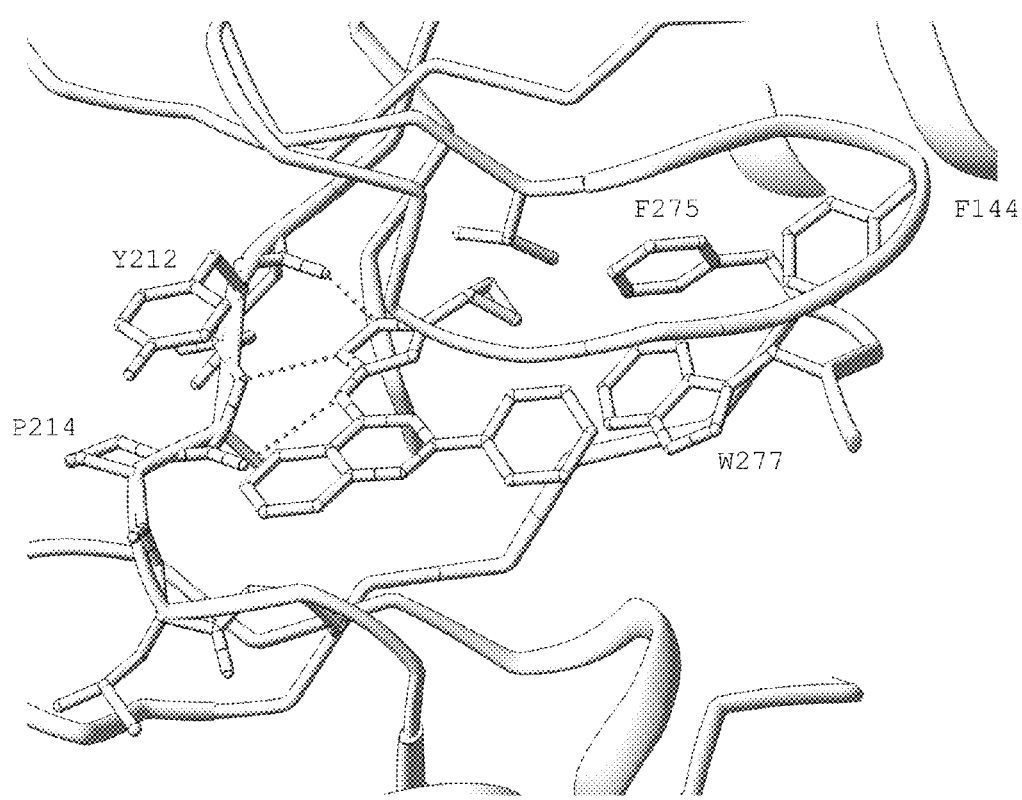

FIG. 6 shows a detailed representation of pockets in the catalytic active site of the Aurora-2-(5-Cyclopropyl-2H-pyrazol-3-yl)-(2-phenyl-quinazolin-4-yl)-amine complex.

Figure 7:
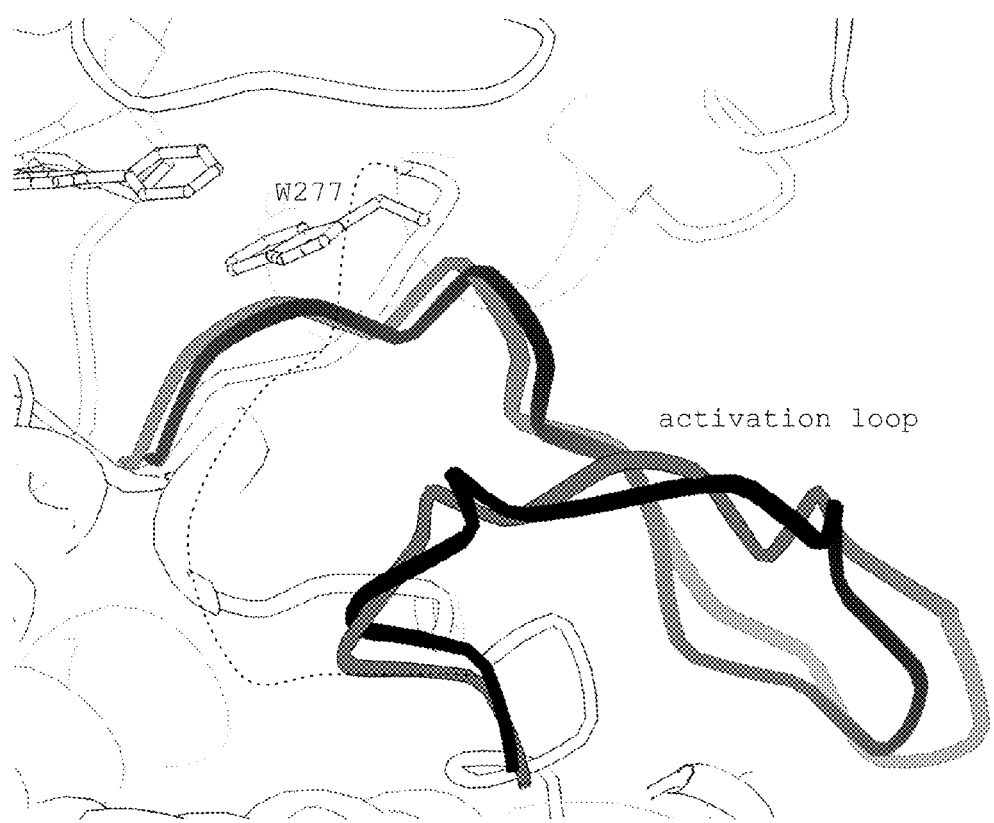

FIG. 7 shows a comparison between the activation loops of Aurora-2-(5-Cyclopropyl-2H-pyrazol-3-yl)-(2-phenyl-quinazolin-4-yl)-amine complex in white, unphosphorylated GSK-3β in grey (ter Haar, E. et al., Nat. Struct. Biol. 8, 593-596 (2001)), and activated substrate-bound human CDK2 in black (PDB Accession number 1B38).

Figure 8:

FIG. 8 shows that in each of the Aurora-2-inhibitor crystal structures, the Aurora-2 catalytic active site is partially occupied by the activation loop region (residues 275-279) which forms a unique hydrophobic pocket in the Aurora-2 catalytic active site. In comparison (see FIG. 7) the activation loops of other kinases adopt a more extended and "open" conformation. Residue W277 is conserved in the Aurora-1, Aurora-2 and Aurora-3 catalytic active sites and plays an important role in forming this unique hydrophobic pocket. FIGS. 8A, B, C and D represent the Aurora-2-adenosine, Aurora-2-(5-Cyclopropyl-2H-pyrazol-3-yl)-(2-phenyl-quinazolin-4-yl)-amine, Aurora-2-(5-Methyl-2H-pyrazol-3-yl)-[2-(pyridin-3-ylmethylamino)-quinazolin-4-yl]-amine, Aurora-2-(5-Methylthiazol-2-yl)-(2-phenyl-quinazolin-4-yl)-amine complexes, respectively.

Figure 9:
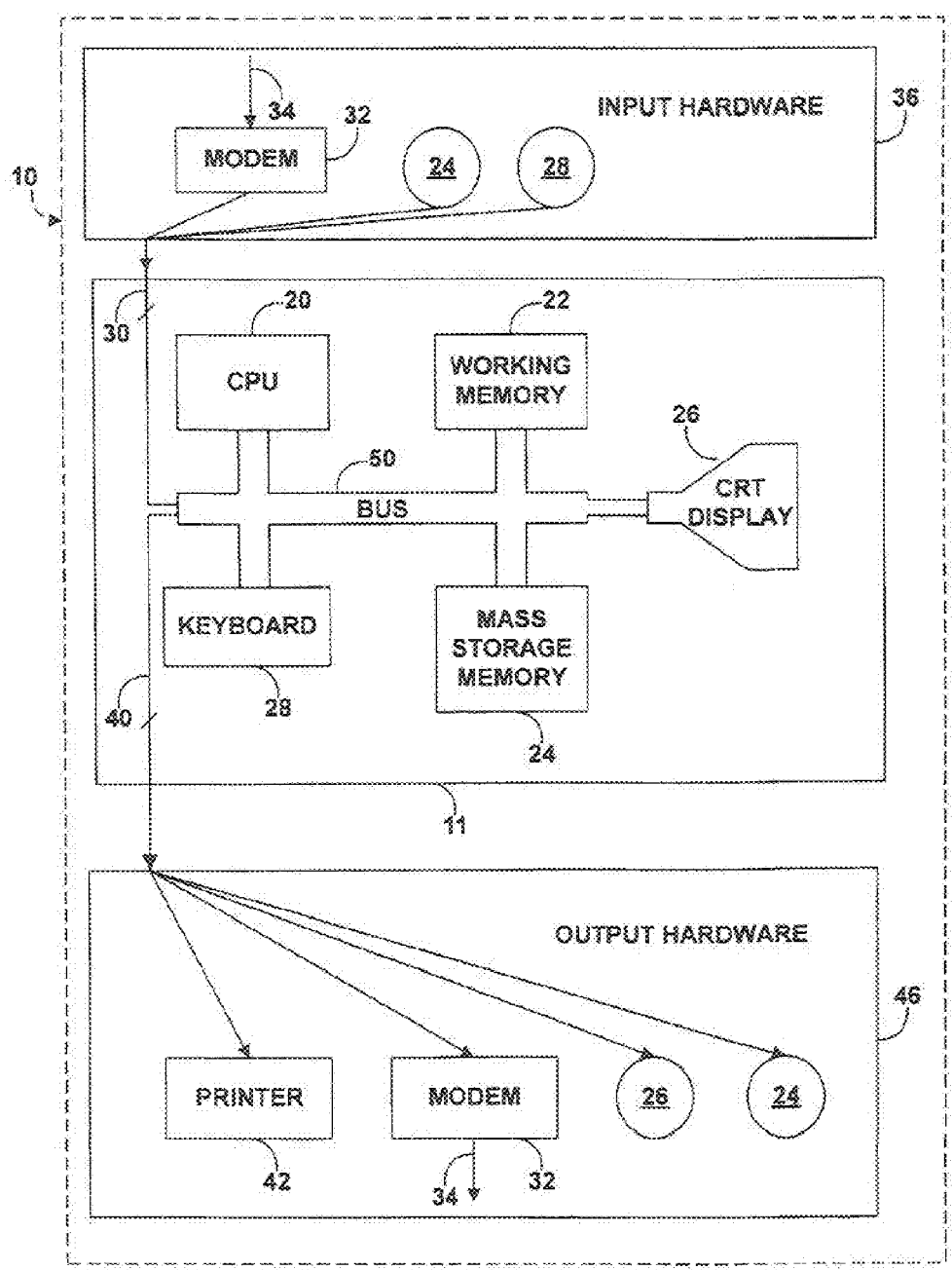
Figure 10:
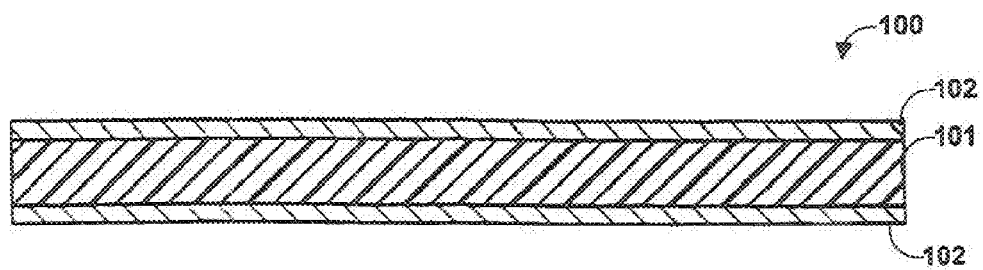
Figure 11:
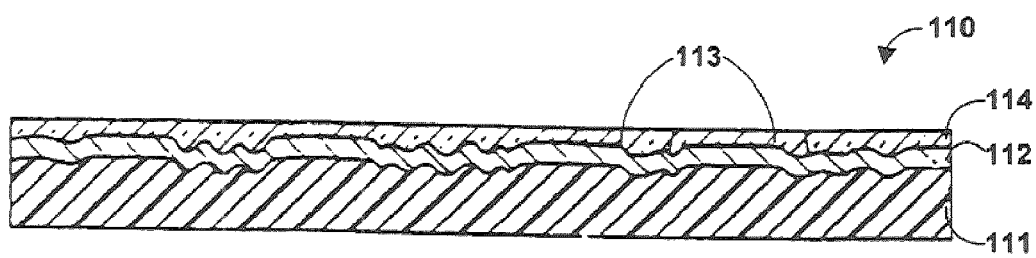

FIG. 9 shows a diagram of a system used to carry out the instructions encoded by the storage medium of FIGS. 10 and 11.

FIG. 10 shows a cross section of a magnetic storage medium.

FIG. 11 shows a cross section of an optically-readable data storage medium.

DETAILED DESCRIPTION OF THE INVENTION

In order that the invention described herein may be more fully understood, the following detailed description is set forth.

Throughout the specification, the word "comprise", or variations such as "comprises" or "comprising" will be understood to imply the inclusion of a stated integer or groups of integers but not exclusion of any other integer or groups of integers.

The following abbreviations are used throughout the application:

| | |
|---|---|
| A = Ala = Alanine | T = Thr = Threonine |
| V = Val = Valine | C = Cys = Cysteine |
| L = Leu = Leucine | Y = Tyr = Tyrosine |
| I = Ile = Isoleucine | N = Asn = Asparagine |
| P = Pro = Proline | Q = Gln = Glutamine |
| F = Phe = Phenylalanine | D = Asp = Aspartic Acid |
| W = Trp = Tryptophan | E = Glu = Glutamic Acid |
| M = Met = Methionine | K = Lys = Lysine |
| G = Gly = Glycine | R = Arg = Arginine |
| S = Ser = Serine | H = His = Histidine |

As used herein, the following definitions shall apply unless otherwise indicated.

The term "about" when used in the context of RMSD values takes into consideration the standard error of the RMSD value, which is ±0.1 Å.

The term "associating with" refers to a condition of proximity between a chemical entity or compound, or portions thereof, and a binding pocket or binding site on a protein. The association may be non-covalent—wherein the juxtaposition is energetically favored by hydrogen bonding or van der Waals or electrostatic interactions—or it may be covalent.

The term "ATP analogue" refers to a compound derived from adenosine-5'-triphosphate (ATP). The compound can be ADP, or a non-hydrolyzable analogue, such as, but not limited to adenylyl imidodiphosphate (AMPPNP). The analogue may be in complex with magnesium or manganese ions.

The term "Aurora protein" refers to kinases from the Aurora kinase family. Examples of this family of kinases include but are not limited to Aurora-1, Aurora-2, and Aurora-3.

The "Aurora-2 ATP-binding pocket" refers to a binding pocket of a molecule or molecular complex defined by the structure coordinates of a certain set of amino acid residues present in the Aurora-2 structure, as described below. In general, the ligand for the ATP-binding pocket is a nucleotide such as ATP. This binding pocket is in the catalytic active site of the kinase domain. In the protein kinase family, the ATP-binding pocket is generally located at the interface of the α-helical and β-strand sub-domains, and is bordered by the glycine rich loop and the hinge (See, Xie et al., Structure, 6, pp. 983-991 (1998), incorporated herein by reference).

The term "Aurora-2 kinase domain" or "Aurora-2-like kinase domain" refers to the catalytic domain of Aurora-2 or Aurora-2-like kinase, respectively. The kinase domain includes, for example, the catalytic active site which comprises the catalytic residues, the activation loop or phosphorylation lip, the DFGWSxxxxxxxRxTxCGTxDYLPPE or DFG motif, and the glycine-rich phosphate anchor or glycine-rich loop (See, Xie et al., Structure, 6, pp. 983-991 (1998); R. Giet and C. Prigent, J. Cell Sci., 112, pp. 3591-3601 (1999), incorporated herein by reference). The kinase domain in the Aurora-2 protein comprises amino acid residues selected from the group consisting of amino acids residues 107-403, 127-403, 107-387, and 127-387 according to SEQ ID NO: 1.

The term "Aurora-2-like" refers to all or a portion of a molecule or molecular complex that has a commonality of shape to all or a portion of the Aurora-2 protein. For example, in the Aurora-2-like ATP-binding pocket, the commonality of shape is defined by a root mean square deviation of the structure coordinates of the backbone atoms between the amino acids in the Aurora-2-like ATP-binding pocket and the amino acids in the Aurora-2 ATP-binding pocket (as set forth in FIG. 1, 2, 3 or 4). Compared to an amino acid in the Aurora-2 ATP-binding pocket, the corresponding amino acids in the Aurora-2-like ATP-binding pocket may or may not be identical. Depending on the Aurora-2 amino acid residues that define the Aurora-2-ATP binding pocket, one skilled in the art would be able to locate the corresponding amino acid residues that define an Aurora-2-like-ATP binding pocket in a protein based upon sequence and structural homology.

The term "Aurora-2 protein complex" or "Aurora-2 homologue complex" refers to a molecular complex formed by associating the Aurora-2 protein or Aurora-2 homologue with a chemical entity, for example, a ligand, a substrate, nucleotide triphosphate, nucleotide diphosphate, phosphate, an agonist or antagonist, inhibitor, antibody, drug or compound. In one embodiment, the chemical entity is selected from the group consisting of ATP, an ATP analogue, a nucleotide triphosphate and ATP-binding pocket inhibitor. In another embodiment, the inhibitor is an ATP analogue such as MgAMP-PNP (adenylyl imidodiphosphate), adenosine, (5-Methyl-2H-pyrazol-3-yl)-(2-(pyridin-3-ylmethylamino)-quinazolin-4-yl)-amine, (5-Cyclopropyl-2H-pyrazol-3-yl)-(2-phenyl-quinazolin-4-yl)-amine or (5-methylthiazol-2-yl)-(2-phenyl-quinazolin-4-yl)-amine.

The term "binding pocket" refers to a region of a molecule or molecular complex, that, as a result of its shape and charge, favorably associates with another chemical entity or compound. The term "pocket" includes, but is not limited to, cleft, channel or site. Aurora-2 or Aurora-2-like molecules may have binding pockets which include, but are not limited to, peptide or substrate binding, ATP-binding and antibody binding sites.

The term "catalytic active site" or "active site" refers to the portion of the protein kinase to which nucleotide substrates bind. For example, the catalytic active site of Aurora-2 is at the interface between the N-terminal, β-strand sub-domain and the C-terminal, α-helical sub-domain, and is bordered by the glycine rich loop and the hinge (See, Xie et al., Structure, 6, pp. 983-991 (1998).

The term "chemical entity" refers to chemical compounds, complexes of at least two chemical compounds, and fragments of such compounds or complexes. The chemical entity may be, for example, a ligand, a substrate, a nucleotide triphosphate, a nucleotide diphosphate, phosphate, a nucleotide, an agonist, antagonist, inhibitor, antibody, drug, peptide, protein or compound.

"Conservative substitutions" refers to residues that are physically or functionally similar to the corresponding reference residues. That is, a conservative substitution and its reference residue have similar size, shape, electric charge, chemical properties including the ability to form covalent or hydrogen bonds, or the like. Preferred conservative substitutions are those fulfilling the criteria defined for an accepted point mutation in Dayhoff et al., Atlas of Protein Sequence and Structure, 5, pp. 345-352 (1978 & Supp.), which is incorporated herein by reference. Examples of conservative substitutions are substitutions including but not limited to the following groups: (a) valine, glycine; (b) glycine, alanine; (c) valine, isoleucine, leucine; (d) aspartic acid, glutamic acid; (e) asparagine, glutamine; (f) serine, threonine; (g) lysine, arginine, methionine; and (h) phenylalanine, tyrosine.

The term "corresponding amino acid" or "residue which corresponds to" refers to a particular amino acid or analogue thereof in an Aurora-2 protein or Aurora-2 homologue that is identical or functionally equivalent to an amino acid in Aurora-2 according to SEQ ID NO: 1.

Methods for identifying a corresponding amino acid are known in the art and are based upon sequence, structural alignment, its functional position or a combination thereof as compared to the Aurora-2 kinase. For example, corresponding amino acids may be identified by superimposing the backbone atoms of the amino acids in Aurora-2 and the Aurora-2 homologue using well known software applications, such as QUANTA (Accelrys, San Diego, Calif. ©2001, 2002). The corresponding amino acids may also be identified using sequence alignment programs such as the "bestfit" program available from the Genetics Computer Group which uses the local homology algorithm described by Smith and Waterman in Advances in Applied Mathematics 2, 482 (1981), which is incorporated herein by reference.

The term "crystallization solution" refers to a solution which promotes crystallization comprising at least one agent including a buffer, one or more salts, a precipitating agent, one or more detergents, sugars or organic compounds, lanthanide ions, a poly-ionic compound, and/or stabilizer.

The term "domain" refers to a portion of the Aurora-2 protein or homologue that can be separated based on its biological function, for example, catalysis. The domain may comprise a binding pocket, a sequence or a structural motif.

The term "fitting operation" refers to an operation that utilizes the structure coordinates of a chemical entity, binding pocket, molecule or molecular complex, or portion thereof, to associate the chemical entity with the binding pocket, molecule or molecular complex, or portion thereof. This may be achieved by positioning, rotating or translating the chemical entity in the binding pocket to match the shape and electrostatic complementarity of the binding pocket. Covalent interactions, non-covalent interactions such as hydrogen bond, electrostatic, hydrophobic, van der Waals interactions, and non-complementary electrostatic interactions such as repulsive charge-charge, dipole-dipole and charge-dipole interactions may be optimized. Alternatively, one may minimize the deformation energy of binding of the chemical entity to the binding pocket.

The term "generating a three-dimensional structure" or "generating a three-dimensional representation" refers to converting the lists of structure coordinates into structural models or graphical representation in three-dimensional space. This can be achieved through commercially or publicly available software. The three-dimensional structure may be displayed or used to perform computer modeling or fitting operations. In addition, the structure coordinates themselves may be used to perform computer modeling and fitting operations.

The term "homology model" refers to a structural model derived from known three-dimensional structure(s). Generation of the homology model, termed "homology modeling", can include sequence alignment, residue replacement, residue conformation adjustment through energy minimization, or a combination thereof.

The term "homologue of Aurora-2" or "Aurora-2 homologue" refers to a molecule that is homologous to Aurora-2 by structure or sequence, but retains the kinase activity of an Aurora protein. Examples of homologues include but are not limited to human Aurora-2 and Aurora-2 from another species with conservative substitutions, additions, deletions or a combination thereof; or another member of the Aurora family of protein kinases including, but not limited to, Aurora-1 and Aurora-3, with conservative substitutions, additions, deletions or a combination thereof.

The term "homologue of Aurora-2 kinase domain" or "Aurora-2 kinase domain homologue" refers to a molecule having amino acids which correspond to the amino acids in the Aurora-2 kinase domain. Examples of homologues include but are not limited to the kinase domain of human Aurora-2 and Aurora-2 from another species with conservative substitutions; or the kinase domain of another member of the Aurora family of protein kinases including, but not limited to, Aurora-1 and Aurora-3, or with conservative substitutions.

The term "molecular complex" or "complex" refers to a molecule associated with at least one chemical entity.

The term "motif" refers to a portion of the Aurora-2 protein or homologue that defines a structural compartment or carries out a function in the protein, for example, catalysis, structural stabilization, or phosphorylation. The motif may be conserved in sequence, structure and function. The motif can be contiguous in primary sequence or three-dimensional space. Examples of a motif include but are not limited to the phosphorylation lip or activation loop, the glycine-rich phosphate anchor loop, the catalytic loop, the DFG or DFGWSxxxxxxxRxTxCGTxDYLPPE loop (See, Xie et al., Structure, 6, pp. 983-991 (1998); R. Giet and C. Prigent, J. Cell Sci., 112, pp. 3591-3601 (1999)), and the degradation box.

The term "part of a binding pocket" refers to less than all of the amino acid residues that define the binding pocket. For example, the structure coordinates of residues that constitute part of a binding pocket may be specific for defining the chemical environment of the binding pocket, or useful in designing fragments of an inhibitor that may interact with those residues. For example, the portion of residues may be key residues that play a role in ligand binding, or may be residues that are spatially related and define a three-dimensional compartment of the binding pocket. The residues may be contiguous or non-contiguous in primary sequence.

The term "part of an Aurora-2 kinase domain" or "part of an Aurora-2-like kinase domain" refers to less than all of the Aurora-2 or Aurora-2-like catalytic domain, respectively. The structure coordinates of residues that constitute part of an Aurora-2 or Aurora-2-like kinase domain may be specific for defining the chemical environment of the domain, or useful in designing fragments of an inhibitor that interact with those residues. For example, the portion of residues may be residues that play a role in ligand binding, or may be residues that are spatially related and define a three-dimensional compartment of the domain. The residues may be contiguous or non-contiguous in primary sequence. For example, part of an Aurora-2 kinase domain can be the active site, the DFG or DFGWSxxxxxxxRxTxCGTxDYLPPE motif, the glycine-rich loop, the activation loop, or the catalytic loop (see Xie et al., supra).

The term "part of an Aurora-2 protein" or "part of an Aurora-2 homologue" refers to less than all of the amino acid residues of an Aurora-2 protein or homologue. In one embodiment, part of an Aurora-2 protein or homologue defines the binding pockets, domains, sub-domains, and motifs of the protein or homologue. The structure coordinates of residues that constitute part of an Aurora-2 protein or homologue may be specific for defining the chemical environment of the protein, or useful in designing fragments of an inhibitor that may interact with those residues. The portion of residues may also be residues that are spatially related and define a three-dimensional compartment of a binding pocket, motif or domain. The residues may be contiguous or non-contiguous in primary sequence. For example, the portion of residues may be key residues that play a role in ligand or substrate binding, peptide binding, antibody binding, catalysis, structural stabilization or degradation.

The term "root mean square deviation" or "RMSD" means the square root of the arithmetic mean of the squares of the deviations from the mean. It is a way to express the deviation or variation from a trend or object. For purposes of this invention, the "root mean square deviation" defines the variation in the backbone of a protein from the backbone of Aurora-2, a binding pocket, a motif, a domain, or portion thereof, as defined by the structure coordinates of Aurora-2 described herein. It would be apparent to the skilled worker that the calculation of RMSD involves a standard error.

The term "soaked" refers to a process in which the crystal is transferred to a solution containing a compound of interest.

The term "structure coordinates" refers to Cartesian coordinates derived from mathematical equations related to the patterns obtained on diffraction of a monochromatic beam of X-rays by the atoms (scattering centers) of a protein or protein complex in crystal form. The diffraction data are used to calculate an electron density map of the repeating unit of the crystal. The electron density maps are then used to establish the positions of the individual atoms of the molecule or molecular complex.

The term "sub-domain" refers to a portion of the domain as defined above in the Aurora-2 protein or homologue. The catalytic kinase domain (amino acid residues selected from the group consisting of amino acids residues 107-403, 127-403, 107-387 and 127-387 according to SEQ ID NO: 1) of Aurora-2 is a bi-lobal structure consisting of an N-terminal, β-strand sub-domain (amino acid residues 127 to 215) and a C-terminal, α-helical sub-domain (amino acid residues 216 to 390).

The term "sufficiently homologous to Aurora-2" refers to a protein that has a sequence homology of at least 20% compared to Aurora-2 protein. In one embodiment, the sequence homology is at least 40%.

The term "three-dimensional structural information" refers to information obtained from the structure coordinates. Structural information generated can include the three-dimensional structure or graphical representation of the structure. Structural information can also be generated when subtracting distances between atoms in the structure coordinates, calculating chemical energies for an Aurora-2 molecule or molecular complex or homologues thereof, calculating or minimizing energies for an association of an Aurora-2 molecule or molecular complex or homologues thereof to a chemical entity.

Crystallizable Compositions and Crystals of Aurora-2 Protein and Protein Complexes According to one embodiment, the invention provides a crystallizable composition or crystal comprising Aurora-2 kinase domain or Aurora-2 kinase domain homologue in the presence or absence of a chemical entity. The Aurora-2 kinase domain may be phosphorylated or unphosphorylated. Preferably, the chemical entity is an ATP analogue, nucleotide triphosphate, nucleotide diphosphate, phosphate, or an ATP-binding pocket inhibitor. More preferably, the chemical entity is MgAMP-PNP (adenylyl imidodiphosphate), adenosine, (5-Methyl-2H-pyrazol-3-yl)-(2-(pyridin-3-ylmethylamino)-quinazolin-4-yl)-amine, (5-Cyclopropyl-2H-pyrazol-3-yl)-(2-phenyl-quinazolin-4-yl)-amine or (5-Methylthiazol-2-yl)-(2-phenyl-quinazolin-4-yl)-amine. In another embodiment, the crystal has a unit cell dimension of a=b=87 Å, c=76 Å, $\alpha=\beta=90°$, $\gamma=120°$ and belongs to space group $P3_221$. It will be readily apparent to those skilled in the art that the unit cells of the crystal compositions may deviate ±1-2 Å from the above cell dimensions depending on the deviation in the unit cell calculations.

The Aurora-2 protein or its homologue may be produced by any well-known method, including synthetic methods, such as solid phase, liquid phase and combination solid phase/liquid phase syntheses; recombinant DNA methods, including cDNA cloning, optionally combined with site directed mutagenesis; and/or purification of the natural products. In a preferred embodiment, the protein is overexpressed in a baculovirus system or an *E. coli* system. In a more preferred embodiment, the protein is overexpressed in a baculovirus system.

The invention also provides a method of making crystals of Aurora-2 protein or a homologue thereof in the presence or absence of a chemical entity. Such methods comprise the steps of:

a. producing and purifying Aurora-2 protein;

b. combining said Aurora-2 protein, or a homologue thereof in the presence or absence of a chemical entity with a crystallization solution to produce a crystallizable composition; and c. subjecting said crystallizable composition to conditions which promote crystallization.

The crystallization solution may include, but is not limited to, polyethylene glycol (PEG) at between about 10% to 30% v/v, 100-300 mM ammonium sulphate and a buffer that maintains pH at between about 4.0 and 8.0. In one embodiment, the crystallization solution comprises 25% PEG 3350, 50 mM 2-(N-morpholino) ethanesulfonic acid (MES) at pH 6.0 and 200 mM ammonium sulphate.

According to one embodiment, the crystallizable composition comprises Aurora-2 protein or a homologue thereof in the presence or absence of a chemical entity. In another embodiment, the crystallizable composition comprises Aurora-2 protein and a chemical entity. In one embodiment, the crystallizable composition further comprises a precipitant, polyethylene glycol (PEG) at between about 10 to 30% v/v, 100-300 mM ammonium sulphate and a buffer that maintains pH at between about 4.0 and 8.0, and optionally a reducing agent, such as dithiothreitol (DTT) at between about 1 to 20 mM. The Aurora-2 protein may be phosphorylated or unphosphorylated. The Aurora-2 protein or complex is preferably 85-100% pure prior to forming the composition. More preferably, the Aurora-2 protein or complex is 90-100% pure. Even more preferably, the Aurora-2 protein or complex is 95-100% pure.

In a preferred embodiment, the crystallizable composition comprises unphosphorylated Aurora-2 protein kinase domain, 25% PEG 3350, 50 mM 2-(N-morpholino)ethanesulfonic acid (MES) at pH 6.0, and 200 mM ammonium sulphate. In a more preferred embodiment, the crystallizable composition comprises unphosphorylated Aurora-2 protein kinase domain, 25% PEG 3350, 50 mM 2-(N-morpholino) ethanesulfonic acid (MES) at pH 6.0, 200 mM ammonium sulphate and a chemical entity selected from the group consisting of an inhibitor and substrate analogue.

In another embodiment, the method of making crystals of Aurora-2 proteins or a homologue thereof in the presence or absence of a chemical entity includes the use of a device for promoting crystallizations. Devices for promoting crystallization can include but are not limited to the hanging-drop, sitting-drop, sandwich-drop, dialysis, microbatch or microtube batch devices (U.S. Pat. Nos. 4,886,646, 5,096,676, 5,130,105, 5,221,410 and 5,400,741; Pav et al., *Proteins: Structure, Function, and Genetics*, 20, pp. 98-102 (1994); Chayen, *Acta. Cryst.*, D54, pp. 8-15 (1998), Chayen, *Structure*, 5, pp. 1269-1274 (1997), D'Arcy et al., *J. Cryst. Growth*, 168, pp. 175-180 (1996) and Chayen, *J. Appl. Cryst.*, 30, pp. 198-202 (1997), incorporated herein by reference). The hanging-drop, sitting-drop and some adaptations of the microbatch methods (D'Arcy et al., *J. Cryst. Growth*, 168, pp. 175-180 (1996) and Chayen, *J. Appl. Cryst.*, 30, pp. 198-202 (1997)) produce crystals by vapor diffusion. The hanging drop and sitting drop containing the crystallizable composition is equilibrated against a reservoir containing a higher or lower concentration of precipitant. As the drop approaches equilibrium with the reservoir, the saturation of protein in the solution leads to the formation of crystals.

Microseeding may be used to increase the size and quality of crystals. In this instance, micro-crystals are crushed to yield a stock seed solution. The stock seed solution is diluted in series. Using a needle, glass rod or strand of hair, a small sample from each diluted solution is added to a set of equilibrated drops containing a protein concentration equal to or less than a concentration needed to create crystals without the presence of seeds. The aim is to end up with a single seed crystal that will act to nucleate crystal growth in the drop.

It would be readily apparent to one of skill in the art to vary the crystallization conditions disclosed above to identify other crystallization conditions that would produce crystals of Aurora-2 protein or a homologue thereof in the presence or absence of a chemical entity. Such variations include, but are not limited to, adjusting pH, protein concentration and/or crystallization temperature, changing the identity or concentration of salt and/or precipitant used, using a different method for crystallization, or introducing additives such as detergents (e.g., TWEEN 20 (monolaurate), LDOA, Brji 30 (4 lauryl ether)), sugars (e.g., glucose, maltose), organic compounds (e.g., dioxane, dimethylformamide), lanthanide ions, or poly-ionic compounds that aid in crystallizations. High throughput crystallization assays may also be used to assist in finding or optimizing the crystallization condition.

Binding Pockets of Aurora-2 Protein, Protein Complexes or Homologues Thereof.

As disclosed above, applicants have provided the three-dimensional X-ray crystal structures of three Aurora-2-inhibitor complexes and an Aurora-2-adenosine complex. The crystal structures of Aurora-2 presented here are the first reported within the Aurora subfamily. The invention will be useful for inhibitor design and to study the role of Aurora-1, Aurora-2 and Aurora-3 in cell signaling. The atomic coordinate data is presented in FIGS. 1-4.

In order to use the structure coordinates generated for Aurora-2, its complexes, one of its binding pockets, or an Aurora-2-like binding pocket thereof, it is often times necessary to convert the structure coordinates into a three-dimensional shape. This is achieved through the use of commercially available software that is capable of generating three-dimensional graphical representations of molecules or portions thereof from a set of structure coordinates.

Binding pockets, also referred to as binding sites in the present invention, are of significant utility in fields such as drug discovery. The association of natural ligands or substrates with the binding pockets of their corresponding receptors or enzymes is the basis of many biological mechanisms of action. Similarly, many drugs exert their biological effects through association with the binding pockets of receptors and enzymes. Such associations may occur with all or part of the binding pocket. An understanding of such associations will help lead to the design of drugs having more favorable associations with their target receptor or enzyme, and thus, improved biological effects. Therefore, this information is valuable in designing potential inhibitors of the binding pockets of biologically important targets. The ATP and substrate binding pockets of this invention will be important for drug design.

In one embodiment, part of binding pocket is at least two amino acid residues, preferably, E211 and A213. In another embodiment, the ATP-binding pocket comprises amino acids of L139, L194, L210, E211, A213, L263 and W277 according to any one of FIGS. 1-4. These were common residues found in the ATP-binding pockets of each of the protein complexes described in the present invention.

In another embodiment, the ATP-binding pocket comprises amino acids L139, G140, F144, V147, A160, K162, L194, L210, E211, Y212, A213, P214, L215, T217, R220, L263, A273, and W277 according to the structure of Aurora-2-(5-Methyl-2H-pyrazol-3-yl)-(2-(pyridin-3-ylmethylamino)-quinazolin-4-yl)-amine complex in FIG. 3. In another embodiment, the ATP-binding pocket comprises amino acids L139, G140, F144, V147, A160, K162, L194, L210, E211, Y212, A213, P214, L215, T217, R220, L263, A273, W277 and S278 according to the structure of Aurora-2-(5-Cyclopropyl-2H-pyrazol-3-yl)-(2-phenyl-quinazolin-4-yl)-amine complex in FIG. 1, or Aurora-2-adenosine complex in FIG. 4. In yet another embodiment, the ATP-binding pocket comprises amino acids L139, G140, F144, V147, A160, K162, L194, L210, E211, Y212, A213, P214, L215, T217, R220, L263, A273, W277, S278, and V279 according to the structure of Aurora-2-(5-Methylthiazol-2-yl)-(2-phenyl-quinazolin-4-yl)-amine complex in FIG. 2. The above-identified amino acid residues were within 5 Å ("5 Å sphere amino acids") of the inhibitor bound in the ATP-binding pockets. These residues were identified using the program QUANTA (Molecular Simulations, Inc., San Diego, Calif. ©1998, 2000), O (T. A. Jones et al., *Acta Cryst., A*47, pp. 110-119 (1991)) and RIBBONS (Carson, *J. Appl. Cryst.*, 24, pp. 958-961 (1991)), which allow the display and output of all residues within 5 Å from the inhibitor.

In another embodiment, the ATP-binding pocket comprises amino acids R137, L139, G140, G142, F144, G145, N146, V147, Y148, L149, I158, L159, A160, L161, K162, L194, R195, L208, I209, L210, E211, Y212, A213, P214, L215, T217, V218, Y219, R220, E260, N261, L262, L263, L264, K271, I272, A273, D274, F275 and W277 according to the structure of Aurora-2-(5-Methyl-2H-pyrazol-3-yl)-(2-(pyridin-3-ylmethylamino)-quinazolin-4-yl)-amine complex in FIG. 3. In another embodiment, the ATP-binding pocket comprises amino acids R137, L139, G140, G142, F144, G145, N146, V147, Y148, L149, I158, L159, A160, L161, K162, L194, R195, L208, I209, L210, E211, Y212, A213, P214, L215, T217, V218, Y219, R220, E260, N261, L262, L263, L264, K271, I272, A273, D274, F275, W277, and S278 according to the structure of Aurora-2-(5-Cyclopropyl-2H-pyrazol-3-yl)-(2-phenyl-quinazolin-4-yl)-amine complex in FIG. 1, or Aurora-2-adenosine complex in FIG. 4. In yet another embodiment, the ATP-binding pocket comprises amino acids R137, L139, G140, G142, F144, G145, N146, V147, Y148, L149, I158, L159, A160, L161, K162, L194, R195, L208, I209, L210, E211, Y212, A213, P214, L215, T217, V218, Y219, R220, E260, N261, L262, L263, L264, K271, I272, A273, D274, F275, W277, S278, and V279 according to the structure of Aurora-2-(5-Methylthiazol-2-yl)-(2-phenyl-quinazolin-4-yl)-amine complex in FIG. 2. These amino acids residues were within 8 Å ("8 Å sphere amino acids") of the inhibitor bound in the ATP-binding pockets. These residues were identified using the programs QUANTA, O and RIBBONS, supra.

Using a multiple alignment program to compare each Aurora-2 structure and structures of other members of the protein kinase family (Gerstein et al., *J. Mol. Biol.*, 251, pp. 161-175 (1995), incorporated herein by reference), the above amino acids were identified as the ATP-binding pocket. For the comparison, first, a sequence alignment between members of the protein kinase family including GSK-3β (PDB Accession number 1IO9), p38 (K. P. Wilson et al., *J. Biol. Chem.*, 271, pp. 27696-27700 (1996); Z. Wang et al., *Proc. Natl. Acad. Sci. U.S.A.*, 94, pp. 2327-32 (1997)), cdk2 (PDB Accession number 1B38), SRC (Xu, W., et al., *Cell* 3, pp. 629-638 (1999); PDB Accession number 2SRC), MAPKAP2 (U.S. Provisional application 60/337,513), and ERK2 (Zhang et al., *Nature*, 367, pp. 704-711 (1994); PDB Accession number 1ERK) is performed. Second, a putative core is constructed by superimposing a series of corresponding structures in the protein kinase family. Third, residues of high spatial variation are discarded, and the core alignment is iteratively refined. The amino acids that make up the final core structure have low structural variance and have the same local and global conformation relative to the corresponding residues in the protein family.

Therefore, in another embodiment, the ATP-binding pocket comprises amino acids F133, I135, G136, R137, F144, N146, V147, Y148, L149, A150, R151, E152, I158, L159, A160, L161, K162, V163, V182, E183, Q185, H190, N192, I193, L194, R195, L196, Y197, G198, Y199, F200, V206, Y207, L208, I209, L210, E211, Y212, A213, P214, L215, T217, V218, Y219, R220, E221, D229, E230, Q231, R232, T233, A234, T235, Y236, I237, T238, E239, L240, A241, N242, A243, L244, S245, Y246, C247, H248, S249, K250, R251, V252, I253, H254, R255, D256, I257, K258, P259, E260, N261, L262, L263, L264, G265, S266, G268, E269, L270, K271, I272, A273, D274, F275 and W277 according to the structure of the Aurora-2-(5-Methyl-2H-pyrazol-3-yl)-(2-(pyridin-3-ylmethylamino)-quinazolin-4-yl)-amine complex in FIG. 3.

In another embodiment, the ATP-binding pocket comprises amino acids F133, I135, G136, R137, F144, N146, V147, Y148, L149, A150, R151, E152, I158, L159, A160, L161, K162, V163, V182, E183, Q185, H190, N192, I193, L194, R195, L196, Y197, G198, Y199, F200, V206, Y207, L208, I209, L210, E211, Y212, A213, P214, L215, T217, V218, Y219, R220, E221, D229, E230, Q231, R232, T233, A234, T235, Y236, I237, T238, E239, L240, A241, N242, A243, L244, S245, Y246, C247, H248, S249, K250, R251, V252, I253, H254, R255, D256, I257, K258, P259, E260, N261, L262, L263, L264, G265, S266, G268, E269, L270, K271, I272, A273, D274, F275, W277 and S278 according to the structure of the Aurora-2-(5-Cyclopropyl-2H-pyrazol-3-yl)-(2-phenyl-quinazolin-4-yl)-amine complex in FIG. 1 or Aurora-2-adenosine complex in FIG. 4.

In another embodiment, the ATP-binding pocket comprises amino acids F133, I135, G136, R137, F144, N146, V147, Y148, L149, A150, R151, E152, I158, L159, A160, L161, K162, V163, V182, E183, Q185, H190, N192, I193, L194, R195, L196, Y197, G198, Y199, F200, V206, Y207, L208, I209, L210, E211, Y212, A213, P214, L215, T217, V218, Y219, R220, E221, D229, E230, Q231, R232, T233, A234, T235, Y236, I237, T238, E239, L240, A241, N242, A243, L244, S245, Y246, C247, H248, S249, K250, R251, V252, I253, H254, R255, D256, I257, K258, P259, E260, N261, L262, L263, L264, G265, S266, G268, E269, L270, K271, I272, A273, D274, F275, W277, S278 and V279 according to the structure of the Aurora-2-(5-Methylthiazol-2-yl)-(2-phenyl-quinazolin-4-yl)-amine complex in FIG. 2.

It will be readily apparent to those of skill in the art that the numbering of amino acids in other homologues of Aurora-2 may be different than that set forth for Aurora-2. Corresponding amino acids in homologues of Aurora-2 are easily identified by visual inspection of the amino acid sequences or by using commercially available sequence homology, structural homology or structure superimposition software programs.

Those of skill in the art understand that a set of structure coordinates for a molecule or a molecular-complex or a portion thereof, is a relative set of points that define a shape in three dimensions. Thus, it is possible that an entirely different set of coordinates could define a similar or identical shape. Moreover, slight variations in the individual coordinates will have little effect on overall shape. In terms of binding pockets, these variations would not be expected to significantly alter the nature of ligands that could associate with those pockets.

The variations in coordinates discussed above may be generated as a result of mathematical manipulations of the Aurora-2 structure coordinates. For example, the structure coordinates set forth in FIG. 1, 2, 3 or 4 could be manipulated by crystallographic permutations of the structure coordinates, fractionalization of the structure coordinates, integer additions or subtractions to sets of the structure coordinates, inversion of the structure coordinates or any combination of the above.

Alternatively, modifications in the crystal structure due to mutations, additions, substitutions, and/or deletions of amino acids, or other changes in any of the components that make up the crystal could also account for variations in structure coordinates. If such variations are within a certain root mean square deviation as compared to the original coordinates, the resulting three-dimensional shape is considered encompassed by this invention. Thus, for example, a ligand that binds to the binding pocket of Aurora-2 would also be expected to bind to another binding pocket whose structure coordinates define a shape that falls within the acceptable root mean square deviation.

Various computational analyses may be necessary to determine whether a binding pocket, motif, domain or portion thereof of a molecule or molecular complex is sufficiently similar to the binding pocket, motif, domain or portion thereof of Aurora-2. Such analyses may be carried out using well known software applications, such as ProFit (A. C. R. Martin, SciTech Software, ProFit version 1.8, University College London, http://www.bioinf.org.uk/software), Swiss-Pdb Viewer (Guex et al., *Electrophoresis,* 18, pp. 2714-2723 (1997)), the Molecular Similarity application of QUANTA (Molecular Simulations Inc., San Diego, Calif. © 1998, 2000) and as described in the accompanying User's Guide, which are incorporated herein by reference.

The above programs permit comparisons between different structures, different conformations of the same structure, and different parts of the same structure. The procedure used in QUANTA (Molecular Simulations, Inc., San Diego, Calif. ©1998, 2000) and Swiss-Pdb Viewer to compare structures is divided into four steps: 1) load the structures to be compared; 2) define the atom equivalences in these structures; 3) perform a fitting operation on the structures; and 4) analyze the results.

The procedure used in ProFit to compare structures includes the following steps: 1) load the structures to be compared; 2) specify selected residues of interest; 3) define the atom equivalences in the selected residues; 4) perform a fitting operation on the selected residues; and 5) analyze the results.

Each structure in the comparison is identified by a name. One structure is identified as the target (i.e., the fixed structure); all remaining structures are working structures (i.e., moving structures). Since atom equivalency within the above programs is defined by user input, for the purpose of this invention we will define equivalent atoms as protein backbone atoms (N, Cα, C and O) for Aurora-2 amino acids and corresponding amino acids in the structures being compared.

The corresponding amino acids may be identified by sequence alignment programs such as the "bestfit" program available from the Genetics Computer Group which uses the local homology algorithm described by Smith and Waterman in *Advances in Applied Mathematics* 2, 482 (1981), which is incorporated herein by reference. A suitable amino acid sequence alignment will require that the proteins being aligned share minimum percentage of identical amino acids. Generally, a first protein being aligned with a second protein should share in excess of about 35% identical amino acids [Hanks et al., *Science,* 241, 42 (1988); Hanks and Quinn, *Methods in Enzymology,* 200, 38 (1991)]. The identification of equivalent residues can also be assisted by secondary structure alignment, for example, aligning the α-helices, β-sheets in the structure. The program Swiss-Pdb Viewer has its own best fit algorithm that is based on secondary sequence alignment.

When a rigid fitting method is used, the working structure is translated and rotated to obtain an optimum fit with the target structure. The fitting operation uses an algorithm that computes the optimum translation and rotation to be applied to the moving structure, such that the root mean square difference of the fit over the specified pairs of equivalent atom is an absolute minimum. This number, given in angstroms, is reported by the above programs. The Swiss-Pdb Viewer program sets an RMSD cutoff for eliminating pairs of equivalent atoms that have high RMSD values. An RMSD cutoff value can be used to exclude pairs of equivalent atoms with extreme individual RMSD values. In the program ProFit, the RMSD cutoff value can be specified by the user.

The rigid fitting between structures was performed by QUANTA and then inputted into the program ProFit, from which the RMSD values were determined. For the 5 Å and 8 Å sphere amino acids, the RMSD values of the ATP-binding pocket between the Aurora-2-adenosine complex and the Aurora-2-inhibitor complexes are 0.61-0.77 Å and 0.58-0.64 Å, respectively. The comparison of the entire kinase domain between the Aurora-2 structures in the present invention yields RMSD values in the range of 0.61-0.77 Å using Aurora-2-adenosine as a reference. The RMSD values are averages of individual RMSD values calculated for the backbone atoms (C, O, N and Cα) of all residues in the kinase or ATP-binding pocket between the reference structure and the other Aurora-2-inhibitor complex structures.

For the purpose of this invention, any molecule, molecular complex, binding pocket, motif, domain thereof or portion thereof that is within a root mean square deviation for backbone atoms (N, Cα, C, O) when superimposed on the relevant backbone atoms described by structure coordinates listed in FIGS. 1-4 are encompassed by this invention.

Therefore, one embodiment of this invention provides a molecule or molecular complex comprising all or part of an Aurora-2 ATP-binding pocket defined by structure coordinates of a set of amino acid residues that correspond to Aurora-2 amino acid residues L139, L194, L210, E211, A213, L263, and W277 according to any one of FIGS. 1-4, wherein the root mean square deviation of the backbone atoms between said amino acids of said molecule or molecular complex and said Aurora-2 amino acids is not more than about 3.0 Å. In one embodiment, the RMSD is not greater than about 2.0 Å. In one embodiment, the RMSD is not greater than about 1.0 Å. In one embodiment, the RMSD is not greater than about 0.8 Å. In one embodiment, the RMSD is not greater than about 0.5 Å. In one embodiment, the RMSD is not greater than about 0.3 Å. In one embodiment, the RMSD is not greater than about 0.2 Å.

Another embodiment of this invention provides a molecule or molecular complex comprising all or part of an Aurora-2 ATP-binding pocket defined by structure coordinates of a set of amino acid residues that correspond to Aurora-2 amino acid residues L139, G140, F144, V147, A160, K162, L194, L210, E211, Y212, A213, P214, L215, T217, R220, L263, A273, and W277 according to FIG. 3, wherein the root mean square deviation (RMSD) of the backbone atoms between said amino acid residues of said molecule or molecular complex and said Aurora-2 amino acids is not more than about 3.0 Å. In one embodiment, the RMSD is not greater than about 2.0 Å. In one embodiment, the RMSD is not greater than about 1.0 Å. In one embodiment, the RMSD is not greater than about 0.8 Å. In one embodiment, the RMSD is not greater than about 0.5 Å. In one embodiment, the RMSD is not greater than about 0.3 Å. In one embodiment, the RMSD is not greater than about 0.2 Å.

Another embodiment of this invention provides a molecule or molecular complex comprising all or part of an Aurora-2 ATP-binding pocket defined by structure coordinates of a set of amino acid residues that correspond to Aurora-2 amino acid residues L139, G140, F144, V147, A160, K162, L194, L210, E211, Y212, A213, P214, L215, T217, R220, L263, A273, W277, and S278 according to FIG. 1 or 4, wherein the root mean square deviation of the backbone atoms between said amino acid residues of said molecule or molecular complex and said Aurora-2 amino acids is not more than about 3.0 Å. In one embodiment, the RMSD is not greater than about 2.0 Å. In one embodiment, the RMSD is not greater than about 1.0 Å. In one embodiment, the RMSD is not greater than about 0.8 Å. In one embodiment, the RMSD is not greater than about 0.5 Å. In one embodiment, the RMSD is not greater than about 0.3 Å. In one embodiment, the RMSD is not greater than about 0.2 Å.

Another embodiment of this invention provides a molecule or molecular complex comprising all or part of an Aurora-2 ATP-binding pocket defined by structure coordinates of a set of amino acid residues that correspond to Aurora-2 amino acid residues L139, G140, F144, V147, A160, K162, L194, L210, E211, Y212, A213, P214, L215, T217, R220, L263, A273, W277, and V279 according to FIG. 2, wherein the root mean square deviation (RMSD) of the backbone atoms between said amino acid residues of said molecule or molecular complex and said Aurora-2 amino acids is not more than about 3.0 Å. In one embodiment, the RMSD is not greater than about 2.0 Å. In one embodiment, the RMSD is not greater than about 1.0 Å. In one embodiment, the RMSD is not greater than about 0.8 Å. In one embodiment, the RMSD is not greater than about 0.5 Å. In one embodiment, the RMSD is not greater than about 0.3 Å. In one embodiment, the RMSD is not greater than about 0.2 Å.

Another embodiment of this invention provides a molecule or molecular complex comprising all or part of an Aurora-2 ATP-binding pocket defined by structure coordinates of a set of amino acid residues that correspond to Aurora-2 amino acid residues R137, L139, G140, G142, F144, G145, N146, V147, Y148, L149, I158, L159, A160, L161, K162, L194, R195, L208, I209, L210, E211, Y212, A213, P214, L215, T217, V218, Y219, R220, E260, N261, L262, L263, L264, K271, I272, A273, D274, F275, and W277 according to FIG. 3, wherein the root mean square deviation of the backbone atoms between said amino acids of said molecule or molecular complex and said Aurora-2 amino acids is not greater than about 3.0 Å. In one embodiment, the RMSD is not greater than about 2.0 Å. In one embodiment, the RMSD is not greater than about 1.0 Å. In one embodiment, the RMSD is not greater than about 0.8 Å. In one embodiment, the RMSD is not greater than about 0.5 Å. In one embodiment, the RMSD is not greater than about 0.3 Å. In one embodiment, the RMSD is not greater than about 0.2 Å.

Another embodiment of this invention provides a molecule or molecular complex comprising all or part of an Aurora-2 ATP-binding pocket defined by structure coordinates of a set of amino acid residues that correspond to Aurora-2 amino acid residues R137, L139, G140, G142, F144, G145, N146, V147, Y148, L149, I158, L159, A160, L161, K162, L194, R195, L208, I209, L210, E211, Y212, A213, P214, L215, T217, V218, Y219, R220, E260, N261, L262, L263, L264, K271, I272, A273, D274, F275, W277 and S278 according to FIG. 1 or 4, wherein the root mean square deviation of the backbone atoms between said amino acids of said molecule or molecular complex and said Aurora-2 amino acids is not greater than about 3.0 Å. In one embodiment, the RMSD is not greater than about 2.0 Å. In one embodiment, the RMSD is not greater than about 1.0 Å. In one embodiment, the RMSD is not greater than about 0.8 Å. In one embodiment, the RMSD is not greater than about 0.5 Å. In one embodiment, the RMSD is not greater than about 0.3 Å. In one embodiment, the RMSD is not greater than about 0.2 Å.

Another embodiment of this invention provides a molecule or molecular complex comprising all or part of an Aurora-2 ATP-binding pocket defined by structure coordinates of a set of amino acid residues that correspond to Aurora-2 amino acid residues R137, L139, G140, G142, F144, G145, N146, V147, Y148, L149, I158, L159, A160, L161, K162, L194, R195, L208, I209, L210, E211, Y212, A213, P214, L215, T217, V218, Y219, R220, E260, N261, L262, L263, L264, K271, I272, A273, D274, F275, W277, S278, and V279 according to FIG. 2, wherein the root mean square deviation of the backbone atoms between said amino acids of said molecule or molecular complex and said Aurora-2 amino acids is not greater than about 3.0 Å. In one embodiment, the RMSD is not greater than about 2.0 Å. In one embodiment, the RMSD is not greater than about 1.0 Å. In one embodiment, the RMSD is not greater than about 0.8 Å. In one embodiment, the RMSD is not greater than about 0.5 Å. In one embodiment, the RMSD is not greater than about 0.3 Å. In one embodiment, the RMSD is not greater than about 0.2 Å.

Another embodiment of this invention provides a molecule or molecular complex comprising all or part of an Aurora-2 ATP-binding pocket defined by structure coordinates of a set of amino acid residues that correspond to Aurora-2 amino acid residues F133, I135, G136, R137, F144, N146, V147, Y148, L149, A150, R151, E152, I158, L159, A160, L161, K162, V163, V182, E183, Q185, H190, N192, I193, L194, R195, L196, Y197, G198, Y199, F200, V206, Y207, L208, I209, L210, E211, Y212, A213, P214, L215, T217, V218, Y219, R220, E221, D229, E230, Q231, R232, T233, A234, T235, Y236, I237, T238, E239, L240, A241, N242, A243, L244, S245, Y246, C247, H248, S249, K250, R251, V252, I253, H254, R255, D256, I257, K258, P259, E260, N261, L262, L263, L264, G265, S266, G268, E269, L270, K271, I272, A273, D274, F275, and W277 according to FIG. 3, wherein the root mean square deviation of the backbone atoms between said amino acids of said molecular complex and said Aurora-2 amino acids is not more than about 3.0 Å. In one embodiment, the RMSD is not greater than about 2.0 Å. In one embodiment, the RMSD is not greater than about 1.0 Å. In one embodiment, the RMSD is not greater than about 0.8 Å. In one embodiment, the RMSD is not greater than about 0.5 Å. In one embodiment, the RMSD is not greater than about 0.3 Å. In one embodiment, the RMSD is not greater than about 0.2 Å.

Another embodiment of this invention provides a molecule or molecular complex comprising all or part of an Aurora-2 ATP-binding pocket defined by structure coordinates of a set of amino acid residues that correspond to Aurora-2 amino acid residues F133, I135, G136, R137, F144, N146, V147, Y148, L149, A150, R151, E152, I158, L159, A160, L161, K162, V163, V182, E183, Q185, H190, N192, I193, L194, R195, L196, Y197, G198, Y199, F200, V206, Y207, L208, I209, L210, E211, Y212, A213, P214, L215, T217, V218, Y219, R220, E221, D229, E230, Q231, R232, T233, A234, T235, Y236, I237, T238, E239, L240, A241, N242, A243, L244, S245, Y246, C247, H248, S249, K250, R251, V252, I253, H254, R255, D256, I257, K258, P259, E260, N261, L262, L263, L264, G265, S266, G268, E269, L270, K271, I272, A273, D274, F275, W277, and S278 according to FIG. 1 or 4, wherein the root mean square deviation of the backbone atoms between said amino acids of said molecule or molecular complex and said Aurora-2 amino acids is not more than about 3.0 Å. In one embodiment, the RMSD is not greater than about 2.0 Å. In one embodiment, the RMSD is not greater than about 1.0 Å. In one embodiment, the RMSD is not greater than about 0.8 Å. In one embodiment, the RMSD is not greater than about 0.5 Å. In one embodiment, the RMSD is not greater than about 0.3 Å. In one embodiment, the RMSD is not greater than about 0.2 Å.

Another embodiment of this invention provides a molecule or molecular complex comprising all or part of an Aurora-2 ATP-binding pocket defined by structure coordinates of a set of amino acid residues that correspond to Aurora-2 amino acid residues F133, I135, G136, R137, F144, N146, V147, Y148, L149, A150, R151, E152, I158, L159, A160, L161, K162, V163, V182, E183, Q185, H190, N192, I193, L194, R195, L196, Y197, G198, Y199, F200, V206, Y207, L208, I209, L210, E211, Y212, A213, P214, L215, T217, V218, Y219, R220, E221, D229, E230, Q231, R232, T233, A234, T235, Y236, I237, T238, E239, L240, A241, N242, A243, L244, S245, Y246, C247, H248, S249, K250, R251, V252, I253, H254, R255, D256, I257, K258, P259, E260, N261, L262, L263, L264, G265, S266, G268, E269, L270, K271, I272, A273, D274, F275, W277, S278, and V279 according to FIG. 2, wherein the root mean square deviation of the backbone atoms between said amino acids of said molecule or molecular complex and said Aurora-2 amino acids is not more than about 3.0 Å. In one embodiment, the RMSD is not greater than about 2.0 Å. In one embodiment, the RMSD is not greater than about 1.0 Å. In one embodiment, the RMSD is not greater than about 0.8 Å. In one embodiment, the RMSD is not greater than about 0.5 Å. In one embodiment, the RMSD is not greater than about 0.3 Å. In one embodiment, the RMSD is not greater than about 0.2 Å.

Another embodiment of this invention provides a molecule or molecular complex comprising a protein defined by structure coordinates of a set of amino acid residues which correspond to Aurora-2 amino acid residues according to FIG. 1, 2, 3 or 4, wherein the root mean square deviation between said set of amino acid residues of said molecule or molecular complex and said Aurora-2 amino acid residues is not more than about 5 Å. In one embodiment, the RMSD is not greater than about 4 Å. In one embodiment, the RMSD is not greater than about 3 Å. In one embodiment, the RMSD is not greater than about 2 Å. In one embodiment, the RMSD is not greater than about 1.5 Å. In another embodiment, the RMSD is not greater than about 1 Å. In one embodiment, the RMSD is not greater than about 0.8 Å. In one embodiment, the RMSD is not greater than about 0.5 Å.

In one embodiment, the above molecules or molecular complexes are in crystalline form.

Computer Systems

According to another embodiment, this invention provided a machine-readable data storage medium, comprising a data storage material encoded with machine-readable data, wherein said data defines the above-mentioned molecules or molecular complexes. In one embodiment, the data defines the above-mentioned binding pockets by comprising the structure coordinates of said amino acid residues according to any one of FIG. 1-4. To use the structure coordinates generated for Aurora-2, homologues thereof, or one of its binding pockets, it is at times necessary to convert them into a three-dimensional shape. This is achieved through the use of commercially or publicly available software that is capable of generating a three-dimensional structure of molecules or potions thereof from a set of structure coordinates. The three-dimensional structure may be displayed as a graphical representation.

Therefore, according to another embodiment, this invention provides a machine-readable data storage medium comprising a data storage material encoded with machine readable data. In one embodiment, a machine programmed with instructions for using said data, is capable of generating a three-dimensional structure of any of the molecule or molecular complexes, or binding pockets thereof, that are described herein.

This invention also provides a computer comprising:

(a) a machine-readable data storage medium comprising a data storage material encoded with machine-readable data, wherein said data defines any one of the above molecules or molecular complexes;

(b) a working memory for storing instructions for processing said machine-readable data;

(c) a central processing unit (CPU) coupled to said working memory and to said machine-readable data storage medium for processing said machine readable data and means for generating three-dimensional structural information of said molecule or molecular complex; and (d) output hardware coupled to said central processing unit for outputting three-dimensional structural information of said molecule or molecular complex, or information produced using said three-dimensional structural information of said molecule or molecular complex.

In one embodiment, the data defines the binding pocket or protein of the molecule or molecular complex.

Three-dimensional data generation may be provided by an instruction or set of instructions such as a computer program or commands for generating a three-dimensional structure or graphical representation from structure coordinates, or by subtracting distances between atoms, calculating chemical energies for an Aurora-2 molecule or molecular complex or homologues thereof, or calculating or minimizing energies for an association of an Aurora-2 molecule or molecular complex or homologues thereof to a chemical entity. The graphical representation can be generated or displayed by commercially available software programs. Examples of software programs include but are not limited to QUANTA [Accelrys ©2001, 2002], O [Jones et al., *Acta Crystallogr.* A47, pp. 110-119 (1991)] and RIBBONS [Carson, *J. Appl. Crystallogr.*, 24, pp. 9589-961 (1991)], which are incorporated herein by reference. Certain software programs may imbue this representation with physico-chemical attributes which are known from the chemical composition of the molecule, such as residue charge, hydrophobicity, torsional and rotational degrees of freedom for the residue or segment, etc. Examples of software programs for calculating chemical energies are described in the Rational Drug Design section.

In one embodiment, the computer is executing an instruction such as a computer program for three dimensional data generation.

Information of said binding pocket or information produced by using said binding pocket can be outputted through display terminals, touchscreens, facsimile machines, modems, CD-ROMs printers or disk drives. The information can be in graphical or alphanumeric form.

FIG. 9 demonstrates one version of these embodiments. System (10) includes a computer (11) comprising a central processing unit ("CPU") (20), a working memory (22) which may be, e.g., RAM (random-access memory) or "core" memory, mass storage memory (24) (such as one or more disk drives or CD-ROM drives), one or more cathode-ray tube ("CRT") display terminals (26), one or more keyboards (28), one or more input lines (30), and one or more output lines (40), all of which are, interconnected by a conventional bi-directional system bus (50).

Input hardware (36), coupled to computer (11) by input lines (30), may be implemented in a variety of ways. Machine-readable data of this invention may be inputted via the use of a modem or modems (32) connected by a telephone line or dedicated data line (34). Alternatively or additionally, the input hardware (36) may comprise CD-ROM drives or disk drives (24). In conjunction with display terminal (26), keyboard (28) may also be used as an input device.

Output hardware (46), coupled to computer (11) by output lines (40), may similarly be implemented by conventional devices. By way of example, output hardware (46) may include CRT display terminal (26) for displaying a graphical representation of a binding pocket of this invention using a program such as QUANTA as described herein. Output hardware may also include a printer (42), so that hard copy output may be produced, or a disk drive (24), to store system output for later use. Output hardware may also include a CD or DVD recorder, ZIP™ or JAZ™ drive, or other machine-readable data storage device.

In operation, CPU (20) coordinates the use of the various input and output devices (36), (46), coordinates data accesses from mass storage (24) and accesses to and from working memory (22), and determines the sequence of data processing steps. A number of programs may be used to process the machine-readable data of this invention. Such programs are discussed in reference to the computational methods of drug discovery as described herein. Specific references to components of the hardware system (10) are included as appropriate throughout the following description of the data storage medium.

FIG. 10 shows a cross section of a magnetic data storage medium (100) which can be encoded with a machine-readable data that can be carried out by a system such as system (10) of FIG. 9. Medium (100) can be a conventional floppy diskette or hard disk, having a suitable substrate (101), which may be conventional, and a suitable coating (102), which may be conventional, on one or both sides, containing magnetic domains (not visible) whose polarity or orientation can be altered magnetically. Medium (100) may also have an opening (not shown) for receiving the spindle of a disk drive or other data storage device (24).

The magnetic domains of coating (102) of medium (100) are polarized or oriented so as to encode in manner which may be conventional, machine readable data such as that described herein, for execution by a system such as system (10) of FIG. 9.

FIG. 11 shows a cross section of an optically-readable data storage medium (110) which also can be encoded with such a machine-readable data, or set of instructions, which can be carried out by a system such as system (10) of FIG. 9. Medium (110) can be a conventional compact disk read only memory (CD-ROM) or a rewritable medium such as a magneto-optical disk which is optically readable and magneto-optically writable. Medium (100) preferably has a suitable substrate (111), which may be conventional, and a suitable coating (112), which may be conventional, usually of one side of substrate (111).

In the case of CD-ROM, as is well known, coating (112) is reflective and is impressed with a plurality of pits (113) to encode the machine-readable data. The arrangement of pits is read by reflecting laser light off the surface of coating (112). A protective coating (114), which preferably is substantially transparent, is provided on top of coating (112).

In the case of a magneto-optical disk, as is well known, coating (112) has no pits (113), but has a plurality of magnetic domains whose polarity or orientation can be changed magnetically when heated above a certain temperature, as by a laser (not shown). The orientation of the domains can be read by measuring the polarization of laser light reflected from coating (112). The arrangement of the domains encodes the data as described above.

In one embodiment, the structure coordinates of said molecules or molecular complexes are produced by homology modeling of at least a portion of the structure coordinates of FIG. 1, 2, 3 or 4. Homology modeling can be used to generate structural models of Aurora-2 homologues or other homologous proteins based on the known structure of Aurora-2. This can be achieved by performing one or more of the following steps: performing sequence alignment between the amino acid sequence of an unknown molecule against the amino acid sequence of Aurora-2; identifying conserved and variable regions by sequence or structure; generating structure co-ordinates for structurally conserved residues of the unknown structure from those of Aurora-2; generating conformations for the structurally variable residues in the unknown structure; replacing the non-conserved residues of Aurora-2 with residues in the unknown structure; building side chain conformations; and refining and/or evaluating the unknown structure.

For example, since the protein sequence of the catalytic domains of Aurora-2 and Aurora-1 or Aurora-3 can be aligned relative to each other, it is possible to construct models of the structures of Aurora-1 or Aurora-3, particularly in the regions of the active site, using the Aurora-2 structure. Software programs that are useful in homology modeling include XALIGN [Wishart, D. S. et al., *Comput. Appl. Biosci.,* 10, pp. 687-88 (1994)] and CLUSTAL W Alignment Tool [Higgins D. G. et al., *Methods Enzymol.,* 266, pp. 383-402 (1996)]. See also, U.S. Pat. No. 5,884,230. These references are incorporated herein by reference.

To perform the sequence alignment, programs such as the "bestfit" program available from the Genetics Computer Group [Waterman in *Advances in Applied Mathematics* 2, 482 (1981), which is incorporated herein by reference] and CLUSTAL W Alignment Tool [Higgins D. G. et al., *Methods Enzymol.,* 266, pp. 383-402 (1996), which is incorporated by reference] can be used. To model the amino acid side chains of Aurora-1 or Aurora-3, the amino acid residues in Aurora-2 can be replaced, using a computer graphics program such as "O" [Jones et al, (1991) *Acta Cryst. Sect. A,* 47: 110-119], by those of the homologous protein, where they differ. The same orientation or a different orientation of the amino acid can be used. Insertions and deletions of amino acid residues may be necessary where gaps occur in the sequence alignment. However, certain portions of the active site of Aurora-2 and its homologues are highly conserved with essentially no insertions and deletions.

Homology modeling can be performed using, for example, the computer programs SWISS-MODEL available through Glaxo Wellcome Experimental Research in Geneva, Switzerland; WHATIF available on EMBL servers; Schnare et al., *J. Mol. Biol,* 256: 701-719 (1996); Blundell et al., *Nature* 326: 347-352 (1987); Fetrow and Bryant, *Bio/Technology* 11:479-484 (1993); Greer, *Methods in Enzymology* 202: 239-252 (1991); and Johnson et al, *Crit. Rev. Biochem. Mol Biol.* 29:1-68 (1994). An example of homology modeling can be found, for example, in Szklarz G. D., *Life Sci.* 61: 2507-2520 (1997). These references are incorporated herein by reference.

Thus, in accordance with the present invention, data capable of generating the three dimensional structure of the above molecules or molecular complexes, or binding pockets thereof, can be stored in a machine-readable storage medium, which is capable of displaying a graphical three-dimensional representation of the structure.

Rational Drug Design

The Aurora-2 structure coordinates or the three-dimensional graphical representation generated from these coordinates may be used in conjunction with a computer for a variety of purposes, including drug discovery.

For example, the structure encoded by the data may be computationally evaluated for its ability to associate with chemical entities. Chemical entities that associate with Aurora-2 may inhibit Aurora-2 or its homologues, and are potential drug candidates. Alternatively, the structure encoded by the data may be displayed in a graphical three-dimensional representation on a computer screen. This allows visual inspection of the structure, as well as visual inspection of the structure's association with chemical entities.

Thus, according to another embodiment, the invention provides a method for designing, selecting and/or optimizing a chemical entity that binds to all or part of the molecule or molecular complex comprising the steps of:

(a) providing the structure coordinates of said molecule or molecular complex on a computer comprising the means for generating three-dimensional structural information of all or part of said molecule or molecular complex from said structure coordinates; and (b) designing, selecting and/or optimizing said chemical entity by employing means for performing a fitting operation between said chemical entity and said three-dimensional structural information of all or part of said molecule or molecular complex.

In one embodiment, the method is for designing, selecting and or optimizing a chemical entity that binds with the binding pocket of a molecule or molecular complex. In one embodiment, the above method further comprises the following steps before step (a):

(c) producing a crystal of a molecule or molecular complex comprising Aurora-2 or homologue thereof;

(d) determining the three-dimensional structure coordinates of the molecule or molecular complex by X-ray diffraction of the crystal; and (e) identifying all or part of said binding pocket.

Three-dimensional structural information in step (a) may be generated by instructions such as a computer program or commands that can generate a three-dimensional structure or graphical representation; subtract distances between atoms; calculate chemical energies for an Aurora-2 molecule, molecular complex or homologues thereof; or calculate or minimize energies of an association of Aurora-2 molecule, molecular complex or homologues thereof to a chemical entity. These types of computer programs are known in the art. The graphical representation can be generated or displayed by commercially available software programs. Examples of software programs include but are not limited to QUANTA [Accelrys ©2001, 2002], O [Jones et al., *Acta Crystallogr.* A47, pp. 110-119 (1991)] and RIBBONS [Carson, *J. Appl. Crystallogr.,* 24, pp. 9589-961 (1991)], which are incorporated herein by reference. Certain software programs may imbue this representation with physico-chemical attributes which are known from the chemical composition of the molecule, such as residue charge, hydrophobicity, torsional and rotational degrees of freedom for the residue or segment, etc. Examples of software programs for calculating chemical energies are described below.

Thus, according to another embodiment, the invention provides a method for evaluating the potential of a chemical entity to associate with all or part of a molecule or molecular complex as described previously in the different embodiments.

This method comprises the steps of: (a) employing computational means to perform a fitting operation between the chemical entity and all or part of the molecule or molecular complex described before; (b) analyzing the results of said fitting operation to quantify the association between the chemical entity and all or part of the molecule or molecular complex; and optionally (c) outputting said quantified association to a suitable output hardware, such as a CRT display terminal, a CD or DVD recorder, ZIP™ or JAZ™ drive, a disk drive, or other machine-readable data storage device, as described previously. The method may further comprise generating a three-dimensional structure, graphical representation thereof, or both of all or part of the molecule or molecular complex prior to step (a). In one embodiment, the method is for evaluating the ability of a chemical entity to associate with all or part of the binding pocket of a molecule or molecular complex.

In another embodiment, the invention provides a method for screening a plurality of chemical entities to associate at a deformation energy of binding of less than −7 kcal/mol with said binding pocket:
  (a) employing computational means, which utilize said structure coordinates to perform a fitting operation between one of said chemical entities from the plurality of chemical entities and said binding pocket;
  (b) quantifying the deformation energy of binding between the chemical entity and the binding pocket;
  (c) repeating steps (a) and (b) for each remaining chemical entity; and
  (d) outputting a set of chemical entities that associate with the binding pocket at a deformation energy of binding of less than −7 kcal/mol to a suitable output hardware.

In another embodiment, the method comprises the steps of:
  (a) constructing a computer model of a binding pocket of the molecule or molecular complex;
  (b) selecting a chemical entity to be evaluated by a method selected from the group consisting of assembling said chemical entity; selecting a chemical entity from a small molecule database; de novo ligand design of said chemical entity; and modifying a known agonist or inhibitor, or a portion thereof, of an Aurora-2 protein or homologue thereof;
  (c) employing computational means to perform a fitting operation between computer models of said chemical entity to be evaluated and said binding pocket in order to provide an energy-minimized configuration of said chemical entity in the binding pocket; and
  (d) evaluating the results of said fitting operation to quantify the association between said chemical entity and the binding pocket model, whereby evaluating the ability of said chemical entity to associate with said binding pocket.

In another embodiment, the invention provides a method of using a computer for evaluating the ability of a chemical entity to associate with all or part of the molecule or molecular complex, wherein said computer comprises a machine-readable data storage medium comprising a data storage material encoded with said structure coordinates defining said binding pocket and means for generating a three-dimensional graphical representation of the binding pocket, and wherein said method comprises the steps of:
  (a) positioning a first chemical entity within all or part of said binding pocket using a graphical three-dimensional representation of the structure of the chemical entity and the binding pocket;
  (b) performing a fitting operation between said chemical entity and said binding pocket by employing computational means;
  (c) analyzing the results of said fitting operation to quantitate the association between said chemical entity and all or part of the binding pocket; and
  (d) outputting said quantitated association to a suitable output hardware.

The above method may further comprise the steps of:
  (e) repeating steps (a) through (d) with a second chemical entity; and
  (f) selecting at least one of said first or second chemical entity that associates with all or part of said binding pocket based on said quantitated association of said first or second chemical entity.

Alternatively, the structure coordinates of the Aurora-2 binding pockets may be utilized in a method for identifying an agonist or antagonist of a molecule comprising a binding pocket of Aurora-2. This method comprises the steps of:
  (a) using a three-dimensional structure of the molecule or molecular complex to design or select a chemical entity;
  (b) contacting the chemical entity with the molecule and molecular complex;
  (c) monitoring the activity of the molecule or molecular complex; and
  (d) classifying the chemical entity as an agonist or antagonist based on the effect of the chemical entity on the activity of the molecule or molecular complex.

In one embodiment, step (a) is using a three-dimensional structure of the binding pocket of the molecule or molecular complex. In another embodiment, the three-dimensional structure is displayed as a graphical representation.

In another embodiment, the method comprises the steps of:
  (a) constructing a computer model of a binding pocket of the molecule or molecular complex;
  (b) selecting a chemical entity to be evaluated by a method selected from the group consisting of assembling said chemical entity; selecting a chemical entity from a small molecule database; de novo ligand design of said chemical entity; and modifying a known agonist or inhibitor, or a portion thereof, of an Aurora-2 protein or homologue thereof;
  (c) employing computational means to perform a fitting operation between computer models of said chemical entity to be evaluated and said binding pocket in order to provide an energy-minimized configuration of said chemical entity in the binding pocket; and
  (d) evaluating the results of said fitting operation to quantify the association between said chemical entity and the binding pocket model, whereby evaluating the ability of said chemical entity to associate with said binding pocket;
  (e) synthesizing said chemical entity; and
  (f) contacting said chemical entity with said molecule or molecular complex to determine the ability of said compound to activate or inhibit said molecule.

In one embodiment, the invention provides a method of designing a compound or complex that associates with all or part of the binding pocket comprising the steps of:
  (a) providing the structure coordinates of said binding pocket or protein on a computer comprising the means for generating three-dimensional structural information from said structure coordinates; and
  (b) using the computer to perform a fitting operation to associate a first chemical entity with all or part of the binding pocket;

(c) performing a fitting operation to associate at least a second chemical entity with all or part of the binding pocket;
(d) quantifying the association between the first and second chemical entity and all or part of the binding pocket;
(e) optionally repeating steps (b) to (d) with another first and second chemical entity, selecting a first and a second chemical entity based on said quantified association of all of said first and second chemical entity;
(f) optionally, visually inspecting the relationship of the first and second chemical entity to each other in relation to the binding pocket on a computer screen using the three-dimensional graphical representation of the binding pocket and said first and second chemical entity; and
(g) assembling the first and second chemical entity into a compound or complex that associates with all or part of said binding pocket by model building.

For the first time, the present invention permits the use of molecular design techniques to identify, select and design chemical entities, including inhibitory compounds, capable of binding to Aurora-2 or Aurora-2-like binding pockets, motifs and domains.

Applicants' elucidation of binding pockets on Aurora-2 provides the necessary information for designing new chemical entities and compounds that may interact with Aurora-2 substrate or ATP-binding pockets or Aurora-2-like substrate or ATP-binding pockets, in whole or in part. Due to the homology in the kinase core between Aurora-2, Aurora-1 and Aurora-3, compounds that inhibit Aurora-2 are also expected to inhibit Aurora-1 and Aurora-3, especially those compounds that bind the ATP-binding pocket.

Throughout this section, discussions about the ability of a chemical entity to bind to, associate with or inhibit Aurora-2 binding pockets refer to features of the entity alone. Assays to determine if a compound binds to Aurora-2 are well known in the art and are exemplified below.

The design of compounds that bind to or inhibit Aurora-2 binding pockets according to this invention generally involves consideration of two factors. First, the chemical entity must be capable of physically and structurally associating with parts or all of the Aurora-2 binding pockets. Non-covalent molecular interactions important in this association include hydrogen bonding, van der Waals interactions, hydrophobic interactions and electrostatic interactions.

Second, the chemical entity must be able to assume a conformation that allows it to associate with the Aurora-2 binding pockets directly. Although certain portions of the chemical entity will not directly participate in these associations, those portions of the chemical entity may still influence the overall conformation of the molecule. This, in turn, may have a significant impact on potency. Such conformational requirements include the overall three-dimensional structure and orientation of the chemical entity in relation to all or a portion of the binding pocket, or the spacing between functional groups of a chemical entity comprising several chemical entities that directly interact with the Aurora-2 or Aurora-2-like binding pockets.

The potential inhibitory or binding effect of a chemical entity on Aurora-2 binding pockets may be analyzed prior to its actual synthesis and testing by the use of computer modeling techniques. If the theoretical structure of the given entity suggests insufficient interaction and association between it and the Aurora-2 binding pockets, testing of the entity is obviated. However, if computer modeling indicates a strong interaction, the molecule may then be synthesized and tested for its ability to bind to an Aurora-2 binding pocket. This may be achieved by testing the ability of the molecule to inhibit Aurora-2 using the assays described in Example 8. In this manner, synthesis of inoperative compounds may be avoided.

A potential inhibitor of an Aurora-2 binding pocket may be computationally evaluated by means of a series of steps in which chemical entities or fragments are screened and selected for their ability to associate with the Aurora-2 binding pockets.

One skilled in the art may use one of several methods to screen chemical entities or fragments for their ability to associate with an Aurora-2 binding pocket. This process may begin by visual inspection of, for example, an Aurora-2 binding pocket on the computer screen based on the Aurora-2 structure coordinates in any of FIGS. 1-4 or other coordinates which define a similar shape generated from the machine-readable storage medium. Selected fragments or chemical entities may then be positioned in a variety of orientations, or docked, within that binding pocket as defined supra. Docking may be accomplished using software such as QUANTA (Molecular Simulations, Inc., San Diego, Calif. ©1998, 2000) and Sybyl (Tripos Associates, St. Louis, Mo.), followed by energy minimization and molecular dynamics with standard molecular mechanics force fields, such as CHARMM and AMBER.

Specialized computer programs may also assist in the process of selecting fragments or chemical entities. These include:

1. GRID (P. J. Goodford, "A Computational Procedure for Determining Energetically Favorable Binding Sites on Biologically Important Macromolecules", *J. Med. Chem.*, 28, pp. 849-857 (1985)). GRID is available from Oxford University, Oxford, UK.

2. MCSS (A. Miranker et al., "Functionality Maps of Binding Sites: A Multiple Copy Simultaneous Search Method." *Proteins: Structure, Function and Genetics*, 11, pp. 29-34 (1991)). MCSS is available from Molecular Simulations, San Diego, Calif.

3. AUTODOCK (D. S. Goodsell et al., "Automated Docking of Substrates to Proteins by Simulated Annealing", *Proteins: Structure, Function, and Genetics*, 8, pp. 195-202 (1990)). AUTODOCK is available from Scripps Research Institute, La Jolla, Calif.

4. DOCK (I. D. Kuntz et al., "A Geometric Approach to Macromolecule-Ligand Interactions", *J. Mol. Biol.*, 161, pp. 269-288 (1982)). DOCK is available from University of California, San Francisco, Calif.

Once suitable chemical entities or fragments have been selected, they can be assembled into a single compound or complex. Assembly may be preceded by visual inspection of the relationship of the fragments to each other on the three-dimensional image displayed on a computer screen in relation to the structure coordinates of Aurora-2. This would be followed by manual model building using software such as QUANTA (Molecular Simulations, Inc., San Diego, Calif. ©1998, 2000) or Sybyl (Tripos Associates, St. Louis, Mo.).

Useful programs to aid one of skill in the art in connecting the individual chemical entities or fragments include:

1. CAVEAT (P. A. Bartlett et al., "CAVEAT: A Program to Facilitate the Structure-Derived Design of Biologically Active Molecules", in *Molecular Recognition in Chemical and Biological Problems*, Special Pub., Royal Chem. Soc., 78, pp. 182-196 (1989); G. Lauri and P. A. Bartlett, "CAVEAT: a Program to Facilitate the Design of Organic Molecules", *J. Comput. Aided Mol. Des.*, 8, pp. 51-66 (1994)). CAVEAT is available from the University of California, Berkeley, Calif.

2. 3D Database systems such as ISIS (MDL Information Systems, San Leandro, Calif.). This area is reviewed in Y. C.

Martin, "3D Database Searching in Drug Design", J. Med. Chem., 35, pp. 2145-2154 (1992).

3. HOOK (M. B. Eisen et al., "HOOK: A Program for Finding Novel Molecular Architectures that Satisfy the Chemical and Steric Requirements of a Macromolecule Binding Site", Proteins: Struct., Funct., Genet., 19, pp. 199-221 (1994)). HOOK is available from Molecular Simulations, San Diego, Calif.

Instead of proceeding to build an inhibitor of an Aurora-2 binding pocket in a step-wise fashion one fragment or chemical entity at a time as described above, inhibitory or other Aurora-2 binding compounds may be designed as a whole or "de novo" using either an empty binding pocket or optionally including some portion(s) of a known inhibitor(s). There are many de novo ligand design methods including:

1. LUDI (H.-J. Bohm, "The Computer Program LUDI: A New Method for the De Novo Design of Enzyme Inhibitors", J. Comp. Aid. Molec. Design, 6, pp. 61-78 (1992)). LUDI is available from Molecular Simulations Incorporated, San Diego, Calif.

2. LEGEND (Y. Nishibata et al., Tetrahedron, 47, p. 8985 (1991)). LEGEND is available from Molecular Simulations Incorporated, San Diego, Calif.

3. LeapFrog (available from Tripos Associates, St. Louis, Mo.).

4. SPROUT (V. Gillet et al., "SPROUT: A Program for Structure Generation", J. Comput. Aided Mol. Design, 7, pp. 127-153 (1993)). SPROUT is available from the University of Leeds, UK.

Other molecular modeling techniques may also be employed in accordance with this invention (see, e.g., N. C. Cohen et al., "Molecular Modeling Software and Methods for Medicinal Chemistry, J. Med. Chem., 33, pp. 883-894 (1990); see also, M. A. Navia and M. A. Murcko, "The Use of Structural Information in Drug Design", Current Opinions in Structural Biology, 2, pp. 202-210 (1992); L. M. Balbes et al., "A Perspective of Modern Methods in Computer-Aided Drug Design", Reviews in Computational Chemistry, Vol. 5, K. B. Lipkowitz and D. B. Boyd, Eds., VCH, New York, pp. 337-380 (1994); see also, W. C. Guida, "Software For Structure-Based Drug Design", Curr. Opin. Struct. Biology, 4, pp. 777-781 (1994)).

Once a chemical entity has been designed or selected by the above methods, the efficiency with which that chemical entity may bind to an Aurora-2 binding pocket may be tested and optimized by computational evaluation. For example, an effective Aurora-2 binding pocket inhibitor must preferably demonstrate a relatively small difference in energy between its bound and free states (i.e., a small deformation energy of binding). Thus, the most efficient Aurora-2 binding pocket inhibitors should preferably be designed with a deformation energy of binding of not greater than about 10 kcal/mole, more preferably, not greater than 7 kcal/mole. Aurora-2 binding pocket inhibitors may interact with the binding pocket in more than one conformation that is similar in overall binding energy. In those cases, the deformation energy of binding is taken to be the difference between the energy of the free chemical entity and the average energy of the conformations observed when the inhibitor binds to the protein.

A chemical entity designed or selected as binding to an Aurora-2 binding pocket may be further computationally optimized so that in its bound state it would preferably lack repulsive electrostatic interaction with the target enzyme and with the surrounding water molecules. Such non-complementary electrostatic interactions include repulsive charge-charge, dipole-dipole and charge-dipole interactions.

Specific computer software is available in the art to evaluate compound deformation energy and electrostatic interactions. Examples of programs designed for such uses include: Gaussian 94, revision C (M. J. Frisch, Gaussian, Inc., Pittsburgh, Pa. ©1995); AMBER, version 4.1 (P. A. Kollman, University of California at San Francisco, ©1995); QUANTA/CHARMM (Molecular Simulations, Inc., San Diego, Calif. ©1998, 2000); Insight II/Discover (Molecular Simulations, Inc., San Diego, Calif. ©1998); DelPhi (Molecular Simulations, Inc., San Diego, Calif. ©1998); and AMSOL (Quantum Chemistry Program Exchange, Indiana University). These programs may be implemented, for instance, using a Silicon Graphics workstation such as an Indigo2 with "IMPACT" graphics. Other hardware systems and software packages will be known to those skilled in the art.

Another approach enabled by this invention, is the computational screening of small molecule databases for chemical entities or compounds that can bind in whole, or in part, to an Aurora-2 binding pocket. In this screening, the quality of fit of such entities to the binding pocket may be judged either by shape complementarity or by estimated interaction energy (E. C. Meng et al., J. Comp. Chem., 13, pp. 505-524 (1992)).

According to another embodiment, the invention provides compounds which associate with an Aurora-2 binding pocket produced or identified by the method set forth above.

Another particularly useful drug design technique enabled by this invention is iterative drug design. Iterative drug design is a method for optimizing associations between a protein and a compound by determining and evaluating the three-dimensional structures of successive sets of protein/compound complexes.

In iterative drug design, crystals of a series of protein or protein complexes are obtained and then the three-dimensional structures of each crystal is solved. Such an approach provides insight into the association between the proteins and compounds of each complex. This is accomplished by selecting compounds with inhibitory activity, obtaining crystals of this new protein/compound complex, solving the three-dimensional structure of the complex, and comparing the associations between the new protein/compound complex and previously solved protein/compound complexes. By observing how changes in the compound affected the protein/compound associations, these associations may be optimized.

In some cases, iterative drug design is carried out by forming successive protein-compound complexes and then crystallizing each new complex. High throughput crystallization assays may be used to find a new crystallization condition or to optimize the original protein or complex crystallization condition for the new complex. Alternatively, a pre-formed protein crystal may be soaked in the presence of an inhibitor, thereby forming a protein/compound complex and obviating the need to crystallize each individual protein/compound complex.

Structure Determination of Other Molecules

The structure coordinates set forth in FIGS. 1-4 can also be used to aid in obtaining structural information about other crystallized molecules or molecular complexes. This may be achieved by any of a number of well-known techniques, including molecular replacement.

According to an alternate embodiment, the machine-readable data storage medium comprises a data storage material encoded with a first set of machine readable data which comprises the Fourier transform of at least a portion of the structure coordinates set forth in FIGS. 1-4 or homology model thereof, and which, when using a machine programmed with instructions for using said data, can be combined with a second set of machine readable data comprising the X-ray diffraction pattern of a molecule or molecular complex to determine at least a portion of the structure coordinates corresponding to the second set of machine readable data.

In another embodiment, the invention provides a computer for determining at least a portion of the structure coordinates corresponding to X-ray diffraction data obtained from a molecule or molecular complex, wherein said computer comprises:
 (a) a machine-readable data storage medium comprising a data storage material encoded with machine-readable data, wherein said data comprises at least a portion of the structure coordinates of Aurora-2 according to any one of FIGS. 1-4 or homology model thereof;
 (b) a machine-readable data storage medium comprising a data storage material encoded with machine-readable data, wherein said data comprises X-ray diffraction data obtained from said molecule or molecular complex; and
 (c) instructions for performing a Fourier transform of the machine-readable data of (a) and for processing said machine-readable data of (b) into structure coordinates.

For example, the Fourier transform of at least a portion of the structure coordinates set forth in any one of FIGS. 1-4 or homology model thereof may be used to determine at least a portion of the structure coordinates of Aurora-2 homologues. In one embodiment, the molecule is an Aurora-2 homologue. In another embodiment, the molecular complex is selected from the group consisting of Aurora-2 complex and Aurora-2 homologue complex.

Therefore, in another embodiment this invention provides a method of utilizing molecular replacement to obtain structural information about a molecule or a molecular complex of unknown structure wherein the molecule or molecular complex is sufficiently homologous to Aurora-2, comprising the steps of:
 (a) crystallizing said molecule or molecular complex of unknown structure;
 (b) generating an X-ray diffraction pattern from said crystallized molecule or molecular complex;
 (c) applying at least a portion of the Aurora-2 structure coordinates set forth in one of FIGS. 1-4 or a homology model thereof to the X-ray diffraction pattern to generate a three-dimensional electron density map of at least a portion of the molecule or molecular complex whose structure is unknown; and
 (d) generating a structural model of the molecule or molecular complex from the three-dimensional electron density map.

In one embodiment, the method is performed using a computer. In another embodiment, the molecule is selected from the group consisting of Aurora-2 and Aurora-2 homologues. In another embodiment, the molecule is an Aurora molecular complex or homologue thereof.

By using molecular replacement, all or part of the structure coordinates of the Aurora-2 as provided by this invention or homology model thereof (and set forth in any one of FIGS. 1-4) can be used to determine the structure of a crystallized molecule or molecular complex whose structure is unknown more quickly and efficiently than attempting to determine such information ab initio.

Molecular replacement provides an accurate estimation of the phases for an unknown structure. Phases are a factor in equations used to solve crystal structures that can not be determined directly. Obtaining accurate values for the phases, by methods other than molecular replacement, is a time-consuming process that involves iterative cycles of approximations and refinements and greatly hinders the solution of crystal structures. However, when the crystal structure of a protein containing at least a homologous portion has been solved, the phases from the known structure may provide a satisfactory estimate of the phases for the unknown structure.

Thus, this method involves generating a preliminary model of a molecule or molecular complex whose structure coordinates are unknown, by orienting and positioning the relevant portion of the Aurora-2 according to any one of FIGS. 1-4 within the unit cell of the crystal of the unknown molecule or molecular complex so as best to account for the observed X-ray diffraction pattern of the crystal of the molecule or molecular complex whose structure is unknown. Phases can then be calculated from this model and combined with the observed X-ray diffraction pattern amplitudes to generate an electron density map of the structure whose coordinates are unknown. This, in turn, can be subjected to any well-known model building and structure refinement techniques to provide a final, accurate structure of the unknown crystallized molecule or molecular complex (E. Lattman, "Use of the Rotation and Translation Functions", in *Meth. Enzymol.*, 115, pp. 55-77 (1985); M. G. Rossmann, ed., "The Molecular Replacement Method", Int. Sci. Rev. Ser., No. 13, Gordon & Breach, New York (1972)).

The structure of any portion of any crystallized molecule or molecular complex that is sufficiently homologous to any portion of the Aurora-2 can be resolved by this method.

In one embodiment, the method of molecular replacement is utilized to obtain structural information about an Aurora-2 homologue. The structure coordinates of Aurora-2 as provided by this invention are particularly useful in solving the structure of Aurora-2 complexes that are bound by ligands, substrates and inhibitors.

Furthermore, the structure coordinates of Aurora-2 as provided by this invention are useful in solving the structure of Aurora-2 proteins that have amino acid substitutions, additions and/or deletions (referred to collectively as "Aurora-2 mutants", as compared to naturally occurring Aurora-2). These Aurora-2 mutants may optionally be crystallized in co-complex with a chemical entity, such as a non-hydrolyzable ATP analogue or a suicide substrate. The crystal structures of a series of such complexes may then be solved by molecular replacement and compared with that of wild-type Aurora-2. Potential sites for modification within the various binding pockets of the enzyme may thus be identified. This information provides an additional tool for determining the most efficient binding interactions, for example, increased hydrophobic interactions, between Aurora-2 and a chemical entity or compound.

The structure coordinates are also particularly useful in solving the structure of crystals of Aurora-2 or Aurora-2 homologues co-complexed with a variety of chemical entities. This approach enables the determination of the optimal sites for interaction between chemical entities, including candidate Aurora-2 inhibitors. For example, high resolution X-ray diffraction data collected from crystals exposed to different types of solvent allows the determination of where each type of solvent molecule resides. Small molecules that bind tightly to those sites can then be designed and synthesized and tested for their Aurora-2 inhibition activity.

All of the complexes referred to above may be studied using well-known X-ray diffraction techniques and may be refined using 1.5-3.4 Å resolution X-ray data to an R value of about 0.30 or less using computer software, such as X-PLOR (Yale University, ©1992, distributed by Molecular Simulations, Inc.; see, e.g., Blundell & Johnson, supra; *Meth. Enzy-* mol., vol. 114 & 115, H. W. Wyckoff et al., eds., Academic Press (1985)) or CNS (Brunger et al., *Acta Cryst.*, D54, pp. 905-921, (1998)).

In order that this invention be more fully understood, the following examples are set forth. These examples are for the purpose of illustration only and are not to be construed as limiting the scope of the invention in any way.

Example 1

Expression and Purification of Aurora-2

The expression of Aurora-2 was carried out using standard procedures known in the art. A truncated Aurora-2 (amino acid residues 107-403) (full length sequence: GenBank AF011468; SEQ ID NO: 1) with an N-terminal hexa-histidine tag and a thrombin cleavage site was overexpressed in a baculovirus expression system.

Aurora-2 was purified using Ni/NTA agarose metal affinity chromatography (Qiagen, Hilden, Germany) followed by size-exclusion on a Superdex 200 column (Amersham Pharmacia Biotech, Uppsala, Sweden). The hexa-histidine tag was removed by incubation with thrombin (Calbiochem, La Jolla, Calif.). Incubation overnight incubation at 4° C. with 5 units/mg thrombin produced more than 90% Aurora-2 (amino acid residues 107-403), which was used for crystallographic studies. The reaction was quenched with PMSF (phenylmethylsulfonyl fluoride or α-toluenesulfonyl fluoride) and thrombin was removed with benzamidine sepharose (Pharmacia, Uppsala, Sweden). The protein was applied to a MonoS 10/10 column (Pharmacia, Uppsala, Sweden) equilibrated in 20 mM HEPES, pH 7.3, 10% Glycerol (v/v), 2 mM DTT, and eluted with a linear gradient from 0 to 500 mM NaCl in 80 column volumes. Unphosphorylated Aurora-2 (107-403) eluted at 148 mM NaCl. The protein was dialyzed against 25 mM Tris pH 8.0 containing 200 mM NaCl and 2 mM DTT at 4° C., concentrated to 15 mg/ml, and centrifuged at 100,000×g prior to crystallization. All protein molecular weights were confirmed by electrospray mass spectrometry.

Example 2

Formation of Aurora-2-Inhibitor Complex for Crystallization

Crystals of Aurora-2-inhibitor complex crystals were formed by co-crystallizing the protein with the inhibitors or with adenosine. The inhibitor was added to the Aurora-2 protein solution immediately after the final Mono-S purification step and prior to protein concentration (Example 1). Alternatively, inhibitor may be added to the concentrated Aurora-2 protein solution immediately before setting up the crystallization drop.

Example 3

Crystallization of Aurora-2 and Aurora-2-Inhibitor Complexes

Crystallization of Aurora-2 was carried out using the hanging drop vapor diffusion technique. The Aurora-2 formed diamond shaped or hexagonal plate-like crystals over a reservoir containing 25% PEG 3350, 50 mM MES pH 6.0, 200 mM ammonium sulphate. The crystallization droplet contained 1 µl of 15 mg ml$^{-1}$ protein solution and 1 µl of reservoir solution. Crystals formed in less than 48 hours.

The formed crystals were transferred to a reservoir solution containing 15% glycerol. After soaking the crystals in 15% glycerol for less than 2 minutes, the crystals were scooped up with a cryo-loop, frozen in liquid nitrogen and stored for data collection.

Example 4

X-Ray Data Collection and Structure Determination

The Aurora-2-inhibitor complex structures and the Aurora-2-adenosine structure were solved by molecular replacement using X-ray diffraction data collected either (i) at beam line 5.0.2 of the Advanced Light Source Lawrence Berkeley Laboratory, Berkeley, Calif., USA, (ii) at beam line 14.2 of the CCLRC Synchrotron Radiation Source, Daresbury, Cheshire, UK, or (iii) at beamline X31, DESY, EMBL Outstation, Hamburg, Germany. The diffraction images were processed with the program MOSFLM (A. G. Leslie, *Acta Cryst.*, D55, pp. 1696-1702 (1999)) and the data was scaled using SCALA (Collaborative Computational Project, N., *Acta Cryst.*, D50, pp. 760-763 (1994)).

The data statistics, unit cell parameters and spacegroup of the Aurora-2-(5-Cyclopropyl-2H-pyrazol-3-yl)-(2-phenyl-quinazolin-4-yl)-amine crystal structure is given in Table 1. The starting phases for the Aurora-2 complexes were obtained by molecular replacement using coordinates of GSK-3β (PDB Accession number 1I09) (E. ter Haar, et al., *Nat. Struct. Biol.*, 8, pp. 593-596 (2001)) as a search model in the program AMoRe (J. Navaza, *Acta. Cryst. A,* 50, pp. 157-163 (1994)). The asymmetric unit contained a single Aurora-2 complex. Multiple rounds of rebuilding with QUANTA (Molecular Simulations, Inc., San Diego, Calif. ©1998, 2000) and refinement with CNX (Accelrys Inc., San Diego, Calif. ©2000) resulted in a final model that included residues 127 to 279 and residues 288 to 390. The refined model has a crystallographic R-factor of 26.3% and R-free of 33.2%.

The data statistics, unit cell parameters and spacegroup of the Aurora-2-(5-Methylthiazol-2-yl)-(2-phenyl-quinazolin-4-yl)-amine crystal structure is given in Table 2. The starting phases were obtained by molecular replacement using coordinates of the Aurora-2-(5-Cyclopropyl-2H-pyrazol-3-yl)-(2-phenyl-quinazolin-4-yl)-amine complex as a search model in the program AMoRe. Multiple rounds of rebuilding with QUANTA (Molecular Simulations, Inc., San Diego, Calif. ©1998, 2000) and refinement with CNX (Accelrys Inc., San Diego, Calif. ©2000) resulted in a final model that included residues 120 to 279 and residues 287 to 388. The refined model has a crystallographic R-factor of 25.9% and R-free of 32.8%.

The data statistics, unit cell parameters and spacegroup of the Aurora-2-(5-Methyl-2H-pyrazol-3-yl)-(2-(pyridin-3-yl-methylamino)-quinazolin-4-yl)-amine crystal structure is given in Table 3. The starting phases were obtained by molecular replacement using coordinates of the Aurora-2-(5-Cyclopropyl-2H-pyrazol-3-yl)-(2-phenyl-quinazolin-4-yl)-amine complex as a search model in the program AMoRe. Multiple rounds of rebuilding with QUANTA (Molecular Simulations, Inc., San Diego, Calif. ©1998, 2000) and refinement with CNX (Accelrys Inc., San Diego, Calif. ©2000) resulted in a final model that included residues 128 to 277 and residues 291 to 388. The refined model has a crystallographic R-factor of 23.6% and R-free of 29.1%.

The data statistics, unit cell parameters and spacegroup of the Aurora-2-adenosine crystal structure is given in Table 4. The starting phases were obtained by molecular replacement using coordinates of the Aurora-2-(5-Cyclopropyl-2H-pyrazol-3-yl)-(2-phenyl-quinazolin-4-yl)-amine complex as a search model in the program AMoRe. Multiple rounds of rebuilding with QUANTA (Molecular Simulations, Inc., San Diego, Calif. ©1998, 2000) and refinement with CNX (Accelrys Inc., San Diego, Calif. ©2000) resulted in a final model that included residues 127 to 278 and residues 289 to 387. The refined model has a crystallographic R-factor of 26.4% and R-free of 31.7%.

In the above models, disordered residues were not included in the model. Alanine or glycine residues were used in the model if the side chains of certain residues could not be located in the electron density.

Example 5

Overall Structure of Aurora-2

Aurora-2 has the typical bi-lobal catalytic kinase fold or structural domain (S. K. Hanks, et al., *Science*, 241, pp. 42-52 (1988); Hanks, S. K. and A. M. Quinn, *Meth. Enzymol.*, 200, pp. 38-62 (1991)) with a β-strand sub-domain (residues 127-215) at the N-terminal end and an α-helical sub-domain at the C-terminal end (residues 216-385) (FIG. 5). The ATP-binding pocket is at the interface of the α-helical and β-strand domains, and is bordered by the glycine rich loop and the hinge. The activation loop runs along the surface of the catalytic active site. The β-strand domain consists of five antiparallel β-strands that form a β-barrel structure.

Comparison of the Aurora-2 Structure with Other Kinases

Comparison with other kinases such as GSK-3β, CDK2 and p38 revealed that the structure of Aurora-2 closely resembles the substrate-bound activated, form of a kinase. However, a unique feature that is present in all four Aurora-2 crystal structures is the unusual conformation of the activation loop (amino acid residues 273-292). Amino acid residues 275-290 act like a flexible flap that partially occludes the catalytic active site and creates a novel hydrophobic binding pocket in the catalytic active site (FIG. 6). This hydrophobic pocket is unique in that it partially overlaps with the triphosphate binding pocket of the catalytic active site. Comparison of the activation loops of GSK-3β (PDB Accession number 1IO9) (E. ter Haar, et al., *Nat. Struct. Biol.*, 8, pp. 593-596 (2001)), P38 (PDB Accession number 1CM8) (Bellon, S., et al., *Struct. Fold Des.*, 7, pp. 1057-65 (1999)) and substrate-bound activated CDK2 (PDB Accession number 1B38) (N. R. Brown et al., *J. Biol. Chem.*, 274, pp. 8746-8756 (1999)) shows that in other closely related kinases, the activation loop adopts a more extended conformation, irrespective of whether activated protein was used in the crystal structure determination (FIG. 7).

Example 6

Catalytic Active Site of Aurora-2-Inhibitor Complexes

The inhibitor (5-Cyclopropyl-2H-pyrazol-3-yl)-(2-phenyl-quinazolin-4-yl)-amine is bound in the deep cleft of the catalytic active site in the Aurora-2 structure (FIG. 6). The inhibitor forms three hydrogen bonds with the hinge portion of the ATP-binding pocket (dotted lines). The 1H pyrazole nitrogen shares a proton with the E211 backbone carbonyl. The other pyrazole nitrogen (position 2) accepts a proton from the A213 backbone nitrogen. Comparison with the adenosine-bound crystal structure reveals that the pyrazole mimics the binding of adenosine, a constituent of the natural ATP substrate.

The side chains of L210 and K162 are positioned inside the ATP-binding pocket. K162 is a catalytically important residue and is unable to make a salt bridge with D274 due to the formation of a unique hydrophobic binding pocket in the Aurora-2 catalytic active site. This lysine-glutamic acid salt bridge is seen in other kinase crystal structures.

FIG. 8 represents the binding pockets for each Aurora-2 complex in the present invention.

Example 7

The Use of Aurora-2 Coordinates for Inhibitor Design

The coordinates of any one of FIGS. 1-4 are used to design compounds, including inhibitory compounds, that associate with Aurora-1, Aurora-2, Aurora-3, or homologues of Aurora-1, Aurora-2 or Aurora-3. This process may be aided by using a computer comprising a machine-readable data storage medium encoded with a set of machine-executable instructions, wherein the recorded instructions are capable of displaying a three-dimensional representation of the Aurora-2 or a portion thereof. The graphical representation is used according to the methods described herein to design compounds. Such compounds associate with the Aurora-2 at the ATP-binding pocket or substrate binding pocket.

Example 8

Aurora-2 Activity Inhibition Assay

Compounds were screened for their ability to inhibit full length Aurora-2 (AA 1-403) activity using a standard coupled enzyme system (Fox et al., *Protein Sci.*, 7, pp. 2249 (1998)). Reactions were carried out in a solution containing 100 mM HEPES (pH 7.5), 10 mM $MgCl_2$, 25 mM NaCl, 300 μM NADH, 1 mM DTT and 3% DMSO. Final substrate concentrations in the assay were 200 μM ATP (Sigma Chemicals, St Louis, Mo.) and 800 μM peptide (LRRASLG, American Peptide, Sunnyvale, Calif.). Reactions were carried out at 30° C. and with 35 nM Aurora-2. Final concentrations of the components of the coupled enzyme system were 2.5 mM phosphoenolpyruvate, 200 μM NADH, 60 μg/ml pyruvate kinase and 20 μg/ml lactate dehydrogenase.

An assay stock buffer solution was prepared containing all of the reagents listed above with the exception of ATP and the test compound of interest. The assay stock buffer solution (60 μl) was incubated in a 96 well plate with 2 μl of the test compound of interest at final concentrations spanning 0.002 μM to 30 μM at 30° C. for 10 min. Typically, a 12 point titration was conducted by preparing serial dilutions (from 1 mM compound stocks) with DMSO of the test compounds in daughter plates. The reaction was initiated by the addition of 5 μl of ATP (final concentration 200 μM). Rates of reaction were obtained using a Molecular Devices Spectramax plate reader (Sunnyvale, Calif.) over 10 min at 30° C. The Ki values were determined from the rate data as a function of inhibitor concentration using computerized nonlinear regression (Prism 3.0, Graphpad Software, San Diego, Calif.).

Example 9

The Use of Aurora-2 Coordinates in the Design of Aurora-Specific Antibodies

The atomic coordinates in any one of FIGS. 1-4 also define, in great detail, the external solvent-accessible, hydrophilic, and mobile surface regions of the Aurora-2 catalytic kinase domain. Anti-peptide antibodies are known to react strongly against highly mobile regions but do not react with well-ordered regions of proteins. Mobility is therefore a major factor in the recognition of proteins by anti-peptide antibodies (J. A. Tainer et al., *Nature,* 312, pp. 127-134 (1984))

One skilled in the art would therefore be able to use the X-ray crystallography data to determine possible antigenic sites in the Aurora-2 kinase domain. Possible antigenic sites are exposed, small and mobile regions on the kinase surface which have atomic B-factors of greater than about 80 Å$^2$ in FIGS. 1, 2, 3 and 4. This information can be used in conjunction with data from immunological studies to design and produce specific monoclonal or polyclonal antibodies.

This process may be aided by using a computer comprising a machine-readable data storage medium encoded with a set of machine-executable instructions, wherein the recorded instructions are capable of displaying a three-dimensional representation of the Aurora-2 or a portion thereof.

TABLE 1

Summary of data collection for Aurora-2 - (5-Cyclopropyl-2H-pyrazol-3-yl)-(2-phenyl-quinazolin-4-yl)-amine complex

| Source | ALS 5.0.2 |
|---|---|
| Wavelength (Å) | 1.1 |
| Resolution (Å) | 2.7 |
| No. of Reflections (measured/unique) | 62,585/9,773 |
| Completeness (%) (overall/outer shell) | 99.4/99.4 |
| I/σ(I) (overall/outer shell) | 23.1/1.9 |
| R$_{merge}$ * (%) (overall/outer shell) | 4.9/39 |
| Molecules per asymmetric unit | 1 |
| Structure refinement | |
| Resolution (Å) | 30-2.7 |
| No. of reflections | 7381 |
| R factor | 26.3 |
| Free R factor † | 33.2 |
| RMSD values Bond lengths/angles | 0.005/2.5° |

Space Group: P3$_2$21
Unit Cell: a = b = 87 Å, c = 76 Å; α = β = 90°, γ = 120°
* R$_{merge}$ = 100 × Σ$_h$Σ$_i$ @I$_{hi}$ − <I$_h$> @/Σ$_h$Σ$_i$I$_{hi}$.
† The Free R factor was calculated with 7.9% of the data.

TABLE 2

Summary of data collection for Aurora-2 - (5-Methylthiazol-2-yl)-(2-phenyl-quinazolin-4-yl)-amine complex

| Source | Daresbury SRS 14.2 |
|---|---|
| Wavelength (Å) | 0.98 |
| Resolution (Å) | 2.5 |
| No. of Reflections (measured/unique) | 113,308/12,094 |

TABLE 2-continued

Summary of data collection for Aurora-2 - (5-Methylthiazol-2-yl)-(2-phenyl-quinazolin-4-yl)-amine complex

| Source | Daresbury SRS 14.2 |
|---|---|
| Completeness (%) (overall/outer shell) | 99.8/99.8 |
| I/σ(I) (overall/outer shell) | 18.2/1.5 |
| R$_{merge}$ * (%) (overall/outer shell) | 8.2/46 |
| Molecules per asymmetric unit | 1 |
| Structure refinement | |
| Resolution (Å) | 30-2.5 |
| No. of reflections | 9318 |
| R factor | 25.9 |
| Free R factor †† | 32.8 |
| RMSD values Bond lengths/angles | 0.011/1.9° |

Space Group: P3$_2$21
Unit Cell: a = b = 87 Å, c = 76 Å; α = β = 90°, γ = 120°
* R$_{merge}$ = 100 × Σ$_h$Σ$_i$ @I$_{hi}$ − <I$_h$> @/Σ$_h$Σ$_i$I$_{hi}$.
†† The Free R factor was calculated with 8.1% of the data.

TABLE 3

Summary of data collection for Aurora-2 - (5-Methyl-2H-pyrazol-3-yl)-(2-(pyridin-3-ylmethylamino)-quinazolin-4-yl)-amine complex

| Source | Daresbury SRS 14.2 |
|---|---|
| Wavelength (Å) | 0.98 |
| Resolution (Å) | 3.1 |
| No. of Reflections (measured/unique) | 23,387/5,359 |
| Completeness (%) (overall/outer shell) | 99.8/99.8 |
| I/σ(I) (overall/outer shell) | 15.9/2.5 |
| R$_{merge}$ * (%) (overall/outer shell) | 8.6/41 |
| Molecules per asymmetric unit | 1 |
| Structure refinement | |
| Resolution (Å) | 30-3.3 |
| No. of reflections | 4409 |
| R factor | 23.6 |
| Free R factor ††† | 29.1 |
| RMSD values Bond lengths/angles | 0.011/1.78° |

Space Group: P3$_2$21
Unit Cell: a = b = 87 Å, c = 76 Å; α = β = 90°, γ = 120°
* R$_{merge}$ = 100 × Σ$_h$Σ$_i$ @I$_{hi}$ − <I$_h$> @/Σ$_h$Σ$_i$I$_{hi}$.
††† The Free R factor was calculated with 4.3% of the data.

TABLE 4

Summary of data collection for Aurora-2 - adenosine complex

| Source | EMBL Hamburg X31 |
|---|---|
| Wavelength (Å) | 0.8 |
| Resolution (Å) | 3.2 |
| No. of Reflections (measured/unique) | 12,545/5,355 |
| Completeness (%) (overall/outer shell) | 96.5/96.5 |
| I/σ(I) (overall/outer shell) | 14.5/1.2 |
| R$_{merge}$ * (%) (overall/outer shell) | 5.0/46.8 |
| Molecules per asymmetric unit | 1 |

TABLE 4-continued

Summary of data collection for Aurora-2 - adenosine complex

| Source | EMBL Hamburg X31 |
|---|---|
| Structure refinement | |
| Resolution (Å) | 20-3.2 |
| No. of reflections | 4016 |
| R factor | 26.4 |
| Free R factor ††† | 31.7 |
| Source | EMBL Hamburg X31 |
| RMSD values Bond lengths/angles | 0.013/1.65° |

Space Group: P3₂21
Unit Cell: a = b = 87 Å, c = 76 Å; α = β = 90°, γ =120°
* $R_{merge} = 100 \times \Sigma_h\Sigma_i @I_{hi} - <I_h> @/\Sigma_h\Sigma_iI_{hi}$.
††† The Free R factor was calculated with 4.0% of the data.

---

We claim:

1. A method for designing, selecting and/or optimizing a chemical entity that binds to all or part of an Aurora-2 kinase binding pocket or protein comprising the steps of:
   (a) employing the structural coordinates of said Aurora-2 kinase binding pocket or protein according to any one of FIGS. 1-4 to generate a three-dimensional model of said Aurora-2 kinase binding pocket or protein on a computer, wherein said computer comprises the means for generating said three-dimensional model;
   (b) identifying a binding pocket for said chemical entity, wherein said binding pocket comprises: F133, I135, G136, R137, L139, G140, G142, F144, G145, N146, V147, Y148, L149, A150, R151, E152, I158, L159, A160, L161, K162, V163, V182, E183, Q185, H190, N192, I193, L194, R195, L196, Y197, G198, Y199, F200, V206, Y207, L208, I209, L210, E211, Y212, A213, P214, L215, T217, V218, Y219, R220, E221, D229, E230, Q231, R232, T233, A234, T235, Y236, I237, T238, E239, L240, A241, N242, A243, L244, S245, Y246, C247, H248, S249, K250, R251, V252, I253, H254, R255, D256, I257, K258, P259, E260, N261, L262, L263, L264, G265, S266, G268, E269, L270, K271, I272, A273, D274, F275, W277, S278, or V279 or combinations thereof; and
   (c) employing the residues identified in (b) to design, select and/or optimize said chemical entity by performing a fitting operation between said chemical entity and said three-dimensional structural information of all or part of said binding pocket or protein.

2. A method for evaluating the ability of a chemical entity to associate with all or part of an Aurora-2 kinase binding pocket or protein comprising the steps of:

(a) employing the structural coordinates of said Aurora-2 kinase binding pocket or protein according to any one of FIGS. 1-4 to generate a three-dimensional model of said Aurora-2 kinase binding pocket or protein on a computer, wherein said computer comprises the means for generating said three-dimensional model;

(b) identifying a binding pocket for said chemical entity, wherein said binding pocket comprises: F133, I135, G136, R137, L139, G140, G142, F144, G145, N146, V147, Y148, L149, A150, R151, E152, I158, L159, A160, L161, K162, V163, V182, E183, Q185, H190, N192, I193, L194, R195, L196, Y197, G198, Y199, F200, V206, Y207, L208, I209, L210, E211, Y212, A213, P214, L215, T217, V218, Y219, R220, E221, D229, E230, Q231, R232, T233, A234, T235, Y236, I237, T238, E239, L240, A241, N242, A243, L244, S245, Y246, C247, H248, S249, K250, R251, V252, I253, H254, R255, D256, I257, K258, P259, E260, N261, L262, L263, L264, G265, S266, G268, E269, L270, K271, I272, A273, D274, F275, W277, S278, or V279 or combinations thereof;

(c) employing computational means to perform a fitting operation between the chemical entity and all or part of the binding pocket or protein identified in (b); and (d) analyzing the results of said fitting operation to quantitate the association between the chemical entity and all or part of the binding pocket or protein.

3. A method of employing a computer for evaluating the ability of a chemical entity to associate with all or part of the binding pocket or protein of an Aurora-2 kinase, wherein said computer comprises a machine-readable data storage medium comprising a data storage material encoded with the structure coordinates of an Aurora-2 kinase binding pocket or protein according to any one of FIGS. 1-4 and means for generating a three-dimensional graphical representation of the binding pocket or protein, wherein said method comprises the steps of:

(a) employing the structural coordinates of said Aurora-2 kinase binding pocket or protein according to any one of FIGS. 1-4 to generate a three-dimensional model of said Aurora-2 kinase binding pocket or protein on said computer;

(b) identifying a binding pocket for said chemical entity, wherein said binding pocket comprises: F133, I135, G136, R137, L139, G140, G142, F144, G145, N146, V147, Y148, L149, A150, R151, E152, I158, L159, A160, L161, K162, V163, V182, E183, Q185, H190, N192, I193, L194, R195, L196, Y197, G198, Y199, F200, V206, Y207, L208, I209, L210, E211, Y212, A213, P214, L215, T217, V218, Y219, R220, E221, D229, E230, Q231, R232, T233, A234, T235, Y236, I237, T238, E239, L240, A241, N242, A243, L244, S245, Y246, C247, H248, S249, K250, R251, V252, I253, H254, R255, D256, I257, K258, P259, E260, N261, L262, L263, L264, G265, S266, G268, E269, L270, K271, I272, A273, D274, F275, W277, S278, or V279 or combinations thereof;

(c) employing computational means to perform a fitting operation between the chemical entity and all or part of the binding pocket or protein identified in (b); and (d) analyzing the results of said fitting operation to quantitate the association between said chemical entity and all or part of the binding pocket or protein.

4. The method according to claim 3, further comprising the steps of:

(e) repeating steps (a) through (d) with a second chemical entity; and (f) selecting at least one of said first or second chemical entity that associates with said all or part of said binding pocket or protein based on said quantitated association of said first or second chemical entity.

5. A method for identifying a potential agonist or antagonist of an Aurora-2 kinase or Aurora-2 kinase complex comprising the steps of:

(a) employing the structural coordinates of an Aurora-2 kinase binding pocket or protein according to any one of FIGS. 1-4 to generate a three-dimensional in silico model of said Aurora-2 kinase and to design or select a chemical entity, wherein the binding pocket of said Aurora-2 kinase comprises: F133, I135, G136, R137, L139, G140, G142, F144, G145, N146, V147, Y148, L149, A150, R151, E152, I158, L159, A160, L161, K162, V163, V182, E183, Q185, H190, N192, I193, L194, R195, L196, Y197, G198, Y199, F200, V206, Y207, L208, I209, L210, E211, Y212, A213, P214, L215, T217, V218, Y219, R220, E221, D229, E230, Q231, R232, T233, A234, T235, Y236, I237, T238, E239, L240, A241, N242, A243, L244, S245, Y246, C247, H248, S249, K250, R251, V252, I253, H254, R255, D256, I257, K258, P259, E260, N261, L262, L263, L264, G265, S266, G268, E269, L270, K271, I272, A273, D274, F275, W277, S278, or V279 or combinations thereof;

(b) contacting the chemical entity with said Aurora-2 kinase or Aurora-2 kinase complex;

(c) monitoring the catalytic activity of said Aurora-2 kinase or Aurora-2 kinase complex; and (d) classifying the chemical entity as an agonist or antagonist based on the effect of the chemical entity on the catalytic activity of said Aurora-2 kinase or Aurora-2 kinase complex.

6. A method of designing a compound or complex that associates with all or part of the binding pocket of an Aurora-2 kinase comprising the steps of:

(a) employing the structural coordinates of an Aurora-2 kinase binding pocket or protein according to any one of FIGS. 1-4 on a computer comprising the means for generating three-dimensional structural information from said structure coordinates;

(b) identifying a binding pocket for said chemical entity, wherein said binding pocket comprises: F133, I135, G136, R137, L139, G140, G142, F144, G145, N146, V147, Y148, L149, A150, R151, E152, I158, L159, A160, L161, K162, V163, V182, E183, Q185, H190, N192, I193, L194, R195, L196, Y197, G198, Y199, F200, V206, Y207, L208, I209, L210, E211, Y212, A213, P214, L215, T217, V218, Y219, R220, E221, D229, E230, Q231, R232, T233, A234, T235, Y236, I237, T238, E239, L240, A241, N242, A243, L244, S245, Y246, C247, H248, S249, K250, R251, V252, I253, H254, R255, D256, I257, K258, P259, E260, N261, L262, L263, L264, G265, S266, G268, E269, L270, K271, I272, A273, D274, F275, W277, S278, or V279 or combinations thereof;

(c) using the computer to perform a fitting operation to associate a first chemical entity with all or part of the binding pocket;

(d) performing a fitting operation to associate at least a second chemical entity with all or part of the binding pocket;

(e) quantifying the association between the first and second chemical entity and all or part of the binding pocket;

(f) optionally repeating steps (b) to (e) with another first and second chemical entity, selecting a first and a second chemical entity based on said quantified association of all of said first and second chemical entity;

(g) optionally, visually inspecting the relationship of the first and second chemical entity to each other in relation to the binding pocket on a computer screen using the three-dimensional graphical representation of the binding pocket and said first and second chemical entity; and (h) assembling the first and second chemical entity into a compound or complex that associates with all or part of said binding pocket by model building.

* * * * *

SEQUENCE LISTING

<160> NUMBER OF SEQ ID NOS: 2

<210> SEQ ID NO 1
<211> LENGTH: 403
<212> TYPE: PRT
<213> ORGANISM: Homo sapiens

<400> SEQUENCE: 1

```
Met Asp Arg Ser Lys Glu Asn Cys Ile Ser Gly Pro Val Lys Ala Thr
1               5                   10                  15

Ala Pro Val Gly Gly Pro Lys Arg Val Leu Val Thr Gln Gln Ile Pro
            20                  25                  30

Cys Gln Asn Pro Leu Pro Val Asn Ser Gly Gln Ala Gln Arg Val Leu
        35                  40                  45

Cys Pro Ser Asn Ser Ser Gln Arg Val Pro Leu Gln Ala Gln Lys Leu
    50                  55                  60

Val Ser Ser His Lys Pro Val Gln Asn Gln Lys Gln Lys Gln Leu Gln
65                  70                  75                  80

Ala Thr Ser Val Pro His Pro Val Ser Arg Pro Leu Asn Asn Thr Gln
                85                  90                  95

Lys Ser Lys Gln Pro Leu Pro Ser Ala Pro Glu Asn Asn Pro Glu Glu
            100                 105                 110

Glu Leu Ala Ser Lys Gln Lys Asn Glu Glu Ser Lys Lys Arg Gln Trp
        115                 120                 125

Ala Leu Glu Asp Phe Glu Ile Gly Arg Pro Leu Gly Lys Gly Lys Phe
    130                 135                 140

Gly Asn Val Tyr Leu Ala Arg Glu Lys Gln Ser Lys Phe Ile Leu Ala
145                 150                 155                 160

Leu Lys Val Leu Phe Lys Ala Gln Leu Glu Lys Ala Gly Val Glu His
                165                 170                 175

Gln Leu Arg Arg Glu Val Glu Ile Gln Ser His Leu Arg His Pro Asn
            180                 185                 190

Ile Leu Arg Leu Tyr Gly Tyr Phe His Asp Ala Thr Arg Val Tyr Leu
        195                 200                 205

Ile Leu Glu Tyr Ala Pro Leu Gly Thr Val Tyr Arg Glu Leu Gln Lys
    210                 215                 220

Leu Ser Lys Phe Asp Glu Gln Arg Thr Ala Thr Tyr Ile Thr Glu Leu
225                 230                 235                 240

Ala Asn Ala Leu Ser Tyr Cys His Ser Lys Arg Val Ile His Arg Asp
                245                 250                 255

Ile Lys Pro Glu Asn Leu Leu Leu Gly Ser Ala Gly Glu Leu Lys Ile
            260                 265                 270
```

```
Ala Asp Phe Gly Trp Ser Val His Ala Pro Ser Ser Arg Arg Thr Thr
        275                 280                 285

Leu Cys Gly Thr Leu Asp Tyr Leu Pro Pro Glu Met Ile Glu Gly Arg
        290                 295                 300

Met His Asp Glu Lys Val Asp Leu Trp Ser Leu Gly Val Leu Cys Tyr
305                 310                 315                 320

Glu Phe Leu Val Gly Lys Pro Pro Phe Glu Ala Asn Thr Tyr Gln Glu
                325                 330                 335

Thr Tyr Lys Arg Ile Ser Arg Val Glu Phe Thr Phe Pro Asp Phe Val
            340                 345                 350

Thr Glu Gly Ala Arg Asp Leu Ile Ser Arg Leu Leu Lys His Asn Pro
        355                 360                 365

Ser Gln Arg Pro Met Leu Arg Glu Val Leu Glu His Pro Trp Ile Thr
    370                 375                 380

Ala Asn Ser Ser Lys Pro Ser Asn Cys Gln Asn Lys Glu Ser Ala Ser
385                 390                 395                 400

Lys Gln Ser

<210> SEQ ID NO 2
<211> LENGTH: 26
<212> TYPE: PRT
<213> ORGANISM: human
<220> FEATURE:
<221> NAME/KEY: misc_feature
<222> LOCATION: (6)..(12)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid

<400> SEQUENCE: 2

Asp Phe Gly Trp Ser Xaa Xaa Xaa Xaa Xaa Xaa Xaa Arg Xaa Thr Xaa
1               5                   10                  15

Cys Gly Thr Xaa Asp Tyr Leu Pro Pro Glu
                20                  25
```